United States Patent
Zhang et al.

(10) Patent No.: US 10,508,085 B2
(45) Date of Patent: Dec. 17, 2019

(54) COMPOUNDS AND METHODS FOR IDO AND TDO MODULATION, AND INDICATIONS THEREFOR

(71) Applicant: Plexxikon Inc., Berkeley, CA (US)

(72) Inventors: Jiazhong Zhang, Foster City, CA (US); Hannah Powers, San Francisco, CA (US); Aaron Albers, San Francisco, CA (US); Phuongly Pham, San Francisco, CA (US); Guoxian Wu, Foster City, CA (US); John Buell, San Francisco, CA (US); Wayne Spevak, Berkeley, CA (US); Zuojun Guo, Pasadena, CA (US); Jack Walleshauser, San Ramon, CA (US); Ying Zhang, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/713,502

(22) Filed: Sep. 22, 2017

(65) Prior Publication Data

US 2018/0099939 A1  Apr. 12, 2018

Related U.S. Application Data

(60) Provisional application No. 62/398,409, filed on Sep. 22, 2016.

(51) Int. Cl.

| | | |
|---|---|---|
| *A61K 31/337* | (2006.01) | |
| *A61K 31/38* | (2006.01) | |
| *A61K 31/416* | (2006.01) | |
| *A61K 31/4184* | (2006.01) | |
| *C07D 231/12* | (2006.01) | |
| *C07D 403/06* | (2006.01) | |
| *C07D 233/54* | (2006.01) | |
| *C07D 407/04* | (2006.01) | |
| *C07D 409/04* | (2006.01) | |
| *C07D 487/04* | (2006.01) | |
| *C07D 487/08* | (2006.01) | |
| *C07D 487/10* | (2006.01) | |
| *C07D 231/56* | (2006.01) | |
| *C07D 401/06* | (2006.01) | |
| *C07D 401/14* | (2006.01) | |
| *C07D 403/04* | (2006.01) | |
| *C07D 403/14* | (2006.01) | |
| *C07D 491/044* | (2006.01) | |
| *C07D 491/056* | (2006.01) | |
| *C07D 519/00* | (2006.01) | |

(52) U.S. Cl.
CPC ......... *C07D 231/56* (2013.01); *C07D 231/12* (2013.01); *C07D 233/54* (2013.01); *C07D 401/06* (2013.01); *C07D 401/14* (2013.01); *C07D 403/04* (2013.01); *C07D 403/06* (2013.01); *C07D 403/14* (2013.01); *C07D 407/04* (2013.01); *C07D 409/04* (2013.01); *C07D 487/04* (2013.01); *C07D 487/08* (2013.01); *C07D 487/10* (2013.01); *C07D 491/044* (2013.01); *C07D 491/056* (2013.01); *C07D 519/00* (2013.01)

(58) Field of Classification Search
CPC .... A61K 31/337; A61K 31/38; A61K 31/416; A61K 31/4184; C07D 231/12; C07D 403/06; C07D 403/14; C07D 233/54; C07D 407/04; C07D 409/04; C07D 487/04; C07D 487/08; C07D 487/10
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |

(Continued)

FOREIGN PATENT DOCUMENTS

| | | |
|---|---|---|
| WO | WO 02/098350 | 12/2002 |
| WO | WO 2005/066136 | 7/2005 |

(Continued)

OTHER PUBLICATIONS

U.S. Appl. No. 15/851,639, filed Dec. 21, 2017, Wu et al.

(Continued)

*Primary Examiner* — Brenda L Coleman
(74) *Attorney, Agent, or Firm* — Sheppard Mullin Richter & Hampton LLP

(57) ABSTRACT

Disclosed are compounds of Formula I(a):

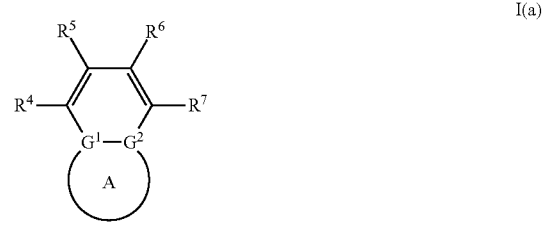

or a pharmaceutically acceptable salt, a solvate, a tautomer, an isomer or a deuterated analog thereof, wherein $R^4$, $R^5$, $R^6$, $R^7$, $G^1$, $G^2$ and Ring A are as described in any of the embodiments described in this disclosure; compositions thereof; and uses thereof.

37 Claims, No Drawings

Specification includes a Sequence Listing.

(56) References Cited

U.S. PATENT DOCUMENTS

| | | |
|---|---|---|
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,450,351 B2 | 5/2013 | Combs et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0182882 A1 | 7/2008 | Combs et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128390 A1 | 5/2014 | Lin et al. |
| 2014/0213554 A1 | 7/2014 | Wu et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0133400 A1 | 5/2015 | Zhang et al. |
| 2015/0183793 A1 | 7/2015 | Zhang et al. |
| 2015/0284397 A1 | 10/2015 | Lin et al. |
| 2015/0290205 A1 | 10/2015 | Ibrahim et al. |
| 2015/0368243 A1 | 12/2015 | Ibrahim |
| 2016/0068528 A1 | 3/2016 | Zhang et al. |
| 2016/0075712 A1 | 3/2016 | Shi et al. |
| 2016/0176865 A1 | 6/2016 | Ibrahim et al. |
| 2016/0243092 A1 | 8/2016 | Bollag et al. |
| 2016/0326162 A1 | 11/2016 | Lin et al. |
| 2016/0326168 A1 | 11/2016 | Ibrahim et al. |
| 2016/0326169 A1 | 11/2016 | Ibrahim et al. |
| 2016/0339025 A1 | 11/2016 | Ibrahim et al. |
| 2016/0340357 A1 | 11/2016 | Ibrahim et al. |
| 2016/0340358 A1 | 11/2016 | Ibrahim et al. |
| 2016/0355513 A1 | 12/2016 | Desai et al. |
| 2017/0029413 A1 | 2/2017 | Holladay et al. |
| 2017/0056382 A1 | 3/2017 | Wu et al. |
| 2017/0081326 A1 | 3/2017 | Ibrahim et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |

FOREIGN PATENT DOCUMENTS

| | | | |
|---|---|---|---|
| WO | WO 2006/042150 | 4/2006 | |
| WO | WO 2007/013896 | 2/2007 | |
| WO | WO 2007/117560 | 10/2007 | |
| WO | WO 2008/008431 | 1/2008 | |
| WO | WO 2009/073620 | 6/2009 | |
| WO | WO 2009/132238 | 10/2009 | |
| WO | WO 2010/111527 | 9/2010 | |
| WO | WO 2010/129467 | 11/2010 | |
| WO | WO 2011/056652 | 5/2011 | |
| WO | WO 2012/142237 | 10/2012 | |
| WO | WO 2014/006625 | 1/2014 | |
| WO | WO 2014/141110 | 9/2014 | |
| WO | WO 2014/159248 | 10/2014 | |
| WO | WO 2014/186035 | 11/2014 | |
| WO | WO 2015/188085 | 12/2015 | |
| WO | WO 2016/027241 | 2/2016 | |
| WO | WO-2016049524 A1 * | 3/2016 | ........... C07D 295/10 |
| WO | WO 2016/071293 | 5/2016 | |
| WO | WO 2016/161960 | 10/2016 | |
| WO | WO 2016/165613 | 10/2016 | |
| WO | WO 2017/007700 | 1/2017 | |
| WO | WO 2017/048612 | 3/2017 | |
| WO | WO 2018/057973 | 3/2018 | |

OTHER PUBLICATIONS

U.S. Appl. No. 15/925,270, filed Mar. 19, 2018, Lin.
U.S. Appl. No. 15/977,772, filed May 11, 2018, Ibrahim et al.
U.S. Appl. No. 16/001,534, filed Jun. 6, 2018, Zhang et al.
U.S. Appl. No. 16/024,197, filed Jun. 29, 2018, Ibrahim et al.
CAS Registry # 1505499-61-5. Entry date Dec. 27, 2013.
Dias, et al. Synthesis and Biological Activity of New Potential Antimalarial: 1h-Pyrazolo[3,4-B]pyridine Derivatives. Boll Chim Farm. Jan.-Feb. 2000;139(1):14-20.
G. W. Gribble, in Science of Synthesis, eds. V. Snieckus and M. Majewski, Georg Thieme Verlag KG, Stuttgart, 2006, vol. 8a (Jan. 8, 2014), pp. 357-426.
Higashino, et al. Studies on Pyrazolo [3, 4-d] pyrimidine Derivatives. XV. Reactions Involving the Formation of the Anion of the

(56) References Cited

OTHER PUBLICATIONS

Reissert Compound Derived from 1H-Pyrazolo [3, 4-d] pyrimidine. Chem. Pharm. Bull. 1987; 35(10):4078-4086.

Higashino, et al. Studies on Pyrazolo [3, 4-d] pyrimidine Derivatives. XIII. Aryl Migration of 4-Aroyl-1H-pyrazolo [3, 4-d] pyrimidines to 4-Aryl-4, 5-dihydro-1H-pyrazolo [3, 4-d] pyrimidine-4-carboxylic Acids. Chem. Pharm. Bull. 1983; 31(11):3951-3958.

Higashino, et al. Studies on Pyrazolo[3, 4-d]pyrimidine Derivatives. XIV. : Preparation and Reactions of 1-Phenyl-1H-pyrazolo-[3, 4-d]pyrimidine Reissert Compound. Chem. Pharm. Bull. 1986; 34(11):4569-4576.

Higashino, et al. Studies on the Reaction of π-Deficient Heterocycles with Aromatic Aldehyde in the Presence of Cyanide Ion. Chem. Pharm. Bull. 1976; 24(2):238-252.

International search report and written opinion dated Feb. 12, 2018 for PCT/US2017/053080. 14 pages.

Menezes, et al. Molecular modeling of novel 1H-pyrazolo[3,4-b]pyridine derivatives designed as isosters of the antimalarial mefloquine. Journal of Molecular Structure: Theochem. Mar. 1, 2002; 579(1-3):31-39.

Miyashita, et al. Carbon-carbon bond cleavage of α-hydroxybenzylheteroarenes to ketones and heteroarenes by catalytic action of cyanide ion based on retrobenzoin condensation. Heterocycles. 1997; 45(1):1-5.

Miyashita, et al. Studies on Pyrazolo[3, 4-d]pyrimidne Derivatives. XVII. : Reactions of 5-Benzoyl-4, 5-dihydro-6-methyl-1-phenyl-1H-pyrazolo[3, 4-d]pyrimidine-4-carbonitrile : The 6-Methylpyrazolopyrimidine Reissert Compound. Chem. Pharm. Bull. 1990; 38(1):230-233.

Sugimoto, et al. A facile halogenation of some hydroxyheterocycles using triphenylphosphine and N-halosuccinimide. Tetrahedron 1999; 40:7477-7478.

Sugimoto, et al. The tellurium—lithium exchange reaction: selective functionalization of electron-deficient heteroaromatics. Tetrahedron 2001; 57(11):2133-2138.

Suzuki, et al. Carbon-Carbon Bond Cleavage of α-Hydroxybenzylheteroarenes Catalyzed by Cyanide Ion : Retro-Benzoin Condensation Affords Ketones and Heteroarenes and Benzyl Migration Affords Benzylheteroarenes and Arenecarbaldehydes. Chem. Pharm. Bull. 1998; 46(2):199-206.

Suzuki. Studies on pyrazolo[3,4-d]pyrimidine derivatives. XII. On 1-phenyl-1H-pyrazolo[3,4-d]pyrimidine-4-carboxylic acid. Yakugaku Zasshi. 1978; 98(9):1274-1278. (in Japanese with English abstract).

U.S. Appl. No. 15/605,856, filed May 25, 2017, Ibrahim.
U.S. Appl. No. 15/606,682, filed May 26, 2017, Desai.
U.S. Appl. No. 15/669,353, filed Aug. 4, 2017, Bollag.
U.S. Appl. No. 15/689,931, filed Aug. 29, 2017, Ibrahim et al.
U.S. Appl. No. 15/705,097, filed Sep. 14, 2017, Ibrahim et al.
U.S. Appl. No. 15/725,197, filed Oct. 4, 2017, Ibrahim et al.
U.S. Appl. No. 15/814,179, filed Nov. 15, 2017, Zhang et al.
U.S. Appl. No. 15/838,268, filed Dec. 11, 2017, Zhang.
U.S. Appl. No. 16/058,945, filed Aug. 8, 2018, Wu.
U.S. Appl. No. 16/109,199, filed Aug. 22, 2018, Wu.
U.S. Appl. No. 16/043,821, filed Jul. 24, 2018, Ibrahim et al.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/158,107, filed Oct. 11, 2018, Ibrahim et al.
U.S. Appl. No. 16/172,573, filed Oct. 26, 2018, Rezaei et al.
U.S. Appl. No. 16/219,730, filed Dec. 13, 2018, Ibrahim et al.
U.S. Appl. No. 16/358,608, filed Mar. 19, 2019, Zhang et al.
U.S. Appl. No. 16/400,801, filed May 1, 2019, Ibrahim et al.

* cited by examiner

SEQUENCE LISTING

<160> NUMBER OF SEQ ID NOS: 4

<210> SEQ ID NO 1
<211> LENGTH: 403
<212> TYPE: PRT
<213> ORGANISM: Homo sapiens

<400> SEQUENCE: 1

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Asp Pro Asn Lys Pro Leu Thr
130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Thr Asp Leu
    370                 375                 380

Met Asn Phe Leu Lys Thr Val Arg Ser Thr Thr Glu Lys Ser Leu Leu
385                 390                 395                 400

Lys Glu Gly

<210> SEQ ID NO 2
<211> LENGTH: 1944
<212> TYPE: DNA
<213> ORGANISM: Homo sapiens

<400> SEQUENCE: 2
aatttctcac tgcccctgtg ataaactgtg gtcactggct gtggcagcaa ctattataag       60
atgctctgaa aactcttcag acactgaggg gcaccagagg agcagactac aagaatggca      120
cacgctatgg aaaactcctg acaatcagt aaagagtacc atattgatga agaagtgggc      180

```
tttgctctgc caaatccaca ggaaaatcta cctgattttt ataatgactg gatgttcatt    240
gctaaacatc tgcctgatct catagagtct ggccagcttc gagaaagagt tgagaagtta    300
aacatgctca gcattgatca tctcacagac cacaagtcac agcgccttgc acgtctagtt    360
ctgggatgca tcaccatggc atatgtgtgg ggcaaaggtc atggagatgt ccgtaaggtc    420
ttgccaagaa atattgctgt tccttactgc caactctcca gaaactggaa actgcctcct    480
attttggttt atgcagactg tgtcttggca aactggaaga aaaaggatcc taataagccc    540
ctgacttatg agaacatgga cgttttgttc tcatttcgtg atggagactg cagtaaagga    600
ttcttcctgg tctctctatt ggtggaaata gcagctgctt ctgcaatcaa gtaattcct     660 actgtattca aggcaatgca aatgcaagaa cgggacactt tgctaaaggc gctgttggaa    720
atagcttctt gcttggagaa agcccttcaa gtgtttcacc aaatccacga tcatgtgaac    780
ccaaaagcat ttttcagtgt tcttcgcata tatttgtctg gctggaaagg caaccccag    840 ctatcagacg gtctggtgta tgaagggttc tgggaagacc caaggagtt tgcagggggc    900 agtgcaggcc aaagcagcgt ctttcagtgc tttgacgtcc tgctgggcat ccagcagact    960
gctggtggag acatgctgc tcagttcctc caggacatga aagatatat gccaccagct   1020 cacaggaact tcctgtgctc attagagtca atccctcag tccgtgagtt tgtcctttca   1080
aaaggtgatg ctggcctgcg ggaagcttat gacgcctgtg tgaaagctct ggtctccctg   1140
aggagctacc atctgcaaat cgtgactaag tacatcctga ttcctgcaag ccagcagcca   1200
aaggagaata gacctctga agaccccttca aaactggaag ccaaaggaac tggaggcact   1260
gatttaatga atttcctgaa gactgtaaga agtacaactg agaaatccct tttgaaggaa   1320
ggttaatgta acccaacaag agcacatttt atcatagcag agacatctgt atgcattcct   1380
gtcattaccc attgtaacag agccacaaac taatactatg caatgttta ccaataatgc    1440 aatacaaaag acctcaaaat acctgtgcat ttcttgtagg aaaacaacaa aaggtaatta   1500
tgtgtaatta tactagaagt tttgtaatct gtatcttatc attggaataa aatgacattc   1560
aataaataaa aatgcataag atatattctg tcggctgggc gcggtggctc acgcctgtaa   1620
tcccagcact ttgggaggcc gaggcgggcg gatcacaagg tcaggagatc gagaccatct   1680
tggctaacac ggtgaaaccc cgtctctact aaaaatacaa aaaattagcc gggcgcggtg   1740
gcgggcacct gtagtcccag ctactcggga ggctgaggca ggagaatggc gtgaacctgg   1800
gaggcggagc ttgcagtgag ccaagattgt gccactgcaa tccggcctgg gctaaagagc   1860
gggactccgt ctcaaaaaaa aaaaaaaaaa gatatattct gtcataataa ataaaaatgc   1920
ataagatata aaaaaaaaaa aaaa                                          1944
```

<210> SEQ ID NO 3
<211> LENGTH: 406
<212> TYPE: PRT
<213> ORGANISM: Homo sapiens

<400> SEQUENCE: 3

```
Met Ser Gly Cys Pro Phe Leu Gly Asn Asn Phe Gly Tyr Thr Phe Lys
1               5                   10                  15

Lys Leu Pro Val Glu Gly Ser Glu Glu Asp Lys Ser Gln Thr Gly Val
            20                  25                  30

Asn Arg Ala Ser Lys Gly Gly Leu Ile Tyr Gly Asn Tyr Leu His Leu
        35                  40                  45

Glu Lys Val Leu Asn Ala Gln Glu Leu Gln Ser Glu Thr Lys Gly Asn
```

```
            50                  55                  60
Lys Ile His Asp Glu His Leu Phe Ile Ile Thr His Gln Ala Tyr Glu
 65                  70                  75                  80

Leu Trp Phe Lys Gln Ile Leu Trp Glu Leu Asp Ser Val Arg Glu Ile
                 85                  90                  95

Phe Gln Asn Gly His Val Arg Asp Glu Arg Asn Met Leu Lys Val Val
            100                 105                 110

Ser Arg Met His Arg Val Ser Val Ile Leu Lys Leu Leu Val Gln Gln
        115                 120                 125

Phe Ser Ile Leu Glu Thr Met Thr Ala Leu Asp Phe Asn Asp Phe Arg
130                 135                 140

Glu Tyr Leu Ser Pro Ala Ser Gly Phe Gln Ser Leu Gln Phe Arg Leu
145                 150                 155                 160

Leu Glu Asn Lys Ile Gly Val Leu Gln Asn Met Arg Val Pro Tyr Asn
                165                 170                 175

Arg Arg His Tyr Arg Asp Asn Phe Lys Gly Glu Glu Asn Glu Leu Leu
            180                 185                 190

Leu Lys Ser Glu Gln Glu Lys Thr Leu Leu Glu Leu Val Glu Ala Trp
        195                 200                 205

Leu Glu Arg Thr Pro Gly Leu Glu Pro His Gly Phe Asn Phe Trp Gly
210                 215                 220

Lys Leu Glu Lys Asn Ile Thr Arg Gly Leu Glu Glu Glu Phe Ile Arg
225                 230                 235                 240

Ile Gln Ala Lys Glu Glu Ser Glu Glu Lys Glu Glu Gln Val Ala Glu
                245                 250                 255

Phe Gln Lys Gln Lys Glu Val Leu Leu Ser Leu Phe Asp Glu Lys Arg
            260                 265                 270

His Glu His Leu Leu Ser Lys Gly Glu Arg Arg Leu Ser Tyr Arg Ala
        275                 280                 285

Leu Gln Gly Ala Leu Met Ile Tyr Phe Tyr Arg Glu Glu Pro Arg Phe
290                 295                 300

Gln Val Pro Phe Gln Leu Leu Thr Ser Leu Met Asp Ile Asp Ser Leu
305                 310                 315                 320

Met Thr Lys Trp Arg Tyr Asn His Val Cys Met Val His Arg Met Leu
                325                 330                 335

Gly Ser Lys Ala Gly Thr Gly Gly Ser Ser Gly Tyr His Tyr Leu Arg
            340                 345                 350

Ser Thr Val Ser Asp Arg Tyr Lys Val Phe Val Asp Leu Phe Asn Leu
        355                 360                 365

Ser Thr Tyr Leu Ile Pro Arg His Trp Ile Pro Lys Met Asn Pro Thr
370                 375                 380

Ile His Lys Phe Leu Tyr Thr Ala Glu Tyr Cys Asp Ser Ser Tyr Phe
385                 390                 395                 400

Ser Ser Asp Glu Ser Asp
                405
```

<210> SEQ ID NO 4
<211> LENGTH: 1703
<212> TYPE: DNA
<213> ORGANISM: Homo sapiens

<400> SEQUENCE: 4

```
ggaaggtcaa tgatagcatc tgcctagagt caaacctccg tgcttctcag acagtgcctt      60
ttcaccatga gtgggtgccc atttttagga aacaactttg gatatacttt taaaaaactc     120
```

```
cccgtagaag gcagcgaaga agacaaatca caaactggtg tgaatagagc cagcaaagga    180
ggtcttatct atgggaacta cctgcatttg gaaaaagttt tgaatgcaca agaactgcaa    240
agtgaaacaa aaggaaataa aatccatgat gaacatcttt ttatcataac tcatcaagct    300
tatgaactct ggtttaagca aatcctctgg gagttggatt ctgttcgaga gatctttcag    360
aatggccatg tcagagatga aaggaacatg cttaaggttg tttctcggat gcaccgagtg    420
tcagtgatcc tgaaactgct ggtgcagcag ttttccattc tggagacgat gacagccttg    480
gacttcaatg acttcagaga gtacttatct ccagcatcag gcttccagag tttgcaattc    540
cgactattag aaaacaagat aggtgttctt cagaacatga gagtcccttta taacagaaga    600
cattatcgtg ataacttcaa aggagaagaa aatgaactgc tacttaaatc tgagcaggaa    660
aagcacttc tggaattagt ggaggcatgg ctggaaagaa ctccaggttt agagccacat    720
ggatttaact tctggggaaa gcttgaaaaa aatatcacca gaggcctgga agaggaattc    780
ataaggattc aggctaaaga agagtctgaa gaaaaagagg aacaggtggc tgaatttcag    840
aagcaaaaag aggtgctact gtccttattt gatgagaaac gtcatgaaca tctccttagt    900
aaaggtgaaa gacggctgtc atacagagca cttcagggag cattgatgat atattttttac    960
agggaagagc ctaggttcca ggtgccttttt cagttgctga cttctcttat ggacatagat   1020
tcactgatga ccaaatggag atataaccat gtgtgcatgg tgcacagaat gctgggcagc   1080
aaagctggca ccggtggttc ctcaggctat cactacctgc gatcaactgt gagtgatagg   1140
tacaaggtat ttgtagattt atttaatctt tcaacatacc tgattccccg acactggata   1200
ccgaagatga acccaaccat tcacaaattt ctatatacag cagaatactg tgatagctcc   1260
tacttcagca gtgatgaatc agattaaaat cgtctgcaaa atctatgaag aatactggtt   1320
tcacagccta tttttttattt tctatggatt ttcataaata cagtttgaat atatgtatgc   1380
atatattgtt cagcaccacg atgctctgat ttaattctag aaacaatttg attacctctt   1440
gtttgtgaca agactaagca ttaagatgag aaagaataca tttaaatagt aacattgtac   1500
atagggtgtt ttcctattaa aaattcagtt tcccctgaga cttaatgtaa ccacttaatg   1560
taatcactat ctcattgttt catctttata aacttgtaaa cttcatctat ttcaaatatt   1620
ttatgcagta cattatatta ttctgtacaa aggctttcaa acaaaatttt taaaataata   1680
aagtattaat ctttctccct gta                                            1703
```

COMPOUNDS AND METHODS FOR IDO AND TDO MODULATION, AND INDICATIONS THEREFOR

CROSS-REFERENCE TO RELATED APPLICATIONS

This application claims the benefit under 35 U.S.C. § 119(e) of United States Provisional Application 62/398,409, filed Sep. 22, 2016, of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 13, 2017, is named 37JF-242669-US_SL.TXT and is 12,291 bytes in size.

FIELD

The present disclosure relates to heme-containing oxidoreductase enzymes and compounds which selectively modulate such enzymes, and uses therefor. Particular embodiments contemplate disease indications which are amenable to treatment by modulation of enzymatic activity by the compounds of the present disclosure.

BACKGROUND

The present disclosure relates to novel compounds which inhibit indoleamine-2,3-dioxygenase (IDO), specifically indoleamine 2,3-dioxygenase 1 (IDO1), and tryptophan-2,3-dioxygenase (TDO). The disclosure also contemplates the use of such compounds to treat disease indications mediated by activity of IDO1 or TDO.

The essential amino acid tryptophan is degraded through the kynurenine pathway, of which the first and rate limiting step is catalyzed by heme-containing oxidoreductase enzymes, including indoleamine-2,3-dioxygenase (IDO) and tryptophan-2,3-dioxygenase (TDO), that convert tryptophan to N-formylkynurenine. Although these enzymes perform the same biochemical function, they share limited homology and their expression is compartmentalized in different locations of the body. Whereas IDO1 is expressed in placenta, gut, lungs, epididymis, lymph nodes and tumor cells, TDO expression is found mainly in the liver and the brain. IDO1 and TDO control tryptophan concentration, and also the balance of kynurenine pathway metabolites. Dysregulation of the kynurenine pathway or an imbalance in favor of kynurenine metabolites due to IDO1 and TDO activity leads to numerous disease indications related to immunosuppression.

The local depletion of tryptophan and the accumulation of kynurenine pathway metabolites due to dioxygenase activity induce immune tolerance and suppression. It has been shown in experiments concerning gut immunity, mammalian pregnancy, tumor immune evasion, chronic infection, neurological disorders, inflammatory and autoimmune diseases, etc., that expression of IDO can induce immune tolerance through suppression of T cells by depletion of tryptophan, an obligate amino acid for effector T cells. General control non-derepressible-2 kinase (GCN2) prevents T cell proliferation after detecting tryptophan depletion. Furthermore, kynurenine metabolites promote helper T cell conversion into regulatory T cells (Tregs), which are also responsible for immune suppression.

The human body houses ten times more bacterial cells than human cells and many of these bacterial cells comprise the human gut microbiota. Although these bacterial cells are distinguishable from the self, the human body must maintain immunological tolerance with respect to these bacteria. IDO-deficient mice had elevated baseline levels of immunoglobulin A (IgA) and IgG in the serum and increased IgA in intestinal secretions. These mutant mice expressing higher levels of natural secretory IgA were more resistant to intestinal colonization by *Citrobacter rodentium* and experienced significantly attenuated colitis due to *C. rodentium*. Distinct from disease resistance, IDO has also been shown to induce disease tolerance, the reduction of the impact of infection on host fitness. IDO1 knockout (KO) mice failed to exhibit LPS endotoxin tolerance, whereas LPS tolerant IDO1 expressing mice were able to mount a fully protective tolerance state when infected by LPS-expressing *Salmonella enterica* Typhimurium. These findings suggest that pharmacological modulation of IDO activity may provide solutions to dysregulation of intestinal immunity and to diseases caused by enteric pathogens.

Immunosuppression by IDO is also exemplified by maternal tolerance towards allogeneic fetuses. The general laws of tissue transplantation suggest that allogeneic mammalian conceptus should not survive. However, implications of IDO expression at the maternal-fetal interface suggest that IDO prevents immunologic rejection of allogeneic fetuses from the uterus. Dosing pregnant mice with 1-methyl-tryptophan (1-MT) resulted in rejection of allogeneic fetuses through a T cell-mediated response. Tryptophan catabolism by IDO1 appears to suppress immunological rejection by maternal T cells, allowing survival of allogeneic concepti. Maternal tolerance towards the fetus due to IDO1 expression suggests that IDO1/TDO inhibitory compounds may be of use in abortion or contraception.

HIV infection chronically induces IDO1 expression, resulting in chronic depletion of tryptophan and T cell dysfunction. Tryptophan depletion favors the development of Tregs over other CD4+ helper T cell subsets that offer protective immune functions. Constitutive expression of IDO1 continuously shifts the equilibrium of tryptophan metabolism towards kynurenines, inducing immunosuppression and allowing for progression of HIV infection. However, it has been demonstrated that IDO inhibition enhances the level of virus-specific CD8+ T cells and concomitantly reduces the number of virally infected macrophages in a mouse model of HIV. These lines of evidence suggest that IDO1 inhibitors, possibly in combination with other antiretroviral agents, may provide utility in treatment of HIV disease.

Tumors, while normally under immune surveillance, have been shown to have the ability to express IDO1 to create a local microenvironment favorable for tumor growth and metastasis. Depletion of tryptophan and accumulation of kynurenines blocks proliferation of effector T cells and promotes the development of Tregs, inducing an immunosuppressed state in which tumors can evade normal immune mechanisms.

Although IFN-g exhibits anti-tumor properties, the cytokine has also been shown to be a potent inducer of IDO expression, and therefore may have limited effects in the immunosuppressive tumor microenvironment. Recent studies, however, have indicated that treatment of dendritic cells using selective IDO1 inhibitor epacadostat resulted in more potent activation of tumor associated antigen-specific T cells, along with an increase in production of both IFN-g and tumor cell lysis. Combinatorial therapy using an IDO inhibitor and anti-CTLA-4 or anti-PD-1/PD-L1 antibodies improved tumor control, IL-2 production and CD8+ T cell proliferation in a mouse model of melanoma compared to single agent therapy. Additionally, blocking IDO during chemo-radiation therapy increases the anti-tumor efficacy of such treatment by causing widespread deposition of C3 complement responsible for tumor destruction. These lines of evidence suggest that IDO1 inhibition can reverse tumor resistance and when used in combination with therapeutic agents may control tumor growth and metastasis.

Tryptophan degradation using tryptophan-2,3-dioxygenase (TDO) also influences tumor immune resistance in a manner similar to that catalyzed by IDO. TDO expressed by neurons and liver cells catabolizes tryptophan into kynurenine, which in turn functions as an endogenous ligand of human aryl hydrocarbon receptor (AHR) in an autocrine and paracrine fashion. Activation of AHR by TDO-derived kynurenine suppresses antitumor immune responses and promotes tumor cell survival and motility. Accordingly, it has been shown that TDO inhibition promotes tumoral immune rejection. Data from a series of 104 tumor cell lines shows that 20 tumors expressed only TDO2, 17 expressed only IDO1 and 16 expressed both. This suggests that a method of therapy involving dual inhibition of both IDO and TDO could be effective against a greater proportion of tumors.

Infectious diseases often trigger inflammation, which in turn can induce IDO activity. Infection by Epstein-Barr virus has been demonstrated to be able to induce IDO expression due to upregulation of TNF-α and IL-6 through p38/MAPK and NF-κB pathways in monocyte-derived macrophages. IDO suppression of T cell proliferation and impairment of CD8+ T cell cytotoxic function may be important in creating an immunosuppressive microenvironment for virus survival. In a mouse model, infection by influenza A virus stimulated IDO activity in the lungs and lung-draining mediastinal lymph nodes. In this mouse model, influenza-induced IDO activity in the lungs enhanced morbidity, slowed recovery, restrained effector T cell responses, and altered the repertoire of virus-specific memory CD8 T cells. Given the correlation between IDO activity and weakened host immunity, IDO inhibitors may be useful in combating infectious diseases.

Additionally, IDO has been implicated in non-infectious inflammatory diseases. IDO KO mice do not display spontaneous disorders of classical inflammation. Instead of eliciting generalized inflammatory reactions, small molecule inhibitors of IDO alleviate disease severity in the models of skin cancer promoted by chronic inflammation, and in models of inflammation-associated arthritis and allergic airway disease. IDO has also been implicated in autoimmune arthritis. IDO2 mediates production of autoreactive antibodies, but IDO2 KO mice have been shown to maintain their ability to mount productive antibody responses against model antigens. Very common autoimmune diseases include rheumatoid arthritis, type 1 diabetes, lupus, Hashimoto's thyroid disease, multiple sclerosis (MS), inflammatory bowel disease (IBD, which includes Crohn's disease and ulcerative colitis), celiac disease, and asthma. Therefore, IDO inhibitors may prove to be useful in the treatment of classical or autoimmune inflammatory diseases.

Studies have shown tryptophan catabolites to be of neurological significance. Tryptophan degraded through the kynurenine pathway produces metabolites that are neuroactive and neurotoxic. Kynurenine can be synthesized into kynurenic acid (KYNA) by kynurenine aminotransferases. KYNA has been shown to exert a non-competitive antagonistic effect on a7-nicotinic acetylcholine receptors and may offer protection against glutamate induced excitotoxicity. Also acting as a free radical scavenger, KYNA is generally understood to be a protective agent in neurodegenerative mechanisms. In a different branch of the kynurenine pathway, kynurenine can be converted to 3-hydroxykynurenine (3-HK) which undergoes auto-oxidation. 3-HK is generally considered to be neurotoxic due to the production of free radicals during auto-oxidation. 3-HK can also be converted to 3-hydroxyanthronilic acid (3-HA) which has similar oxidative reactivity as 3-HK, and can interfere with T cell survival. Downstream processing of 3-HA leads to production of quinolinic acid (QUIN). QUIN is a weak endogenous agonist of N-methyl-D-aspartate (NMDA) receptors and causes greatest excitotocity in regions of the brain rich in NMDA receptors. An imbalance in kynurenine metabolites reflected by higher concentrations of neurotoxic species may result in neurodegenerative disease indications. Because IDO and TDO are responsible for kynurenine production, inhibitors of these enzymes could be beneficial for neuropathic patients.

Alzheimer's disease (AD) is a chronic neurodegenerative disease that most commonly manifests in the elderly population and is characterized by progressive memory loss. Hallmarks of AD pathology include amyloid β (Aβ) plaques and phosphorylated tau-constituted neurofibrillary tangles, and the kynurenine pathway may play an important role in the neurodegenerative process. AD mice exhibit a greater density of TDO immune-density cells and an increased expression of TDO mRNA in the cerebellum. TDO co-localizes with QUIN, neurofibrillary tangles and amyloid deposits in the hippocampus of human AD brains. Furthermore, QUIN has been demonstrated to be capable of inducing tau phosphorylation in the human brain. Activated microglia in AD may produce excessive amounts of kynurenine pathway metabolites, including QUIN, in response to phosphorylated tau and Aβ plaques, resulting in a progressive disease cycle. These lines of evidence suggest that increased tryptophan catabolism through the kynurenine pathway may be responsible for Aβ pathology, and inhibitors of TDO or IDO could be useful in halting disease progression.

Parkinson's disease (PD) is a neurodegenerative disorder that impairs the motor system. PD is characterized by loss of dopaminergic neurons and neuroinflammation, which can occur several years before the onset of symptoms. Activated microglia can utilize the kynurenine pathway to generate neuroactive compounds. In PD, QUIN production by microglia is increased, leading to excitotoxicity by acting as a NMDA agonist. KYNA is a neuroprotective tryptophan catabolite, but its synthesis by astrocytes is concomitantly decreased in PD. PD is associated with an imbalance between these two branches of the kynurenine pathway within the brain, and pharmacological modulation of this pathway may be a new therapeutic strategy to treat the disease.

Huntington's disease (HD) is an autosomal dominantly inherited neurodegenerative disorder caused by expansion of CAG repeats in the HD gene on chromosome 4. HD is associated with loss of muscle coordination and cognitive decline. Evidence of increased ratio of kynurenine to tryptophan in the peripheral blood plasma of human patients with HD suggests a possible role of abnormal tryptophan metabolism in contributing to neuronal dysfunction and damage in HD. Gene expression analysis of YAC128 mouse model of HD reveals increased striatal-specific Ido1 mRNA. Further studies continue to examine the role of kynurenine pathway in HD, showing that the striatum of IDO KO mice is less sensitive to NMDA receptor-mediated excitotoxicity induce by QUIN compared to wild-type littermate controls. Although activity of TDO is generally thought to be limited to the liver, ablation of TDO2 is neuroprotective in a *Drosophila* model of HD. These findings implicate dysregulation of tryptophan catabolism in HD neuropathology and suggest that IDO or TDO could be therapeutic targets in cases of HD.

Amyotrophic lateral sclerosis (ALS), also known as Lou Gehrig's disease, is a neurodegenerative disease that specifically targets neurons that control voluntary muscle movement. Symptoms of ALS include varying degrees of muscle stiffness and weakening, but the long term prognosis can be bleak, and often fatal. Although ALS is a multifactorial disease and its exact mechanism of pathology is yet to be understood, tryptophan catabolites have been implicated in ALS studies. Compared to samples from control subjects, cerebral spinal fluid (CSF) and serum samples of ALS patients show elevated levels of L-kynurenine and QUIN, and decreased levels of neuroprotective species picolinic acid (PIC). Furthermore, the neurons and microglia of the ALS motor cortex and spinal cord express greater levels of IDO and QUIN, implicating neuroinflammation and kynurenine pathway involvement in ALS. A separate study reveals that CSF samples of patients with bulbar onset of ALS contained higher levels of KYNA compare to those of patients with severe clinical status, suggesting a neuroprotective role of KYNA against excitotoxicity in ALS. Involvement of kynurenines in ALS has been brought to attention, and inhibition of IDO or TDO responsible for synthesis of neurotoxic kynurenines may be a new option for therapeutic intervention.

Multiple sclerosis (MS) is a complex autoimmune disease driven by Th1 cells targeting oligodendrocytes and the myelin sheath, resulting in an inflammatory response that leads to the formation of sclerotic plaques in the central nervous system. Early research on kynurenine pathway involvement in MS shows that patients with chronic disease have lower levels of tryptophan in serum and CSF samples, suggesting activation of the kynurenine pathway. Ex vivo CSF samples of human MS patients indicate a possible correlation between KYNA and disease progression: induction of the kynurenine pathway in early active phases of MS leads to increased KYNA production but later shifts to a decrease in KYNA levels, causing the kynurenine pathway to exert neurotoxic effects. Activated macrophages and microglia have been shown be present along the boundaries of MS lesions, and may be able to produce QUIN at concentrations sufficient to induce brain cell death. In the autoimmune encephalomyelitis (EAE) mouse model of MS, inhibition of IDOL using 1-methyl-tryptophan has been shown to exacerbate disease status and allow proliferation of T-cell responses. Because the various branches of the kynurnine pathway can produce either neurotoxic or neuroprotective tryptophan catabolites, it is unclear whether activation of the pathway is beneficial in MS treatment. However, modulation of the kynurenine pathway may still be a valid strategy to treat MS.

Tryptophan degradation has also been implicated in neuropsychiatric disorders. An imbalanced kynurenine pathway may be a pathophysiological promoter in schizophrenia: CSF samples of schizophrenic patients contain higher ratios of KYNA to QUIN compared to controls, possibly due to compromised function of enzymes involved in QUIN synthesis. Since KYNA is an antagonist of the NMDA receptor, while QUIN is an agonist, a shift in this ratio may be reflected in the behavioral domain. A single nucleotide polymorphism in kynurenine 3-monooxygenase (KMO), one enzyme responsible for QUIN production, correlates with decreased KMO expression and increased CSF KYNA levels, and may be responsible for lifetime psychotic features in bipolar disorder patients.

Tryptophan can also be converted to 5-hydroxytryptamine (5-HT) and later into serotonin and then melatonin. Depletion of tryptophan can cause episodes of depression, and IDO activity in the kynurenine pathway can decrease serotonin and trigger depression. In inflammation-associated depression, tryptophan catabolites can trigger the mood swing independently of serotonin. Conversion of tryptophan into kynurenine and later QUIN and 3HK is neurotoxic, and can induce a depressive state. Although the mechanisms of neuropsychiatric disorders differ from those of inflammation-associated neurodegenerative disorders, new methods of therapy may still involve modulation of the kynurenine pathway.

There has also been evidence of the kynurenine pathway influencing cardiovascular health. Especially in patients with end-stage renal disease, induction of IDO activity and consequent increase in serum kynurenines lead to a number of cardiovascular complications. Kynurenines have been associated with hyperfibrinolysis, which has been causally related to the development of atherosclerosis. Elevated levels of kynurenine, QUIN, matrix metalloproteinases (MMPs) and a tissue inhibitor of MMPs have been discovered in continuous ambulatory peritoneal dialysis patients with cardiovascular disease (CVD) than patients without CVD and controls. Additionally, it has been demonstrated that QUIN is positively correlated with MMP-2 and the tissue inhibitor of MMP-2, which are responsible for the degradation of the extracellular matrix components involved in vascular wall remodeling. These lines of evidence suggest a connection between activation of the kynurenine pathway and cardiovascular disease prevalence in patients with chronic kidney disease. Given the above discussion of disease indications relating to dysregulation of tryptophan catabolism, there exists a strong unmet need for new compounds that inhibit IDO or TDO, two enzymes that are responsible for activation of the kynurenine pathway and tryptophan depletion. Development of TDO and IDO inhibitors and methods of treatment using such inhibitors is a key step in combating the aforementioned diseases and disorders.

There has been a considerable amount of effort towards making new IDO1 and TDO inhibitors for human use since the discovery of indoleamine 2,3-dioxygenase 1 as an important target for anticancer therapy in 2003. However, only a few potent IDO1 inhibiting compounds have entered clinical trials, and none have been approved by the FDA as of date.

Accordingly, there remains a strong unmet need for new IDO1 and TDO inhibiting compounds.

SUMMARY

One embodiment of the disclosure relates to novel compounds, as described in any of the embodiments herein, or a pharmaceutically acceptable salt, a solvate, a tautomer, an isomer or a deuterated analog thereof, wherein these novel compounds can modulate IDO1, TDO, or both IDO1 and TDO.

Another embodiment of this disclosure relates to a compound of Formula I(a):

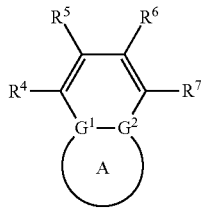

I(a)

or a pharmaceutically acceptable salt, a solvate, a tautomer, an isomer or a deuterated analog thereof, wherein $R^4$, $R^5$, $R^6$, $R^7$, $G^1$, $G^2$ and Ring A are as described in any of the embodiments described in this disclosure.

Other embodiments and subembodiments of Formula I(a) are further described herein in this disclosure.

Another embodiment of the disclosure relates to a pharmaceutical composition comprising a compound according to Formula I(a) or any embodiment and sub-embodiment of Formula I(a) described herein in this disclosure, or a pharmaceutically acceptable salt, a solvate, a tautomer, an isomer or a deuterated analog of any of these compounds, and a pharmaceutically acceptable carrier or excipient.

Another embodiment of the disclosure relates to a pharmaceutical composition comprising a compound according to Formula I(a), or any embodiment of Formula I(a) described herein in this disclosure, or a pharmaceutically acceptable salt, a solvate, a tautomer, an isomer or a deuterated analog of any of these compounds, and another therapeutic agent.

Another embodiment of this disclosure relates to a method for treating a subject with a disease or condition mediated by IDO1, TDO or both IDO1 and TDO, said method comprising administering to the subject an effective amount of a compound according to Formula I(a), or any embodiment of Formula I(a) described herein in this disclosure, or a pharmaceutically acceptable salt, a solvate, a tautomer, an isomer or a deuterated analog of any of these compounds, or a pharmaceutical composition of any of the compounds as described in this disclosure, wherein the disease or condition express aberrantly or otherwise IDO1, TDO, or both IDO1 and TDO, or activating mutations or translocations of any of the foregoing. In other embodiments of this embodiment, the disease or condition can be any one or more of the disease or conditions described in this disclosure. In other embodiments, the disease or condition is an inflammatory disease, an inflammatory condition, an autoimmune disease or cancer. In other embodiments, the disease or condition is selected from the group consisting of immunosuppression, autoimmune diseases (for example, rheumatoid arthritis, type 1 diabetes, lupus, Hashimoto's thyroid disease, multiple sclerosis (MS), inflammatory bowel disease (IBD), Crohn's disease, ulcerative colitis, celiac disease, autoimmune disorders of the intestines, diseases caused by enteric pathogens, and asthma), HIV, tumor growth, tumor metastasis, infectious diseases (for example, infectious disease caused by a virus such as Epstein Barr virus or influenza A virus), non-infectious inflammatory disease, skin cancer promoted by chronic inflammation, neurodegenerative disorders (for example, Alzheimer's disease, Parkinson's disease and Huntington's disease), amyotrophic lateral sclerosis, multiple sclerosis), neuropsychiatric disorders (for example, schizophrenia, bipolar disorder, depression, and inflammation-associated depression), cardiovascular disease, end-stage renal disease, chronic kidney disease and atherosclerosis.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I(a) of this disclosure, and all the embodiments thereof, are to be read from left to right, wherein the right hand side is directly attached to the parent structure as defined. However, if a point of attachment is shown on the left hand side of the chemical moiety (e.g., -alkyloxy-($C_1$-$C_{25}$)alkyl), then the left hand side of this chemical moiety is attached directly to the parent moiety as defined. It is assumed that when considering generic descriptions of compounds of the described herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl (or $C_1$-$C_6$ alkyl) refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom. In some embodiments, $C_0$-alkylene refers a bond.

"Alkenyl" refers to a linear monovalent hydrocarbon radical or a branched monovalent hydrocarbon radical having the number of carbon atoms indicated in the prefix and containing at least one double bond. For example, $C_2$-$C_6$ alkenyl is meant to include ethenyl, propenyl, and the like. In some embodiments, alkenyl may have from 2 to 20 carbon atoms or from 2 to 10 carbon atoms (e.g. 2 to 6 carbon atoms) and may have from 1 to 6 carbon-carbon double bonds, e.g. 1, 2 or 3 carbon-carbon double bonds.

The term "alkenylene" refers to a linear monovalent hydrocarbon radical or a branched monovalent hydrocarbon radical containing at least one double bond and having the number of carbon atoms indicated in the prefix. In some embodiments, alkenylene may have from 2 to 20 carbon atoms or from 2 to 10 carbon atoms (e.g. 2 to 6 carbon atoms) and may have from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkynylene" refers to a linear monovalent hydrocarbon radical or a branched monovalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers.

"Alkoxy" or "alkoxyl" refers to a —O-alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

The term "alkoxyalkyl" refers to an alkyl group substituted with one or more, such as one to three alkoxy groups.

"Alkylamino" refers to a —NH-alkyl group, where alkyl is as defined herein. Exemplary alkylamino groups include $CH_3NH$—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like. "Cycloalkylamino" denotes the group —$NR^{dd}R^{ee}$, where $R^{dd}$ and $R^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Amino" or "amine" denotes the group —$NH_2$.

"Cycloalkyl" or "Carbocycle" or "Carbocyclic" by itself, or as part of another substituent, unless otherwise stated, refers to saturated or unsaturated, non-aromatic monocyclic, or fused rings, such as bicyclic or tricyclic carbon ring systems, or cubane, having the number of carbon atoms indicated in the prefix or if unspecified having 3-10, also 3-8, and also 3-6, ring members per ring, such as cyclopropyl, cyclopentyl, cyclohexyl, 1-cyclohexenyl and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). In one embodiment, cycloalkyl is saturated.

The term "cycloalkenyl" refers to a cycloalkyl having at least one point of unsaturation.

"Cycloalkylalkyl" refers to an -(alkylene)-cycloalkyl group where alkylene as defined herein has the indicated number of carbon atoms or if unspecified having six or fewer, or four or fewer main chain carbon atoms; and cycloalkyl is as defined herein has the indicated number of carbon atoms or if unspecified having 3-10, also 3-8, and also 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

The term "alkylcycloalkyl" refers to a cycloalkyl group which is substituted with an alkyl group, where alkyl and cycloalkyl are as defined herein.

The term "cyano" refers to the group —CN. The term "cyanoalkyl" refers to an alkyl, as defined herein, that is substituted with at least one cyano group, for example, 1, 2 or 3 cyano groups. For example, "$C_{1-4}$ cyanoalkyl" refers to a $C_1$-$C_4$alkyl group that is substituted with at least one cyano group, for example, 1, 2 or 3 cyano groups.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl and 2-naphthyl. The term "arylene" refers to a divalent aryl, wherein the aryl is as defined herein.

"Arylalkyl" or "aralkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

The term "haloalkyl" refers to an alkyl substituted by one to seven halogen atoms. Haloalkyl includes monohaloalkyl or polyhaloalkyl. For example, the term "$C_{1-6}$ haloalkyl" is meant to include trifluoromethyl, difluoromethyl, 2,2,2-trifluoroethyl, 4-chlorobutyl, 3-bromopropoyl, and the like. The term "fluoroalkyl" refers to an alkyl substituted by one to seven fluoro.

"Halogen" or "halo" refers to all halogens, that is, chloro (Cl), fluoro (F), bromo (Br), or iodo (I).

"Heteroatom" is meant to include oxygen (O), nitrogen (N), and sulfur (S).

"Heteroaryl" by itself, or as part of another substituent, refers to a monocyclic aromatic ring radical containing 5 or 6 ring atoms, or a bicyclic aromatic radical having 8 to 10 atoms, containing one or more, 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any of the heteroatoms is N.

"Heteroarylene" by itself or as part of another substituent, refers to a divalent heteroaryl, where the heteroaryl is as defined herein.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein.

"Heterocycloalkyl" refers to a saturated or unsaturated non-aromatic cycloalkyl group that contains from one to five heteroatoms selected from N, O, S (including SO and $SO_2$), or P (including phosphine oxide) wherein the nitrogen and sulfur atoms are optionally oxidized, and the nitrogen atom(s) are optionally quarternized, the remaining ring atoms being C, where one or two C atoms may optionally be replaced by a carbonyl. The heterocycloalkyl may be substituted with an oxo group. The heterocycloalkyl may be a monocyclic, a fused bicyclic or a fused polycyclic ring system of 3 to 12, or 4 to 10 ring atoms, or 5 to 8 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, benzofuranyl, pyrazolidinyl, morpholinyl, and the like. A heterocycloalkyl group can be attached to the remainder of the molecule through a ring carbon or a heteroatom.

"Heterocycloalkylalkyl" or "heterocyclylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein.

"Hydroxyl" or "hydroxy" refers to the group —OH. The term "hydroxyalkyl" or "hydroxyalkylene" refers to an alkyl group or alkylene group, respectively as defined herein, substituted with 1-5 hydroxy groups.

The term "—SO$_2$-alkyl" refers to a moiety wherein the point of attachment to the parent moiety is represented by the bond on the sulfur atom, and wherein alkyl is as defined herein.

The term "—SO$_2$-cycloalkyl" refers to a moiety wherein the point of attachment to the parent moiety is represented by the bond on the sulfur atom, and wherein cycloalkyl is as defined herein.

The term "—SO$_2$-haloalkyl" refers to a moiety wherein the point of attachment to the parent moiety is represented by the bond on the sulfur atom, and wherein haloalkyl is as defined herein.

The term "—NHSO$_2$-alkyl" refers to a moiety wherein the point of attachment to the parent moiety is represented by the bond on the nitrogen atom, and wherein alkyl is as defined herein.

The term "—NHSO$_2$-cycloalkyl" refers to a moiety wherein the point of attachment to the parent moiety is represented by the bond on the nitrogen atom, and wherein cycloalkyl is as defined herein.

The term "—NHSO$_2$-haloalkyl" refers to a moiety wherein the point of attachment to the parent moiety is represented by the bond on the nitrogen atom, and wherein haloalkyl is as defined herein.

The term "alkoxycarbonyl" refers to a moiety —C(O)-alkoxy, and wherein alkoxy is as defined herein. The term "$C_1$-$C_4$alkoxycarbonyl" refers to a moiety —C(O)—$C_1$-$C_{34}$alkoxy, and wherein $C_1$-$C_4$alkoxy is as defined herein.

A "bridged ring" or a "bridged compound" is a carbocyclic or heterocyclic compound having two or more rings containing a bridge of one to four carbon atoms that connect two bridgehead atoms. In this disclosure, the phrase "bridged carbocyclic or heterocyclic ring" in this disclosure has the same meaning as the phrase "bridged carbocylic ring or bridged heterocyclic ring. For purposes of this disclosure, bridgehead atoms cannot be two adjacent atoms on any particular ring. For purposes of this disclosure, two bridgehead atoms in a bridged ring cannot the same atom on any particular ring. A bridged heterocyclic ring refers to a bridged compound having at least one heteroatom. The bridgehead atoms are part of the skeletal framework of the molecule. Bridged rings (or compounds) may be fully carbocyclic (all carbon skeletal atoms). Below is an example of a bridged ring showing each of the bridge and bridgehead atoms.

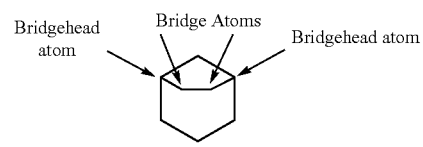

For purposes of this disclosure, a bridged ring is meant to include rings that may optionally have by 1-2 $C_1$-$C_3$ alkyl groups which are not attached on either its bridge atoms and bridgehead atoms, and these bridged rings can be substituted as described in this disclosure. Other non-limiting examples of bridged rings include bicyclo[1.1.1]pentane, adamantyl, (1s,5s)-bicyclo[3.3.1]nonane, (1R,5S)-6,6-dimethylbicyclo[3.1.1]heptane, (1R,5S)-6,6-dimethylbicyclo[3.1.1]heptane, (1r,2R,4S,5r,6R,8S)-tetracyclo[3.3.1.02,4.06,8]nonane, bicyclo[2.2.1]heptane, bicyclo[2.2.2]octane, and 1-fluorobicyclo[2.2.2]octane.

Substitutions of chemical groups with more then one variable:

For purposes of this disclosure, chemical groups that are substituted with more than one variable, such as what is described within one of the embodiments of $R^{12}$ (a) below (with optional substituents $Z^2$, $Z^5$ and $Z^6$, are meant to include the following substitution patterns:

By way of example, in one of the embodiments of $R^{12}$(a), the phrase "a saturated cycloalkyl optionally substituted with 1-8 $Z^2$, and optionally substituted with 1 $Z^5$ or 1-2 $Z^6$;" is meant to include the following possible substitution patterns (1)-(8) for the saturated cycloalkyl:

(1) a saturated cycloalkyl that is not substituted;

(2) a saturated cycloalkyl substituted with 1-8 $Z^2$, wherein each $Z^2$ can be the same or different;

(3) a saturated cycloalkyl substituted with 1 $Z^5$;

(4) a saturated cycloalkyl substituted with 1-2 $Z^6$, wherein each $Z^6$ can be the same or different;

(5) a saturated cycloalkyl substituted with (i) 1-8 $Z^2$, wherein each $Z^2$ can be the same or different; and (ii) 1 $Z^5$;

(6) a saturated cycloalkyl substituted with (i) 1-8 $Z^2$, wherein each $Z^2$ can be the same or different; and (ii) 1-2 $Z^6$, wherein each $Z^6$ can be the same or different;

(7) a saturated cycloalkyl substituted substituted with (i) 1 $Z^5$; and (ii) 1-2 $Z^6$, wherein each $Z^6$ can be the same or different; or (8) a saturated cycloalkyl substituted with (i) 1-8 $Z^2$, wherein each $Z^2$ can be the same or different; (ii) 1 $Z^5$; and (iii) 1-2 $Z^6$, wherein each $Z^6$ can be the same or different.

For purposes of this disclosure, and by way of example, the phrase "a saturated cycloalkyl optionally substituted with 1-9 $Z^2$, and further optionally substituted with 1 $Z^5$ or 1-2 $Z^6$" is meant to mean the same as the phrase "a saturated cycloalkyl optionally substituted with 1-9 $Z^2$, and optionally substituted with 1 $Z^5$ or 1-2 $Z^6$."

The term "oxo" refers to C(=O) or (O). In some embodiments, two possible points of attachment on a carbon form an oxo group.

A "spiro ring system" refers to two rings (carbocyclic rings, heterocyclic rings, or combinations thereof), wherein the spiro ring system is joined by one common spiro carbon atom.

A fused ring system refers to two rings (carbocyclic rings, heterocyclic rings, or combinations thereof) wherein the two rings are fused together by two adjacent carbon atoms that are shared between the two fused rings.

"Optional" or "Optionally" as used throughout the disclosure means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein in connection with compounds of the disclosure, the term "synthesizing" and like terms means chemical synthesis from one or more precursor materials.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group. In some embodiments, provided herein are deuterated analogs of compounds of Formula I(a), and any sub-embodiments thereof, wherein a deuterium can substitute any hydrogen on such compounds. While in some instances, deuterium (D) is explicitly recited as a possible substituent, it is not meant to exclude the possibility of deuterium at other positions.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen," the position is understood to have hydrogen at its natural abundance isotopic composition or its isotopes, such as deuterium (D) or tritium ($^3$H). Certain isotopically-labeled compounds of the present disclosure (e.g., those labeled with $^3$H and $^{14}$C) are useful in compound and/or substrate tissue distribution assays. Tritiated (i.e., $^3$H) and carbon-14 (i.e., $^{14}$C) and fluorine-18 ($^{18}$F) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I(a) in vivo when such prodrug is administered to a subject. Prodrugs of a compound of Formula I(a) are prepared by modifying functional groups present in the compound of Formula I(a) in such a way, either in routine manipulation or in vivo, that the modifications may be cleaved in vivo to release the parent compound. Prodrugs may proceed from prodrug form to active form in a single step or may have one or more intermediate forms which may themselves have activity or may be inactive. Some prodrugs are activated enzymatically to yield the active compound, or a compound which, upon further chemical reaction, yields the active compound. Prodrugs include compounds of Formula I(a) wherein a hydroxy, amino, carboxyl or sulfhydryl group in a compound of Formula I(a) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I(a), and the like. Other examples of prodrugs include, without limitation, carbonates, ureides, solvates, or hydrates of the active compound. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J Med. Chem.*, 40:2011-2016; Shan et al., 1997, *J Pharm Sci* 86(7):756-757; Bagshawe, 1995, *Drug Dev. Res.*, 34:220-230; Wermuth.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism (tautomerism) can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." As another example, stereoisomers include geometric isomers, such as cis- or trans-orientation of substituents on adjacent carbons of a double bond. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

"Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as those described herein. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 1 mM or less, 1 µM or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "modulate," "modulation," and the like refer to the ability of a compound to increase or decrease the function and/or expression of an enzyme, such as IDO1 or TDO, where such function may include transcription regulatory activity and/or binding. Modulation may occur in vitro or in vivo. Modulation, as described herein, includes the inhibition, antagonism, partial antagonism, activation, agonism or partial agonism of a function or characteristic associated with IDO1 or TDO, either directly or indirectly, and/or the upregulation or downregulation of the expression of IDO1 or TDO, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

As used herein, the term "subject," "animal subject," and the like refers to a living organism including, but not limited to, human and non-human vertebrates, e.g. any mammal, such as a human, other primates, sports animals and animals of commercial interest such as cattle, horses, ovines, or porcines, rodents, or pets such as dogs and cats.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

The term "IDO1" refers to the enzyme, indoleamine 2,3-dioxygenase 1. Human IDO1 is discussed, for example, in Tone et al., Nucleic Acids Research, 18(2):367 (1990).

The term "TDO" refers to the enzyme, tryptophan 2,3-dioxygenase. Human TDO is discussed, for example, in Comings et al., Genomics 29(2), 390-396 (1995).

The ability of a compound to inhibit the function of IDO1 and/or TDO can be demonstrated in a biochemical assay, e.g., binding assay, or a cell-based assay.

As used herein, the term "IDO1 or TDO mediated disease or condition" refers to a disease or condition in which the biological function of IDO1 or TDO affects the development and/or course of the disease or condition, and/or in which modulation of IDO1 or TDO alters the development, course, and/or symptoms. These mutations attenuate the intrinsic activity of the receptor to different degrees and are models for the effect of modulation of IDO1 or TDO activity. An IDO1 or TDO mediated disease or condition includes a disease or condition for which IDO1 or TDO inhibition provides a therapeutic benefit, e.g. wherein treatment with IDO1 or TDO inhibitors, including compounds described herein, provides a therapeutic benefit to the subject suffering from or at risk of the disease or condition.

The term "IDO1 mediated disease or disorder" includes a disease associated with or that implicates IDO1 activity, for example, the overactivity of IDO1, and conditions that accompany with these diseases. The term "overactivity of IDO1" refers to either: 1) IDO1 expression in cells which normally do not express IDO1; 2) increased IDO1 expression leading to unwanted cell proliferation; or 3) mutations leading to constitutive activation of IDO1. Examples of an IDO1 mediated diseases or disorders include a disorder resulting from over stimulation of IDO1 or from abnormally high amount of IDO1 activity, due to abnormally high amount of IDO1. It is known that overactivity of IDO1 has been implicated in the pathogenesis of a number of diseases, including inflammatory and autoimmune diseases, cell proliferative disorders, neoplastic disorders and cancers as described herein.

The term "TDO mediated disease or disorder" includes a disease associated with or that implicates TDO activity, for example, the overactivity of TDO, and conditions that accompany with these diseases. The term "overactivity of TDO" refers to either 1) TDO expression in cells which normally do not express TDO; 2) increased TDO expression leading to unwanted cell proliferation; or 3) mutations leading to constitutive activation of TDO. Examples of a TDO-mediated disease or disorder include a disorder resulting from overstimulation of TDO or from abnormally high amount of TDO activity, due to abnormally high amount of TDO. It is known that overactivity of TDO has been implicated in the pathogenesis of a number of diseases, including inflammatory and autoimmune diseases, cell proliferative disorders, neoplastic disorders and cancers as described herein.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of IDO1 or TDO, or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for IDO1," and terms of like import mean that a particular compound binds to IDO1 to a statistically greater extent than to other enzymes that may be present in a particular sample. Also, where biological activity other than binding is indicated, the term "specific for IDO1" indicates that a particular compound has greater biological effect associated with binding IDO1 than to other enzymes, e.g., enzyme activity inhibition. The specificity is also with respect to other biomolecules (not limited to IDO1 enzymes) that may be present in a particular sample.

As used herein in connection with binding compounds or ligands, the term "specific for TDO," and terms of like import mean that a particular compound binds to TDO to a statistically greater extent than to other enzymes that may be present in a particular sample. Also, where biological activity other than binding is indicated, the term "specific for TDO" indicates that a particular compound has greater biological effect associated with binding TDO than to other enzymes, e.g., enzyme activity inhibition. The specificity is also with respect to other biomolecules (not limited to TDO enzymes) that may be present in a particular sample.

The term "first line cancer therapy" refers to therapy administered to a subject as an initial regimen to reduce the number of cancer cells. First line therapy is also referred to as induction therapy, primary therapy and primary treatment. First-line therapy can be an administered combination with one or more agents. A summary of currently accepted approaches to first line treatment for certain disease can be found in the NCI guidelines for such diseases.

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy." A summary of the currently accepted approaches to second line treatment for certain diseases is described in the NCI guidelines for such diseases.

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

In addition, abbreviations as used herein have respective meanings as follows:

| | |
|---|---|
| ° C. | Degree Celsius |
| Ac | Acetyl |
| BOC | tert-Butoxycarbonyl |
| DEAE | Diethylaminoethyl |
| DMEM | Dulbecco's Modified Eagle's Medium |
| DMSO | Dimethylsulfoxide |
| FBS | Fetal bovine serum |

| | |
|---|---|
| HPLC | High Performance Liquid Chromatography |
| LCMS | Liquid Chromatography Mass Spectrometry |
| L-Trp | L-tryptophan |
| [M + H+]+ or (MH)+ | Mass peak plus hydrogen |
| [M − H−]− or (MH)− | Mass peak minus hydrogen |
| MEM | Minimum essential medium |
| PBS | Phosphate buffered saline |
| TCA | Trichloroacetic acid |
| THF | Tetrahydrofuran |
| n-Bu | n-Butyl |
| Me | Methyl |
| MS | Mass spectrometry |
| ES | Electrospray ionization |
| N | Normal |
| IDO | indoleamine 2,3-dioxygenase |
| TDO | tryptophan-2,3-dioxygenase |
| DMEM | Dulbecco's Modified Eagle's Medium |
| IC$_{50}$ | Half minimal (50%) inhibitory concentration |
| ESI | Electrospray ionization |
| MS | Mass spectrometry |
| RP | Reverse phase |
| T3P | 1-Propanephosphonic anhydride |
| LC | Liquid chromatography |
| HATU | 1-[Bis(dimethylamino)methylene]-1H-1,2,3-triazolo[4,5-b]pyridinium 3-oxid hexafluorophosphate |
| DMF | dimethylformamide |

II. Compounds

Embodiment 1 of this disclosure relates to a compound of Formula I(a):

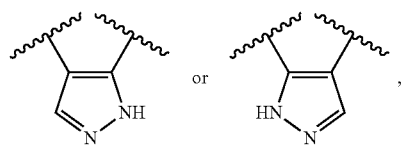
(I(a))

or a pharmaceutically acceptable salt, a solvate, a tautomer, an isomer or a deuterated analog thereof, wherein:

ring A is

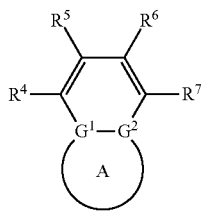

is wherein $G^1$ and $G^2$ are each C;

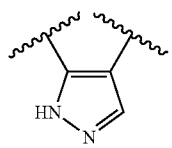, wherein $G^1$ and $G^2$ are each C;

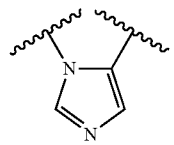

wherein $G^1$ is N and $G^2$ is C; or

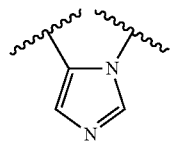

wherein $G^1$ is C and $G^2$ is N;

$R^4$, $R^5$ and $R^6$ are each independently H, halogen, alkyl, haloalkyl, —OCH$_3$ optionally substituted with 1-3 halogens, or C$_3$-C$_6$cycloalkyl optionally substituted with 1-3 halogens, provided that when ring A

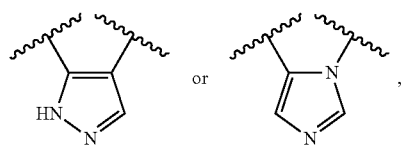 [SMILES: *c1cn[nH]c1* ; *c1cncn1*]

is at least one of $R^4$, $R^5$ or $R^6$ is not H; and
provided that when ring A is

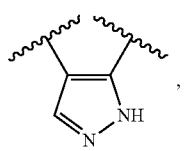

$R^7$ is

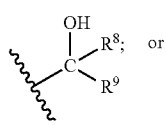
(e)

or

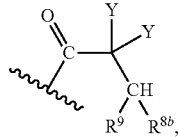
(f)

or
$R^5$ and $R^6$, together with the carbon atoms to which they are attached, join to form a 4-6 membered carbocyclic or heterocyclic ring each being optionally substituted on its carbon atoms with one or more substituents selected from the group consisting of halogen, alkyl and haloalkyl;
or $R^4$ and $R^5$, together with the carbon atoms to which they are attached, join to form a 4-6 membered carbocyclic or heterocyclic ring each being optionally substituted on its carbon atoms with one or more substituents selected from the group consisting of halogen, alkyl and haloalkyl;

$R^7$ is one of the following groups (a)-(f):
(a) cycloalkenyl optionally substituted with 1-7 $Z^1$ and optionally substituted with 1 $Z^4$;
(b) heterocycloalkyl optionally substituted with 1-9 $Z^2$ and optionally substituted with 1 $Z^5$;
(c) a bridged heterocyclic ring optionally substituted with 1-5 $Z^2$ and optionally substituted with 1 $Z^5$;
(d) a spiro ring system containing two heterocycloalkyl groups joined by one common spiro carbon atom, wherein the spiro ring system is optionally substituted on its carbon atoms with 1-8 $Z^3$, and wherein the spiro ring system is optionally N-substituted with alkyl, haloalkyl, —CO$_2$-alkyl, —C(O)NR$^{10}$R$^{11}$, —SO$_2$NR$^{10}$R$^{11}$, —SO$_2$-alkyl, SO$_2$-haloalkyl, or —SO$_2$-cycloalkyl substituted with 1-6 halogens;

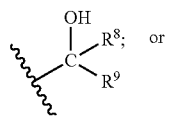
(e)

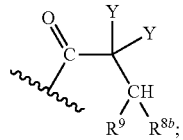
(f)

$R^8$ is H, —CH$_3$, —CFH$_2$, —CF$_2$H or —CF$_3$;
$R^{8b}$ is H, F, Cl, —CH$_3$, —CFH$_2$, —CF$_2$H or —CF$_3$;
$R^9$ is —(CY$_2$)$_{0-3}$—R$^{12}$;
or $R^8$ and $R^9$ join together with the carbon atom to which they are attached to form one of the following groups (a)-(e):
(a) a cycloalkyl optionally substituted with 1-9 $Z^2$ and optionally substituted with 1 $Z^5$ or 1-2 $Z^6$;
(b) a heterocycloalkyl optionally substituted with 1-9 $Z^2$ and optionally substituted with 1 $Z^5$;
(c) a spiro ring system containing two cycloalkyl groups joined by one common spiro carbon atom, wherein the spiro ring system is optionally substituted with 1-9 $Z^2$ and optionally substituted with 1 $Z^5$ or 1-2 $Z^6$;
(d) a spiro ring system containing one cycloalkyl and one heterocycloalkyl joined by one common spiro carbon atom, wherein the spiro ring system is optionally substituted on its carbon atoms with 1-9 $Z^3$, and wherein the spiro ring system is optionally N-substituted with alkyl, haloalkyl, —CO$_2$-alkyl, —C(O)NR$^{10}$R$^{11}$, —SO$_2$NR$^{10}$R$^{11}$, —SO$_2$-alkyl, —SO$_2$-haloalkyl, or —SO$_2$-cycloalkyl substituted with 1-6 halogens; or
(e) a spiro ring system containing one cycloalkyl and one bridged ring joined by one common spiro carbon atom, wherein the spiro ring system is optionally substituted with 1-5 $Z^2$ and optionally substituted with 1 $Z^5$;

$R^{10}$ is H, alkyl, or haloalkyl;
$R^{11}$ is H, alkyl, haloalkyl, cyanoalkyl, CN, alkynyl, phenyl optionally substituted with 1-4 $J^3$, heteroaryl optionally substituted with 1-4 $J^3$, heterocycloalkyl optionally substituted with 1-4 $J^3$, -alkylene-C(O)—OH, -alkylene-C(O)—NH$_2$, -alkylene-C(O)—N(H)-alkyl, -alkylene-C(O)—N (alkyl)$_2$, alkoxy, -alkylene-C(O)-phenyl optionally substituted with 1-4 $J^3$, —C(O)—O-alkyl, alkylene-C(O)—O-alkyl, hydroxyalkyl, cycloalkyl optionally substituted with 1-4 $J^3$, cycloalkylalkyl optionally substituted with 1-4 $J^3$, -alkylene-phenyl optionally substituted with 1-4 $J^3$, -alkylene-SO$_2$-phenyl optionally substituted with 1-4 $J^3$, -alkylene-NH—SO$_2$—C$_1$-C$_6$ alkyl, -alkylene-SO$_2$-alkyl, -alkylene-NH—SO$_2$—C$_1$-C$_6$ alkyl, alkoxyalkyl, alkoxycarbonyl, alkylcycloalkyl optionally substituted with 1-4 $J^3$, -alkylene-heterocycloalkyl optionally substituted with 1-4 $J^3$, -alkylene-heteroaryl optionally substituted with 1-4 $J^3$, or —C(O)-phenyl optionally substituted with 1-4 $J^3$;

$R^{12}$ is one of the following groups (a)-(g):
(a) a saturated cycloalkyl optionally substituted with 1-9 $Z^2$ and optionally substituted with 1 $Z^5$ or 1-2 $Z^6$;
(b) an unsaturated cycloalkyl optionally substituted with 1-7 $Z^2$ and optionally substituted with 1 $Z^5$;
(c) a heterocycloalkyl optionally substituted 1-9 $Z^2$ and optionally substituted with 1 $Z^5$;
(d) phenyl optionally substituted with 1-2 $Z^2$;
(e) a bridged ring optionally substituted with 1-5 $Z^2$ and the bridged ring is optionally substituted on a carbon atom with —N(H)(SO)$_2$-alkyl and the bridged ring is optionally N-substituted with alkyl, haloalkyl, —SO$_2$-alkyl, —SO$_2$-haloalkyl, —CO$_2$-alkyl, —C(O)NR$^{10}$R$^{11}$, —SO$_2$NR$^{10}$R$^{11}$, or —SO$_2$-cycloalkyl substituted with 1-5 halogens;
(f) heteroaryl optionally substituted with 1-2 $Z^2$; or
(g) alkyl optionally substituted with 1-2 G groups;

each G is independently —CF$_3$, C$_{3-6}$cycloalkyl, CN, NH$_2$, N(H)alkyl, —N(H)C(O)-alkyl or —N(C$_1$-C$_6$alkyl)$_2$;

$J^1$ is C$_1$-C$_6$alkyl optionally substituted with 1-4 $J^3$, —C$_1$-C$_6$alkylene-C$_1$-C$_6$alkoxy, C$_1$-C$_6$cyanoalkyl, C$_1$-C$_6$hydroxyalkyl, C$_0$-C$_3$ alkylene-C$_3$-C$_6$ cycloalkyl optionally substituted with 1-4 $J^3$, C$_0$-C$_3$ alkylene-phenyl optionally substituted with 1-4 $J^3$, —C$_0$-C$_3$ alkylene-5-6 membered heteroaryl optionally substituted with 1-4 $J^3$, —C$_0$-C$_3$ alkylene-4-6 membered heterocycloalkyl optionally substituted with 1-4 $J^3$;

$J^2$ is H, C$_1$-C$_6$alkyl, or C$_1$-C$_6$haloalkyl;

each $J^3$ is independently halogen, C$_1$-C$_6$alkyl, C$_1$-C$_6$haloalkyl, OH, C$_1$-C$_6$alkoxy optionally substituted with 1-3 halogens, CN, —C$_0$-C$_3$ alkylene-4-6 membered heterocycloalkyl optionally substituted with C$_1$-C$_3$alkyl, —S(O)$_2$—C$_1$-C$_6$alkyl, —NH$_2$, —N(H)—C$_1$-C$_6$alkyl, or —N(C$_1$-C$_6$alkyl)$_2$, provided that when $J^3$ is attached to nitrogen, $J^3$ cannot be halogen, OH, CN, NH$_2$, —N(H)—C$_1$-C$_6$alkyl, or —N(C$_1$-C$_6$alkyl)$_2$;

each Y is independently H, D, halogen, alkyl, or haloalkyl, or 2 Y groups join together with the carbon atom to which they are attached to form a cycloalkyl optionally substituted with 1-3 halogens;

each $Z^1$ is independently CN, halogen, alkyl, or haloalkyl;

each $Z^2$ is independently —OH, CN, halogen, alkyl, cycloalkyl optionally substituted with 1-3 halogens, hydroxyalkyl, haloalkyl, —NH$_2$, —N(H)alkyl, —N(alkyl)$_2$, alkoxyl optionally substituted with halo or phenyl, 5-6 membered heterocycloalkyl, or 5-6 membered heteroaryl, provided that when $Z^2$ is attached to nitrogen, $Z^2$ cannot be —OH, CN, halogen, alkoxyl, —NH$_2$, —N(H)alkyl, or —N(alkyl)$_2$;

each $Z^3$ is independently CN, halogen, alkyl or haloalkyl;

$Z^4$ is alkoxyalkyl, phenyl optionally substituted with 1-3 halogens, —SO$_2$-alkyl, —SO$_2$-haloalkyl, —SO$_2$-cycloalkyl optionally substituted with 1-6 halogens, —C(O)NR$^{10}$R$^{11}$, —SO$_2$NR$^{10}$R$^{11}$, —N(H)SO$_2$-alkyl, —N(H)SO$_2$-cycloalkyl optionally substituted with 1-6 halogens, or —N(H)SO$_2$-haloalkyl;

$Z^5$ is alkoxyalkyl, —SO$_2$-alkyl, —CO$_2$-alkyl, —C(O)J$^1$, —CO$_2$J$^2$, —C$_0$-C$_4$alkylene-phenyl optionally substituted with 1-4 J³, —C₀-C₄alkylene-CH(phenyl)₂ optionally substituted with 1-4 J³, —C₀-C₄alkylene-CH(C₃-C₆cycloalkyl)₂ optionally substituted with 1-4 J³, —SO₂-haloalkyl, —SO₂-cycloalkyl optionally substituted with 1-6 J³, —SO₂-heterocycloalkyl optionally substituted with 1-6 J³, —SO₂-heteroaryl optionally substituted with 1-6 J³, —SO₂-aryl optionally substituted with 1-6 J³, —C(O)NR¹⁰R¹¹, —SO₂NR¹⁰R¹¹, —N(H)SO₂-alkyl optionally substituted with 1-6 J³, —N(H)SO₂-aryl optionally substituted with 1-6 J³, —N(H)SO₂-cycloalkyl optionally substituted with 1-6 J³, —N(H)SO₂-heterocyloalkyl optionally substituted with 1-6 J³, —N(H)SO₂-heteroaryl optionally substituted with 1-6 J³, —N(H)SO₂-haloalkyl, optionally substituted with 1-6 J³, —C(O)—N(H)SO₂-alkyl optionally substituted with 1-6 J³, —C(O)—N(H)SO₂-aryl optionally substituted with 1-6 J³, —C(O)—N(H)SO₂-cycloalkyl optionally substituted with 1-6 J³, —C(O)—N(H)SO₂-heterocyloalkyl optionally substituted with 1-6 J³, —C(O)N(H)SO₂-heteroaryl optionally substituted with 1-6 J³, —C(O)N(H)SO₂-haloalkyl, or —C(NW₂)=N-T, provided that when Z⁵ is attached to nitrogen, Z⁵ cannot be —N(H)SO₂-alkyl, —N(H)SO₂-aryl, —N(H)SO₂-cycloalkyl, —N(H)SO₂-heterocyloalkyl, —N(H)SO₂-heteroaryl, or —N(H)SO₂-haloalkyl;

each W is independently H, alkyl or haloalkyl;

T is alkyl, haloalkyl, hydroxyalkyl, alkoxy or CN; and each Z⁶ is independently halo, alkyl, haloalkyl, CN, OH, cycloalkyl, aryl or heteroaryl, provided that only one Z⁶ can be OH.

Sub-Embodiments of Embodiment 1

Embodiment 1(a) of this disclosure relates to embodiment 1, wherein R⁷ is group (a):

(a) cycloalkenyl optionally substituted with 1-7 Z¹, and optionally substituted with 1 Z⁴.

Embodiment 1(b) of this disclosure relates to embodiment 1, wherein R⁷ is group (b):

(b) heterocycloalkyl optionally substituted with 1-9 Z², and optionally substituted with 1 Z⁵.

Embodiment 1(c) of this disclosure relates to embodiment 1, wherein R⁷ is group (c):

(c) a bridged heterocyclic ring optionally substituted with 1-5 Z², and optionally substituted with 1 Z⁵.

Embodiment 1(d) of this disclosure relates to embodiment 1, wherein R⁷ is group (d):

(d) a spiro ring system containing two heterocycloalkyl groups joined by one common spiro carbon atom, wherein the spiro ring system is optionally substituted on its carbon atoms with 1-8 Z³, and wherein the spiro ring system can also be optionally N-substituted with alkyl, haloalkyl, —CO₂-alkyl, —C(O)NR¹⁰R¹¹, —SO₂NR¹⁰R¹¹, —SO₂-alkyl, SO₂-haloalkyl, or —SO₂-cycloalkyl substituted with 1-6 halogens.

Embodiment 1(e) of this disclosure relates to embodiment 1, wherein R⁷ is group (e):

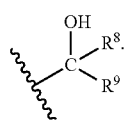

(e)

Embodiment 1(e)(a) of this disclosure relates to Embodiment 1(e), wherein R⁸ and R⁹ join together with the carbon atom to which they are attached to form group (a):

(a) a cycloalkyl optionally substituted with 1-9 Z², and optionally substituted with 1 Z⁵ or 1-2 Z⁶.

Embodiment 1(e)(b) of this disclosure relates to Embodiment 1(e), wherein R⁸ and R⁹ join together with the carbon atom to which they are attached to form group (b):

(b) a heterocycloalkyl optionally substituted with 1-9 Z², and optionally substituted with 1 Z⁵.

Embodiment 1(e)(c) of this disclosure relates to Embodiment 1(e), wherein R⁸ and R⁹ join together with the carbon atom to which they are attached to form group (c):

(c) a spiro ring system containing two cycloalkyl groups joined by one common spiro carbon atom, wherein the spiro ring system is optionally substituted with 1-9 Z², and optionally substituted with 1 Z⁵ or 1-2 Z⁶.

Embodiment 1(e)(d) of this disclosure relates to Embodiment 1(e), wherein R⁸ and R⁹ join together with the carbon atom to which they are attached to form group (d):

(d) a spiro ring system containing one cycloalkyl and one heterocycloalkyl joined by one common spiro carbon atom, wherein the spiro ring system is optionally substituted on its carbon atoms with 1-9 Z³, and wherein the spiro ring system can also be optionally N-substituted with alkyl, haloalkyl, —CO₂-alkyl, —C(O)NR¹⁰R¹¹, —SO₂NR¹⁰R¹¹, —SO₂-alkyl, —SO₂-haloalkyl, or —SO₂-cycloalkyl substituted with 1-6 halogens.

Embodiment 1(e)(e) of this disclosure relates to Embodiment 1(e), wherein R⁸ and R⁹ join together with the carbon atom to which they are attached to form group (e):

(e) a spiro ring system containing one cycloalkyl and one a bridged ring joined by one common spiro carbon atom, wherein the spiro ring system is optionally substituted with 1-5 Z², and optionally substituted with 1 Z⁵.

Embodiment 1(e)(2) of this disclosure relates to Embodiment 1(e), wherein R⁹ is —(CY₂)₀₋₃—R¹², and R⁸ is H, —CH₃, —CFH₂, —CF₂H or —CF₃.

Embodiment 1(e)(2)(a) of this disclosure relates to Embodiment 1(e)(2), wherein R¹² is group (a):

(a) a saturated cycloalkyl optionally substituted with 1-9 Z², and optionally substituted with 1 Z⁵ or 1-2 Z⁶.

Embodiment 1(e)(2)(b) of this disclosure relates to Embodiment 1(e)(2), wherein R¹² is group (b):

(b) an unsaturated cycloalkyl optionally substituted with 1-7 Z², and optionally substituted with 1 Z⁵.

Embodiment 1(e)(2)(c) of this disclosure relates to Embodiment 1(e)(2), wherein R¹² is group (c):

(c) a heterocycloalkyl optionally substituted 1-9 Z², and optionally substituted with 1 Z⁵.

Embodiment 1(e)(2)(d) of this disclosure relates to Embodiment 1(e)(2), wherein R¹² is group (d):

(d) phenyl optionally substituted with 1-2 Z².

Embodiment 1(e)(2)(e) of this disclosure relates to Embodiment 1(e)(2), wherein R¹² is group (e):

(e) a bridged ring optionally substituted with 1-5 Z²; and the bridged ring is optionally N-substituted with alkyl, haloalkyl, —SO₂-alkyl, —SO₂-haloalkyl; —CO₂-alkyl, —C(O)NR¹⁹R¹¹, —SO₂NR¹⁰R¹¹, or —SO₂-cycloalkyl substituted with 1-5 halogens.

Embodiment 1(e)(2)(f) of this disclosure relates to Embodiment 1(e)(2), wherein R¹² is group (f):

(f) heteroaryl optionally substituted with 1-2 Z².

Embodiment 1(e)(2)(g) of this disclosure relates to Embodiment 1(e)(2), wherein R¹² is group (g):

(g) alkyl optionally substituted with 1-3 G groups.

Embodiment 1(f) of this disclosure relates to Embodiment 1, wherein $R^7$ is group (f):

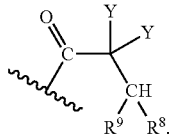
(f)

Embodiment 1(g) of this disclosure relates to Embodiment 1, wherein when $R^{12}$ is (c) a saturated cycloalkyl optionally substituted with 1-8 $Z^2$, and optionally substituted with 1 $Z^5$ or 1-2 $Z^6$, then $R^8$ is H and $R^9$ is —$(CY_2)_{1-3}$—$R^{12}$.

Embodiment 2 of this disclosure relates to a compound of Formula (Ic),

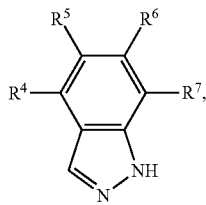
(Ic)

or a pharmaceutically acceptable salt, a solvate, a tautomer, an isomer or a deuterated analog thereof, wherein:

$R^4$ is H, F, Cl, Br, —$OCH_3$ optionally substituted with 1-3 halogens, cyclopropyl, $C_1$-$C_3$alkyl, or $C_1$-$C_3$haloalkyl;

$R^5$ and $R^6$ are each independently H, F, Cl, Br, —$OCH_3$ optionally substituted with 1-3 halogens, $C_1$-$C_3$alkyl, $C_1$-$C_3$haloalkyl, or $C_3$-$C_5$cycloalkyl optionally substituted with 1-3 halogens, provided that at least one of $R^5$ or $R^6$ is not H;

or $R^5$ and $R^6$, together with the carbon atoms to which they are attached, join to form a 4-6 membered carbocyclic or a heterocyclic ring containing at least one oxygen or sulfur atom, each ring being optionally substituted on its carbon atoms with 1-4 substituents selected from the group consisting of F, Cl, $C_1$-$C_3$alkyl and $C_1$-$C_3$haloalkyl;

or $R^4$ and $R^5$, together with the carbon atoms to which they are attached, join to form a 4-6 membered carbocyclic or a heterocyclic ring containing at least one oxygen or sulfur atom, each ring being optionally substituted on its carbon atoms with 1-4 substituents selected from the group consisting of F, Cl, $C_1$-$C_3$alkyl and $C_1$-$C_3$haloalkyl;

$R^7$ is one of the following groups (a)-(f):
(a) cycloalkenyl optionally substituted with 1-6 $Z^1$, and optionally substituted with 1 $Z^4$;
(b) heterocycloalkyl optionally substituted with 1-8 $Z^2$, and optionally substituted with 1 $Z^5$;
(c) a bridged nitrogen-containing heterocyclic ring optionally substituted with 1-4 $Z^2$, and optionally substituted with 1 $Z^5$; or
(d) a spiro ring system containing two nitrogen-containing heterocycloalkyl groups joined by one common spiro carbon atom, wherein the spiro ring system is optionally substituted on its carbon atoms with 1-7 $Z^3$, and wherein the spiro ring system is optionally N-substituted with alkyl, haloalkyl, —$SO_2$-alkyl, —$SO_2$-haloalkyl, —$CO_2$-alkyl, —$C(O)NR^{10}R^{11}$, —$SO_2NR^{10}R^{11}$, or —$SO_2$-cycloalkyl substituted with 1-5 halogens;

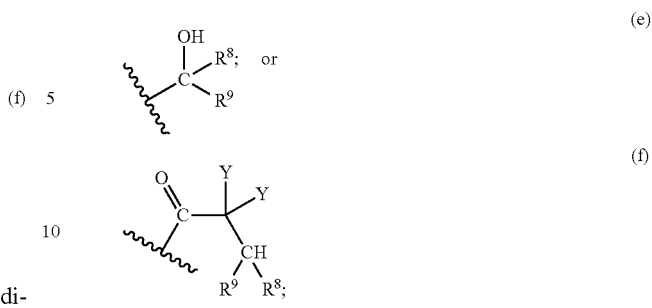

$R^8$ is H or $CH_3$;
$R^9$ is —$(CY_2)_{0-2}$—$R^{12}$;
or $R^8$ and $R^9$ join together with the carbon atom to which they are attached to form one of the following groups (a)-(e):
(a) a cycloalkyl optionally substituted with 1-8 $Z^2$, and optionally substituted with 1 $Z^5$ or 1-2 $Z^6$;
(b) a heterocycloalkyl optionally substituted with 1-8 $Z^2$, and optionally substituted with 1 $Z^5$;
(c) a spiro ring system containing two cycloalkyl groups joined by one common spiro carbon atom, wherein the spiro ring system is optionally substituted with 1-8 $Z^2$, and optionally substituted with 1 $Z^5$ or 1-2 $Z^6$;
(d1) a spiro ring system containing one cycloalkyl and one nitrogen-containing heterocycloalkyl joined by one common spiro carbon atom, wherein the spiro ring system is optionally substituted on its carbon atoms with 1-8 $Z^3$, and wherein the spiro ring system is optionally N-substituted with alkyl, haloalkyl, —$SO_2$-alkyl, —$SO_2$-haloalkyl, —$CO_2$-alkyl, —$C(O)NR^{10}R^{11}$, —$SO_2NR^{10}R^{11}$, or —$SO_2$-cycloalkyl substituted with 1-5 halogens;
(d2) a spiro ring system containing one cycloalkyl and one heterocycloalkyl containing —O—, —S—, —S(O)— or —$S(O)_2$—, wherein the spiro ring system is joined by one common spiro carbon atom, and wherein the spiro ring system is optionally substituted on its carbon atoms with 1-8 $Z^3$; or
(e) a spiro ring system containing one cycloalkyl and one bridged ring joined by one common spiro carbon atom, wherein the spiro ring system is optionally substituted with 1-4 $Z^2$, and optionally substituted with 1 $Z^5$;

$R^{10}$ is H, $C_1$-$C_6$alkyl, or $C_1$-$C_6$haloalkyl;
$R^{11}$ is H, $C_1$-$C_6$alkyl, $C_1$-$C_6$haloalkyl, $C_1$-$C_6$cyanoalkyl, CN, $C_2$-$C_6$alkynyl, $C_1$-$C_6$alkylene-C(O)—OH, -alkylene-C(O)—$NH_2$, -alkylene-C(O)—N(H)—$C_1$-$C_6$alkyl, —$C_1$-$C_6$alkylene-C(O)—N($C_1$-$C_6$alkyl)$_2$, alkoxy, —$C_0$-$C_6$ alkylene-C(O)—O—$C_1$-$C_6$ alkyl, $C_1$-$C_6$hydroxyalkyl, —$C_0$-$C_6$alkylene-phenyl optionally substituted with 1-4 $J^3$, —$C_1$-$C_3$ alkylene-$SO_2$-phenyl optionally substituted with 1-4 $J^3$, —$C_1$-$C_3$ alkylene-$SO_2$—$C_1$-$C_6$ alkyl, —$C_1$-$C_3$ alkylene-NH—$SO_2$—$C_1$-$C_6$ alkyl, —$C_1$-$C_6$alkylene-$C_1$-$C_6$alkoxy, $C_1$-$C_6$alkoxycarbonyl, —$C_0$-$C_6$ alkylene-$C_3$-$C_6$cycloalkyl optionally substituted with 1-4 $J^3$, —$C_0$-$C_6$ alkylene-$C_3$-$C_6$heterocycloalkyl optionally substituted with 1-4 $J^3$, —$C_0$-$C_6$ alkylene-5-6 membered heteroaryl optionally substituted with 1-4 $J^3$, or —$C_0$-$C_6$ alkylene-C(O)-phenyl optionally substituted with 1-4 $J^3$;

$R^{12}$ is one of the following groups (a)-(g):
(a) a saturated cycloalkyl optionally substituted with 1-8 $Z^2$, and optionally substituted with 1 $Z^5$ or 1-2 $Z^6$;
(b) a cycloalkenyl optionally substituted with 1-6 $Z^2$, and optionally substituted with 1 $Z^5$;
(c) a heterocycloalkyl optionally substituted with 1-8 $Z^2$, and optionally substituted with 1 $Z^5$;

(d) phenyl optionally substituted with 1-2 substituents independently selected from the group consisting of CN, halogen, $C_1$-$C_4$alkyl, $C_1$-$C_4$haloalkyl, —$NH_2$, —N(H)$C_1$-$C_4$alkyl, —N($C_1$-$C_4$alkyl)$_2$, $C_1$-$C_4$alkoxyl optionally substituted with phenyl, 5-6 membered heterocycloalkyl, and 5-6 membered heteroaryl;

(e) a bridged ring optionally substituted with 1-4 $Z^2$, wherein the bridged ring is optionally N-substituted with alkyl, haloalkyl, —$SO_2$-alkyl, —$SO_2$-haloalkyl, —$CO_2$-alkyl, —C(O)NR$^{10}$R$^{11}$, —$SO_2$NR$^{10}$R$^{11}$, or —$SO_2$-cycloalkyl substituted with 1-5 halogens; or (g) alkyl optionally substituted with 1-2 G groups;

each G is independently —$CF_3$, cyclopropyl, CN, $NH_2$, —N(H)alkyl, —N(H)C(O)-alkyl or —N($C_1$-$C_6$alkyl)$_2$;

$J^1$ is $C_1$-$C_6$alkyl optionally substituted with 1-4 $J^3$, —$C_1$-$C_6$alkylene-$C_1$-$C_6$alkoxy, $C_1$-$C_6$cyanoalkyl, $C_1$-$C_6$hydroxyalkyl, $C_0$-$C_3$ alkylene-$C_3$-$C_6$ cycloalkyl optionally substituted with 1-4 $J^3$, $C_0$-$C_3$ alkylene-phenyl optionally substituted with 1-4 $J^3$, —$C_0$-$C_3$ alkylene-5-6 membered heteroaryl optionally substituted with 1-4 $J^3$, —$C_0$-$C_3$ alkylene-4-6 membered heterocycloalkyl optionally substituted with 1-4 $J^3$;

$J^2$ is H, $C_1$-$C_6$alkyl, or $C_1$-$C_6$haloalkyl;

each $J^3$ is independently halogen, $C_1$-$C_6$alkyl, $C_1$-$C_6$haloalkyl, OH, $C_1$-$C_6$alkoxy optionally substituted with 1-3 halogens, CN, 4-6 membered heterocycloalkyl, —S(O)$_2$—$C_1$-$C_6$alkyl, —$NH_2$, —N(H)$C_1$-$C_{36}$alkyl, —N($C_1$-$C_6$alkyl)$_2$ provided that when $J^3$ is attached to nitrogen, $J^3$ cannot be halogen, OH, CN, $NH_2$, —N(H)—$C_1$-$C_6$alkyl, or —N($C_1$-$C_6$alkyl)$_2$;

each Y is independently H, F, Cl, $C_1$-$C_3$alkyl or $C_1$-$C_3$haloalkyl, or 2 Y groups join together with the carbon atom to which they are attached to form a $C_3$-$C_5$cycloalkyl optionally substituted with 1-3 halogens;

each $Z^1$ is independently CN, F, Cl, alkyl, or haloalkyl;

each $Z^2$ is independently —OH, CN, F, Cl, alkyl, alkoxy, $C_3$-$C_6$ cycloalkyl optionally substituted with 1-3 halogens, cyclopropyl, hydroxyalkyl, or haloalkyl, provided that when $Z^2$ is attached to nitrogen, $Z^2$ cannot be —OH, CN, F, Cl, or alkoxy;

each $Z^3$ is independently CN, F, Cl, alkyl or haloalkyl;

$Z^4$ is —$C_1$-$C_3$alkylene-$C_1$-$C_3$alkoxy, —$SO_2$-alkyl, —$SO_2$-haloalkyl, —C(O)NR$^{10}$R$^{11}$, —$SO_2$NR$^{10}$R$^{11}$, —$SO_2$-cycloalkyl optionally substituted with 1-5 halogens, —N(H)SO$_2$-alkyl, —N(H)SO$_2$-cycloalkyl optionally substituted with 1-5 halogens, or —N(H)SO$_2$-haloalkyl;

$Z^5$ is —$C_1$-$C_3$ alkylene-$C_1$-$C_3$ alkoxy, —$C_0$-$C_3$ alkylene-phenyl optionally substituted with 1-3 $J^3$, —$SO_2$-alkyl, $SO_2$-haloalkyl, —$C_0$-$C_3$alkylene-CH(phenyl)$_2$ optionally substituted with 1-3 $J^3$, —$C_0$-$C_3$alkylene-CH($C_3$-$C_6$cycloalkyl)$_2$ optionally substituted with 1-3 $J^3$, —C(O)NR$^{10}$R$^{11}$, —$CO_2$-alkyl, —C(O)$J^1$, $CO_2J^2$, —$SO_2$NR$^{10}$R$^{11}$, —$SO_2$-cycloalkyl optionally substituted with 1-5 $J^3$, —$SO_2$-heterocycloalkyl optionally substituted with 1-5 $J^3$, —$SO_2$-heteroaryl optionally substituted with 1-5 $J^3$, —$SO_2$-phenyl optionally substituted with 1-3 $J^3$, —C(O)N(H)SO$_2$-cycloalkyl optionally substituted with 1-5 $J^3$, —C(O)N(H)SO$_2$-heterocycloalkyl optionally substituted with 1-5 $J^3$, —C(O)N(H)SO$_2$-heteroaryl optionally substituted with 1-5 $J^3$, —C(O)N(H)SO$_2$-phenyl optionally substituted with 1-3 $J^3$, —N(H)SO$_2$-alkyl, —N(H)SO$_2$-cycloalkyl optionally substituted with 1-5 $J^3$, —N(H)SO$_2$-heterocycloalkyl optionally substituted with 1-5 $J^3$, —N(H)SO$_2$-heteroaryl optionally substituted with 1-5 $J^3$, —N(H)SO$_2$-haloalkyl, or —C(NW$_2$)=N-T, provided that when $Z^5$ is attached to nitrogen, $Z^5$ cannot be —N(H)SO$_2$-alkyl, —N(H)SO$_2$-cycloalkyl, —N(H)SO$_2$-heterocycloalkyl, —N(H)SO$_2$-heteroaryl, or N(H)SO$_2$—$C_1$-$C_6$haloalkyl;

each W is independently H, $C_1$-$C_3$alkyl, or $C_1$-$C_3$haloalkyl;

T is $C_1$-$C_6$alkyl, $C_1$-$C_6$haloalkyl, $C_1$-$C_6$hydroxyalkyl, $C_1$-$C_6$alkoxy or CN; and each $Z^6$ is independently halo, $C_1$-$C_3$alkyl, $C_1$-$C_3$haloalkyl, CN, OH, $C_3$-$C_5$cycloalkyl, phenyl or 5-6 membered heteroaryl, provided that only one $Z^6$ can be OH.

Sub-Embodiments of Embodiment 2

Embodiment 2(a) of this disclosure relates to Embodiment 2 wherein $R^7$ is group (a):

(a) cycloalkenyl optionally substituted with 1-6 $Z^1$, and optionally substituted with 1 $Z^4$.

Embodiment 2(b) of this disclosure relates to Embodiment 2 wherein $R^7$ is group (b):

(b) heterocycloalkyl optionally substituted with 1-8 $Z^2$, and optionally substituted with 1 $Z^5$.

Embodiment 2(c) of this disclosure relates to Embodiment 2 wherein $R^7$ is group (c):

(c) a bridged nitrogen-containing heterocyclic ring optionally substituted with 1-4 $Z^2$, and optionally substituted with 1 $Z^5$.

Embodiment 2(d) of this disclosure relates to Embodiment 2 wherein $R^7$ is group (d):

(d) a spiro ring system containing two nitrogen-containing heterocycloalkyl groups joined by one common spiro carbon atom, wherein the spiro ring system is optionally substituted on its carbon atoms with 1-7 $Z^3$, and wherein the spiro ring system is optionally N-substituted with alkyl, haloalkyl, —$SO_2$-alkyl, —$SO_2$-haloalkyl, —$CO_2$-alkyl, —C(O)NR$^{10}$R$^{11}$, —$SO_2$NR$^{10}$R$^{11}$, or —$SO_2$-cycloalkyl substituted with 1-5 halogens.

Embodiment 2(e)(a) of this disclosure relates to Embodiment 2(e) wherein $R^8$ and $R^9$ join together with the carbon atom to which they are attached to form group (a):

(a) a cycloalkyl optionally substituted with 1-8 $Z^2$, and optionally substituted with 1 $Z^5$ or 1-2 $Z^6$.

Embodiment 2(e)(b) of this disclosure relates to Embodiment 2(e) wherein $R^8$ and $R^9$ join together with the carbon atom to which they are attached to form groups (b):

(b) a heterocycloalkyl optionally substituted with 1-8 $Z^2$, and optionally substituted with 1 $Z^5$.

Embodiment 2(e)(c) of this disclosure relates to Embodiment 2(e) wherein $R^8$ and $R^9$ join together with the carbon atom to which they are attached to form group (c):

(c) a spiro ring system containing two cycloalkyl groups joined by one common spiro carbon atom, wherein the spiro ring system is optionally substituted with 1-8 $Z^2$, and optionally substituted with 1 $Z^5$ or 1-2 $Z^6$.

Embodiment 2(e)(d1) of this disclosure relates to Embodiment 2(e) wherein $R^8$ and $R^9$ join together with the carbon atom to which they are attached to form group (d1):

(d1) a spiro ring system containing one cycloalkyl and one nitrogen-containing heterocycloalkyl joined by one common spiro carbon atom, wherein the spiro ring system is optionally substituted on its carbon atoms with 1-8 $Z^3$, and wherein the spiro ring system can also be optionally N-substituted with alkyl, haloalkyl, —$SO_2$-alkyl, —$SO_2$-haloalkyl, —$CO_2$-alkyl, —C(O)NR$^{10}$R$^{11}$, —$SO_2$NR$^{10}$R$^{11}$, or —$SO_2$-cycloalkyl substituted with 1-5 halogens.

Embodiment 2(e)(d2) of this disclosure relates to Embodiment 2(e) wherein $R^8$ and $R^9$ join together with the carbon atom to which they are attached to form group (d2):

(d2) a spiro ring system containing one cycloalkyl and one heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-8 $Z^3$.

Embodiment 2(e)(e) of this disclosure relates to Embodiment 2(e) wherein $R^8$ and $R^9$ join together with the carbon atom to which they are attached to form group (e):

(e) a spiro ring system containing one cycloalkyl and one bridged ring joined by one common spiro carbon atom, wherein the spiro ring system is optionally substituted with 1-4 $Z^2$, and optionally substituted with 1 $Z^5$.

Embodiment 2(e)(2) of this disclosure relates to Embodiment 2(e) wherein:

$R^8$ is H, or CH$_3$; and
$R^9$ is —(CY$_2$)$_{0-2}$—R$^{12}$.

Embodiment 2(e)(2)(a) of this disclosure relates to Embodiment 2(e)(2) wherein $R^{12}$ is group (a):

(a) a saturated cycloalkyl optionally substituted with 1-8 $Z^2$, and optionally substituted with 1 $Z^5$ or 1-2 $Z^6$.

Embodiment 2(e)(2)(b) of this disclosure relates to Embodiment 2(e) wherein $R^{12}$ is group (b):

(b) a cycloalkenyl optionally substituted with 1-6 $Z^2$, and optionally substituted with 1 $Z^5$.

Embodiment 2(e)(2)(c) of this disclosure relates to Embodiment 2(e) wherein $R^{12}$ is group (c):

(c) a heterocycloalkyl optionally substituted with 1-8 $Z^2$, and optionally substituted with 1 $Z^5$.

Embodiment 2(e)(2)(d) of this disclosure relates to Embodiment 2(e) wherein $R^{12}$ is group (d):

(d) phenyl optionally substituted with 1-2 substituents independently selected from the group consisting of CN, halogen, C$_1$-C$_4$alkyl, C$_1$-C$_4$haloalkyl, —NH$_2$, —N(H)C$_1$-C$_4$alkyl, —N(C$_1$-C$_4$alkyl)$_2$, C$_1$-C$_4$alkoxyl optionally substituted with phenyl, 5-6 membered heterocycloalkyl, and 5-6 membered heteroaryl.

Embodiment 2(e)(2)(e) of this disclosure relates to Embodiment 2(e) wherein $R^{12}$ is group (e):

(e) a bridged ring optionally substituted with 1-4 $Z^2$, wherein the bridged ring is optionally N-substituted with alkyl, haloalkyl, —SO$_2$-alkyl, —SO$_2$-haloalkyl, —CO$_2$-alkyl, —C(O)NR$^{10}$R$^{11}$, —SO$_2$NR$^{10}$R$^{11}$, or —SO$_2$-cycloalkyl substituted with 1-5 halogens.

Embodiment 2(e)(2)(g) of this disclosure relates to Embodiment 2(e) wherein $R^{12}$ is group (g):

(g) alkyl optionally substituted with 1-3 G groups.

Embodiment 2(f) of this disclosure relates to Embodiment 2 wherein $R^7$ is group (f):

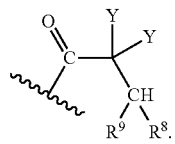

(f)

Embodiment 2(g) of this disclosure relates to Embodiment 1, wherein when $R^{12}$ is (c) a heterocycloalkyl optionally substituted with 1-8 $Z^2$ and optionally substituted with 1 $Z^5$; then $R^8$ is H and $R^9$ is —(CY$_2$)$_{1-3}$—R$^{12}$.

Embodiment 3 of this disclosure relates to a compound of any one of Embodiments 1 and 2, wherein:

$R^7$ is one of the following groups (a), (b), (c), or (e):

(a) C$_5$-C$_6$cycloalkenyl optionally substituted with 1-5 $Z^1$, and optionally substituted with 1 $Z^4$;

(b) 5 or 6-membered nitrogen-containing heterocycloalkyl optionally substituted with 1-7 $Z^2$, and optionally substituted with 1 $Z^5$;

(c) a 5-9 membered nitrogen-containing bridged heterocyclic ring optionally substituted with 1-3 $Z^2$, and optionally substituted with 1 $Z^5$; or

(e)

$R^8$ is H;
$R^9$ is —(CY$_2$)$_{0-2}$—R$^{12}$;
or $R^8$ and $R^9$ join together with the carbon atom to which they are attached to form one of the following groups (a)-(e):

(a) a C$_3$-C$_6$cycloalkyl optionally substituted with 1-7 $Z^2$, and optionally substituted with 1 $Z^5$ or 1-2 $Z^6$;

(b) a 4-6 membered heterocycloalkyl optionally substituted with 1-7 $Z^2$, and optionally substituted with 1 $Z^5$;

(c) a spiro ring system containing two C$_4$-C$_6$cycloalkyl groups joined by one common spiro carbon atom, wherein the spiro ring system is optionally substituted with 1-7 $Z^2$, and optionally substituted with 1 $Z^5$ or 1-2 $Z^6$;

(d1) a spiro ring system containing one C$_4$-C$_6$cycloalkyl and one 4-6 membered nitrogen-containing heterocycloalkyl joined by one common spiro carbon atom, wherein the spiro ring system is optionally substituted on its carbon atoms with 1-7 $Z^3$, and wherein the spiro ring system is optionally N-substituted with C$_1$-C$_6$alkyl, C$_1$-C$_6$haloalkyl, —SO$_2$—C$_1$-C$_6$alkyl, —SO$_2$—C$_1$-C$_6$haloalkyl, —C(O)NR$^{10}$R$^{11}$, —SO$_2$NR$^{10}$R$^{11}$, or —SO$_2$—C$_3$-C$_6$cycloalkyl substituted with 1-4 halogens;

(d2) a spiro ring system containing one cycloalkyl and one heterocycloalkyl containing —O—, —S—, —S(O)—, or —S(O)$_2$—, wherein the spiro ring system is joined by one common spiro carbon atom, and wherein the spiro ring system is optionally substituted on its carbon atoms with 1-7 $Z^3$; or (e) a spiro ring system containing one cycloalkyl and one bridged ring joined by one common spiro carbon atom, wherein the spiro ring system is optionally substituted with 1-3 $Z^2$;

$R^{10}$ is H, C$_1$-C$_3$alkyl, or C$_1$-C$_3$haloalkyl;
is H, C$_1$-C$_3$alkyl, C$_1$-C$_3$haloalkyl, C$_1$-C$_4$cyanoalkyl, C$_2$-C$_4$alkynyl, —C$_1$-C$_4$alkylene-C(O)—NH$_2$, —C$_1$-C$_4$alkylene-C(O)—N(H)—C$_1$-C$_4$alkyl, —C$_1$-C$_4$alkylene-C(O)—N(C$_1$-C$_4$alkyl)$_2$, —C$_0$-C$_4$ alkylene-C(O)—O—C$_1$-C$_4$alkyl, C$_1$-C$_4$hydroxyalkyl, —C$_0$-C$_4$alkylene-phenyl optionally substituted with 1-4 J$^3$, —C$_1$-C$_3$ alkylene-SO$_2$-phenyl optionally substituted with 1-4 J$^3$, —C$_1$-C$_3$ alkylene-SO$_2$—C$_1$-C$_{36}$ alkyl, —C$_1$-C$_3$ alkylene-NH—SO$_2$—C$_1$-C$_6$ alkyl, —C$_1$-C$_4$alkylene-C$_1$-C$_4$alkoxy, C$_1$-C$_4$alkoxycarbonyl, —C$_0$-C$_4$ alkylene-C$_3$-C$_6$cycloalkyl optionally substituted with 1-4 J$^3$, —C$_0$-C$_4$ alkylene-5-6 membered heterocycloalkyl optionally substituted with 1-4 J$^3$, —C$_0$-C$_4$ alkylene-5-6 membered heteroaryl optionally substituted with 1-4 J$^3$, or —C(O)-phenyl optionally substituted with 1-4 J$^3$;

$R^{12}$ is one of the following groups (a)-(e):

(a) a saturated C$_3$-C$_6$cycloalkyl optionally substituted with 1-7 $Z^2$, and optionally substituted with 1 $Z^5$ or 1-2 $Z^6$;

(b) a $C_5$-$C_6$cycloalkenyl optionally substituted with 1-5 $Z^2$, and optionally substituted with 1 $Z^5$;

(c) a 4-6 membered heterocycloalkyl optionally substituted with 1-7 $Z^2$, and optionally substituted with 1 $Z^5$;

(d) phenyl optionally substituted with 1-2 substituents independently selected from the group consisting of CN, halogen, $C_1$-$C_4$alkyl, and $C_1$-$C_4$haloalkyl; or (e) a 5-10 membered bridged carbocyclic or heterocyclic ring, wherein the 5-10 membered bridged carbocyclic or heterocyclic ring are each optionally substituted with 1-3 $Z^2$, and wherein the bridged heterocyclic ring is optionally N-substituted with $C_1$-$C_6$alkyl, $C_1$-$C_6$haloalkyl, —$SO_2$—$C_1$-$C_6$alkyl, —$SO_2$—$C_1$-$C_6$haloalkyl, —C(O)NR$^{10}$R$^{11}$, —$SO_2$NR$^{10}$R$^{11}$, or —$SO_2$—$C_3$-$C_6$cycloalkyl substituted with 1-4 halogens;

$J^1$ is $C_1$-$C_5$alkyl optionally substituted with 1-4 $J^3$, —$C_1$-$C_5$alkylene-$C_1$-$C_5$alkoxy, $C_1$-$C_5$cyanoalkyl, $C_1$-$C_5$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, —$C_0$-$C_3$ alkylene-5-6 membered heteroaryl optionally substituted with 1-3 $J^3$, —$C_0$-$C_3$ alkylene-4-6 membered heterocycloalkyl optionally substituted with 1-3 $J^3$;

$J^2$ is H, $C_1$-$C_5$alkyl, or $C_1$-$C_5$haloalkyl; each $J^3$ is independently halogen, $C_1$-$C_5$alkyl, $C_1$-$C_5$haloalkyl, OH, $C_1$-$C_5$alkoxy optionally substituted with 1-3 halogens, CN, 4-6 membered heterocycloalkyl, —S(O)$_2$—$C_1$-$C_5$alkyl, —NH$_2$, —N(H)—$C_1$-$C_5$alkyl, or —N($C_1$-$C_5$alkyl)$_2$ provided that when $J^3$ is attached to nitrogen, $J^3$ cannot be halogen, OH, CN, NH$_2$, —N(H)—$C_1$-$C_5$alkyl, or —N($C_1$-$C_5$alkyl)$_2$;

each Y is independently H, D, F, Cl, $C_1$-$C_2$alkyl or $C_1$-$C_2$haloalkyl, or 2 Y groups join together with the carbon atom to which they are attached to form a $C_3$-$C_4$cycloalkyl optionally substituted with 1-3 halogens;

each $Z^1$ is independently CN, halogen, $C_1$-$C_6$alkyl, or $C_1$-$C_6$haloalkyl;

each $Z^2$ is independently —OH, CN, halogen, $C_1$-$C_6$alkyl, alkoxy, $C_3$-$C_6$ cycloalkyl optionally substituted with 1-3 halogens, cyclopropyl, hydroxyalkyl, or $C_1$-$C_6$haloalkyl, provided that when $Z^2$ is attached to nitrogen, $Z^2$ cannot be —OH, CN, F, Cl, or alkoxy;

each $Z^3$ is independently CN, F, Cl, $C_1$-$C_6$alkyl or $C_1$-$C_6$haloalkyl;

$Z^4$ is —$SO_2$—$C_1$-$C_6$alkyl, —$SO_2$—$C_3$-$C_6$cycloalkyl optionally substituted with 1-3 halogens, —$SO_2$—$C_1$-$C_6$haloalkyl, —N(H)$SO_2$—$C_1$-$C_6$alkyl, —N(H)$SO_2$—$C_3$-$C_6$cycloalkyl optionally substituted with 1-3 halogens, or —N(H)$SO_2$—$C_1$-$C_6$haloalkyl;

$Z^5$ is —$C_1$-$C_2$alkylene-$C_1$-$C_2$alkoxy, —$C_0$-$C_2$alkylene phenyl optionally substituted with 1-3 $J^3$, —$SO_2$—$C_1$-$C_6$alkyl, —$SO_2$—$C_1$-$C_6$haloalkyl, —$SO_2$—($C_3$-$C_6$cycloalkyl) optionally substituted with 1-3 $J^3$, —$SO_2$-4-6 membered heterocycloalkyl optionally substituted with 1-3 $J^3$, —$SO_2$-5-6 membered heteroaryl optionally substituted with 1-3 $J^3$, —C(O)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_3$alkylene-CH(phenyl)$_2$ optionally substituted with 1-3 $J^3$, —$C_0$-$C_3$alkylene-CH($C_3$-$C_6$cycloalkyl)$_2$ optionally substituted with 1-3 $J^3$, —C(O)NR$^{10}$R$^{11}$, —C(O)$J^1$, —CO$_2J^2$, —$SO_2$NR$^{10}$R$^{11}$, —$SO_2$-phenyl optionally substituted with 1-3 $J^3$, —N(H)$SO_2$—$C_1$-$C_6$alkyl, —N(H)$SO_2$—$C_3$-$C_6$cycloalkyl optionally substituted with 1-3 $J^3$, —N(H)$SO_2$—$C_1$-$C_6$haloalkyl, or —C(NH$_2$)=N-T; provided that when $Z^5$ is attached to nitrogen, $Z^5$ cannot be —N(H)$SO_2$—$C_1$-$C_6$alkyl, —N(H)$SO_2$—$C_3$-$C_6$cycloalkyl optionally substituted with 1-3 $J^3$, or —N(H)$SO_2$—$C_1$-$C_6$haloalkyl;

T is $C_1$-$C_3$alkyl, $C_1$-$C_3$haloalkyl, $C_1$-$C_3$hydroxyalkyl, $C_1$-$C_3$alkoxy or CN; and each $Z^6$ is independently halo, $C_1$-$C_2$alkyl, $C_1$-$C_2$haloalkyl, CN, OH, $C_3$-$C_6$cycloalkyl, phenyl or 5-6 membered heteroaryl, provided that only one $Z^6$ can be OH.

Sub-Embodiments of Embodiment 3

Embodiment 3(a) of this disclosure relates to Embodiment 3, wherein $R^7$ is group (a):

(a) $C_5$-$C_6$cycloalkenyl optionally substituted with 1-5 $Z^1$, and optionally substituted with 1 $Z^4$.

Embodiment 3(b) of this disclosure relates to Embodiment 3, wherein $R^7$ is group (b):

(b) 5 or 6-membered nitrogen-containing heterocycloalkyl optionally substituted with 1-7 $Z^2$, and optionally substituted with 1 $Z^5$.

Embodiment 3(c) of this disclosure relates to Embodiment 3, wherein $R^7$ is group (c):

(c) a 5-9 membered nitrogen-containing bridged heterocyclic ring optionally substituted with 1-3 $Z^2$, and optionally substituted with 1 $Z^5$.

Embodiment 3(e) of this disclosure relates to Embodiment 3, wherein $R^7$ is group (e):

(e)

Embodiment 3(e)(a) of this disclosure relates to Embodiment 3(e), wherein $R^8$ and $R^9$ join together with the carbon atom to which they are attached to form group (a):

(a) a $C_3$-$C_6$cycloalkyl optionally substituted with 1-7 $Z^2$, and optionally substituted with 1 $Z^5$ or 1-2 $Z^6$.

Embodiment 3(e)(a) of this disclosure relates to Embodiment 3(e), wherein $R^8$ and $R^9$ join together with the carbon atom to which they are attached to form group (b):

(b) a 4-6 membered heterocycloalkyl optionally substituted with 1-7 $Z^2$, and optionally substituted with 1 $Z^5$.

Embodiment 3(e)(c) of this disclosure relates to Embodiment 3(e), wherein $R^8$ and $R^9$ join together with the carbon atom to which they are attached to form group (c):

(c) a spiro ring system containing two $C_4$-$C_6$cycloalkyl groups joined by one common spiro carbon atom, wherein the spiro ring system is optionally substituted with 1-7 $Z^2$, and optionally substituted with 1 $Z^5$ or 1-2 $Z^6$.

Embodiment 3(e)(d1) of this disclosure relates to Embodiment 3(e), wherein $R^8$ and $R^9$ join together with the carbon atom to which they are attached to form group (d1):

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-7 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_1$-$C_6$haloalkyl, —C(O)NR$^{10}$R$^{11}$, —$SO_2$NR$^{10}$R$^{11}$, or —$SO_2$—$C_3$-$C_6$cycloalkyl substituted with 1-4 halogens.

Embodiment 3(e)(d2) of this disclosure relates to Embodiment 3(e), wherein $R^8$ and $R^9$ join together with the carbon atom to which they are attached to form group (d2):

(d2) a spiro ring system containing one cycloalkyl and one heterocycloalkyl containing —O—, —S—, —S(O)—, or —S(O)$_2$—, wherein the spiro ring system is joined by one common spiro carbon atom, and wherein the spiro ring system is optionally substituted on its carbon atoms with 1-7 $Z^3$.

Embodiment 3(e)(e) of this disclosure relates to Embodiment 3(e), wherein $R^8$ and $R^9$ join together with the carbon atom to which they are attached to form group (e):

(e) a spiro ring system containing one cycloalkyl and one bridged ring joined by one common spiro carbon atom, wherein the spiro ring system is optionally substituted with 1-3 $Z^2$ Embodiment 3(e)(2) of this disclosure relates to Embodiment 3(e), wherein $R^8$ is H; and $R^9$ is —(CY$_2$)$_{0-2}$—R$^{12}$.

Embodiment 3(e)(2)(a) of this disclosure relates to Embodiment 3(e)(2), wherein $R^{12}$ is group (a):

(a) a saturated C$_3$-C$_6$cycloalkyl optionally substituted with 1-7 $Z^2$, and optionally substituted with 1 $Z^5$ or 1-2 $Z^6$.

Embodiment 3(e)(2)(b) of this disclosure relates to Embodiment 3(e)(2), wherein $R^{12}$ is group (b):

(b) a C$_5$-C$_6$cycloalkenyl optionally substituted with 1-5 $Z^2$, and optionally substituted with 1 $Z^5$.

Embodiment 3(e)(2)(c) of this disclosure relates to Embodiment 3(e)(2), wherein $R^{12}$ is group (c):

(c) a 4-6 membered heterocycloalkyl optionally substituted with 1-7 $Z^2$, and optionally substituted with 1 $Z^5$.

Embodiment 3(e)(2)(d) of this disclosure relates to Embodiment 3(e)(2), wherein $R^{12}$ is group (d):

(d) phenyl optionally substituted with 1-2 substituents independently selected from the group consisting of CN, halogen, C$_1$-C$_4$alkyl, and C$_1$-C$_4$haloalkyl.

Embodiment 3(e)(2)(e) of this disclosure relates to Embodiment 3(e)(2), wherein $R^{12}$ is group (e):

(e) a 5-10 membered bridged carbocyclic or heterocyclic ring, wherein the 5-10 membered bridged carbocyclic or heterocyclic ring are each optionally substituted with 1-3 $Z^2$, and wherein the bridged heterocyclic ring is optionally N-substituted with C$_1$-C$_6$alkyl, C$_1$-C$_6$haloalkyl, —SO$_2$—C$_1$-C$_6$alkyl, —SO$_2$—C$_1$-C$_6$haloalkyl, —C(O)NR$^{10}$R$^{11}$, —SO$_2$NR$^{10}$R$^{11}$, or —SO$_2$—C$_3$-C$_6$cycloalkyl substituted with 1-4 halogens.

Embodiment 3(f) of this disclosure relates to Embodiment 1, wherein when $R^{12}$ is (c) a 4-6 membered heterocycloalkyl optionally substituted with 1-7 $Z^2$ and optionally substituted with 1 $Z^5$, then $R^9$ is —(CY$_2$)$_{1-3}$—R$^{12}$.

Embodiment 4 of this disclosure relates to a compound according to any one of Embodiments 1-3 having one of Formula (IIa), (IIb), (IIc), (IId), (IIj), or (IIi):

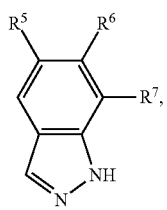
(IIa)

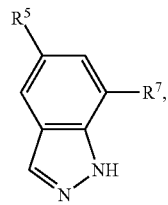
(IIb)

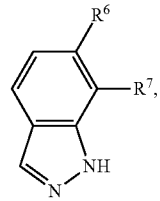
(IIc)

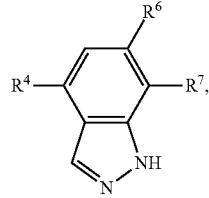
(IId)

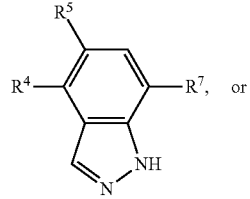
(IIj)

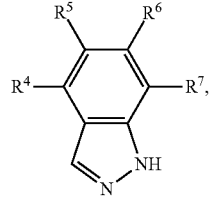
(IIi)

or a pharmaceutically acceptable salt, a solvate, a tautomer, an isomer or a deuterated analog thereof, wherein:

$R^4$, $R^5$ and $R^6$ are each independently F, Cl, C$_1$-C$_3$alkyl, C$_1$-C$_3$haloalkyl, —OCH$_3$ optionally substituted with 1-3 F, or cyclopropyl;

or $R^4$ and $R^5$, when they both exist, join together with the carbon atoms to which they are attached to form a 4-6 membered carbocyclic ring optionally substituted with 1-4 substituents selected from the group consisting of F, Cl, C$_1$-C$_3$alkyl and C$_1$-C$_3$haloalkyl;

or $R^4$ and $R^5$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, C$_1$-C$_3$alkyl and C$_1$-C$_3$haloalkyl;

or $R^5$ and $R^6$, when they both exist, join together with the carbon atoms to which they are attached to form a 4-6 membered carbocyclic ring optionally substituted with 1-4 substituents selected from the group consisting of F, Cl, C$_1$-C$_3$alkyl and C$_1$-C$_3$haloalkyl;

or $R^5$ and $R^6$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, $C_1$-$C_3$alkyl and $C_1$-$C_3$haloalkyl.

Sub-Embodiments of Embodiment 4

Embodiment 4(b) of this disclosure relates to a compound according to Embodiment 4 having Formula (IIa), or a pharmaceutically acceptable salt, a solvate, a tautomer, an isomer or a deuterated analog thereof, wherein: $R^5$ and $R^6$ are each independently F, Cl, $C_1$-$C_3$alkyl, $C_1$-$C_3$haloalkyl, or —$OCH_3$ optionally substituted with 1-3 F.

Embodiment 4(c) of this disclosure relates to a compound according to Embodiment 4 having Formula (IIb), or a pharmaceutically acceptable salt, a solvate, a tautomer, an isomer or a deuterated analog thereof, wherein: $R^5$ is F, Cl, $C_1$-$C_3$alkyl, $C_1$-$C_3$haloalkyl, or —$OCH_3$ optionally substituted with 1-3 F.

Embodiment 4(d) of this disclosure relates to a compound according to Embodiment 4 having Formula (IIc), or a pharmaceutically acceptable salt, a solvate, a tautomer, an isomer or a deuterated analog thereof, wherein: $R^6$ is F, Cl, $C_1$-$C_3$alkyl, $C_1$-$C_3$haloalkyl, or —$OCH_3$ optionally substituted with 1-3 F.

Embodiment 4(e) of this disclosure relates to a compound according to Embodiment 4 having Formula (IId), or a pharmaceutically acceptable salt, a solvate, a tautomer, an isomer or a deuterated analog thereof, wherein: $R^4$ and $R^6$ are each independently F, Cl, $C_1$-$C_3$alkyl, $C_1$-$C_3$haloalkyl, or —$OCH_3$ optionally substituted with 1-3 F.

Embodiment 4(f) of this disclosure relates to a compound according to Embodiment 4 having Formula (IIj), or a pharmaceutically acceptable salt, a solvate, a tautomer, an isomer or a deuterated analog thereof, wherein: $R^4$ and $R^5$ are each independently F, Cl, $C_1$-$C_3$alkyl, $C_1$-$C_3$haloalkyl, or —$OCH_3$ optionally substituted with 1-3 F.

Embodiment 4(g) of this disclosure relates to a compound according to Embodiment 4 having Formula (IIi), or a pharmaceutically acceptable salt, a solvate, a tautomer, an isomer or a deuterated analog thereof, wherein: $R^4$, $R^5$, and $R^5$ are each independently F, Cl, $C_1$-$C_3$alkyl, $C_1$-$C_3$haloalkyl, or —$OCH_3$ optionally substituted with 1-3 F.

Embodiment 5 of this disclosure relates to a compound according to Embodiment 4, wherein:

$R^4$, $R^5$ and $R^6$ are each independently F, Cl, methyl optionally substituted with 1-3 F, —$OCH_3$ optionally substituted with 1-3 F, or cyclopropyl;

or $R^4$ and $R^5$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^4$ and $R^5$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$;

$R^7$ is one of the following groups (a), (b), (c), or (e):

(a) cyclohexenyl optionally substituted with 1-4 $Z^1$, and optionally substituted with 1 $Z^4$;

(b) a six-membered nitrogen-containing heterocycloalkyl optionally substituted with 1-6 $Z^2$, and optionally substituted with 1 $Z^5$;

(c) an 8-9 membered nitrogen containing bridged heterocyclic ring optionally substituted with 1-2 $Z^2$, and optionally substituted with 1 $Z^5$; or

(e)

$R^8$ is H;
$R^9$ is —$(CY_2)_{0-2}$—$R^{12}$;
or $R^8$ and $R^9$ join together with the carbon atom to which they are attached to form one of the following groups (a)-(e):

(a) a $C_3$-$C_6$cycloalkyl optionally substituted with 1-7 $Z^2$, and optionally substituted with 1 $Z^5$ or 1-2 $Z^6$;

(b) a 4-6 membered nitrogen-containing heterocycloalkyl optionally substituted with 1-6 $Z^2$, and optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-6 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl; or (d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-6 $Z^3$; or (e) a spiro ring system containing one $C_4$-$C_6$cycloalkyl and one 7-10 membered bridged ring joined by one common spiro carbon atom, wherein the spiro ring system is optionally substituted with 1-2 $Z^2$;

$R^{10}$ is H, $C_1$-$C_2$alkyl, or $C_1$-$C_2$haloalkyl;
$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—N($C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_4$alkylene phenyl optionally substituted with 1-3 $J^3$, —$C_1$-$C_3$ alkylene-$SO_2$-phenyl optionally substituted with 1-3 $J^3$, —$C_1$-$C_3$ alkylene-$SO_2$—$C_1$-$C_{36}$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-3 $J^3$, —$C_0$-$C_4$ alkylene-$C_3$-$C_6$heterocycloalkyl optionally substituted with 1-3 $J^3$, —$C_0$-

$C_4$ alkylene-5-6 membered heteroaryl optionally substituted with 1-3 $J^3$, or —C(O)-phenyl optionally substituted with 1-3 $J^3$;

$R^{12}$ is one of the following groups (a)-(e):

(a) a saturated $C_3$-$C_8$cycloalkyl optionally substituted with 1-6 $Z^2$, and optionally substituted with 1 $Z^5$ or 1-2 $Z^6$;

(b) $C_5$-$C_6$cycloalkenyl optionally substituted with 1-6 $Z^2$, and optionally substituted with 1 $Z^5$;

(c) a 4-6 membered nitrogen-containing heterocycloalkyl optionally substituted with 1-6 $Z^2$, and optionally substituted with 1 $Z^5$;

(d) phenyl optionally substituted with 1-2 $Z^2$; or (e) a 6-9 membered bridged carbocyclic or nitrogen-containing heterocyclic ring, wherein the bridged carbocyclic or nitrogen-containing heterocyclic ring are each optionally substituted with 1-2 $Z^2$, and wherein 6-9 membered bridged nitrogen-containing heterocyclic ring is optionally N-substituted with $C_1$-$C_4$alkyl, $C_1$-$C_4$haloalkyl, —$SO_2$—$C_1$-$C_4$alkyl, —$SO_2$—$C_1$-$C_4$haloalkyl, —C(O)NR$^{10}$R$^{11}$, —$SO_2$NR$^{10}$R$^{11}$, or —$SO_2$—$C_3$-$C_6$cycloalkyl optionally substituted with 1-3 halogens;

$J^1$ is $C_1$-$C_4$alkyl optionally substituted with 1-4 $J^3$, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, —$C_0$-$C_3$ alkylene-5-6 membered heteroaryl optionally substituted with 1-3 $J^3$, —$C_0$-$C_3$ alkylene-4-6 membered heterocycloalkyl optionally substituted with 1-3 $J^3$;

$J^2$ is H, $C_1$-$C_4$alkyl, or $C_1$-$C_4$haloalkyl;

each $J^3$ is independently halogen, $C_1$-$C_4$alkyl, $C_1$-$C_4$haloalkyl, OH, $C_1$-$C_4$alkoxy optionally substituted with 1-3 halogens, CN, 4-6 membered heterocycloalkyl, —S(O)$_2$—$C_1$-$C_4$alkyl, —NH$_2$, —N(H)—$C_1$-$C_4$alkyl, —N($C_1$-$C_4$alkyl)$_2$ provided that when $J^3$ is attached to nitrogen, $J^3$ cannot be halogen, OH, CN, NH$_2$, —N(H)—$C_1$-$C_4$alkyl, or —N($C_1$-$C_4$alkyl)$_2$;

each Y is independently H, D, F, $CH_3$, —$CFH_2$, —$CF_2H$ or —$CF_3$, or 2 Y groups join together with the carbon atom to which they are attached to form a $C_3$-$C_4$cycloalkyl optionally substituted with 1-3 F;

each $Z^1$ is independently CN, F, Cl, $C_1$-$C_4$alkyl, of $C_1$-$C_4$haloalkyl;

each $Z^2$ is independently —OH, CN, F, Cl, $C_1$-$C_4$alkyl, or $C_1$-$C_4$haloalkyl;

each $Z^3$ is independently CN, F, Cl, $C_1$-$C_4$alkyl or $C_1$-$C_4$haloalkyl;

$Z^4$ is —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

$Z^5$ is —$C_1$-$C_2$alkylene-$C_1$-$C_2$alkoxy, —$C_0$-$C_1$alkylene phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 memberedheterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 memberedheteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)NR$^{10}$R$^{11}$, —$SO_2$NR$^{10}$R$^{11}$, —$SO_2$—$C_3$-$C_6$cycloalkyl optionally substituted with 1-3 halogens, —$CO_2$-alkyl, $COJ^1$, —$CO_2J^2$, —N(H)$SO_2$—$C_1$-$C_4$alkyl, —N(H)$SO_2$—$C_3$-$C_6$cycloalkyl optionally substituted with 1-3 $J^3$, —N(H)$SO_2$—$C_1$-$C_4$haloalkyl, or $C(NH_2)$=N-T, provided that when $Z^5$ is attached to nitrogen, $Z^5$ cannot be —N(H)$SO_2$—$C_1$-$C_4$alkyl, —N(H)$SO_2$—$C_3$-$C_6$cycloalkyl optionally substituted with 1-3 $J^3$, or —N(H)$SO_2$—$C_1$-$C_4$haloalkyl;

T is $C_1$-$C_2$alkyl, $C_1$-$C_2$haloalkyl, $C_1$-$C_2$hydroxyalkyl, $C_1$-$C_2$alkoxy or CN; and and each $Z^6$ is independently halo, $C_1$-$C_2$alkyl, $C_1$-$C_2$haloalkyl, CN, OH, $C_3$-$C_6$cycloalkyl, phenyl or 5-6 membered heteroaryl, provided that only one $Z^6$ can be OH.

Sub-Embodiments of Embodiment 5

Embodiment 5(a) of this disclosure relates to Embodiment 5, wherein $R^7$ is group (a):

(a) cyclohexenyl optionally substituted with 1-4 $Z^1$, and optionally substituted with 1 $Z^4$.

Embodiment 5(b) of this disclosure relates to Embodiment 5, wherein $R^7$ is group (b):

(b) a six-membered nitrogen-containing heterocycloalkyl optionally substituted with 1-6 $Z^2$, and optionally substituted with 1 $Z^5$.

Embodiment 5(c) of this disclosure relates to Embodiment 5, wherein $R^7$ is group (c):

(c) an 8-9 membered nitrogen containing bridged heterocyclic ring optionally substituted with 1-2 $Z^2$, and optionally substituted with 1 $Z^5$.

Embodiment 5(e) of this disclosure relates to Embodiment 5, wherein $R^7$ is group (e):

(e)

Embodiment 5(e)(a) of this disclosure relates to Embodiment 5(e), wherein $R^8$ and $R^9$ join together with the carbon atom to which they are attached to form group (a):

(a) a $C_3$-$C_6$cycloalkyl optionally substituted with 1-7 $Z^2$, and optionally substituted with 1 $Z^5$ or 1-2 $Z^6$.

Embodiment 5(e)(b) of this disclosure relates to Embodiment 5(e), wherein $R^8$ and $R^9$ join together with the carbon atom to which they are attached to form group (b):

(b) a 4-6 membered nitrogen-containing heterocycloalkyl optionally substituted with 1-6 $Z^2$, and optionally substituted with 1 $Z^5$.

Embodiment 5(e)(c) of this disclosure relates to Embodiment 5(e), wherein $R^8$ and $R^9$ join together with the carbon atom to which they are attached to form group (c):

(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$.

Embodiment 5(e)(d1) of this disclosure relates to Embodiment 5(e), wherein $R^8$ and $R^9$ join together with the carbon atom to which they are attached to form group (d1):

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-6 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl.

Embodiment 5(e)(d2) of this disclosure relates to Embodiment 5(e), wherein $R^8$ and $R^9$ join together with the carbon atom to which they are attached to form group (d2):

(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-6 $Z^3$.

Embodiment 5(e)(e) of this disclosure relates to Embodiment 5(e), wherein $R^8$ and $R^9$ join together with the carbon atom to which they are attached to form group (e):

(e) a spiro ring system containing one $C_4$-$C_6$cycloalkyl and one 7-10 membered bridged ring joined by one common spiro carbon atom, wherein the spiro ring system is optionally substituted with 1-2 $Z^2$.

Embodiment 5(e)(2) of this disclosure relates to Embodiment 5(e), wherein:
$R^8$ is H; and
$R^9$ is —$(CY_2)_{0-2}$—$R^{12}$.

Embodiment 5(e)(2)(a) of this disclosure relates to Embodiment 5(e)(2), wherein $R^{12}$ is group (a):
(a) a saturated $C_3$-$C_8$cycloalkyl optionally substituted with 1-6 $Z^2$, and optionally substituted with 1 $Z^5$ or 1-2 $Z^6$.

Embodiment 5(e)(2)(b) of this disclosure relates to Embodiment 5(e)(2), wherein $R^{12}$ is group (b):
(b) $C_5$-$C_6$cycloalkenyl optionally substituted with 1-6 $Z^2$, and optionally substituted with 1 $Z^5$.

Embodiment 5(e)(2)(c) of this disclosure relates to Embodiment 5(e)(2), wherein $R^{12}$ is group (c):
(c) a 4-6 membered nitrogen-containing heterocycloalkyl optionally substituted with 1-6 $Z^2$, and optionally substituted with 1 $Z^5$.

Embodiment 5(e)(2)(d) of this disclosure relates to Embodiment 5(e)(2), wherein $R^{12}$ is group (d):
(d) phenyl optionally substituted with 1-2 $Z^2$.

Embodiment 5(e)(2)(e) of this disclosure relates to Embodiment 5(e)(2), wherein $R^{12}$ is group (e):
(e) a 6-9 membered bridged carbocyclic or nitrogen-containing heterocyclic ring, wherein the bridged carbocyclic or nitrogen-containing heterocyclic ring are each optionally substituted with 1-2 $Z^2$, and wherein 6-9 membered bridged nitrogen-containing heterocyclic is optionally N-substituted with $C_1$-$C_4$alkyl, $C_1$-$C_4$haloalkyl, —$SO_2$—$C_1$-$C_4$alkyl, —$SO_2$—$C_1$-$C_4$haloalkyl, —$C(O)NR^{10}R^{11}$, —$SO_2NR^{10}R^{11}$, or —$SO_2$—$C_3$-$C_6$cycloalkyl optionally substituted with 1-3 halogens.

Embodiment 5(f) of this disclosure relates to Embodiment 1, wherein when $R^{12}$ is (c) a 4-6 membered nitrogen-containing heterocycloalkyl optionally substituted with 1-6 $Z^2$, and optionally substituted with 1 $Z^5$, then $R^9$ is —$(CY_2)_{1-3}$—$R^{12}$.

Embodiment 6 of this disclosure relates to Embodiment 4, wherein:
$R^4$ and $R^5$, when they both exist, join together with the carbon atoms to which they are attached to form a 4-6 membered carbocyclic or a 5-6 membered heterocyclic ring containing 1-2 oxygen atoms, each ring being optionally substituted on its carbon atoms with 1-4 substituents selected from the group consisting of F, Cl, —$CH_3$, —$CFH_2$, —$CF_2H$, —$CF_3$, —O—$CH_3$, —O—$CFH_2$, —$OCF_2H$ and —$OCF_3$;
$R^6$ is F, Cl, —$CH_3$, —$CFH_2$, —$CF_2H$, —$CF_3$, —O—$CH_3$, —O—$CFH_2$, —$OCF_3$, or cyclopropyl;

$R^7$ is one of the following groups (a), (b), (c), or (e):
(a) cyclohexenyl optionally substituted with 1-3 $Z^1$, and optionally substituted with 1 $Z^4$;
(b) a six-membered nitrogen-containing heterocycloalkyl optionally substituted with 1-5 $Z^2$, and optionally substituted with 1 $Z^5$;
(c) an 8 membered bridged heterocyclic ring containing 1-2 nitrogen atoms, said 8 membered bridged heterocyclic ring optionally substituted with 1 $Z^2$, and optionally substituted with 1 $Z^5$; or

(e)

$R^8$ is H;
$R^9$ is —$(CY_2)_{0-2}$—$R^{12}$;
or $R^8$ and $R^9$ join together with the carbon atom to which they are attached to form one of the following groups (a)-(e):
(a) a $C_3$-$C_6$cycloalkyl optionally substituted with 1-6 $Z^2$, and optionally substituted with 1 $Z^5$ or 1-2 $Z^6$;
(b) a 4-6 membered nitrogen-containing heterocycloalkyl optionally substituted with 1-5 $Z^2$, and optionally substituted with 1 $Z^5$;
(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$;
(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl; or
(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$; or
(e) a spiro ring system containing one $C_4$-$C_6$cycloalkyl and one 7-10 membered bridged ring joined by one common spiro carbon atom, wherein the spiro ring system is optionally substituted with 1 $Z^2$,
$R^{12}$ is one of the following groups (a)-(e):
(a) a saturated $C_3$-$C_8$cycloalkyl optionally substituted with 1-6 $Z^2$, and optionally substituted with 1 $Z^5$ or 1-2 $Z^6$;
(b) a $C_5$-$C_6$cycloalkenyl optionally substituted with 1-3 $Z^2$, and optionally substituted with 1 $Z^5$;
(c) a 4-6 membered nitrogen-containing heterocycloalkyl optionally substituted with 1-5 $Z^2$, and optionally substituted with 1 $Z^5$;
(d) phenyl optionally substituted with 1-2 $Z^2$;
(e1) a 5-10 membered bridged carbocyclic ring, wherein the bridged carbocyclic ring is optionally substituted with 1 $Z^2$; or
(e2) a 6-9 membered bridged nitrogen-containing heterocyclic ring optionally N-substituted with $C_1$-$C_3$alkyl, $C_1$-$C_3$haloalkyl, —$SO_2$—$C_1$-$C_3$alkyl, —$SO_2$—$C_1$-$C_3$haloalkyl, —$C(O)NR^{10}R^{11}$, —$SO_2NR^{10}R^{11}$, or —$SO_2$—$C_3$-$C_6$cycloalkyl optionally substituted with 1-3 halogens;

each Y is independently H, D, F, $CH_3$, $-CFH_2$, $-CF_2H$ or $-CF_3$, or 2 Y groups join together with the carbon atom to which they are attached to form a $C_3$-$C_4$cycloalkyl optionally substituted with 1-2 F; and each $Z^6$ is independently F, $C_1$-$C_2$alkyl, $C_1$-$C_2$haloalkyl, CN, OH, $C_3$-$C_6$cycloalkyl, phenyl or 6 membered heteroaryl, provided that only one $Z^6$ can be OH.

Sub-Embodiments of Embodiment 6

Embodiment 6(a) of this disclosure relates to Embodiment 6, wherein $R^7$ is group (a):
(a) cyclohexenyl optionally substituted with 1-3 $Z^1$, and optionally substituted with 1 $Z^4$.

Embodiment 6(b) of this disclosure relates to Embodiment 6, wherein $R^7$ is group (b):
(b) a six-membered nitrogen-containing heterocycloalkyl optionally substituted with 1-5 $Z^2$, and optionally substituted with 1 $Z^5$.

Embodiment 6(c) of this disclosure relates to Embodiment 6, wherein $R^7$ is group (c):
(c) an 8 membered bridged heterocyclic ring containing 1-2 nitrogen atoms, said 8 membered bridged heterocyclic ring optionally substituted with 1 $Z^2$, and furter optionally substituted with 1 $Z^5$.

Embodiment 6(e) of this disclosure relates to Embodiment 6, wherein $R^7$ is group (e):

(e)

Embodiment 6(e)(1)(a) of this disclosure relates to Embodiment 6(e), wherein $R^8$ and $R^9$ join together with the carbon atom to which they are attached to form group (a):
(a) a $C_3$-$C_6$cycloalkyl optionally substituted with 1-6 $Z^2$, and optionally substituted with 1 $Z^5$ or 1-2 $Z^6$;

Embodiment 6(e)(1)(b) of this disclosure relates to Embodiment 6(e), wherein $R^8$ and $R^9$ join together with the carbon atom to which they are attached to form group (b):
(b) a 4-6 membered nitrogen-containing heterocycloalkyl optionally substituted with 1-5 $Z^2$, and optionally substituted with 1 $Z^5$.

Embodiment 6(e)(1)(c) of this disclosure relates to Embodiment 6(e), wherein $R^8$ and $R^9$ join together with the carbon atom to which they are attached to form group (c):
(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$;

Embodiment 6(e)(1)(d1) of this disclosure relates to Embodiment 6(e), wherein $R^8$ and $R^9$ join together with the carbon atom to which they are attached to form group (d1):
(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system is optionally N-substituted with $C_1$-$C_6$alkyl, $C_1$-$C_6$haloalkyl, $-SO_2$—$C_1$-$C_6$alkyl, $-SO_2$—$C_3$-$C_6$cycloalkyl optionally substituted with 1-3 halogens, or $-SO_2$—$C_1$-$C_6$haloalkyl.

Embodiment 6(e)(1)(d2) of this disclosure relates to Embodiment 6(e), wherein $R^8$ and $R^9$ join together with the carbon atom to which they are attached to form group (d2):
(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$.

Embodiment 6(e)(1)(e) of this disclosure relates to Embodiment 6(e), wherein $R^8$ and $R^9$ join together with the carbon atom to which they are attached to form group (e):
(e) a spiro ring system containing one $C_4$-$C_6$cycloalkyl and one 7-10 membered bridged ring joined by one common spiro carbon atom, wherein the spiro ring system is optionally substituted with 1 $Z^2$.

Embodiment 6(e)(2) of this disclosure relates to Embodiment 6(e), wherein $R^8$ is H; and $R^9$ is $-(CY_2)_{0-2}$—$R^{12}$.

Embodiment 6(e)(2)(a) of this disclosure relates to Embodiment 6(e)(2), wherein $R^{12}$ is group (a):
(a) a saturated $C_3$-$C_8$cycloalkyl optionally substituted with 1-6 $Z^2$, and optionally substituted with 1 $Z^5$ or 1-2 $Z^6$.

Embodiment 6(e)(2)(a) of this disclosure relates to Embodiment 6(e)(2), wherein $R^{12}$ is group (b):
(b) a $C_5$-$C_6$cycloalkenyl optionally substituted with 1-3 $Z^2$, and optionally substituted with 1 $Z^5$.

Embodiment 6(e)(2)(c) of this disclosure relates to Embodiment 6(e)(2), wherein $R^{12}$ is group (c):
(c) a 4-6 membered nitrogen-containing heterocycloalkyl optionally substituted with 1-5 $Z^2$, and optionally substituted with 1 $Z^5$.

Embodiment 6(e)(2)(d) of this disclosure relates to Embodiment 6(e)(2), wherein $R^{12}$ is group (d):
(d) phenyl optionally substituted with 1-2 $Z^2$;

Embodiment 6(e)(2)(e1) of this disclosure relates to Embodiment 6(e)(2), wherein $R^{12}$ is group (e1):
(e1) a 5-10 membered bridged carbocyclic ring, wherein the bridged carbocyclic ring is optionally substituted with 1 $Z^2$.

Embodiment 6(e)(2)(e2) of this disclosure relates to Embodiment 6(e)(2), wherein $R^{12}$ is group (e2):
(e2) a 6-9 membered bridged nitrogen-containing heterocyclic ring optionally N-substituted with $C_1$-$C_3$alkyl, $C_1$-$C_3$haloalkyl, $-SO_2$—$C_1$-$C_3$alkyl, $-SO_2$—$C_1$-$C_3$haloalkyl, $-C(O)NR^{10}R^{11}$, $-SO_2R^{10}R^{11}$, or $-SO_2$—$C_3$-$C_6$cycloalkyl optionally substituted with 1-3 halogens.

Embodiment 6(f) of this disclosure relates to Embodiment 1, wherein when $R^{12}$ is (c) a 4-6 membered nitrogen-containing heterocycloalkyl optionally substituted with 1-5 $Z^2$, and optionally substituted with 1 $Z^5$; then $R^9$ is $-(CY_2)_{1-3}$—$R^{12}$.

Embodiment 7 of this disclosure relates to Embodiment 4, wherein:
$R^5$ and $R^6$, when they both exist, join together with the carbon atoms to which they are attached to form a 4-6 membered carbocyclic or a 5-6 membered heterocyclic ring containing 1-2 oxygen atoms, each ring being optionally substituted on its carbon atoms with 1-4 substituents selected from the group consisting of F, Cl, $-CH_3$, $-CFH_2$, $-CF_2H$, $-CF_3$, $-OCH_3$, $-OCFH_2$, and $-OCF_3$;
$R^6$ is F, Cl, $-CH_3$, $-CFH_2$, $-CF_2H$, $-CF_3$, $-OCH_3$, $-OCFH_2$, $-OCF_3$, or cyclopropyl;
$R^7$ is one of the following groups (a), (b), (c), or (e):
(a) cyclohexenyl optionally substituted with 1-3 $Z^1$, and optionally substituted with 1 $Z^4$;

(b) a six-membered nitrogen-containing heterocycloalkyl optionally substituted with 1-4 $Z^2$, and optionally substituted with 1 $Z^5$;

(c) an 8 membered bridged heterocyclic ring containing 1-2 nitrogen atoms, said 8 membered bridged heterocyclic ring optionally N-substituted with 1 $Z^5$; or

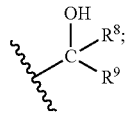

(e)

$R^8$ is H;
$R^9$ is —$(CY_2)_{0-2}$—$R^{12}$;
or $R^8$ and $R^9$ join together with the carbon atom to which they are attached to form one of the following groups (a)-(e):

(a) a $C_3$-$C_6$cycloalkyl optionally substituted with 1-6 $Z^2$, and optionally substituted with 1 $Z^5$ or 1-2 $Z^6$;

(b) a 4-6 membered nitrogen-containing heterocycloalkyl optionally substituted with 1-5 $Z^2$, and optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system can also be optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl; or (d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$; or (e) a spiro ring system containing one $C_4$-$C_6$cycloalkyl and one 7-10 membered bridged ring joined by one common spiro carbon atom, wherein the spiro ring system is optionally substituted with 1 $Z^2$;

$R^{12}$ is one of the following groups (a)-(e):

(a1) a saturated $C_3$-$C_6$cycloalkyl optionally substituted with 1-5 $Z^2$, and optionally substituted with 1 $Z^5$ or 1-2 $Z^6$;

(a2) cubane;

(b) a $C_5$-$C_6$cycloalkenyl optionally substituted with 1-3 $Z^2$, and optionally substituted with 1 $Z^5$;

(c) a 4-6 membered nitrogen-containing heterocycloalkyl optionally substituted with 1-5 $Z^2$, and optionally substituted with 1 $Z^5$;

(d) phenyl optionally substituted with 1-2 $Z^2$; or (e) a 5-10 membered bridged carbocyclic ring, wherein the bridged carbocyclic ring is optionally substituted with 1 $Z^2$;

each Y is independently H, F, $CH_3$, —$CFH_2$, —$CF_2H$ or —$CF_3$, or 2 Y groups join together with the carbon atom to which they are attached to form a cyclopropyl or cyclobutyl group;

each $Z^1$ is independently CN, F, Cl, $C_1$-$C_4$alkyl, or $C_1$-$C_4$haloalkyl;

each $Z^2$ is independently OH, CN, F, Cl, $C_1$-$C_4$alkyl, or $C_1$-$C_4$haloalkyl;

each $Z^3$ is independently CN, F, Cl, $C_1$-$C_4$alkyl or $C_1$-$C_4$haloalkyl;

$Z^4$ is —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

$Z^5$ is —$SO_2$—$C_1$-$C_4$alkyl, $SO_2$—$C_1$-$C_4$haloalkyl, —$SO_2$—$C_3$-$C_6$cycloalkyl optionally substituted with 1-3 $J^3$, —C(O)$NR^{10}R^{11}$, —$CO_2$-alkyl, $COJ^1$, $CO_2J^2$, —N(H)$SO_2$—$C_1$-$C_4$alkyl, —N(H)$SO_2$—$C_3$-$C_6$cycloalkyl optionally substituted with 1-3 $J^3$, or —N(H)$SO_2$—$C_1$-$C_4$haloalkyl, provided that when $Z^5$ is attached to nitrogen, $Z^5$ cannot be —N(H)$SO_2$—$C_1$-$C_4$alkyl, —N(H)$SO_2$—$C_3$-$C_6$cycloalkyl optionally substituted with 1-3 $J^3$, or —N(H)$SO_2$—$C_1$-$C_4$haloalkyl; and each $Z^6$ is independently F, $CH_3$ optionally substituted with 1-3 F, CN, OH, $C_3$-$C_4$cycloalkyl, phenyl or 6 membered heteroaryl, provided that only one $Z^6$ can be OH.

Sub-Embodiments of Embodiment 7

Embodiment 7(a) of this disclosure relates to Embodiment 7, wherein $R^7$ is group (a):

(a) cyclohexenyl optionally substituted with 1-3 $Z^1$, and optionally substituted with 1 $Z^4$.

Embodiment 7(b) of this disclosure relates to Embodiment 7, wherein $R^7$ is group (b):

(b) a six-membered nitrogen-containing heterocycloalkyl optionally substituted with 1-4 $Z^2$, and optionally substituted with 1 $Z^5$.

Embodiment 7(c) of this disclosure relates to Embodiment 7, wherein $R^7$ is group (c):

(c) an 8 membered bridged heterocyclic ring containing 1-2 nitrogen atoms, said 8 membered bridged heterocyclic ring optionally N-substituted with 1 $Z^5$ Embodiment 7(e) of this disclosure relates to Embodiment 7, wherein $R^7$ is group (e):

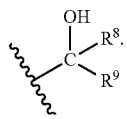

(e)

Embodiment 7(e)(a) of this disclosure relates to Embodiment 7(e), wherein or $R^8$ and $R^9$ join together with the carbon atom to which they are attached to form group (a):

(a) a $C_3$-$C_6$cycloalkyl optionally substituted with 1-6 $Z^2$, and optionally substituted with 1 $Z^5$ or 1-2 $Z^6$.

Embodiment 7(e)(b) of this disclosure relates to Embodiment 7(e), wherein or $R^8$ and $R^9$ join together with the carbon atom to which they are attached to form group (b):

(b) a 4-6 membered nitrogen-containing heterocycloalkyl optionally substituted with 1-5 $Z^2$, and optionally substituted with 1 $Z^5$.

Embodiment 7(e)(c) of this disclosure relates to Embodiment 7(e), wherein or $R^8$ and $R^9$ join together with the carbon atom to which they are attached to form group (c):

(c) a spiro ring system containing two $C_4$-$C_6$cycloalkyl groups joined by one common spiro carbon atom, wherein the spiro ring system is optionally substituted with 1-6 $Z^2$, and optionally substituted with 1 $Z^5$ or 1-2 $Z^6$.

Embodiment 7(e)(d1) of this disclosure relates to Embodiment 7(e), wherein or $R^8$ and $R^9$ join together with the carbon atom to which they are attached to form group (d1):

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl.

Embodiment 7(e)(d2) of this disclosure relates to Embodiment 7(e), wherein or $R^8$ and $R^9$ join together with the carbon atom to which they are attached to form group (d2):

(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$.

Embodiment 7(e)(e) of this disclosure relates to Embodiment 7(e), wherein or $R^8$ and $R^9$ join together with the carbon atom to which they are attached to form group (e):

(e) a spiro ring system containing one $C_4$-$C_6$cycloalkyl and one 7-10 membered bridged ring joined by one common spiro carbon atom, wherein the spiro ring system is optionally substituted with 1 $Z^2$.

Embodiment 7(e)(2) of this disclosure relates to Embodiment 7(e), wherein $R^8$ is H; and $R^9$ is —$(CY_2)_{0-2}$—$R^{12}$.

Embodiment 7(e)(2)(a1) of this disclosure relates to Embodiment 7(e)(2), wherein $R^{12}$ is group (a1):

(a1) a saturated $C_3$-$C_6$cycloalkyl optionally substituted with 1-5 $Z^2$, and optionally substituted with 1 $Z^5$ or 1-2 $Z^6$.

Embodiment 7(e)(2)(a2) of this disclosure relates to Embodiment 7(e)(2), wherein $R^{12}$ is group (a2):

(a2) cubane.

Embodiment 7(e)(2)(b) of this disclosure relates to Embodiment 7(e)(2), wherein $R^{12}$ is group (b):

(b) a $C_5$-$C_6$cycloalkenyl optionally substituted with 1-3 $Z^2$, and optionally substituted with 1 $Z^5$.

Embodiment 7(e)(2)(c) of this disclosure relates to Embodiment 7(e)(2), wherein $R^{12}$ is group (c):

(c) a 4-6 membered nitrogen-containing heterocycloalkyl optionally substituted with 1-5 $Z^2$, and optionally substituted with 1 $Z^5$.

Embodiment 7(e)(2)(d) of this disclosure relates to Embodiment 7(e)(2), wherein $R^{12}$ is group (d):

(d) phenyl optionally substituted with 1-2 $Z^2$.

Embodiment 7(e)(2)(e) of this disclosure relates to Embodiment 7(e)(2), wherein $R^{12}$ is group (e):

(e) a 5-10 membered bridged carbocyclic ring, wherein the bridged carbocyclic ring is optionally substituted with 1 $Z^2$.

Embodiment 7(f) of this disclosure relates to Embodiment 1, wherein when $R^{12}$ is (c) a 4-6 membered nitrogen-containing heterocycloalkyl optionally substituted with 1-5 $Z^2$ and optionally substituted with 1 $Z^5$, then $R^9$ is —$(CY_2)_{1-3}$—$R^{12}$.

Embodiment 8 of this disclosure relates to Embodiments 1-4 having any one of the following Formulae:

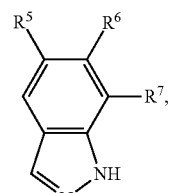

(IIIa)

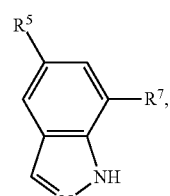

(IIIb)

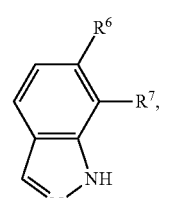

(IIIc)

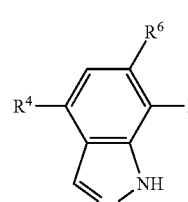

(IIId)

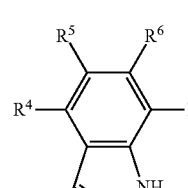

(IIIe)

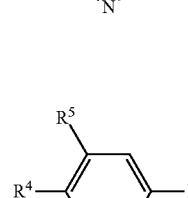

(IIIf)

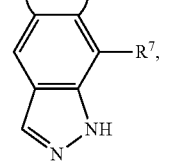

(IIIo)

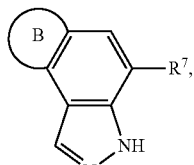
(IIIq)

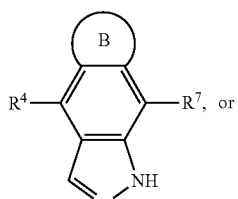
(IIIs)

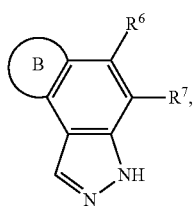
(IIIu)

or a pharmaceutically acceptable salt, a solvate, a tautomer, an isomer or a deuterated analog thereof, wherein:

$R^4$, $R^5$ and $R^6$ are each independently F, Cl, —CH$_3$, —CFH$_2$, —CF$_2$H, —CF$_3$, —OCH$_3$, —OCFH$_2$, —OCF$_2$H or —OCF$_3$;

ring B is a 4-6 membered carbocyclic or a 5 membered heterocyclic ring containing 1-2 oxygen atoms, wherein each ring is optionally substituted on its carbon atoms with 1-4 substituents selected from the group consisting of F, Cl, —CH$_3$, —CFH$_2$, —CF$_2$H, —CF$_3$, —OCH$_3$, —OCFH$_2$, —OCF$_2$H and —OCF$_3$.

Sub-Embodiments of Embodiment 8

Embodiment 8(a) of this disclosure relates to Embodiment 8 having Formula (IIIa).

Embodiment 8(a)(1) of this disclosure relates to Embodiment 8(a) wherein $R^5$ is Cl and $R^6$ is Cl.

Embodiment 8(a)(3) of this disclosure relates to Embodiment 8(a) wherein $R^5$ is F and $R^6$ is Cl.

Embodiment 8(a)(4) of this disclosure relates to Embodiment 8(a) wherein $R^5$ is F and $R^6$ is F.

Embodiment 8(a)(5) of this disclosure relates to Embodiment 8(a) wherein $R^5$ is Cl and $R^6$ is CH3.

Embodiment 8(b) of this disclosure relates to Embodiment 8 having Formula (IIIb).

Embodiment 8(b)(1) of this disclosure relates to Embodiment 8(b) wherein $R^5$ is Cl.

Embodiment 8(b)(2) of this disclosure relates to Embodiment 8(b) wherein $R^5$ is F.

Embodiment 8(b)(3) of this disclosure relates to Embodiment 8(b) wherein $R^5$ is CH$_3$.

Embodiment 8(c) of this disclosure relates to Embodiment 8 having Formula (IIIc).

Embodiment 8(d) of this disclosure relates to Embodiment 8 having Formula (IIId).

Embodiment 8(e) of this disclosure relates to Embodiment 8 having Formula (IIIe).

Embodiment 8(f) of this disclosure relates to Embodiment 8 having Formula (IIIf).

Embodiment 8(g) of this disclosure relates to Embodiment 8 having Formula (IIIo).

Embodiment 8(g)(1) of this disclosure relates to Embodiment 8(g) wherein ring B is a 4 membered carbocyclic ring is optionally substituted on its carbon atoms with 1-4 substituents selected from the group consisting of F, Cl, —CH$_3$, —CFH$_2$, —CF$_2$H, and —CF$_3$.

Embodiment 8(h) of this disclosure relates to Embodiments 8 having Formula (IIIq).

Embodiment 8(h)(1) of this disclosure relates to Embodiment 8(h) wherein ring B is a 4 membered carbocyclic ring is optionally substituted on its carbon atoms with 1-4 substituents selected from the group consisting of F, Cl, —CH$_3$, —CFH$_2$, —CF$_2$H, and —CF$_3$.

Embodiment 8(i) of this disclosure relates to Embodiment 8 having Formula (IIIs).

Embodiment 8(i)(1) of this disclosure relates to Embodiment 8(i) wherein ring B is a 4 membered carbocyclic ring is optionally substituted on its carbon atoms with 1-4 substituents selected from the group consisting of F, Cl, —CH$_3$, —CFH$_2$, —CF$_2$H, and —CF$_3$.

Embodiment 8(j) of this disclosure relates to Embodiment 8 having Formula (IIIu).

Embodiment 8(j)(1) of this disclosure relates to Embodiment 8(j) wherein ring B is a 4 membered carbocyclic ring is optionally substituted on its carbon atoms with 1-4 substituents selected from the group consisting of F, Cl, —CH$_3$, —CFH$_2$, —CF$_2$H, amd —CF$_3$.

Embodiment 9 of this disclosure relates to any of Embodiments 1-8, wherein $R^4$ is H; $R^5$ is Cl; and $R^6$ is H, Cl or F.

Embodiment 10 of this disclosure relates to Embodiment 8 having one of the following Formulae:

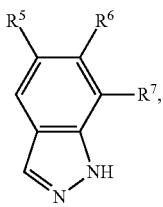
(IIIa)

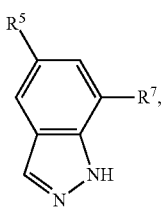
(IIIb)

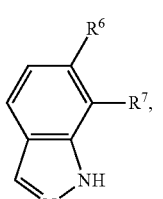
(IIIc)

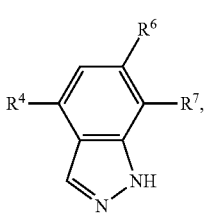
(IIId)

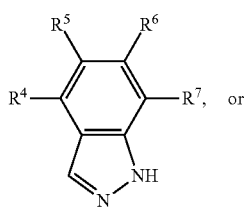 (IIIe)

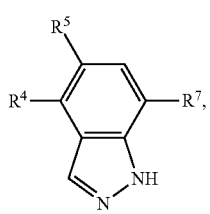 (IIIf)

or a pharmaceutically acceptable salt, a solvate, a tautomer, an isomer or a deuterated analog thereof.

Embodiment 11 of this disclosure relates to Embodiment 8 having one of the following Formulae:

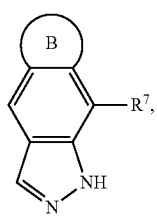 (IIIo)

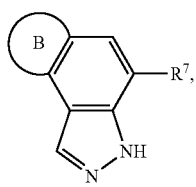 (IIIq)

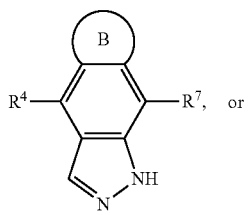 (IIIs) or

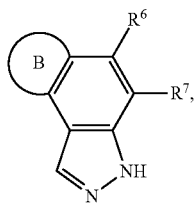 (IIIu)

or a pharmaceutically acceptable salt, a solvate, a tautomer, an isomer or a deuterated analog thereof.

Embodiment 12 of this disclosure relates to Embodiment 11 having one of the following Formulae:

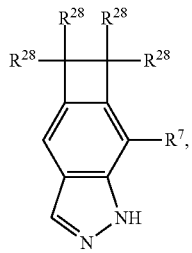 (IVa)

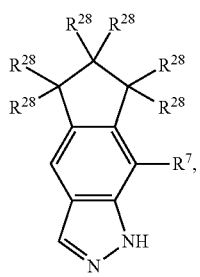 (IVb)

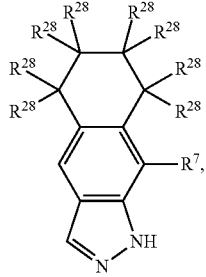 (IVc)

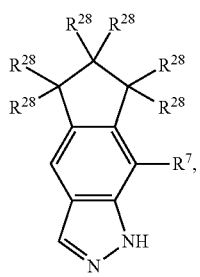 (IVg)

(IVh)

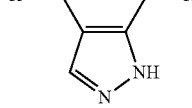 (IVi)

-continued

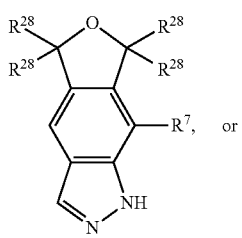
(IVm)

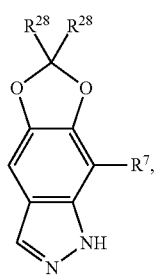
(IVn)

or a pharmaceutically acceptable salt, a solvate, a tautomer, an isomer or a deuterated analog thereof, wherein each $R^{28}$ is independently H, F, Cl, —$CH_3$, —$CFH_2$, —$CF_2H$ or —$CF_3$, provided that no more than three $R^{28}$ groups in each Formula is other than H.

Sub-Embodiments of Embodiment 12

Embodiment 12(a)(1) of this disclosure relates to Embodiment 12 having Formual (IVa), wherein each $R^{28}$ is independently H, F, Cl, or —$CH_3$.

Embodiment 12(a)(2) of this disclosure relates to Embodiment 12 having Formual (IVa), wherein each $R^{28}$ is H.

Embodiment 12(b)(1) of this disclosure relates to Embodiment 12 having Formual (IVb), wherein each $R^{28}$ is independently H, F, Cl, or —$CH_3$.

Embodiment 12(b)(2) of this disclosure relates to Embodiment 12 having Formual (IVb), wherein each $R^{28}$ is H.

Embodiment 12(c)(1) of this disclosure relates to Embodiment 12 having Formual (IVc), wherein each $R^{28}$ is independently H, F, Cl, or —$CH_3$.

Embodiment 12(c)(2) of this disclosure relates to Embodiment 12 having Formual (IVc), wherein each $R^{28}$ is H.

Embodiment 12(d) of this disclosure relates to Embodiment 12 having Formual (IVg), wherein each $R^{28}$ is independently H, F, Cl, or —$CH_3$.

Embodiment 12(e) of this disclosure relates to Embodiment 12 having Formual (IVg), wherein each $R^{28}$ is H.

Embodiment 12(f) of this disclosure relates to Embodiment 12 having Formual (IVh), wherein each $R^{28}$ is independently H, F, Cl, or —$CH_3$.

Embodiment 12(g) of this disclosure relates to Embodiment 12 having Formual (IVh), wherein each $R^{28}$ is H.

Embodiment 12(h) of this disclosure relates to Embodiment 12 having Formual (IVi), wherein each $R^{28}$ is independently H, F, Cl, or —$CH_3$.

Embodiment 12(i) of this disclosure relates to Embodiment 12 having Formual (IVi), wherein each $R^{28}$ is H.

Embodiment 12(j) of this disclosure relates to Embodiment 12 having Formual (IVm), wherein each $R^{28}$ is independently H, F, Cl, or —$CH_3$.

Embodiment 12(k) of this disclosure relates to Embodiment 12 having Formual (IVm), wherein each $R^{28}$ is H.

Embodiment 12(l) of this disclosure relates to Embodiment 12 having Formual (IVn), wherein each $R^{28}$ is independently H, F, Cl, or —$CH_3$.

Embodiment 12(m) of this disclosure relates to Embodiment 12 having Formual (IVn), wherein each $R^{28}$ is H.

Embodiment 13 of this disclosure relates to Embodiment 1 having one of the following Formulae:

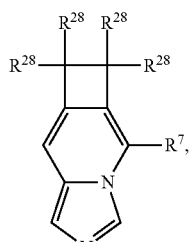
(IVd)

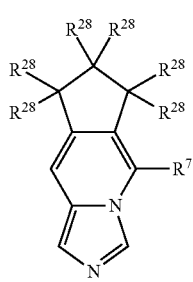
(IVe)

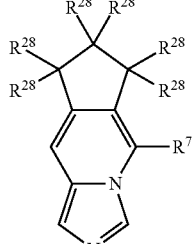
(IVf)

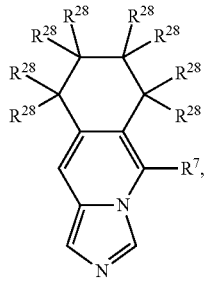
(IVj)

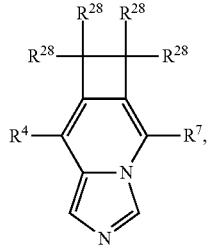
(IVk)

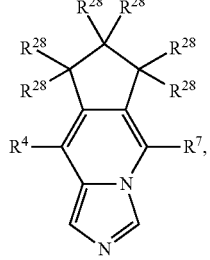

-continued

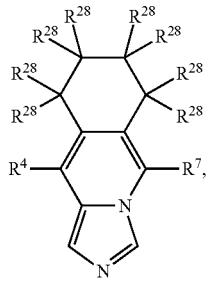
(IVI)

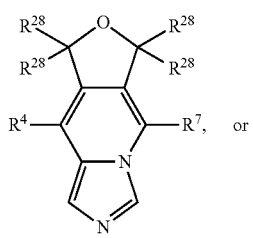
(IVo)

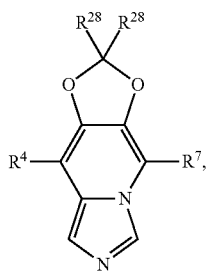
(IVp)

or a pharmaceutically acceptable salt, a solvate, a tautomer, an isomer or a deuterated analog thereof, wherein each $R^{28}$ is independently H, F, Cl, —CH$_3$, —CFH$_2$, —CF$_2$H or —CF$_3$, provided that no more than three $R^{28}$ groups in each Formula is other than H.

Embodiment 14 of this disclosure relates to any of the preceding Embodiments and sub-embodiments, wherein $Z^5$ is:

—C(O)—O—CH$_3$, —C(O)—O—CH$_2$CH$_3$, C(O)—O—C(CH$_3$)$_3$, —C(O)—O—CH$_2$CF$_3$, —C(O)—O—(CH$_2$)$_2$CH$_3$, —C(O)—O—CH(CH$_3$)$_2$, —C(O)—O—C(CH$_3$)$_3$, —C(O)—O—CH$_2$CH(CH$_3$)$_2$, —C(O)—O-cyclopropyl, —C(O)—O-cyclobutyl, —C(O)—O-cyclopentyl, —C(O)—O-cyclohexyl, —C(O)—N(H)—SO$_2$—CH$_3$, —C(O)—N(H)—SO$_2$—CH$_2$CF$_3$, —C(O)—N(H)—SO$_2$—CH$_2$CH$_3$, —C(O)—N(H)—SO$_2$—(CH$_2$)$_2$CH$_3$, —C(O)—N(H)—SO$_2$—CH(CH$_3$)$_2$, —C(O)—N(H)—SO$_2$—C(CH$_3$)$_3$, —C(O)—N(H)—SO$_2$—CH$_2$CH(CH$_3$)$_2$, —C(O)—N(H)—SO$_2$-cyclopropyl, —C(O)—N(H)—SO$_2$-cyclobutyl, —C(O)—N(H)—SO$_2$-cyclopentyl, —C(O)—N(H)—SO$_2$-cyclohexyl, —C(O)—N(H)—SO$_2$-phenyl, —C(O)—N(H)—SO$_2$-tetrahydro-2H-pyran, —C(O)—N(H)—SO$_2$-tetrahydro-2H-thiopyran, —C(O)—N(H)—SO$_2$-piperidinyl, —C(O)—N(H)—SO$_2$-piperazinyl, —C(O)—N(H)—SO$_2$-pyridyl, —C(O)—N(H)—SO$_2$-isoxazolyl, —C(O)—N(H)—SO$_2$-thiophenyl, —SO$_2$—CH$_3$, —SO$_2$—CH$_2$CH$_3$, —SO$_2$—CH$_2$CF$_3$, —SO$_2$—(CH$_2$)$_2$—CH$_3$, —SO$_2$—CH(CH$_3$)$_2$, —SO$_2$—CH$_2$CH(CH$_3$)$_2$, —SO$_2$-cyclopropyl, —SO$_2$-cyclobutyl, —SO$_2$-cyclopentyl, —SO$_2$-cyclohexyl, —SO$_2$-phenyl, —SO$_2$-tetrahydro-2H-pyran, —SO$_2$-tetrahydro-2H-thiopyran, —SO$_2$-pyridyl, —SO$_2$-isoxazole, —SO$_2$-thiophene, —C(O)—CH$_2$—OH, —C(O)(CH$_2$)$_2$—OH, —C(O)CH$_2$—C(CH$_3$)$_2$—OH, —CH(phenyl)$_2$, —CH (cycloalkyl)$_2$, —SO$_2$—N(CH$_3$)$_2$, —C(O)CH$_3$, —C(O) CH$_2$CH$_3$, —C(O)CH$_2$CF$_3$, —C(O)(CH$_2$)$_2$CH$_3$, —C(O)CH (CH$_3$)$_2$, —C(O)C(CH$_3$)$_3$, —C(O)CH$_2$CH(CH$_3$)$_2$, —C(O)-cyclopropyl, —C(O)cyclobutyl, C(O)cyclopentyl, —C(O) cyclohexyl, —C(O)phenyl, —C(O)tetrahydro-2H-pyran, —C(O)-tetrahydro-2H-thiopyranyl, —C(O)-piperidinyl, —C(O)piperazinyl, —C(O)-pyridyl, —C(O)-isoxazolyl, —C(O)-thiophenyl, —C(O)N(H)CH$_3$, —C(O)N(H)—CH$_2$CF$_3$, —C(O)—N(H)—CH$_2$CH$_3$, —C(O)N(H)—(CH$_2$)$_2$CH$_3$, —C(O)—N(H)—CH(CH$_3$)$_2$, —C(O)—N(H)—C(CH$_3$)$_3$, —C(O)—N(H)—CH$_2$CH(CH$_3$)$_2$, C(O)—N(H)-cyclopropyl, —C(O)—N(H)-cyclobutyl, —C(O)—N(H)-cyclopentyl, —C(O)—N(H)-cyclohexyl, —C(O)—N(H)-phenyl, —C(O)—N(H)-heterocycloalkyl, C(O)—N(H)-tetrahydro-2H-pyran, C(O)—N(H)-tetrahydro-2H-thiopyran, C(O)—N(H)-piperidinyl, C(O)—N(H)-piperazinyl, —C(O)—N(H)-pyridyl, —C(O)—N(H)-isoxazole, or —C(O)—N(H)-thiophene, wherein the cycloalkyl, heterocycloalkyl, phenyl or heteroaryl moieties of $Z^5$ can be optionally substituted with 1-3 substituents independently selected from the group consisting of F, Cl, CN or CH$_3$, CF$_3$, OH, OCH$_3$ and OCF$_3$.

Embodiment 15 of this disclosure relates to any of Embodiment 1-14, including any of the sub-embodiments of these Embodiments where applicable, wherein $R^{11}$ is —(CH$_2$)$_2$—CF$_3$, CH$_2$—CF$_3$, CH$_3$, —CH(CH$_3$)$_2$, —CH$_2$—CH$_3$, —CH(CH$_3$)$_2$, —C(CH$_3$)$_3$, —CH$_2$CH$_2$CH$_3$, —CH(CH$_3$)-phenyl, —C(O)—N(H)propyl, —C$_3$-C$_6$cycloalkyl, phenyl optionally substituted with 0-2 $J^3$, —(CH$_2$)$_{0-1}$cyclopropyl, —(CH$_2$)$_{0-1}$cyclobutyl, —(CH$_2$)$_{0-1}$cyclopentyl, —(CH$_2$)$_{0-1}$cyclohexyl, —(CH$_2$)$_{0-1}$tetrahydro-2H-thiopyran 1,1-dioxide, —(CH$_2$)$_{0-1}$tetrahydro-2H-pyran, —(CH$_2$)$_{0-1}$oxetane, —(CH$_2$)$_{0-1}$morpholinyl, —(CH$_2$)$_{0-1}$ thiomorpholinyl 1,1-dioxide, —(CH$_2$)$_{0-1}$ isothiozolidine 1,1-dioxide, CH$_3$—CN, methoxymethyl, methoxypropyl, methoxyethyl, morpholinyl, pyridyl, —C(O)isoxazolyl optionally substituted with 1-3 methyl, phenyl optionally substituted with 1-3 F, Cl, alkoxy, CN, —SO$_2$-phenyl optionally substituted with 1-3 substituents independently selected from the group consisting of F, Cl, alkoxy, and CN.

Embodiment 16 of this disclosure relates to any one of Embodiments 1-15, including any of the sub-embodiments of these Embodiments where applicable, wherein $R^7$ is:

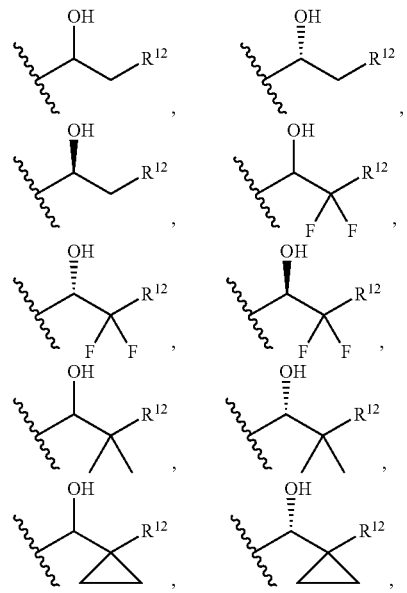

-continued

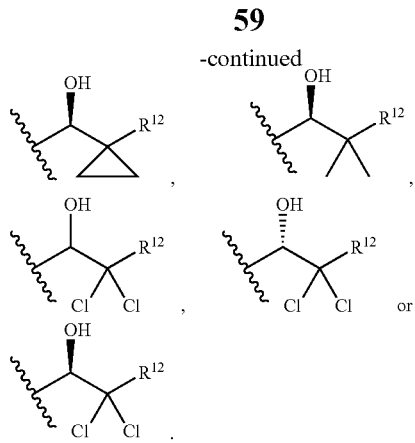

Embodiment 17 of this disclosure relates to any of Embodiments 1-15, including any of the sub-embodiments of these Embodiments where applicable, wherein $R^7$ is:

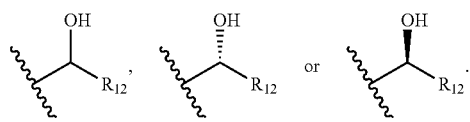

Embodiment 18 of this disclosure relates to any one of Embodiments 1-5, and 8-13, including any of the sub-embodiments of Embodiments 4 and 8, wherein $R^7$ is one of the following groups:

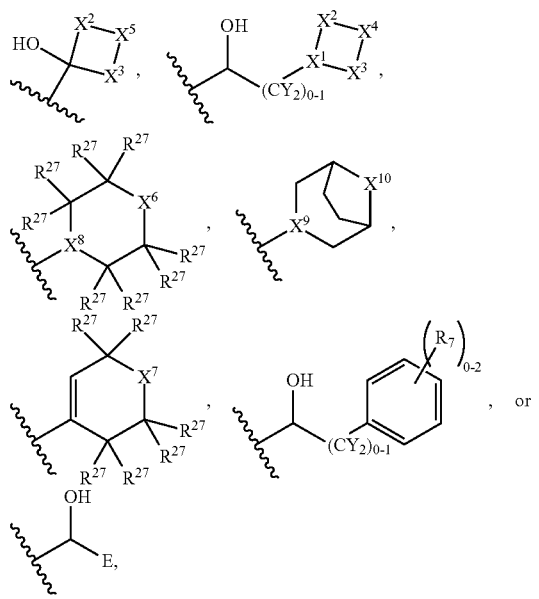

wherein:

E is bicyclo[2.2.2]octane-1-yl, bicyclo[2.2.1]heptan-1-yl, 1-fluorobicyclo[2.2.2]octan-1-yl, (1r,2R,4S,5r,6R,8S)-tetracyclo[3.3.1.0²,⁴.0⁶,⁸]nonan-9-yl, (1s,5s)-bicyclo[3.3.1]nonan-9-yl, cuban-1-yl, bicyclo[1.1.1]pentan-2-yl, adamantanyl, (1R,5S)-8-azabicyclo[3.2.1]octanyl, (1R,5S)-3,8-diazabicyclo[3.2.1]octanyl, or (1R,5S)-3-azabicyclo[3.2.1]octane;

$X^1$ is —$CR^{13}$—;

$X^2$ is —$C(R^{14})_2$— or —$C(R^{14})_2$—$C(R^{14})_2$—;
$X^3$ is —$C(R^{14})_2$— or —$C(R^{14})_2$—$C(R^{14})_2$—;
$X^4$ is —$N(R^{15})$— or —$C(R^{16})(R^{17})$—;
$X^5$ is —$N(R^{18})$— or —$C(R^{19})(R^{20})$—;
$X^6$ is —$N(R^{21})$—, —O— or —$C(R^{22})(R^{23})$—;
$X^7$ is N—$C(R^{25})(R^{26})$—;
$X^8$ is —C(H)— or

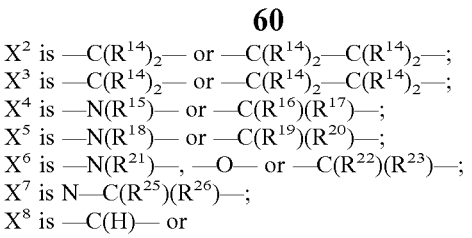

$X^9$ is CH or N;
$X^{10}$ is $CH_2$, $CH(CH_3)$, CHF, CHCl, or $NR^{21}$;
$R^{19}$ is H, $C_1$-$C_3$alkyl, or $C_1$-$C_3$haloalkyl;
$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—N($C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_3$ alkylene-$C_3$-$C_6$cycloalkyl optionally substituted with 1-4 $J^3$, —$C_0$-$C_4$alkylene phenyl optionally substituted with 1-3 $J^3$, —$C_1$-$C_3$ alkylene-$SO_2$-phenyl optionally substituted with 1-3 $J^3$, —$C_1$-$C_3$ alkylene-$SO_2$—$C_1$-$C_6$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-3 $J^3$, —$C_0$-$C_4$ alkylene-$C_3$-$C_6$heterocycloalkyl optionally substituted with 1-3 $J^3$, —$C_0$-$C_4$ alkylene-5-6 membered heteroaryl optionally substituted with 1-3 $J^3$, or —C(O)-phenyl optionally substituted with 1-3 $J^3$;

$R^{13}$ is H, F, $CH_3$, $CFH_2$, $CF_2H$, or $CF_3$;
each $R^{14}$ is independently H, halogen, $CH_3$, —$CFH_2$, —$CF_2H$ or —$CF_3$, provided that no more than four $R^{14}$ is other than H;

$R^{15}$ is $C_1$-$C_2$alkylene-$C_1$-$C_2$alkoxy, —$C_0$-$C_1$alkyl-phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 memberedheterocycloalkyl optionally substituted with 1-3 $J^3$, —C(O)N(H) $SO_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)$NR^{10}R^{11}$, —C(O)$J^1$, $CO_2J^2$, —$SO_2NR^{10}R^{11}$, —$SO_2$—$C_3$-$C_6$cycloalkyl optionally substituted with 1-3 halogens, —$CO_2$-alkyl, or —$C(NW_2)$=N-T, $R^{16}$ is H, halogen, CN, OH, cyclopropyl, cyclobutyl, $C_1$-$C_4$alkyl or $C_1$-$C_4$haloalkyl;

$R^{17}$ is H, halogen, CN, OH, cyclopropyl, cyclobutyl, $C_1$-$C_4$alkyl, $C_1$-$C_4$haloalkyl, $SO_2$—$C_1$-$C_4$alkyl, $SO_2$—$C_1$-$C_4$haloalkyl, —$SO_2$—$C_3$-$C_6$cycloalkyl optionally substituted with 1-3 halogens, —C(O)$NR^{10}R^{11}$, —$CO_2$-alkyl, $COJ^1$, $CO_2J^2$, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkylene;

or $R^{16}$ and $R^{17}$ join together with the carbon atom to which they are attached to form one of the following groups (a)-(c):

(a) a $C_3$-$C_6$cycloalkyl optionally substituted with 1-6 groups independently selected from the group consisting of CN, F, $C_1$-$C_4$alkyl, and $C_1$-$C_4$haloalkyl, and wherein the $C_3$-$C_6$cycloalkyl is optionally substituted with —N(H)SO$_2$—$C_1$-$C_3$alkyl, —N(H)SO$_2$—$C_3$-$C_6$cycloalkyl optionally substituted with 1-3 halogens, or —N(H)SO$_2$—$C_1$-$C_3$haloalkyl;

(b) a 4-6 membered nitrogen-containing heterocycloalkyl optionally substituted on its carbon atoms with 1-4 groups independently selected from the group consisting of CN, F, $C_1$-$C_4$alkyl, and $C_1$-$C_4$haloalkyl, and wherein the nitrogen-containing heterocycloalkyl is optionally N-substituted with —SO$_2$—$C_1$-$C_3$alkyl, —SO$_2$—$C_3$-$C_6$cycloalkyl optionally substituted with 1-3 halogens, or —SO$_2$—$C_1$-$C_3$haloalkyl; or (c) a 4-6 membered heterocycloalkyl containing —O—, —S—, —SO—, or SO$_2$—, wherein the 4-6 membered heterocycloalkyl is optionally substituted on its carbon atoms with 1-3 groups independently selected from the group consisting of CN, F, $C_1$-$C_4$alkyl, and $C_1$-$C_4$haloalkyl;

each Y is independently H, F, CH$_3$, —CFH$_2$, —CF$_2$H or —CF$_3$, or two Y groups join together, with the carbon atom to which they are attached, to form a cyclopropyl or cyclobutyl group;

$R^{18}$ is H, $C_1$-$C_4$alkyl, $C_1$-$C_4$haloalkyl, —SO$_2$—$C_1$-$C_4$alkyl, —SO$_2$—$C_3$-$C_6$cycloalkyl optionally substituted with 1-3 halogens, —SO$_2$—$C_1$-$C_4$haloalkyl, $C_3$-$C_6$cycloalkyl optionally substituted with 1-3 halogens, —C(O)NR$^{10}$R$^{11}$, —CO$_2$-alkyl, COJ$^1$, or CO$_2$J$^2$;

$R^{19}$ is H, halogen, CN, OH, cyclopropyl, cyclobutyl, $C_1$-$C_4$alkyl, or —$C_1$-$C_4$haloalkyl;

$R^{20}$ is H, halogen, CN, OH, cyclopropyl, cyclobutyl, $C_1$-$C_4$alkyl, $C_1$-$C_4$haloalkyl, —SO$_2$—$C_1$-$C_4$alkyl, SO$_2$—$C_1$-$C_4$haloalkyl, —SO$_2$—$C_3$-$C_6$cycloalkyl optionally substituted with 1-3 halogens, —CO$_2$-alkyl, COJ$^1$, CO$_2$J$^2$, —N(H)SO$_2$—$C_1$-$C_4$alkyl, —N(H)SO$_2$—$C_3$-$C_6$cycloalkyl optionally substituted with 1-3 halogens, or —N(H)SO$_2$—$C_1$-$C_4$haloalkyl;

or $R^{19}$ and $R^{20}$ join together with the carbon atom to which they are attached to form one of the following groups (a)-(d):

(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl is optionally substituted with —N(H)SO$_2$—$C_1$-$C_3$alkyl, —N(H)SO$_2$—$C_1$-$C_3$haloalkyl, or —N(H)SO$_2$—$C_3$-$C_6$cycloalkyl optionally substituted with 1-3 halogens;

(b) a 4-6 membered nitrogen-containing heterocycloalkyl optionally substituted on its carbon atoms with 1-3 groups independently selected from the group consisting of CN, F, $C_1$-$C_4$alkyl, and $C_1$-$C_4$haloalkyl, and wherein the nitrogen-containing heterocycloalkyl can also be optionally N-substituted with —SO$_2$—$C_1$-$C_3$alkyl, —SO$_2$—$C_1$-$C_3$haloalkyl or —SO$_2$—$C_3$-$C_6$cycloalkyl optionally substituted with 1-3 halogens;

(c) a 4-6 membered heterocycloalkyl containing —O—, —S—, —SO—, or SO$_2$—, wherein the 4-6 membered heterocycloalkyl is optionally substituted on its carbon atoms with 1-3 groups independently selected from the group consisting of CN, F, $C_1$-$C_4$alkyl, and $C_1$-$C_4$haloalkyl; or (d) a 7-10 membered bridged ring;

$R^{21}$ is $C_1$-$C_3$alkylene-$C_1$-$C_3$alkoxy, —$C_0$-$C_2$alkylene phenyl optionally substituted with 1-3 J$^3$, —SO$_2$—$C_1$-$C_6$alkyl, —SO$_2$—$C_1$-$C_6$haloalkyl, —SO$_2$—$C_3$-$C_6$cycloalkyl optionally substituted with 1-3 J$^3$, —SO$_2$-5-6 membered heterocycloalkyl optionally substituted with 1-3 J$^3$, —SO$_2$-5-6 membered heteroaryl optionally substituted with 1-3 J$^3$, —SO$_2$-phenyl optionally substituted with 1-3 J$^3$, —(CO)N(H)SO$_2$—$C_1$-$C_6$alkyl, —C(O)N(H)SO$_2$—$C_1$-$C_6$haloalkyl, —C(O)N(H)SO$_2$—$C_3$-$C_6$cycloalkyl optionally substituted with 1-3 J$^3$, —C(O)N(H)SO$_2$-4-6 memberedheterocycloalkyl optionally substituted with 1-3 J$^3$, —C(O)N(H)SO$_2$-5-6 memberedheteroaryl optionally substituted with 1-3 J$^3$, —$C_0$-$C_2$alkylene-CH(phenyl)$_2$ optionally substituted with 1-3 J$^3$, —$C_0$-$C_2$alkylene-CH($C_3$-$C_6$cycloalkyl)$_2$ optionally substituted with 1-3 J$^3$, —C(O)NR$^{10}$R$^{11}$, —C(O)J$^1$, —SO$_2$NR$^{10}$R$^{11}$, —SO$_2$—$C_3$-$C_6$cycloalkyl optionally substituted with 1-3 halogens, or —CO$_2$-alkyl;

$R^{22}$ is H, halogen, $C_1$-$C_4$alkyl, or $C_1$-$C_4$haloalkyl;

$R^{23}$ is H, halogen, $C_1$-$C_4$alkyl, $C_1$-$C_4$haloalkyl, —CN, —SO$_2$—$C_1$-$C_4$alkyl, SO$_2$—$C_1$-$C_4$haloalkyl, —SO$_2$—$C_3$-$C_6$cycloalkyl optionally substituted with 1-3 halogens, —CO$_2$-alkyl, COJ$^1$, CO$_2$J$^2$, —N(H)SO$_2$—$C_1$-$C_4$alkyl, —N(H)SO$_2$—$C_3$-$C_6$cycloalkyl optionally substituted with 1-3 halogens, or —N(H)SO$_2$—$C_1$-$C_4$haloalkyl;

$R^{25}$ is H, halogen, $C_1$-$C_4$alkyl, or $C_1$-$C_4$haloalkyl;

$R^{26}$ is H, halogen, $C_1$-$C_4$alkyl, $C_1$-$C_4$haloalkyl, CN, —N(H)SO$_2$—$C_1$-$C_4$alkyl, —N(H)SO$_2$—$C_1$-$C_4$haloalkyl, —N(H)SO$_2$—$C_3$-$C_6$cycloalkyl optionally substituted with 1-3 halogens, or $C_3$-$C_6$cycloalkyl optionally substituted with 1-3 halogens;

each $R^{27}$ is independently H, D, F, Cl, CH$_3$, —CFH$_2$, —CF$_2$H or —CF$_3$, provided that no more than four $R^{27}$ is other than H;

each W is independently H, alkyl or haloalkyl;

T is alkyl, haloalkyl, hydroxyalkyl, alkoxy or CN;

J$^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 J$^3$, $C_0$-$C_3$ alkylene-phenyl optionally substituted with 1-3 J$^3$, —$C_0$-$C_3$ alkylene-5-6 membered heteroaryl optionally substituted with 1-3 J$^3$, —$C_0$-$C_3$ alkylene-4-6 membered heterocycloalkyl optionally substituted with 1-3 J$^3$;

J$^2$ is H, $C_1$-$C_4$alkyl, or $C_1$-$C_4$haloalkyl; and each J$^3$ is independently halogen, $C_1$-$C_4$alkyl, $C_1$-$C_4$haloalkyl, OH, $C_1$-$C_4$alkoxy optionally substituted with 1-3 halogens, CN, 4-6 membered heterocycloalkyl, —S(O)$_2$—$C_1$-$C_4$alkyl, —NH$_2$, —N(H)—$C_1$-$C_4$alkyl, —N($C_1$-$C_4$alkyl)$_2$ provided that when J$^3$ is attached to nitrogen, J$^3$ cannot be halogen, OH, CN, NH$_2$, —N(H)—$C_1$-$C_4$alkyl, or —N($C_1$-$C_4$alkyl)$_2$.

Embodiment 19 of this disclosure relates to Embodiment 18, wherein $R^7$ is one of the following groups:

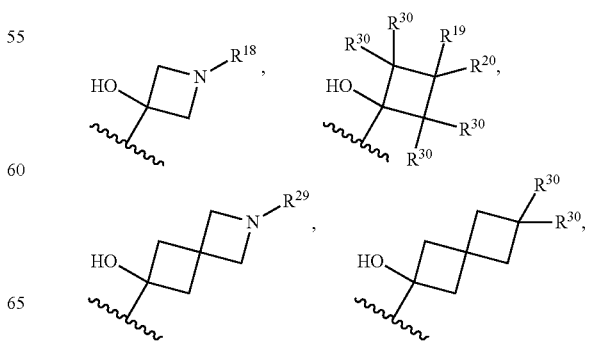

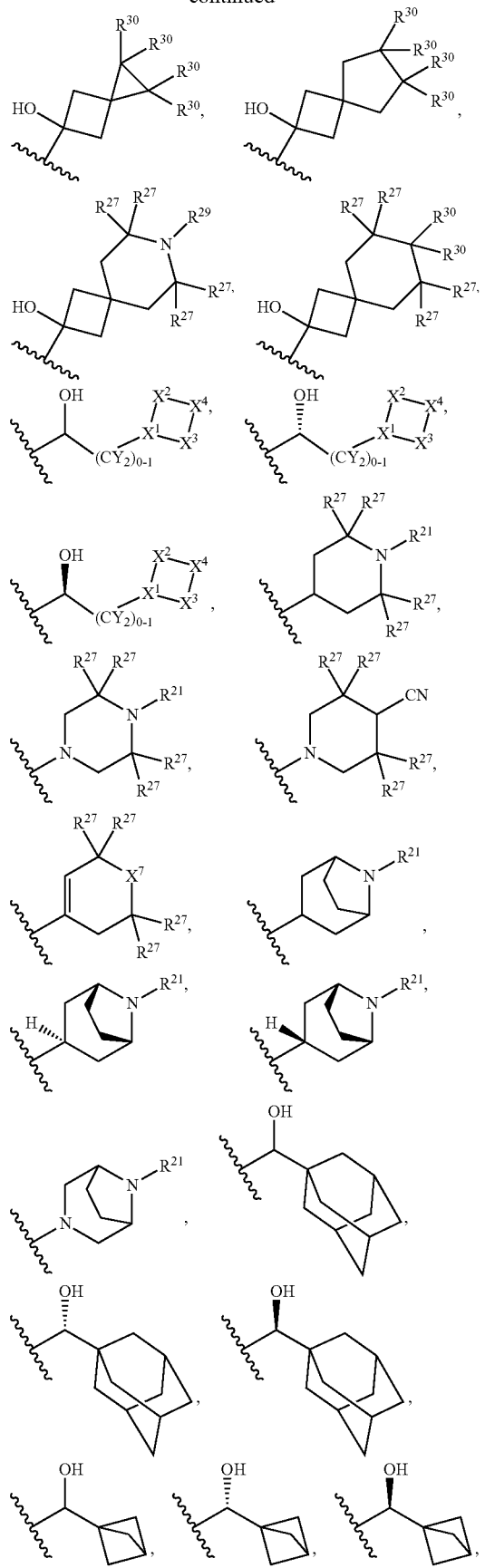
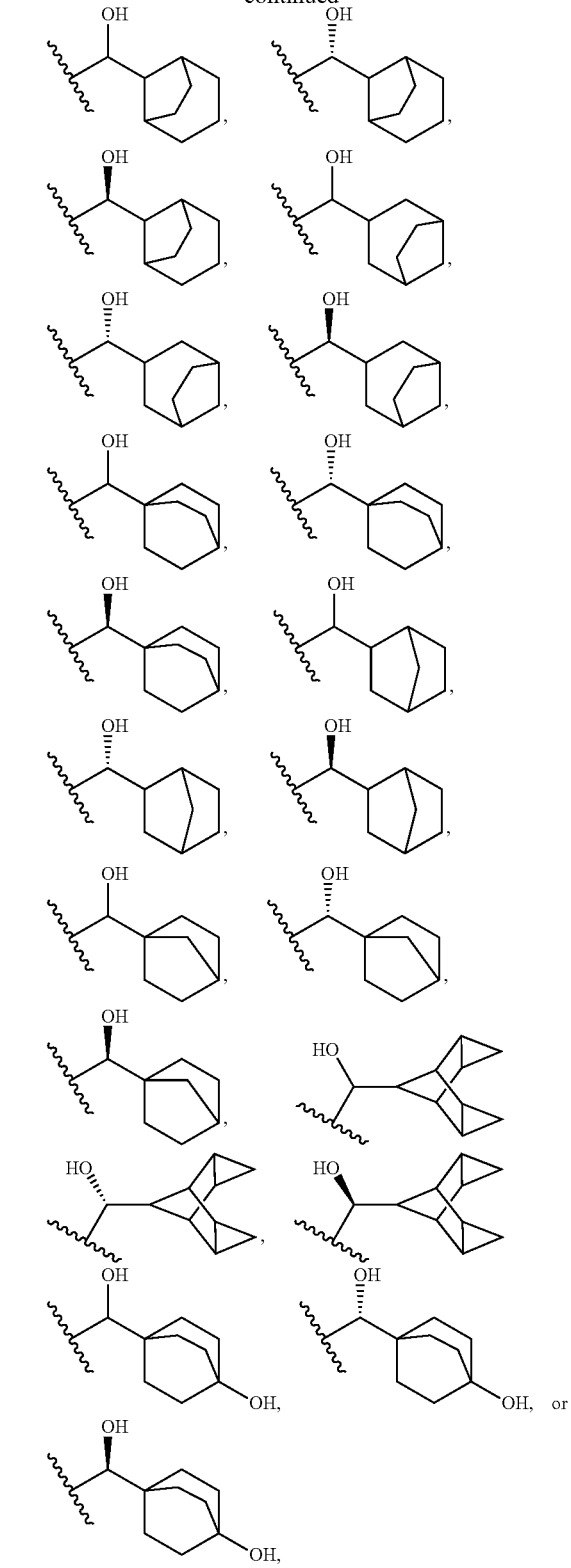
wherein:
each Y is independently H, F, CH$_3$, —CFH$_2$, —CF$_2$H or —CF$_3$, or two Y groups join together, with the carbon atom to which they are attached, to form a cyclopropyl or cyclobutyl group;
X$^7$ is N—C(R$^{25}$)(R$^{26}$)—;

$R^{10}$ is H, $C_1$-$C_2$alkyl, or $C_1$-$C_2$haloalkyl;

$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—N($C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_4$alkylene phenyl optionally substituted with 1-3 $J^3$, —$C_1$-$C_3$ alkylene-$SO_2$-phenyl optionally substituted with 1-2 $J^3$, —$C_1$-$C_3$ alkylene-$SO_2$—$C_1$-$C_{36}$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-2 $J^3$, —$C_0$-$C_4$ alkylene-$C_3$-$C_6$heterocycloalkyl optionally substituted with 1-2 $J^3$, —$C_0$-$C_4$ alkylene-5-6 membered heteroaryl optionally substituted with 1-2 $J^3$, or —C(O)-phenyl optionally substituted with 1-2 $J^3$;

$R^{18}$ is H, $C_1$-$C_3$alkyl, $C_1$-$C_3$haloalkyl, —$SO_2$—$C_1$-$C_3$alkyl, —$SO_2$—$C_3$-$C_6$cycloalkyl optionally substituted with 1-3 F, —C(O)$NR^{10}R^{11}$, —$CO_2$-alkyl, $COJ^1$, $CO_2J^2$, —$SO_2$—$C_1$-$C_3$fluoroalkyl, or $C_3$-$C_6$cycloalkyl optionally substituted with 1-3 F; $SO_2$—$C_1$-$C_4$alkyl, $SO_2$—$C_1$-$C_4$haloalkyl, —$SO_2$—$C_3$-$C_6$cycloalkyl optionally substituted with 1-3 halogens, $R^{19}$ is H, F, CN, cyclopropyl, cyclobutyl, $C_1$-$C_3$alkyl, or —$C_1$-$C_3$fluoroalkyl;

$R^{20}$ is H, F, CN, cyclopropyl, cyclobutyl, $C_1$-$C_3$alkyl, $C_1$-$C_3$fluoroalkyl, —N(H)$SO_2$—$C_1$-$C_6$alkyl, —N(H)$SO_2$—$C_3$-$C_6$cycloalkyl optionally substituted with 1-3 halogens, —N(H)$SO_2$—$C_1$-$C_4$fluoroalkyl, or $C_3$-$C_6$cycloalkyl optionally substituted with 1-3 F;

or $R^{19}$ and $R^{20}$ join together with the carbon atom to which they are attached to form one of the following groups (a)-(d):

(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl is optionally substituted with —N(H)$SO_2$—$C_1$-$C_3$alkyl, —N(H)$SO_2$—$C_1$-$C_3$haloalkyl, or —N(H)$SO_2$—$C_3$-$C_6$cycloalkyl optionally substituted with 1-3 halogens;

(b) a 4-6 membered nitrogen-containing heterocycloalkyl optionally substituted on its carbon atoms with 1-3 groups independently selected from the group consisting of CN, F, $C_1$-$C_3$alkyl, and $C_1$-$C_3$fluoroalkyl, and wherein the nitrogen-containing heterocycloalkyl can also be optionally N-substituted with —$SO_2$—$C_1$-$C_3$alkyl, —$SO_2$—$C_1$-$C_3$fluoroalkyl or —$SO_2$—$C_3$-$C_6$cycloalkyl optionally substituted with 1-3 F;

(c) a 4-6 membered heterocycloalkyl containing —O—, —S—, —SO—, or $SO_2$—, wherein the 4-6 membered heterocycloalkyl is optionally substituted on its carbon atoms with 1-3 groups independently selected from the group consisting of CN, F, $C_1$-$C_3$alkyl, and $C_1$-$C_3$fluoroalkyl; or (d) a 7-10 membered bridged ring;

$R^{21}$ is H, $C_1$-$C_2$alkylene-$C_1$-$C_2$alkoxy, —$C_0$-$C_1$alkylene phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)$NR^{19}R^{11}$, —C(O)$J^1$, $CO_2J^2$, —$SO_2NR^{19}R^{11}$, —$SO_2$—$C_3$-$C_6$cycloalkyl optionally substituted with 1-3 halogens, —$CO_2$-alkyl, or —C($NH_2$)=N-T;

$R^{25}$ is H, F, $C_1$-$C_3$alkyl, or $C_1$-$C_3$fluoroalkyl;

$R^{26}$ is H, F, $C_1$-$C_3$alkyl, $C_1$-$C_3$fluoroalkyl, CN, —N(H)$SO_2$—$C_1$-$C_3$alkyl, —N(H)$SO_2$—$C_1$-$C_3$fluoroalkyl, —N(H)$SO_2$—$C_3$-$C_6$cycloalkyl optionally substituted with 1-3 F, or $C_3$-$C_6$cycloalkyl optionally substituted with 1-3 F;

each $R^{27}$ is independently H, D, F, $CH_3$, —$CFH_2$, —$CF_2H$ or —$CF_3$, provided that no more than two $R^{27}$ is other than H;

$R^{29}$ is H, $C_1$-$C_3$alkyl, $C_1$-$C_3$fluoroalkyl, —$SO_2$—$C_1$-$C_3$alkyl, —$SO_2$—$C_1$-$C_3$fluoroalkyl, —$SO_2$—$C_3$-$C_6$cycloalkyl optionally substituted with 1-3 F, —C(O)$NR^{19}R^{11}$, —$CO_2$-alkyl, $COJ^1$, $CO_2J^2$, or —$C_3$-$C_6$cycloalkyl optionally substituted with 1-3 F;

$R^{30}$ is H, F, or $C_1$-$C_3$ alkyl optionally substituted with 1-3 F;

T is $C_1$-$C_3$alkyl, $C_1$-$C_3$haloalkyl, $C_1$-$C_3$hydroxyalkyl, $C_1$-$C_3$alkoxy or CN;

$J^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, $C_0$-$C_3$ alkylene-5-6 membered heteroaryl optionally substituted with 1-3 $J^3$, —$C_0$-$C_3$ alkylene-4-6 membered heterocycloalkyl optionally substituted with 1-3 $J^3$;

$J^2$ is H, $C_1$-$C_4$alkyl, or $C_1$-$C_4$haloalkyl; and each $J^3$ is independently halogen, $C_1$-$C_4$alkyl, $C_1$-$C_4$haloalkyl, OH, —$C_1$-$C_4$alkoxy optionally substituted with 1-3 halogens, CN, 4-6 membered heterocycloalkyl, —S(O)$_2$—$C_1$-$C_4$alkyl, —$NH_2$, —N(H)—$C_1$-$C_4$alkyl, —N($C_1$-$C_4$alkyl)$_2$ provided that when $J^3$ is attached to nitrogen, $J^3$ cannot be halogen, OH, CN, $NH_2$, —N(H)—$C_1$-$C_4$alkyl, or —N($C_1$-$C_4$alkyl)$_2$.

Embodiment 20 of this disclosure relates to Embodiment 19, wherein $R^7$ is one of the following groups:

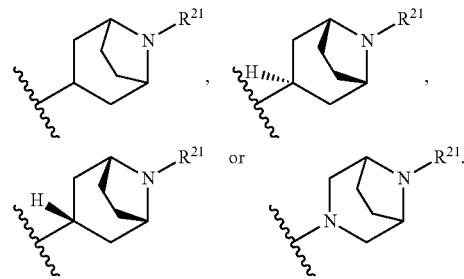

Embodiment 21 of this disclosure relates to Embodiment 19, wherein $R^7$ is one of the following groups:

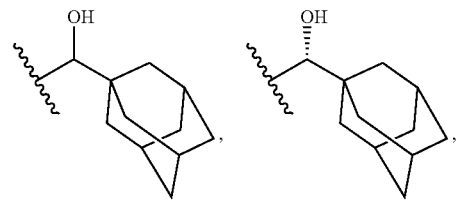

67
-continued
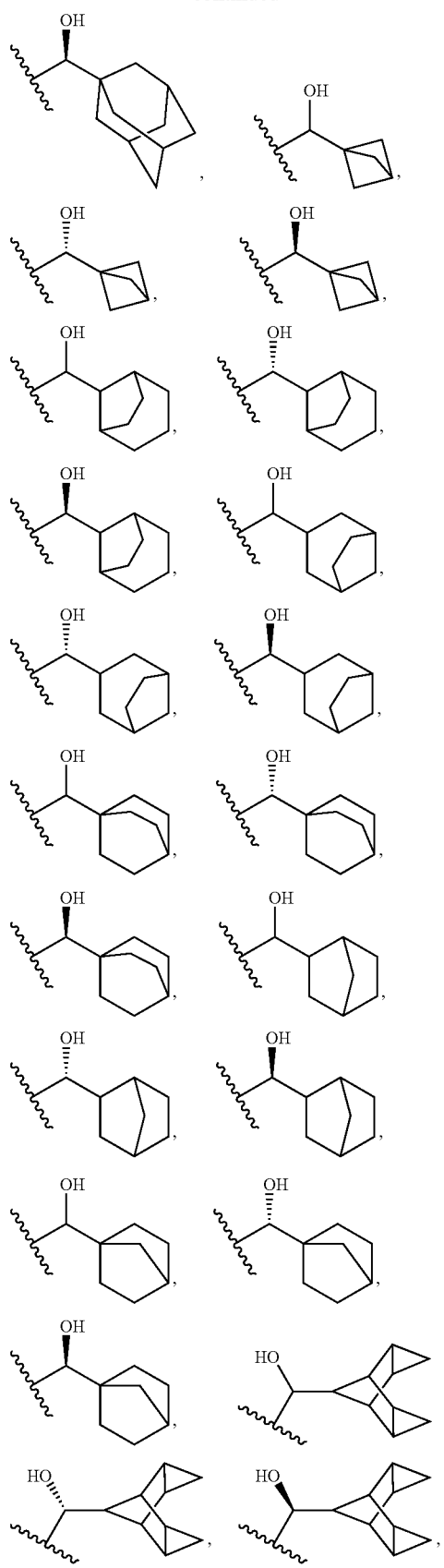
68
-continued
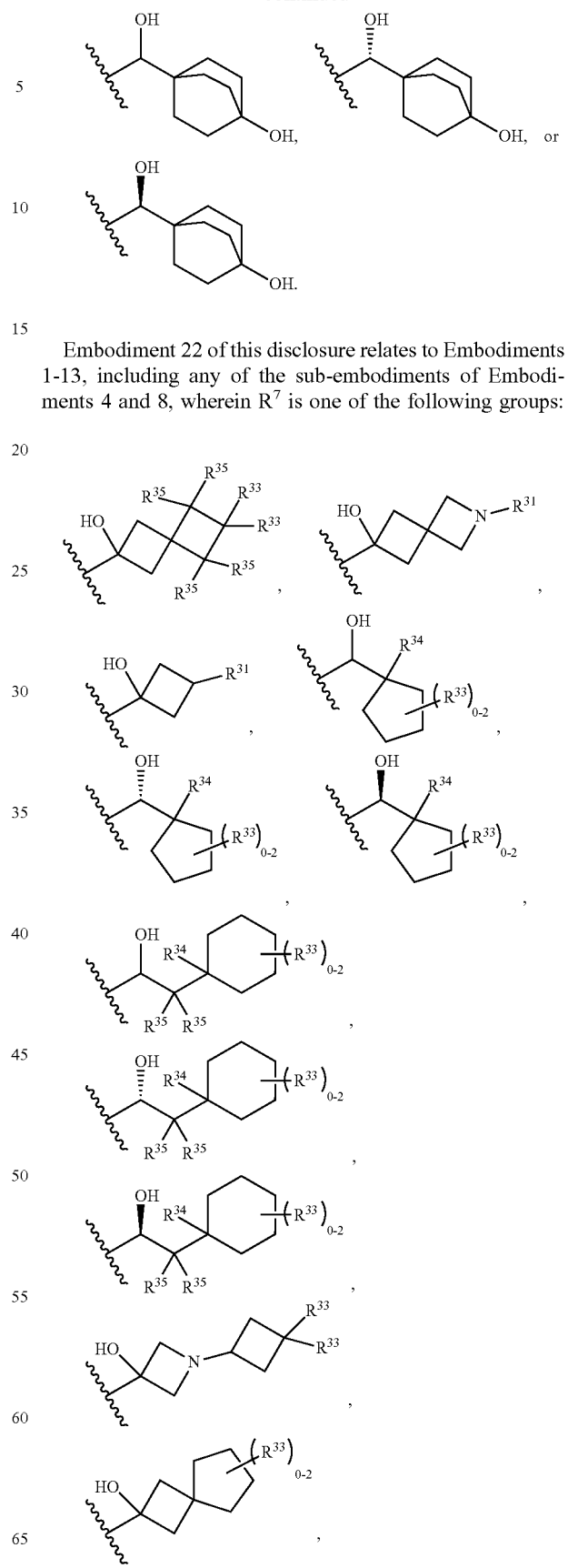
Embodiment 22 of this disclosure relates to Embodiments 1-13, including any of the sub-embodiments of Embodiments 4 and 8, wherein $R^7$ is one of the following groups:

-continued

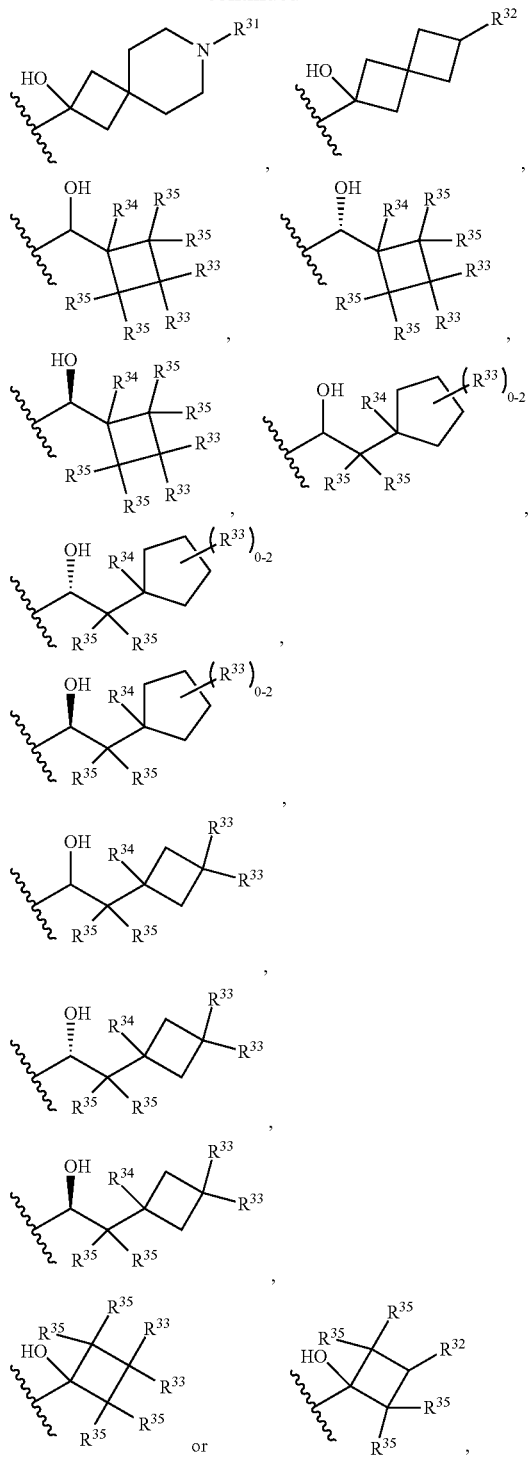

$R^{31}$ is H, $C_1$-$C_3$ alkyl optionally substituted with 1-3 F, —$SO_2$—$R^{35}$ or $C_3$-$C_6$ cycloalkyl optionally substituted with 1-3 F;

$R^{32}$ is —$SO_2$—$R^{35}$ or —N(H)$SO_2$—$R^{35}$;

$R^{33}$ is H, F, CN, cyclopropyl, or $C_1$-$C_3$ alkyl optionally substituted with 1-3 F;

$R^{34}$ is H, F, or $C_1$-$C_3$ alkyl optionally substituted with 1-3 F; and $R^{35}$ is H, F, methyl optionally substituted with 1-3 F, or two $R^{35}$ groups, together with the carbon atom to which they are attached, join together to form a cyclopropyl group.

Embodiment 23 of this disclosure relates to any one of Embodiment 1-13, wherein $R^7$ is one of the following groups:

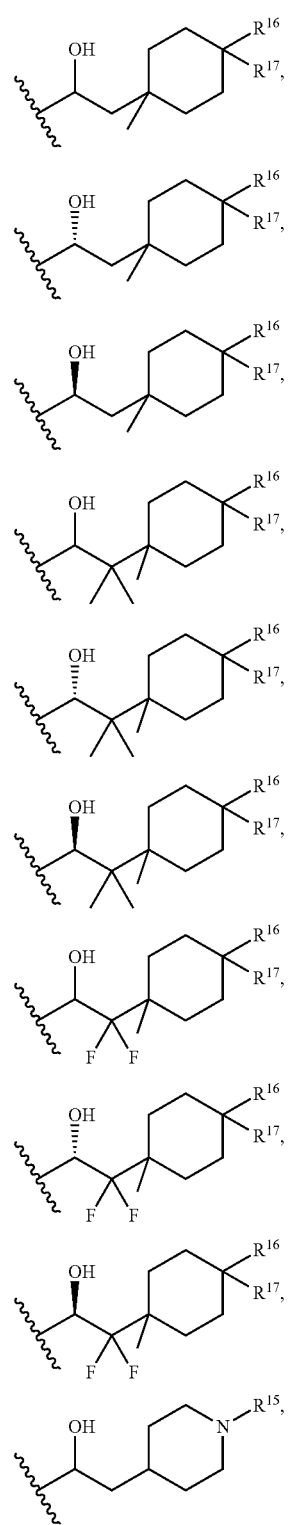

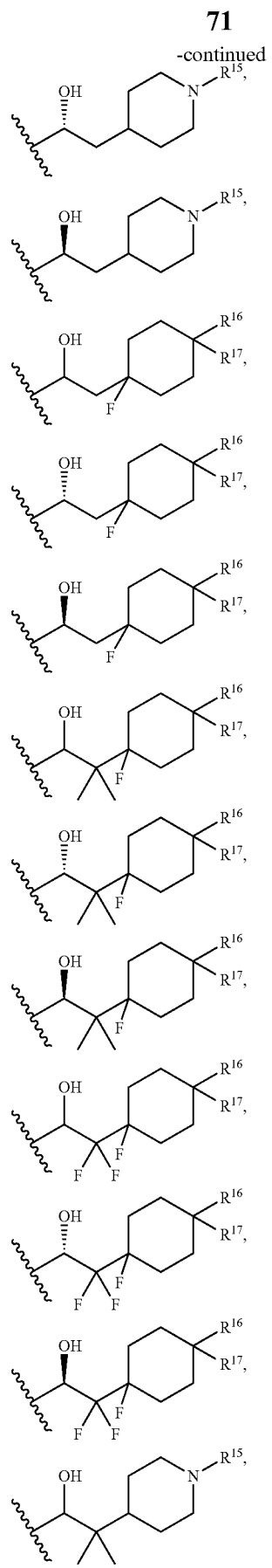
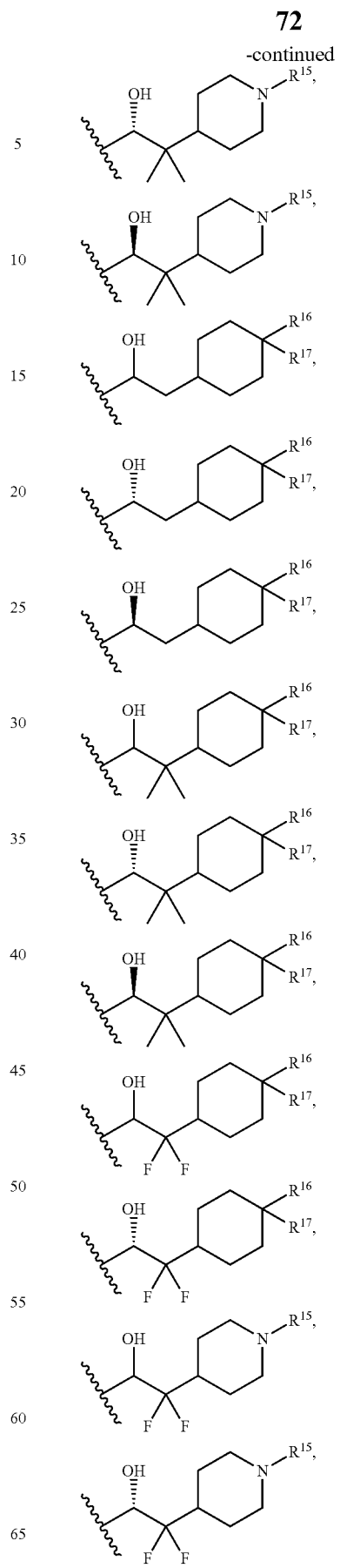

-continued
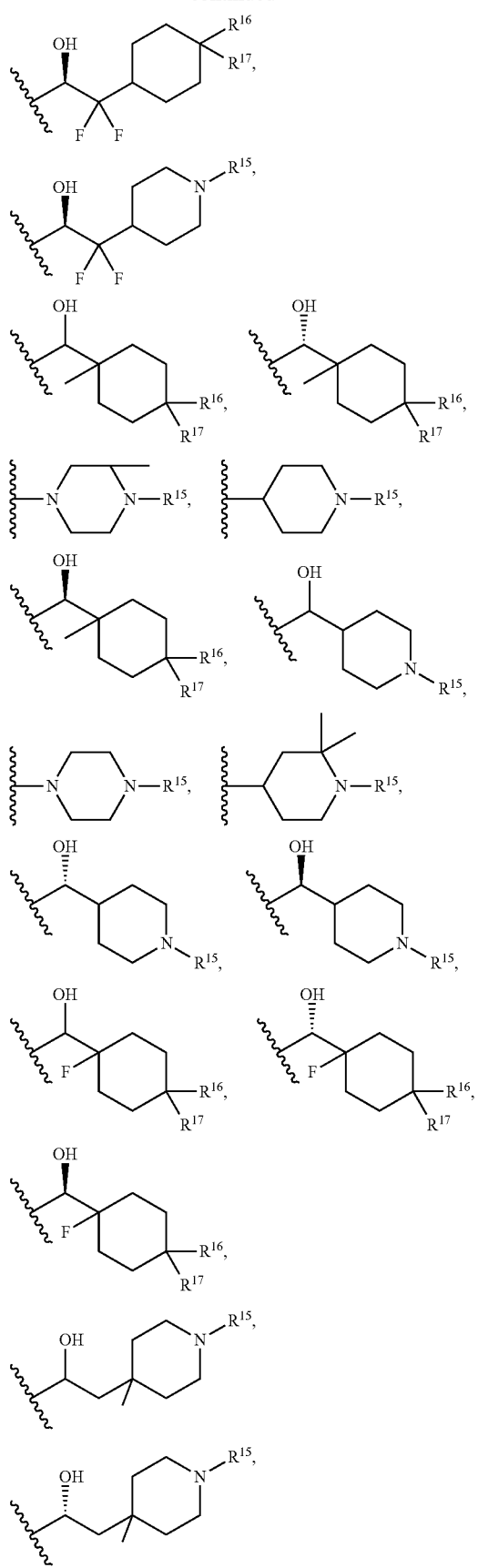
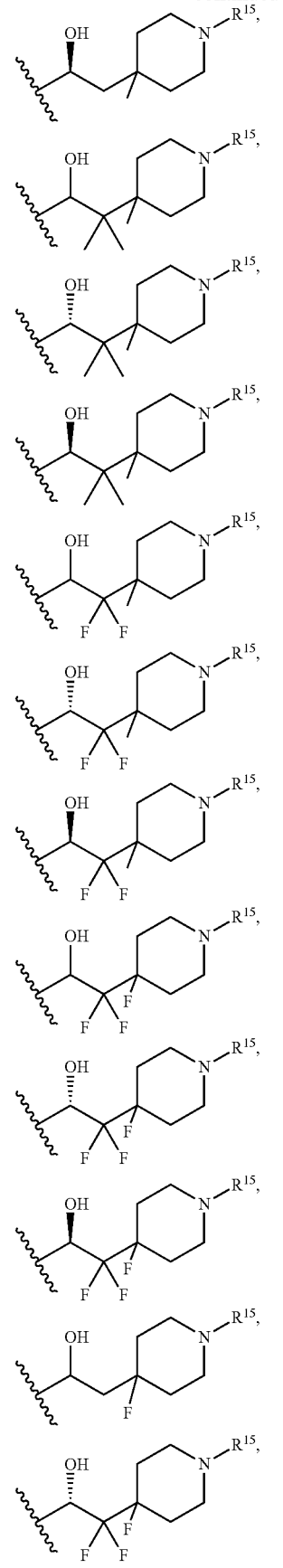

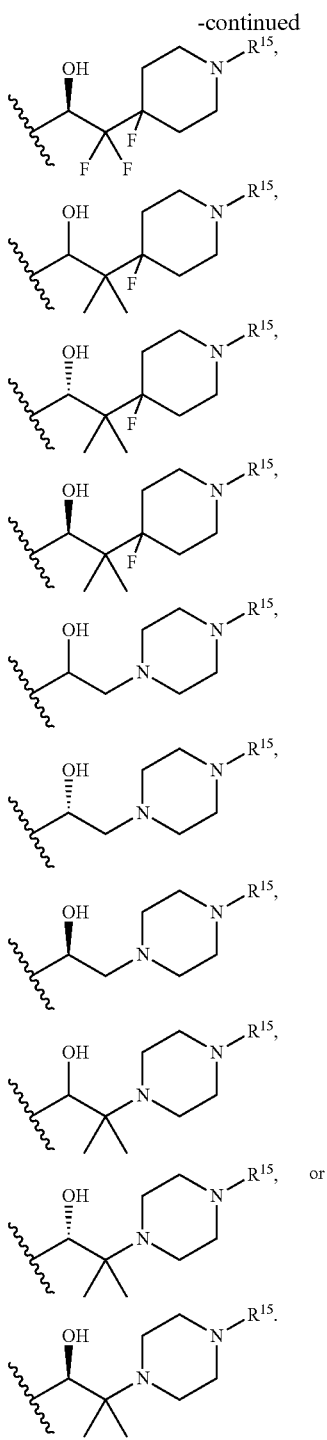

wherein:

$R^{10}$ is H or $C_1$-$C_2$alkyl;

$R^{11}$ is H, $C_1$-$C_3$alkyl, $C_1$-$C_3$haloalkyl, $C_1$-$C_3$cyanoalkyl, $C_2$-$C_3$alkynyl, —$C_1$-$C_3$alkylene-C(O)—NH$_2$, —$C_1$-$C_3$alkylene-C(O)—N(H)—$C_1$-$C_3$alkyl, —$C_1$-$C_3$alkylene-C(O)—N($C_1$-$C_3$alkyl)$_2$, —$C_0$-$C_3$ alkylene-C(O)—O—$C_1$-$C_3$alkyl, $C_1$-$C_3$hydroxyalkyl, —$C_0$-$C_3$ alkylene-$C_3$-$C_6$cycloalkyl optionally substituted with 1-2 $J^3$, —$C_0$-$C_4$alkylene phenyl optionally substituted with 1 $J^3$, —$C_1$-$C_3$ alkylene-SO$_2$-phenyl optionally substituted with 1 $J^3$, —$C_1$-$C_3$ alkylene-SO$_2$—$C_1$-$C_3$ alkyl, —$C_1$-$C_3$ alkylene-NH—SO$_2$—$C_1$-$C_3$ alkyl, $C_1$-$C_3$alkylene-$C_1$-$C_3$alkoxy, $C_1$-$C_3$alkoxycarbonyl, —$C_0$-$C_3$ alkylene-$C_3$-$C_6$cycloalkyl optionally substituted with 1 $J^3$, —$C_0$-$C_3$ alkylene-$C_3$-$C_6$heterocycloalkyl optionally substituted with 1 $J^3$, —$C_0$-$C_3$ alkylene-5-6 membered heteroaryl optionally substituted with 1 $J^3$, or —C(O)-phenyl optionally substituted with 1 $J^3$;

$R^{15}$ is —$C_1$-$C_2$alkylene-$C_1$-$C_2$alkoxy, —$C_0$-$C_1$alkylene phenyl optionally substituted with 1-3 $J^3$, —SO$_2$—$C_1$-$C_3$alkyl, —SO$_2$—$C_1$-$C_3$haloalkyl, —SO$_2$—$C_3$-$C_6$cycloalkyl optionally substituted with 1-3 $J^3$, —SO$_2$-5-6 membered heterocycloalkyl optionally substituted with 1-3 $J^3$, —SO$_2$-5-6 membered heteroaryl optionally substituted with 1-3 $J^3$, —SO$_2$-phenyl optionally substituted with 1-3 $J^3$, —C(O)N(H)SO$_2$—$C_1$-$C_6$alkyl, —C(O)N(H)SO$_2$—$C_1$-$C_6$haloalkyl, —C(O)N(H)SO$_2$—$C_3$-$C_6$cycloalkyl optionally substituted with 1-3 $J^3$, —C(O)N(H)SO$_2$-4-6 membered heterocycloalkyl optionally substituted with 1-3 $J^3$, —C(O)N(H)SO$_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)NR$^{10}$R$^{11}$, —SO$_2$NR$^{10}$R$^{11}$, —SO$_2$—$C_3$-$C_6$cycloalkyl optionally substituted with 1-3 halogens, —CO$_2$-alkyl, COJ$^1$, —CO$_2$J$^2$, or —C(NH$_2$)=N—CN;

$R^{16}$ is H, F, $C_1$-$C_3$alkyl or $C_1$-$C_3$fluoroalkyl;

$R^{17}$ is H, F, $C_1$-$C_3$ alkyl, $C_1$-$C_3$fluoroalkyl, —N(H)SO$_2$—$C_1$-$C_3$alkyl, —SO$_2$—$C_3$-$C_6$cycloalkyl optionally substituted with 1-3 F, —N(H)SO$_2$—$C_1$-$C_3$haloalkyl, or $C_3$-$C_6$cycloalkyl optionally substituted with 1-3 F;

or $R^{16}$ and $R^{17}$, when they both exist, join together with the carbon atom to which they are attached to form one of the following groups (a)-(c):

(a) a $C_3$-$C_6$cycloalkyl optionally substituted with 1-3 groups independently selected from the group consisting of CN, F, $C_1$-$C_3$alkyl, and $C_1$-$C_3$fluoroalkyl, and wherein the $C_3$-$C_6$cycloalkyl is optionally substituted with —N(H)SO$_2$—$C_1$-$C_3$alkyl, —N(H)SO$_2$—$C_3$-$C_6$cycloalkyl optionally substituted with 1-3 F, or —N(H)SO$_2$—$C_1$-$C_3$fluoroalkyl;

(b) a 4-6 membered nitrogen-containing heterocycloalkyl optionally substituted on its carbon atoms with 1-3 groups independently selected from the group consisting of CN, F, $C_1$-$C_3$alkyl, and $C_1$-$C_3$fluoroalkyl, and wherein the nitrogen-containing heterocycloalkyl is optionally N-substituted with —SO$_2$—$C_1$-$C_3$alkyl, —SO$_2$—$C_3$-$C_6$cycloalkyl optionally substituted with 1-3 F, or —SO$_2$—$C_1$-$C_3$fluoroalkyl; or (c) a 4-6 membered heterocycloalkyl containing —O—, —S—, —SO—, or SO$_2$—, wherein the 4-6 membered heterocycloalkyl is optionally substituted on its carbon atoms with 1-3 groups independently selected from the group consisting of CN, F, $C_1$-$C_3$alkyl, and $C_1$-$C_3$fluoroalkyl;

$J^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_1$alkylene-phenyl optionally substituted with 1-3 $J^3$, —$C_0$-$C_1$alkylene-5-6 membered heteroaryl optionally substituted with 1 $J^3$, —$C_0$-$C_3$alkylene-4-6 membered heterocycloalkyl optionally substituted with 1-3 $J^3$;

$J^2$ is H, $C_1$-$C_3$ alkyl, or $C_1$-$C_3$ haloalkyl; and each $J^3$ is independently halogen, $C_1$-$C_4$alkyl, $C_1$-$C_4$haloalkyl, OH, —$C_1$-$C_3$ alkoxy optionally substituted with 1-3 halogens, CN, 5-6 membered heterocycloalkyl, —S(O)$_2$—$C_1$-$C_4$alkyl, —NH$_2$, —N(H)—$C_1$-$C_3$ alkyl, —N($C_1$-$C_3$ alkyl)$_2$ provided that when $J^3$ is attached to nitrogen, $J^3$ cannot be halogen, OH, CN, NH$_2$, —N(H)—$C_1$-$C_3$ alkyl, or —N($C_1$-$C_3$ alkyl)$_2$.

Embodiment 24 of this disclosure relates to Embodiment 23, wherein R⁷ is one of the following groups:
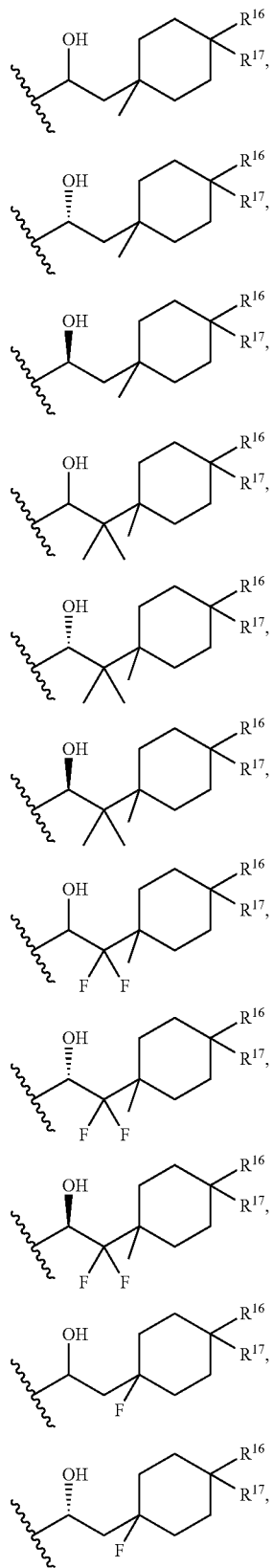
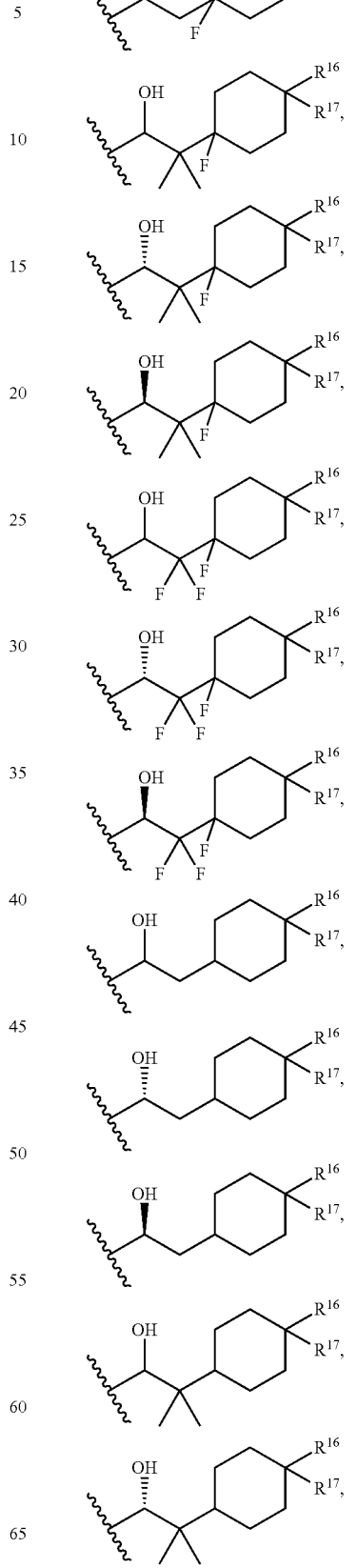

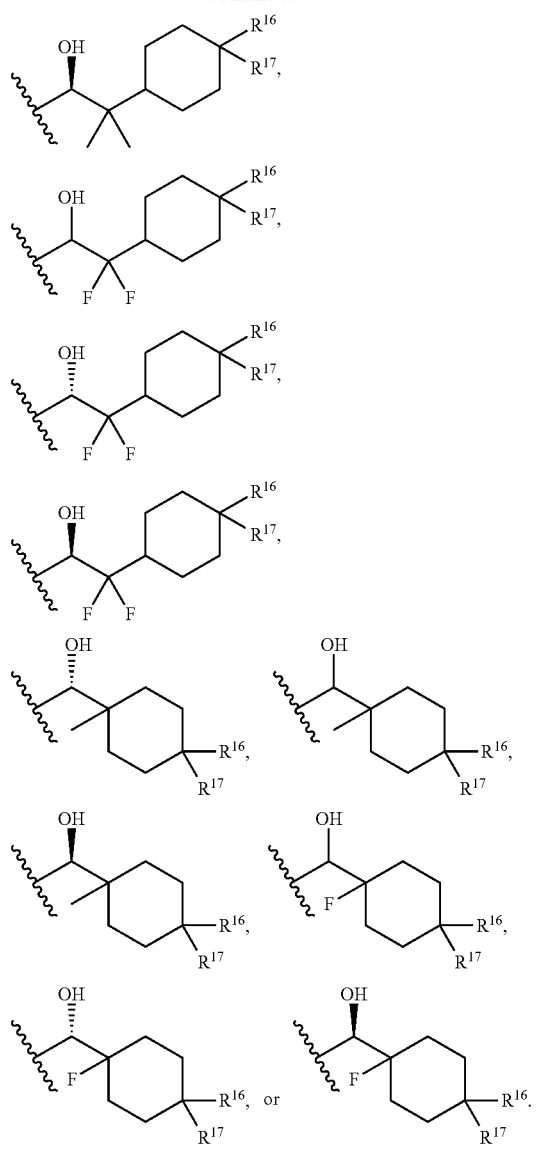
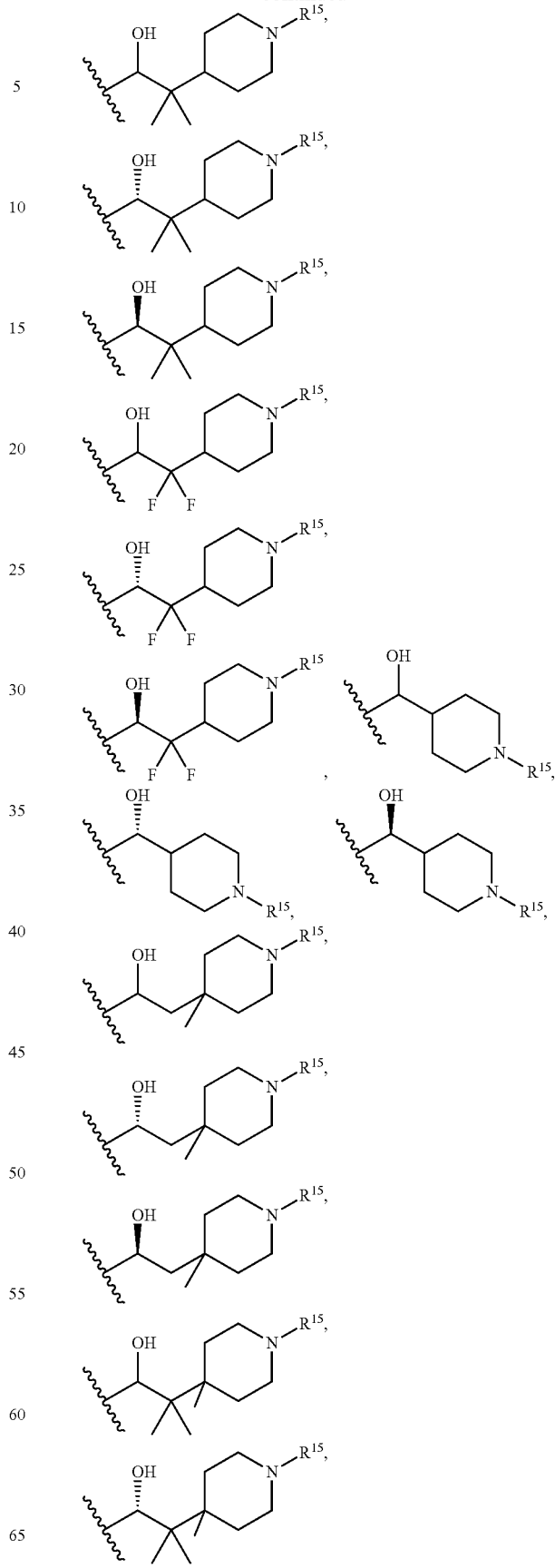
Embodiment 25 of this disclosure relates to Embodiment 24, wherein R⁷ is one of the following groups:
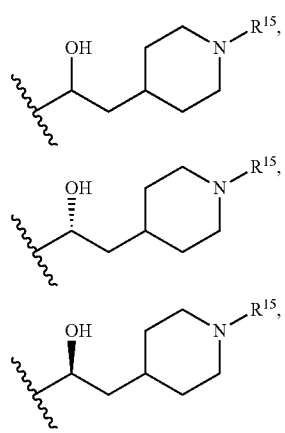

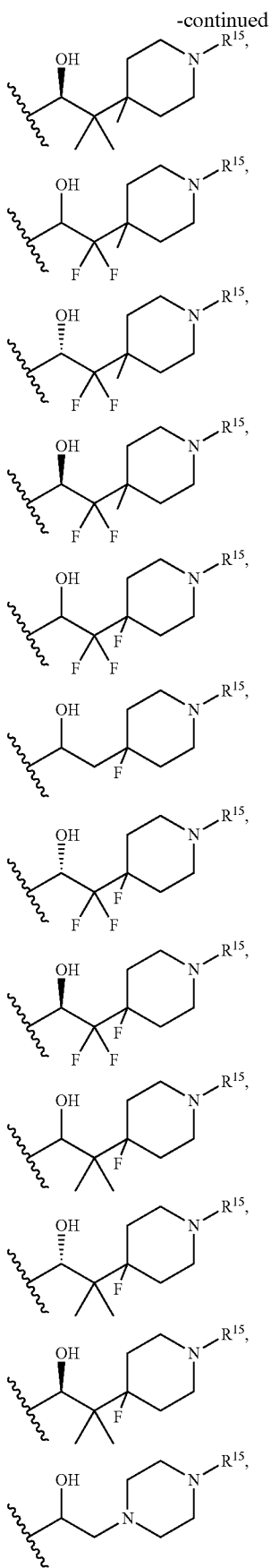
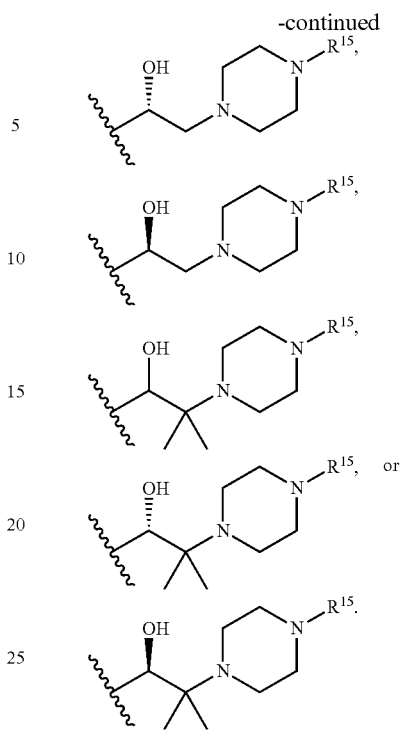

Embodiment 26 of this disclosure relates to any one of Embodiments 18, 19, 20, 23 or 25, wherein $R^{15}$ or $R^{21}$ are one of the following groups: —S(O)$_2$—(CH$_2$)$_2$—CF$_3$, —S(O)$_2$—CH$_2$—CF$_3$, —S(O)$_2$—CH$_3$, —S(O)$_2$—CH(CH$_3$)$_2$, —S(O)$_2$—CH$_2$—CH$_3$, —S(O)$_2$—CH(CH$_3$)$_2$, —S(O)$_2$—C(CH$_3$)$_3$, —S(O)$_2$—CH$_2$CH$_2$CH$_3$, —S(O)$_2$—CH(CH$_3$)-phenyl, —S(O)$_2$—N(H)propyl, —S(O)$_2$—C$_3$-C$_6$cycloalkyl, —S(O)$_2$—(CH$_2$)$_{0-1}$cyclopropyl, —S(O)$_2$—(CH$_2$)$_{0-1}$cyclobutyl, —S(O)$_2$—(CH$_2$)$_{0-1}$cyclopentyl, —S(O)$_2$—(CH$_2$)$_{0-1}$cyclohexyl, —S(O)$_2$—(CH$_2$)$_{0-1}$ tetrahydro-2H-thiopyran 1,1-dioxide, —S(O)$_2$—(CH$_2$)$_{0-1}$tetrahydro-2H-pyran, —S(O)$_2$—(CH$_2$)$_{0-1}$oxetane, —S(O)$_2$—(CH$_2$)$_{0-1}$morpholinyl, —S(O)$_2$—(CH$_2$)$_{0-1}$thiomorpholinyl 1,1-dioxide, —S(O)$_2$—(CH$_2$)$_{0-1}$ isothiozolidine 1,1-dioxide, —S(O)$_2$—CH$_3$—CN, —S(O)$_2$-methoxymethyl, —S(O)$_2$-methoxypropyl, —S(O)$_2$-methoxyethyl, —S(O)$_2$-morpholinyl, —S(O)$_2$-pyridyl, —S(O)$_2$-isoxazolyl optionally substituted with 1-3 methyl, —S(O)$_2$-phenyl optionally substituted with 1-3 substituents selected from the group consisting of F, Cl, alkoxy, and CN, —C(O)—(CH$_2$)$_2$—CF$_3$, —C(O)—CH$_2$—CF$_3$, —C(O)—CH$_3$, —C(O)—CH(CH$_3$)$_2$, —C(O)—CH$_2$—CH$_3$, —C(O)—CH(CH$_3$)$_2$, —C(O)—C(CH$_3$)$_3$, —C(O)—CH$_2$CH$_2$CH$_3$, —C(O)—CH(CH$_3$)-phenyl, —C(O)—N(H)propyl, —C(O)—C$_3$-C$_6$cycloalkyl, —C(O)—(CH$_2$)$_{0-1}$cyclopropyl, —C(O)—(CH$_2$)$_{0-1}$cyclobutyl, —C(O)—(CH$_2$)$_{0-1}$cyclopentyl, —C(O)—(CH$_2$)$_{0-1}$cyclohexyl, —C(O)—(CH$_2$)$_{0-1}$ tetrahydro-2H-thiopyran 1,1-dioxide, —C(O)—(CH$_2$)$_{0-1}$tetrahydro-2H-pyran, —C(O)—(CH$_2$)$_{0-1}$oxetane, —C(O)—(CH$_2$)$_{0-1}$morpholinyl, —C(O)—(CH$_2$)$_{0-1}$ thiomorpholinyl 1,1-dioxide, —C(O)—(CH$_2$)$_{0-1}$ isothiozolidine 1,1-dioxide, —C(O)—CH$_3$—CN, —C(O)-methoxymethyl, —C(O)-methoxypropyl, —C(O)-methoxyethyl, —C(O)-morpholinyl, —C(O)-pyridyl, —C(O)-isoxazolyl optionally substituted with 1-3 methyl, —C(O)-phenyl optionally substituted with 1-3 substituents independently selected from the group consisting of F, Cl, alkoxy, and CN, —S(O)$_2$—N(H)—(CH$_2$)$_2$—CF$_3$, —S(O)$_2$—N(H)—CH$_2$—CF$_3$, —S(O)$_2$—N(H)—CH$_3$, —S(O)$_2$—N(H)—CH(CH$_3$)$_2$, —S(O)$_2$—N(H)—CH$_2$—CH$_3$, —S(O)$_2$—N(H)—CH(CH$_3$)$_2$, —S(O)$_2$—N(H)—C(CH$_3$)$_3$, —S(O)$_2$—N(H)—CH$_2$CH$_2$CH$_3$, —S(O)$_2$—N(H)—CH(CH$_3$)-phenyl, —S(O)$_2$—N(H)-propyl, —S(O)$_2$—N(H)—C$_3$-C$_6$cycloalkyl, —S(O)$_2$—N(H)—(CH$_2$)$_{0-1}$cyclopropyl, —S(O)$_2$—N(H)—(CH$_2$)$_{0-1}$cyclobutyl, —S(O)$_2$—N(H)—(CH$_2$)$_{0-1}$cyclopentyl, —S(O)$_2$—N(H)—(CH$_2$)$_{0-1}$cyclohexyl, —S(O)$_2$—N(H)—(CH$_2$)$_{0-1}$ tetrahydro-2H-thiopyran 1,1-dioxide, —S(O)$_2$—N(H)—(CH$_2$)$_{0-1}$tetrahydro-2H-pyran, —S(O)$_2$—N(H)—(CH$_2$)$_{0-1}$oxetane, —S(O)$_2$—N(H)—(CH$_2$)$_{0-1}$morpholinyl, —S(O)$_2$—N(H)—(CH$_2$)$_{0-1}$ thiomorpholinyl 1,1-dioxide, —S(O)$_2$—N(H)—(CH$_2$)$_{0-1}$ isothiozolidine 1,1-dioxide, —S(O)$_2$—N(H)—CH$_3$—CN, —S(O)$_2$—N(H)-methoxymethyl, —S(O)$_2$—N(H)-methoxypropyl, —S(O)$_2$—N(H)-methoxyethyl, —S(O)$_2$—N(H)-morpholinyl, —S(O)$_2$—N(H)-pyridyl, —S(O)$_2$—N(H)-isoxazolyl optionally substituted with 1-3 methyl, —S(O)$_2$—N(H)-phenyl optionally substituted with 1-3 substituents independently selected from the group consisting of F, Cl, alkoxy, and CN, —C(O)—N(H)(CH$_2$)$_2$—CF$_3$, —C(O)—N(H)CH$_2$—CF$_3$, —C(O)—N(H)CH$_3$, —C(O)—N(H)CH(CH$_3$)$_2$, —C(O)—N(H)CH$_2$—CH$_3$, —C(O)—N(H)CH(CH$_3$)$_2$, —C(O)—N(H)C(CH$_3$)$_3$, —C(O)—N(H)CH$_2$CH$_2$CH$_3$, —C(O)—N(H)—CH$_2$—CH$_2$—S(O)$_2$—CH$_3$, —C(O)—N(H)—CH$_2$—CN, —C(O)—N(H)—CH$_2$—CH$_2$—F, —C(O)—NH$_2$, —C(O)—N(H)CH(CH$_3$)-phenyl, —C(O)—N(H)propyl, —C(O)—N(H)C$_3$-C$_6$cycloalkyl, —C(O)—N(H)(CH$_2$)$_{0-1}$cyclopropyl, —C(O)—N(H)(CH$_2$)$_{0-1}$cyclobutyl, —C(O)—N(H)(CH$_2$)$_{0-1}$cyclopentyl, —C(O)—N(H)(CH$_2$)$_{0-1}$cyclohexyl, —C(O)—N(H)(CH$_2$)$_{0-1}$tetrahydro-2H-thiopyran 1,1-dioxide, —C(O)—N(H)(CH$_2$)$_{0-1}$tetrahydro-2H-pyran, —C(O)—N(H)(CH$_2$)$_{0-1}$oxetane, —C(O)—N(H)(CH$_2$)$_{0-1}$morpholinyl, —C(O)—N(H)(CH$_2$)$_{0-1}$thiomorpholinyl 1,1-dioxide, —C(O)—N(H)(CH$_2$)$_{0-1}$isothiozolidine 1,1-dioxide, —C(O)—N(H)CH$_3$—CN, —C(O)—N(H)-methoxymethyl, —C(O)—N(H)-methoxypropyl, —C(O)—N(H)-methoxyethyl, —C(O)—N(H)-morpholinyl, —C(O)—N(H)-pyridyl, —C(O)—N(H)isoxazolyl optionally substituted with 1-3 methyl, —C(O)—N(H)phenyl optionally substituted with 1-3 substituents independently selected from the group consisting of F, Cl, alkoxy, and CN, —C(O)—N(H)—SO$_2$—(CH$_2$)$_2$—CF$_3$, —C(O)—N(H)—SO$_2$—CH$_2$—CF$_3$, —C(O)—N(H)—SO$_2$—CH$_3$, —C(O)—N(H)—SO$_2$—CH(CH$_3$)$_2$, —C(O)—N(H)—SO$_2$—CH$_2$—CH$_3$, —C(O)—N(H)—SO$_2$—CH(CH$_3$)$_2$, —C(O)—N(H)—SO$_2$—C(CH$_3$)$_3$, —C(O)—N(H)—SO$_2$—CH$_2$CH$_2$CH$_3$, —C(O)—N(H)—SO$_2$—CH(CH$_3$)-phenyl, —C(O)—N(H)—SO$_2$—N(H)propyl, —C(O)—N(H)—SO$_2$—C$_3$-C$_6$cycloalkyl, —C(O)—N(H)—SO$_2$—(CH$_2$)$_{0-1}$cyclopropyl, —C(O)—N(H)—SO$_2$—(CH$_2$)$_{0-1}$cyclobutyl, —C(O)—N(H)—SO$_2$—(CH$_2$)$_{0-1}$-cyclopentyl, —C(O)—N(H)—SO$_2$—(CH$_2$)$_{0-1}$cyclohexyl, —C(O)—N(H)—SO$_2$—(CH$_2$)$_{0-1}$ tetrahydro-2H-thiopyran 1,1-dioxide, —C(O)—N(H)—SO$_2$—(CH$_2$)$_{0-1}$tetrahydro-2H-pyran, —C(O)—N(H)—SO$_2$—(CH$_2$)$_{0-1}$oxetane, —C(O)—N(H)—SO$_2$—(CH$_2$)$_{0-1}$morpholinyl, —C(O)—N(H)—SO$_2$—(CH$_2$)$_{0-1}$ thiomorpholinyl 1,1-dioxide, —C(O)—N(H)—SO$_2$—(CH$_2$)$_{0-1}$ isothiozolidine 1,1-dioxide, —C(O)—N(H)—SO$_2$—CH$_3$—CN, —C(O)—N(H)—SO$_2$-methoxymethyl, —C(O)—N(H)—SO$_2$-methoxypropyl, —C(O)—N(H)—SO$_2$-methoxyethyl, —C(O)—N(H)—SO$_2$-morpholinyl, —C(O)—N(H)—SO$_2$-pyridyl, —C(O)—N(H)—SO$_2$-isoxazolyl optionally substituted with 1-3 methyl, —C(NH$_2$)=N—CN, —C(O)—N(H)—CO-phenyl optionally substituted with 1-3 substituents independently selected from the group consisting of F, Cl, alkoxy, and CN, or —C(O)—N(H)—SO$_2$-phenyl optionally substituted with 1-3 substituents independently selected from the group consisting of F, Cl, alkoxy, and CN.

Sub-Embodiments of Embodiment 26

Embodiment 26(a) of this disclosure relates to Embodiment 26, wherein R$^{15}$ is one of the following groups: —S(O)$_2$—(CH$_2$)$_2$—CF$_3$, —S(O)$_2$—CH$_2$—CF$_3$, —S(O)$_2$—CH$_3$, —S(O)$_2$—CH(CH$_3$)$_2$, —S(O)$_2$—CH$_2$—CH$_3$, —S(O)$_2$—CH(CH$_3$)$_2$, —S(O)$_2$—C(CH$_3$)$_3$, —S(O)$_2$—CH$_2$CH$_2$CH$_3$, —S(O)$_2$—CH(CH$_3$)-phenyl, —S(O)$_2$—N(H)propyl, —S(O)$_2$—C$_3$-C$_6$cycloalkyl, —S(O)$_2$—(CH$_2$)$_{0-1}$cyclopropyl, —S(O)$_2$—(CH$_2$)$_{0-1}$cyclobutyl, —S(O)$_2$—(CH$_2$)$_{0-1}$cyclopentyl, —S(O)$_2$—(CH$_2$)$_{0-1}$cyclohexyl, —S(O)$_2$—(CH$_2$)$_{0-1}$ tetrahydro-2H-thiopyran 1,1-dioxide, —S(O)$_2$—(CH$_2$)$_{0-1}$tetrahydro-2H-pyran, —S(O)$_2$—(CH$_2$)$_{0-1}$oxetane, —S(O)$_2$—(CH$_2$)$_{0-1}$morpholinyl, —S(O)$_2$—(CH$_2$)$_{0-1}$ thiomorpholinyl 1,1-dioxide, —S(O)$_2$—(CH$_2$)$_{0-1}$ isothiozolidine 1,1-dioxide, —S(O)$_2$—CH$_3$—CN, —S(O)$_2$-methoxymethyl, —S(O)$_2$-methoxypropyl, —S(O)$_2$-methoxyethyl, —S(O)$_2$-morpholinyl, —S(O)$_2$-pyridyl, —S(O)$_2$-isoxazolyl optionally substituted with 1-3 methyl, or —S(O)$_2$-phenyl optionally substituted with 1-3 substituents selected from the group consisting of F, Cl, alkoxy, and CN.

Embodiment 26(b) of this disclosure relates to Embodiment 26, wherein R$^{15}$ is one of the following groups: —C(O)—(CH$_2$)$_2$—CF$_3$, —C(O)—CH$_2$—CF$_3$, —C(O)—CH$_3$, —C(O)—CH(CH$_3$)$_2$, —C(O)—CH$_2$—CH$_3$, —C(O)—CH(CH$_3$)$_2$, —C(O)—C(CH$_3$)$_3$, —C(O)—CH$_2$CH$_2$CH$_3$, —C(O)—CH(CH$_3$)-phenyl, —C(O)—N(H)propyl, —C(O)—C$_3$-C$_6$cycloalkyl, —C(O)—(CH$_2$)$_{0-1}$cyclopropyl, —C(O)—(CH$_2$)$_{0-1}$cyclobutyl, —C(O)—(CH$_2$)$_{0-1}$cyclopentyl, —C(O)—(CH$_2$)$_{0-1}$cyclohexyl, —C(O)—(CH$_2$)$_{0-1}$ tetrahydro-2H-thiopyran 1,1-dioxide, —C(O)—(CH$_2$)$_{0-1}$tetrahydro-2H-pyran, —C(O)—(CH$_2$)$_{0-1}$oxetane, —C(O)—(CH$_2$)$_{0-1}$morpholinyl, —C(O)—(CH$_2$)$_{0-1}$ thiomorpholinyl 1,1-dioxide, —C(O)—(CH$_2$)$_{0-1}$ isothiozolidine 1,1-dioxide, —C(O)—CH$_3$—CN, —C(O)-methoxymethyl, —C(O)-methoxypropyl, —C(O)-methoxyethyl, —C(O)-morpholinyl, —C(O)-pyridyl, —C(O)-isoxazolyl optionally substituted with 1-3 methyl, or —C(O)-phenyl optionally substituted with 1-3 substituents independently selected from the group consisting of F, Cl, alkoxy, and CN.

Embodiment 26(c) of this disclosure relates to Embodiment 26, wherein R$^{15}$ or R$^{21}$ are one of the following groups: —S(O)$_2$—N(H)—(CH$_2$)$_2$—CF$_3$, —S(O)$_2$—N(H)—CH$_2$—CF$_3$, —S(O)$_2$—N(H)—CH$_3$, —S(O)$_2$—N(H)—CH(CH$_3$)$_2$, —S(O)$_2$—N(H)—CH$_2$—CH$_3$, —S(O)$_2$—N(H)—CH(CH$_3$)$_2$, —S(O)$_2$—N(H)—C(CH$_3$)$_3$, —S(O)$_2$—N(H)—CH$_2$CH$_2$CH$_3$, —S(O)$_2$—N(H)—CH(CH$_3$)-phenyl, —S(O)$_2$—N(H)-propyl, —S(O)$_2$—N(H)—C$_3$-C$_6$cycloalkyl, —S(O)$_2$—N(H)—(CH$_2$)$_{0-1}$cyclopropyl, —S(O)$_2$—N(H)—(CH$_2$)$_{0-1}$cyclobutyl, —S(O)$_2$—N(H)—(CH$_2$)$_{0-1}$cyclopentyl, —S(O)$_2$—N(H)—(CH$_2$)$_{0-1}$cyclohexyl, —S(O)$_2$—N(H)—(CH$_2$)$_{0-1}$ tetrahydro-2H-thiopyran 1,1-dioxide, —S(O)$_2$—N(H)—(CH$_2$)$_{0-1}$tetrahydro-2H-pyran, —S(O)$_2$—N(H)—(CH$_2$)$_{0-1}$oxetane, —S(O)$_2$—N(H)—(CH$_2$)$_{0-1}$morpholinyl, —S(O)$_2$—N(H)—(CH$_2$)$_{0-1}$ thiomorpholinyl 1,1-dioxide, —S(O)$_2$—N(H)—(CH$_2$)$_{0-1}$ isothiozolidine 1,1-dioxide, —S(O)$_2$—N(H)—CH$_3$—CN, —S(O)$_2$—N(H)-methoxymethyl, —S(O)$_2$—N(H)-methoxypropyl, —S(O)$_2$—N(H)-methoxyethyl, —S(O)$_2$—N(H)-morpholinyl, —S(O)$_2$—N(H)-pyridyl, —S(O)$_2$—N(H)-isoxazolyl optionally substituted with 1-3 methyl, or —S(O)₂—N(H)-phenyl optionally substituted with 1-3 substituents independently selected from the group consisting of F, Cl, alkoxy, and CN.

Embodiment 26(d) of this disclosure relates to Embodiments 26, wherein R¹⁵ is one of the following groups: —C(O)—N(H)(CH₂)₂—CF₃, —C(O)—N(H)CH₂—CF₃, —C(O)—N(H)CH₃, —C(O)—N(H)CH(CH₃)₂, —C(O)—N(H)CH₂—CH₃, —C(O)—N(H)CH(CH₃)₂, —C(O)—N(H)C(CH₃)₃, —C(O)—N(H)CH₂CH₂CH₃, —C(O)—N(H)C(CH₃)₃, —C(O)—N(H)CH₂CH₂CH₃, —C(O)—N(H)CH(CH₃)-phenyl, —C(O)—N(H)propyl, —C(O)—N(H)C₃-C₆cycloalkyl, —C(O)—N(H)(CH₂)₀₋₁cyclopropyl, —C(O)—N(H)(CH₂)₀₋₁cyclobutyl, —C(O)—N(H)(CH₂)₀₋₁cyclopentyl, —C(O)—N(H)(CH₂)₀₋₁cyclohexyl, —C(O)—N(H)(CH₂)₀₋₁tetrahydro-2H-thiopyran 1,1-dioxide, —C(O)—N(H)(CH₂)₀₋₁tetrahydro-2H-pyran, —C(O)—N(H)(CH₂)₀₋₁oxetane, —C(O)—N(H)(CH₂)₀₋₁morpholinyl, —C(O)—N(H)(CH₂)₀₋₁ thiomorpholinyl 1,1-dioxide, —C(O)—N(H)(CH₂)₀₋₁ isothiozolidine 1,1-dioxide, —C(O)—N(H)CH₃—CN, —C(O)—N(H)-methoxymethyl, —C(O)—N(H)-methoxypropyl, —C(O)—N(H)-methoxyethyl, —C(O)—N(H)-morpholinyl, —C(O)—N(H)-pyridyl, —C(O)—N(H)isoxazolyl optionally substituted with 1-3 methyl, or —C(O)—N(H)phenyl optionally substituted with 1-3 substituents independently selected from the group consisting of F, Cl, alkoxy, and CN.

Embodiment 26(e) of this disclosure relates to Embodiment 26, wherein R¹⁵ is one of the the following groups: —C(O)—N(H)—SO₂—(CH₂)₂—CF₃, —C(O)—N(H)—SO₂—CH₂—CF₃, —C(O)—N(H)—SO₂—CH₃, —C(O)—N(H)—SO₂—CH(CH₃)₂, —C(O)—N(H)—SO₂—CH₂—CH₃, —C(O)—N(H)—SO₂—CH(CH₃)₂, —C(O)—N(H)—SO₂—C(CH₃)₃, —C(O)—N(H)—SO₂—CH₂CH₂CH₃, —C(O)—N(H)—SO₂—CH(CH₃)-phenyl, —C(O)—N(H)—SO₂—N(H)propyl, —C(O)—N(H)—SO₂—C₃-C₆cycloalkyl, —C(O)—N(H)—SO₂—(CH₂)₀₋₁cyclopropyl, —C(O)—N(H)—SO₂—(CH₂)₀₋₁cyclobutyl, —C(O)—N(H)—SO₂—(CH₂)₀₋₁cyclopentyl, —C(O)—N(H)—SO₂—(CH₂)₀₋₁cyclohexyl, —C(O)—N(H)—SO₂—(CH₂)₀₋₁ tetrahydro-2H-thiopyran 1,1-dioxide, —C(O)—N(H)—SO₂—(CH₂)₀₋₁tetrahydro-2H-pyran, —C(O)—N(H)—SO₂—(CH₂)₀₋₁oxetane, —C(O)—N(H)—SO₂—(CH₂)₀₋₁morpholinyl, —C(O)—N(H)—SO₂—(CH₂)₀₋₁ thiomorpholinyl 1,1-dioxide, —C(O)—N(H)—SO₂—(CH₂)₀₋₁ isothiozolidine 1,1-dioxide, —C(O)—N(H)—SO₂—CH₃—CN, —C(O)—N(H)—SO₂-methoxymethyl, —C(O)—N(H)—SO₂-methoxypropyl, —C(O)—N(H)—SO₂-methoxyethyl, —C(O)—N(H)—SO₂-morpholinyl, —C(O)—N(H)—SO₂-pyridyl, —C(O)—N(H)—SO₂-isoxazolyl optionally substituted with 1-3 methyl, or C(O)—N(H)—SO₂-phenyl optionally substituted with 1-3 substituents independently selected from the group consisting of F, Cl, alkoxy, and CN, or —C(O)—N(H)—SO₂-phenyl optionally substituted with 1-3 substituents independently selected from the group consisting of F, Cl, alkoxy, and CN.

Embodiment 27 relates to any one of Embodiments 1-13, including any of the sub-embodiments of Embodiments 4 and 8, wherein R⁷ is one of the following groups:

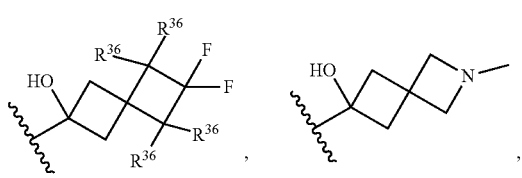

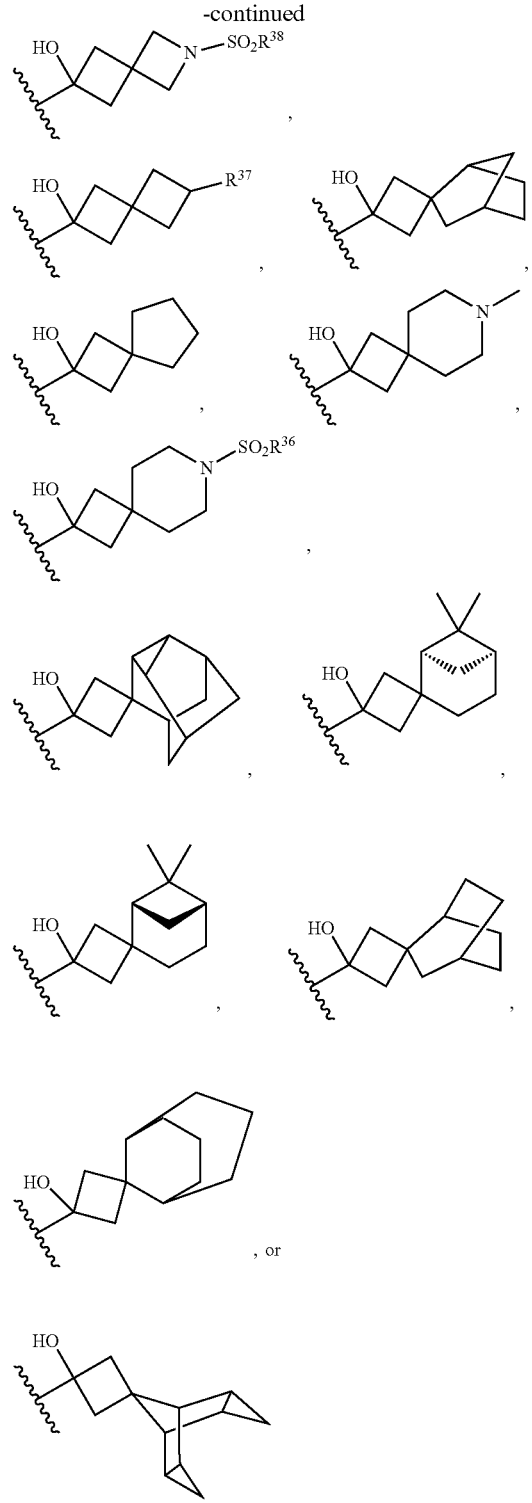

wherein:

R³⁶ is H or C₁-C₃ alkyl optionally substituted with 1-3 F; and

R³⁷ is H, —N(H)SO₂R³⁶ or —SO₂R³⁶; and

R³⁸ is C₁-C₃ alkyl optionally substituted with 1-3 F.

Embodiment 28 of this disclosure relates to Embodiment 26, wherein R⁷ is one of the following groups:

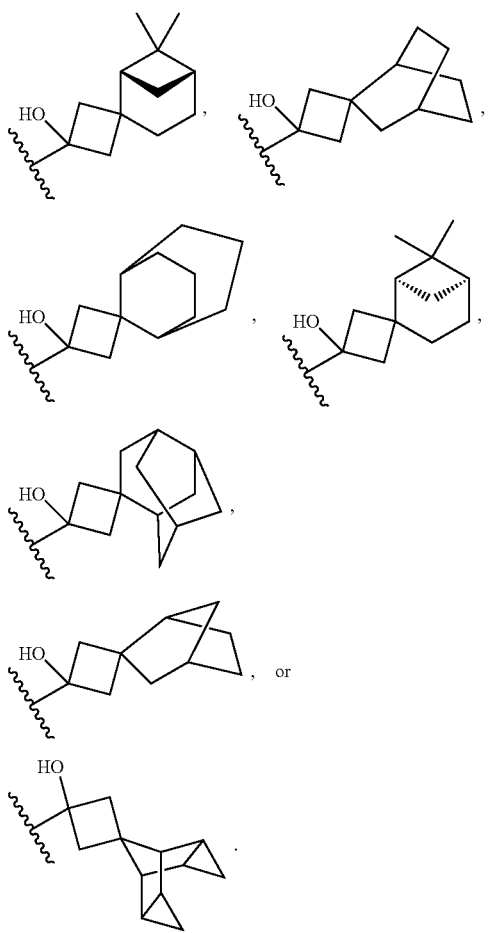

Embodiment 29 relates to any one of Embodiments 1-13, including any of the sub-embodiments of Embodiments 4 and 8, wherein $R^7$ is one of the following groups:

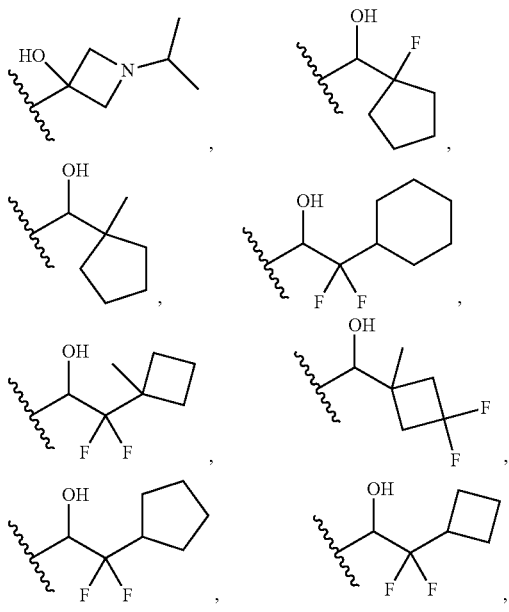

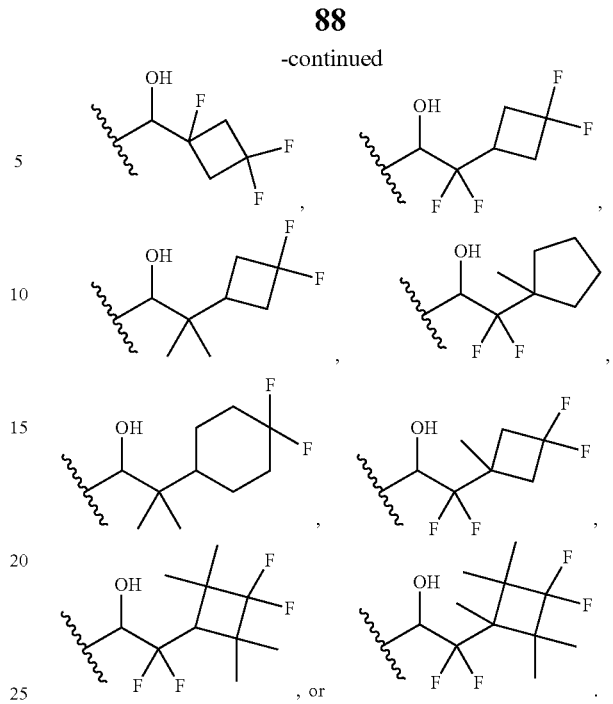

Embodiment 30 of this disclosure relates to Embodiment 1 selected from Table 1.

In other sub-embodiments of Embodiments 4, 8 and 12, including any of the sub-embodiments thereof, $Z^5$ is —SO$_2$—C$_1$-C$_4$alkyl.

In other sub-embodiments of Embodiments 4, 8 and 12, including any of the sub-embodiments thereof, $Z^5$ is —SO$_2$—CH$_3$.

In other sub-embodiments of Embodiments 4, 8 and 12, including any of the sub-embodiments thereof, $Z^5$ is SO$_2$—C$_1$-C$_4$haloalkyl.

In other sub-embodiments of Embodiments 4, 8 and 12, including any of the sub-embodiments thereof, $Z^5$ is —SO$_2$—C$_3$-C$_6$cycloalkyl optionally substituted with 1-3 J$^3$, wherein J$^3$ is as defined in the respective embodiment.

In other sub-embodiments of Embodiments 4, 8 and 12, including any of the sub-embodiments thereof, $Z^5$ is —C(O)NHR$^{11}$, wherein R$^{11}$ H.

In other sub-embodiments of Embodiments 4, 8 and 12, including any of the sub-embodiments thereof, $Z^5$ is —C(O)NHR$^{11}$, wherein R$^{11}$ is C$_1$-C$_3$alkyl.

In other sub-embodiments of Embodiments 4, 8 and 12, including any of the sub-embodiments thereof, $Z^5$ is —C(O)NHR$^{11}$, wherein R$^{11}$ is C$_1$-C$_3$haloalkyl.

In other sub-embodiments of Embodiments 4, 8 and 12, including any of the sub-embodiments thereof, $Z^5$ is —C(O)N$^{11}$R$^{11}$, wherein R$^{11}$ is C$_1$-C$_4$cyanoalkyl.

In other sub-embodiments of Embodiments 4, 8 and 12, including any of the sub-embodiments thereof, $Z^5$ is —C(O)NHR$^{11}$, wherein R$^{11}$ is C$_2$-C$_4$alkynyl.

In other sub-embodiments of Embodiments 4, 8 and 12, including any of the sub-embodiments thereof, $Z^5$ is —C(O)NHR$^{11}$, wherein R$^{11}$ is —C$_1$-C$_4$alkylene-C(O)—NH$_2$.

In other sub-embodiments of Embodiments 4, 8 and 12, including any of the sub-embodiments thereof, $Z^5$ is —C(O)NHR$^{11}$, wherein R$^H$ is —C$_1$-C$_4$alkylene-C(O)—N(H)—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C$_1$-C$_4$alkylene-C(O)—N(C$_1$-C$_4$alkyl)$_2$.

In other sub-embodiments of Embodiments 4, 8 and 12, including any of the sub-embodiments thereof, $Z^5$ is —C(O)NHR$^{11}$, wherein R$^{11}$ is —C$_0$-C$_4$ alkylene-C(O)—O—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is C$_1$-C$_4$hydroxyalkyl.

In other sub-embodiments of Embodiments 4, 8 and 12, including any of the sub-embodiments thereof, $Z^5$ is —C(O)NHR$^{11}$, wherein R$^{11}$ is —C$_0$-C$_4$alkylene-phenyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C$_1$-C$_3$ alkylene-SO$_2$-phenyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C$_1$-C$_3$ alkylene-SO$_2$—C$_1$-C$_6$ alkyl.

In other sub-embodiments of Embodiments 4, 8 and 12, including any of the sub-embodiments thereof, $Z^5$ is —C(O)NHR$^{11}$, wherein R$^{11}$ is —C$_1$-C$_3$ alkylene-NH—SO$_2$—C$_1$-C$_6$ alkyl.

In other sub-embodiments of Embodiments 4, 8 and 12, including any of the sub-embodiments thereof, $Z^5$ is —C(O)NHR$^{11}$, wherein R$^{11}$ is —C$_1$-C$_4$alkylene-C$_1$-C$_4$alkoxy.

In other sub-embodiments of Embodiments 4, 8 and 12, including any of the sub-embodiments thereof, $Z^5$ is —C(O)NHR$^{11}$, wherein R$^{11}$ is C$_1$-C$_4$alkoxycarbonyl.

In other sub-embodiments of Embodiments 4, 8 and 12, including any of the sub-embodiments thereof, $Z^5$ is —C(O)NHR$^{11}$, wherein R$^{11}$ is —C$_0$-C$_4$ alkylene-C$_3$-C$_6$cycloalkyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C$_0$-C$_4$ alkylene-3-6 membered heterocycloalkyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C$_0$-C$_4$ alkylene-5-6 membered heteroaryl.

In other sub-embodiments of Embodiments 4, 8 and 12, including any of the sub-embodiments thereof, $Z^5$ is —C(O)NHR$^{11}$, wherein R$^{11}$ is optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —C(O)NHR$^{11}$, wherein R$^{11}$ is —C(O)-phenyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is —CO$_2$-alkyl.

In other sub-embodiments of Embodiments 4, 8 and 12, including any of the sub-embodiments thereof, $Z^5$ is COJ$^1$, wherein J$^1$ is as defined in the respective embodiment.

In other sub-embodiments of Embodiments 4, 8 and 12, including any of the sub-embodiments thereof, $Z^5$ is COJ$^1$, wherein J$^1$ is is C$_1$-C$_4$alkyl.

In other sub-embodiments of Embodiments 4, 8 and 12, including any of the sub-embodiments thereof, $Z^5$ is COJ$^1$, wherein J$^1$ is —C$_1$-C$_4$alkylene-C$_1$-C$_4$alkoxy.

In other sub-embodiments of Embodiments 4, 8 and 12, including any of the sub-embodiments thereof, $Z^5$ is COJ$^1$, wherein J$^1$ is C$_1$-C$_4$cyanoalkyl.

In other sub-embodiments of Embodiments 4, 8 and 12, including any of the sub-embodiments thereof, $Z^5$ is COJ$^1$, wherein J$^1$ is C$_1$-C$_4$hydroxyalkyl.

In other sub-embodiments of Embodiments 4, 8 and 12, including any of the sub-embodiments thereof, $Z^5$ is COJ$^1$, wherein J$^1$ is C$_0$-C$_3$ alkylene-C$_3$-C$_6$ cycloalkyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is COJ$^1$, wherein J$^1$ is C$_0$-C$_3$ alkylene-phenyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is COJ$^1$, wherein J$^1$ is —C$_0$-C$_3$ alkylene-5-6 membered heteroaryl optionally substituted with 1-3 J$^3$, wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is COJ$^1$, wherein J$^1$ is —C$_0$-C$_3$ alkylene-4-6 membered heterocycloalkyl optionally substituted with 1-3 J$^3$, and wherein each J$^3$ is independently halogen, C$_1$-C$_4$alkyl, C$_1$-C$_4$haloalkyl, OH, C$_1$-C$_4$alkoxy optionally substituted with 1-3 halogens, CN, 4-6 membered heterocycloalkyl, or —S(O)$_2$—C$_1$-C$_4$alkyl.

In other sub-embodiments of Embodiments 4, 8 and 12, including any of the sub-embodiments thereof, $Z^5$ is CO$_2$J$^2$, wherein J$^2$ is as defined in the respective embodiment.

In other sub-embodiments of Embodiments 4, 8 and 12, including any of the sub-embodiments thereof, $Z^5$ is CO$_2$J$^2$, wherein J$^2$ is H.

In other sub-embodiments of Embodiments 4, 8 and 12, including any of the sub-embodiments thereof, $Z^5$ is CO$_2$J$^2$, wherein J$^2$ is C$_1$-C$_4$alkyl.

In other sub-embodiments of Embodiments 4, 8 and 12, including any of the sub-embodiments thereof, $Z^5$ is CO$_2$J$^2$, wherein J$^2$ is or C$_1$-C$_4$haloalkyl.

Embodiment 1Z of this disclosure relates to a compound of I(a):

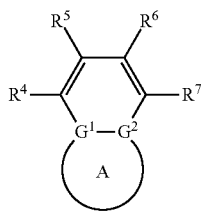

I(a)

or a pharmaceutically acceptable salt, a solvate, a tautomer, an isomer or a deuterated analog thereof, wherein:
ring A is

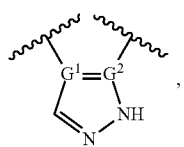

wherein $G^1$ and $G^2$ are each C; or
ring A

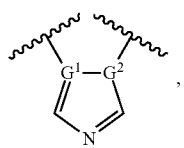

is wherein $G^1$ is C and $G^2$ is N; or
ring A is

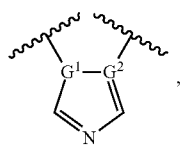

wherein $G^1$ is N and $G^2$ is C;
$R^4$, $R^5$ and $R^6$ are each independently H, halogen, alkyl, haloalkyl, —OCH$_3$ optionally substituted with 1-3 halogens, or $C_3$-$C_6$cycloalkyl optionally substituted with 1-3 halogens, provided that when ring A is

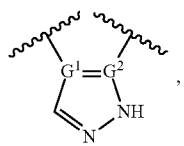

at least one of $R^4$, $R^5$ or $R^6$ is not H;
or $R^5$ and $R^6$, together with the carbon atoms to which they are attached, join to form a 4-6 membered carbocyclic or heterocyclic ring each being optionally substituted on its carbon atoms with one or more substituents selected from the group consisting of halogen, alkyl and haloalkyl;
or $R^4$ and $R^5$, together with the carbon atoms to which they are attached, join to form a 4-6 membered carbocyclic or heterocyclic ring each being optionally substituted on its carbon atoms with one or more substituents selected from the group consisting of halogen, alkyl and haloalkyl;
$R^7$ is one of the following groups (a)-(e):
(a) cycloalkenyl optionally substituted with 1-7 $Z^1$, and further optionally substituted with 1 $Z^4$;
(b) heterocycloalkyl optionally substituted with 1-9 $Z^2$, and further optionally substituted with 1 $Z^5$;
(c) a bridged heterocyclic ring optionally substituted with 1-5 $Z^2$, and further optionally substituted with 1 $Z^5$;
(d) a spiro ring system containing two heterocycloalkyl groups joined by one common spiro carbon atom, wherein the spiro ring system is optionally substituted on its carbon atoms with 1-8 $Z^3$ and wherein the spiro ring system can also be optionally N-substituted with alkyl, haloalkyl, —CO$_2$-alkyl, —C(O)NR$^{10}$R$^{11}$, —SO$_2$NR$^{10}$R$^{11}$, —SO$_2$-alkyl, SO$_2$-haloalkyl, or —SO$_2$-cycloalkyl substituted with 1-6 halogens; or (e)

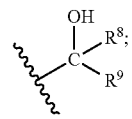

$R^8$ is H, F, Cl, —CH$_3$, —CFH$_2$, —CF$_2$H or —CF$_3$;
$R^9$ is —(CY$_2$)$_{0-3}$—R$^{12}$;
or $R^8$ and $R^9$ join together with the carbon atom to which they are attached to form one of the following groups (a)-(e):
(a) a cycloalkyl optionally substituted with 1-9 $Z^2$, and further optionally substituted with 1 $Z^5$ or 1-2 $Z^6$;
(b) a heterocycloalkyl optionally substituted with 1-9 $Z^2$, and further optionally substituted with 1 $Z^5$;
(c) a spiro ring system containing two cycloalkyl groups joined by one common spiro carbon atom, wherein the spiro ring system is optionally substituted with 1-9 $Z^2$, and further optionally substituted with 1 $Z^5$ or 1-2 $Z^6$;
(d) a spiro ring system containing one cycloalkyl and one heterocycloalkyl joined by one common spiro carbon atom, wherein the spiro ring system is optionally substituted on its carbon atoms with 1-9 $Z^3$, and wherein the spiro ring system can also be optionally N-substituted with alkyl, haloalkyl, —CO$_2$-alkyl, —C(O)NR$^{10}$R$^{11}$, —SO$_2$NR$^{10}$R$^{11}$, —SO$_2$-alkyl, SO$_2$-haloalkyl, or —SO$_2$-cycloalkyl substituted with 1-6 halogens; or
(e) a spiro ring system containing one cycloalkyl and one a bridged ring joined by one common spiro carbon atom, wherein the spiro ring system is optionally substituted with 1-5 $Z^2$, and further optionally substituted with 1 $Z^5$;
$R^{10}$ is H, alkyl, or haloalkyl;
$R^{11}$ is H, alkyl or haloalkyl;
$R^{12}$ is one of the following groups (a)-(f):
(a) a saturated cycloalkyl optionally substituted with 1-9 $Z^2$, and further optionally substituted with 1 $Z^5$ or 1-2 $Z^6$;
(b) an unsaturated cycloalkyl optionally substituted with 1-7 $Z^2$, and further optionally substituted with 1 $Z^5$;
(c) a heterocycloalkyl optionally substituted 1-9 $Z^2$, and further optionally substituted with 1 $Z^5$;
(d) phenyl optionally substituted with 1-2 $Z^2$;
(e) a bridged ring optionally substituted with 1-5 $Z^2$; or
(f) heteroaryl optionally substituted with 1-2 $Z^2$;
each Y is independently H, halogen, alkyl, or haloalkyl, or 2 Y groups join together with the carbon atom to which they are attached to form a cycloalkyl optionally substituted with 1-3 halogens;
each $Z^1$ is independently CN, halogen, alkyl, or haloalkyl;

each $Z^2$ is independently CN, halogen, alkyl, cycloalkyl, haloalkyl, —NH$_2$, —N(H)alkyl, —N(alkyl)$_2$, alkoxyl optionally substituted with halo or phenyl, 5-6 membered heterocycloalkyl, or 5-6 membered heteroaryl;

each $Z^3$ is independently CN, halogen, alkyl or haloalkyl;

$Z^4$ is alkoxyalkyl, phenyl optionally substituted with 1-3 halogens, —SO$_2$-alkyl, —SO$_2$-haloalkyl, —SO$_2$-cycloalkyl optionally substituted with 1-6 halogens, —C(O)NR$^{10}$R$^{11}$, —SO$_2$NR$^{10}$R$^{11}$, —NHSO$_2$-alkyl, —NHSO$_2$-cycloalkyl optionally substituted with 1-6 halogens, or —NHSO$_2$-haloalkyl;

$Z^5$ is alkoxyalkyl, —SO$_2$-alkyl, —CO$_2$-alkyl, —SO$_2$-haloalkyl, —C(O)NR$^{10}$R$^{11}$, —SO$_2$NR$^{10}$R$^{11}$, —SO$_2$-cycloalkyl optionally substituted with 1-6 halogens, —C(O)NR$^{10}$R$^{11}$, —SO$_2$NR$^{10}$R$^{11}$, —NHSO$_2$-alkyl, —NHSO$_2$-aryl, —NHSO$_2$-cycloalkyl optionally substituted with 1-6 halogens, or —NHSO$_2$-haloalkyl, provided that when $Z^5$ is attached to nitrogen, $Z^5$ cannot be halogen, —NHSO$_2$-alkyl, —NHSO$_2$-aryl, —NHSO$_2$-cycloalkyl optionally substituted with 1-6 halogens, or —NHSO$_2$-haloalkyl; and each $Z^6$ is independently halo, alkyl, haloalkyl, CN, OH, cycloalkyl, aryl or heteroaryl, provided that only one $Z^6$ can be OH.

Embodiment 1(b)Z of this disclosure relates to Embodiment 1Z, wherein:

$R^5$ and $R^6$, together with the carbon atoms to which they are attached, join to form a 4-6 membered carbocyclic or heterocyclic ring each being optionally substituted on its carbon atoms with one or more substituents selected from the group consisting and halogen, alkyl and haloalkyl;

or $R^4$ and $R^5$, together with the carbon atoms to which they are attached, join to form a 4-6 membered carbocyclic or heterocyclic ring each being optionally substituted on its carbon atoms with one or more substituents selected from the group consisting of halogen, alkyl and haloalkyl.

Embodiment 1(c)Z of this disclosure relates to Embodiment 1 Z, wherein $R^7$ is group (e):

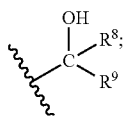
(e)

$R^8$ is H, F, —CH$_3$, —CFH$_2$, —CF$_2$H or —CF$_3$;
$R^9$ is —(CY$_2$)$_{0-2}$—R$^{12}$;
or $R^8$ and $R^9$ join together with the carbon atom to which they are attached to form group (e):
(e) a spiro ring system containing one cycloalkyl and one a bridged ring joined by one common spiro carbon atom, wherein the spiro ring system is optionally substituted with 1-5 $Z^2$, and further optionally substituted with 1 $Z^5$; and
$R^{12}$ is group (e):
(e) a bridged ring optionally substituted with 1-5 $Z^2$.

It has been found that the compounds the of this disclosure, wherein ring A is

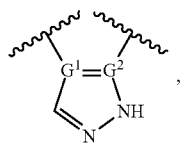

and wherein $G^1$ and $G^2$ are each C; have surprising and unexpected IDO1 biochemical and cellular potency, as measured by the biochemical and cellular assays described in this disclosure, when compared to compounds wherein the only difference is when ring A is

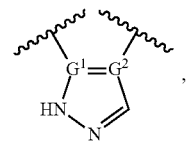

wherein $G^1$ and $G^2$ are each C.

Embodiment 2 Z of this disclosure relates to Embodiment 1 Z having Formula (Ib), (Ic), or (Id):

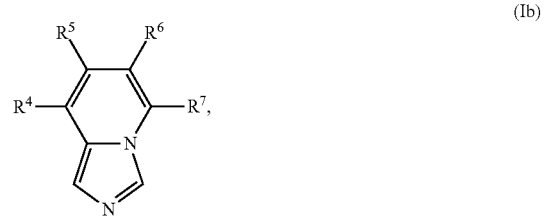
(Ib)

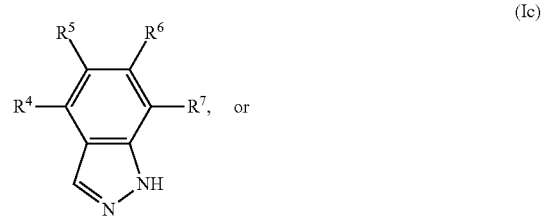
(Ic)

(Id)

or a pharmaceutically acceptable salt, a solvate, a tautomer, an isomer or a deuterated analog thereof, wherein:

$R^4$ is H, F, Cl, Br, —OCH$_3$ optionally substituted with 1-3 halogens, cyclopropyl, C$_1$-C$_3$alkyl, or C$_1$-C$_3$haloalkyl;

$R^5$ and $R^6$ are each independently H, F, Cl, Br, —OCH$_3$ optionally substituted with 1-3 halogens, C$_1$-C$_3$alkyl, C$_1$-C$_3$haloalkyl, or C$_3$-C$_5$cycloalkyl optionally substituted with 1-3 halogens, provided that at least one of $R^5$ or $R^6$ is not H;

or $R^5$ and $R^6$, together with the carbon atoms to which they are attached, join to form a 4-6 membered carbocyclic or a heterocyclic ring containing at least one oxygen or sulfur atom, each ring being optionally substituted on its carbon atoms with 1-4 substituents selected from the group consisting of F, Cl, C$_1$-C$_3$alkyl and C$_1$-C$_3$haloalkyl;

or $R^4$ and $R^5$, together with the carbon atoms to which they are attached, join to form a 4-6 membered carbocyclic or an heterocyclic ring containing at least one oxygen or sulfur atom, each ring being optionally substituted on its carbon atoms with 1-4 substituents selected from the group consisting of F, Cl, C$_1$-C$_3$alkyl and C$_1$-C$_3$haloalkyl;

$R^7$ is one of the following groups (a)-(e):
(a) cycloalkyenyl optionally substituted with 1-6 $Z^1$, and further optionally substituted with 1 $Z^4$;

(b) heterocycloalkyl optionally substituted with 1-8 $Z^2$, and further optionally substituted with 1 $Z^5$;

(c) a bridged nitrogen-containing heterocyclic ring optionally substituted with 1-4 $Z^2$, and further optionally substituted with 1 $Z^5$;

(d) a spiro ring system containing two nitrogen-containing heterocycloalkyl groups joined by one common spiro carbon atom, wherein the spiro ring system is optionally substituted on its carbon atoms with 1-7 $Z^3$, and wherein the spiro ring system can also be optionally N-substituted with alkyl, haloalkyl, —SO$_2$-alkyl, —SO$_2$-haloalkyl; —CO$_2$-alkyl, —C(O)NR$^{10}$R$^{11}$, —SO$_2$NR$^{10}$R$^{11}$, or —SO$_2$-cycloalkyl substituted with 1-5 halogens; or

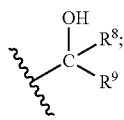
(e)

$R^8$ is H, F or CH$_3$;
$R^9$ is —(CY$_2$)$_{0-2}$—R$^{12}$;
or $R^8$ and $R^9$ join together with the carbon atom to which they are attached to form one of the following groups (a)-(e):

(a) a cycloalkyl optionally substituted with 1-8 $Z^2$, and further optionally substituted with 1 $Z^5$ or 1-2 $Z^6$;

(b) a heterocycloalkyl optionally substituted with 1-8 $Z^2$, and further optionally substituted with 1 $Z^5$;

(c) a spiro ring system containing two cycloalkyl groups joined by one common spiro carbon atom, wherein the spiro ring system is optionally substituted with 1-8 $Z^2$, and further optionally substituted with 1 $Z^5$ or 1-2 $Z^6$;

(d1) a spiro ring system containing one cycloalkyl and one nitrogen-containing heterocycloalkyl joined by one common spiro carbon atom, wherein the spiro ring system is optionally substituted on its carbon atoms with 1-8 $Z^3$, and wherein the spiro ring system can also be optionally N-substituted with alkyl, haloalkyl, —SO$_2$-alkyl, —SO$_2$-haloalkyl; —CO$_2$-alkyl, —C(O)NR$^{10}$R$^{11}$, —SO$_2$NR$^{10}$R$^{11}$, or —SO$_2$-cycloalkyl substituted with 1-5 halogens;

(d2) a spiro ring system containing one cycloalkyl and one heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-8 $Z^3$; or (e) a spiro ring system containing one cycloalkyl and one bridged ring joined by one common spiro carbon atom, wherein the spiro ring system is optionally substituted with 1-4 $Z^2$, and further optionally substituted with 1 $Z^5$;

$R^{10}$ is H, C$_1$-C$_6$alkyl, or C$_1$-C$_6$haloalkyl;
$R^{11}$ is H, C$_1$-C$_6$alkyl, or C$_1$-C$_6$haloalkyl;
$R^{12}$ is one of the following groups (a)-(f):

(a) a saturated cycloalkyl optionally substituted with 1-8 $Z^2$, and further optionally substituted with 1 $Z^5$ or 1-2 $Z^6$;

(b) a cycloalkenyl optionally substituted with 1-6 $Z^2$, and further optionally substituted with 1 $Z^5$;

(c) a heterocycloalkyl optionally substituted with 1-8 $Z^2$, and further optionally substituted with 1 $Z^5$;

(d) phenyl optionally substituted with 1-2 substituents independently selected from the group consisting of CN, halogen, C$_1$-C$_4$alkyl, C$_1$-C$_4$haloalkyl, —NH$_2$, —N(H)C$_1$-C$_4$alkyl, —N(C$_1$-C$_4$alkyl)$_2$, C$_1$-C$_4$alkoxyl optionally substituted with phenyl, 5-6 membered heterocycloalkyl, and 5-6 membered heteroaryl;

(e) a bridged ring optionally substituted with 1-4 $Z^2$; or
(f) heteroaryl optionally substituted with 1-2 $Z^2$;

each Y is independently H, F, Cl, C$_1$-C$_3$alkyl or C$_1$-C$_3$haloalkyl, or 2 Y groups join together with the carbon atom to which they are attached to form a C$_3$-C$_5$cycloalkyl optionally substituted with 1-3 halogens;

each $Z^1$ is independently CN, F, Cl, alkyl, or haloalkyl;
each $Z^2$ is independently CN, F, Cl, alkyl, cyclopropyl, or haloalkyl;
each $Z^3$ is independently CN, F, Cl, alkyl, or haloalkyl;

$Z^4$ is —C$_1$-C$_3$alkyl-C$_1$-C$_3$alkoxy, —SO$_2$-alkyl, —SO$_2$-haloalkyl, —C(O)NR$^{10}$R$^{11}$, —SO$_2$NR$^{10}$R$^{11}$, —SO$_2$-cycloalkyl optionally substituted with 1-5 halogens, —NHSO$_2$-alkyl, —NHSO$_2$-cycloalkyl optionally substituted with 1-5 halogens, or —NHSO$_2$-haloalkyl;

$Z^5$ is —C$_1$-C$_3$alkyl-C$_1$-C$_3$alkoxy, phenyl optionally substituted with 1-3 F, —SO$_2$-alkyl, —SO$_2$-haloalkyl, —C(O)NR$^{10}$R$^{11}$, —SO$_2$NR$^{10}$R$^{11}$, —SO$_2$-cycloalkyl optionally substituted with 1-5 halogens, —NHSO$_2$-alkyl, —NHSO$_2$-cycloalkyl optionally substituted with 1-5 halogens, or —NHSO$_2$-haloalkyl, provided that when $Z^5$ is attached to nitrogen, $Z^5$ cannot be halogen, —NHSO$_2$-alkyl, —NHSO$_2$-cycloalkyl optionally substituted with 1-6 halogens, or —NHSO$_2$-haloalkyl; and each $Z^6$ is independently halo, C$_1$-C$_3$alkyl, C$_1$-C$_3$haloalkyl, CN, OH, C$_3$-C$_5$cycloalkyl, phenyl or 5-6 membered heteroaryl, provided that only one $Z^6$ can be OH.

Embodiment 2(b) Z of this disclosure relates to Embodiment 2 Z, wherein:

$R^5$ and $R^6$, together with the carbon atoms to which they are attached, join to form a 4-6 membered carbocyclic or a heterocyclic ring containing at least one oxygen or sulfur atom, each ring being optionally substituted on its carbon atoms with 1-4 substituents selected from the group consisting of F, Cl, C$_1$-C$_3$alkyl and C$_1$-C$_3$haloalkyl;

or $R^4$ and $R^5$, together with the carbon atoms to which they are attached, join to form a 4-6 membered carbocyclic or an heterocyclic ring containing at least one oxygen or sulfur atom, each ring being optionally substituted on its carbon atoms with 1-4 substituents selected from the group consisting of F, Cl, C$_1$-C$_3$alkyl and C$_1$-C$_3$haloalkyl.

Embodiment 2(b) Z of this disclosure relates to Embodiment 2 Z, wherein:

$R^7$ is group (c) or (e):
(c) a bridged nitrogen-containing heterocyclic ring optionally substituted with 1-4 $Z^2$, and further optionally substituted with 1 $Z^5$; or

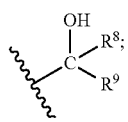
(e)

$R^8$ is H, F, or CH$_3$;
$R^9$ is —(CY$_2$)$_{0-2}$—R$^{12}$;
or $R^8$ and $R^9$ join together with the carbon atom to which they are attached to form group (e):

(e) a spiro ring system containing one cycloalkyl and one bridged ring joined by one common spiro carbon atom, wherein the spiro ring system is optionally substituted with 1-4 $Z^2$, and further optionally substituted with 1 $Z^5$; and $R^{12}$ is group (e):
(e) a bridged ring optionally substituted with 1-4 $Z^2$.

It has been found that the compounds having Formula (Ic)

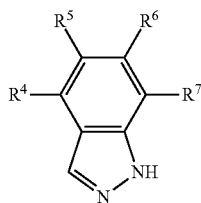
(Ic)

have surprising and unexpected better IDO1 biochemical and cellular potency, as measured by the biochemical and cellular assays described in this disclosure, when compared to compounds having Formula (Ie)

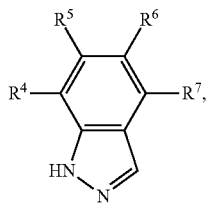
(Ie)

wherein $R^4$, $R^5$, $R^6$, and $R^7$ are the same for each of Formulae (Ic) and (Ie).

Embodiment 3 Z of this disclosure relates to Embodiments 1 Z or 2 Z, wherein:

$R^7$ is one of the following groups (a), (b), (c) or (e):

(a) $(C_5-C_6)$cycloalkyenyl optionally substituted with 1-5 $Z^1$, and further optionally substituted with 1 $Z^4$;

(b) 5 or 6-membered nitrogen-containing heterocycloalkyl optionally substituted with 1-7 $Z^2$, and further optionally substituted with 1 $Z^5$;

(c) a 5-9 membered nitrogen containing bridged heterocyclic ring optionally substituted with 1-3 $Z^2$, and further optionally substituted with 1 $Z^5$; or

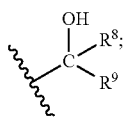
(e)

$R^8$ is H;
$R^9$ is $-(CY_2)_{0-2}-R^{12}$;
or $R^8$ and $R^9$ join together with the carbon atom to which they are attached to form one of the following groups (a)-(e):

(a) a $C_3-C_6$cycloalkyl optionally substituted with 1-7 $Z^2$, and further optionally substituted with 1 $Z^5$ or 1-2 $Z^6$;

(b) a 4-6 membered heterocycloalkyl optionally substituted with 1-7 $Z^2$, and further optionally substituted with 1 $Z^5$;

(c) a spiro ring system containing two $C_4-C_6$cycloalkyl groups joined by one common spiro carbon atom, wherein the spiro ring system is optionally substituted with 1-7 $Z^2$, and further optionally substituted with 1 $Z^5$ or 1-2 $Z^6$;

(d1) a spiro ring system containing one $C_4-C_6$cycloalkyl and one 4-6 membered nitrogen-containing heterocycloalkyl joined by one common spiro carbon atom, wherein the spiro ring system is optionally substituted on its carbon atoms with 1-7 $Z^3$, and wherein the spiro ring system can also be optionally N-substituted with $C_1-C_6$alkyl, $C_1-C_6$haloalkyl, $-SO_2-C_1-C_6$alkyl, $-SO_2-C_1-C_6$haloalkyl, $-C(O)NR^{10}R^{11}$, $-SO_2NR^{10}R^{11}$, or $-SO_2-C_3-C_6$cycloalkyl substituted with 1-4 halogens;

(d2) a spiro ring system containing one cycloalkyl and one heterocycloalkyl containing $-O-$, $-S-$, $-S(O)-$, or $-S(O)_2-$, wherein the spiro ring system is joined by one common spiro carbon atom, and wherein the spiro ring system is optionally substituted on its carbon atoms with 1-7 $Z^3$; or (e) a spiro ring system containing one cycloalkyl and one bridged ring joined by one common spiro carbon atom, wherein the spiro ring system is optionally substituted with 1-3 $Z^2$;

$R^{10}$ is H, $C_1-C_3$alkyl, or $C_1-C_3$haloalkyl;
$R^{11}$ is H, $C_1-C_3$alkyl, or $C_1-C_3$haloalkyl;
$R^{12}$ is one of the following groups (a)-(e):

(a) a saturated $C_3-C_6$cycloalkyl optionally substituted with 1-7 $Z^2$, and further optionally substituted with 1 $Z^5$ or 1-2 $Z^6$;

(b) a $C_5-C_6$cycloalkenyl optionally substituted with 1-5 $Z^2$, and further optionally substituted with 1 $Z^5$;

(c) a 4-6 membered heterocycloalkyl optionally substituted with 1-7 $Z^2$, and further optionally substituted with 1 $Z^5$;

(d) phenyl optionally substituted with 1-2 substituents independently selected from the group consisting of CN, halogen, $C_1-C_4$alkyl, and $C_1-C_4$haloalkyl; or (e) a 5-10 membered bridged carbocyclic or heterocyclic ring, wherein the 5-10 membered bridged carbocyclic or heterocyclic ring are each optionally substituted with 1-3 $Z^2$;

each Y is independently H, F, Cl, $C_1-C_2$alkyl or $C_1-C_2$haloalkyl, or 2 Y groups join together with the carbon atom to which they are attached to form a $C_3-C_4$cycloalkyl optionally substituted with 1-3 halogens;

each $Z^1$ is independently CN, halogen, $C_1-C_6$alkyl, or $C_1-C_6$haloalkyl; each $Z^2$ is independently CN, halogen, $C_1-C_6$alkyl, or $C_1-C_6$haloalkyl; each $Z^3$ is independently CN, F, Cl, $C_1-C_6$alkyl or $C_1-C_6$haloalkyl;

$Z^4$ is $-SO_2-C_1-C_6$alkyl, $-SO_2-C_3-C_6$cycloalkyl optionally substituted with 1-3 halogens, $-SO_2-C_1-C_6$haloalkyl, $-NHSO_2-C_1-C_6$alkyl, $-NHSO_2-C_3-C_6$cycloalkyl optionally substituted with 1-3 halogens, or $-NHSO_2-C_1-C_6$haloalkyl;

$Z^5$ is $-C_1-C_3$alkyl-$OCH_3$, phenyl optionally substituted with 1-2 F, $-SO_2-C_1-C_6$alkyl, $-SO_2-C_1-C_6$haloalkyl, $-C(O)NR^{10}R^{11}$, $-SO_2NR^{10}R^{11}$, $-SO_2-C_3-C_6$cycloalkyl optionally substituted with 1-3 halogens, $-NHSO_2-C_1-C_6$alkyl, $-NHSO_2-C_3-C_6$cycloalkyl optionally substituted with 1-3 halogens, or $-NHSO_2-C_1-C_6$haloalkyl, provided that when $Z^5$ is attached to nitrogen, $Z^5$ cannot be halogen, $-NHSO_2-C_1-C_6$alkyl, $-NHSO_2-C_3-C_6$cycloalkyl optionally substituted with 1-3 halogens, or $-NHSO_2-C_1-C_6$haloalkyl; and each $Z^6$ is independently halo, $C_1-C_2$alkyl, $C_1-C_2$haloalkyl, CN, OH, $C_3-C_3$cycloalkyl, $C_3-C_6$cycloalkyl, phenyl or 5-6 membered heteroaryl, provided that only one $Z^6$ can be OH.

Embodiment 3(b) Z of this disclosure relates to Embodiment 3 Z, wherein:

$R^7$ is group (c) or (e):

(c) a 5-9 membered nitrogen containing bridged heterocyclic ring optionally substituted with 1-3 $Z^2$, and further optionally substituted with 1 $Z^5$; or

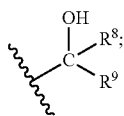 (e)

R[8] is H;
R[9] is —(CY$_2$)$_{0-2}$—R[12];
or R[8] and R[9] join together with the carbon atom to which they are attached to form group (e):
(e) a spiro ring system containing one cycloalkyl and one bridged ring joined by one common spiro carbon atom, wherein the spiro ring system is optionally substituted with 1-3 Z[2]; and
R[12] is group (e):
(e) a 5-10 membered bridged carbocyclic or heterocyclic ring, wherein the 5-10 membered bridged carbocyclic or heterocyclic ring are each optionally substituted with 1-3 Z[2].

Embodiment 4 Z of this disclosure relates to the compound according to any one of Embodiments 1-3 Z having one of Formula (IIa)-(IIm):

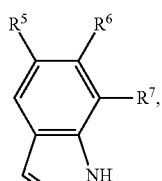 (IIa)

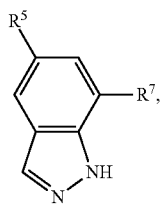 (IIb)

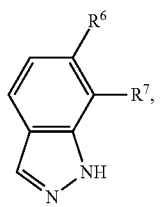 (IIc)

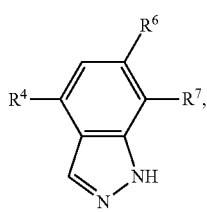 (IId)

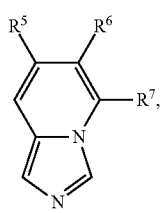 (IIe)

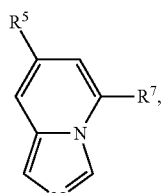 (IIf)

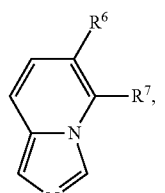 (IIg)

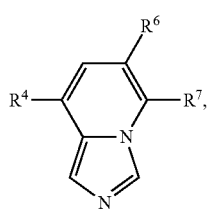 (IIf)

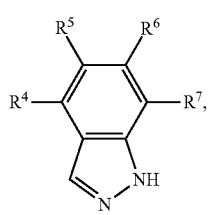 (IIi)

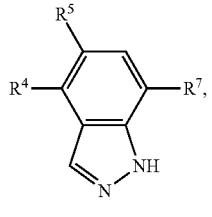 (IIj)

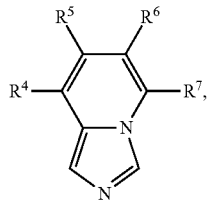 (IIk)

(IIl), or

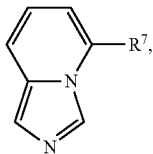

(IIm)

or a pharmaceutically acceptable salt, a solvate, a tautomer, an isomer or a deuterated analog thereof, wherein:

$R^4$, $R^5$ and $R^6$ are each independently F, Cl, $C_1$-$C_3$alkyl, —$C_1$-$C_3$haloalkyl, —$OCH_3$ optionally substituted with 1-3 F, or cyclopropyl;

or $R^4$ and $R^5$, when they both exist, join together with the carbon atoms to which they are attached to form a 4-6 membered carbocyclic ring optionally substituted with 1-4 substituents selected from the group consisting of F, Cl, $C_1$-$C_3$alkyl and $C_1$-$C_3$haloalkyl;

or $R^4$ and $R^5$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, $C_1$-$C_3$alkyl and $C_1$-$C_3$haloalkyl;

or $R^5$ and $R^6$, when they both exist, join together with the carbon atoms to which they are attached to form a 4-6 membered carbocyclic ring optionally substituted with 1-4 substituents selected from the group consisting of F, Cl, $C_1$-$C_3$alkyl and $C_1$-$C_3$haloalkyl;

or $R^5$ and $R^6$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, $C_1$-$C_3$alkyl and $C_1$-$C_3$haloalkyl.

Embodiment 4(b) Z of this disclosure relates to Embodiment 4 Z, wherein:

$R^4$ and $R^5$, when they both exist, join together with the carbon atoms to which they are attached to form a 4-6 membered carbocyclic ring optionally substituted with 1-4 substituents selected from the group consisting of F, Cl, $C_1$-$C_3$alkyl and $C_1$-$C_3$haloalkyl;

or $R^4$ and $R^5$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, $C_1$-$C_3$alkyl and $C_1$-$C_3$haloalkyl;

or $R^5$ and $R^6$, when they both exist, join together with the carbon atoms to which they are attached to form a 4-6 membered carbocyclic ring optionally substituted with 1-4 substituents selected from the group consisting of F, Cl, $C_1$-$C_3$alkyl and $C_1$-$C_3$haloalkyl;

or $R^5$ and $R^6$, when they both exist, join together with the carbon atoms to which they are attached to form a 5-6 membered heterocyclic ring containing 1 or 2 oxygen atoms, and optionally substituted with 1-4 substituents selected from the group consisting of F, Cl, $C_1$-$C_3$alkyl and $C_1$-$C_3$haloalkyl.

Embodiment 5 Z of this disclosure relates to the compound according to Embodiment 4 Z, wherein:

$R^4$, $R^5$ and $R^6$ are each independently F, Cl, methyl optionally substituted with 1-3 F, —$OCH_3$ optionally substituted with 1-3 F, or cyclopropyl;

or $R^4$ and $R^5$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^4$ and $R^5$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$;

$R^7$ is one of the following groups (a), (b), (c), or (e):

(a) cyclohexenyl optionally substituted with 1-4 $Z^2$, and further optionally substituted with 1 $Z^5$;

(b) a six-membered nitrogen-containing heterocycloalkyl optionally substituted with 1-6 $Z^2$, and further optionally substituted with 1 $Z^5$;

(c) an 8-9 membered nitrogen containing bridged heterocyclic ring optionally substituted with 1-2 $Z^2$, and further optionally substituted with 1 $Z^5$; or (e)

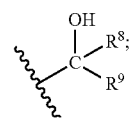

$R^8$ is H;

$R^9$ is —$(CY_2)_{0-2}$—$R^{12}$;

or $R^8$ and $R^9$ join together with the carbon atom to which they are attached to form one of the following groups (a)-(e):

(a) a $C_3$-$C_6$cycloalkyl optionally substituted with 1-7 $Z^2$, and further optionally substituted with 1 $Z^5$ or 1-2 $Z^6$;

(b) a 4-6 membered nitrogen-containing heterocycloalkyl optionally substituted with 1-6 $Z^2$, and further optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$, and further optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-6 $Z^3$, and wherein the spiro ring system can also be optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl;

(d2) a spiro ring system containing one $C_4$-$C_6$cycloalkyl and one 4-6 membered heterocycloalkyl containing —O—, —S—, —S(O)— or —$S(O)_2$—, wherein the spiro ring system is joined by one common spiro carbon atom, and wherein the spiro ring system is optionally substituted on its carbon atoms with 1-6 $Z^3$; or (e) a spiro ring system containing one $C_4$-$C_6$cycloalkyl and one 7-10 membered bridged ring joined by one common spiro carbon atom, wherein the spiro ring system is optionally substituted with 1-2 $Z^2$;

$R^{12}$ is one of the following groups (a)-(e):

(a) a saturated $C_3$-$C_6$cycloalkyl optionally substituted with 1-6 $Z^2$, and further optionally substituted with 1 $Z^5$ or 1-2 $Z^6$;

(b) $C_5$-$C_6$cycloalkenyl optionally substituted with 1-6 $Z^2$, and further optionally substituted with 1 $Z^5$;

(c) a 4-6 membered nitrogen-containing heterocycloalkyl optionally substituted with 1-6 $Z^2$, and further optionally substituted with 1 $Z^5$;

(d) phenyl optionally substituted with 1-2 $Z^2$; or (e) a 6-9 membered bridged carbocyclic or nitrogen-containing heterocyclic ring, wherein the bridged carbocyclic or nitrogen-containing heterocyclic ring are each optionally substituted with 1-2 $Z^2$;

each Y is independently H, F, $CH_3$, —$CFH_2$, —$CF_2H$ or —$CF_3$, or 2 Y groups join together with the carbon atom to which they are attached to form a $C_3$-$C_4$cycloalkyl optionally substituted with 1-3 F;

each $Z^1$ is independently CN, F, Cl, $C_1$-$C_4$alkyl, or $C_1$-$C_4$haloalkyl;

each $Z^2$ is independently CN, F, Cl, $C_1$-$C_4$alkyl, or $C_1$-$C_4$haloalkyl;

each $Z^3$ is independently CN, F, Cl, —$C_1$-$C_4$alkyl or —$C_1$-$C_4$haloalkyl $Z^4$ is —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl;

$Z^5$ is —$SO_2$—$C_1$-$C_4$alkyl, —$SO_2$—$C_1$-$C_4$haloalkyl, —$SO_2$—$C_3$-$C_6$cycloalkyl optionally substituted with 1-3 halogens, —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl, provided that when $Z^5$ is attached to nitrogen, $Z^5$ cannot be —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl; and each $Z^6$ is independently halo, $C_1$-$C_2$alkyl, $C_1$-$C_2$haloalkyl, CN, OH, $C_3$-$C_3$cycloalkyl or $C_3$-$C_6$cycloalkyl, phenyl or 5-6 membered heteroaryl, provided that only one $Z^6$ can be OH.

Embodiment 5(b) Z of this disclosure relates to Embodiment 5 Z, wherein:

$R^4$ and $R^5$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^4$ and $R^5$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 4-6 membered carbocyclic ring optionally substituted with 1-4 substituents selected from the group consisting of F, Cl, —$CH_3$, —$CFH_2$, —$CF_2H$ and —$CF_3$;

or $R^5$ and $R^6$ when they both exist, join together with the carbon atoms to which they are attached to form a 5 membered heterocyclic ring containing 1-2 oxygen atoms and optionally substituted with 1-4 substituents selected from the group consisting of F, Cl, —$CH_3$, —$CFH_2$, —$CF_2H$ and —$CF_3$.

Embodiment 5(c) Z of this disclosure relates to Embodiment 5 Z, wherein:

$R^7$ is group (c) or (e):

(c) an 8-9 membered nitrogen containing bridged heterocyclic ring optionally substituted with 1-2 $Z^2$, and further optionally substituted with 1 $Z^5$; or

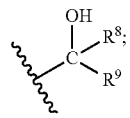

(e)

$R^8$ is H;

$R^9$ is —$(CY_2)_{0-2}$—$R^{12}$;

or $R^8$ and $R^9$ join together with the carbon atom to which they are attached to form group (e):

(e) a spiro ring system containing one $C_4$-$C_6$cycloalkyl and one 7-10 membered bridged ring joined by one common spiro carbon atom, wherein the spiro ring system is optionally substituted with 1-2 $Z^2$; and $R^{12}$ is group (e):

(e) a 6-9 membered bridged carbocyclic or nitrogen-containing heterocyclic ring, wherein the bridged carbocyclic or nitrogen-containing heterocyclic ring are each optionally substituted with 1-2 $Z^2$.

Embodiment 6 Z of this disclosure relates to Embodiment 4 Z, wherein:

$R^4$ and $R^5$, when they both exist, join together with the carbon atoms to which they are attached to form a 4-6 membered carbocyclic or a 5-6 membered-heterocyclic containing 1-2 oxygen atoms, each ring being optionally substituted on its carbon atoms with 1-4 substituents selected from the group consisting of F, Cl, —$CH_3$, —$CFH_2$, —$CF_2H$, —$CF_3$, —O—$CH_3$, —O—$CFH_2$, —$OCF_2H$ and —$OCF_3$;

$R^6$ is F, Cl, —$CH_3$, —$CFH_2$, —$CF_2H$, —$CF_3$, —O—$CH_3$, —O—$CFH_2$, —$OCF_3$, or cyclopropyl;

$R^7$ is one of the following groups (a), (b), (c), or (e):

(a) cyclohexenyl optionally substituted with 1-3 $Z^1$, and further optionally substituted with 1 $Z^4$;

(b) a six-membered nitrogen-containing heterocycloalkyl optionally substituted with 1-5 $Z^2$, and further optionally substituted with 1 $Z^5$;

(c) an 8 membered bridged heterocyclic ring containing 1-2 nitrogen atoms, said 8 membered bridged heterocyclic ring optionally substituted with 1 $Z^2$, and further optionally substituted with 1 $Z^5$; or

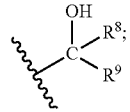

(e)

$R^8$ is H;

$R^9$ is —$(CY_2)_{0-2}$—$R^{12}$;

or $R^8$ and $R^9$ join together with the carbon atom to which they are attached to form one of the following groups (a)-(e):

(a) a $C_3$-$C_6$cycloalkyl optionally substituted with 1-6 $Z^2$, and further optionally substituted with 1 $Z^5$ or 1-2 $Z^6$;

(b) a 4-6 membered nitrogen-containing heterocycloalkyl optionally substituted with 1-5 $Z^2$, and further optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$, and further optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system can also be optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl;

(d2) a spiro ring system containing one $C_4$-$C_6$cycloalkyl and one 4-6 membered heterocycloalkyl containing —O—, —S—, —S(O)— or —$S(O)_2$—, wherein the spiro ring system is joined by one common spiro carbon atom, and wherein the spiro ring system is optionally substituted on its carbon atoms with 1-5 $Z^3$; or (e) a spiro ring system containing one $C_4$-$C_6$cycloalkyl and one 7-10 membered bridged ring joined by one common spiro carbon atom, wherein the spiro ring system is optionally substituted with $1Z^2$;

$R^{12}$ is one of the following groups (a)-(e):

(a) a saturated $C_3$-$C_6$cycloalkyl optionally substituted with 1-6 $Z^2$, and further optionally substituted with 1 $Z^5$ or 1-2 $Z^6$;

(b) a $C_5$-$C_6$cycloalkenyl optionally substituted with 1-3 $Z^2$, and further optionally substituted with 1 $Z^5$;

(c) a 4-6 membered nitrogen-containing heterocycloalkyl optionally substituted with 1-5 $Z^2$, and further optionally substituted with 1 $Z^5$;

(d) phenyl optionally substituted with 1-2 $Z^2$; or (e) a 5-10 membered bridged carbocyclic ring, wherein the bridged carbocyclic ring is optionally substituted with 1 $Z^2$;

each Y is independently H, F, $CH_3$, —$CFH_2$, —$CF_2H$ or —$CF_3$, or 2 Y groups join together with the carbon atom to which they are attached to form a $C_3$-$C_4$cycloalkyl optionally substituted with 1-2 F;

each $Z^1$ is independently CN, F, Cl, $C_1$-$C_4$alkyl, or $C_1$-$C_4$haloalkyl;

each $Z^2$ is independently CN, F, Cl, $C_1$-$C_4$alkyl, or $C_1$-$C_4$haloalkyl;

each $Z^3$ is independently CN, F, Cl, —$C_1$-$C_4$alkyl or —$C_1$-$C_4$haloalkyl;

$Z^4$ is —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl;

$Z^5$ is —$SO_2$—$C_1$-$C_4$alkyl, $SO_2$—$C_1$-$C_4$haloalkyl, —$SO_2$—$C_3$-$C_6$cycloalkyl optionally substituted with 1-3 halogens, —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl, provided that when $Z^5$ is attached to nitrogen, $Z^5$ cannot be —$NHSO_2$—$C_1$-$C_4$alkyl, —$NHSO_2$—$C_3$-$C_6$cycloalkyl optionally substituted with 1-3 halogens, or —$NHSO_2$—$C_1$-$C_4$haloalkyl; and each $Z^6$ is independently F, $C_1$-$C_2$alkyl, $C_1$-$C_2$haloalkyl, CN, OH, $C_3$-$C_3$cycloalkyl, $C_3$-$C_6$cycloalkyl, phenyl or 6 membered heteroaryl, provided that only one $Z^6$ can be OH.

Embodiment 7 Z of this disclosure relates to Embodiment 4 Z, wherein:

$R^5$ and $R^6$, when they both exist, join together with the carbon atoms to which they are attached to form a 4-6 membered carbocyclic or a 5-6 membered-heterocyclic ring containing 1-2 oxygen atoms, each ring being optionally substituted on its carbon atoms with 1-4 substituents selected from the group consisting of F, Cl, —$CH_3$, —$CFH_2$, —$CF_2H$, —$CF_3$, —$OCH_3$, —$OCFH_2$, and —$OCF_3$;

$R^6$ is F, Cl, —$CH_3$, —$CFH_2$, —$CF_2H$, —$CF_3$, —$OCH_3$, —$OCFH_2$, —$OCF_3$, or cyclopropyl;

$R^7$ is one of the following groups (a), (b), (c), or (e):

(a) cyclohexenyl optionally substituted with 1-3 $Z^1$, and further optionally substituted with 1 $Z^4$;

(b) a six-membered nitrogen-containing heterocycloalkyl optionally substituted with 1-4 $Z^2$, and further optionally substituted with 1 $Z^5$;

(c) an 8 membered bridged heterocyclic ring containing 1-2 nitrogen atoms, said 8 membered bridged heterocyclic ring optionally N-substituted with 1 $Z^5$; or

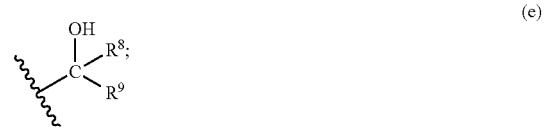

(e)

$R^8$ is H;

$R^9$ is —$(CY_2)_{0-2}$—$R^{12}$;

or $R^8$ and $R^9$ join together with the carbon atom to which they are attached to form one of the following groups (a)-(e):

(a) a $C_3$-$C_6$cycloalkyl optionally substituted with 1-6 $Z^2$, and further optionally substituted with 1 $Z^5$ or 1-2 $Z^6$;

(b) a 4-6 membered nitrogen-containing heterocycloalkyl optionally substituted with 1-5 $Z^2$, and further optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$, and further optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system can also be optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl;

(d2) a spiro ring system containing one $C_4$-$C_6$cycloalkyl and one 4-6 membered heterocycloalkyl containing —O—, —S—, —S(O)— or —$S(O)_2$—, wherein the spiro ring system is joined by one common spiro carbon atom, and wherein the spiro ring system is optionally substituted on its carbon atoms with 1-5 $Z^3$; or (e) a spiro ring system containing one $C_4$-$C_6$cycloalkyl and one 7-10 membered bridged ring joined by one common spiro carbon atom;

$R^{12}$ is one of the following groups(a1), (a2), or (b)-(e):

(a1) a saturated $C_3$-$C_6$cycloalkyl optionally substituted with 1-5 $Z^2$, and further optionally substituted with 1 $Z^5$ or 1-2 $Z^6$;

(a2) cubane;

(b) a $C_5$-$C_6$cycloalkenyl optionally substituted with 1-3 $Z^2$, and further optionally substituted with 1 $Z^5$;

(c) a 4-6 membered nitrogen-containing heterocycloalkyl optionally substituted with 1-5 $Z^2$, and further optionally substituted with 1 $Z^5$;

(d) phenyl optionally substituted with 1-2 $Z^2$; or (e) a 5-10 membered bridged carbocyclic ring;

each Y is independently H, F, $CH_3$, $-CFH_2$, $-CF_2H$ or $-CF_3$, or 2 Y groups join together with the carbon atom to which they are attached to form a cyclopropyl or cyclobutyl group;

each $Z^1$ is independently CN, F, Cl, $C_1$-$C_4$alkyl, or $C_1$-$C_4$haloalkyl;

each $Z^2$ is independently CN, F, Cl, $C_1$-$C_4$alkyl, or $C_1$-$C_4$haloalkyl;

each $Z^3$ is independently CN, F, Cl, $-C_1$-$C_4$alkyl, or $-C_1$-$C_4$haloalkyl;

$Z^4$ is $-SO_2-C_1$-$C_4$alkyl, $-SO_2-C_3$-$C_6$cycloalkyl optionally substituted with 1-3 halogens, $-SO_2-C_1$-$C_4$haloalkyl, $-NHSO_2-C_1$-$C_4$alkyl, $-NHSO_2-C_3$-$C_6$cycloalkyl optionally substituted with 1-3 halogens, or $-NHSO_2-C_1$-$C_4$haloalkyl;

$Z^5$ is $-SO_2-C_1$-$C_4$alkyl, $SO_2-C_1$-$C_4$haloalkyl, $-SO_2-C_3$-$C_6$cycloalkyl optionally substituted with 1-3 halogens, $-NHSO_2-C_1$-$C_4$alkyl, $-NHSO_2-C_3$-$C_6$cycloalkyl optionally substituted with 1-3 halogens, or $-NHSO_2-C_1$-$C_4$haloalkyl, provided that when $Z^5$ is attached to nitrogen, $Z^5$ cannot be $-NHSO_2-C_1$-$C_4$alkyl, or $-NHSO_2-C_3$-$C_6$cycloalkyl optionally substituted with 1-3 halogens; and each $Z^6$ is independently F, $CH_3$ optionally substituted with 1-3 F, CN, OH, $C_3$-$C_4$cycloalkyl, phenyl or 6 membered heteroaryl, provided that only one $Z^6$ can be OH.

Embodiment 8 Z of this disclosure relates to the compound according to one of Embodiments 1-4 Z having any one of Formulae (IIIa)-(IIIu):

(IIIa)

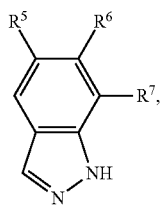

(IIIb)

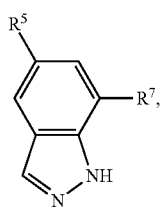

(IIIc)

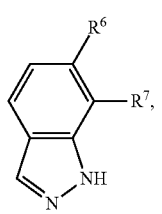

(IIId)

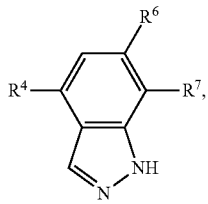

(IIIe)

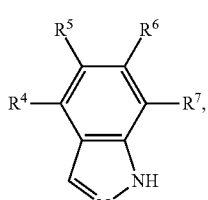

(IIIf)

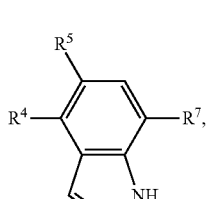

(IIIg)

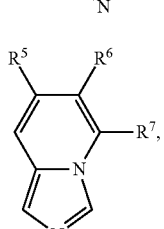

(IIIh)

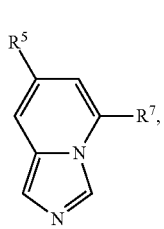

(IIIi)

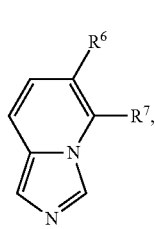

(IIIj)

-continued

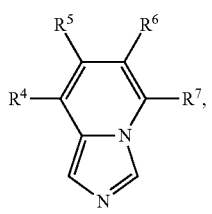
(IIIk)

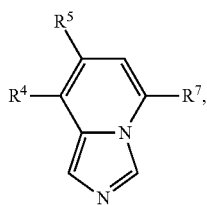
(IIIl)

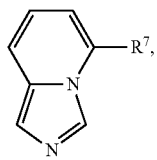
(IIIm)

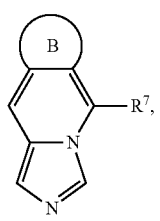
(IIIn)

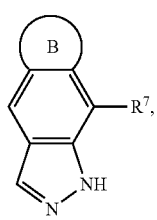
(IIIo)

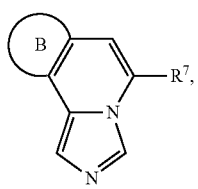
(IIIp)

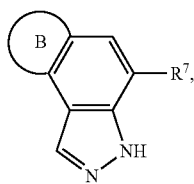
(IIIq)

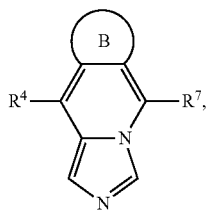
(IIIr)

-continued

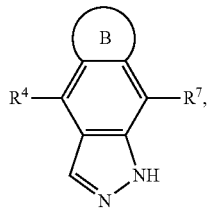
(IIIs)

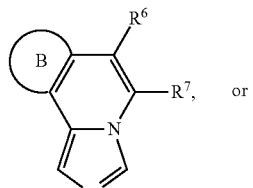
(IIIt)

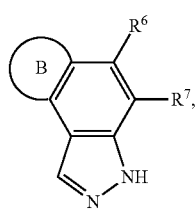
(IIIu)

or a pharmaceutically acceptable salt, a solvate, a tautomer, an isomer or a deuterated analog thereof, wherein:

$R^4$, $R^5$ and $R^6$ are each independently F, —$CH_3$, —$CFH_2$, —$CF_2H$, —$CF_3$, —$OCH_3$, —$OCFH_2$, —$OCF_2H$ or —$OCF_3$;

ring B is a 4-6 membered carbocyclic or a 5 membered heterocyclic ring containing 1-2 oxygen atoms, wherein each ring is optionally substituted on its carbon atoms with 1-4 substituents selected from the group consisting of F, Cl, —$CH_3$, —$CFH_2$, —$CF_2H$, —$CF_3$, —$OCH_3$, —$OCFH_2$, —$OCF_2H$ and —$OCF_3$.

Embodiment 9 Z of this disclosure relates to Embodiment 8 Z having one of the following Formulae:

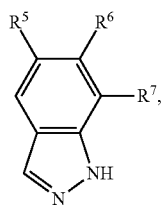
(IIIa)

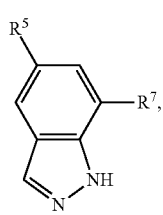
(IIIb)

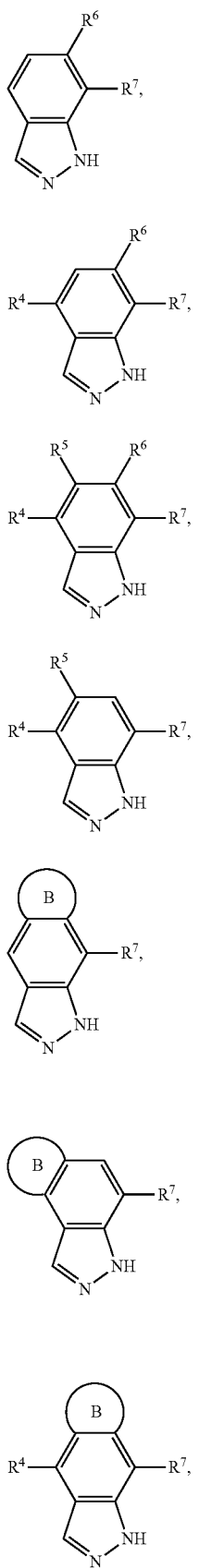
or a pharmaceutically acceptable salt, a solvate, a tautomer, an isomer or a deuterated analog thereof.
Embodiment 10 Z of this disclosure relates to Embodiment 8 Z having one of the following Formulae:

(IIIl)
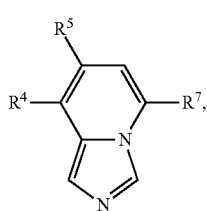

(IIIm)
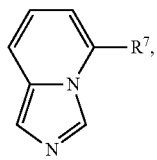

(IIIn)
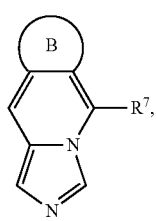

(IIIp)
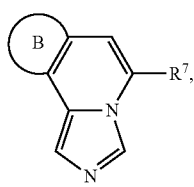

(IIIr)
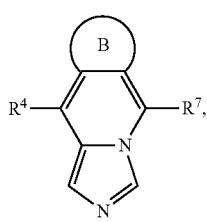

(IIIt)
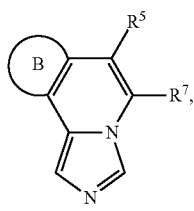

or a pharmaceutically acceptable salt, a solvate, a tautomer, an isomer or a deuterated analog thereof.

Embodiment 11Z of this disclosure relates to the compound according to Embodiment 8Z having one of the following Formulae:

(IIIo)
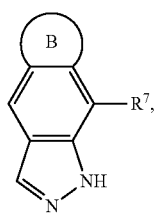

(IIIq)
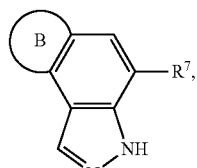

(IIIs)
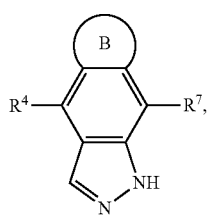

(IIIu)
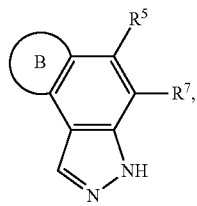

(IIIn)
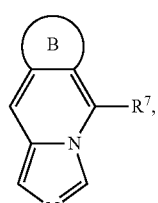

(IIIp)
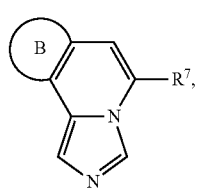

(IIIr)
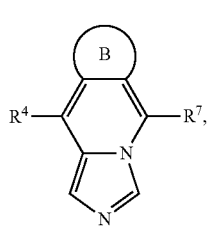

(IIIt)
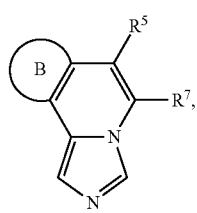

or a pharmaceutically acceptable salt, a solvate, a tautomer, an isomer or a deuterated analog thereof.

Embodiment 12 Z of this disclosure relates to t compound according to Embodiment 11Z having one of Formulae (IVa)-(IVp):

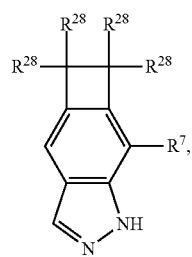
(IVa)
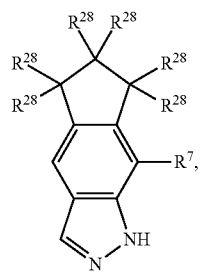
(IVb)
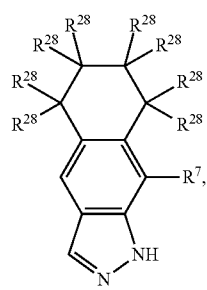
(IVc)
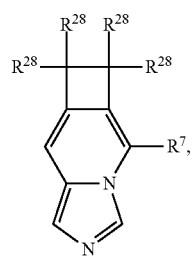
(IVd)
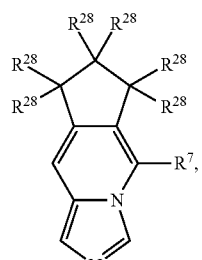
(IVe)
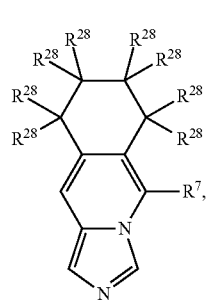
(IVf)
-continued
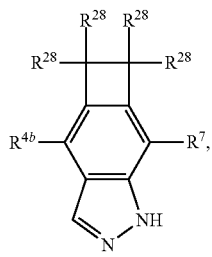
(IVg)
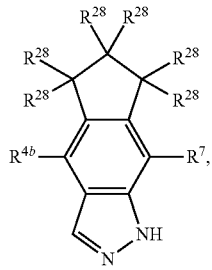
(IVh)
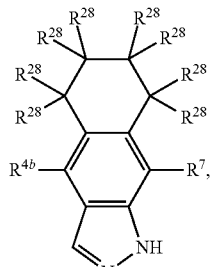
(IVi)
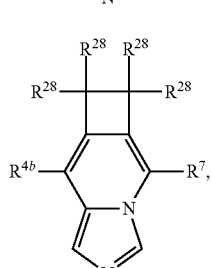
(IVj)
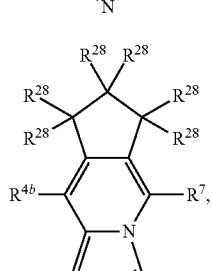
(IVk)
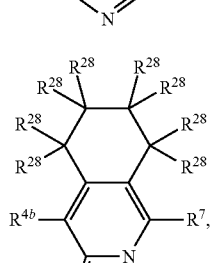
(IVl)

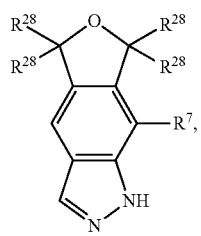

(IVm)

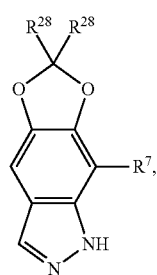

(IVn)

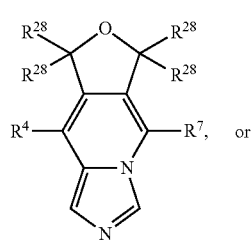

(IVo)

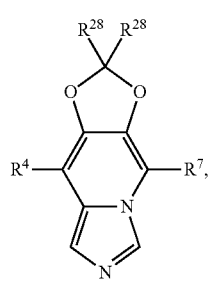

(IVp)

or a pharmaceutically acceptable salt, a solvate, a tautomer, an isomer or a deuterated analog thereof, wherein each $R^{28}$ is independently H, F, Cl, —$CH_3$, —$CFH_2$, —$CF_2H$, or —$CF_3$, provided that no more than three $R^{28}$ groups in each Formula is other than H.

Embodiment 12(b) Z of this disclosure relates to Embodiment 13 Z, wherein two $R^{28}$ groups, that are attached to the same carbon atom, are each independently F, Cl, —$CH_3$, —$CFH_2$, —$CF_2H$ or —$CF_3$.

Embodiment 12(c) Z of this disclosure relates to Embodiment 13, wherein two $R^{28}$ groups, that are attached to the same carbon atom, are each independently F, Cl, —$CH_3$, —$CFH_2$, —$CF_2H$ or —$CF_3$, and all remaining $R^{28}$ groups are H.

Embodiment 13Z of this disclosure relates to Embodiment 11 Z having one of Formulae (Va)-(Vp):

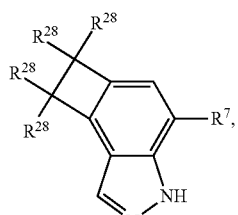

(Va)

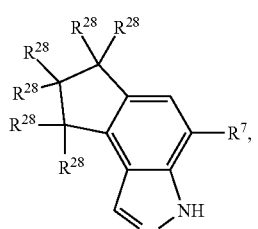

(Vb)

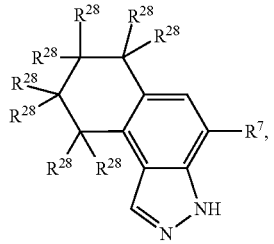

(Vc)

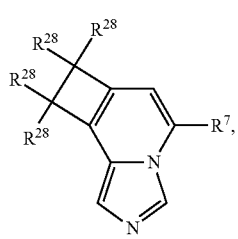

(Vd)

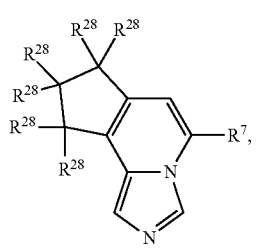

(Ve)

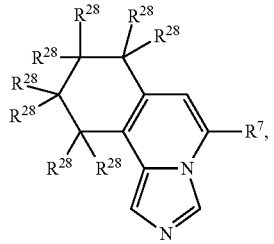

(Vf)

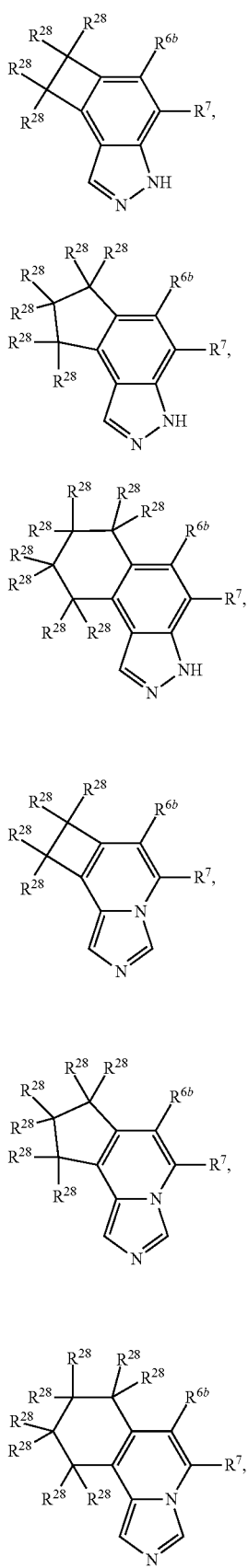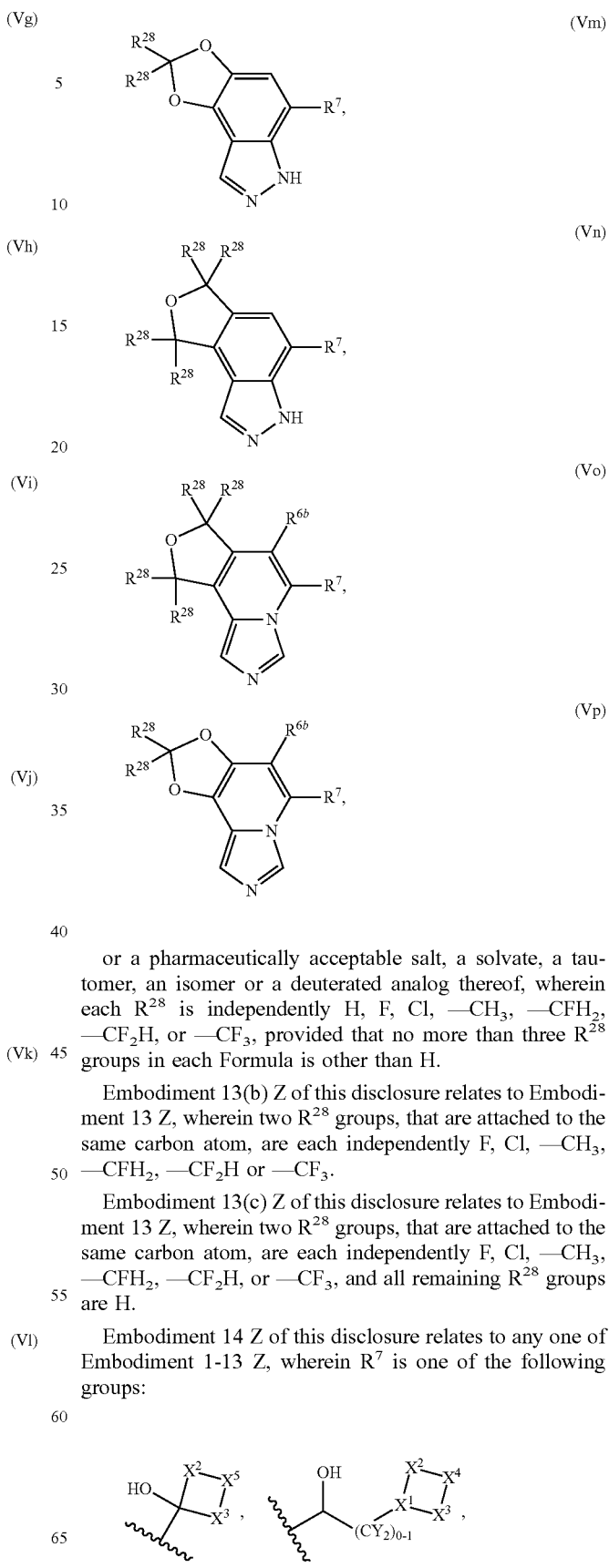

or a pharmaceutically acceptable salt, a solvate, a tautomer, an isomer or a deuterated analog thereof, wherein each $R^{28}$ is independently H, F, Cl, —$CH_3$, —$CFH_2$, —$CF_2H$, or —$CF_3$, provided that no more than three $R^{28}$ groups in each Formula is other than H.

Embodiment 13(b) Z of this disclosure relates to Embodiment 13 Z, wherein two $R^{28}$ groups, that are attached to the same carbon atom, are each independently F, Cl, —$CH_3$, —$CFH_2$, —$CF_2H$ or —$CF_3$.

Embodiment 13(c) Z of this disclosure relates to Embodiment 13 Z, wherein two $R^{28}$ groups, that are attached to the same carbon atom, are each independently F, Cl, —$CH_3$, —$CFH_2$, —$CF_2H$, or —$CF_3$, and all remaining $R^{28}$ groups are H.

Embodiment 14 Z of this disclosure relates to any one of Embodiment 1-13 Z, wherein $R^7$ is one of the following groups:

-continued

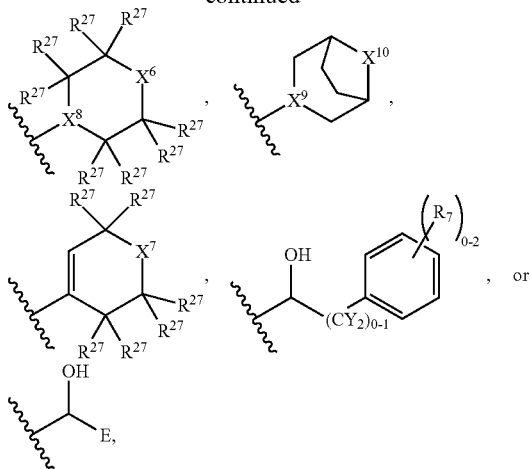

wherein:
E is bicyclo[2.2.2]octane-1-yl, bicyclo[2.2.1]heptan-1-yl, 1-fluorobicyclo[2.2.2]octan-1-yl, (1r,2R,4S,5r,6R,8S)-tetracyclo[3.3.1.02,4.06,8]nonan-9-yl, (1s,5s)-bicyclo[3.3.1]nonan-9-yl, cuban-1-yl, bicyclo[1.1.1]pentan-2-yl, or adamantanyl;

$X^1$ is —$CR^{13}$—;
$X^2$ is —$C(R^{14})_2$— or —$C(R^{14})_2$—$C(R^{14})_2$—;
$X^3$ is —$C(R^{14})_2$— or —$C(R^{14})_2$—$C(R^{14})_2$—;
$X^4$ is —$N(R^{15})$— or —$C(R^{16})(R^{17})$—;
$X^5$ is —$N(R^{18})$— or —$C(R^{19})(R^{20})$—;
$X^6$ is —$N(R^{21})$— or —$C(R^{22})(R^{23})$—;
$X^7$ is N—$C(R^{25})(R^{26})$—;
$X^8$ is —C(H)— or

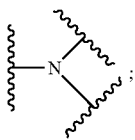 [SMILES: *N(*)*]

$X^9$ is CH or N;
$X^{19}$ is $CH_2$ or $NR^{21}$;
$R^{13}$ is H, F, $CH_3$, $CFH_2$, $CF_2H$, or $CF_3$;
each $R^{14}$ is independently H, halogen, $CH_3$, —$CFH_2$, —$CF_2H$ or —$CF_3$, provided that no more than four $R^{14}$ is other than H;
$R^{15}$ is H, $C_1$-$C_4$alkyl, $C_1$-$C_6$haloalkyl, —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, or $C_3$-$C_6$cycloalkyl optionally substituted with 1-3 halogens;
$R^{16}$ is H, halogen, CN, OH, cyclopropyl, cyclobutyl, $C_1$-$C_4$alkyl or $C_1$-$C_4$haloalkyl;
$R^{17}$ is H, halogen, CN, OH, cyclopropyl, cyclobutyl, $C_1$-$C_4$ alkyl, $C_1$-$C_4$haloalkyl, —$NHSO_2$—$C_1$-$C_4$alkyl, —$SO_2$—$C_3$-$C_6$cycloalkyl optionally substituted with 1-3 halogens, —$NHSO_2$—$C_1$-$C_4$haloalkyl, or $C_3$-$C_6$cycloalkyl optionally substituted with 1-3 halogens;
or $R^{16}$ and $R^{17}$ join together with the carbon atom to which they are attached to form one of the following groups (a)-(c):
(a) a $C_3$-$C_6$cycloalkyl optionally substituted with 1-6 groups independently selected from the group consisting of CN, F, $C_1$-$C_4$alkyl, and $C_1$-$C_4$haloalkyl, and wherein the $C_3$-$C_6$cycloalkyl can also be optionally substituted with —$NHSO_2$—$C_1$-$C_3$alkyl, —$NHSO_2$—$C_3$-$C_6$cycloalkyl optionally substituted with 1-3 halogens, or —$NHSO_2$—$C_1$-$C_3$haloalkyl;
(b) a 4-6 membered nitrogen-containing heterocycloalkyl optionally substituted on its carbon atoms with 1-4 groups independently selected from the group consisting of CN, F, $C_1$-$C_4$alkyl, and $C_1$-$C_4$haloalkyl, and wherein the nitrogen-containing heterocycloalkyl can also be optionally N-substituted with —$SO_2$—$C_1$-$C_3$alkyl, —$SO_2$—$C_3$-$C_6$cycloalkyl optionally substituted with 1-3 halogens, or —$SO_2$—$C_1$-$C_3$haloalkyl; or
(c) a 4-6 membered heterocycloalkyl containing —O—, —S—, —SO—, or $SO_2$—, wherein the 4-6 membered heterocycloalkyl is optionally substituted on its carbon atoms with 1-3 groups independently selected from the group consisting of CN, F, $C_1$-$C_4$alkyl, and $C_1$-$C_4$haloalkyl;
each Y is independently H, F, $CH_3$, —$CFH_2$, —$CF_2H$ or —$CF_3$, or two Y groups join together, with the carbon atom to which they are attached, to form a cyclopropyl or cyclobutyl group;
$R^{18}$ is H, $C_1$-$C_4$alkyl, $C_1$-$C_4$haloalkyl, —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, or $C_3$-$C_6$cycloalkyl optionally substituted with 1-3 halogens;
$R^{19}$ is H, halogen, CN, OH, cyclopropyl, cyclobutyl, $C_1$-$C_4$alkyl, or —$C_1$-$C_4$haloalkyl;
$R^{20}$ is H, halogen, CN, OH, cyclopropyl, cyclobutyl, $C_1$-$C_4$alkyl, $C_1$-$C_4$haloalkyl, —$NHSO_2$—$C_1$-$C_4$alkyl, —$NHSO_2$—$C_3$-$C_6$cycloalkyl optionally substituted with 1-3 halogens, —$NHSO_2$—$C_1$-$C_4$haloalkyl, or $C_3$-$C_6$cycloalkyl optionally substituted with 1-3 halogens;
or $R^{19}$ and $R^{20}$ join together with the carbon atom to which they are attached to form one of the following groups (a)-(d):
(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl can also be optionally substituted with —$NHSO_2$—$C_1$-$C_3$alkyl, —$NHSO_2$—$C_1$-$C_3$haloalkyl, or —$NHSO_2$—$C_3$-$C_6$cycloalkyl optionally substituted with 1-3 halogens;
(b) a 4-6 membered nitrogen-containing heterocycloalkyl optionally substituted on its carbon atoms with 1-3 groups independently selected from the group consisting of CN, F, $C_1$-$C_4$alkyl, and $C_1$-$C_4$haloalkyl, and wherein the nitrogen-containing heterocycloalkyl can also be optionally N-substituted with —$SO_2$—$C_1$-$C_3$alkyl, —$SO_2$—$C_1$-$C_3$haloalkyl or —$SO_2$—$C_3$-$C_6$cycloalkyl optionally substituted with 1-3 halogens;
(c) a 4-6 membered heterocycloalkyl containing —O—, —S—, —SO—, or $SO_2$—, wherein the 4-6 membered heterocycloalkyl is optionally substituted on its carbon atoms with 1-3 groups independently selected from the group consisting of CN, F, $C_1$-$C_4$alkyl, and $C_1$-$C_4$haloalkyl; or
(d) a 7-10 membered bridged ring;
$R^{21}$ is H, $C_1$-$C_6$alkyl, $C_1$-$C_3$haloalkyl, —$SO_2$—$C_1$-$C_3$alkyl, —$SO_2$—$C_1$-$C_3$haloalkyl, —$SO_2$—$C_3$-$C_6$cycloalkyl optionally substituted with 1-3 halogens, —$C_3$-$C_3$cycloalkyl optionally substituted with 1-3 halogens or $C_3$-$C_6$cycloalkyl optionally substituted with 1-3 halogens;
$R^{22}$ is H, halogen, $C_1$-$C_4$alkyl, or $C_1$-$C_4$haloalkyl;
$R^{23}$ is H, halogen, $C_1$-$C_4$alkyl, $C_1$-$C_4$haloalkyl, —CN, —$NHSO_2$—$C_1$-$C_4$alkyl, —$NHSO_2$—$C_1$-$C_4$haloalkyl, —$NHSO_2$—$C_3$-$C_6$cycloalkyl optionally substituted with 1-3 halogens, or $C_3$-$C_6$cycloalkyl optionally substituted with 1-3 halogens;

$R^{25}$ is H, halogen, $C_1$-$C_4$alkyl, or $C_1$-$C_4$haloalkyl;

$R^{26}$ is H, halogen, $C_1$-$C_4$alkyl, $C_1$-$C_4$haloalkyl, CN, —NHSO$_2$—$C_1$-$C_4$alkyl, —NHSO$_2$—$C_1$-$C_4$haloalkyl, —NHSO$_2$—$C_3$-$C_6$cycloalkyl optionally substituted with 1-3 halogens, or $C_3$-$C_6$cycloalkyl optionally substituted with 1-3 halogens; and each $R^{27}$ is independently H, F, Cl, CH$_3$, —CFH$_2$, —CF$_2$H or —CF$_3$, provided that no more than four $R^{27}$ is other than H.

Embodiment 15Z of this disclosure relates to Embodiment 14 Z, wherein $R^7$ is one of the following groups:

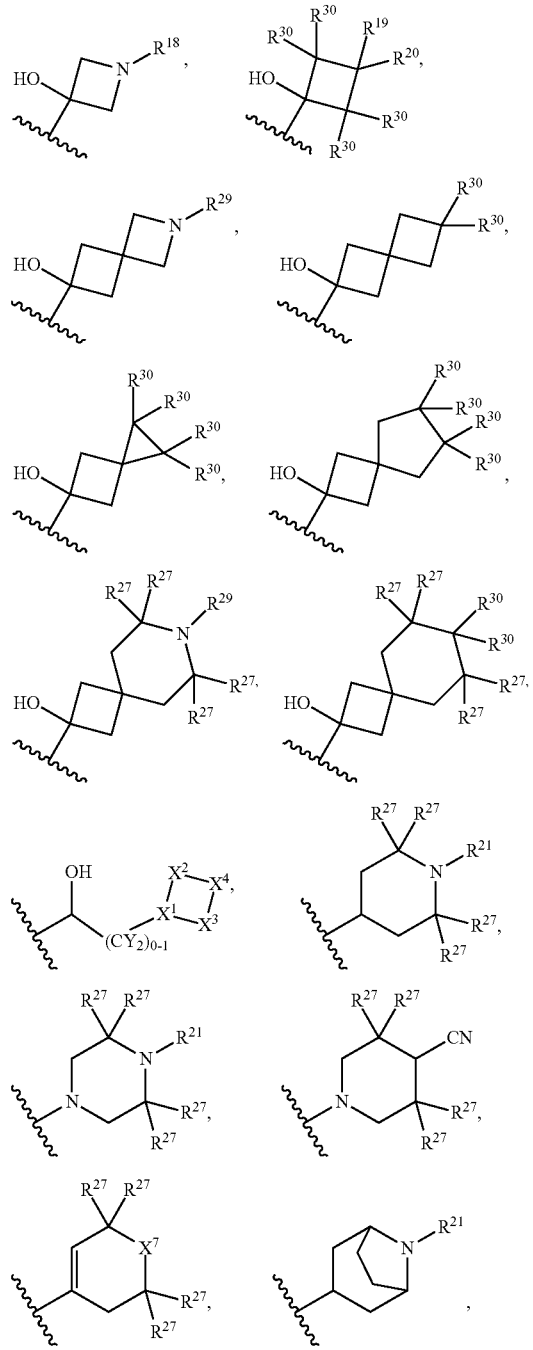

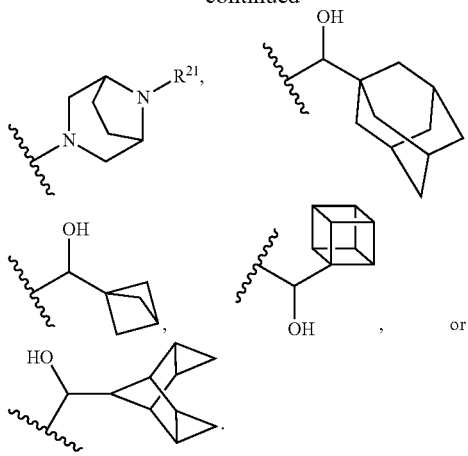

wherein:

each Y is independently H, F, CH$_3$, —CFH$_2$, —CF$_2$H or —CF$_3$, or two Y groups join together, with the carbon atom to which they are attached, to form a cyclopropyl or cyclobutyl group;

$X^7$ is N—C($R^{25}$)($R^{26}$)—;

$R^{18}$ is H, $C_1$-$C_3$alkyl, $C_1$-$C_3$haloalkyl, —SO$_2$—$C_1$-$C_3$alkyl, —SO$_2$—$C_3$-$C_6$cycloalkyl optionally substituted with 1-3 F, —SO$_2$—$C_1$-$C_3$fluoroalkyl, or $C_3$-$C_6$cycloalkyl optionally substituted with 1-3 F;

$R^{19}$ is H, F, CN, cyclopropyl, cyclobutyl, $C_1$-$C_3$alkyl, or —$C_1$-$C_{33}$fluoroalkyl;

$R^{20}$ is H, F, CN, cyclopropyl, cyclobutyl, $C_1$-$C_3$alkyl, $C_1$-$C_3$fluoroalkyl, —NHSO$_2$—$C_1$-$C_4$alkyl, —NHSO$_2$—$C_3$-$C_6$cycloalkyl optionally substituted with 1-3 halogens, —NHSO$_2$—$C_1$-$C_4$fluoroalkyl, or $C_3$-$C_6$cycloalkyl optionally substituted with 1-3 F;

or $R^{19}$ and $R^{20}$ join together with the carbon atom to which they are attached to form one of the following groups (a)-(d):

(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl can also be optionally substituted with —NHSO$_2$—$C_1$-$C_3$alkyl, —NHSO$_2$—$C_1$-$C_3$haloalkyl, or —NHSO$_2$—$C_3$-$C_6$cycloalkyl optionally substituted with 1-3 halogens;

(b) a 4-6 membered nitrogen-containing heterocycloalkyl optionally substituted on its carbon atoms with 1-3 groups independently selected from the group consisting of CN, F, $C_1$-$C_3$alkyl, and $C_1$-$C_3$fluoroalkyl, and wherein the nitrogen-containing heterocycloalkyl can also be optionally N-substituted with —SO$_2$—$C_1$-$C_3$alkyl, —SO$_2$—$C_1$-$C_3$fluoroalkyl or —SO$_2$—$C_3$-$C_6$cycloalkyl optionally substituted with 1-3 F;

(c) a 4-6 membered heterocycloalkyl containing —O—, —S—, —SO—, or SO$_2$—, wherein the 4-6 membered heterocycloalkyl is optionally substituted on its carbon atoms with 1-3 groups independently selected from the group consisting of CN, F, $C_1$-$C_3$alkyl, and $C_1$-$C_3$fluoroalkyl; or (d) a 7-10 membered bridged ring;

$R^{21}$ is H, $C_1$-$C_3$alkyl, $C_1$-$C_3$fluoroalkyl, —SO$_2$—$C_1$-$C_3$alkyl, —SO$_2$—$C_1$-$C_3$fluoroalkyl, —SO$_2$—$C_3$-$C_6$cycloalkyl optionally substituted with 1-3 F, —$C_3$-$C_3$cycloalkyl optionally substituted with 1-3 F or $C_3$-$C_6$cycloalkyl optionally substituted with 1-3 F;

$R^{25}$ is H, F, $C_1$-$C_3$alkyl, or $C_1$-$C_3$fluoroalkyl;

$R^{26}$ is H, F, $C_1$-$C_3$alkyl, $C_1$-$C_3$fluoroalkyl, CN, —NHSO$_2$—$C_1$-$C_3$alkyl, —NHSO$_2$—$C_1$-$C_3$fluoroalkyl, —NHSO$_2$—$C_3$-$C_6$cycloalkyl optionally substituted with 1-3 F, or $C_3$-$C_6$cycloalkyl optionally substituted with 1-3 F;

each $R^{27}$ is independently H, F, CH$_3$, —CFH$_2$, —CF$_2$H or —CF$_3$, provided that no more than two $R^{27}$ is other than H;

$R^{29}$ is H, $C_1$-$C_3$alkyl, $C_1$-$C_3$fluoroalkyl, —SO$_2$—$C_1$-$C_3$alkyl, —SO$_2$—$C_1$-$C_3$fluoroalkyl, —SO$_2$—$C_3$-$C_6$cycloalkyl optionally substituted with 1-3 F, $C_3$-$C_3$cycloalkyl optionally substituted with 1-3 F, or $C_3$-$C_6$cycloalkyl optionally substituted with 1-3 F; and $R^{30}$ is H, F, or $C_1$-$C_3$ alkyl optionally substituted with 1-3 F.

Embodiment 16 Z relates to Embodiment 15 Z, wherein $R^7$ is one of the following groups:

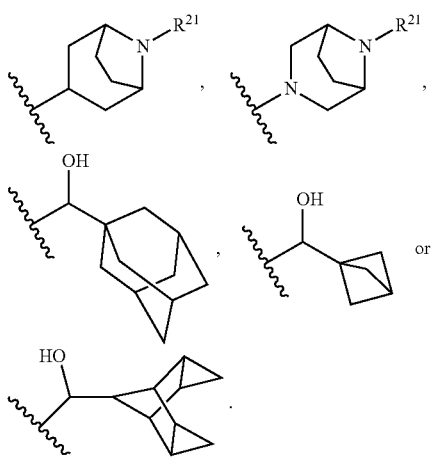

Embodiment 17 Z relates to any one of Embodiments 1-13Z, wherein $R^7$ is one of the following groups:

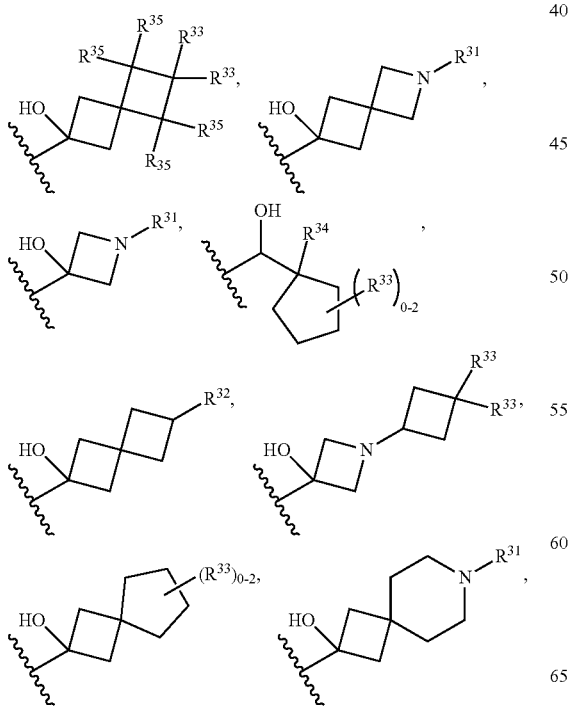

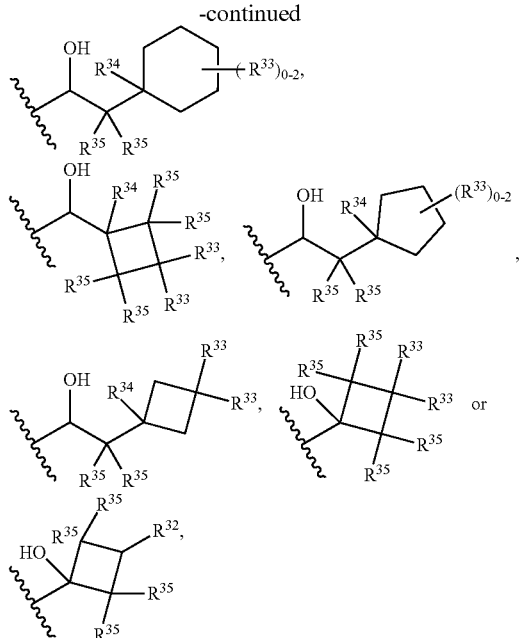

$R^{31}$ is H, $C_1$-$C_3$ alkyl optionally substituted with 1-3 F, —SO$_2$—$R^{35}$ or $C_3$-$C_6$ cycloalkyl optionally substituted with 1-3 F;

$R^{32}$ is —SO$_2$—$R^{35}$ or —NHSO$_2$—$R^{35}$;

$R^{33}$ is H, F, CN, cyclopropyl, or $C_1$-$C_3$ alkyl optionally substituted with 1-3 F;

$R^{34}$ is H, F, or $C_1$-$C_3$ alkyl optionally substituted with 1-3 F; and $R^{35}$ is H, F, methyl optionally substituted with 1-3 F, or two $R^{35}$ groups, together with the carbon atom to which they are attached, join together to form a cyclopropyl group.

Embodiment 18Z of this disclosure relates to any one of Embodiments 1-13Z, wherein $R^7$ is one of the following groups:

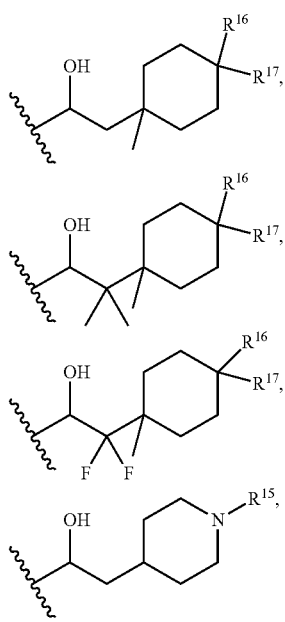

-continued

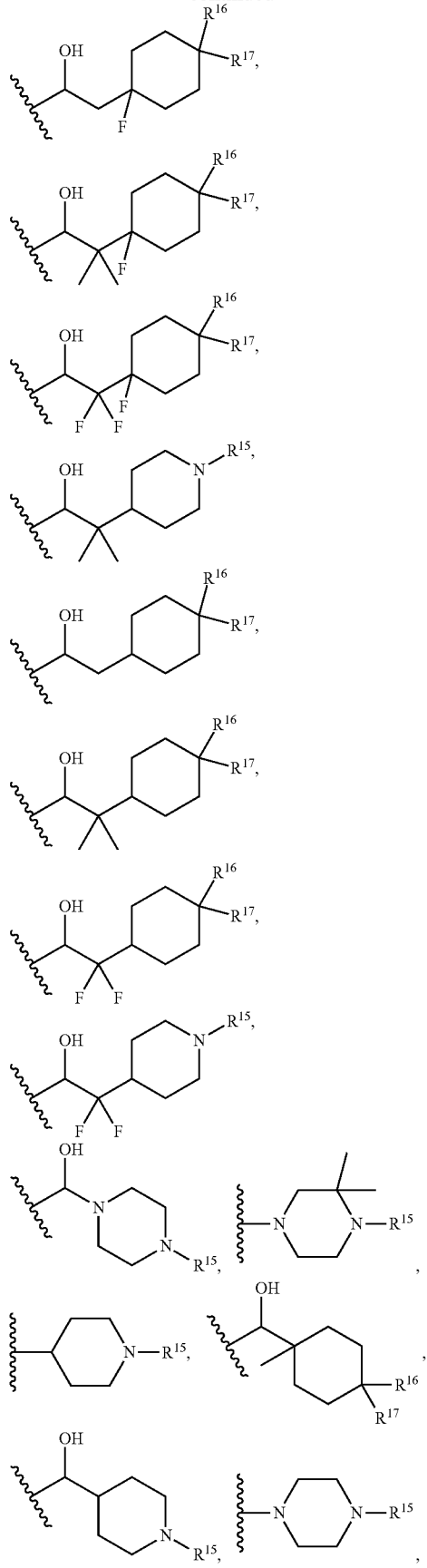

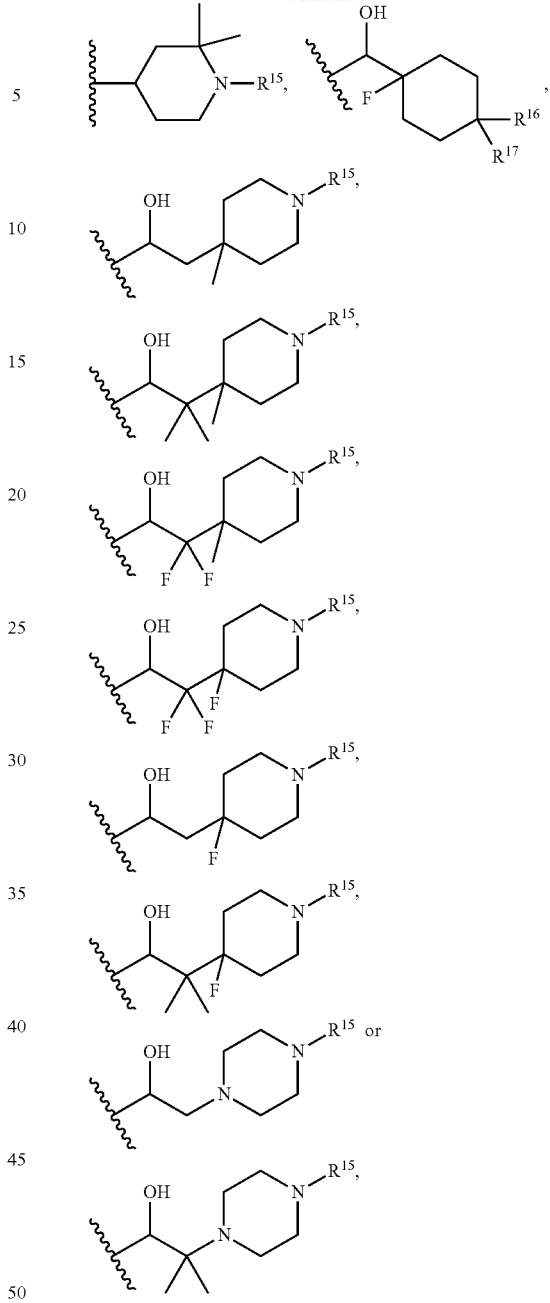

wherein:

R[15] is H, $C_1$-$C_3$alkyl, $C_1$-$C_3$fluoroalkyl, —$SO_2$—$C_1$-$C_3$alkyl, —$SO_2$—$C_3$-$C_6$cycloalkyl optionally substituted with 1-3 F, —$SO_2$—$C_1$-$C_3$fluoroalkyl, or $C_3$-$C_6$cycloalkyl optionally substituted with 1-3 F;

R[16] is H, F, $C_1$-$C_3$alkyl, or $C_1$-$C_3$fluoroalkyl;

R[17] is H, F, $C_1$-$C_3$ alkyl, $C_1$-$C_3$fluoroalkyl, —$NHSO_2$—$C_1$-$C_3$alkyl, —$SO_2$—$C_3$-$C_3$cycloalkyl optionally substituted with 1-3 F, —$SO_2$—$C_3$-$C_6$cycloalkyl optionally substituted with 1-3 F, —$NHSO_2$—$C_1$-$C_3$haloalkyl, or $C_3$-$C_6$cycloalkyl optionally substituted with 1-3 F;

or R[16] and R[17], when they both exist, join together with the carbon atom to which they are attached to form one of the following groups (a)-(c):

(a) a $C_3$-$C_6$cycloalkyl optionally substituted with 1-3 groups independently selected from the group consisting of CN, F, C$_1$-C$_3$alkyl, and C$_1$-C$_3$fluoroalkyl, and wherein the C$_3$-C$_6$cycloalkyl can also be optionally substituted with —NHSO$_2$—C$_1$-C$_3$alkyl, —NHSO$_2$—C$_3$-C$_6$cycloalkyl optionally substituted with 1-3 F, or —NHSO$_2$—C$_1$-C$_3$fluoroalkyl;

(b) a 4-6 membered nitrogen-containing heterocycloalkyl optionally substituted on its carbon atoms with 1-3 groups independently selected from the group consisting of CN, F, C$_1$-C$_3$alkyl, and C$_1$-C$_3$fluoroalkyl, and wherein the nitrogen-containing heterocycloalkyl can also be optionally N-substituted with —SO$_2$—C$_1$-C$_3$alkyl, —SO$_2$—C$_3$-C$_6$cycloalkyl optionally substituted with 1-3 F, or —SO$_2$—C$_1$-C$_3$fluoroalkyl; or (c) a 4-6 membered heterocycloalkyl containing —O—, —S—, —SO—, or SO$_2$—, wherein the 4-6 membered heterocycloalkyl is optionally substituted on its carbon atoms with 1-3 groups independently selected from the group consisting of CN, F, C$_1$-C$_3$alkyl, and C$_1$-C$_3$fluoroalkyl; and each Y is independently H, F, CH$_3$, —CFH$_2$, —CF$_2$H or —CF$_3$.

Embodiment 19 Z of this disclosure relates to the compound according to any one of embodiments 1-13Z, wherein R$^7$ is one of the following groups:

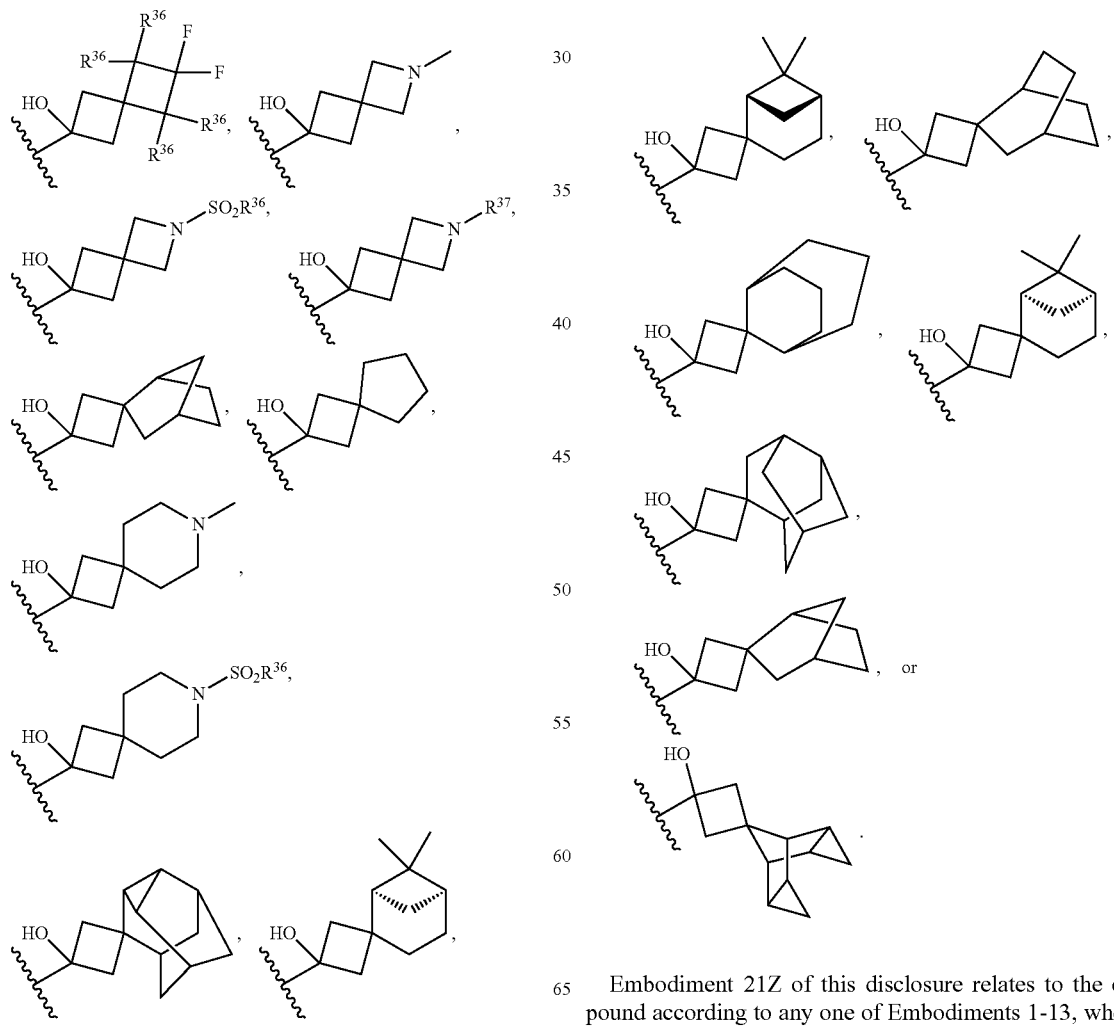

wherein:

R$^{36}$ is H or C$_1$-C$_3$ alkyl optionally substituted with 1-3 F; and

R$^{37}$ is H, —NHSO$_2$R$^{36}$ or —SO$_2$R$^{36}$.

Embodiment 20Z of this disclosure relates to the compound according to Embodiment 19, wherein R$^7$ is one of the following groups:

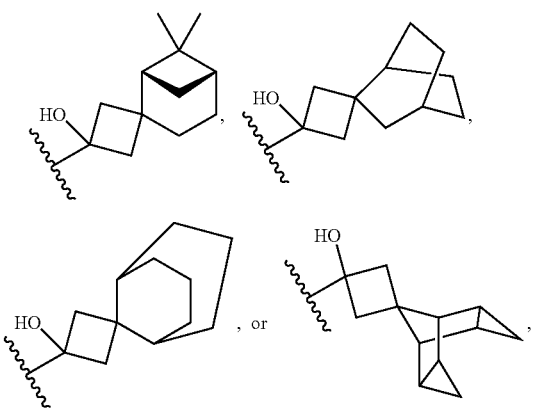

Embodiment 21Z of this disclosure relates to the compound according to any one of Embodiments 1-13, wherein R$^7$ is one of the following groups:

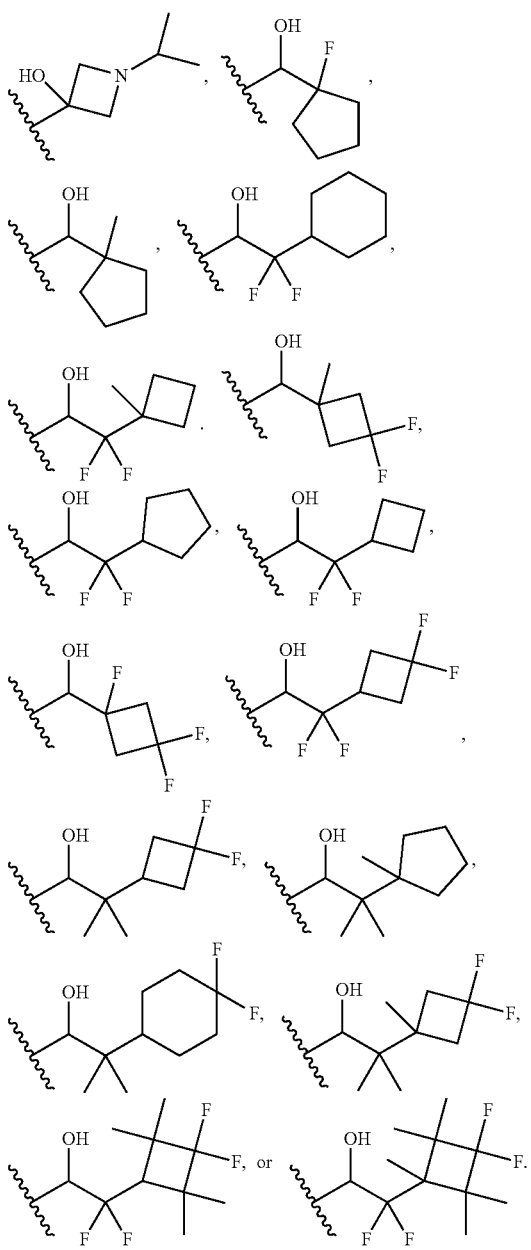

Embodiment 22z of this disclosure relates to Embodiment 1Z selected from Table 1.

Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, different crystal forms or polymorphs, and active metabolites.

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers as defined herein. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

In addition to the present formulae and compounds described herein, the disclosure also includes prodrugs (generally pharmaceutically acceptable prodrugs), active metabolic derivatives (active metabolites), and their pharmaceutically acceptable salts.

Unless specified to the contrary, specification of a compound herein includes pharmaceutically acceptable salts of such compound.

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae.

In some embodiments, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex can be formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

III. Formulations and Administration

Embodiment 31 of this disclosure relates to a pharmaceutical composition comprising a compound in one of Embodiments 1-30, and a pharmaceutically acceptable carrier. In some embodiments, embodiment 31z of this disclosure relates to a pharmaceutical composition comprising a compound in one of Embodiments 1Z-21Z, and a pharmaceutically acceptable carrier. In some embodiments, embodiment 31z of this disclosure relates to a pharmaceutical composition comprising a compound in one of Embodiments 1Z-22Z, and a pharmaceutically acceptable carrier.

Embodiment 32 of this disclosure relates to a pharmaceutical composition of Embodiment 31, further comprising a second pharmaceutical agent. In some embodiments, embodiment 32z of this disclosure relates to a pharmaceutical composition of Embodiment 31z, further comprising a second pharmaceutical agent.

Embodiment 33 of this disclosure relates to the pharmaceutical composition according to Embodiment 32, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor; xv) a Mek inhibitor; xvi) a tyrosine kinase inhibitor; xvii) an EGFR inhibitor; or xviii) an anti-retroviral agent selected from entry inhibitors, fusion inhibitors, reverse transcriptase inhibitors, nucleoside/nucleotide reverse transcriptase inhibitors, non-nucleoside reverse transcriptase inhibitors, integrase inhibitors, protease inhibitors, and multi-class combination products. In some embodiments, embodiment 33z of this disclosure relates to the pharmaceutical composition according to Embodiment 32z, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor; xv) a Mek inhibitor; xvi) a tyrosine kinase inhibitor; xvii) an EGFR inhibitor; or xviii) an anti-retroviral agent selected from entry inhibitors, fusion inhibitors, reverse transcriptase inhibitors, nucleoside/nucleotide reverse transcriptase inhibitors, non-nucleoside reverse transcriptase inhibitors, integrase inhibitors, protease inhibitors, and multi-class combination products.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21st edition, Lippincott, Williams and Wilkins, Philadelphia, Pa., 2005 (hereby incorporated by reference herein).

Compounds of the present disclosure (i.e. any of the compounds described in Embodiments 1-30 can be formulated as pharmaceutically acceptable salts. Compounds of the present disclosure (i.e. any of the compounds described in Embodiments 1Z to 21Z can be formulated as pharmaceutically acceptable salts. Compounds of the present disclosure (i.e. any of the compounds described in Embodiments 1Z to 22Z can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Methods of Use

The methods and compounds will typically be used in therapy for human subjects. However, they may also be used to treat similar or identical indications in other animal subjects.

Embodiment 34 of this disclosure relates to a method for treating a subject with a disease or condition mediated by IDO1, TDO or both IDO1 and TDO, said method comprising administering to the subject an effective amount of a compound in one of Embodiments 1-30, or a pharmaceutically acceptable salt, deuterated analog, a tautomer or an isomer thereof, or a pharmaceutical composition in one of Embodiments 31-33, wherein the disease or condition express aberrantly or otherwise IDO1, TDO, or both IDO1 and TDO, or activating mutations or translocations of any of the foregoing. Embodiment 34Z of this disclosure relates to a method for treating a subject with a disease or condition mediated by IDO1, TDO or both IDO1 and TDO, said method comprising administering to the subject an effective amount of a compound in one of Embodiments 1Z-21Z or 1Z to 22Z, or a pharmaceutically acceptable salt, deuterated analog, a tautomer or an isomer thereof, or a pharmaceutical composition in one of Embodiments 31Z-33Z, wherein the disease or condition express aberrantly or otherwise IDO1, TDO, or both IDO1 and TDO, or activating mutations or translocations of any of the foregoing.

Embodiment 35 of this disclosure relates to a method for treatment of a disease or condition according to Embodiment 34, wherein the disease or condition is an inflammatory disease, an inflammatory condition, an autoimmune disease or cancer. Embodiment 35Z of this disclosure relates to a method for treatment of a disease or condition according to Embodiment 34Z, wherein the disease or condition is an inflammatory disease, an inflammatory condition, an autoimmune disease or cancer.

Embodiment 36 of this disclosure relates to a method for treatment of a disease or condition according to Embodiment 35, wherein the disease or condition is selected from the group consisting of immunosuppression, rheumatoid arthritis, type 1 diabetes, lupus, Hashimoto's thyroid disease, multiple sclerosis, inflammatory bowel disease, Crohn's disease, ulcerative colitis, celiac disease, autoimmune disorders of the intestines, diseases caused by enteric pathogens, asthma, HIV, tumor growth, tumor metastasis, infectious diseases, non-infectious inflammatory disease, skin cancer promoted by chronic inflammation, Alzheimer's disease, Parkinson's disease, Huntington's disease, amyotrophic lateral sclerosis, multiple sclerosis, schizophrenia, bipolar disorder, depression, inflammation-associated depression, cardiovascular disease, end-stage renal disease, chronic kidney disease and atherosclerosis. Embodiment 36Z of this disclosure relates to a method for treatment of a disease or condition according to Embodiment 35Z, wherein the disease or condition is selected from the group consisting of immunosuppression, rheumatoid arthritis, type 1 diabetes, lupus, Hashimoto's thyroid disease, multiple sclerosis, inflammatory bowel disease, Crohn's disease, ulcerative colitis, celiac disease, autoimmune disorders of the intestines, diseases caused by enteric pathogens, asthma, HIV, tumor growth, tumor metastasis, infectious diseases, noninfectious inflammatory disease, skin cancer promoted by chronic inflammation, Alzheimer's disease, Parkinson's disease, Huntington's disease, amyotrophic lateral sclerosis, multiple sclerosis, schizophrenia, bipolar disorder, depression, inflammation-associated depression, cardiovascular disease, end-stage renal disease, chronic kidney disease and atherosclerosis.

Embodiment 37 of the disclosure relates to a contraceptive or abortion method, said method comprising administering to the subject an effective amount of a compound in one of Embodiments 1-30, or a pharmaceutically acceptable salt, deuterated analog, a tautomer or an isomer thereof, or a pharmaceutical composition in one of Embodiments 31-33. Embodiment 37Z of the disclosure relates to a contraceptive or abortion method, said method comprising administering to the subject an effective amount of a compound in one of Embodiments 1Z-21Z or 1Z-22Z, or a pharmaceutically acceptable salt, deuterated analog, a tautomer or an isomer thereof, or a pharmaceutical composition in one of Embodiments 31Z-33Z.

There are six major types of anti-retroviral agents used to treat HIV/AIDS. These agents are called anti-retrovirals because they act against the retrovirus HIV. Anti-retroviral agents are grouped by how they interfere with steps in HIV replication.

1. Entry Inhibitors interfere with the virus' ability to bind to receptors on the outer surface of the cell it tries to enter. When receptor binding fails, HIV cannot infect the cell. A non-limiting examples of Entry Inhibitors is maraviroc.
2. Fusion Inhibitors interfere with the virus's ability to fuse with a cellular membrane, preventing HIV from entering a cell. Non-limiting example of a Fusion Inhibitor includes enfuvirtide, T-20.
3. Reverse Transcriptase Inhibitors prevent the HIV enzyme reverse transcriptase (RT) from converting single-stranded HIV RNA into double-stranded HIV DNA—a process called reverse transcription. There are two types of RT inhibitors described below in (3a) and (3b):

(3a) Nucleoside/nucleotide RT inhibitors (NRTIs) are faulty DNA building blocks. When one of these faulty building blocks is added to a growing HIV DNA chain, no further correct DNA building blocks can be added on, halting HIV DNA synthesis. Non-limiting examples of nucleoside reverse transcriptase inhibitors include lamivudine and zidovudine; emtricitabine, FTC; lamivudine, 3TC; abacavir and lamivudine; zalcitabine, dideoxycytidine, ddC; zidovudine, azidothymidine, AZT, ZDV; abacavir, zidovudine, and lamivudine; tenofovir disoproxil fumarate and emtricitabine; enteric coated didanosine, ddI EC; didanosine, dideoxyinosine, ddI; tenofovir disoproxil fumarate, TDF; stavudine, d4T; and abacavir sulfate, ABC.

(3b) Non-nucleoside RT inhibitors (NNRTIs) bind to RT, interfering with its ability to convert HIV RNA into HIV DNA. Non-limiting examples of non-nucleoside RT inhibitor include rilpivirine; etravirine; delavirdine, DLV; efavirenz, EFV; and nevirapine, NVP.

4. Integrase Inhibitors block the HIV enzyme integrase, which the virus uses to integrate its genetic material into the DNA of the cell it has infected. Non-limiting examples of HIV integrase inhibitors include raltegravir, dolutegravir, and elvitegravir.
5. Protease Inhibitors interfere with the HIV enzyme called protease, which normally cuts long chains of HIV proteins into smaller individual proteins. When protease does not work properly, new virus particles cannot be assembled. Non-limiting examples of protease inhibitors include amprenavir, APV; tipranavir, TPV; indinavir, IDV; saquinavir; saquinavir mesylate, SQV; lopinavir and ritonavir; LPV/RTV; Fosamprenavir Calcium; p FOS-APV; ritonavir, RTV; darunavir; atazanavir sulfate, ATV; and nelfinavir mesylate, NFV.
6. Multi-class Combination Products combine HIV drugs from two or more classes, or types, into a single product. Non-limiting examples of Multi-class Combination Products include efavirenz, emtricitabine and tenofovir disoproxil fumarate; emtricitabine, rilpivirine, and tenofovir disoproxil fumarate; atazanavir sulfate, combicistat; cobicistat, darunavir ethanolate; and elvitegravir, cobicistat, emtricitabine, tenofovir disoproxil fumarate.

Embodiment 38 of this disclosure relates to a method for treating a subject with HIV, said method comprising administering to the subject an effective amount of a compound in one of Embodiments 1-30, or a pharmaceutically acceptable salt, deuterated analog, a tautomer or an isomer thereof, or a pharmaceutical composition in one of Embodiments 34-36, in combination with one or more anti-retroviral agents. Embodiment 38Z of this disclosure relates to a method for treating a subject with HIV, said method comprising administering to the subject an effective amount of a compound in one of Embodiments 1Z-22Z, or a pharmaceutically acceptable salt, deuterated analog, a tautomer or an isomer thereof, or a pharmaceutical composition in one of Embodiments 34Z-36Z, in combination with one or more anti-retroviral agents.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per dosage. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by IDO1 and/or TDO by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in a compound in one of Embodiments 1Z-22Z, or a pharmaceutically acceptable salt, deuterated analog, a tautomer or an isomer thereof, and wherein the compound is administered on an empty stomach. In certain embodiments, provided herein is a method for treating a diseases or condition mediated by IDO1 and/or TDO by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in a compound in one of Embodiments 1-30, or a pharmaceutically acceptable salt, deuterated analog, a tautomer or an isomer thereof, and wherein the compound is administered on an empty stomach.

Other embodiments of this disclosure relate to compounds that are IDO1/TDO dual inhibitors in any of Embodiments 1Z-22Z. Other embodiments of this disclosure relate to compounds that are IDO1/TDO dual inhibitors in any of Embodiments 1-30.

Other embodiments of this disclosure relate compounds that are IDO1 selective inhibitors over TDO in any of Embodiments 1Z-22Z. Other embodiments of this disclosure relate compounds that are IDO1 selective inhibitors over TDO in any of Embodiments 1-30.

As used herein, the term IDO1 or TDO mediated disease or condition refers to a disease or condition in which the biological function of IDO1 or TDO affects the development and/or course of the disease or condition, and/or in which modulation of IDO1 or TDO alters the development, course, and/or symptoms. These mutations attenuate the intrinsic activity of the receptor to different degrees and are models for the effect of modulation of IDO1 or TDO activity. An IDO1 or TDO mediated disease or condition includes a disease or condition for which IDO1 or TDO inhibition provides a therapeutic benefit, e.g. wherein treatment with IDO1 or TDO inhibitors, including compounds described herein, provides a therapeutic benefit to the subject suffering from or at risk of the disease or condition.

V. Combination Therapy

IDO and TDO modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides a composition comprising one or more compounds as described in any of Embodiments 1-30, or a pharmaceutically acceptable salt, deuterated analog, a tautomer or an isomer thereof, or a pharmaceutical composition thereof, and one or more agents. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustinc, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-.alpha., and interleukin-2; IDO inhibitors, including, but not limited to, indoximod, and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); and MEK inhibitors (e.g., AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), TAK-733). In some embodiments, the present disclosure provides a composition comprising one or more compounds as described in any of Embodiments 1Z-22Z, or a pharmaceutically acceptable salt, deuterated analog, a tautomer or an isomer thereof, or a pharmaceutical composition thereof, and one or more agents. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustinc, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-alpha, and interleukin-2; IDO inhibitors, including, but not limited to, indoximod, and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); and MEK inhibitors (e.g., AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), TAK-733).

In one embodiment, the present disclosure provides methods for treating a disease or condition mediated by IDO1 and/or TDO, by administering to the subject an effective amount of a composition including any one or more compound(s) as described herein in combination with one or more other suitable therapies for treating the disease.

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, gamma-ray, or electron, proton, neutron, or .alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

VI. Kits

In another aspect, the present disclosure provides kits that include one or more compounds as described in any one of a compound in one of Embodiments 1Z-22Z, or a pharmaceutically acceptable salt, deuterated analog, a tautomer or an isomer thereof, or a pharmaceutical composition in one of Embodiments 23Z-25Z. In another aspect, the present disclosure provides kits that include one or more compounds as described in any one of a compound in one of Embodiments 1-30, or a pharmaceutically acceptable salt, deuterated analog, a tautomer or an isomer thereof, or a pharmaceutical composition in one of Embodiments 31-33. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a an IDO or TDO mediated disease or condition; the kits described herein may include written instructions for use and/or other indication that the compound or composition is suitable or approved for administration to a mammal, e.g., a human, for an IDO1 and/or TD an IDO or TDO-mediated disease or condition; and the compound or composition may be packaged in unit dose or single dose form, e.g., single dose pills, capsules, or the like.

VII. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 μM under standard conditions. By "very low activity" is meant an $IC_{50}$ or $EC_{50}$ of above 100 μM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owickiet al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

VIII. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

IX. Manipulation of IDO1 or TDO

Techniques for the manipulation of nucleic acids, such as, e.g., subcloning, labeling probes (e.g. random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the disclosure can be performed by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the present disclosure can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the present disclosure can also be provided in expression vectors and cloning vehicles, e.g., sequences encoding the polypeptides used to practice the methods of the present disclosure. Expression vectors and cloning vehicles used to practice the methods of the present disclosure can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors used to practice the methods of the present disclosure can include chromosomal, non-chromosomal and synthetic DNA sequences. Large numbers of suitable vectors are known to those of skill in the art, and are commercially available.

The nucleic acids used to practice the methods of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435:10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the present disclosure can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids used to practice the methods of the present disclosure are administered in vivo for in situ expression of the peptides or polypeptides used to practice the methods of the disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, selected from baculoviridiae, parvoviridiae, picornoviridiae, herpesveridiae, poxviridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the present disclosure; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) J. Virol. 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present disclosure also relates to use of fusion proteins, and nucleic acids encoding them. A polypeptide used to practice the methods of the present disclosure can be fused to a heterologous peptide or polypeptide, such as N-terminal identification peptides which impart desired characteristics, such as increased stability or simplified purification. Peptides and polypeptides used to practice the methods of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif 12:404-414). The histidine residues facilitate detection and purification while the enterokinase cleavage site provides a means for purifying the epitope from the remainder of the fusion protein. In one aspect, a nucleic acid encoding a polypeptide used to practice the methods of the present disclosure is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll (1993) DNA Cell. Biol. 12:441-53.

The nucleic acids and polypeptides used to practice the methods of the present disclosure can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl) aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding polypeptides and peptides used to practice the methods of the present disclosure to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides used to practice the methods of the present disclosure can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the present disclosure. For example, in one aspect of the disclosure, a monitored parameter is transcript expression of a gene comprising a nucleic acid used to practice the methods of the present disclosure. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the present disclosure. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the present disclosure, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The present disclosure also provides a transformed cell comprising a nucleic acid sequence used to practice the methods of the present disclosure, e.g., a sequence encoding a polypeptide used to practice the methods of the present disclosure, or a vector used to practice the methods of the present disclosure. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the present disclosure. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the present disclosure may or may not also include an initial methionine amino acid residue.

Cell-free translation systems can also be employed to produce a polypeptide used to practice the methods of the present disclosure. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y, pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/mL), 100 μM chloroquine, 10% NuSerum, DNA (0.4 mg/mL) in DMEM/F12 medium is then applied on the cells 10 mL volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/mL). Individual colonies of G418-resistant cells are isolated about 2-3 weeks later, clonally selected and then propagated for assay purposes.

EXAMPLES

The examples below depict the general synthetic procedure for the compounds described herein. Synthesis of the compounds described herein is not limited by these examples and schemes. One skilled in the art will know that other procedures can be used to synthesize the compounds described herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. Unless otherwise specified, intermediate compounds in the examples below, that do not contain a description of how they are made, are either commercially available to one skilled in the art, or can otherwise be synthesized by the skilled artisan using commercially available precursor molecules and synthetic methods known in the art.

The following Generic Schemes and synthetic examples are intended to be illustrative and are not limiting or restrictive to the scope of the disclosure.

Generic Schemes

General Scheme 1

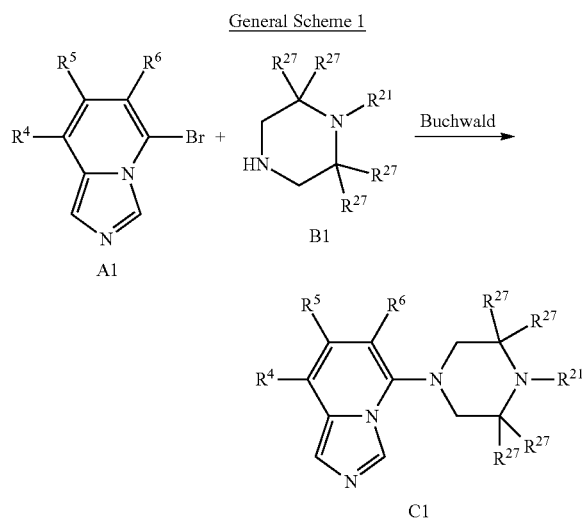

Added together are compound A1, compound B1, a palladium catalyst base (such as chloro(2-dicyclohexylphosphino-2',6'-di-i-propoxy-1,1'-biphenyl)[2-(2-aminoethyl-phenyl]palladium(II)), an appropriate ether adduct (such as methyl-t-butyl ether adduct), an appropriate base (such as sodium tert-butoxide), and an appropriate solvent (such as THF). The reaction mixture is then placed under appropriate reaction conditions to form compound C1.

General Scheme 2

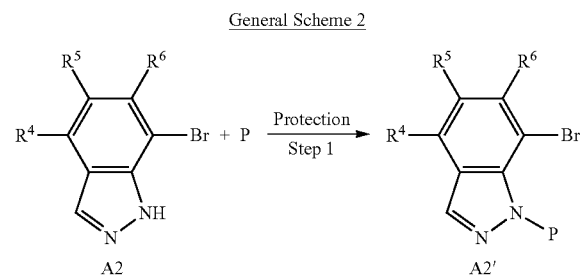

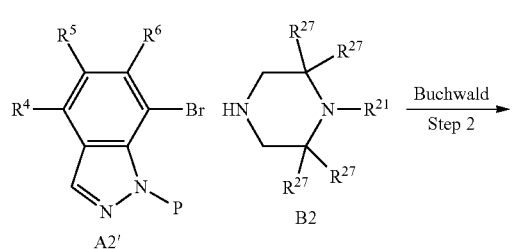

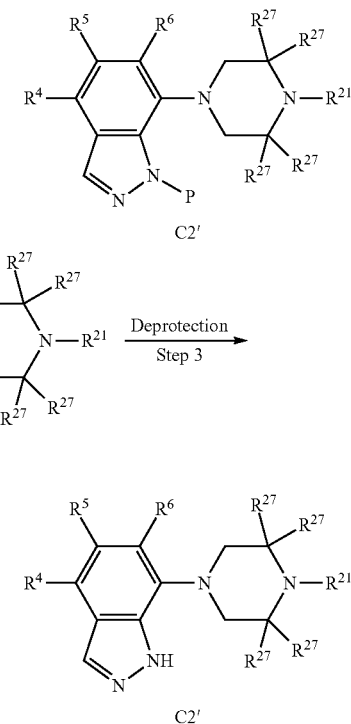

Step 1:
To starting material A2 is added protecting group P (such as 3,4-dihydro-2h-pyran) by combining A2 and P with an appropriate acid (such as methane sulfonic acid) in an appropriate solvent (such as THF). The reaction mixture is put under appropriate reaction conditions to form compound A2'.

Step 2:
Added together are compound A2', compound B2, a palladium catalyst base (such as chloro(2-dicyclohexylphosphino-2',6'-di-i-propoxy-1,1'-biphenyl)[2-(2-aminoethyl-phenyl)]palladium(II)), an appropriate ether adduct (such as methyl-t-butyl ether adduct), an appropriate base (such as sodium tert-butoxide), and an appropriate solvent (such as THF). The reaction mixture is then placed under appropriate reaction conditions to form compound C2'.

Step 3:
To compound C2' is added an appropriate solvent (such as MeOH and THF) and an appropriate acid (such as HCl) under appropriate reaction conditions to remove protecting group P and form compound C2'.

General Scheme 3

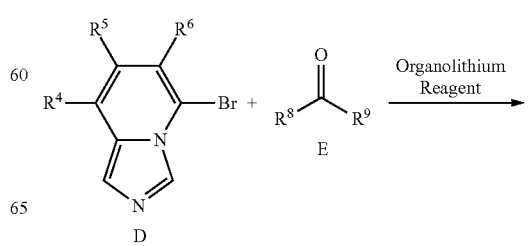

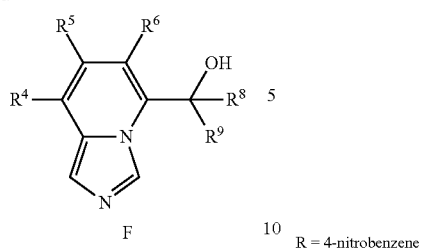

F

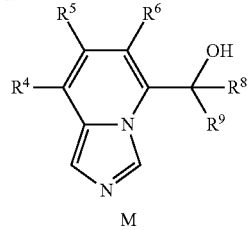

R = 4-nitrobenzene

M

To compound D in an appropriate solvent (such as THF) is added an appropriate organolithium reagent (an alkyllithium reagent such as butyllithium), or an appropriate Grignard reagent (such as chloro(isopropyl)magnesium). To the reaction mixture is added a ketone compound E, and the reaction mixture is placed under appropriate reaction conditions to form compound F.

Step 1:
To compound G in an appropriate solvent (such as dichloromethane) is added 1-isothiocyanato-4-nitro-benzene. The reaction mixture is placed under appropriate reaction conditions to give compound H.

Step 2:
To compound H is added N-ethyl-N-isopropyl-propan-2-amine and isopropanol. The reaction mixture is placed under appropriate reaction conditions to yield compound I.

Step 3:
To compound I is added an appropriate base (such as potassium carbonate) and an appropriate alkylating agent (such as iodoethane). The reaction mixture is placed under appropriate reaction conditions to give compound J.

Step 4:
To compound J in an appropriate solvent, such as THF (5 mL) under appropriate reaction conditions, is added an appropriate organolithium reagent (an alkylithium reagent such as butyllithium). Compound K is then added to the reaction mixture, and the reaction mixture is placed under appropriate reaction conditions to yield compound L.

Step 5:
To compound L in an appropriate solvent is added raney nickel. The reaction mixture is placed under appropriate reaction conditions to yield compound M.

General Scheme 4

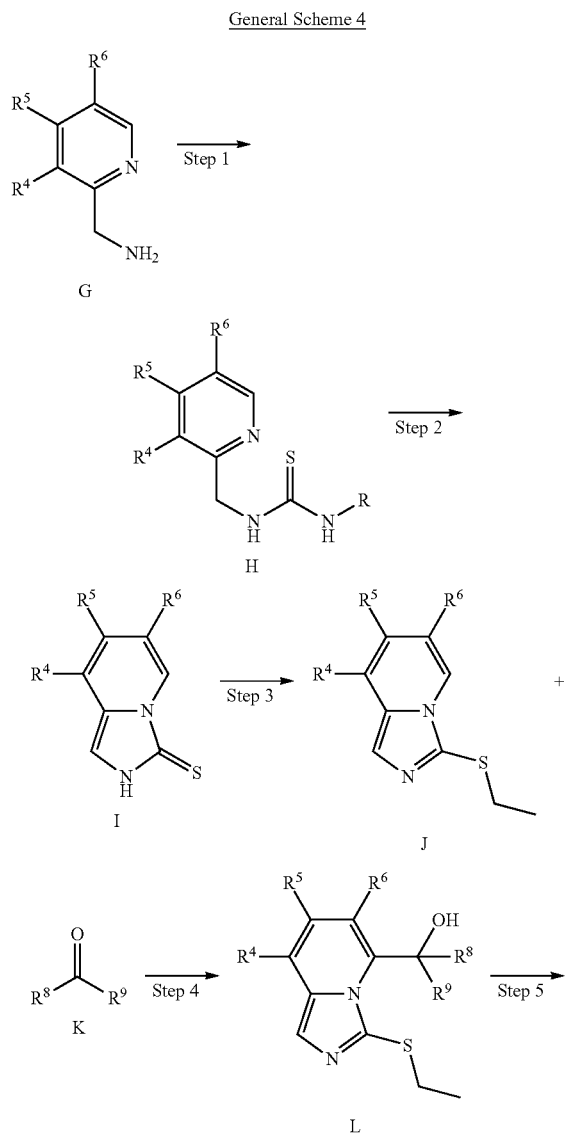

Synthetic Examples

Standard abbreviations and acronyms as defined in *J. Org. Chem.* 2007 72(1): 23A-24A are used herein. Other abbreviations and acronyms used herein are described above.

The preparation of the tricyclic compounds depicted in Examples 1-4 below required significant experimentation, including a number of attempts and modifications of reaction conditions, in order to achieve successful results.

Example 1

(5,6-dihydro-1H-cyclobuta[f]indazol-7-yl)(1-methyl-cyclohexyl)methanol (P-0054)

Scheme 1

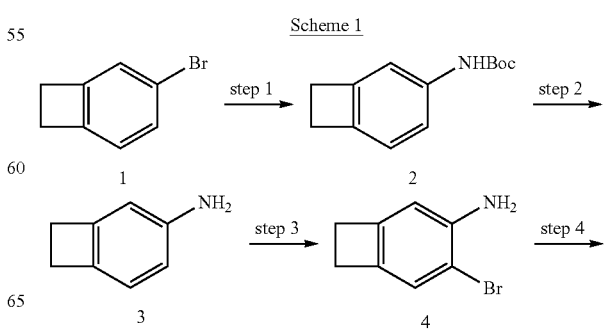

-continued

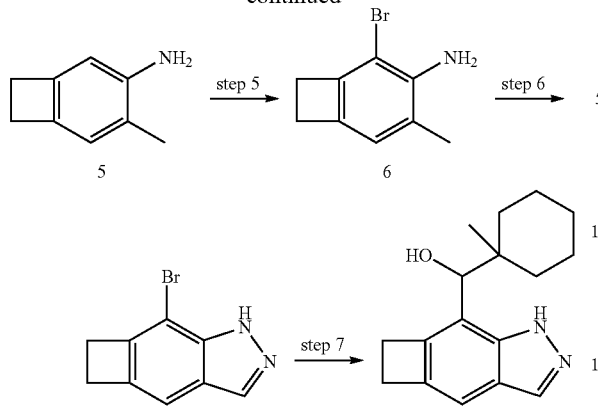

P-0054

Step 1—Preparation of tert-butyl N-(4-bicyclo[4.2.0]octa-1,3,5-trienyl)carbamate (2)

To 4-bromobicyclo[4.2.0]octa-1,3,5-triene (1, 3.25 g, 17.76 mmol) in dioxane (30 mL) were added tert-butyl carbamate (2.53 g, 21.6 mmol), cesium carbonate (9.2 g, 28.24 mmol), 4,5-bis(diphenylphosphino)-9,9-dimethylxanthene (0.5 g, 0.86 mmol), and tris(dibenzylideneacetone)dipalladium-chloroform adduct (0.3 g, 0.29 mmol). The reaction mixture was stirred at 105° C. under nitrogen overnight. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (2).

Step 2—Preparation of bicyclo[4.2.0]octa-1,3,5-trien-4-amine (3)

To tert-butyl N-(4-bicyclo[4.2.0]octa-1,3,5-trienyl)carbamate (2, 1.64 g, 7.48 mmol) in dichloromethane (20 mL) was added 2,2,2-trifluoroacetic acid (2 g, 17.54 mmol). The reaction mixture was stirred at room temperature overnight. The reaction mixture was poured into aqueous potassium carbonate, and extracted with ethyl acetate. The organic layer was washed with brine, dried over sodium sulfate, and filtered. The filtrate was concentrated to give product (3) that was used in the next step without further purification. $[M+H^+]+=120.0$.

Step 3—Preparation of 4-bromobicyclo[4.2.0]octa-1,3,5-trien-3-amine (4)

To bicyclo[4.2.0]octa-1,3,5-trien-4-amine (3, 0.89 g, 7.47 mmol) in acetonitrile (60 mL), cooled to −30° C. under nitrogen, was added 1-bromopyrrolidine-2,5-dione (1.36 g, 7.62 mmol). The reaction mixture was allowed to warm to room temperature overnight. LCMS showed the reaction was complete. The reaction mixture was poured into water, and extracted with ethyl acetate. The organic layer was washed with brine, dried over sodium sulfate, and filtered. The filtrate was concentrated to give crude product around (4). $[M+H^+]+=197.8, 199.8$.

Step 4—Preparation of 3-methylbicyclo[4.2.0]octa-1,3,5-trien-4-amine (5)

To 4-bromobicyclo[4.2.0]octa-1,3,5-trien-3-amine (4, 1.6 g, 8.08 mmol) and methylboronic acid (1.5 g, 25.06 mmol) in 1,4-dioxane (15 mL) and water (5.0 mL) were added [1,1'-bis(diphenylphosphino)ferrocene]dichloropalladium (II) (0.5 g, 0.68 mmol), and potassium carbonate (5 g, 36.18 mmol). The reaction mixture was stirred at 90° C. under nitrogen for 3 hours. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (5). $[M+H^+]+=134.0$.

Step 5—Preparation of 5-bromo-3-methyl-bicyclo[4.2.0]octa-1(6),2,4-trien-4-amine (6)

To 3-methylbicyclo[4.2.0]octa-1,3,5-trien-4-amine (5, 0.25 g, 1.84 mmol) in acetonitrile (15 mL), cooled to −30° C. under nitrogen, was added 1-bromopyrrolidine-2,5-dione (0.33 g, 1.88 mmol). The reaction mixture was allowed to warm to room temperature for 1 hour. LCMS showed the reaction was complete. The reaction mixture was poured into water, and extracted with ethyl acetate. The organic layer was washed with brine and potassium carbonate 5 times, dried over sodium sulfate, and filtered. The filtrate was concentrated to give crude product (6). $[M+H^+]+=211.8, 213.8$.

Step 6—Preparation of 7-bromo-5,6-dihydro-1H-cyclobuta[f]indazole (7)

To 5-bromo-3-methyl-bicyclo[4.2.0]octa-1(6),2,4-trien-4-amine (6, 0.38 g, 1.79 mmol) in acetic acid (10 mL) was added sodium nitite (0.4 g, 5.83 mmol) dissolved in water (1.0 mL). The reaction mixture was stirred at room temperature for 3 hours. The reaction mixture was concentrated, poured into aqueous potassium carbonate, and extracted with ethyl acetate. The organic layer was washed with brine, dried over sodium sulfate, and filtered. The filtrate was concentrated, and purified with silica gel column chromatography eluting with 1% to 10% methanol in methylene chloride, and then further purified with reverse C18 column to give product (7). $[M+H^+]+=222.8, 224.8$.

Step 7—Preparation of (5,6-dihydro-1H-cyclobuta[f]indazol-7-yl)(1-methylcyclohexyl)methanol (8, P-0054)

To 7-bromo-5,6-dihydro-1H-cyclobuta[f]indazole (7, 0.07 g, 0.31 mmol) in THF (4 mL), cooled to −78° C. under nitrogen, was added 2.5 M n-BuLi in hexane (0.3 mL). After 30 minutes, 1-methylcyclohexanecarbaldehyde (0.08 g, 0.63 mmol) was added to the reaction. The reaction mixture was then allowed to warm to room temperature in 1 hour. The reaction mixture was poured into water, and extracted with ethyl acetate. The organic layer was washed with brine, dried over sodium sulfate, and filtered. The filtrate was concentrated, and purified with silica gel column chromatography eluting with 1% to 12% methanol in methylene chloride to give desired product (8, P-0054). $[M+H^+]^+=271.2$.

Example 2

(1-methylcyclohexyl)(6,7,8,9-tetrahydro-3H-benzo[e]indazol-4-yl)methanol (P-0050)

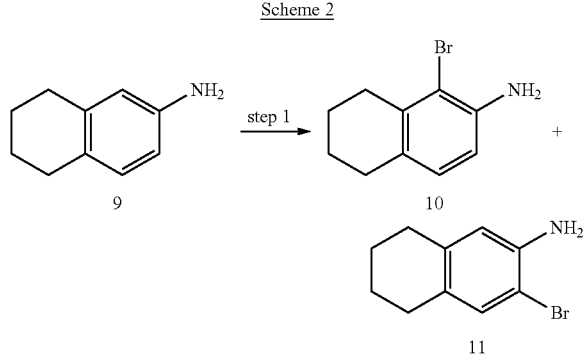

Step 1—Preparation of 5-bromotetralin-6-amine (10)

To tetralin-6-amine (9, 2.3 g, 15.62 mmol) in acetonitrile (60 mL), cooled to −20° C. under nitrogen, was added 1-bromopyrrolidine-2,5-dione (2.78 g, 15.62 mmol) slowly. The reaction mixture was allowed to warm to 0° C. in 2 hours. LCMS showed the reaction was complete. The reaction mixture was poured into water, and extracted with ethyl acetate. The organic layer was washed with brine, dried over sodium sulfate, and filtered. The filtrate was concentrated to give a mixture of 10 and 11 with a ratio of 85:15 according to $^1$H NMR. [M+H$^+$]$^+$=225.8, 227.8.

Step 2—Preparation of 5-methyltetralin-6-amine (12)

To 5-bromotetralin-6-amine (10, 1.2 g, 5.31 mmol, 85% pure from previous step) in 1,4-dioxane (15 mL) and water (2.0 mL) were added [1,1'-bis(diphenylphosphino)ferrocene]dichloropalladium(II) (0.4 g, 0.55 mmol) and 2,4,6-trimethyl-1,3,5,2,4,6-trioxatriborinane (0.72 g, 5.75 mmol) and potassium carbonate (3.25 g, 23.52 mmol). The reaction mixture was stirred at 90° C. under nitrogen 3 days. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (12). [M+H$^+$]$^+$=162.0.

Step 3—Preparation of 7-bromo-5-methyl-tetralin-6-amine (13)

To 5-methyltetralin-6-amine (12, 1.9 g, 11.78 mmol, 85% purity) in acetonitrile (30 mL), cooled to −50° C. under nitrogen, was added 1-bromopyrrolidine-2,5-dione (2.1 g, 11.8 mmol). The reaction mixture was allowed to warm to 0° C. in 2 hours. LCMS showed the reaction was complete. The reaction mixture was poured into aqueous potassium carbonate, and extracted with ethyl acetate. The organic layer was washed with brine, dried over sodium sulfate, and filtered. The filtrate was concentrated to give crude product (13%) that was used directly in the next step without further purification. [M+H$^+$]$^+$=240.0, 241.9.

Step 4—Preparation of 4-bromo-6,7,8,9-tetrahydro-3H-benzo[e]indazole (14)

To 7-bromo-5-methyl-tetralin-6-amine (13, 1.4 g, 5.83 mmol, 85% purity) in acetic acid (30 mL) was added sodium nitrite (0.4 g, 5.83 mmol) dissolved in water (1.0 mL). The reaction mixture was stirred at room temperature for 3 hours. The reaction mixture was concentrated, poured into aqueous potassium carbonate, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (14). [M+H$^+$]$^+$=251.0, 253.0.

Step 5—Preparation of (1-methylcyclohexyl)(6,7,8,9-tetrahydro-3H-benzo[e]indazol-4-yl)methanol (15, P-0050)

To 4-bromo-6,7,8,9-tetrahydro-3H-benzo[e]indazole (14, 0.3 g, 1.19 mmol) in THF (6 mL), cooled to −78° C. under nitrogen, was added 11 M n-BuLi in THF (0.25 mL). After 20 minutes 1-methylcyclohexanecarbaldehyde (0.3 g, 2.38 mmol) was added to the reaction. The reaction mixture was allowed to warm to room temperature in 1 hour. The reaction mixture was poured into water, and extracted with ethyl acetate. The organic layer was washed with brine, dried over sodium sulfate, and filtered. The filtrate was concentrated, and purified by silica gel column chromatography eluting with 5% to 100% ethyl acetate in hexane, and then further purified with reverse phase C18 column to give product (15, P-0050), and recovery of starting material 210 mg. MS (ESI) [M+H]$^+$=299.1.

Example 3

9-bromo-5,6,7,8-tetrahydro-1H-benzo[f]indazole (Intermediate 24)

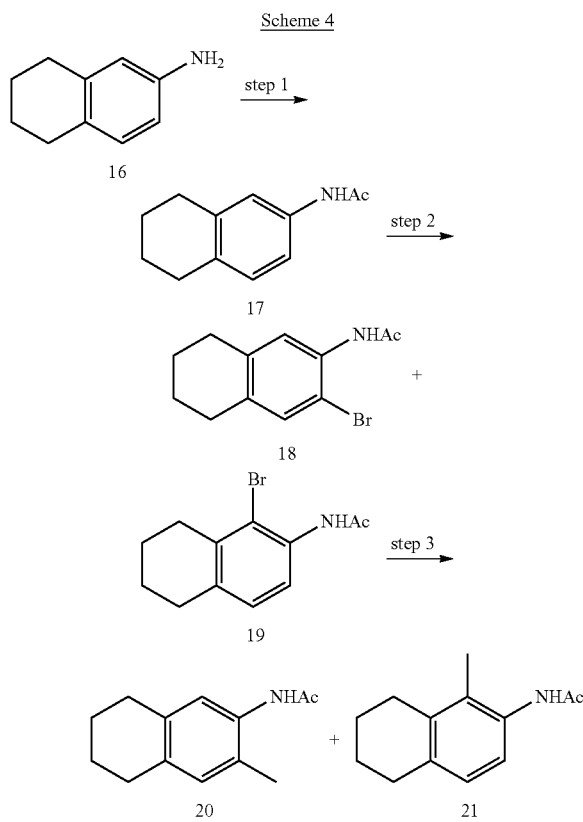

Step 1—Preparation of N-tetralin-6-ylacetamide (17)

To tetralin-6-amine (16, 5 g, 33.96 mmol) in ethyl acetate (50 mL), were added pyridine (3.7 mL, 45.98 mmol) and acetyl acetate (3.53 mL, 37.36 mmol). The reaction mixture was stirred at room temperature overnight. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (17). [M+H]$^+$=190.2.

Step 2—Preparation of N-(7-bromotetralin-6-yl)acetamide (18)

To N-tetralin-6-ylacetamide (17, 2.4 g, 12.68 mmol) in acetic acid (30 mL), cooled to 10° C., was added bromine (0.78 mL, 15.22 mmol) slowly. The reaction mixture was allowed to warm to 0° C. for 2 hours. The reaction mixture was poured into water, and extracted with ethyl acetate. The organic layer was washed with brine, dried over sodium sulfate, and filtered. The filtrate was concentrated to give a mixture of product 18 and 19 with the ratio of approximately 1:2. This mixture was used directly in the next step without further purification. [M+H]$^+$=267.9, 269.9.

Step 3—Preparation of N-(7-methyltetralin-6-yl)acetamide (20)

To a mixture of N-(7-bromotetralin-6-yl)acetamide (18) and N-(5-bromotetralin-6-yl)acetamide (19) (3.3 g, 12.3 mmol, 18:19~1:2) in 1,4-dioxane (15 mL) and water (5.0 mL) were added [1,1'-bis(diphenylphosphino)ferrocene]dichloropalladium(II) (0.5 g, 0.68 mmol), methylboronic acid (1.47 g, 24.56 mmol) and potassium carbonate (5.5 g, 39.8 mmol). The reaction mixture was stirred at 90° C. under nitrogen for 3 hours. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (20) and product (21). Product 20: [M+H]$^+$=204.0.

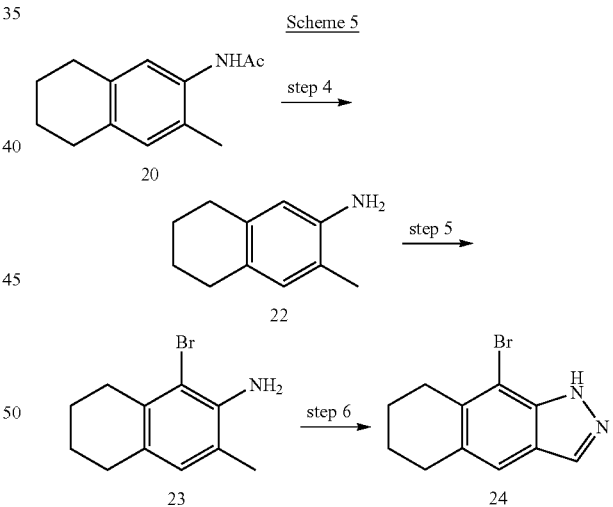

Step 4—Preparation of 7-methyltetralin-6-amine (22)

To N-(7-methyltetralin-6-yl)acetamide (20, 0.75 g, 3.69 mmol) was added 6N hydrogen chloride in water (40 mL). The reaction mixture was stirred at 110° C. for 6 hours. The reaction mixture was concentrated, and then poured into aqueous potassium carbonate, and extracted with ethyl acetate. The organic layer was washed with brine, dried over sodium sulfate, and filtered. The filtrate was concentrated to give product (22). [M+H]$^+$=162.1.

Step 5—Preparation of 5-bromo-7-methyl-tetralin-6-amine (23)

To 7-methyltetralin-6-amine (22, 0.46 g, 2.85 mmol) in acetonitrile (15 mL) at −40° C. was added 1-bromopyrrolidine-2,5-dione (4.55 g, 25.57 mmol) slowly. The reaction mixture was allowed to warm to room temperature and then stirred overnight. LCMS showed the reaction was complete. The reaction mixture was poured into aqueous potassium carbonate, and extracted with ethyl acetate. The organic layer was washed with brine, dried over sodium sulfate, and filtered. The filtrate was concentrated to give crude product (23) that was used directly in the next step. [M+H$^+$]$^+$=239.8, 241.8.

Step 6—Preparation of 9-bromo-5,6,7,8-tetrahydro-1H-benzo[f]indazole (24)

To 5-bromo-7-methyl-tetralin-6-amine (23, 0.66 g, 2.75 mmol) in acetic acid (30 mL) was added sodium nitite (0.19 g, 2.75 mmol). The reaction mixture was stirred at room temperature for 3 hours. The reaction mixture was concentrated, poured into aqueous potassium carbonate, and extracted with ethyl acetate. The organic layer was washed with brine, dried over sodium sulfate, and filtered. The filtrate was concentrated, and purified by silica gel column chromatography eluting with 20% to 100% ethyl acetate in hexane to give product (24). [M+H$^+$]$^+$=250.9, 252.9.

Example 4

(1-methylcyclohexyl)(1,5,6,7-tetrahydrocyclopenta[f]indazol-8-yl)methanol (P-0099)

Scheme 6

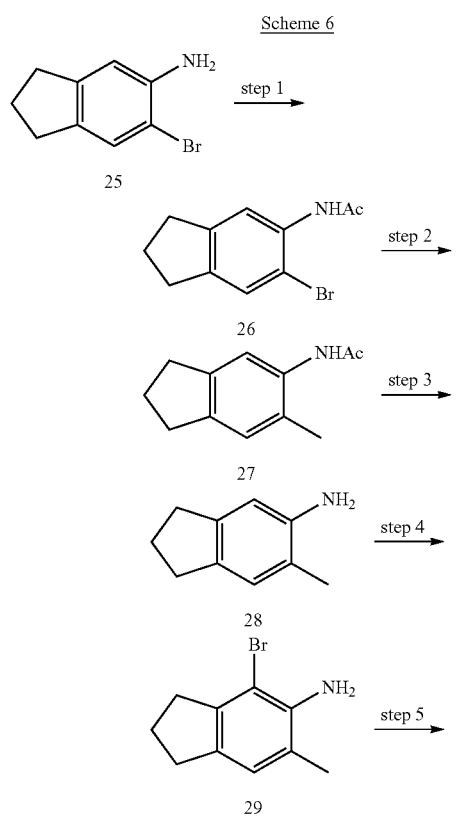

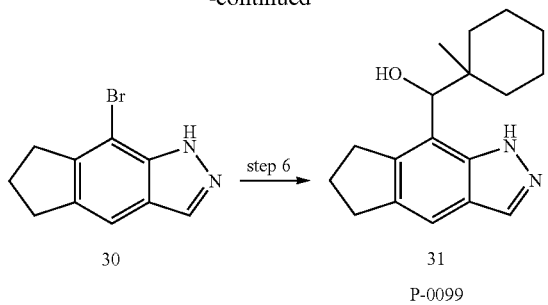

P-0099

Step 1—Preparation of N-(6-bromoindan-5-yl)acetamide (26)

To 6-bromoindan-5-amine (25, 1.3 g, 6.13 mmol) in ethyl acetate (20 mL), were added pyridine (0.9 mL, 11.17 mmol) and acetyl acetate (0.65 mL, 6.88 mmol). The reaction mixture was stirred at room temperature for 3 days. The reaction mixture was poured into water, and extracted with ethyl acetate. The organic layer was washed with brine, dried over sodium sulfate, and filtered. The filtrate was concentrated to give product (26). MS (ESI) [M+H$^+$]$^+$=253.9, 255.9.

Step 2—Preparation of N-(6-methylindan-5-yl)acetamide (27)

To N-(6-bromoindan-5-yl)acetamide (26, 1.4 g, 5.51 mmol) and methylboronic acid (1 g, 16.71 mmol) in 1,4-dioxane (15 mL) and water (5 mL) were added [1,1'-bis(diphenylphosphino)ferrocene]dichloropalladium(II) (0.5 g, 0.68 mmol), and potassium carbonate (3.5 g, 25.32 mmol). The reaction mixture was stirred at 90° C. under nitrogen for 2 hours. The reaction mixture was poured into water, and extracted with ethyl acetate. The organic layer was washed with brine, dried over sodium sulfate, and filtered. The filtrate was concentrated, and purified with silica gel column chromatography eluting with 20% to 100% ethyl acetate in hexane to give product (27). MS (ESI) [M+H$^+$]$^+$=190.1.

Step 3—Preparation of 6-methylindan-5-amine (28)

To N-(6-methylindan-5-yl)acetamide (27, 0.7 g, 3.7 mmol) was added 6M hydrogen chloride in H$_2$O (25 mL). The reaction mixture was stirred at 110° C. overnight. The reaction mixture was concentrated, and then poured into aqueous potassium carbonate, and extracted with ethyl acetate. The organic layer was washed with brine, dried over sodium sulfate, and filtered. The filtrate was concentrated to give product (28). MS (ESI) [M+H$^+$]$^+$=148.0.

Step 4—Preparation of 4-bromo-6-methyl-indan-5-amine (29)

To 6-methylindan-5-amine (28, 0.47 g, 3.19 mmol) in acetonitrile (15 mL), cooled to −30° C. under nitrogen, was added 1-bromopyrrolidine-2,5-dione (0.58 g, 3.26 mmol). The reaction mixture was allowed to warm to room temperature for 1 hour. The reaction mixture was poured into water, and extracted with ethyl acetate. The organic layer was washed with brine and potassium carbonate 5 times, dried over sodium sulfate, and filtered. The filtrate was concentrated to give crude product (29). [M+H⁺]⁺=225.8, 227.8.

Step 5—Preparation of 8-bromo-1,5,6,7-tetrahydrocyclopenta[f]indazole (30)

To 4-bromo-6-methyl-indan-5-amine (29, 0.72 g, 3.18 mmol) in acetic acid (10 mL) was added sodium nitrite (0.22 g, 3.25 mmol) dissolved in water (1.0 mL). The reaction mixture was stirred at room temperature for 1 hour. The reaction mixture was concentrated, poured into aqueous potassium carbonate (around 1 mL of 1 M solution), and extracted with ethyl acetate. The organic layer was washed with brine, dried over sodium sulfate, and filtered. The filtrate was concentrated, and purified by silica gel column chromatography eluting with 5% to 100% ethyl acetate in hexane, and then further purified with reverse C18 column chromatography to give product (30). [M+H⁺]⁺=236.9, 238.9.

Step 6—Preparation of (1-methylcyclohexyl)(1,5,6,7-tetrahydrocyclopenta[f]indazol-8-yl)methanol (31, P-0099)

To 8-bromo-1,5,6,7-tetrahydrocyclopenta[f]indazole (30, 0.03 g, 0.13 mmol) in THF (4 mL), under nitrogen cooled with dry ice/acetone, was added 2.5 M butyllithium in hexane (0.15 mL). After 30 minutes, 1-methylcyclohexanecarbaldehyde (0.05 g, 0.38 mmol) was added to the reaction. The reaction mixture was poured into water, and extracted with ethyl acetate. The organic layer was washed with brine, dried over sodium sulfate, and filtered. The filtrate was concentrated, and purified by silica gel column chromatography eluting with 1% to 15% methanol in methylene chloride, and then further purified with RP-HPLC to give product (31, P-0099). MS (ESI) [M+H⁺]⁺=284.9.

Example 5

((1S,3s)-adamantan-1-yl)(imidazo[1,5-a]pyridin-5-yl)methanol (P-0087)

Scheme 7

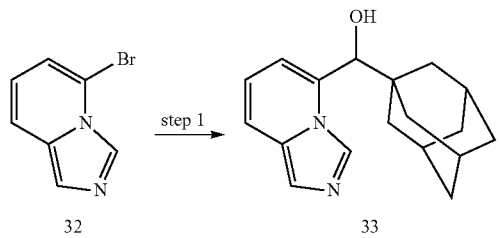

To 5-bromoimidazo[1,5-a]pyridine (32, 0.27 g, 1.37 mmol) in THF (5 mL) under an atmosphere of nitrogen at −30° C., was added 2M chloro(isopropyl)magnesium in THF (0.75 mL). The reaction mixture was allowed to warm to 0° C. for 1 hour, followed by adding adamantane-1-carbaldehyde (0.18 g, 1.1 mmol) in THF (1.0 mL). After 1 hour, the reaction mixture was allowed to warm to room temperature for 10 minutes. The reaction mixture was poured into water, extracted with ethyl acetate. The organic layer was washed with brine, and the organic layer was dried over sodium sulfate, concentrated, and purified with silica gel column chromatography eluting with 20% to 100% ethyl acetate in hexane to give product (33, P-0087). MS (ESI) [M+H⁺]⁺=283.0.

Example 6

2-(5-chloro-1H-indazol-7-yl)spiro[3.3]heptan-2-ol (P-0012)

Scheme 8

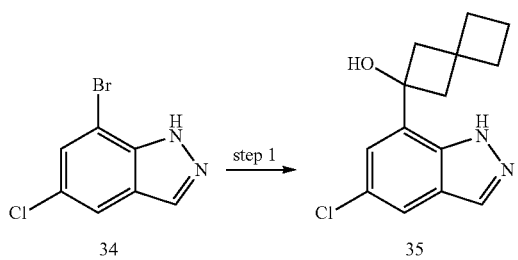

To 7-bromo-5-chloro-1H-indazole (34, 0.64 g, 2.76 mmol) in THF (6 mL), cooled to −78° C. under nitrogen, was added 10 M n-BuLi in THF (0.53 mL). After 1 hour, spiro[3.3]heptan-6-one (0.34 g, 3.04 mmol) was added to the reaction mixture. The reaction mixture was allowed to warm to room temperature for 1 hour. The reaction mixture was poured into water and extracted with ethyl acetate. The organic layer was washed with brine, dried over sodium sulfate, and filtered. The filtrate was concentrated, and then purified with silica gel column chromatography by eluting it with 10% to 100% ethyl acetate in hexane to give product (35, P-0012). MS (ESI) [M+H⁺]⁺=263.0.

Example 7

5-chloro-6-fluoro-7-(8-(methylsulfonyl)-3,8-diazabicyclo[3.2.1]octan-3-yl)-1H-indazole (P-0096)

Scheme 9

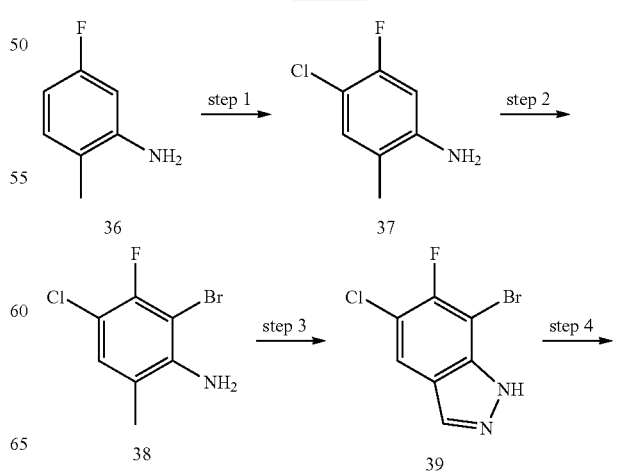

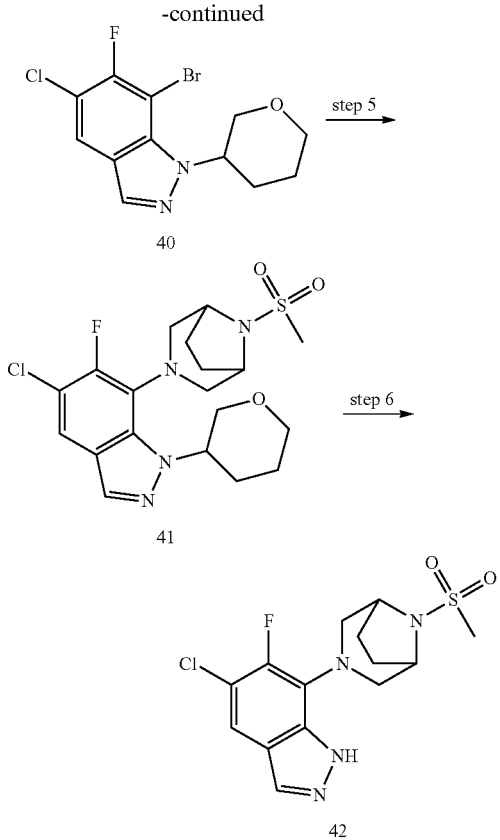

Step 3—Preparation of 7-bromo-5-chloro-6-fluoro-1H-indazole (39)

To 2-bromo-4-chloro-3-fluoro-6-methylaniline (38, 5.03 g, 21.1 mmol) in AcOH (210 mL) at room temperature was added sodium nitrite (1454.5 mg, 21.08 mmol) in H$_2$O (4.0 mL) slowly. The reaction mixture was stirred at room temperature for 17 hours. The reaction mixture was then concentrated, poured into 900 mL of ice water, and stirred vigorously giving a precipitate. The precipitate was collected by vacuum filtration and dissolved in ethyl acetate (300 mL), whereupon the organic fraction was washed with H$_2$O (2×100 mL) and 5 M NaCl (1×100 mL), dried over Na$_2$SO$_4$, filtered, and evaporated to give a solid. The solid was triturated with ether (100 mL), giving a solid that was collected by vacuum filtration and dried (39, 3770 mg, 72% yield). [M+H$^+$]$^+$=250.90. The filtrate was then evaporated, providing additional product as a solid (39). [M+H]+=250.90.

Step 4—Preparation of 7-bromo-5-chloro-6-fluoro-1-tetrahydropyran-2-yl-indazole (40)

To a dried 50 mL heavy walled pressure vessel was added 7-bromo-5-chloro-6-fluoro-1H-indazole (39, 1247.8 mg, 5.002 mmol), 3,4-dihydro-2h-pyran (1.36 mL, 1261.2 mg, 14.99 mmol), methanesulfonic acid (4.0 uL, 4.805 mg, 0.050 mmol), and THF (5.0 mL). The reaction mixture was placed under N$_2$, sealed, and heated to 80° C. for 13 hours. The reaction mixture was poured into water, and extracted with ethyl acetate. The organic layer was washed with brine, dried over sodium sulfate, and filtered. The filtrate was concentrated, and purified with silica gel column chromatography by eluting it with 10% to 100% ethyl acetate in hexane to give product (40). [M+H$^+$]$^+$=333.0, 335.0.

Step 5—Preparation of 5-chloro-6-fluoro-7-(8-methylsulfonyl-3,8-diazabicyclo[3.2.1]octan-3-yl)-1-tetrahydropyran-2-yl-indazole (41)

To a dried 50 mL heavy walled pressure vessel was added 7-bromo-5-chloro-6-fluoro-1-tetrahydropyran-2-yl-indazole (40, 528.2 mg, 1.583 mmol), 8-methylsulfonyl-3,8-diazabicyclo[3.2.1]octane hydrochloride (395.8 mg, 1.746 mmol), chloro(2-dicyclohexylphosphino-2',6'-di-i-propoxy-1,1'-biphenyl)[2-(2-aminoethylphenyl]palladium(II), methyl-t-butyl ether adduct (Strem Chemicals 46-0266, RuPhos Palladacycle Gen 1, 129.9 mg, 0.159 mmol), sodium tert-butoxide (2.0 M in THF, 1.74 mL, 3.48 mmol), and THF (15.0 mL). The pressure vessel was placed under N$_2$, sealed, and heated to 100° C. for 2 hours. The reaction mixture was poured into water, and extracted with ethyl acetate. The organic layer was washed with brine, dried over sodium sulfate, and filtered. The filtrate was concentrated, and purified by silica gel column chromatography eluting with 10% to 100% ethyl acetate in hexane to give product (41). [M+H$^+$]$^+$=443.1.

Step 6—Preparation of 5-chloro-6-fluoro-7-(8-(methylsulfonyl)-3,8-diazabicyclo[3.2.1]octan-3-yl)-1H-indazole (42, P-0096)

To a dried 20 mL glass scintillation vial was added 5-chloro-6-fluoro-7-(8-methylsulfonyl-3,8-diazabicyclo [3.2.1]octan-3-yl)-1-tetrahydropyran-2-yl-indazole (41, 129.0 mg, 0.291 mmol), MeOH (10.0 mL) and THF (3 mL). The reaction was stirred at 20° C., whereupon HCl (3N in

Step 1—Preparation of 4-chloro-5-fluoro-2-methyl-aniline (37)

To 5-fluoro-2-methylaniline (36, 6.53 g, 52.2 mmol) in acetonitrile (100 mL) was added N-chlorosuccinimide (6.68 g, 50.02 mmol). The reaction mixture was stirred at 80° C. for 1 hour. The reaction mixture was poured into water, and extracted with ethyl acetate. The organic layer was washed with brine, dried over sodium sulfate, and filtered. The filtrate was concentrated, and purified with silica gel column chromatography by eluting it with 10% to 100% ethyl acetate in hexane to give product (37). [M+H$^+$]$^+$=160.1.

Step 2—Preparation of 2-bromo-4-chloro-3-fluoro-6-methylaniline (38)

To a dried 250 mL 3 neck round bottom flask was added 4-chloro-5-fluoro-2-methyl-aniline (37, 5.23 g, 32.86 mmol) and acetonitrile (100.0 mL). The reaction vessel was placed under N$_2$ and stirred at 0° C., whereupon N-bromosuccinimide (5.83 g, 32.77 mmol, in acetonitrile 60.0 mL) was added slowly. The reaction mixture was stirred at 0° C. for 2 hours. After completion of the reaction as determined by LC/ESI-MS, the reaction mixture was poured into water, and then extracted with ethyl acetate. The organic layer was washed with brine, dried over sodium sulfate, and filtered. The filtrate was concentrated, and purified with silica gel column chromatography eluting with 10% to 100% ethyl acetate in hexane to give product (38). [M+H$^+$]$^+$=237.8, 239.8.

MeOH, Ampule, Supelco, 0.971 mL, 2.912 mmol) was added dropwise, slowly, by syringe. The reaction vial was placed under $N_2$, sealed, and stirred at 20° C. for 2 hours.

The reaction mixture was poured into water, and extracted with ethyl acetate. The organic layer was washed with brine, dried over sodium sulfate, and filtered. The filtrate was concentrated, and purified by reverse phase flash column chromatography (C18, 0-100% $CH_3CN$ (0.1% $HCO_2H$), $H_2O$ (0.1% $HCO_2H$)) to give product (42, P-0096). $[M+H^+]^+=359.1$.

Example 8

(1R,5S)-3'-(5-chloro-1H-indazol-7-yl)spiro[adamantane-2,1'-cyclobutan]-3'-ol (P-0100)

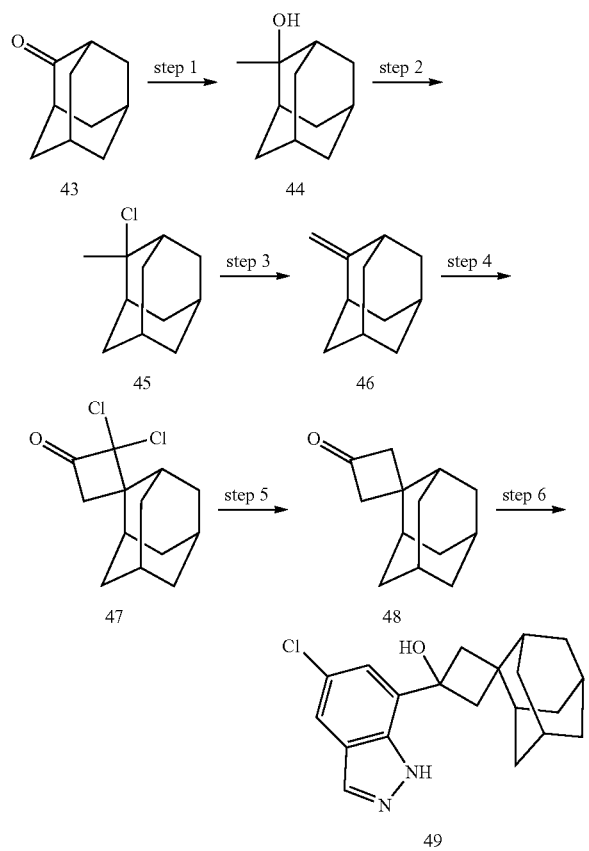

Step 1—Preparation of 2-methyladamantan-2-ol (44)

To adamantan-2-one (43, 5.4 g, 35.95 mmol) in THF (100 mL), cooled with dry ice/acetone under nitrogen, was added 1.6 M methyllithium in ether (24.71 mL) slowly. The reaction mixture was allowed to warm to room temperature overnight. The reaction mixture was poured into water, and extracted with ethyl acetate. The organic layer was washed with brine, dried over sodium sulfate, and filtered. The filtrate was concentrated to give product (44).

Step 2—Preparation of 2-chloro-2-methyl-adamantane (45)

To 2-methyladamantan-2-ol (44, 5.9 g, 35.49 mmol) in methylene chloride (10 mL) was added thionyl chloride (5 mL, 68.92 mmol) slowly. The reaction mixture was stirred at room temperature for 3 hours. The reaction mixture was concentrated to give product (45).

Step 3—Preparation of 2-methyleneadamantane (46)

To 2-chloro-2-methyl-adamantane (45, 6.5 g, 35.19 mmol) in acetonitrile (50 mL), was added potassium carbonate (8 g, 57.89 mmol). The reaction mixture was stirred at reflux overnight. The reaction mixture was poured into water, and extracted with ethyl acetate. The organic layer was washed with brine, dried over sodium sulfate, and filtered. The filtrate was concentrated to give product (46).

Step 4—Preparation of 2',2'-dichlorospiro[adamantane-2,3'-cyclobutane]-1'-one (47)

To 2-methyleneadamantane (46, 1.2 g, 8.09 mmol) in ether (30 mL), were added zinc (1.8 g, 27.53 mmol), and 2,2,2-trichloroacetyl chloride (0.96 mL, 8.55 mmol) slowly. The reaction mixture was sonicated at room temperature for 2 hours. The temperature rose to around 35° C. at the end of 2 hours. The reaction mixture was filtered, concentrated, and purified with silica gel column chromatography by eluting with 5% to 100% ethyl acetate in hexane to give product (47).

Step 5—Preparation of spiro[adamantane-2,3'-cyclobutane]-1'-one (48)

To 2',2'-dichlorospiro[adamantane-2,3'-cyclobutane]-1'-one (47, 1.9 g, 7.33 mmol) in acetic acid (15 mL), was added zinc (1.5 g, 22.94 mmol). The reaction mixture was stirred at room temperature for 2 hours. The reaction mixture was filtered, poured into aqueous potassium carbonate, and extracted with ethyl acetate. The aqueous layer was then acidified to pH around 4 with 6N HCl, and extracted with ethyl acetate. The organic layer was combined, washed with brine, dried over sodium sulfate, and filtered. The filtrate was concentrated to give product (48).

Step 6—Preparation of 1'-(5-chloro-1H-indazol-7-yl)spiro[adamantane-2,3'-cyclobutane]-1'-ol (49, P-0100)

To 7-bromo-5-chloro-1H-indazole (0.85 g, 3.67 mmol) in THF (5 mL), cooled to −78° C. under nitrogen, was added 1M n-BuLi in THF (0.67 mL). After 1 hour, spiro[adamantane-2,3'-cyclobutane]-1'-one (48, 0.4 g, 2.1 mmol) was added to the reaction mixture. The reaction mixture was allowed to warm to room temperature for 1 hour. The reaction mixture was poured into water, and extracted with ethyl acetate. The organic layer was washed with brine, dried over sodium sulfate, and filtered. The filtrate was concentrated, and purified with silica gel column chromatography by eluting it with 10% to 100% ethyl acetate in hexane to give product (49, P-0100). MS (ESI) $[M+H^+]^+=343.0$.

Example 9

(5-chloro-4-fluoro-1H-indazol-7-yl)(3,3-difluoro-1-methylcyclobutyl)methanol (P-650)

Scheme 11

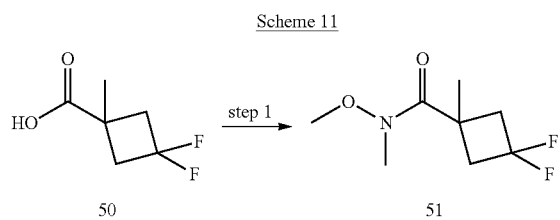

Step 1—Preparation of 3,3-difluoro-N-methoxy-N,1-dimethylcyclobutane-1-carboxamide (51)

To 3,3-difluoro-1-methyl-cyclobutanecarboxylic acid (50, 1 g, 6.63 mmol) was added NMP. To this solution was added N,O-dimethylhydroxylamine HCl (0.65 g, 6.67 mmol), and pyridine (3 mL, 37.1 mmol). After several minutes, 1.68 M 2,4,6-tripropyl-1,3,5,2,4,6-trioxatriphosporinane-2,4,6-trioxide (T3P, 10 mL, in ethyl acetate) was added. The reaction was allowed to stir at room temperature overnight. The reaction was poured into water and extracted with ethyl acetate. The organic phase was washed with water (1×200 mL), saturated ammonium chloride (1×200 mL) and brine (3×200 mL). The organic phase was dried over sodium sulfate and filtered. The solvent was removed under reduced pressure to provide product (51).

Scheme 12

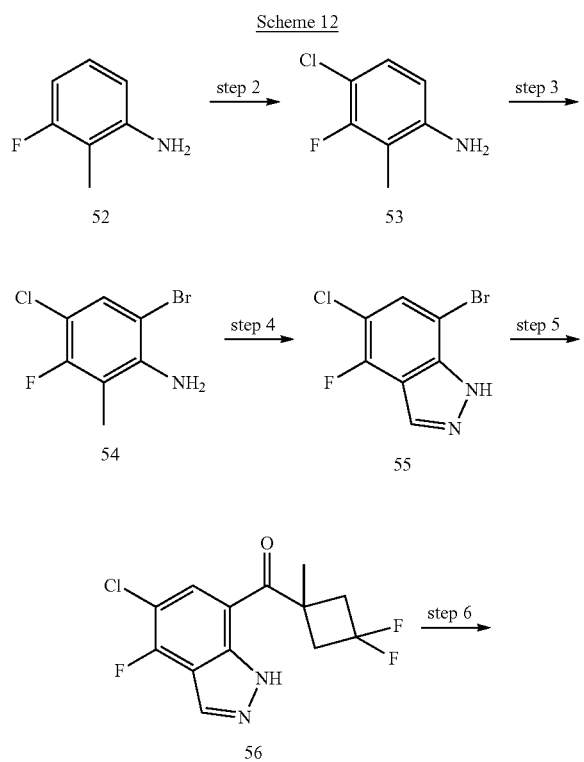

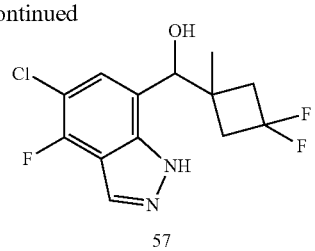

Step 2—Preparation of 4-chloro-3-fluoro-2-methylaniline (53)

To a solution of 3-fluoro-2-methyl-aniline (52, 5.01 g, 40 mmol) in acetonitrile (200 mL) was added N-chlorosuccinimide (2.67 mL, 42 mmol). The mixture was heated to reflux at 110° C. for 3 hours. The mixture was diluted with saturated aqueous sodium thiosulfate and extracted with ethyl acetate. The organic layer was washed with water followed by brine and was dried over anhydrous magnesium sulfate. The organic layer was filtered and concentrated under reduced pressure. The resulting residue was purified by silica gel flash chromatography eluting with 30% dichloromethane in hexane to provide product (53). MS (ESI) $[M+H^+]^+=160.2$.

Step 3—Preparation of 6-bromo-4-chloro-3-fluoro-2-methylaniline (54)

To an ice cold solution of 4-chloro-3-fluoro-2-methylaniline (53, 5.3 g, 33.21 mmol) in acetonitrile (200 mL) was added N-bromosuccinimide (2.96 mL, 34.87 mmol), portion wise. The mixture was allowed to stir and warm to room temperature over 3 hours. The mixture was diluted with saturated aqueous sodium thiosulfate and extracted with ethyl acetate. The organic layer was washed with water followed by brine and was dried over anhydrous magnesium sulfate. The organic layer was filtered and concentrated under reduced pressure. The resulting residue was purified by silica gel flash chromatography eluting with 40% dichloromethane in hexane to provide product (54). MS (ESI) $[M+H^+]^+=239.9$.

Step 4—Preparation of 7-bromo-5-chloro-4-fluoro-1H-indazole (55)

To an ice cold mixture of 6-bromo-4-chloro-3-fluoro-2-methyl-aniline (54, 4.29 g, 17.99 mmol) in acetic acid (50 mL) was added slowly a mixture of sodium nitrite (1.37 g, 19.79 mmol) in water. The mixture was allowed to stir and warm to room temperature for 1 hour. The reaction mixture was poured on to ice water. The precipitated pale solid was collected by vacuum filtration and washed with water to provide product (55). MS (ESI) $[M+H^+]^+=250.9$.

Step 5—Preparation of (5-chloro-4-fluoro-1H-indazol-7-yl)(3,3-difluoro-1-methylcyclobutyl)methanone (56)

To a 50 mL round bottom flask was added 7-bromo-5-chloro-4-fluoro-1H-indazole (55, 0.5 g, 2 mmol) followed by THF (10 mL). The solution was de-gassed, purged with nitrogen and allowed to stir at −78° C. for five minutes. To this solution was added 2.5 M n-BuLi (1.6 mL, THF) and the mixture was allowed to stir at −78° C. for 30 min. To this reaction was added 3,3-difluoro-N-methoxy-N,1-dimethyl-cyclobutanecarboxamide (51, 0.19 g, 1 mmol) and the reaction was allowed to stir for 2 h while warming to room temperature. The mixture was poured into water and extracted with ethyl acetate. The organic phase was washed with saturated ammonium chloride and brine, dried over sodium sulfate and filtered. The volatiles were removed under reduced pressure and the resulting residue was purified by silica gel flash chromatography eluting with 10-100% ethyl acetate in hexanes to provide product (56).

Step 6—Preparation of (5-chloro-4-fluoro-1H-indazol-7-yl)(3,3-difluoro-1-methylcyclobutyl)methanol (57, P-0650)

To (5-chloro-4-fluoro-1H-indazol-7-yl)-(3,3-difluoro-1-methyl-cyclobutyl)methanone (56, 85 mg, 0.28 mmol) was added THF (8 mL). The resulting solution was stirred at 0° C. for five minutes and 1M LiAlH4 in THF (0.7 mL) was added. The mixture was allowed to stir while warming to room temperature for 1 hour. The reaction was quenched with sodium sulfate decahydrate (~1 g) and allowed to stir for an additional thirty minutes. The solid was removed by filtration and the solvent was removed under reduced pressure to yield product (57, P-0650). MS (ESI) [M+H$^+$]$^+$=305.05.

Example 10

(7-Chloroimidazo[1,5-a]pyridin-5-yl)(1-methylcyclohexyl)methanol (P-0083)

Scheme 13

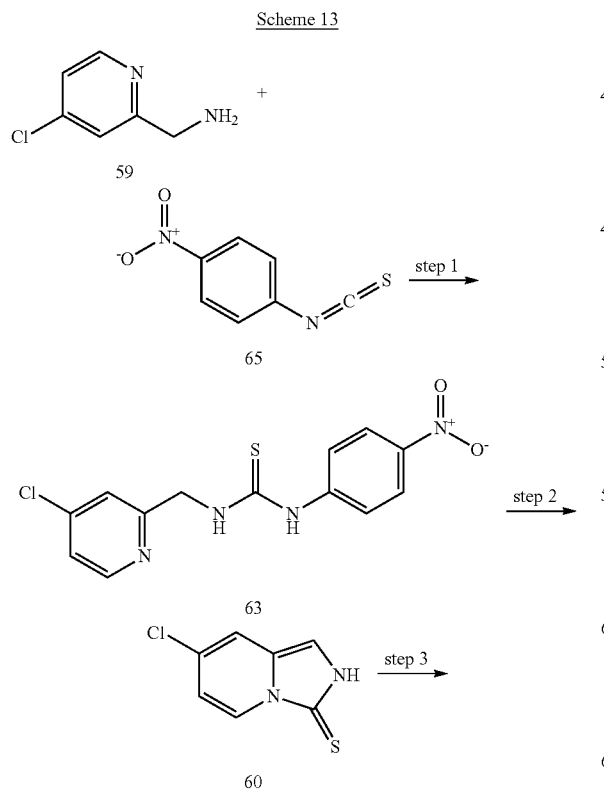

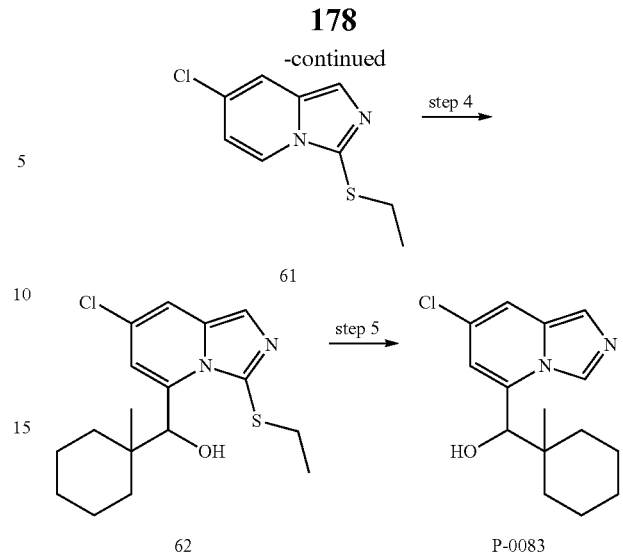

Step 1—Preparation of 1-[(4-chloro-2-pyridyl)methyl]-3-(4-nitrophenyl)thiourea (63)

To (4-chloro-2-pyridyl)methanamine (59, 0.51 g, 3.58 mmol) in dichloromethane (50 mL) was added 1-isothiocyanato-4-nitro-benzene (65, 0.66 g, 3.65 mmol). The reaction mixture was stirred at room temperature for about 1 hour. LCMS showed the reaction was complete. The reaction was concentrated, and washed with ethyl acetate and hexane to give product (63).

Step 2—Preparation of 7-chloro-2H-imidazo[1,5-a]pyridine-3-thione (60)

To 1-[(4-chloro-2-pyridyl)methyl]-3-(4-nitrophenyl)thiourea (63, 1.7 g, 5.27 mmol) were added N-ethyl-N-isopropyl-propan-2-amine (10 mL, 56.02 mmol) and isopropanol (150 mL). The reaction was stirred at 150° C. overnight. The reaction was concentrated, and purified with silica gel column chromatography eluting with 20% to 100% ethyl acetate in hexane to give product (60).

Step 3—Preparation of 7-chloro-3-ethylsulfanyl-imidazo[1,5-a]pyridine (61)

To 7-chloro-2H-imidazo[1,5-a]pyridine-3-thione (60, 0.27 g, 1.44 mmol) in acetone (30 mL) were added potassium carbonate (0.67 g, 4.85 mmol), and iodoethane (0.13 mL, 1.64 mmol). The reaction mixture was stirred at 45° C. for 90 minutes. The reaction was filtered, concentrated, and purified with silica gel column chromatography eluting with 20% to 100% ethyl acetate in hexane to give product (61).

Step 4—Preparation of (7-chloro-3-ethylsulfanyl-imidazo[1,5-a]pyridin-5-yl)-(1-methylcyclohexyl)methanol (62)

To 7-chloro-3-ethylsulfanyl-imidazo[1,5-a]pyridine (61, 0.25 g, 1.15 mmol) in THF (5 mL) under an atmosphere of nitrogen at −78° C., 2.5M butyllithium in hexane (0.55 mL). After 30 minutes, 1-methylcyclohexanecarbaldehyde (0.17 g, 1.38 mmol) was added to the reaction mixture. The reaction mixture was stirred for 2 hours at −78° C., and then allowed to warm to room temperature. The reaction was poured into aqueous potassium carbonate, and extracted with ethyl acetate. The organic layer was washed with brine, dried over sodium sulfate, and filtered. The filtrate was concentrated, and purified with silica gel column chromatography eluting with 2% to 15% methanol in methylene chloride, and then further purified with reverse phase C18 column to give product (62).

Step 5-(7-chloroimidazo[1,5-a]pyridin-5-yl)(1-methylcyclohexyl)methanol (64, P-0083)

To (7-chloro-3-ethylsulfanyl-imidazo[1,5-a]pyridin-5-yl)-(1-methylcyclohexyl)methanol (62, 0.18 g, 0.53 mmol) in ethanol (30 mL) was added excessive amount of raney nickel (4 mL). The reaction was heated to 70° C. for 1 hour. The reaction mixture was filtered, concentrated, and purified with silica gel column chromatography eluting with 2% to 20% methanol in methylene chloride to give product (64, P-0083). MS (ESI) [M+H+]+=279.0.

Example 11 bicyclo[2.2.2]octan-1-yl(5-chloro-6-fluoro-1H-indazol-7-yl)methanol (P-0294)

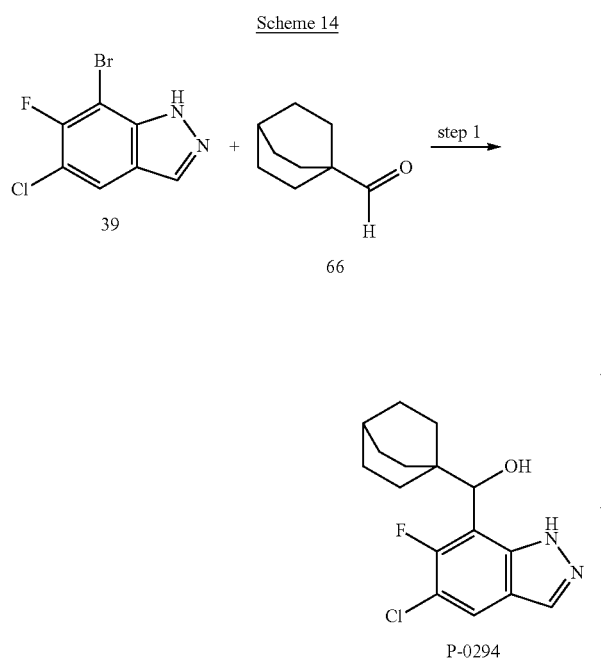

Step 1—Preparation of bicyclo[2.2.2]octan-1-yl(5-chloro-6-fluoro-1H-indazol-7-yl)methanol (P-0294)

To 7-bromo-5-chloro-6-fluoro-1H-indazole (39, 3.79 g, 15.17 mmol) in THF (35 mL) at −20° C. was added sodium hydride (60%, 0.78 g, 19.5 mmol). The reaction was stirred at room temperature for 40 minutes. The reaction was cooled to −78° C., followed by adding 1.7 M tert-butyllithium in hexane (19.0 ml) slowly. After 20 minutes, the reaction was allowed to warm to −25° C. for 20 minutes. The reaction was cooled to −78° C., followed by adding bicyclo[2.2.2]octane-4-carbaldehyde (66, 1.55 g, 11.21 mmol) in THF (5 mL). After 40 minutes at −78° C., the reaction was then allowed to warm to room temperature for 15 minutes. The reaction was poured into aqueous ammonia, and extracted with ethyl acetate. The organic layer was washed with brine, dried over anhydrous sodium sulfate and filtered. The filtrate was concentrated, and purified with silica gel column chromatography eluting with 10% to 100% ethyl acetate in hexane, and further purified by reverse phase C18 flash chromatography to gave product (P-0294). MS (ESI) [M−H+]−=306.9.

Example 12

(R)-bicyclo[2.2.2]octan-1-yl(5-chloro-6-fluoro-1H-indazol-7-yl)methanol (P-0335) and (S)-bicyclo[2.2.2]octan-1-yl(5-chloro-6-fluoro-1H-indazol-7-yl)methanol (P-0334)

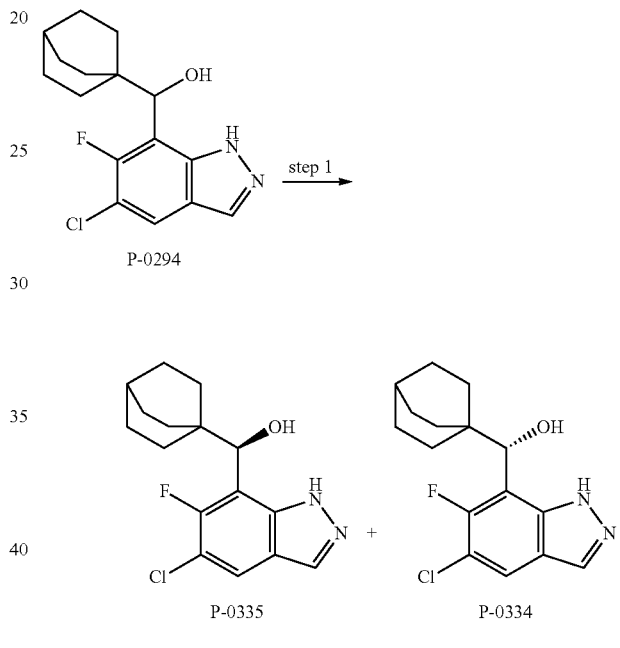

Step 1—Preparation of (R)-bicyclo[2.2.2]octan-1-yl(5-chloro-6-fluoro-1H-indazol-7-yl)methanol (P-0335) and (5)-bicyclo[2.2.2]octan-1-yl(5-chloro-6-fluoro-1H-indazol-7-yl)methanol (P-0334)

Racemic bicyclo[2.2.2]octan-1-yl(5-chloro-6-fluoro-1H-indazol-7-yl)methanol (P-0294, 1.0 g) was separated by preparative supercritical fluid chromatography on a 2.1× 25.0 cm Chiralpak IC column from Chiral Technologies using an isocratic method eluting with CO$_2$ and 15% methanol (with 0.25% isopropylamine) at 120 bar and 25° C. at 90 g/min. This provided (R)-bicyclo[2.2.2]octan-1-yl(5-chloro-6-fluoro-1H-indazol-7-yl)methanol (P-0335) and (S)-bicyclo[2.2.2]octan-1-yl(5-chloro-6-fluoro-1H-indazol-7-yl)methanol (P-0334). The absolute stereochemistry was assigned based on X-Ray crystallography and biological activity.

Example 13 tert-butyl (S)-4-(1-(5-chloro-1H-indazol-7-yl)-1-hydroxy-2-methylpropan-2-yl)piperidine-1-carboxylate (P-0337) and tert-butyl (R)-4-(1-(5-chloro-1H-indazol-7-yl)-1-hydroxy-2-methylpropan-2-yl)piperidine-1-carboxylate (P-0338)

Scheme 16

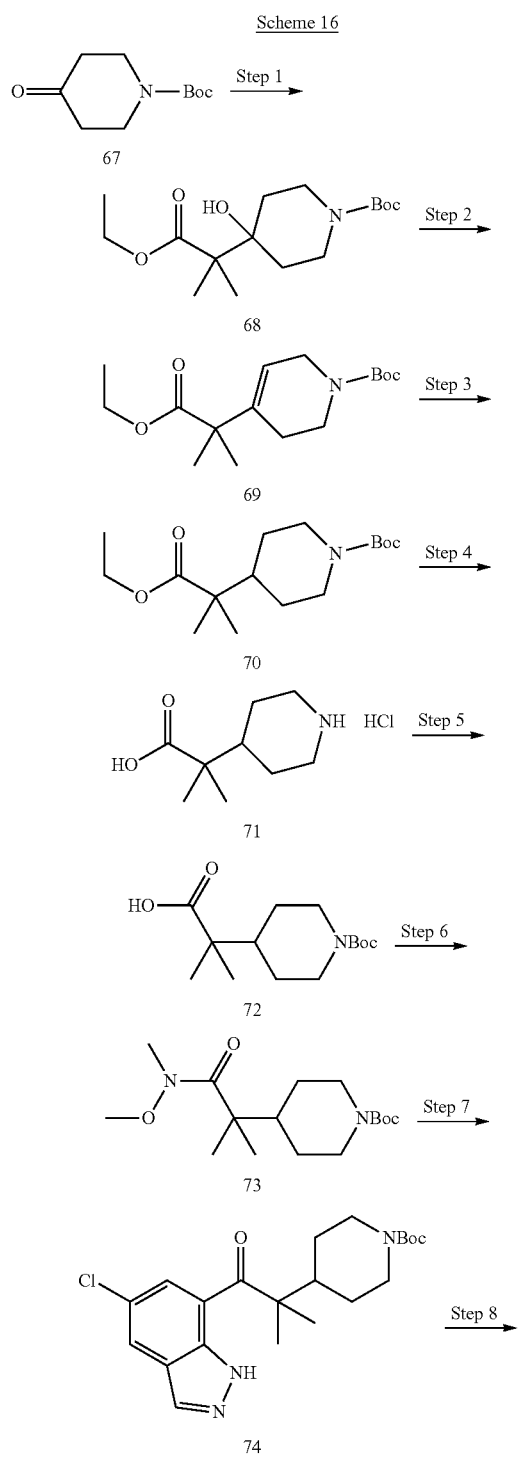

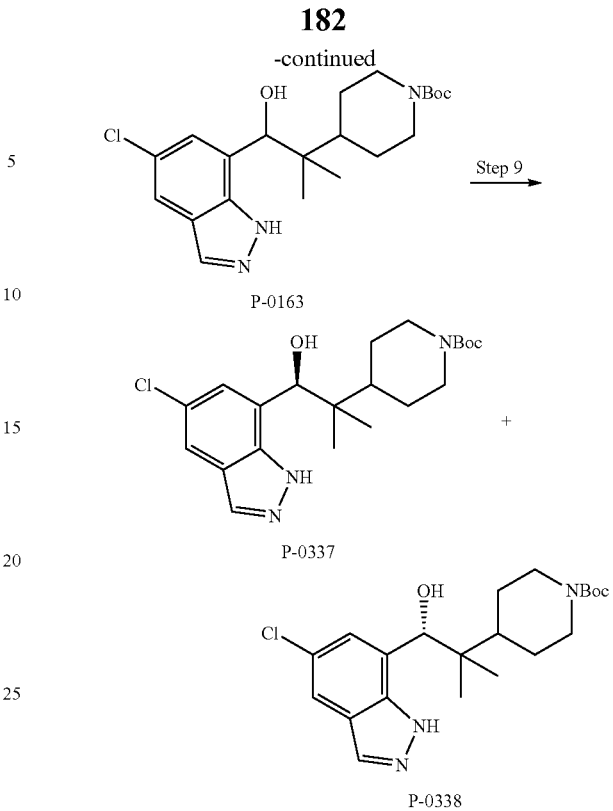

Step 1—Preparation of tert-butyl 4-(2-ethoxy-1,1-dimethyl-2-oxo-ethyl)-4-hydroxy-piperidine-1-carboxylate (68)

To ethyl 2-methylpropanoate (4.60 ml, 34.25 mmol) in tetrahydrofuran (50 ml), at −78° C. under nitrogen, was added slowly a solution of 1.37 M lithium diisopropylamide in THF (28 ml). After stirring at −78° C. for 1 hour, tert-butyl tert-butyl 4-oxopiperidine-1-carboxylate (67, 7.51 g, 37.68 mmol) was added. After 1 hour, the mixture was allowed to warm to room temperature. The reaction was poured into aqueous ammonia chloride, and extracted with ethyl acetate. The organic layer was washed with brine, dried over sodium sulfate, and filtered. The filtrate was concentrated, and purified with silica gel column chromatography eluting with 5% to 100% ethyl acetate in hexane to give product (68).

Step 2—Preparation of tert-butyl 4-(2-ethoxy-1,1-dimethyl-2-oxo-ethyl)-3,6-dihydro-2H-pyridine-1-carboxylate (69)

To a suspension of Burgess reagent (3.41 g, 14.32 mmol) in THF (25 ml) was added tert-butyl 4-(2-ethoxy-1,1-dimethyl-2-oxo-ethyl)-4-hydroxy-piperidine-1-carboxylate (68, 3.00 g, 9.51 mmol) slowly. The mixture was allowed to stir at 70° C. for 1 hour. The reaction was then allowed to stir at room temperature for three days. The mixture was poured into water and extracted with ethyl acetate. The organic phase was washed with brine, dried over sodium sulfate and filtered. The filtrate was concentrated and purified with silica gel column chromatography eluting with 5% to 100% ethyl acetate in hexane to give product (69).

Step 3—Preparation of tert-butyl 4-(2-ethoxy-1,1-dimethyl-2-oxo-ethyl)piperidine-1-carboxylate (70)

To a solution of tert-butyl 4-(2-ethoxy-1,1-dimethyl-2-oxo-ethyl)-3,6-dihydro-2H-pyridine-1-carboxylate (69, 0.88 g, 2.96 mmol) in methanol (50 ml) was added Pearlman's catalyst (0.3 g). The mixture was de-gassed and purged with hydrogen. The reaction mixture was allowed to stir under 1 atm of hydrogen at room temperature overnight. The reaction was filtered, and concentrated to give product (70).

Step 4—Preparation of 2-methyl-2-(4-piperidyl)propanoic acid (71)

To tert-butyl 4-(2-ethoxy-1,1-dimethyl-2-oxo-ethyl)piperidine-1-carboxylate (70, 0.86 g, 2.86 mmol) was added 6N HCl (5 ml). The mixture was stirred at 100° C. for 12 hour. The reaction was concentrated to give product (71).

Step 5—Preparation of 2-(1-tert-butoxycarbonyl-4-piperidyl)-2-methyl-propanoic acid (72)

To a suspension of 2-methyl-2-(4-piperidyl)propanoic acid HCl salt (71, 0.95 g, 5.55 mmol) in THF (35 ml) were added triethylamine (0.93 ml, 6.66 mmol), di-tert-butyl dicarbonate (1.4 ml, 6.1 mmol) and 4-dimethylaminopyridine (68 mg, 0.55 mmol). The mixture was stirred at 70° C. overnight. The mixture was poured into aqueous potassium carbonate, and extracted with ether. The aqueous phase was washed with fresh ether (3×200 ml) and the combined organic extracts were discarded. The aqueous phase was then neutralized with 1 N HCl, and extracted with ether. The organic phase was dried over sodium sulfate, filtered, and concentrated to give product (72).

Step 6—Preparation of tert-butyl 4-[2-[methoxy(methyl)amino]-1,1-dimethyl-2-oxo-ethyl]piperidine-1-carboxylate (73)

To a solution of 2-(1-tert-butoxycarbonyl-4-piperidyl)-2-methyl-propanoic acid (72, 0.55 g, 2.03 mmol) in NMP (15 ml) was added N,O-dimethylhydroxylamine hydrochloride (0.2 g, 2.03 mmol) followed by pyridine (0.73 ml, 9.03 mmol) and 1.68M 2,4,6-tripropyl-1,3,5,2,4,6-trioxatriphosphorinane-2,4,6-trioxide (3.6 ml). The reaction mixture was allowed to stir at room temperature overnight. The reaction mixture was poured into water, and extracted with ethyl acetate. The organic phase was washed with saturated ammonia chloride, brine, dried over sodium sulfate, filtered, and concentrated to give product (73).

Step 7—Preparation of tert-butyl 4-[2-(5-chloro-1H-indazol-7-yl)-1,1-dimethyl-2-oxo-ethyl]piperidine-1-carboxylate (74)

To 7-bromo-5-chloro-1H-indazole (6.3 g, 27.2 mmol) in THF (70 mL) at −20° C. was added sodium hydride (60% in mineral oil, 1.56 g, 39.0 mmol). The reaction was stirred at room temperature for 100 minutes. The reaction was cooled to −78° C., followed by adding 1.7 M tert-butyllithium in hexane (32 ml) slowly. After 30 minutes, the reaction was allowed to warm to −25° C. for 20 minutes. The reaction was cooled to −78° C., followed by adding tert-butyl 4-[2-[methoxy(methyl)amino]-1,1-dimethyl-2-oxo-ethyl]piperidine-1-carboxylate (73, 6 g, 19.1 mmol) in THF (14 mL). After 40 minutes at −78° C., The reaction was then allowed to warm to room temperature for 15 minutes. The reaction was poured into aqueous ammonia chloride, and extracted with ethyl acetate. The organic layer was washed with brine, dried over sodium sulfate, and filtered. The filtrate was concentrated, and purified with silica gel column chromatography eluting with 10% to 100% ethyl acetate in hexane, and then further purified with reverse phase C18 column to give product (74).

Step 8—Preparation of tert-butyl 4-[2-(5-chloro-1H-indazol-7-yl)-2-hydroxy-1,1-dimethyl-ethyl] piperidine-1-carboxylate (P-0163)

To tert-butyl 4-[2-(5-chloro-1H-indazol-7-yl)-1,1-dimethyl-2-oxo-ethyl]piperidine-1-carboxylate (74, 1.07 g, 2.64 mmol) in methanol (40 mL) at −10° C. was added sodium boranuide (0.12 g, 3.16 mmol). The reaction was stirred at room temperature for 2 hours. The reaction was poured into aqueous ammonia, and extracted with ethyl acetate. The organic layer was washed with brine, dried over sodium sulfate, and filtered. The filtrate was concentrated, and washed with ethyl acetate and hexane (P-0163) MS (ESI) [M+H$^+$]$^+$=408.2.

Step 9—Preparation of tert-butyl (R)-4-(1-(5-chloro-1H-indazol-7-yl)-1-hydroxy-2-methylpropan-2-yl)piperidine-1-carboxylate (P-0338) and tert-butyl (S)-4-(1-(5-chloro-1H-indazol-7-yl)-1-hydroxy-2-methylpropan-2-yl)piperidine-1-carboxylate (P-0337)

Racemic tert-butyl 4-[2-(5-chloro-1H-indazol-7-yl)-2-hydroxy-1,1-dimethyl-ethyl]piperidine-1-carboxylate (P-0163) (1.0 g) was separated by preparative supercritical fluid chromatography on a 2.1×25.0 cm Chiralpak IC column from Chiral Technologies using an isocratic method eluting with $CO_2$ and 30% methanol (with 0.25% isopropylamine) at 120 bar and 25° C. at 90 g/min. This provided tert-butyl (R)-4-(1-(5-chloro-1H-indazol-7-yl)-1-hydroxy-2-methylpropan-2-yl)piperidine-1-carboxylate (P-0338) and tert-butyl (S)-4-(1-(5-chloro-1H-indazol-7-yl)-1-hydroxy-2-methylpropan-2-yl)piperidine-1-carboxylate (P-0337). The absolute stereochemistry was assigned based on X-Ray crystallography and biological activity.

Example 14

(S)-4-(1-(5-chloro-1H-indazol-7-yl)-1-hydroxy-2-methylpropan-2-yl)-N-(4-fluorophenyl)piperidine-1-carboxamide (P-0344)

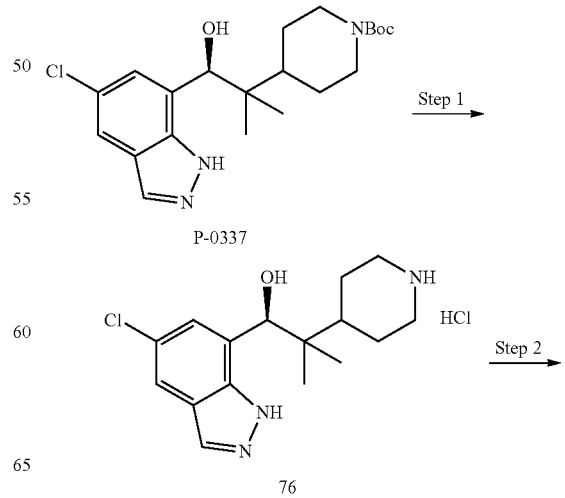

Scheme 17

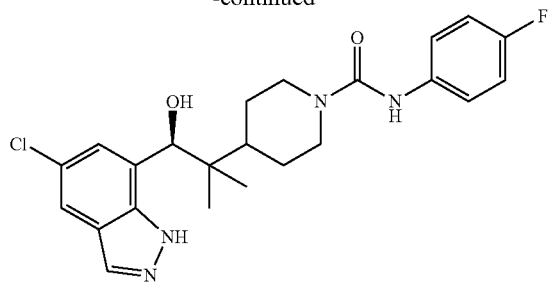

P-0344

P-0498

Step 1—Preparation of (1S)-1-(5-chloro-1H-indazol-7-yl)-2-methyl-2-(4-piperidyl)propan-1-ol hydrochloride (76)

To tert-butyl (S)-4-(1-(5-chloro-1H-indazol-7-yl)-1-hydroxy-2-methylpropan-2-yl)piperidine-1-carboxylate (P-0337, 1.5 g, 3.68 mmol) in methylene chloride (30 mL) at 0° C. was added 4N HCl (8.0 mL). The reaction was stirred at room temperature overnight. The reaction was concentrated under reduced pressure to give product (76).

Step 2—Preparation of (S)-4-(1-(5-chloro-1H-indazol-7-yl)-1-hydroxy-2-methylpropan-2-yl)-N-(4-fluorophenyl)piperidine-1-carboxamide (P-0344)

To (1S)-1-(5-chloro-1H-indazol-7-yl)-2-methyl-2-(4-piperidyl)propan-1-ol hydrochloride (76, 0.1 g, 0.29 mmol) in dichloromethane (5.0 mL) was added triethylamine (0.2 ml, 1.43 mmol). 1-fluoro-4-isocyanato-benzene (43.81 mg, 0.32 mmol) in dichloromethane (2.0 mL) was slowly added to the reaction. The reaction was stirred at room temperature for 3 hours. LCMS showed the reaction was complete. The reaction was poured into aqueous potassium carbonate, and extracted with ethyl acetate. The organic layer was washed with brine, dried over anhydrous sodium sulfate and filtered. The filtrate was concentrated and purified by reverse phase C18 column chromatography to give product (P-0344). [M+H⁺]⁺=445.2.

Example 15

(S)-(4-(1-(5-chloro-1H-indazol-7-yl)-1-hydroxy-2-methylpropan-2-yl)piperidin-1-yl)(cyclobutyl)methanone (P-0498)

Step 1—Preparation of (S)-(4-(1-(5-chloro-1H-indazol-7-yl)-1-hydroxy-2-methylpropan-2-yl)piperidin-1-yl)(cyclobutypmethanone (P-0498)

To the mixture of the cyclobutane carboxylic acid (8.7 mg, 0.087 mmol, 1 eq), (S)-1-(5-chloro-1H-indazol-7-yl)-2-methyl-2-piperidin-4-yl-propan-1-ol (76, 30 mg, 0.087 mmol) and diisopropylethylamine (0.045 mL, 0.261 mmol, 3 eq) in DMF (0.2 mL) was added HATU (40 mg, 0.104 mmol, 1.15 eq) in one portion at room temperature. The material was directly purified by RP-HPLC purification to give product (P-0498). [M+H⁺]⁺=390.4.

Example 16

(S)-4-(1-(5-chloro-1H-indazol-7-yl)-1-hydroxy-2-methylpropan-2-yl)-N-(2-hydroxyethyl)piperidine-1-carboxamide (P-0499)

Scheme 19

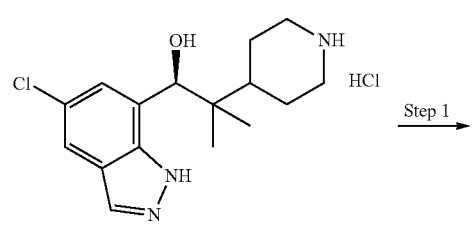

76

Step 1

Scheme 18

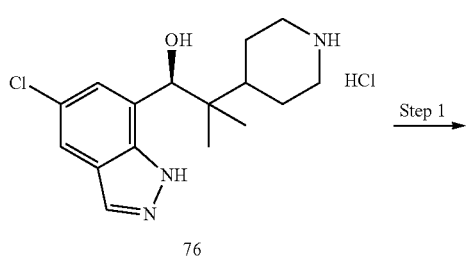

76

Step 1

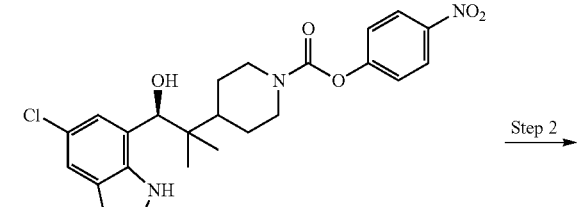

77

Step 2

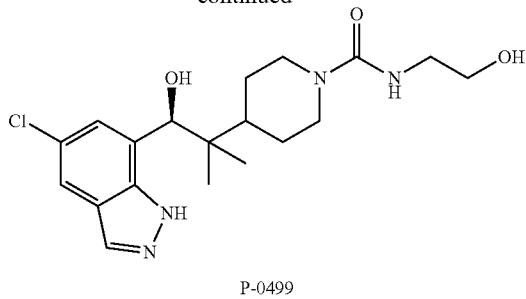

P-0499

Step 1—Preparation of (4-nitrophenyl) 4-[(2S)-2-(5-chloro-1H-indazol-7-yl)-2-hydroxy-1,1-dimethyl-ethyl]piperidine-1-carboxylate (77)

To a solution of 4 nitrophenyl chloroformate (1.41 g, 7.02 mmol) in tetrahydrofuran (45.0 mL) and diisopropylethylamine (3.2 mL) at ice bath temperature was added portion wise (S)-1-(5-chloro-1H-indazol-7-yl)-2-methyl-2-piperidin-4-yl-propan-1-ol (76) 2.2 g, 6.39 mmmol). The solid was slowly dissolved in the solution and the product was formed after one hour at room temperature. The solution was pour onto ice cold solution of 10% ammonium chloride (50 mL) and was extracted with ethyl acetate (70 mL, 3×). The combined organic layers were dried over sodium sulfate, filtered and concentrated to give product (77). [M+H⁺]⁺=473.5.

Step 2—Preparation of (S)-4-(1-(5-chloro-1H-indazol-7-yl)-1-hydroxy-2-methylpropan-2-yl)-N-(2-hydroxyethyl)piperidine-1-carboxamide (P-0499)

4-[(S)-2-(5-Chloro-1H-indazol-7-yl)-2-hydroxy-1,1-dimethyl-ethyl]-piperidine-1-carboxylic acid 4-nitro-phenyl ester (77, 25 mg, 0.053 mmol), ethanolamine (9.6 mg, 0.159 mmol, 3.0 eq) and diisopropyl ethyl amine (0.159 mmol, 0.030 mL, 3.0 eq) was heated in N-methyl pyrrolidine (0.5 mL) at 80° C. overnight. The material was directly purified by RP-HPLC purification to give product (P-0499). [M+H⁺]⁺=395.5.

Example 17

(6-chloro-1H-indazol-4-yl)(cyclohexyl)methanol (P-0173)

Scheme 20

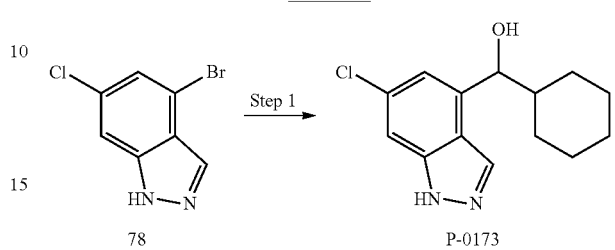

Step 1—Preparation of (6-chloro-1H-indazol-4-yl)(cyclohexyl)methanol (P-0173)

To a solution of 4-bromo-6-chloro-1H-indazole (78, 0.37 g, 1.62 mmol) in THF (6 ml) was added sodium hydride (60% dispersion in mineral oil, 0.08 g, 2.12 mmol). The mixture was allowed to stir at room temperature for 30 min and then was cooled to −78° C. Then, 2.5 M n-butyllithium in hexane (0.65 ml) was added dropwise over 5 min period. The mixture was allowed to stir at −78° C. for 30 min followed by the addition of cyclohexanecarbaldehyde (0.08 g, 0.67 mmol). The reaction mixture was allowed to stir for 1 h at −78° C. and then for 20 min while warming to room temperature. The reaction was quenched with saturated aqueous ammonium chloride and extracted with ethyl acetate and water. The organic phase was washed with brine (3×), dried over anhydrous sodium sulfate and filtered. The filtrate was concentrated under reduced pressure and the resulting crude material was purified by silica gel column chromatography to provide product (P-0173). [M+H⁺]⁺=265.0.

All compounds in Table 1 listed below can be made according to the synthetic examples described in this disclosure, and by making any necessary substitutions of starting materials that the skilled artisan would be able to obtain either commercially or otherwise.

All compounds below have a mass spectrometry (MH)+ value unless specifically indicated otherwise as (MH)−.

TABLE 1

| Compound Number | Compound Name | Compound Structure | (MH)+ |
|---|---|---|---|
| P-0001 | (5-chloro-1H-indazol-7-yl)(pyridin-3-yl)methanol | 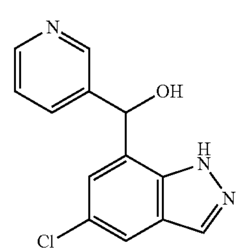 [SMILES: OC(c1cccnc1)c1cc(Cl)cc2cn[nH]c12] | 259.9 |

TABLE 1-continued

| Compound Number | Compound Name | Compound Structure | (MH)+ |
|---|---|---|---|
| P-0002 | (5-chloro-1H-indazol-7-yl)(cyclohexyl)methanol | 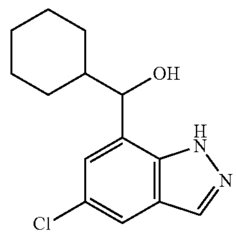 [SMILES: OC(c1cc(Cl)cc2cn[nH]c12)C1CCCCC1] | 262.8 (MH)− |
| P-0003 | (4-chloro-1H-indazol-7-yl)(cyclohexyl)methanol | 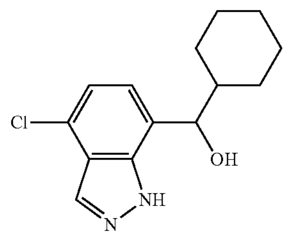 [SMILES: OC(c1ccc(Cl)c2cn[nH]c12)C1CCCCC1] | 298.9 (MH)− |
| P-0004 | (5-chloro-1H-indazol-7-yl)(1-fluorocyclohexyl)methanol | 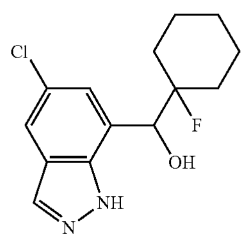 [SMILES: OC(c1cc(Cl)cc2cn[nH]c12)C1(F)CCCCC1] | 327.9 (MH)− |
| P-0005 | (5-chloro-1H-indazol-7-yl)(cyclopentyl)methanol | 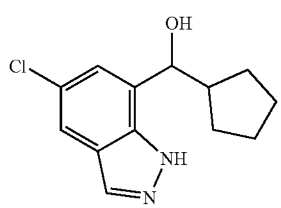 [SMILES: OC(c1cc(Cl)cc2cn[nH]c12)C1CCCC1] | 299.8 (MH)− |
| P-0006 | (5-chloro-1H-indazol-7-yl)(1-methylcyclohexyl)methanol | 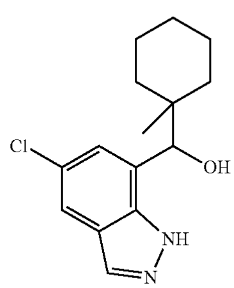 [SMILES: CC1(C(O)c2cc(Cl)cc3cn[nH]c23)CCCCC1] | 314.9 |
| P-0007 | 1-(5-chloro-1H-indazol-7-yl)-2-cyclohexylethan-1-ol | 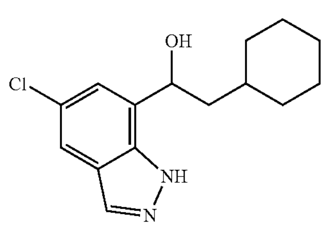 [SMILES: OC(CC1CCCCC1)c1cc(Cl)cc2cn[nH]c12] | 315.1 |

TABLE 1-continued

| Number | Compound Name | Compound Structure | (MH)+ |
|---|---|---|---|
| P-0008 | 1-(5-chloro-1H-indazol-7-yl)-2-cyclohexyl-2-methylpropan-1-ol | 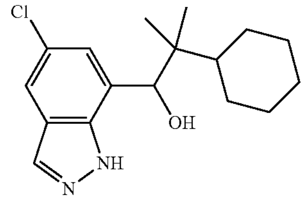 [SMILES: CC(C)(C1CCCCC1)C(O)c1cc(Cl)cc2cn[nH]c12] | 301.1 |
| P-0009 | 1-(5-chloro-1H-indazol-7-yl)-3-cyclohexylpropan-1-ol | 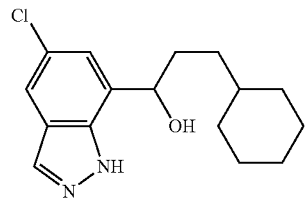 [SMILES: OC(CCC1CCCCC1)c1cc(Cl)cc2cn[nH]c12] | 341.9 |
| P-0010 | ((1S,3s)-adamantan-1-yl)(5-chloro-1H-indazol-7-yl)methanol | 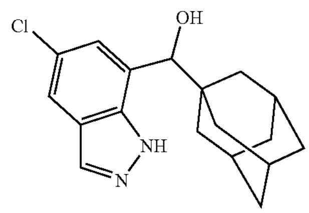 [SMILES: OC(c1cc(Cl)cc2cn[nH]c12)C12CC3CC(CC(C3)C1)C2] | 292.9 |
| P-0011 | 1-(5-chloro-1H-indazol-7-yl)-4,4-difluorocyclohexan-1-ol | 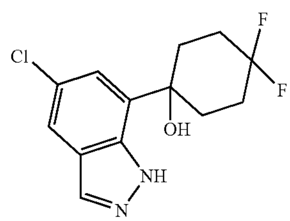 [SMILES: OC1(c2cc(Cl)cc3cn[nH]c23)CCC(F)(F)CC1] | 243.0 |
| P-0012 | 2-(5-chloro-1H-indazol-7-yl)spiro[3.3]heptan-2-ol | 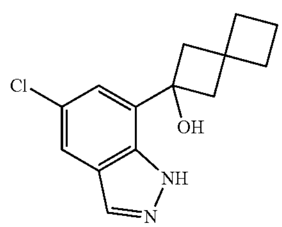 [SMILES: OC1(c2cc(Cl)cc3cn[nH]c23)CC2(CCC2)C1] | 297 |
| P-0013 | (1-methylcyclohexyl)(5-(trifluoromethyl)-1H-indazol-7-yl)methanol | 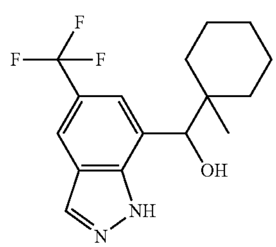 [SMILES: CC1(C(O)c2cc(C(F)(F)F)cc3cn[nH]c23)CCCCC1] | 315.1 |
| P-0014 | (5-methyl-1H-indazol-7-yl)(1-methylcyclohexyl)methanol | 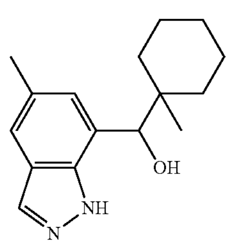 [SMILES: Cc1cc(C(O)C2(C)CCCCC2)c2[nH]ncc2c1] | 319.1 |

TABLE 1-continued

| Number | Compound Name | Compound Structure | (MH)+ |
|---|---|---|---|
| P-0015 | (6-methyl-1H-indazol-7-yl)(1-methylcyclohexyl)methanol | 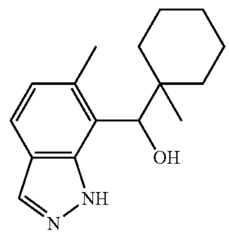 [SMILES: Cc1ccc2cn[nH]c2c1C(O)C1(C)CCCCC1] | 367.9 (MH)− |
| P-0016 | 5-(5-chloro-1H-indazol-7-yl)spiro[2.3]hexan-5-ol | 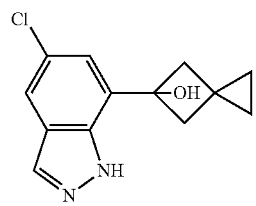 | 393.9 (MH)− |
| P-0017 | (5-chloro-1H-indazol-7-yl)(3,3-difluorocyclobutyl)methanol | 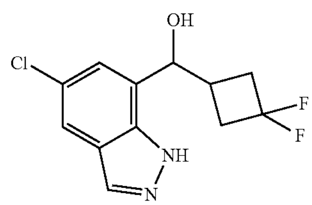 [SMILES: OC(c1cc(Cl)cc2cn[nH]c12)C1CC(F)(F)C1] | 296.9 |
| P-0018 | (5-chloro-1H-indazol-7-yl)(3,3-difluoro-1-methylcyclobutyl)methanol | 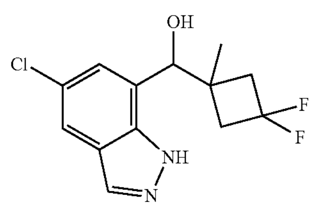 [SMILES: CC1(C(O)c2cc(Cl)cc3cn[nH]c23)CC(F)(F)C1] | 297.0 |
| P-0019 | tert-butyl 2-(5-chloro-1H-indazol-7-yl)-2-hydroxy-7-azaspiro[3.5]nonane-7-carboxylate | 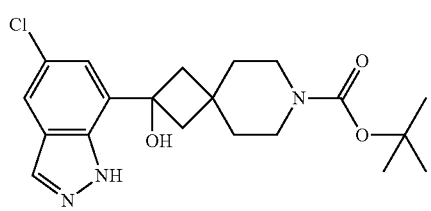 [SMILES: CC(C)(C)OC(=O)N1CCC2(CC1)CC(O)(c1cc(Cl)cc3cn[nH]c13)C2] | 313.9 (MH)− |
| P-0020 | 2-(5-chloro-1H-indazol-7-yl)-7-azaspiro[3.5]nonan-2-ol | 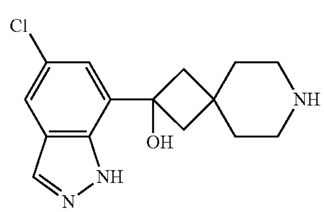 [SMILES: OC1(c2cc(Cl)cc3cn[nH]c23)CC2(CCNCC2)C1] | 262.9 (MH)− |
| P-0021 | (5-chloro-1H-indazol-7-yl)(1-methylcyclopentyl)methanol | 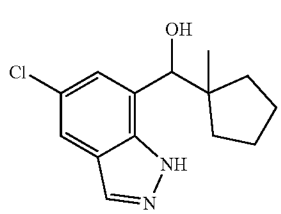 [SMILES: CC1(C(O)c2cc(Cl)cc3cn[nH]c23)CCCC1] | 262.9 (MH)− |

TABLE 1-continued

| Compound Number | Compound Name | Compound Structure | (MH)+ |
|---|---|---|---|
| P-0022 | (5-chloro-1H-indazol-7-yl)(4,4-difluorocyclohexyl)methanol | 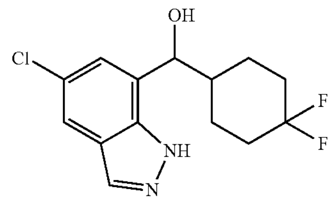 [SMILES: OC(c1cc(Cl)cc2cn[nH]c12)C1CCC(F)(F)CC1] | 282.9 |
| P-0023 | 4-(5-chloro-1H-indazol-7-yl)-1-(methylsulfonyl)piperidin-4-ol | 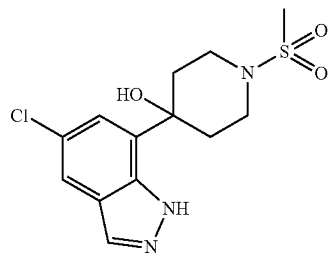 [SMILES: CS(=O)(=O)N1CCC(O)(c2cc(Cl)cc3cn[nH]c23)CC1] | 248.9 (MH)− |
| P-0024 | 3-(5-chloro-1H-indazol-7-yl)-1-(methylsulfonyl)azetidin-3-ol | 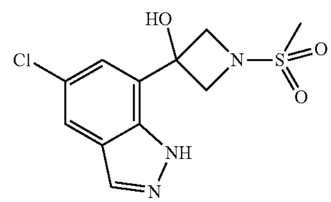 [SMILES: CS(=O)(=O)N1CC(O)(c2cc(Cl)cc3cn[nH]c23)C1] | 276.9 (MH)− |
| P-0025 | (5,6-dichloro-1H-indazol-7-yl)(1-methylcyclohexyl)methanol | 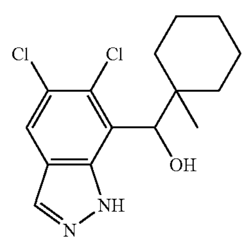 [SMILES: CC1(C(O)c2c(Cl)c(Cl)cc3cn[nH]c23)CCCCC1] | 276.9 (MH)− |
| P-0026 | 1-(5-chloro-1H-indazol-7-yl)-2,2-dimethyl-3-phenylpropan-1-ol | 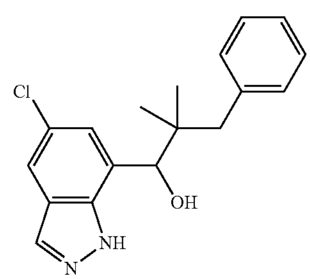 [SMILES: CC(C)(Cc1ccccc1)C(O)c1cc(Cl)cc2cn[nH]c12] | 305.0 (MH)− |
| P-0027 | 1-(5-chloro-1H-indazol-7-yl)-2-methyl-2-phenylpropan-1-ol | 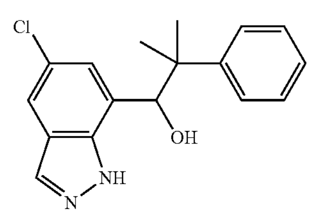 [SMILES: CC(C)(c1ccccc1)C(O)c1cc(Cl)cc2cn[nH]c12] | 290.9 (MH)− |

TABLE 1-continued

| Number | Compound Name | Compound Structure | (MH)+ |
|---|---|---|---|
| P-0028 | 6-(5-chloro-1H-indazol-7-yl)-2-(methylsulfonyl)-2-azaspiro[3.3]heptan-6-ol | 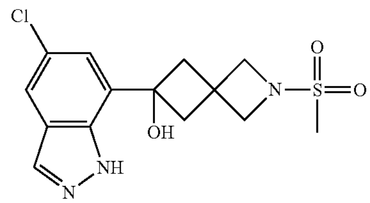 [SMILES: CS(=O)(=O)N1CC2(C1)CC(O)(c1cc(Cl)cc3cn[nH]c13)C2] | 315.0 |
| P-0029 | 2-(5-chloro-1H-indazol-7-yl)-7-oxaspiro[3.5]nonan-2-ol | 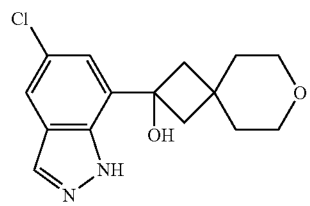 [SMILES: OC1(c2cc(Cl)cc3cn[nH]c23)CC2(CCOCC2)C1] | 286.9 |
| P-0030 | 2-(5-methyl-1H-indazol-7-yl)spiro[3.3]heptan-2-ol | 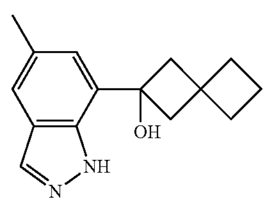 [SMILES: Cc1cc(C2(O)CC3(CCC3)C2)c2[nH]ncc2c1] | 263.0 |
| P-0031 | 2-(5-(trifluoromethyl)-1H-indazol-7-yl)spiro[3.3]heptan-2-ol | 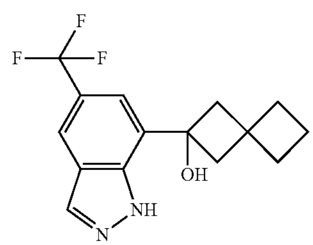 [SMILES: OC1(c2cc(C(F)(F)F)cc3cn[nH]c23)CC2(CCC2)C1] | 313.0 |
| P-0032 | (5-chloro-1H-indazol-7-yl)(4,4-difluoro-1-methylcyclohexyl)methanol | 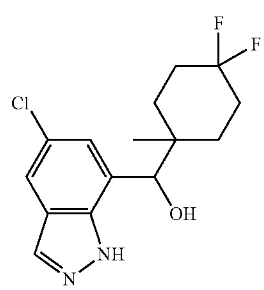 [SMILES: CC1(C(O)c2cc(Cl)cc3cn[nH]c23)CCC(F)(F)CC1] | 259.3 |
| P-0033 | (5-chloro-1H-indazol-7-yl)(1,4,4-trifluorocyclohexyl)methanol | 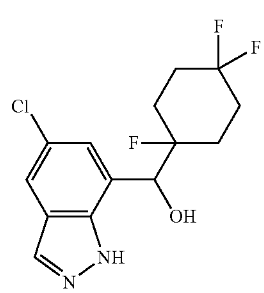 [SMILES: OC(c1cc(Cl)cc2cn[nH]c12)C1(F)CCC(F)(F)CC1] | 259.4 |

TABLE 1-continued

| Compound Number | Compound Name | Compound Structure | (MH)+ |
|---|---|---|---|
| P-0034 | 2-(5-chloro-1H-indazol-7-yl)-7-(methylsulfonyl)-7-azaspiro[3.5]nonan-2-ol | 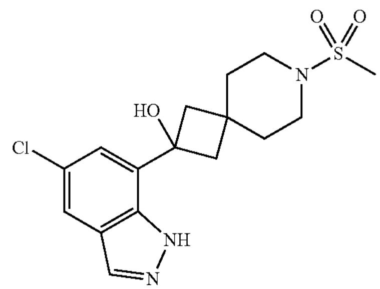 [SMILES: CS(=O)(=O)N1CCC2(CC1)CC(O)(c1cc(Cl)cc3cn[nH]c13)C2] | 248.9 |
| P-0035 | 2-(5-chloro-1H-indazol-7-yl)-7-(cyclopropylsulfonyl)-7-azaspiro[3.5]nonan-2-ol | 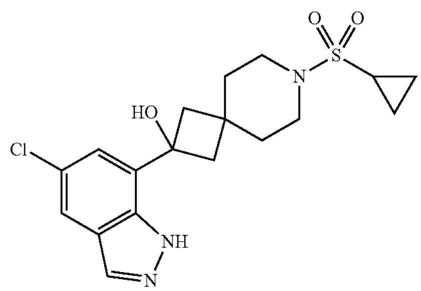 [SMILES: O=S(=O)(C1CC1)N1CCC2(CC1)CC(O)(c1cc(Cl)cc3cn[nH]c13)C2] | 270.9 (MH)− |
| P-0036 | 2-(5,6-dichloro-1H-indazol-7-yl)spiro[3.3]heptan-2-ol | 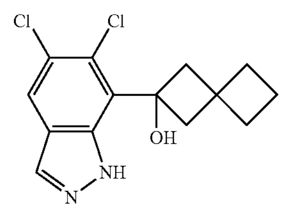 [SMILES: OC1(c2c(Cl)c(Cl)cc3cn[nH]c23)CC2(CCC2)C1] | 284.9 (MH)− |
| P-0037 | ((1s,3s)-adamantan-1-yl)(6-methyl-1H-indazol-7-yl)methanol | 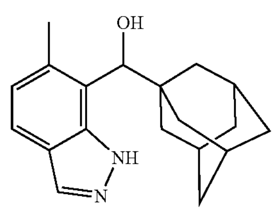 [SMILES: Cc1ccc2cn[nH]c2c1C(O)C12CC3CC(CC(C3)C1)C2] | 392.0 |
| P-0038 | N-(3-(5-chloro-1H-indazol-7-yl)-3-hydroxycyclobutyl)methanesulfonamide | 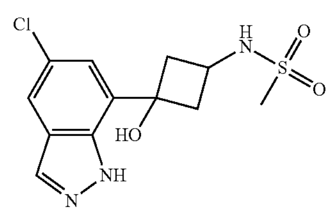 [SMILES: CS(=O)(=O)NC1CC(O)(c2cc(Cl)cc3cn[nH]c23)C1] | 289.9 (MH)− |
| P-0039 | 6-(5-chloro-1H-indazol-7-yl)-2-oxaspiro[3.3]heptan-6-ol | 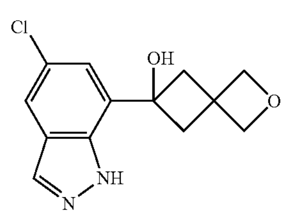 [SMILES: OC1(c2cc(Cl)cc3cn[nH]c23)CC2(COC2)C1] | 262.90 (MH)− |

TABLE 1-continued

| Compound Number | Compound Name | Compound Structure | (MH)+ |
|---|---|---|---|
| P-0040 | 6-(5-chloro-1H-indazol-7-yl)-2-thiaspiro[3.3]heptan-6-ol | 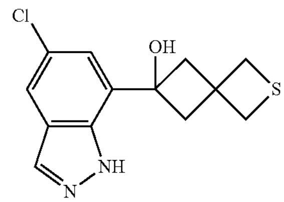 [SMILES: OC1(c2cc(Cl)cc3cn[nH]c23)CC2(CSC2)C1] | 280.9 |
| P-0041 | (5-fluoro-1H-indazol-7-yl)(1-methylcyclohexyl)methanol | 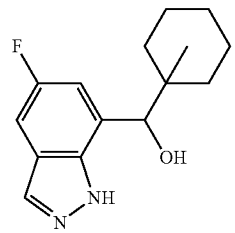 | 263.2 |
| P-0042 | cyclohexyl(5-fluoro-1H-indazol-7-yl)methanol | 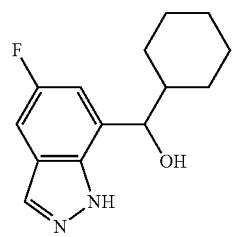 [SMILES: OC(c1cc(F)cc2cn[nH]c12)C1CCCCC1] | 249.2 |
| P-0043 | adamantan-1-yl(5-fluoro-1H-indazol-7-yl)methanol | 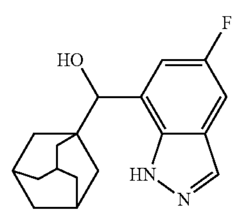 [SMILES: OC(c1cc(F)cc2cn[nH]c12)C12CC3CC(CC(C3)C1)C2] | 301.2 |
| P-0044 | N-(3-(5-chloro-1H-indazol-7-yl)-3-hydroxycyclobutyl)benzenesulfonamide | 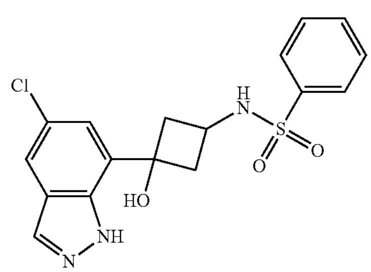 [SMILES: O=S(=O)(NC1CC(O)(c2cc(Cl)cc3cn[nH]c23)C1)c1ccccc1] | 375.9 (MH)− |
| P-0045 | N-(3-(5-chloro-1H-indazol-7-yl)-3-hydroxycyclobutyl)cyclopropanesulfonamide | 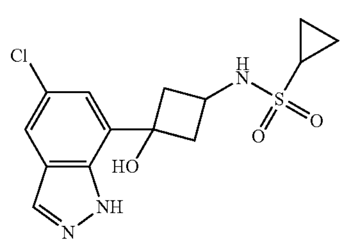 [SMILES: O=S(=O)(NC1CC(O)(c2cc(Cl)cc3cn[nH]c23)C1)C1CC1] | 339.9 (MH)− |

TABLE 1-continued

| Compound Number | Compound Name | Compound Structure | (MH)+ |
|---|---|---|---|
| P-0046 | 4-(5-chloro-1H-indazol-7-yl)-2,2-dimethyl-1-(methylsulfonyl)piperidin-4-ol | 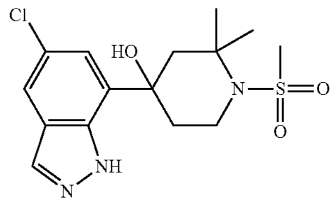 [SMILES: CC1(C)CC(O)(c2cc(Cl)cc3cn[nH]c23)CCN1S(C)(=O)=O] | 358.1 |
| P-0047 | 4-(5-chloro-1H-indazol-7-yl)-4-hydroxytetrahydro-2H-thiopyran 1,1-dioxide | 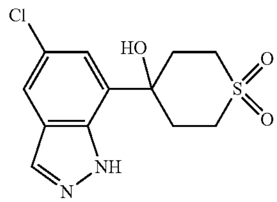 [SMILES: O=S1(=O)CCC(O)(c2cc(Cl)cc3cn[nH]c23)CC1] | 300.8 |
| P-0048 | 2-(5-chloro-1H-indazol-7-yl)spiro[3.4]octan-2-ol | 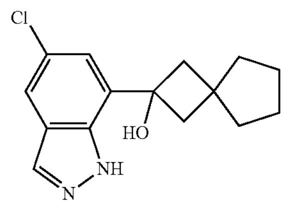 [SMILES: OC1(c2cc(Cl)cc3cn[nH]c23)CC2(CCCC2)C1] | 276.9 |
| P-0049 | (6-methyl-1H-indazol-7-yl)(1-(trifluoromethyl)cyclopentyl)methanol | 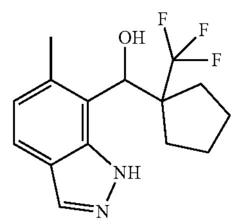 [SMILES: Cc1ccc2cn[nH]c2c1C(O)C1(C(F)(F)F)CCCC1] | 299.0 |
| P-0050 | (1-methylcyclohexyl)(6,7,8,9-tetrahydro-3H-benzo[e]indazol-4-yl)methanol | 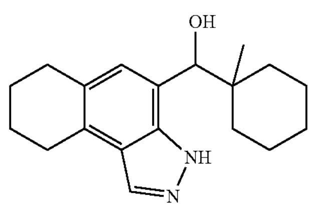 [SMILES: CC1(C(O)c2cc3c(c4cn[nH]c24)CCCC3)CCCCC1] | 299.1 |
| P-0051 | 2-(5-chloro-1H-indazol-7-yl)spiro[3.5]nonan-2-ol | 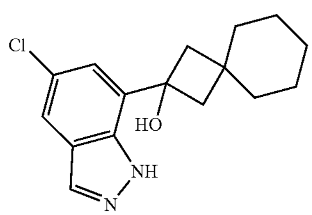 [SMILES: OC1(c2cc(Cl)cc3cn[nH]c23)CC2(CCCCC2)C1] | 290.9 |
| P-0052 | (5-chloro-6-fluoro-1H-indazol-7-yl)(1-methylcyclohexyl)methanol | 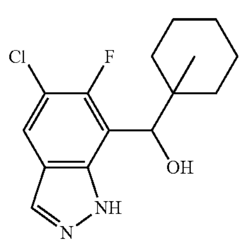 | 297.1 |

TABLE 1-continued

| Compound Number | Compound Name | Compound Structure | (MH)+ |
|---|---|---|---|
| P-0053 | (5-chloro-1H-indazol-7-yl)(1-(trifluoromethyl)cyclopentyl)methanol | 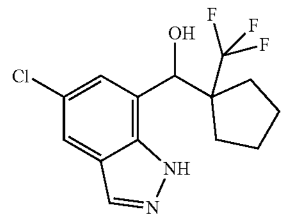 [SMILES: OC(c1cc(Cl)cc2cn[nH]c12)C1(C(F)(F)F)CCCC1] | 316.9 (MH)− |
| P-0054 | (5,6-dihydro-1H-cyclobuta[f]indazol-7-yl)(1-methylcyclohexyl)methanol | 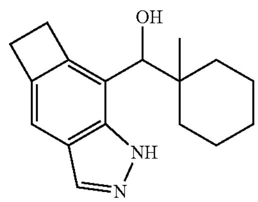 [SMILES: CC1(C(O)c2c3c(cc4cn[nH]c24)CC3)CCCCC1] | 271.2 |
| P-0055 | (5-chloro-4-fluoro-1H-indazol-7-yl)(1-methylcyclohexyl)methanol | 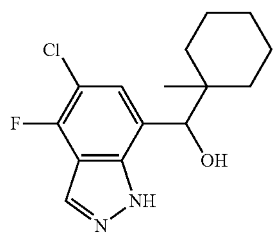 [SMILES: CC1(C(O)c2cc(Cl)c(F)c3cn[nH]c23)CCCCC1] | 295.0 MH(−) |
| P-0056 | 6-(5-chloro-1H-indazol-7-yl)-6-hydroxy-2-thiaspiro[3.3]heptane 2,2-dioxide | 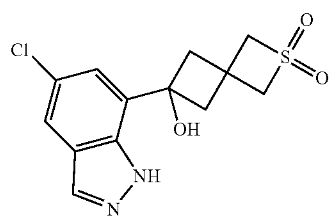 [SMILES: O=S1(=O)CC2(CC(O)(c3cc(Cl)cc4cn[nH]c34)C2)C1] | 312.9 |
| P-0057 | imidazo[1,5-a]pyridin-5-yl(phenyl)methanol | 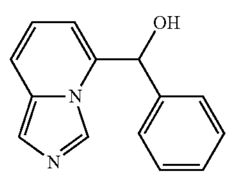 [SMILES: OC(c1ccccc1)c1cccc2cncn12] | 225.0 |
| P-0058 | cyclopentyl(imidazo[1,5-a]pyridin-5-yl)methanol | 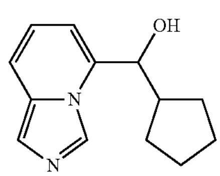 [SMILES: OC(c1cccc2cncn12)C1CCCC1] | 217.1 |
| P-0059 | bicyclo[2.2.1]heptan-2-yl(imidazo[1,5-a]pyridin-5-yl)methanol | 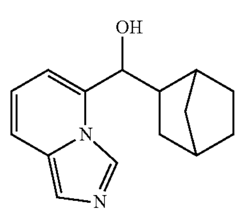 [SMILES: OC(c1cccc2cncn12)C1CC2CCC1C2] | 243.0 |

TABLE 1-continued

| Compound Number | Compound Name | Compound Structure | (MH)+ |
|---|---|---|---|
| P-0060 | cyclohexyl (imidazo[1,5-a]pyridin-5-yl)methanol | 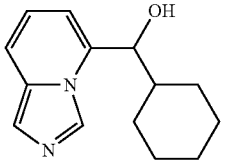 [SMILES: OC(c1cccc2cncn12)C1CCCCC1] | 231.0 |
| P-0061 | imidazo[1,5-a]pyridin-5-yl(1-methylcyclohexyl)methanol | 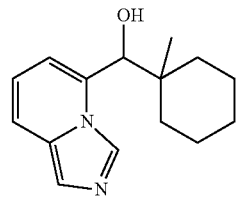 [SMILES: CC1(C(O)c2cccc3cncn23)CCCCC1] | 245.0 |
| P-0062 | imidazo[1,5-a]pyridin-5-yl(1,4,4-trifluorocyclohexyl)methanol | 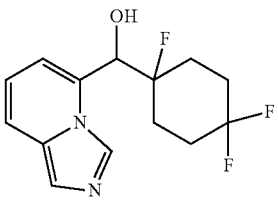 [SMILES: OC(c1cccc2cncn12)C1(F)CCC(F)(F)CC1] | 284.9 |
| P-0063 | cyclooctyl)imidazo[1,5-a]pyridin-5-yl)methanol | 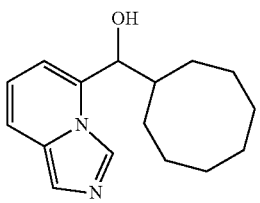 [SMILES: OC(c1cccc2cncn12)C1CCCCCCC1] | 259.1 |
| P-0064 | imidazo[1,5-a]pyridin-5-yl(4-propoxyphenyl)methanol | 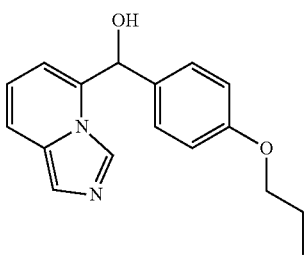 [SMILES: CCCOc1ccc(C(O)c2cccc3cncn23)cc1] | 283.5 |
| P-0065 | imidazo[1,5-a]pyridin-5-yl(4-(trifluoromethoxy)phenyl)methanol | 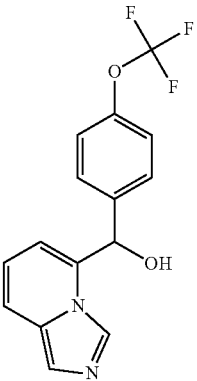 [SMILES: OC(c1ccc(OC(F)(F)F)cc1)c1cccc2cncn12] | 309.3 |

TABLE 1-continued

| Compound Number | Compound Name | Compound Structure | (MH)+ |
|---|---|---|---|
| P-0066 | (2-fluorophenyl)(imidazo[1,5-a]pyridin-5-yl)methanol | 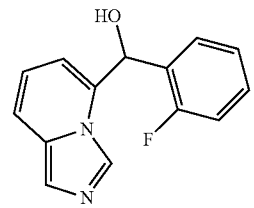 [SMILES: OC(c1ccccc1F)c1cccc2cncn12] | 243.3 |
| P-0067 | imidazo[1,5-a]pyridin-5-yl(2-(trifluoromethyl)phenyl)methanol | 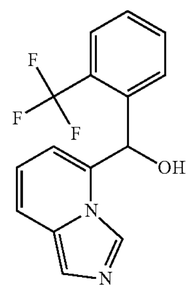 [SMILES: OC(c1ccccc1C(F)(F)F)c1cccc2cncn12] | 293.1 |
| P-0068 | (3-fluorophenyl)(imidazo[1,5-a]pyridin-5-yl)methanol | 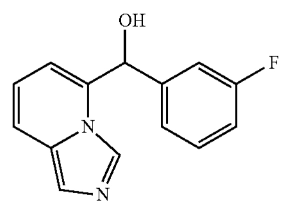 [SMILES: OC(c1cccc(F)c1)c1cccc2cncn12] | 243.2 |
| P-0069 | imidazo[1,5-a]pyridin-5-yl(3-morpholinophenyl)methanol | 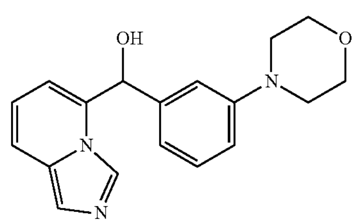 [SMILES: OC(c1cccc(N2CCOCC2)c1)c1cccc2cncn12] | 310.5 |
| P-0070 | (3-(1H-imidazol-1-yl)phenyl)(imidazo[1,5-a]pyridin-5-yl)methanol | 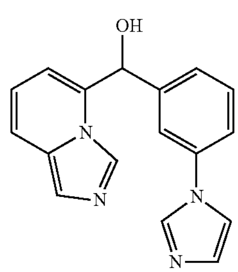 [SMILES: OC(c1cccc(-n2ccnc2)c1)c1cccc2cncn12] | 291.0 |

TABLE 1-continued
| Compound Number | Compound Name | Compound Structure | (MH)+ |
|---|---|---|---|
| P-0071 | (3-(benzyloxy)phenyl)(imidazo[1,5-a]pyridin-5-yl)methanol | 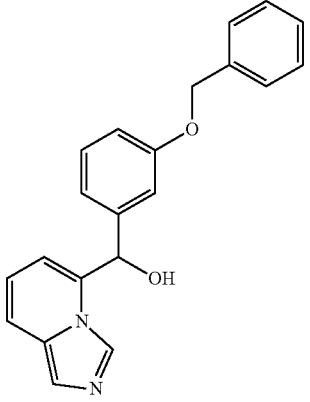 [SMILES: OC(c1cccc(OCc2ccccc2)c1)c1cccc2cncn12] | 331.2 |
| P-0072 | (3-(dimethylamino)phenyl)(imidazo[1,5-a]pyridin-5-yl)methanol | 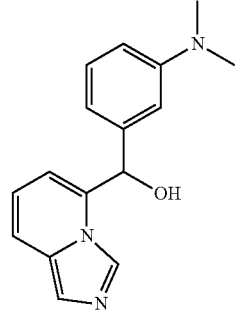 [SMILES: CN(C)c1cccc(C(O)c2cccc3cncn23)c1] | 268.2 |
| P-0073 | imidazo[1,5-a]pyridin-5-yl(3-(piperidin-1-yl)phenyl)methanol | 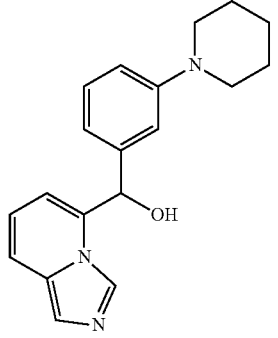 [SMILES: OC(c1cccc(N2CCCCC2)c1)c1cccc2cncn12] | 308.1 |
| P-0074 | 1-(imidazo[1,5-a]pyridin-5-yl)-3-phenylpropan-1-ol | 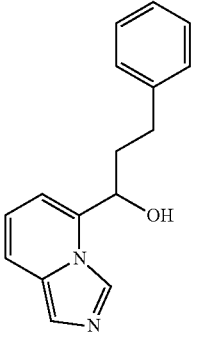 [SMILES: OC(CCc1ccccc1)c1cccc2cncn12] | 253.2 |

TABLE 1-continued

| Compound Number | Compound Name | Compound Structure | (MH)+ |
|---|---|---|---|
| P-0075 | imidazo[1,5-a]pyridin-5-yl(tetrahydro-2H-pyran-4-yl)methanol | 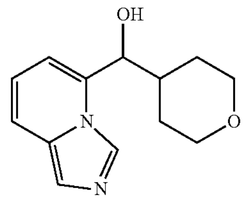 [SMILES: OC(c1cccc2cncn12)C1CCOCC1] | 233.1 |
| P-0076 | tert-butyl 4-(hydroxy(imidazo[1,5-a]pyridin-5-yl)methyl)piperidine-1-carboxylate | 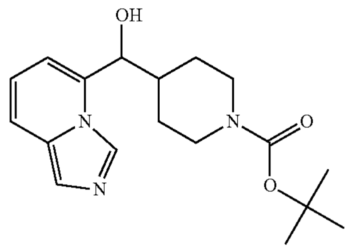 [SMILES: CC(C)(C)OC(=O)N1CCC(C(O)c2cccc3cncn23)CC1] | 332.1 |
| P-0077 | (2-chlorophenyl)(imidazo[1,5-a]pyridin-5-yl)methanol | 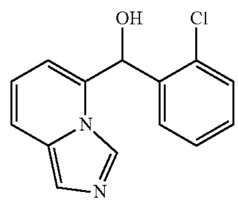 [SMILES: OC(c1ccccc1Cl)c1cccc2cncn12] | 259.2 |
| P-0078 | imidazo[1,5-a]pyridin-5-yl(3-(trifluoromethyl)phenyl)methanol | 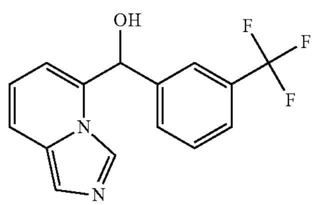 [SMILES: OC(c1cccc(C(F)(F)F)c1)c1cccc2cncn12] | 293.1 |
| P-0079 | 2-cyclohexyl-1-(imidazo[1,5-a]pyridin-5-yl)ethan-1-ol | 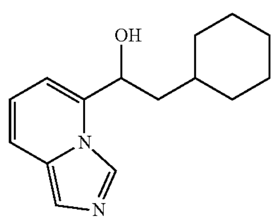 [SMILES: OC(CC1CCCCC1)c1cccc2cncn12] | 245.1 |
| P-0080 | cyclobutyl(imidazo[1,5-a]pyridin-5-yl)methanol | 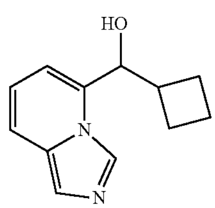 [SMILES: OC(c1cccc2cncn12)C1CCC1] | 203.4 |
| P-0081 | (4,4-difluorocyclohexyl)(imidazo[1,5-a]pyridin-5-yl)methanol | 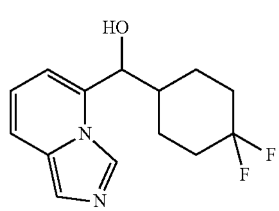 [SMILES: OC(c1cccc2cncn12)C1CCC(F)(F)CC1] | 267.3 |

TABLE 1-continued

| Number | Compound Name | Compound Structure | (MH)+ |
|---|---|---|---|
| P-0082 | (7-bromoimidazo[1,5-a]pyridin-5-yl)(1-methylcyclohexyl)methanol | 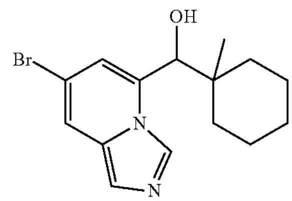 [SMILES: CC1(C(O)c2cc(Br)cc3cncn23)CCCCC1] | 322.9 |
| P-0083 | (7-chloroimidazo[1,5-a]pyridin-5-yl)(1-methylcyclohexyl)methanol | 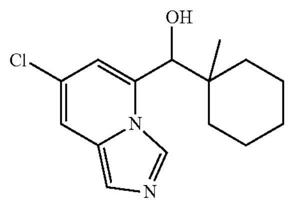 [SMILES: CC1(C(O)c2cc(Cl)cc3cncn23)CCCCC1] | 279.0 |
| P-0084 | 1-(imidazo[1,5-a]pyridin-5-yl)-2-(tetrahydro-2H-pyran-4-yl)ethan-1-ol | 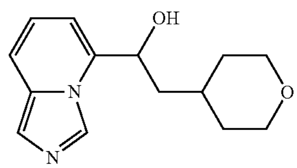 [SMILES: OC(CC1CCOCC1)c1cccc2cncn12] | 247.0 |
| P-0085 | tert-butyl 4-(2-hydroxy-2-(imidazo[1,5-a]pyridin-5-yl)ethyl)piperidine-1-carboxylate | 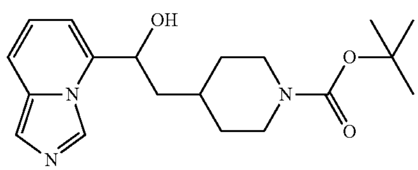 [SMILES: CC(C)(C)OC(=O)N1CCC(CC(O)c2cccc3cncn23)CC1] | 346.1 |
| P-0086 | 1-(7-chloroimidazo[1,5-a]pyridin-5-yl)-2-cyclohexyl-2-methylpropan-1-ol | 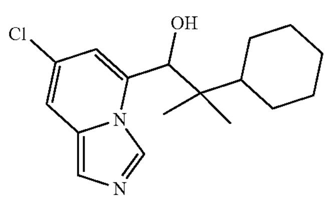 [SMILES: CC(C)(C1CCCCC1)C(O)c1cc(Cl)cc2cncn12] | 307.2 |
| P-0087 | ((1s,3s)-adamantan-1-yl)(imidazo[1,5-a]pyridin-5-yl)methanol | 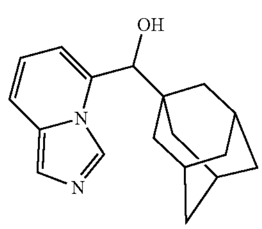 [SMILES: OC(c1cccc2cncn12)C12CC3CC(CC(C3)C1)C2] | 283.0 |
| P-0088 | (6-chloroimidazo[1,5-a]pyridin-5-yl)(1-methylcyclohexyl)methanol | 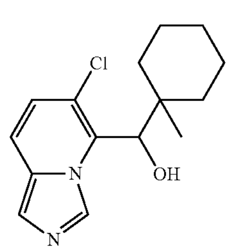 [SMILES: CC1(C(O)c2c(Cl)ccc3cncn23)CCCCC1] | 279.0 |

TABLE 1-continued

| Compound Number | Compound Name | Compound Structure | (MH)+ |
|---|---|---|---|
| P-0089 | 5-chloro-7-(3,3-dimethyl-4-(methylsulfonyl)piperazin-1-yl)-1H-indazole | 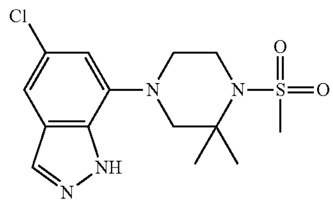 [SMILES: CC1(C)CN(c2cc(Cl)cc3cn[nH]c23)CCN1S(C)(=O)=O] | 323.4 |
| P-0090 | 7-(3,3-dimethyl-4-(methylsulfonyl)piperazin-1-yl)-5-methyl-1H-indazole | 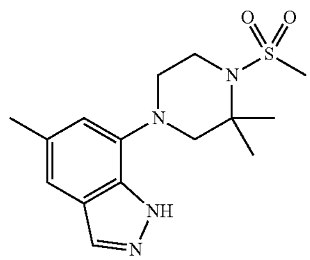 | 343.1 |
| P-0091 | 7-(3,3-dimethyl-4-(methylsulfonyl)piperazin-1-yl)-5-(trifluoromethyl)-1H-indazole | 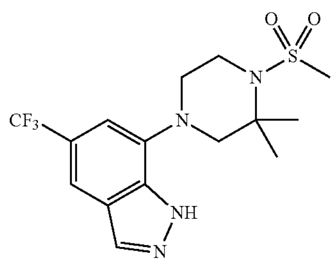 [SMILES: CC1(C)CN(c2cc(C(F)(F)F)cc3cn[nH]c23)CCN1S(C)(=O)=O] | 377.1 |
| P-0092 | 5-chloro-7-(3,3-dimethyl-4-(methylsulfonyl)piperazin-1-yl)-6-fluoro-1H-indazole | 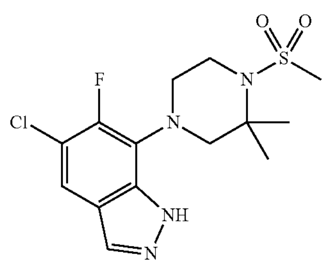 [SMILES: CC1(C)CN(c2c(F)c(Cl)cc3cn[nH]c23)CCN1S(C)(=O)=O] | 361.0 |
| P-0093 | 5-chloro-7-(8-(methylsulfonyl)-3,8-diazabicyclo[3.2.1]octan-3-yl)-1H-indazole | 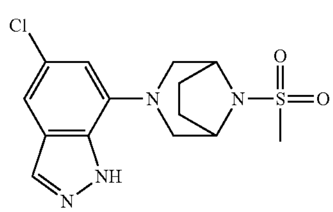 | 341.1 |
| P-0094 | 5-methyl-7-(8-(methylsulfonyl)-3,8-diazabicyclo[3.2.1]octan-3-yl)-1H-indazole | 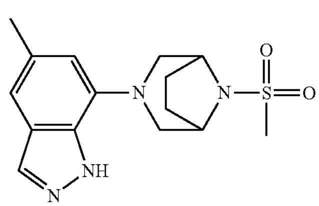 [SMILES: Cc1cc(N2CC3CCC(C2)N3S(C)(=O)=O)c2[nH]ncc2c1] | 321.5 |

TABLE 1-continued

| Compound Number | Compound Name | Compound Structure | (MH)+ |
|---|---|---|---|
| P-0095 | 7-(8-(methylsulfonyl)-3,8-diazabicyclo[3.2.1]octan-3-yl)-5-(trifluoromethyl)-1H-indazole | 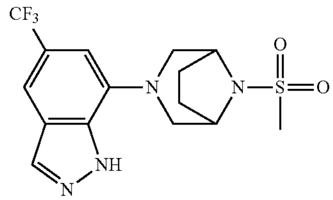 [SMILES: CS(=O)(=O)N1C2CCC1CN(c1cc(C(F)(F)F)cc3cn[nH]c13)C2] | 375.1 |
| P-0096 | 5-chloro-6-fluoro-7-(8-(methylsulfonyl)-3,8-diazabicyclo[3.2.1]octan-3-yl)-1H-indazole | 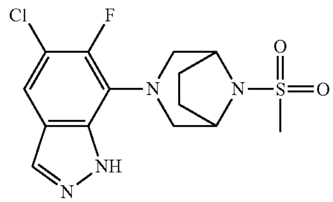 [SMILES: CS(=O)(=O)N1C2CCC1CN(c1c(F)c(Cl)cc3cn[nH]c13)C2] | 359.1 |
| P-0097 | 5-chloro-7-(3,3-dimethyl-4-(methylsulfonyl)piperazin-1-yl)-4-fluoro-1H-indazole | 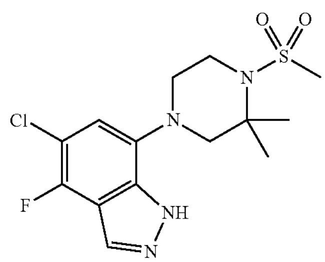 [SMILES: CC1(C)CN(c2cc(Cl)c(F)c3cn[nH]c23)CCN1S(C)(=O)=O] | 361.1 |
| P-0098 | (7-chloroimidazo[1,5-a]pyridin-8-yl)(1-methylcyclohexyl)methanol | 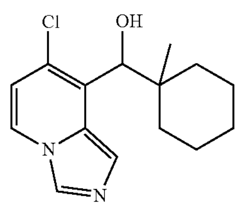 [SMILES: CC1(C(O)c2c(Cl)ccn3cncc23)CCCCC1] | 279 |
| P-0099 | (1-methylcyclohexyl)(1,5,6,7-tetrahydrocyclopenta[f]indazol-8-yl)methanol | 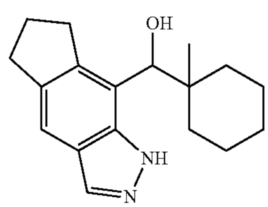 [SMILES: CC1(C(O)c2c3c(cc4cn[nH]c24)CCC3)CCCCC1] | 284.9 |
| P-0100 | (1R,5S)-3'-(5-chloro-1H-indazol-7-yl)spiro[adamantane-2,1'-cyclobutan]-3'-ol | 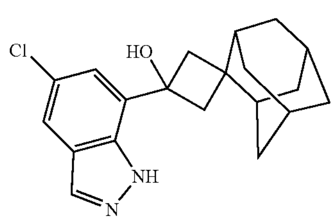 [SMILES: OC1(c2cc(Cl)cc3cn[nH]c23)CC2(C1)C1CC3CC(C1)CC2C3] | 343.0 |
| P-0105 | 4-(5-chloro-1H-indazol-7-yl)cyclohex-3-ene-1-carbonitrile | 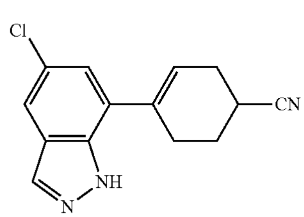 [SMILES: N#CC1CC=C(c2cc(Cl)cc3cn[nH]c23)CC1] | 258.1 |

TABLE 1-continued

| Number | Compound Name | Compound Structure | (MH)+ |
|---|---|---|---|
| P-0106 | 1-(5-chloro-1H-indazol-7-yl)piperidine-4-carbonitrile | 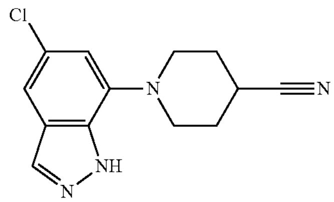 [SMILES: N#CC1CCN(c2cc(Cl)cc3cn[nH]c23)CC1] | 261.1 |
| P-0110 | 5-chloro-7-(1-(methylsulfonyl)-1,2,3,6-tetrahydropyridin-4-yl)-1H-indazole | 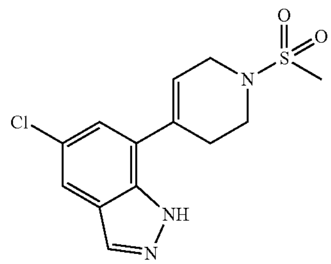 [SMILES: CS(=O)(=O)N1CC=C(c2cc(Cl)cc3cn[nH]c23)CC1] | 309.9 (MH)− |
| P-0111 | 8-(5-chloro-1H-indazol-7-yl)-2,8-diazaspiro[4.5]decan-1-one | 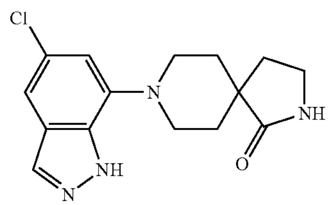 [SMILES: O=C1NCCC12CCN(c1cc(Cl)cc3cn[nH]c13)CC2] | 305.1 |
| P-0112 | (5-chloro-4,6-difluoro-1H-indazol-7-yl)(3,3-difluoro-1-methylcyclobutyl)methanol | 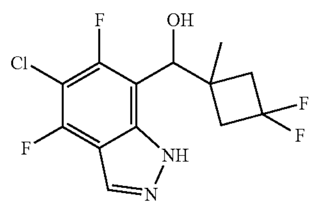 [SMILES: CC1(C(O)c2c(F)c(Cl)c(F)c3cn[nH]c23)CC(F)(F)C1] | 320.9 (MH)− |
| P-0113 | (1r,3r,5r,7r)-3'-(5-chloro-1H-indazol-7-yl)spiro[adamantane-2,1'-cyclobutan]-3'-ol | 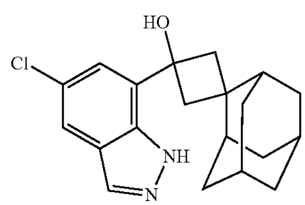 [SMILES: OC1(c2cc(Cl)cc3cn[nH]c23)CC2(C1)C1CC3CC(C1)CC2C3] | 343.0 |
| P-0114 | (5-chloro-6-fluoro-1H-indazol-7-yl)(3,3-difluoro-1-methylcyclobutyl)methanol | 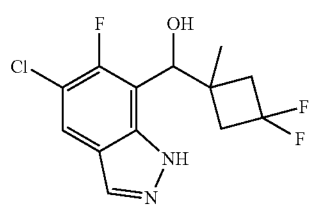 [SMILES: CC1(C(O)c2c(F)c(Cl)cc3cn[nH]c23)CC(F)(F)C1] | 302.9 (MH)− |
| P-0115 | (5-methoxy-1H-indazol-7-yl)(1-methylcyclohexyl)methanol | 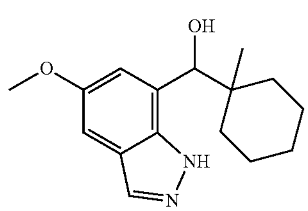 [SMILES: COc1cc(C(O)C2(C)CCCCC2)c2[nH]ncc2c1] | 275.0 |

TABLE 1-continued

| Compound Number | Compound Name | Compound Structure | (MH)+ |
|---|---|---|---|
| P-0116 | (5-chloro-1H-indazol-7-yl)(cyclobutyl)methanol | 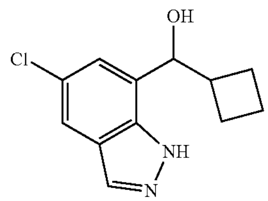 [SMILES: OC(c1cc(Cl)cc2cn[nH]c12)C1CCC1] | 237.0 |
| P-0117 | (5-chloro-1H-indazol-7-yl)(1-methylcyclobutyl)methanol | 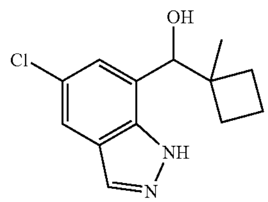 [SMILES: CC1(C(O)c2cc(Cl)cc3cn[nH]c23)CCC1] | 251.4 |
| P-0118 | 1-(5-chloro-1H-indazol-7-yl)-2-cyclobutyl-2-methylpropan-1-ol | 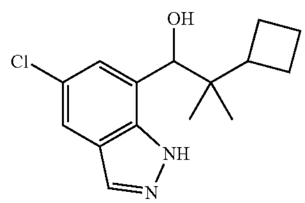 [SMILES: CC(C)(C1CCC1)C(O)c1cc(Cl)cc2cn[nH]c12] | 279.3 |
| P-0119 | (5-chloro-1H-indazol-7-yl)(1-(trifluoromethyl)cyclopropyl)methanol | 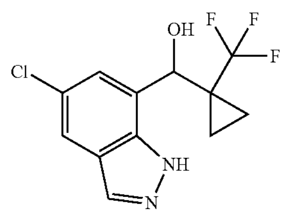 [SMILES: OC(c1cc(Cl)cc2cn[nH]c12)C1(C(F)(F)F)CC1] | 291.0 |
| P-0120 | (5-chloro-1H-indazol-7-yl)(1-(trifluoromethyl)cyclobutyl)methanol | 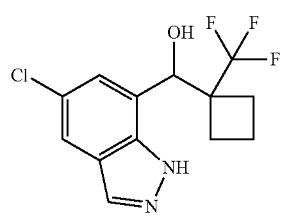 [SMILES: OC(c1cc(Cl)cc2cn[nH]c12)C1(C(F)(F)F)CCC1] | 304.8 |
| P-0121 | (5-chloro-1H-indazol-7-yl)(1-propylcyclobutyl)methanol | 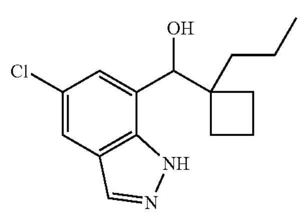 [SMILES: CCCC1(C(O)c2cc(Cl)cc3cn[nH]c23)CCC1] | 279.3 |
| P-0122 | 1-(5-chloro-1H-indazol-7-yl)-3,3-dicyclopropylcyclobutan-1-ol | 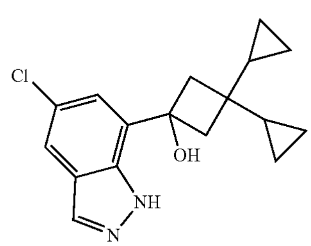 [SMILES: OC1(c2cc(Cl)cc3cn[nH]c23)CC(C2CC2)(C2CC2)C1] | 312.9 (MH)− |

TABLE 1-continued

| Compound Number | Compound Name | Compound Structure | (MH)+ |
|---|---|---|---|
| P-0123 | (5-chloro-4,6-difluoro-1H-indazol-7-yl)(1-methylcyclohexyl)methanol | 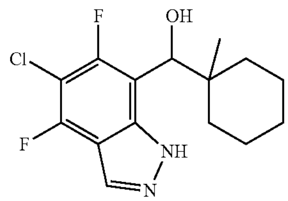 [SMILES: CC1(C(O)c2c(F)c(Cl)c(F)c3cn[nH]c23)CCCCC1] | 305.1 |
| P-0124 | (1s,5s)-3'-(5-chloro-1H-indazol-7-yl)spiro[bicyclo[3.3.1]nonane-9,1'-cyclobutan]-3'-ol | 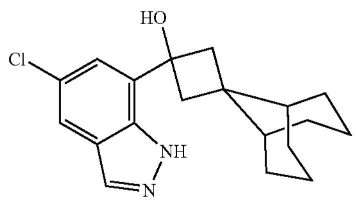 [SMILES: OC1(c2cc(Cl)cc3cn[nH]c23)CC2(C1)C1CCCC2CCC1] | 331.0 |
| P-0125 | 1-(5-chloro-1H-indazol-7-yl)-3,3-dicyclopropylcyclobutan-1-ol | 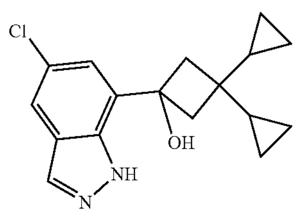 [SMILES: OC1(c2cc(Cl)cc3cn[nH]c23)CC(C2CC2)(C2CC2)C1] | 303.0 |
| P-0126 | 2-(5-chloro-6-fluoro-1H-indazol-7-yl)-7-(methylsulfonyl)-7-azaspiro[3.5]nonan-2-ol | 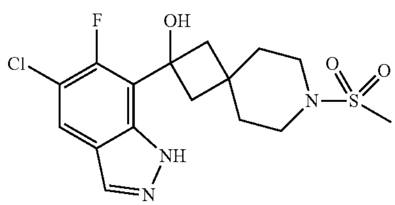 [SMILES: CS(=O)(=O)N1CCC2(CC1)CC(O)(c1c(F)c(Cl)cc3cn[nH]c13)C2] | 385.9 (MH)− |
| P-0127 | 8-(2-(5-chloro-1H-indazol-7-yl)-2-hydroxyethyl)-N-methyl-3-azabicyclo[3.2.1]octane-3-carboxamide | 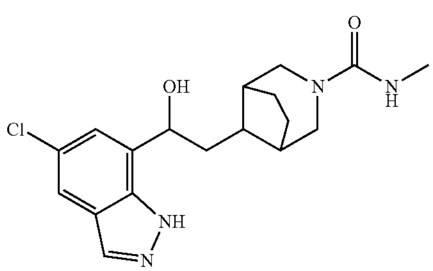 [SMILES: CNC(=O)N1CC2CCC(C1)C2CC(O)c1cc(Cl)cc2cn[nH]c12] | 363.1 |
| P-0128 | 1-(4-(2-(5-chloro-6-fluoro-1H-indazol-7-yl)-1,1-difluoro-2-hydroxyethyl)piperidin-1-yl)ethan-1-one | 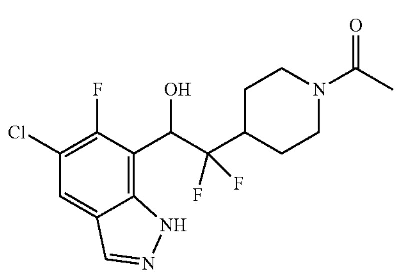 [SMILES: CC(=O)N1CCC(C(F)(F)C(O)c2c(F)c(Cl)cc3cn[nH]c23)CC1] | 376.1 |

TABLE 1-continued

| Number | Compound Name | Compound Structure | (MH)+ |
|---|---|---|---|
| P-0129 | 1-(4-(2-(5,6-dihydro-1H-cyclobuta[f]indazol-7-yl)-1,1-difluoro-2-hydroxyethyl)piperidin-1-yl)ethan-1-one | 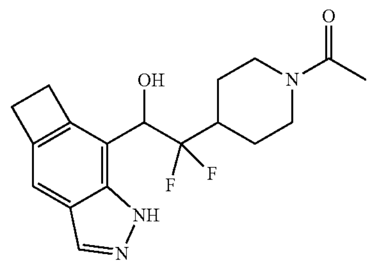 [SMILES: CC(=O)N1CCC(C(F)(F)C(O)c2c3c(cc4cn[nH]c24)CC3)CC1] | 350.2 |
| P-0130 | 1-(4-(1-((5-chloro-1H-indazol-7-yl)(hydroxy)methyl)cyclopropyl)piperidin-1-yl)ethan-1-one | 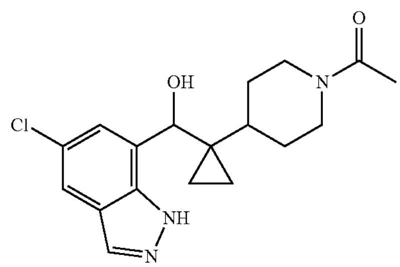 [SMILES: CC(=O)N1CCC(C2(C(O)c3cc(Cl)cc4cn[nH]c34)CC2)CC1] | 348.10 |
| P-0131 | 1-(5-chloro-1H-indazol-7-yl)-2,2-difluoro-2-((1R,5S,8s)-3-(methylsulfonyl)-3-azabicyclo[3.2.1]octan-8-yl)ethan-1-ol | 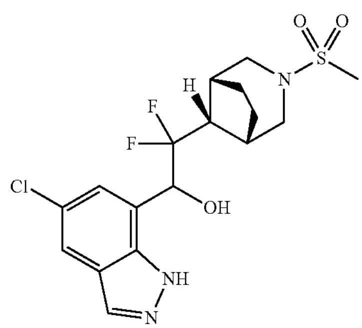 [SMILES: CS(=O)(=O)N1C[C@H]2CC[C@@H](C1)[C@H]2C(F)(F)C(O)c1cc(Cl)cc2cn[nH]c12] | 420.1 |
| P-0132 | 1-(5-chloro-1H-indazol-7-yl)-2,2-difluoro-2-((1R,5S,8r)-3-(methylsulfonyl)-3-azabicyclo[3.2.1]octan-8-yl)ethan-1-ol | 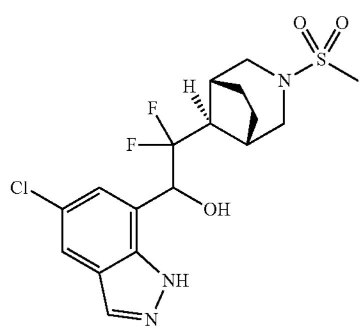 [SMILES: CS(=O)(=O)N1C[C@H]2CC[C@@H](C1)[C@@H]2C(F)(F)C(O)c1cc(Cl)cc2cn[nH]c12] | 420.1 |
| P-0133 | 4-((5-chloro-1H-indazol-7-yl)(hydroxy)methyl)bicyclo[2.2.2]octan-1-ol | 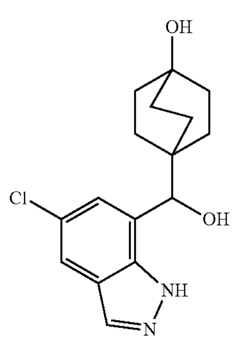 [SMILES: OC(c1cc(Cl)cc2cn[nH]c12)C12CCC(O)(CC1)CC2] | 307.10 |

TABLE 1-continued

| Number | Compound Name | (MH)+ |
|---|---|---|
| P-0134 | 4-(1-((5-chloro-1H-indazol-7-yl)(hydroxy)methyl)cyclopropyl)-N-methylpiperidine-1-carboxamide | 363.10 |
| P-0135 | bicyclo[2.2.2]octan-1-yl(5-chloro-4-fluoro-1H-indazol-7-yl)methanol | 306.9 (MH)− |
| P-0136 | (5-chloro-1H-indazol-7-yl)(4-methoxybicyclo[2.2.2]octan-1-yl)methanol | 319.0 (MH)− |
| P-0137 | (5-chloro-6-fluoro-1H-indazol-7-yl)(4-methoxybicyclo[2.2.2]octan-1-yl)methanol | 336.9 (MH)− |
| P-0138 | 1-((1R,5S,8s)-8-(2-(5-chloro-6-fluoro-1H-indazol-7-yl)-1,1-difluoro-2-hydroxyethyl)-3-azabicyclo[3.2.1]octan-3-yl)ethan-1-one | 402.1 |
| P-0139 | 1-((1R,5S,8r)-8-(2-(5-chloro-6-fluoro-1H-indazol-7-yl)-1,1-difluoro-2-hydroxyethyl)-3-azabicyclo[3.2.1]octan-3-yl)ethan-1-one | 402.10 |

TABLE 1-continued

| Compound Number | Compound Name | Compound Structure | (MH)+ |
|---|---|---|---|
| P-0141 | methyl 4-(2-(5-chloro-1H-indazol-7-yl)-1,1-difluoro-2-hydroxyethyl)piperidine-1-carboxylate | 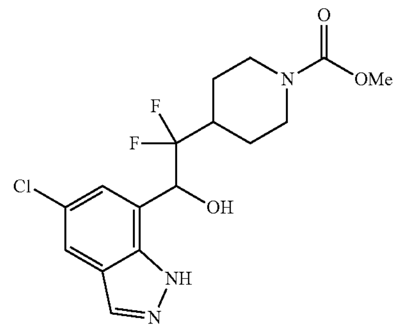 [SMILES: COC(=O)N1CCC(C(F)(F)C(O)c2cc(Cl)cc3cn[nH]c23)CC1] | 374.1 |
| P-0142 | 4-(2-(5-chloro-1H-indazol-7-yl)-1,1-difluoro-hydroxyethyl)-N-methylpiperidine-1-carboxamide | 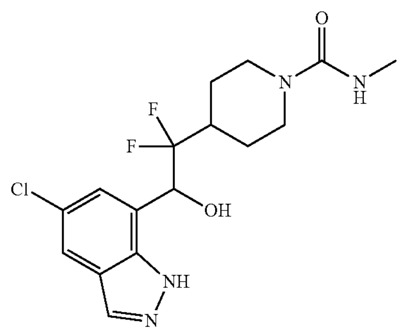 [SMILES: CNC(=O)N1CCC(C(F)(F)C(O)c2cc(Cl)cc3cn[nH]c23)CC1] | 373.1 |
| P-0143 | (4-(2-(5-chloro-1H-indazol-7-yl)-1,1-difluoro-2-hydroxyethyl)piperidin-1-yl)(cyclopropyl)methanone | 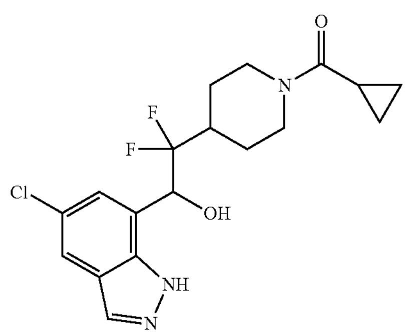 [SMILES: O=C(C1CC1)N1CCC(C(F)(F)C(O)c2cc(Cl)cc3cn[nH]c23)CC1] | 384.1 |
| P-0144 | 4-(2-(5-chloro-1H-indazol-7-yl)-1,1-difluoro-2-hydroxyethyl)piperidine-1-carboxamide | 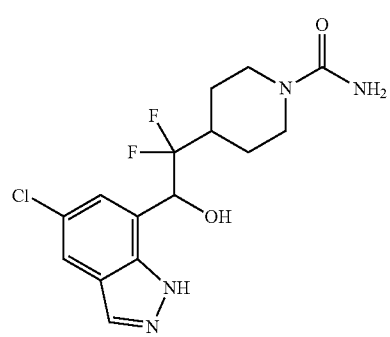 [SMILES: NC(=O)N1CCC(C(F)(F)C(O)c2cc(Cl)cc3cn[nH]c23)CC1] | 359.1 |
| P-0145 | (6-chloro-1H-indazol-4-yl)(1-methylcyclohexyl)methanol | 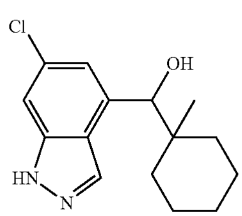 [SMILES: CC1(C(O)c2cc(Cl)cc3[nH]ncc23)CCCCC1] | 276.9 (MH)− |

TABLE 1-continued

| Number | Compound Name | Compound Structure | (MH)+ |
| --- | --- | --- | --- |
| P-0146 | bicyclo[2.2.2]octan-1-yl(6-chloro-1H-indazol-4-yl)methanol | 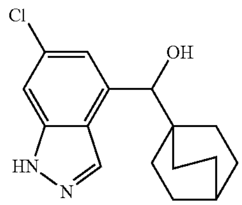 [SMILES: OC(c1cc(Cl)cc2[nH]ncc12)C12CCC(CC1)CC2] | 288.9 (MH)− |
| P-0147 | 1-(4-(2-(5-chloro-1H-indazol-7-yl)-1,1-difluoro-2-hydroxyethyl)piperidin-1-yl)propan-1-one | 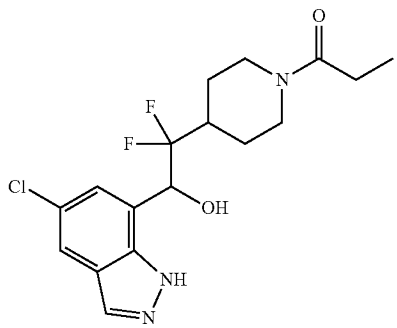 [SMILES: CCC(=O)N1CCC(C(F)(F)C(O)c2cc(Cl)cc3cn[nH]c23)CC1] | 372.1 |
| P-0148 | 1-(4-(2-(5-chloro-1H-indazol-7-yl)-1,1-difluoro-2-hydroxyethyl)piperidin-1-yl)-3-methylbutan-1-one | 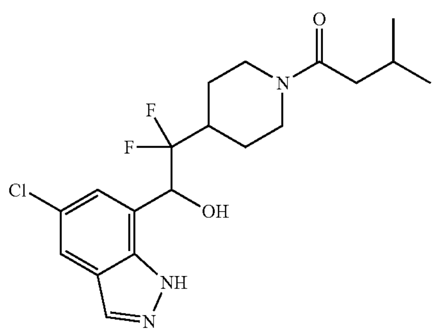 [SMILES: CC(C)CC(=O)N1CCC(C(F)(F)C(O)c2cc(Cl)cc3cn[nH]c23)CC1] | 400.1 |
| P-0149 | 1-(4-(2-(5-chloro-1H-indazol-7-yl)-1,1-difluoro-2-hydroxyethyl)piperidin-1-yl)-2-cyclopropylethan-1-one | 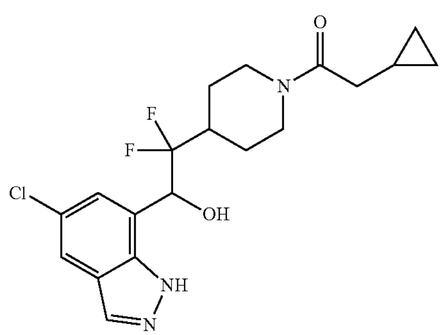 [SMILES: O=C(CC1CC1)N1CCC(C(F)(F)C(O)c2cc(Cl)cc3cn[nH]c23)CC1] | 398.1 |
| P-0150 | 4-(2-(5-chloro-1H-indazol-7-yl)-1,1-difluoro-2-hydroxyethyl)-N-phenylpiperidine-1-carboxamide | 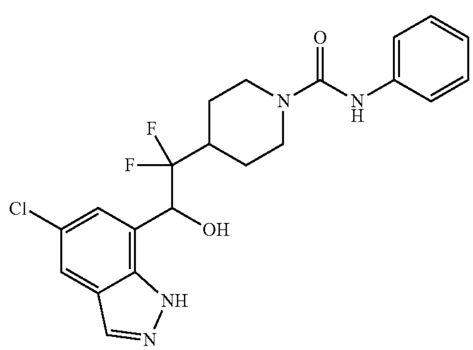 [SMILES: O=C(Nc1ccccc1)N1CCC(C(F)(F)C(O)c2cc(Cl)cc3cn[nH]c23)CC1] | 435.1 |

TABLE 1-continued

| Compound Number | Compound Name | Compound Structure | (MH)+ |
|---|---|---|---|
| P-0151 | 4-(2-(5-chloro-1H-indazol-7-yl)-1,1-difluoro-2-hydroxyethyl)-N-(4-fluorophenyl)piperidine-1-carboxamide | 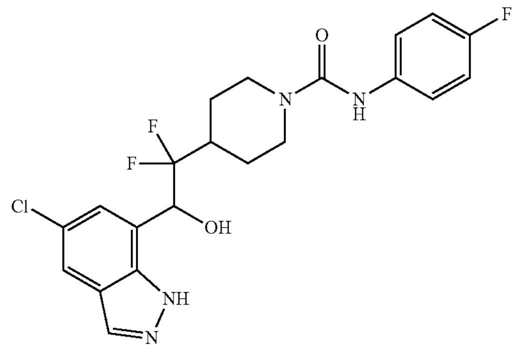 [SMILES: O=C(Nc1ccc(F)cc1)N1CCC(C(F)(F)C(O)c2cc(Cl)cc3cn[nH]c23)CC1] | 435.1 |
| P-0152 | 4-(2-(5-chloro-1H-indazol-7-yl)-1,1-difluoro-2-hydroxyethyl)-N-(3-fluorophenyl)piperidine-1-carboxamide | 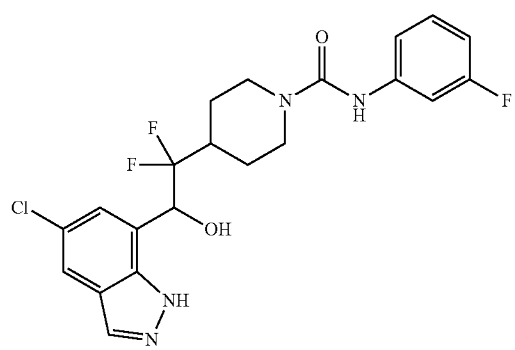 [SMILES: O=C(Nc1cccc(F)c1)N1CCC(C(F)(F)C(O)c2cc(Cl)cc3cn[nH]c23)CC1] | 453.1 |
| P-0153 | 4-(2-(5-chloro-1H-indazol-7-yl)-1,1-difluoro-2-hydroxyethyl)-N-(4-(trifluoromethyl)phenyl)piperidine-1-carboxamide | 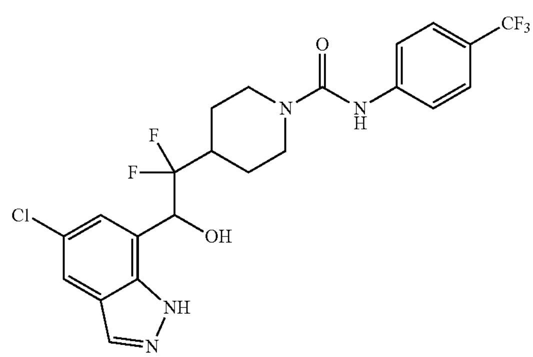 [SMILES: O=C(Nc1ccc(C(F)(F)F)cc1)N1CCC(C(F)(F)C(O)c2cc(Cl)cc3cn[nH]c23)CC1] | 503.1 |
| P-0154 | 4-(2-(5-chloro-1H-indazol-7-yl)-1,1-difluoro-2-hydroxyethyl)-N-(3-(trifluoromethyl)phenyl)piperidine-1-carboxamide | 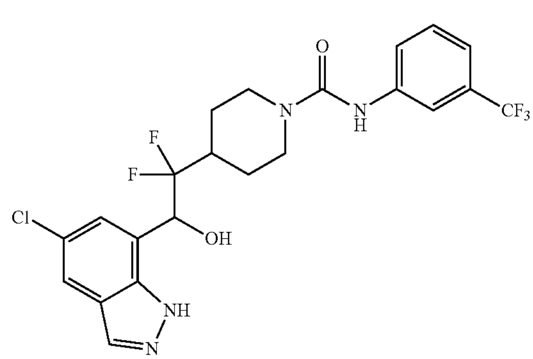 [SMILES: O=C(Nc1cccc(C(F)(F)F)c1)N1CCC(C(F)(F)C(O)c2cc(Cl)cc3cn[nH]c23)CC1] | 503.1 |

TABLE 1-continued

| Compound Number | Compound Name | Compound Structure | (MH)+ |
|---|---|---|---|
| P-0155 | methyl 4-(1-((5-chloro-1H-indazol-7-yl)(hydroxy)methyl)cyclopropyl)piperidine-1-carboxylate | 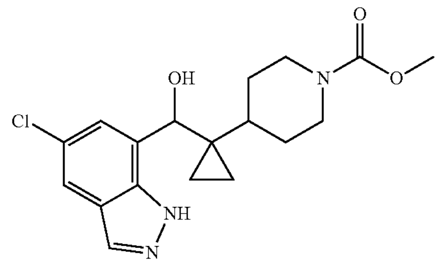 [SMILES: COC(=O)N1CCC(C2(C(O)c3cc(Cl)cc4cn[nH]c34)CC2)CC1] | 361.90 |
| P-0156 | 4-(1-((5-chloro-1H-indazol-7-yl)(hydroxy)methyl)cyclopropyl)piperidine-1-carboxamide | 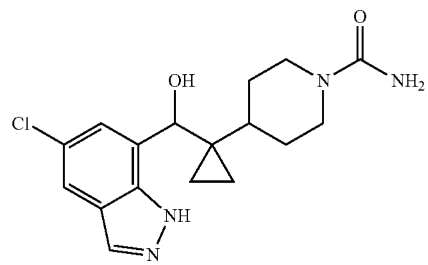 [SMILES: NC(=O)N1CCC(C2(C(O)c3cc(Cl)cc4cn[nH]c34)CC2)CC1] | 349.0 |
| P-0157 | 4-(1-((5-chloro-1H-indazol-7-yl)(hydroxy)methyl)cyclopropyl)-N-(4-fluorophenyl)piperidine-1-carboxamide | 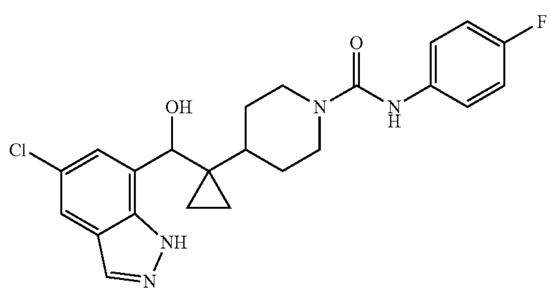 [SMILES: O=C(Nc1ccc(F)cc1)N1CCC(C2(C(O)c3cc(Cl)cc4cn[nH]c34)CC2)CC1] | 443.0 |
| P-0158 | (5-chloro-1H-indazol-7-yl)(1-(1-(methylsulfonyl)piperidin-4-yl)cyclopropyl)methanol | 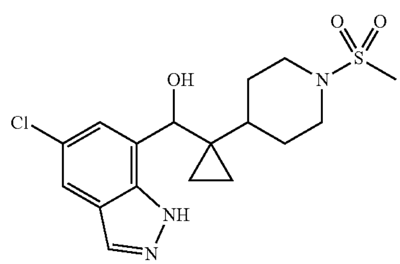 [SMILES: CS(=O)(=O)N1CCC(C2(C(O)c3cc(Cl)cc4cn[nH]c34)CC2)CC1] | 384.0 |
| P-0159 | 1-(4-(1-((5-chloro-6-fluoro-1H-indazol-7-yl)(hydroxy)methyl)cyclopropyl)piperidin-1-yl)ethan-1-one | 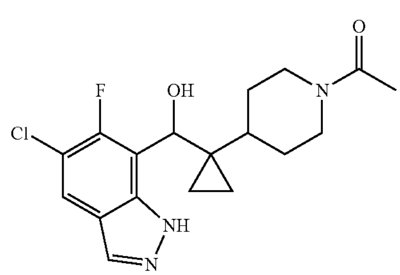 [SMILES: CC(=O)N1CCC(C2(C(O)c3c(F)c(Cl)cc4cn[nH]c34)CC2)CC1] | 366.00 |

TABLE 1-continued

| Compound Number | Compound Name | Compound Structure | (MH)+ |
|---|---|---|---|
| P-0160 | methyl 4-(1-((5-chloro-6-fluoro-1H-indazol-7-yl)(hydroxy)methyl)cyclopropyl)piperidine-1-carboxylate | 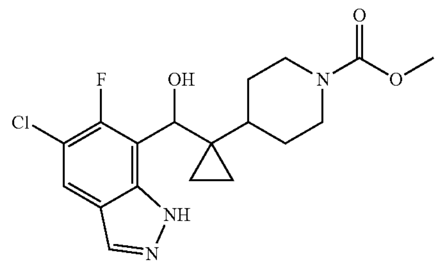 [SMILES: COC(=O)N1CCC(C2(C(O)c3c(F)c(Cl)cc4cn[nH]c34)CC2)CC1] | 379.85 |
| P-0161 | 4-(1-((5-chloro-6-fluoro-1H-indazol-7-yl)(hydroxy)methyl)cyclopropyl)piperidine-1-carboxamide | 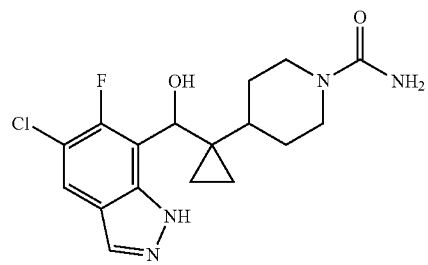 [SMILES: NC(=O)N1CCC(C2(C(O)c3c(F)c(Cl)cc4cn[nH]c34)CC2)CC1] | 367.0 |
| P-0162 | 4-(1-((5-chloro-6-fluoro-1H-indazol-7-yl)(hydroxy)methyl)cyclopropyl)-N-methylpiperidine-1-carboxamide | 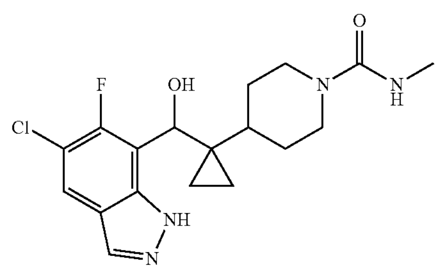 [SMILES: CNC(=O)N1CCC(C2(C(O)c3c(F)c(Cl)cc4cn[nH]c34)CC2)CC1] | 381.0 |
| P-0163 | tert-butyl 4-(1-(5-chloro-1H-indazol-7-yl)-1-hydroxy-2-methylpropan-2-yl)piperidine-1-carboxylate | 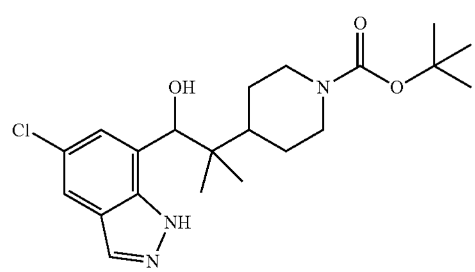 [SMILES: CC(C)(C)OC(=O)N1CCC(C(C)(C)C(O)c2cc(Cl)cc3cn[nH]c23)CC1] | 408.2 |
| P-0164 | 4-(1-((5-chloro-6-fluoro-1H-indazol-7-yl)(hydroxy)methyl)cyclopropyl)-N-(4-fluorophenyl)piperidine-1-carboxamide | 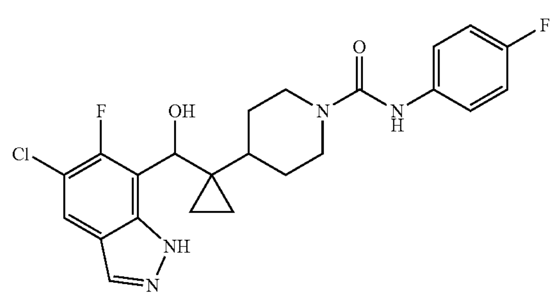 [SMILES: O=C(Nc1ccc(F)cc1)N1CCC(C2(C(O)c3c(F)c(Cl)cc4cn[nH]c34)CC2)CC1] | 461.1 |

TABLE 1-continued

| Compound Number | Compound Name | Compound Structure | (MH)+ |
|---|---|---|---|
| P-0165 | (5-chloro-6-fluoro-1H-indazol-7-yl)(1-(1-(methylsulfonyl)piperidin-4-yl)cyclopropyl)methanol | 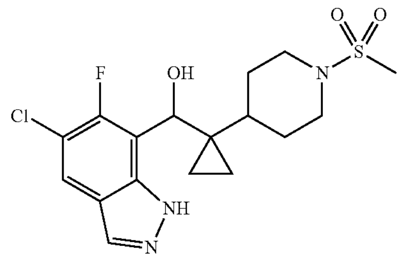 [SMILES: CS(=O)(=O)N1CCC(C2(C(O)c3c(F)c(Cl)cc4cn[nH]c34)CC2)CC1] | 402.0 |
| P-0166 | (2-aminothiazol-4-yl)(4-(1-((5-chloro-1H-indazol-7-yl)(hydroxy)methyl)cyclopropyl)piperidin-1-yl)methanone | 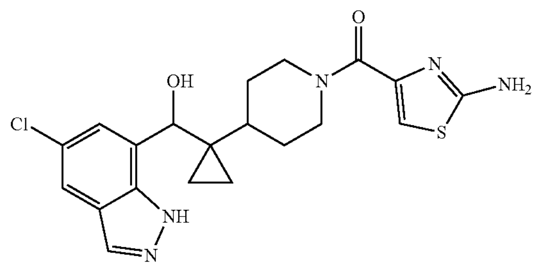 [SMILES: Nc1nc(C(=O)N2CCC(C3(C(O)c4cc(Cl)cc5cn[nH]c45)CC3)CC2)cs1] | 432.0 |
| P-0167 | 4-(1-(5-chloro-1H-indazol-7-yl)-1-hydroxy-2-methylpropan-2-yl)-N-(4-fluorophenyl)piperidine-1-carboxamide | 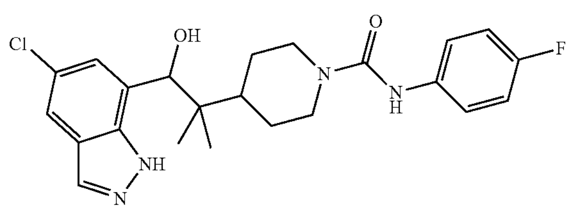 | 445.1 |
| P-0168 | 4-(1-(5-chloro-1H-indazol-7-yl)-1-hydroxy-2-methylpropan-2-yl)-N-(4-cyanophenyl)piperidine-1-carboxamide | 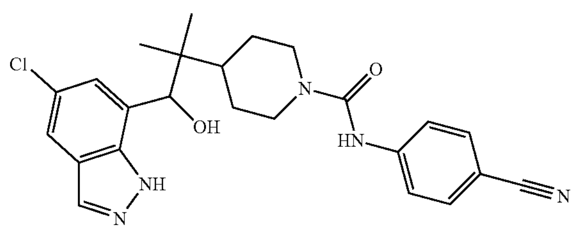 [SMILES: CC(C)(C1CCN(C(=O)Nc2ccc(C#N)cc2)CC1)C(O)c1cc(Cl)cc2cn[nH]c12] | 451.9 |
| P-0169 | 4-(1-(6-chloro-1H-indazol-4-yl)-1-hydroxy-2-methylpropan-2-yl)-N-methylpiperidine-1-carboxamide | 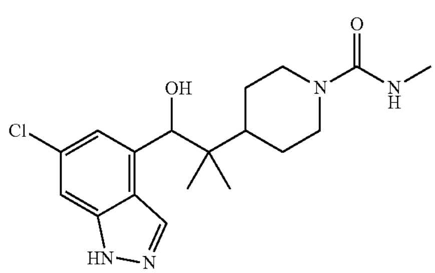 [SMILES: CNC(=O)N1CCC(C(C)(C)C(O)c2cc(Cl)cc3[nH]ncc23)CC1] | 365.1 |
| P-0170 | N-(4-(5-chloro-1H-indazol-7-yl)-4-hydroxy-2-methylbutan-2-yl)propionamide | 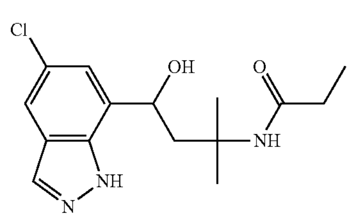 [SMILES: CCC(=O)NC(C)(C)CC(O)c1cc(Cl)cc2cn[nH]c12] | 310.1 |

TABLE 1-continued

| Compound Number | Compound Name | Compound Structure | (MH)+ |
|---|---|---|---|
| P-0171 | 1-(6-chloro-1H-indazol-4-yl)-2-methyl-2-(1-(methylsulfonyl)piperidin-4-yl)propan-1-ol | 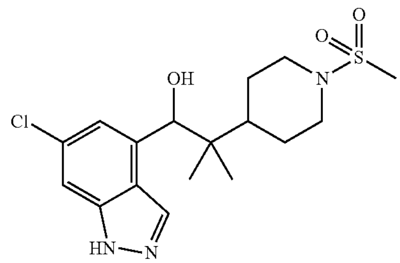 [SMILES: CC(C)(C1CCN(S(C)(=O)=O)CC1)C(O)c1cc(Cl)cc2[nH]ncc12] | 384.0 |
| P-0172 | 1-(4-(1-(6-chloro-1H-indazol-4-yl)-1-hydroxy-2-methylpropan-2-yl)piperidin-1-yl)ethan-1-one | 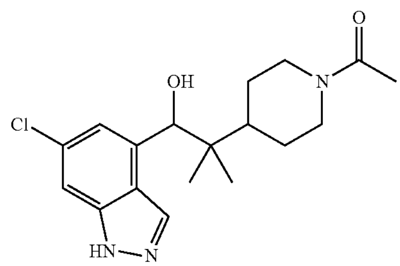 [SMILES: CC(=O)N1CCC(C(C)(C)C(O)c2cc(Cl)cc3[nH]ncc23)CC1] | 347.9 |
| P-0173 | (6-chloro-1H-indazol-4-yl)(cyclohexyl)methanol | 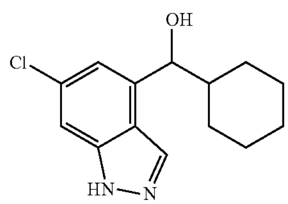 [SMILES: OC(c1cc(Cl)cc2[nH]ncc12)C1CCCCC1] | 265.0 |
| P-0174 | 1-(6-chloro-1H-indazol-4-yl)-2-methyl-2-(tetrahydro-2H-pyran-4-yl)propan-1-ol | 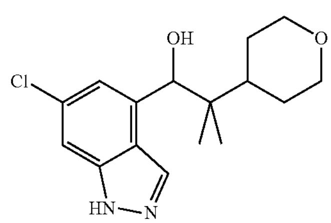 [SMILES: CC(C)(C1CCOCC1)C(O)c1cc(Cl)cc2[nH]ncc12] | 309.0 |
| P-0175 | 4-(1-(5-chloro-1H-indazol-7-yl)-1-hydroxy-2-methylpropan-2-yl)-N-(2,2,2-trifluoroethyl)piperidine-1-carboxamide | 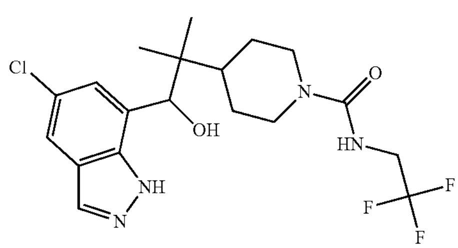 [SMILES: CC(C)(C1CCN(C(=O)NCC(F)(F)F)CC1)C(O)c1cc(Cl)cc2cn[nH]c12] | 433.3 |
| P-0176 | 4-(1-(5-chloro-1H-indazol-7-yl)-1-hydroxy-2-methylpropan-2-yl)-N-cyclopropylpiperidine-1-carboxamide | 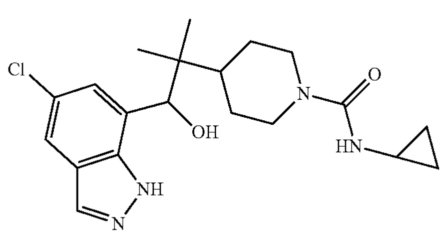 [SMILES: CC(C)(C1CCN(C(=O)NC2CC2)CC1)C(O)c1cc(Cl)cc2cn[nH]c12] | 391.3 |

TABLE 1-continued

| Compound Number | Compound Name | Compound Structure | (MH)+ |
|---|---|---|---|
| P-0177 | 2,2,2-trifluoroethyl 4-(1-(5-chloro-1H-indazol-7-yl)-1-hydroxy-2-methylpropan-2-yl)piperidine-1-carboxylate | 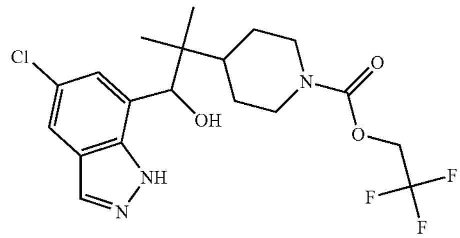 [SMILES: CC(C)(C1CCN(C(=O)OCC(F)(F)F)CC1)C(O)c1cc(Cl)cc2cn[nH]c12] | 434.2 |
| P-0178 | 4-(1-(5-chloro-1H-indazol-7-yl)-1-hydroxy-2-methylpropan-2-yl)-N-(2-fluorophenyl)piperidine-1-carboxamide | 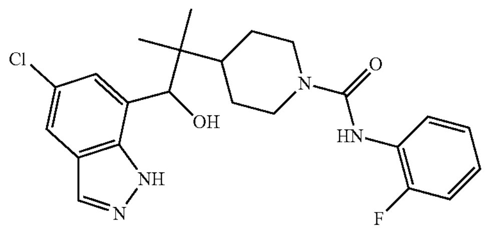 [SMILES: CC(C)(C1CCN(C(=O)Nc2ccccc2F)CC1)C(O)c1cc(Cl)cc2cn[nH]c12] | 445.3 |
| P-0179 | 4-(1-(5-chloro-1H-indazol-7-yl)-1-hydroxy-2-methylpropan-2-yl)-N-(2-methoxyphenyl)piperidine-1-carboxamide | 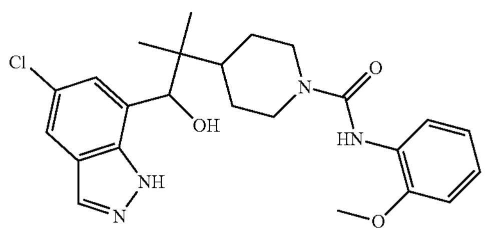 [SMILES: COc1ccccc1NC(=O)N1CCC(C(C)(C)C(O)c2cc(Cl)cc3cn[nH]c23)CC1] | 457.3 |
| P-0180 | 4-(1-(5-chloro-1H-indazol-7-yl)-1-hydroxy-2-methylpropan-2-yl)-N-(2-cyanophenyl)piperidine-1-carboxamide | 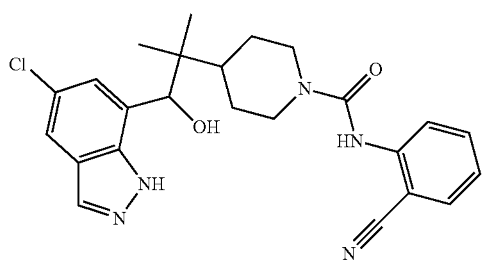 [SMILES: CC(C)(C1CCN(C(=O)Nc2ccccc2C#N)CC1)C(O)c1cc(Cl)cc2cn[nH]c12] | 451.9 |
| P-0181 | 4-(1-(5-chloro-1H-indazol-7-yl)-1-hydroxy-2-methylpropan-2-yl)-N-(m-tolyl)piperidine-1-carboxamide | 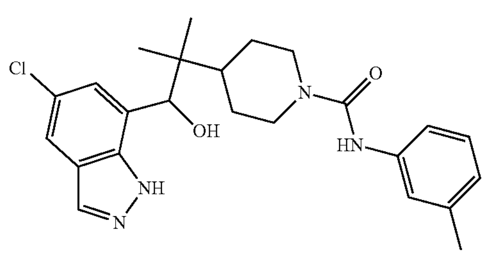 [SMILES: Cc1cccc(NC(=O)N2CCC(C(C)(C)C(O)c3cc(Cl)cc4cn[nH]c34)CC2)c1] | 441.1 |
| P-0182 | 4-(1-(5-chloro-1H-indazol-7-yl)-1-hydroxy-2-methylpropan-2-yl)-N-(3-methoxyphenyl)piperidine-1-carboxamide | 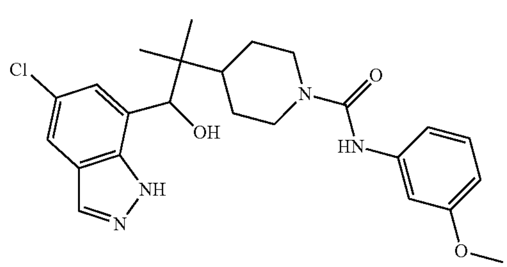 [SMILES: COc1cccc(NC(=O)N2CCC(C(C)(C)C(O)c3cc(Cl)cc4cn[nH]c34)CC2)c1] | 457.3 |

TABLE 1-continued

| Compound Number | Compound Name | Compound Structure | (MH)+ |
|---|---|---|---|
| P-0183 | 4-(1-(5-chloro-1H-indazol-7-yl)-1-hydroxy-2-methylpropan-2-yl)-N-(4-methoxyphenyl)piperidine-1-carboxamide | 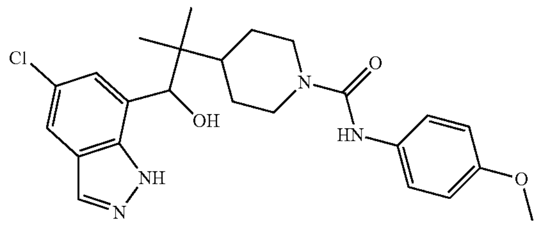 [SMILES: COc1ccc(NC(=O)N2CCC(C(C)(C)C(O)c3cc(Cl)cc4cn[nH]c34)CC2)cc1] | 457.3 |
| P-0184 | 4-(1-(5-chloro-1H-indazol-7-yl)-1-hydroxy-2-methylpropan-2-yl)-N-(2-chlorophenyl)piperidine-1-carboxamide | 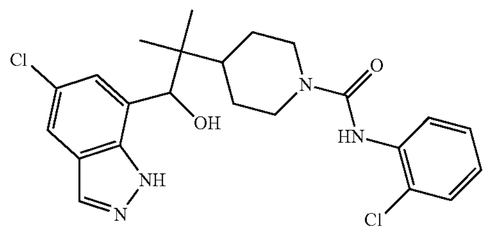 [SMILES: CC(C)(C1CCN(C(=O)Nc2ccccc2Cl)CC1)C(O)c1cc(Cl)cc2cn[nH]c12] | 461.2 |
| P-0185 | 4-(2-(5-chloro-1H-indazol-7-yl)-1,1-difluoro-2-hydroxyethyl)-N-cyclopropylpiperidine-1-carboxamide | 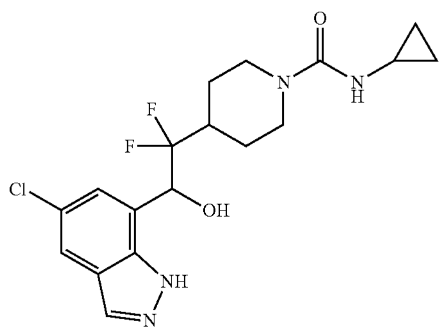 [SMILES: O=C(NC1CC1)N1CCC(C(F)(F)C(O)c2cc(Cl)cc3cn[nH]c23)CC1] | 399.1 |
| P-0186 | [1,1'-bi(cyclobutan)]-1-yl(5-chloro-1H-indazol-7-yl)methanol | 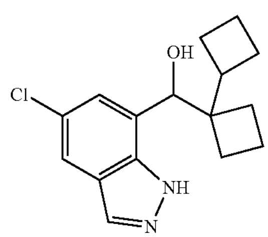 [SMILES: OC(c1cc(Cl)cc2cn[nH]c12)C1(C2CCC2)CCC1] | 291.3 |
| P-0187 | (5-chloro-1H-indazol-7-yl)(1-cyclohexylcyclopropyl)methanol | 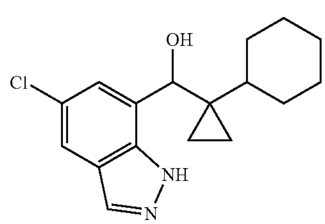 [SMILES: OC(c1cc(Cl)cc2cn[nH]c12)C1(C2CCCCC2)CC1] | 304.8 |
| P-0188 | (5-chloro-1H-indazol-7-yl)(1-(3-fluorobenzyl)cyclobutyl)methanol | 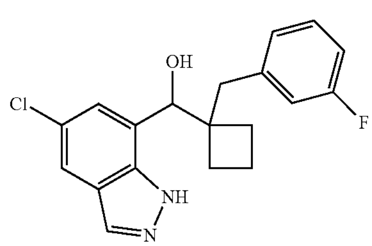 [SMILES: OC(c1cc(Cl)cc2cn[nH]c12)C1(Cc2cccc(F)c2)CCC1] | 344.7 |

TABLE 1-continued

| Number | Compound Name | Compound Structure | (MH)+ |
|---|---|---|---|
| P-0189 | 3-(5-chloro-1H-indazol-7-yl)-3-hydroxythietane 1,1-dioxide | 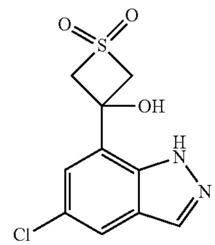 [SMILES: O=S1(=O)CC(O)(c2cc(Cl)cc3cn[nH]c23)C1] | 273.3 |
| P-0190 | (1S,5S)-3'-(5-chloro-1H-indazol-7-yl)-6,6-dimethylspiro[bicyclo3.1.1]heptane-2,1'-cyclobutan]-3'-ol | 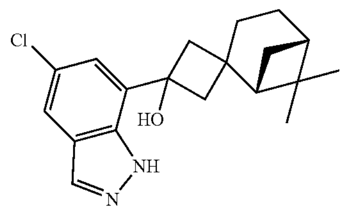 [SMILES: CC1(C)[C@H]2CCC3(CC(O)(c4cc(Cl)cc5cn[nH]c45)C3)[C@@H]1C2] | 329.0 |
| P-0191 | 1-(5-chloro-1H-indazol-7-yl)-2-methyl-2-(tetrahydro-2H-pyran-4-yl)propan-1-ol | 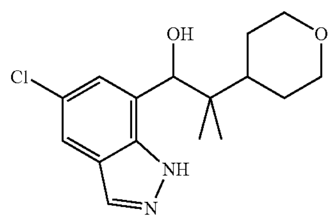 [SMILES: CC(C)(C1CCOCC1)C(O)c1cc(Cl)cc2cn[nH]c12] | 307.0 (MH)− |
| P-0192 | 1-(5-chloro-1H-indazol-7-yl)-2,2-difluoro-2-(tetrahydro-2H-pyran-4-yl)ethan-1-ol | 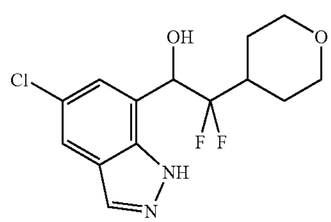 | 317.0 |
| P-0193 | (2s,3's)-3'-(5-chloro-1H-indazol-7-yl)-3,3-dimethylspiro[bicyclo[2.2.1]heptane-2,1'-cyclobutan]-3'-ol | 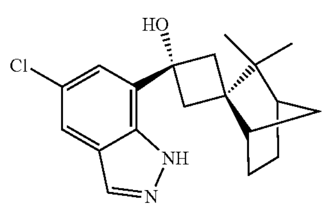 [SMILES: CC1(C)C2CCC(C2)[C@]12C[C@@](O)(c1cc(Cl)cc3cn[nH]c31)C2] | 331.0 |
| P-0194 | (5-chloro-1H-indazol-7-yl)(1-(difluoromethyl)cyclobutyl)methanol | 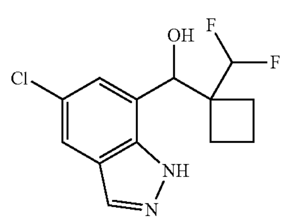 [SMILES: OC(c1cc(Cl)cc2cn[nH]c12)C1(C(F)F)CCC1] | 287.1 |
| P-0195 | (5-chloro-1H-indazol-7-yl)(spiro[3.3]heptan-2-yl)methanol | 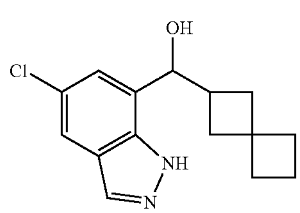 [SMILES: OC(c1cc(Cl)cc2cn[nH]c12)C1CC2(CCC2)C1] | 276.9 |

TABLE 1-continued

| Number | Compound Name | Compound Structure | (MH)+ |
|---|---|---|---|
| P-0196 | (5-chloro-1H-indazol-7-yl)(3,3-dimethylcyclobutyl)methanol | 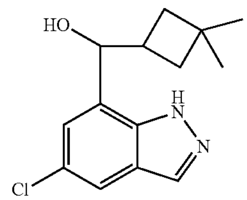 [SMILES: CC1(C)CC(C(O)c2cc(Cl)cc3cn[nH]c23)C1] | 264.9 |
| P-0197 | (5-chloro-1H-indazol-7-yl)(4-(hydroxymethyl)cyclohexyl)methanol | 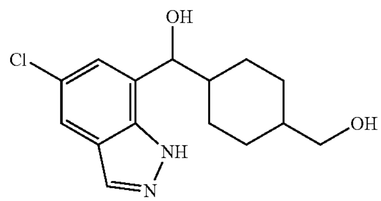 [SMILES: OCC1CCC(C(O)c2cc(Cl)cc3cn[nH]c23)CC1] | 292.9 (MH)− |
| P-0198 | 1-(5-chloro-1H-indazol-7-yl)-2-methyl-2-(1-(methylsulfonyl)piperidin-4-yl)propan-1-ol | 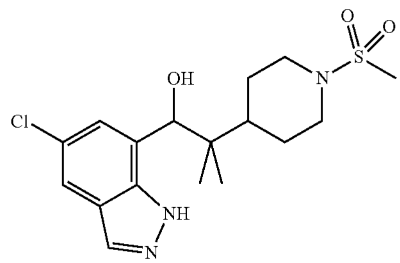 [SMILES: CC(C)(C1CCN(S(C)(=O)=O)CC1)C(O)c1cc(Cl)cc2cn[nH]c12] | 386.1 |
| P-0199 | 1-(5-chloro-1H-indazol-7-yl)-2-cyclopentyl-2-methylpropan-1-ol | 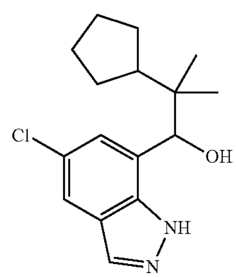 [SMILES: CC(C)(C1CCCC1)C(O)c1cc(Cl)cc2cn[nH]c12] | 292.8 |
| P-0201 | 1-(5-chloro-1H-indazol-7-yl)-3-phenylcyclobutan-1-ol | 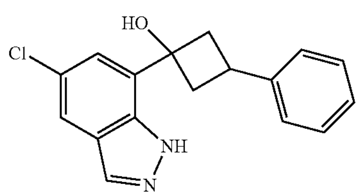 [SMILES: OC1(c2cc(Cl)cc3cn[nH]c23)CC(c2ccccc2)C1] | 299.1 |
| P-0202 | 1-(5-chloro-1H-indazol-7-yl)-2,2-dimethyl-3-(pyrrolidin-1-yl)propan-1-ol | 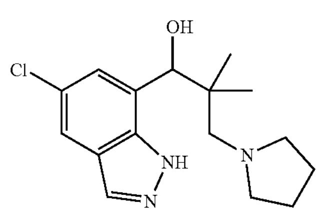 [SMILES: CC(C)(CN1CCCC1)C(O)c1cc(Cl)cc2cn[nH]c12] | 308.4 |
| P-0203 | 1-(5-chloro-1H-indazol-7-yl)-2,2-dicyclobutylethan-1-ol | 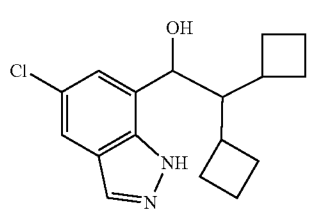 [SMILES: OC(c1cc(Cl)cc2cn[nH]c12)C(C1CCC1)C1CCC1] | 305.1 |

TABLE 1-continued

| Compound Number | Compound Name | Compound Structure | (MH)+ |
|---|---|---|---|
| P-0204 | 1-(5-chloro-1H-indazol-7-yl)-2,2-dicyclopropylethan-1-ol | 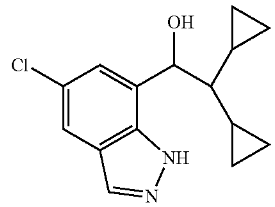 [SMILES: OC(c1cc(Cl)cc2cn[nH]c12)C(C1CC1)C1CC1] | 277.2 |
| P-0205 | 1-(5-chloro-1H-indazol-7-yl)-1-cyclopentylethan-1-ol | 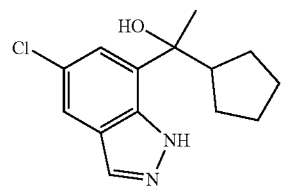 [SMILES: CC(O)(c1cc(Cl)cc2cn[nH]c12)C1CCCC1] | 264.6 |
| P-0206 | 1-(5-chloro-1H-indazol-7-yl)cyclobutan-1-ol | 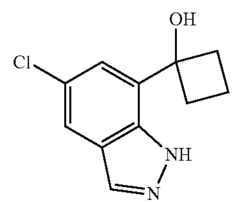 [SMILES: OC1(c2cc(Cl)cc3cn[nH]c23)CCC1] | 223.1 |
| P-0207 | (6-chloro-1H-indazol-7-yl)(1-methylcyclohexyl)methanol | 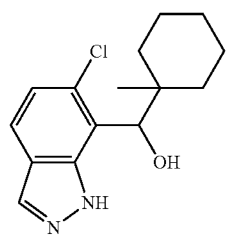 [SMILES: CC1(C(O)c2c(Cl)ccc3cn[nH]c23)CCCCC1] | 279.1 |
| P-0208 | bicyclo[2.2.2]octan-1-yl(5-chloro-1H-indazol-7-yl)methanol | 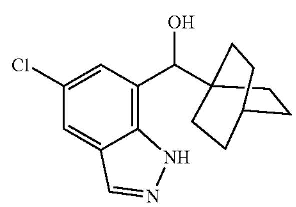 [SMILES: OC(c1cc(Cl)cc2cn[nH]c12)C12CCC(CC1)CC2] | 291.0 |
| P-0209 | bicyclo[1.1.1]pentan-1-yl(5-chloro-1H-indazol-7-yl)methanol | 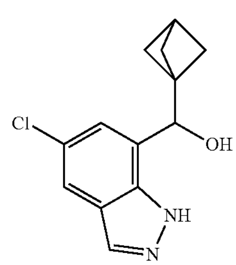 [SMILES: OC(c1cc(Cl)cc2cn[nH]c12)C12CC(C1)C2] | 249.0 |
| P-0210 | 1-(5-chloro-1H-indazol-7-yl)-2-(tetrahydro-2H-pyran-4-yl)ethan-1-ol | 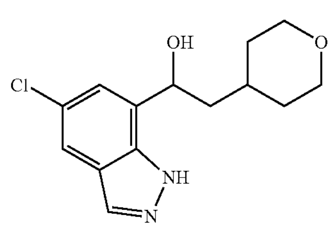 [SMILES: OC(CC1CCOCC1)c1cc(Cl)cc2cn[nH]c12] | 278.9 (MH)− |

TABLE 1-continued

| Compound Number | Compound Name | Compound Structure | (MH)+ |
|---|---|---|---|
| P-0211 | (5-chloro-1H-indazol-7-yl)(3-methyloxetan-3-yl)methanol | 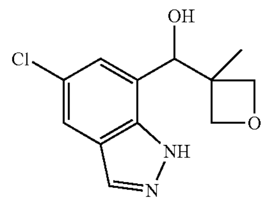 [SMILES: CC1(C(O)c2cc(Cl)cc3cn[nH]c23)COC1] | 252.9 |
| P-0212 | 1-(5-chloro-1H-indazol-7-yl)-2,2-dimethylpropan-1-ol | 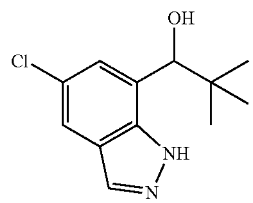 [SMILES: CC(C)(C)C(O)c1cc(Cl)cc2cn[nH]c12] | 239.1 |
| P-0213 | 5-(5-chloro-1H-indazol-7-yl)-5-hydroxy-4,4-dimethylpentanenitrile | 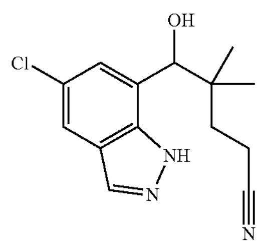 [SMILES: CC(C)(CCC#N)C(O)c1cc(Cl)cc2cn[nH]c12] | 278.1 |
| P-0214 | 3-(tert-butyl)-1-(5-chloro-1H-indazol-7-yl)cyclobutan-1-ol | 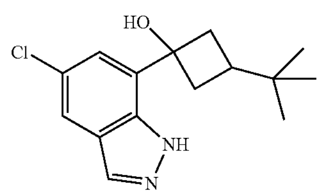 [SMILES: CC(C)(C)C1CC(O)(c2cc(Cl)cc3cn[nH]c23)C1] | 279.0 |
| P-0215 | 1-(5-chloro-1H-indazol-7-yl)-2-methyl-2-morpholinopropan-1-ol | 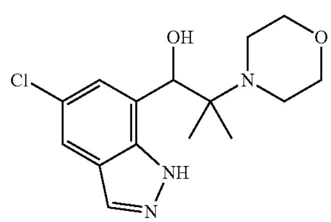 [SMILES: CC(C)(C(O)c1cc(Cl)cc2cn[nH]c12)N1CCOCC1] | 310.0 |
| P-0216 | 1-(5-chloro-1H-indazol-7-yl)-2-methyl-2-(piperidin-1-yl)propan-1-ol | 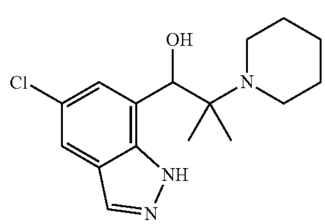 [SMILES: CC(C)(C(O)c1cc(Cl)cc2cn[nH]c12)N1CCCCC1] | 308.2 |
| P-0217 | 1-(5-chloro-4-fluoro-1H-indazol-7-yl)-2-methyl-2-(tetrahydro-2H-pyran-4-yl)propan-1-ol | 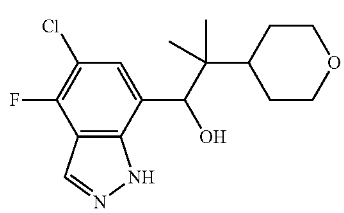 [SMILES: CC(C)(C1CCOCC1)C(O)c1cc(Cl)c(F)c2cn[nH]c12] | 324.9 |

TABLE 1-continued

| Number | Compound Name | Compound Structure | (MH)+ |
|---|---|---|---|
| P-0218 | 1-(5-chloro-4-fluoro-1H-indazol-7-yl)-2,2-difluoro-2-(tetrahydro-2H-pyran-4-yl)ethan-1-ol | 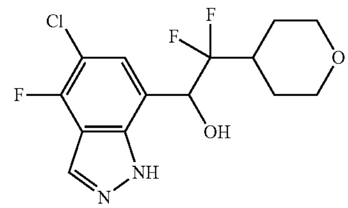 [SMILES: OC(c1cc(Cl)c(F)c2cn[nH]c12)C(F)(F)C1CCOCC1] | 335.1 |
| P-0219 | 4-((5-chloro-1H-indazol-7-yl)(hydroxy)methyl)cyclohexane-1-carboxylic acid | 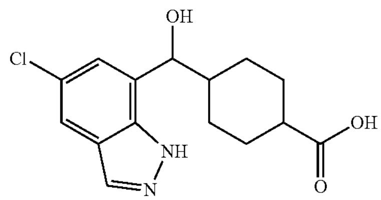 [SMILES: O=C(O)C1CCC(C(O)c2cc(Cl)cc3cn[nH]c23)CC1] | 306.9 ((MH)−) |
| P-0220 | 1-(5,6-dichloro-1H-indazol-7-yl)-2-methyl-2-(tetrahydro-2H-pyran-4-yl)propan-1-ol | 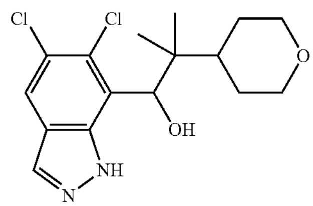 [SMILES: CC(C)(C1CCOCC1)C(O)c1c(Cl)c(Cl)cc2cn[nH]c12] | 343.1 |
| P-0221 | (5-chloro-1H-indazol-7-yl)(1-(tetrahydro-2H-pyran-4-yl)cyclopropyl)methanol | 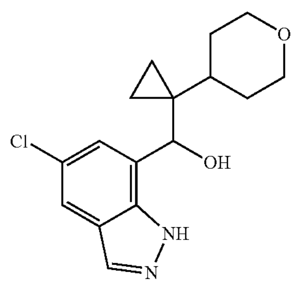 [SMILES: OC(c1cc(Cl)cc2cn[nH]c12)C1(C2CCOCC2)CC1] | 307.2 |
| P-0222 | 1-(5-chloro-1H-indazol-7-yl)-3,3-bis(1,1-difluoroethyl)cyclobutan-1-ol | 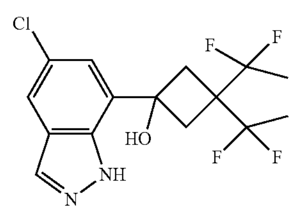 [SMILES: CC(F)(F)C1(C(C)(F)F)CC(O)(c2cc(Cl)cc3cn[nH]c23)C1] | 351.0 |
| P-0223 | (5-chloro-1H-indazol-7-yl)(1-ethylcyclobutyl)methanol | 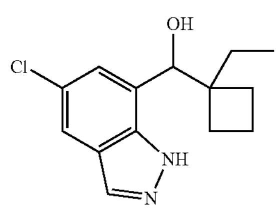 [SMILES: CCC1(C(O)c2cc(Cl)cc3cn[nH]c23)CCC1] | 264.9 |
| P-0224 | 1-(5-chloro-1H-indazol-7-yl)-2-cyclopropyl-2-methylpropan-1-ol | 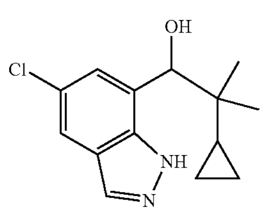 [SMILES: CC(C)(C1CC1)C(O)c1cc(Cl)cc2cn[nH]c12] | 264.9 |

TABLE 1-continued

| Compound Number | Compound Name | Compound Structure | (MH)+ |
|---|---|---|---|
| P-0225 | [1,1'-bi(cyclopropan)]-1-yl(5-chloro-1H-indazol-7-yl)methanol | 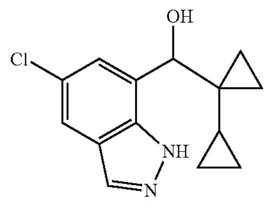 [SMILES: OC(c1cc(Cl)cc2cn[nH]c12)C1(C2CC2)CC1] | 263.1 |
| P-0226 | (5-chloro-1H-indazol-7-yl)(1-(methylsulfonyl)azetidin-3-yl)methanol | 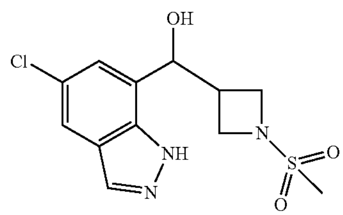 [SMILES: CS(=O)(=O)N1CC(C(O)c2cc(Cl)cc3cn[nH]c23)C1] | 315.9 |
| P-0227 | (5-chloro-1H-indazol-7-yl)(4-fluorobicyclo[2.2.2]octan-1-yl)methanol | 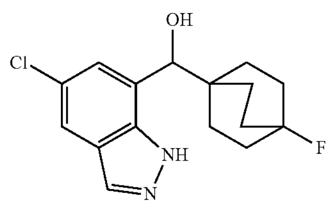 [SMILES: OC(c1cc(Cl)cc2cn[nH]c12)C12CCC(F)(CC1)CC2] | 309.0 |
| P-0228 | (5-chloro-1H-indazol-7-yl)(3-methylbicyclo[3.1.0]hexan-3-yl)methanol | 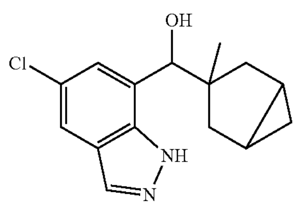 [SMILES: CC1(C(O)c2cc(Cl)cc3cn[nH]c23)CC2CC2C1] | 277.2 |
| P-0229 | bicyclo[2.2.1]heptan-1-yl(5-chloro-1H-indazol-7-yl)methanol | 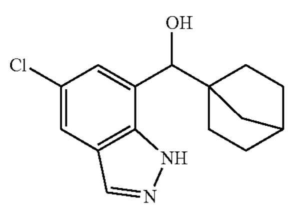 [SMILES: OC(c1cc(Cl)cc2cn[nH]c12)C12CCC(CC1)C2] | 277.2 |
| P-0230 | 1-(5-chloro-1H-indazol-7-yl)-2-(dimethylamino)-2-methylpropan-1-ol | 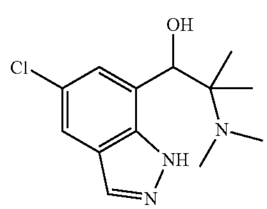 [SMILES: CN(C)C(C)(C)C(O)c1cc(Cl)cc2cn[nH]c12] | 268.2 |
| P-0231 | 1-(5-chloro-1H-indazol-7-yl)-2-methyl-2-(pyrrolidin-1-yl)propan-1-ol | 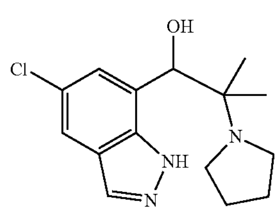 [SMILES: CC(C)(C(O)c1cc(Cl)cc2cn[nH]c12)N1CCCC1] | 294.0 |

TABLE 1-continued

| Compound Number | Compound Name | Compound Structure | (MH)+ |
|---|---|---|---|
| P-0232 | 1-(5-chloro-6-fluoro-1H-indazol-7-yl)-2-methyl-2-(tetrahydro-2H-pyran-4-yl)propan-1-ol | 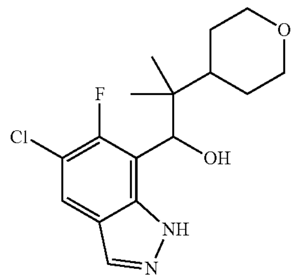 [SMILES: CC(C)(C1CCOCC1)C(O)c1c(F)c(Cl)cc2cn[nH]c12] | 327.1 |
| P-0233 | 3-amino-1-(5-chloro-1H-indazol-7-yl)-3-methylbutan-1-ol | 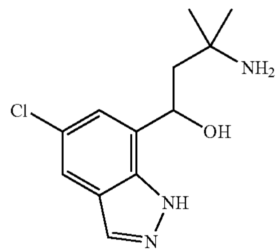 [SMILES: CC(C)(N)CC(O)c1cc(Cl)cc2cn[nH]c12] | 254.1 |
| P-0234 | 2-methyl-1-(6-methyl-1H-indazol-7-yl)-2-(tetrahydro-2H-pyran-4-yl)propan-1-ol | 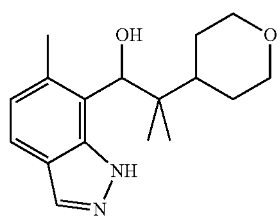 [SMILES: Cc1ccc2cn[nH]c2c1C(O)C(C)(C)C1CCOCC1] | 327.1 |
| P-0235 | (5-chloro-6-fluoro-1H-indazol-7-yl)(1-(tetrahydro-2H-pyran-4-yl)cyclopropyl)methanol | 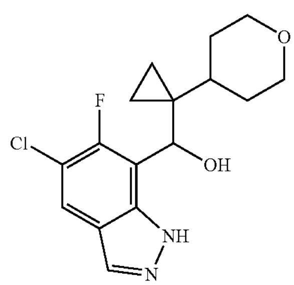 [SMILES: OC(c1c(F)c(Cl)cc2cn[nH]c12)C1(C2CCOCC2)CC1] | 322.9 (MH)− |
| P-0236 | (5-chloro-1H-indazol-7-yl)(4-methyltetrahydro-2H-pyran-4-yl)methanol | 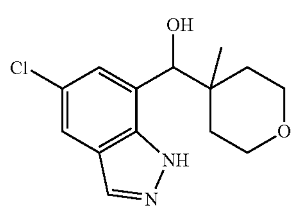 [SMILES: CC1(C(O)c2cc(Cl)cc3cn[nH]c23)CCOCC1] | 281.4 |
| P-0237 | cyclobutyl(5,6-dichloro-1H-indazol-7-yl)methanol | 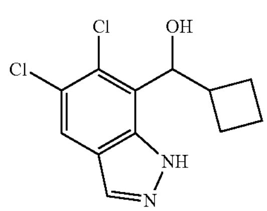 [SMILES: OC(c1c(Cl)c(Cl)cc2cn[nH]c12)C1CCC1] | 271.2 |

TABLE 1-continued

| Compound Number | Compound Name | Compound Structure | (MH)+ |
|---|---|---|---|
| P-0238 | (1-cyclohexylcyclopropyl)(5,6-dichloro-1H-indazol-7-yl)methanol | 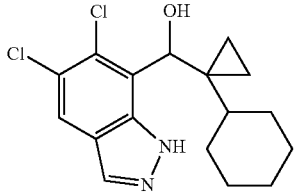 [SMILES: OC(c1c(Cl)c(Cl)cc2cn[nH]c12)C1(C2CCCCC2)CC1] | 339.0 |
| P-0239 | 1-(5,6-dichloro-1H-indazol-7-yl)-2,2-dimethylpropan-1-ol | 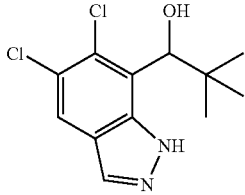 [SMILES: CC(C)(C)C(O)c1c(Cl)c(Cl)cc2cn[nH]c12] | 273.0 |
| P-0240 | bicyclo[2.2.1]heptan-2-yl(5-chloro-1H-indazol-7-yl)methanol | 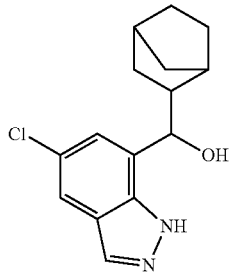 [SMILES: OC(c1cc(Cl)cc2cn[nH]c12)C1CC2CCC1C2] | 277.1 |
| P-0243 | 6-(5-chloro-1H-indazol-7-yl)-1,1,3,3-tetramethyl-2-oxaspiro[3.3]heptan-6-ol | 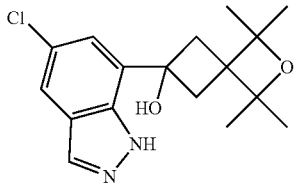 [SMILES: CC1(C)OC(C)(C)C12CC(O)(c1cc(Cl)cc3cn[nH]c13)C2] | 321.0 |
| P-0244 | 1-(5-chloro-1H-indazol-7-yl)-2-methyl-2-(tetrahydro-2H-pyran-4-yl)propan-1-d-1-ol | 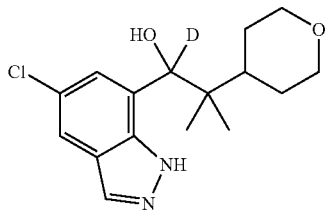 [SMILES: [2H]C(O)(c1cc(Cl)cc2cn[nH]c12)C(C)(C)C1CCOCC1] | 307.9 |
| P-0246 | (5-chloro-4,6-difluoro-1H-indazol-7-yl)(cyclobutyl)methanol | 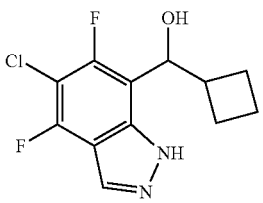 [SMILES: OC(c1c(F)c(Cl)c(F)c2cn[nH]c12)C1CCC1] | 273.3 |
| P-0247 | (5-chloro-4,6-difluoro-1H-indazol-7-yl)(1-cyclohexylcyclopropyl)methanol | 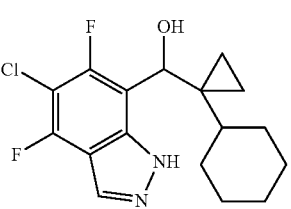 [SMILES: OC(c1c(F)c(Cl)c(F)c2cn[nH]c12)C1(C2CCCCC2)CC1] | 341.1 |

TABLE 1-continued

| Number | Compound Name | Compound Structure | (MH)+ |
|---|---|---|---|
| P-0248 | 1-(5-chloro-4,6-difluoro-1H-indazol-7-yl)-2,2-dimethylpropan-1-ol | 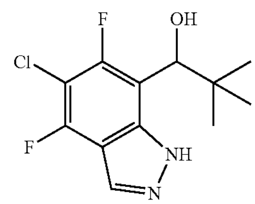 [SMILES: CC(C)(C)C(O)c1c(F)c(Cl)c(F)c2cn[nH]c12] | 275.1 |
| P-0249 | (1s,5s)-3'-(5-chloro-4,6-difluoro-1H-indazol-7-yl)spiro[bicyclo[3.3.1]nonane-9,1'-cyclobutan]-3'-ol | 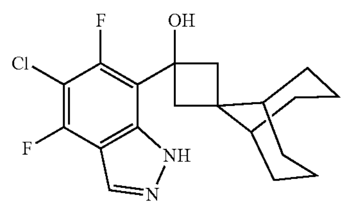 [SMILES: OC1(c2c(F)c(Cl)c(F)c3cn[nH]c23)CC2(C1)C1CCCC2CCC1] | 367.2 |
| P-0250 | 1-(5-chloro-1H-indazol-7-yl)-3,3,3-trifluoro-2,2-dimethylpropan-1-ol | 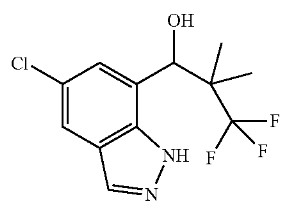 [SMILES: CC(C)(C(O)c1cc(Cl)cc2cn[nH]c12)C(F)(F)F] | 293.1 |
| P-0251 | 1-(5-chloro-4,6-difluoro-1H-indazol-7-yl)-2-cyclobutyl-2-methylpropan-1-ol | 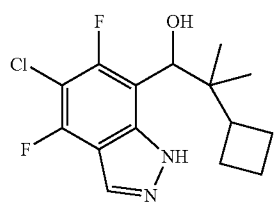 [SMILES: CC(C)(C1CCC1)C(O)c1c(F)c(Cl)c(F)c2cn[nH]c12] | 315.0 |
| P-0252 | 1-(5-chloro-4,6-difluoro-1H-indazol-7-yl)-2-cyclopentyl-2-methylpropan-1-ol | 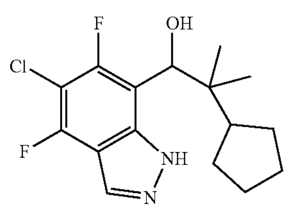 [SMILES: CC(C)(C1CCCC1)C(O)c1c(F)c(Cl)c(F)c2cn[nH]c12] | 329.1 |
| P-0253 | 1-(5-chloro-4,6-difluoro-1H-indazol-7-yl)-2-cyclohexyl-2-methylpropan-1-ol | 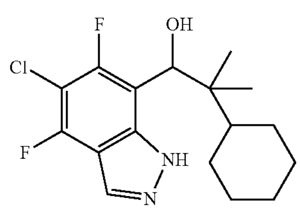 [SMILES: CC(C)(C1CCCCC1)C(O)c1c(F)c(Cl)c(F)c2cn[nH]c12] | 342.9 |
| P-0254 | 1-(5-chloro-1H-indazol-7-yl)-2,2-dimethyl-3-(tetrahydro-2H-pyran-4-yl)propan-1-ol | 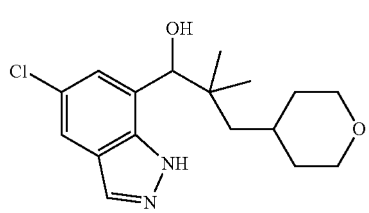 [SMILES: CC(C)(CC1CCOCC1)C(O)c1cc(Cl)cc2cn[nH]c12] | 323.4 |

TABLE 1-continued

| Compound Number | Compound Name | Compound Structure | (MH)+ |
|---|---|---|---|
| P-0255 | 1-(5-chloro-1H-indazol-7-yl)-2-ethyl-2-methylbutan-1-ol | 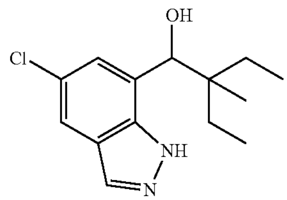 [SMILES: CCC(C)(CC)C(O)c1cc(Cl)cc2cn[nH]c12] | 267.3 |
| P-0256 | 4-((5-chloro-1H-indazol-7-yl)(hydroxy)methyl)-4-ethylhexanenitrile | 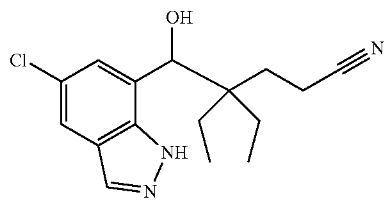 [SMILES: CCC(CC)(CCC#N)C(O)c1cc(Cl)cc2cn[nH]c12] | 306.3 |
| P-0257 | ((1S,3s)-adamantan-1-yl)(5-chloro-6-fluoro-1H-indazol-7-yl)methanol | 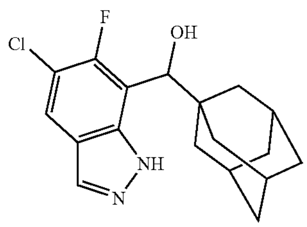 [SMILES: OC(c1c(F)c(Cl)cc2cn[nH]c12)C12CC3CC(CC(C3)C1)C2] | 334.9 |
| P-0258 | bicyclo[2.2.1]heptan-2-yl(5-chloro-6-fluoro-1H-indazol-7-yl)methanol | 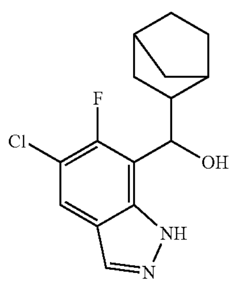 [SMILES: OC(c1c(F)c(Cl)cc2cn[nH]c12)C1CC2CCC1C2] | 292.9 (MH)− |
| P-0259 | 1-(5-chloro-1H-indazol-7-yl)-2,2-dicyclopropylpropan-1-ol | 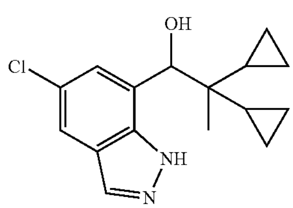 [SMILES: CC(C1CC1)(C1CC1)C(O)c1cc(Cl)cc2cn[nH]c12] | 291.0 |
| P-0260 | 1-(5-chloro-6-fluoro-1H-indazol-7-yl)-2,2-dicyclopropylpropan-1-ol | 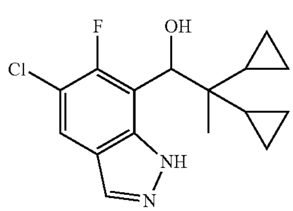 [SMILES: CC(C1CC1)(C1CC1)C(O)c1c(F)c(Cl)cc2cn[nH]c12] | 307.0 |

TABLE 1-continued

| Compound Number | Compound Name | Compound Structure | (MH)+ |
|---|---|---|---|
| P-0261 | 1-(5-chloro-6-fluoro-1H-indazol-7-yl)-2-methyl-2-(1-(methylsulfonyl)piperidin-4-yl)propan-1-ol | 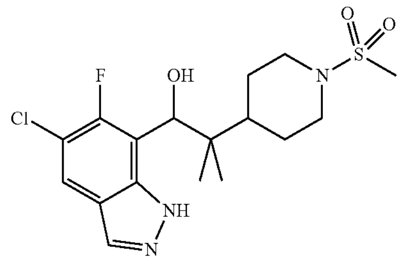 [SMILES: CC(C)(C1CCN(S(C)(=O)=O)CC1)C(O)c1c(F)c(Cl)cc2cn[nH]c12] | 404.0 |
| P-0262 | 1-(5-chloro-6-fluoro-1H-indazol-7-yl)-2,2-difluoro-2-(tetrahydro-2H-pyran-4-yl)ethan-1-ol | 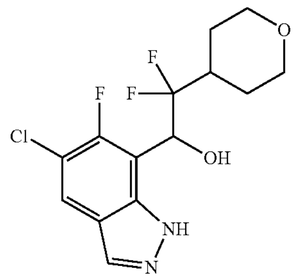 [SMILES: OC(c1c(F)c(Cl)cc2cn[nH]c12)C(F)(F)C1CCOCC1] | 335.1 |
| P-0263 | (5-bromo-1H-indazol-7-yl)(1-methylcyclohexyl)methanol | 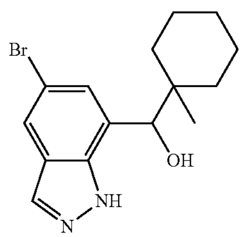 [SMILES: CC1(C(O)c2cc(Br)cc3cn[nH]c23)CCCCC1] | 323.1 |
| P-0264 | (5-chloro-4,6-difluoro-1H-indazol-7-yl)(1-methylcyclobutyl)methanol | 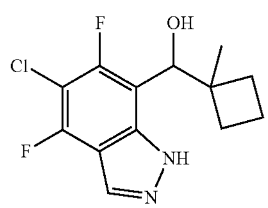 [SMILES: CC1(C(O)c2c(F)c(Cl)c(F)c3cn[nH]c23)CCC1] | 287.1 |
| P-0265 | (5-chloro-4,6-difluoro-1H-indazol-7-yl)(1-(trifluoromethyl)cyclobutyl)methanol | 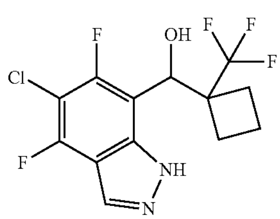 [SMILES: OC(c1c(F)c(Cl)c(F)c2cn[nH]c12)C1(C(F)(F)F)CCC1] | 341.1 |
| P-0266 | (5-chloro-1H-indazol-7-yl)(1-(phenylsulfonyl)cyclopropyl)methanol | 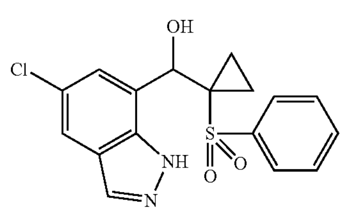 [SMILES: O=S(=O)(c1ccccc1)C1(C(O)c2cc(Cl)cc3cn[nH]c23)CC1] | 363.3 |

TABLE 1-continued

| Compound Number | Compound Name | Compound Structure | (MH)+ |
|---|---|---|---|
| P-0267 | 1-(5-chloro-1H-indazol-7-yl)-2,2-diethylbutan-1-ol | 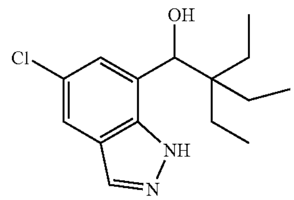 [SMILES: CCC(CC)(CC)C(O)c1cc(Cl)cc2cn[nH]c12] | 281.1 |
| P-0268 | 1-(5-chloro-1H-indazol-7-yl)-2-ethylbutan-1-ol | 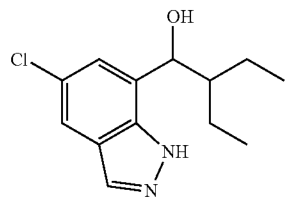 [SMILES: CCC(CC)C(O)c1cc(Cl)cc2cn[nH]c12] | 253.2 |
| P-0269 | (5-chloro-1H-indazol-7-yl)(4-(difluoromethyl)bicyclo[2.2.2]octan-1-yl)methanol | 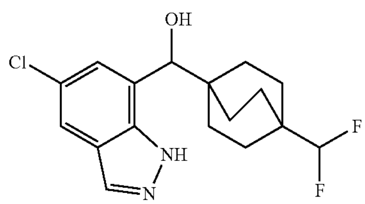 [SMILES: OC(c1cc(Cl)cc2cn[nH]c12)C12CCC(C(F)F)(CC1)CC2] | 359.1 |
| P-0270 | 1-(5-chloro-1H-indazol-7-yl)-2,2-difluoro-2-(1-(methylsulfonyl)piperidin-4-yl)ethan-1-ol | 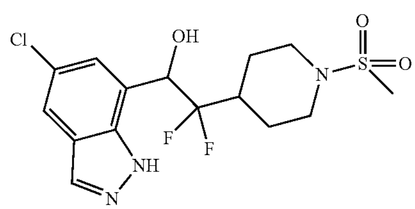 [SMILES: CS(=O)(=O)N1CCC(C(F)(F)C(O)c2cc(Cl)cc3cn[nH]c23)CC1] | 393.9 |
| P-0271 | 1-(5-chloro-1H-indazol-7-yl)-2-methyl-2-((1R,3r,5S)-8-(methylsulfonyl)-8-azabicyclo[3.2.1]octan-3-yl)propan-1-ol | 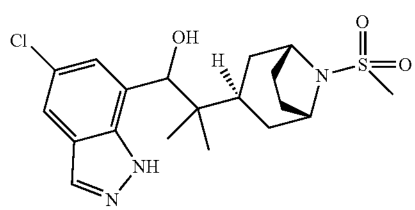 [SMILES: CC(C)(C(O)c1cc(Cl)cc2cn[nH]c12)[C@H]1C[C@H]2CC[C@@H](C1)N2S(C)(=O)=O] | 412.0 |
| P-0272 | 1-(5-chloro-1H-indazol-7-yl)-2-methyl-2-((1R,3s,5S)-8-(methylsulfonyl)-8-azabicyclo[3.2.1]octan-3-yl)propan-1-ol | 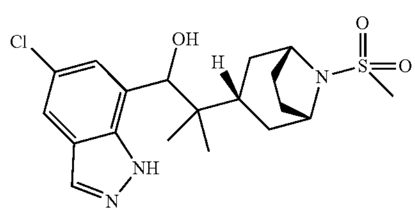 [SMILES: CC(C)(C(O)c1cc(Cl)cc2cn[nH]c12)[C@@H]1C[C@H]2CC[C@@H](C1)N2S(C)(=O)=O] | 412.0 |
| P-0273 | tert-butyl 8-(2-(5-chloro-1H-indazol-7-yl)-2-hydroxyethyl)-3-azabicyclo[3.2.1]octane-3-carboxylate | 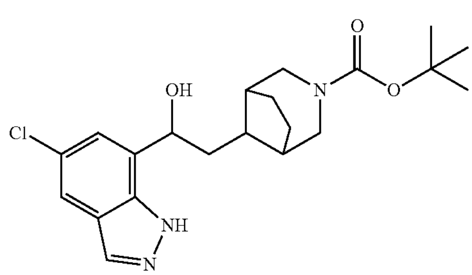 [SMILES: CC(C)(C)OC(=O)N1CC2CCC(C1)C2CC(O)c1cc(Cl)cc2cn[nH]c12] | 406.0 |

TABLE 1-continued

| Number | Compound Name | Compound Structure | (MH)+ |
|---|---|---|---|
| P-0274 | 2-(3-azabicyclo[3.2.1]octan-8-yl)-1-(5-chloro-1H-indazol-7-yl)ethan-1-ol | 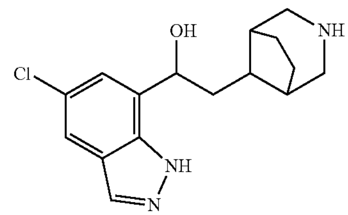 [SMILES: OC(CC1C2CCC1CNC2)c1cc(Cl)cc2cn[nH]c12] | 306.1 |
| P-0275 | 1-(5,6-dihydro-1H-cyclobuta[f]indazol-7-yl)-2,2-difluoro-2-(tetrahydro-2H-pyran-4-yl)ethan-1-one | 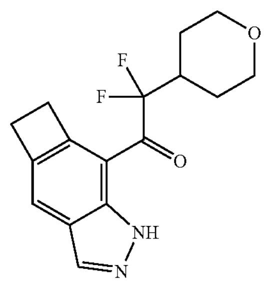 [SMILES: O=C(c1c2c(cc3cn[nH]c13)CC2)C(F)(F)C1CCOCC1] | 307.1 |
| P-0276 | 1-(5-chloro-1H-indazol-7-yl)-2-(1-(ethylsulfonyl)piperidin-4-yl)-2,2-difluoroethan-1-ol | 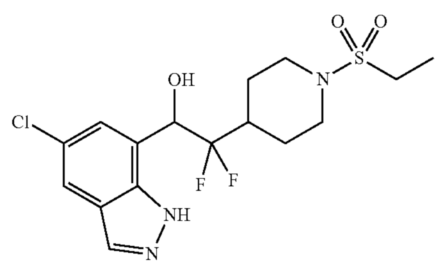 [SMILES: CCS(=O)(=O)N1CCC(C(F)(F)C(O)c2cc(Cl)cc3cn[nH]c23)CC1] | 405.9 (MH)− |
| P-0277 | (5,6-dihydro-1H-cyclobuta[f]indazol-7-yl)(1-(tetrahydro-2H-pyran-4-yl)cyclopropyl)methanol | 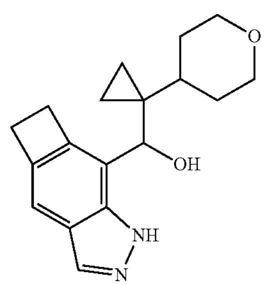 [SMILES: OC(c1c2c(cc3cn[nH]c13)CC2)C1(C2CCOCC2)CC1] | 299.1 |
| P-0278 | 1-(5,6-dihydro-1H-cyclobuta[f]indazol-7-yl)-2,2-difluoro-2-(tetrahydro-2H-pyran-4-yl)ethan-1-ol | 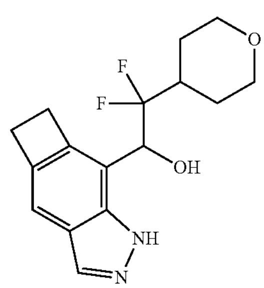 [SMILES: OC(c1c2c(cc3cn[nH]c13)CC2)C(F)(F)C1CCOCC1] | 309.1 |
| P-0279 | bicyclo[2.2.2]octan-1-yl(5,6-dihydro-1H-cyclobuta[f]indazol-7-yl)methanol | 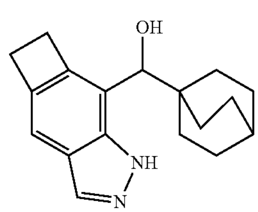 [SMILES: OC(c1c2c(cc3cn[nH]c13)CC2)C12CCC(CC1)CC2] | 283.0 |

TABLE 1-continued

| Compound Number | Compound Name | Compound Structure | (MH)+ |
|---|---|---|---|
| P-0280 | 1-(5,6-dihydro-1H-cyclobuta[f]indazol-7-yl)-2-methyl-2-(1-(methylsulfonyl)piperidin-4-yl)propan-1-ol | 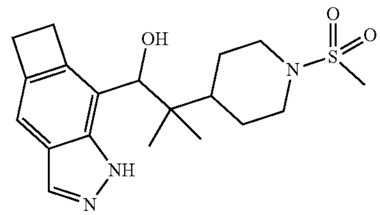 [SMILES: CC(C)(C1CCN(S(C)(=O)=O)CC1)C(O)c1c2c(cc3cn[nH]c13)CC2] | 378.1 |
| P-0281 | 1-(8-(2-(5-chloro-1H-indazol-7-yl)-2-hydroxyethyl)-3-azabicyclo[3.2.1]octan-3-yl)ethan-1-one | 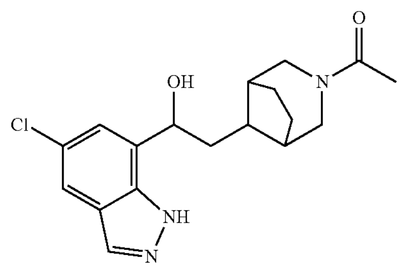 [SMILES: CC(=O)N1CC2CCC(C1)C2CC(O)c1cc(Cl)cc2cn[nH]c12] | 348.1 |
| P-0282 | 1-(5-chloro-1H-indazol-7-yl)-2-(3-(methylsulfonyl)-3-azabicyclo[3.2.1]octan-8-yl)ethan-1-ol | 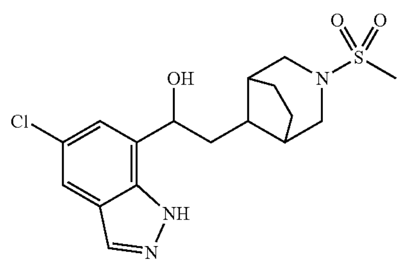 [SMILES: CS(=O)(=O)N1CC2CCC(C1)C2CC(O)c1cc(Cl)cc2cn[nH]c12] | 381.9 (MH)– |
| P-0283 | (5-chloro-1H-indazol-7-yl)(1-(methylsulfonyl)piperidin-4-yl)methanol | 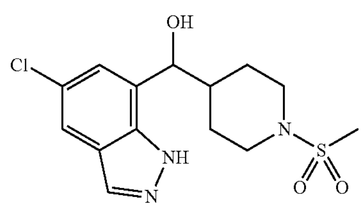 [SMILES: CS(=O)(=O)N1CCC(C(O)c2cc(Cl)cc3cn[nH]c23)CC1] | 341.9 (MH)– |
| P-0284 | 1-(6-fluoro-1H-indazol-7-yl)-2-methyl-2-(1-(methylsulfonyl)piperidin-4-yl)propan-1-ol | 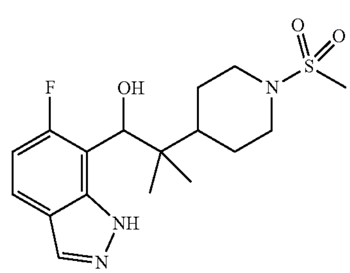 [SMILES: CC(C)(C1CCN(S(C)(=O)=O)CC1)C(O)c1c(F)ccc2cn[nH]c12] | 370.0 |
| P-0285 | 1-(5-chloro-6-fluoro-1H-indazol-7-yl)-2-methyl-2-((1R,3r,5S)-8-(methylsulfonyl)-8-azabicyclo[3.2.1]octan-3-yl)propan-1-ol | 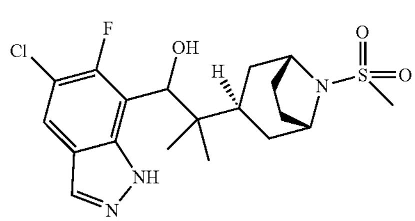 [SMILES: CC(C)(C(O)c1c(F)c(Cl)cc2cn[nH]c12)[C@H]1C[C@H]2CC[C@@H](C1)N2S(C)(=O)=O] | 430.0 |

TABLE 1-continued

| Number | Compound Name | Compound Structure | (MH)+ |
|---|---|---|---|
| P-0286 | (5-chloro-1H-indazol-7-yl)(4-methyl-1-(methylsulfonyl)piperidin-4-yl)methanol | 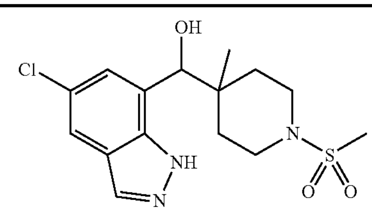 | 355.9 (MH)– |
| P-0287 | (5,6-dichloro-1H-indazol-7-yl)(1-methylcyclohexyl)methanol | 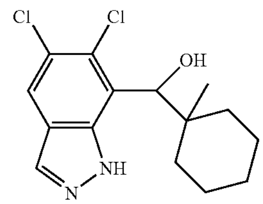 [SMILES: CC1(C(O)c2c(Cl)c(Cl)cc3cn[nH]c23)CCCCC1] | 313.2 |
| P-0288 | 1-(5-chloro-6-fluoro-1H-indazol-7-yl)-2,2-difluoro-2-(1-(methylsulfonyl)piperidin-4-yl)ethan-1-ol | 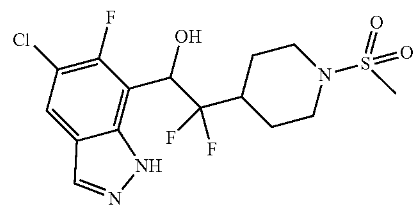 [SMILES: CS(=O)(=O)N1CCC(C(F)(F)C(O)c2c(F)c(Cl)cc3cn[nH]c23)CC1] | 409.9 (MH)– |
| P-0289 | 1-(2-(5-chloro-1H-indazol-7-yl)-1,1-difluoro-2-hydroxyethyl)cyclobutan-1-ol | 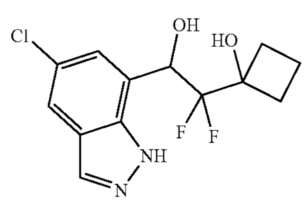 [SMILES: OC(c1cc(Cl)cc2cn[nH]c12)C(F)(F)C1(O)CCC1] | 302.9 |
| P-0290 | 1-(2-(5-chloro-6-fluoro-1H-indazol-7-yl)-1,1-difluoro-2-hydroxyethyl)cyclobutan-1-ol | 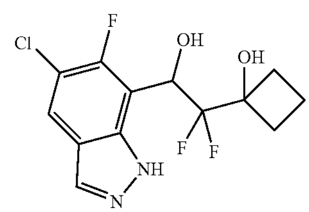 [SMILES: OC(c1c(F)c(Cl)cc2cn[nH]c12)C(F)(F)C1(O)CCC1] | 320.9 |
| P-0291 | 1-(5-chloro-1H-indazol-7-yl)-2-(3-(isopropylsulfonyl)-3-azabicyclo[3.2.1]octan-8-yl)ethan-1-ol | 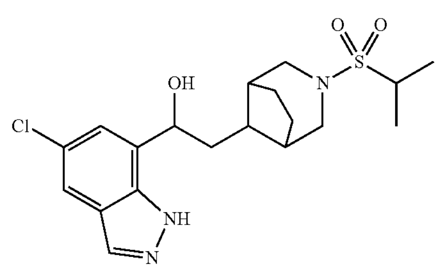 [SMILES: CC(C)S(=O)(=O)N1CC2CCC(C1)C2CC(O)c1cc(Cl)cc2cn[nH]c12] | 412.0 |
| P-0292 | 7-(3,3-dimethyl-4-(methylsulfonyl)piperazin-1-yl)-5,6-dihydro-1H-cyclobuta[f]indazole | 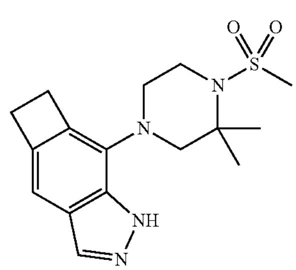 [SMILES: CC1(C)CN(c2c3c(cc4cn[nH]c24)CC3)CCN1S(C)(=O)=O] | 335.2 |

TABLE 1-continued

| Compound Number | Compound Name | Compound Structure | (MH)+ |
|---|---|---|---|
| P-0293 | bicyclo[2.2.1]heptan-2-yl(5,6-dihydro-1H-cyclobuta[f]indazol-7-yl)methanol | 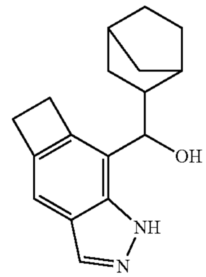 [SMILES: OC(c1c2c(cc3cn[nH]c13)CC2)C1CC2CCC1C2] | 269.2 |
| P-0294 | bicyclo[2.2.2]octan-1-yl(5-chloro-6-fluoro-1H-indazol-7-yl)methanol | 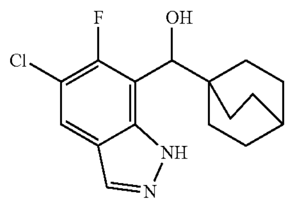 [SMILES: OC(c1c(F)c(Cl)cc2cn[nH]c12)C12CCC(CC1)CC2] | 309.0 |
| P-0295 | 1-(4-(2-(5-chloro-1H-indazol-7-yl)-1,1-difluoro-2-hydroxyethyl)piperidin-1-yl)ethan-1-one | 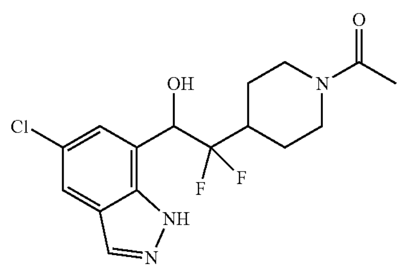 [SMILES: CC(=O)N1CCC(C(F)(F)C(O)c2cc(Cl)cc3cn[nH]c23)CC1] | 358.0 |
| P-0296 | 1-(5,6-dihydro-1H-cyclobuta[f]indazol-7-yl)-2,2-difluoro-2-(1-(methylsulfonyl)piperidin-4-yl)ethan-1-ol | 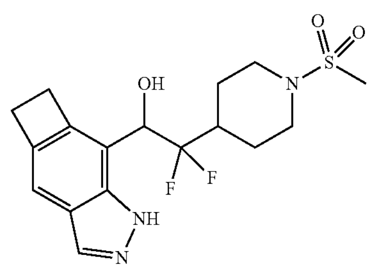 [SMILES: CS(=O)(=O)N1CCC(C(F)(F)C(O)c2c3c(cc4cn[nH]c24)CC3)CC1] | 386.0 |
| P-0297 | 4-(1-(5-chloro-1H-indazol-7-yl)-1-hydroxy-2-methylpropan-2-yl)tetrahydro-2H-thiopyran 1,1-dioxide | 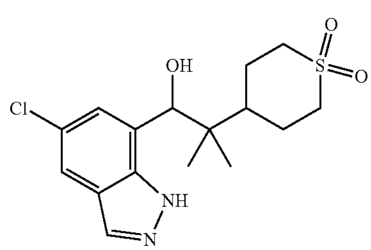 [SMILES: CC(C)(C1CCS(=O)(=O)CC1)C(O)c1cc(Cl)cc2cn[nH]c12] | 354.8 (MH)− |
| P-0298 | 4-(1-(5-chloro-6-fluoro-1H-indazol-7-yl)-1-hydroxy-2-methylpropan-2-yl)tetrahydro-2H-thiopyran 1,1-dioxide | 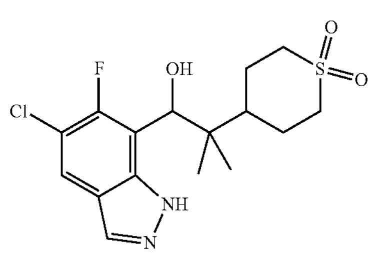 [SMILES: CC(C)(C1CCS(=O)(=O)CC1)C(O)c1c(F)c(Cl)cc2cn[nH]c12] | 372.9 (MH)− |

TABLE 1-continued

| Number | Compound Name | Compound Structure | (MH)+ |
|---|---|---|---|
| P-0299 | (5-chloro-6-fluoro-1H-indazol-7-yl)(4-fluorobicyclo[2.2.2]octan-1-yl)methanol | 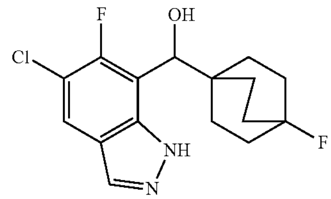 [SMILES: OC(c1c(F)c(Cl)cc2cn[nH]c12)C12CCC(F)(CC1)CC2] | 327.1 |
| P-0300 | 1-(3-(1-(5-chloro-6-fluoro-1H-indazol-7-yl)-1-hydroxy-2-methylpropan-azabicyclo[3.2.1]octan-8-yl)ethan-1-one | 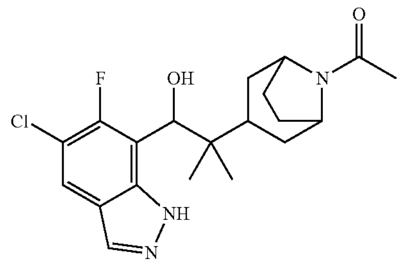 [SMILES: CC(=O)N1C2CCC1CC(C(C)(C)C(O)c1c(F)c(Cl)cc3cn[nH]c13)C2] | 394.1 |
| P-0301 | (5-chloro-6-fluoro-1H-indazol-7-yl)(4-(trifluoromethyl)bicyclo[2.2.2]octan-1-yl)methanol | 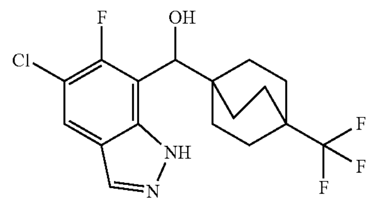 [SMILES: OC(c1c(F)c(Cl)cc2cn[nH]c12)C12CCC(C(F)(F)F)(CC1)CC2] | 374.9 |
| P-0302 | 1-((1R,5S,8s)-8-(2-(5-chloro-1H-indazol-7-yl)-1,1-difluoro-2-hydroxyethyl)-3-azabicyclo[3.2.1]octan-3-yl)ethan-1-one | 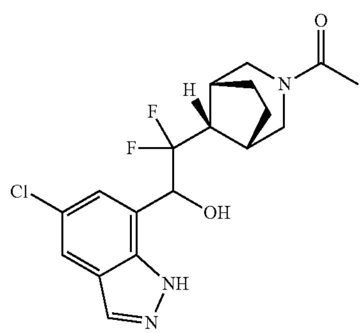 [SMILES: CC(=O)N1C[C@H]2CC[C@@H](C1)[C@H]2C(F)(F)C(O)c1cc(Cl)cc2cn[nH]c12] | 384.1 |
| P-0303 | 1-((1R,5S,8s)-8-(2-(5-chloro-1H-indazol-7-yl)-1,1-difluoro-2-hydroxyethyl)-3-azabicyclo[3.2.1]octan-3-yl)ethan-1-one | 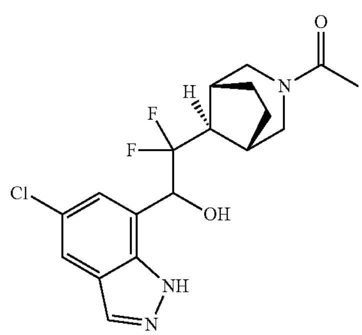 [SMILES: CC(=O)N1C[C@H]2CC[C@@H](C1)[C@@H]2C(F)(F)C(O)c1cc(Cl)cc2cn[nH]c12] | 384.1 |
| P-0304 | 1-(5-chloro-1H-indazol-7-yl)-2-(1-(ethylsulfonyl)piperidin-4-yl)-2-methylpropan-1-ol | 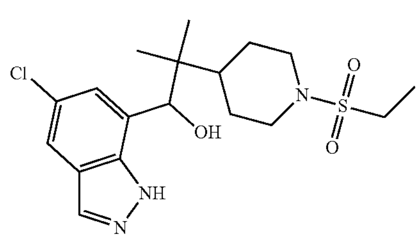 [SMILES: CCS(=O)(=O)N1CCC(C(C)(C)C(O)c2cc(Cl)cc3cn[nH]c23)CC1] | 400.0 |

TABLE 1-continued

| Compound Number | Compound Name | Compound Structure | (MH)+ |
|---|---|---|---|
| P-0305 | 1-(5-chloro-1H-indazol-7-yl)-2-methyl-2-(1-(propylsulfonyl)piperidin-4-yl)propan-1-ol | 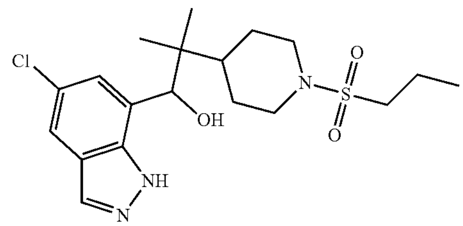 [SMILES: CCCS(=O)(=O)N1CCC(C(C)(C)C(O)c2cc(Cl)cc3cn[nH]c23)CC1] | 414.1 |
| P-0306 | 1-(5-chloro-1H-indazol-7-yl)-2-(1-(cyclopropylsulfonyl)piperidin-methylpropan-1-ol | 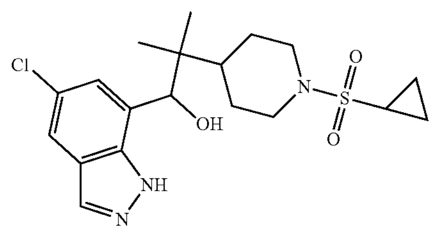 [SMILES: CC(C)(C1CCN(S(=O)(=O)C2CC2)CC1)C(O)c1cc(Cl)cc2cn[nH]c12] | 412.0 |
| P-0307 | 1-(5-chloro-1H-indazol-7-yl)-2-(1-(isopropylsulfonyl)piperidin-4-yl)-2-methylpropan-1-ol | 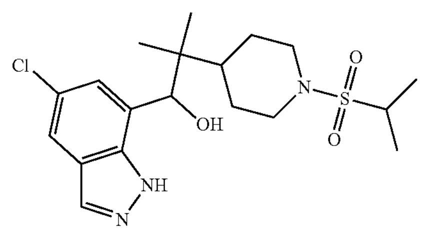 | 414.1 |
| P-0308 | 4-(1-(5-chloro-1H-indazol-7-yl)-1-hydroxy-2-methylpropan-2-yl)-N,N-dimethylpiperidine-1-sulfonamide | 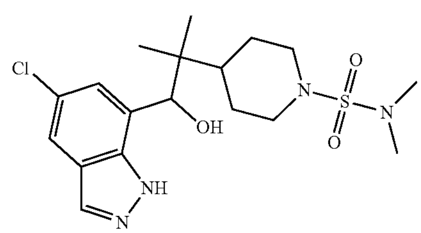 [SMILES: CN(C)S(=O)(=O)N1CCC(C(C)(C)C(O)c2cc(Cl)cc3cn[nH]c23)CC1] | 415.3 |
| P-0309 | 1-(5-chloro-1H-indazol-7-yl)-2-methyl-2-(1-(phenylsulfonyl)piperidin-4-yl)propan-1-ol | 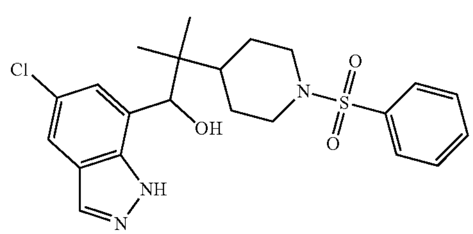 [SMILES: CC(C)(C1CCN(S(=O)(=O)c2ccccc2)CC1)C(O)c1cc(Cl)cc2cn[nH]c12] | 448.0 |
| P-0310 | 1-(4-(1-(5-chloro-1H-indazol-7-yl)-1-hydroxy-2-methylpropan-2-yl)piperidin-1-yl)ethan-1-one | 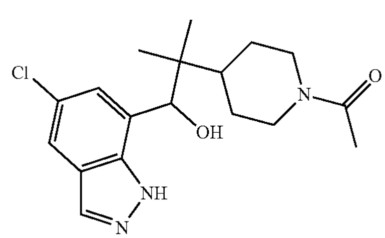 [SMILES: CC(=O)N1CCC(C(C)(C)C(O)c2cc(Cl)cc3cn[nH]c23)CC1] | 350.1 |

TABLE 1-continued

| Compound Number | Compound Name | Compound Structure | (MH)+ |
|---|---|---|---|
| P-0311 | 1-(4-(1-(5-chloro-1H-indazol-7-yl)-1-hydroxy-2-methylpropan-2-yl)piperidin-1-yl)propan-1-one | 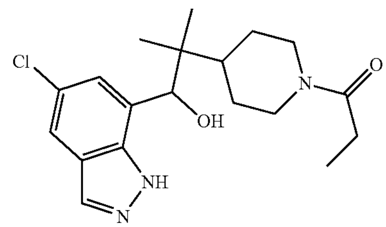 [SMILES: CCC(=O)N1CCC(C(C)(C)C(O)c2cc(Cl)cc3cn[nH]c23)CC1] | 364.2 |
| P-0312 | (4-(1-(5-chloro-1H-indazol-7-yl)-1-hydroxy-2-methylpropan-2-yl)piperidin-1-yl)(cyclopropyl)methanone | 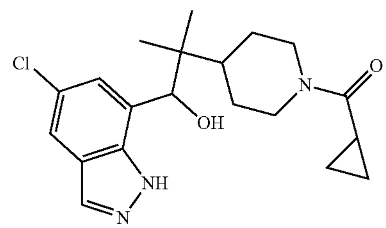 [SMILES: CC(C)(C1CCN(C(=O)C2CC2)CC1)C(O)c1cc(Cl)cc2cn[nH]c12] | 364.2 |
| P-0313 | (4-(1-(5-chloro-1H-indazol-7-yl)-1-hydroxy-2-methylpropan-2-yl)piperidin-1-yl)(phenyl)methanone | 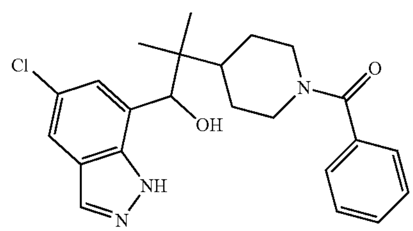 [SMILES: CC(C)(C1CCN(C(=O)c2ccccc2)CC1)C(O)c1cc(Cl)cc2cn[nH]c12] | 412.3 |
| P-0314 | 4-(1-(5-chloro-1H-indazol-7-yl)-1-hydroxy-2-methylpropan-2-yl)-N-methylpiperidine-1-carboxamide | 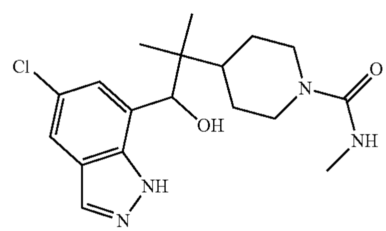 | 365.1 |
| P-0315 | 4-(1-(5-chloro-1H-indazol-7-yl)-1-hydroxy-2-methylpropan-2-yl)-N-isopropylpiperidine-1-carboxamide | 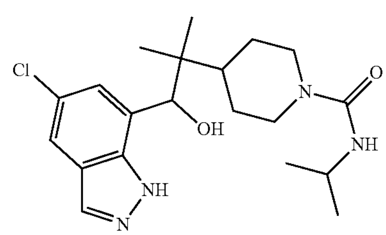 [SMILES: CC(C)NC(=O)N1CCC(C(C)(C)C(O)c2cc(Cl)cc3cn[nH]c23)CC1] | 393.1 |
| P-0316 | 4-(1-(5-chloro-1H-indazol-7-yl)-1-hydroxy-2-methylpropan-2-yl)-N-cyclopentylpiperidine-1-carboxamide | 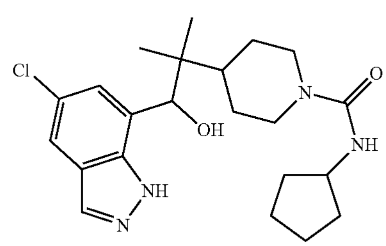 [SMILES: CC(C)(C1CCN(C(=O)NC2CCCC2)CC1)C(O)c1cc(Cl)cc2cn[nH]c12] | 419.2 |

TABLE 1-continued

| Compound Number | Compound Name | Compound Structure | (MH)+ |
|---|---|---|---|
| P-0317 | 4-(1-(5-chloro-1H-indazol-7-yl)-1-hydroxy-2-methylpropan-2-yl)-N-phenylpiperidine-1-carboxamide | 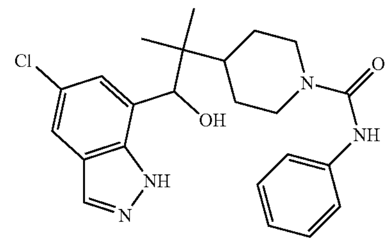 [SMILES: CC(C)(C1CCN(C(=O)Nc2ccccc2)CC1)C(O)c1cc(Cl)cc2cn[nH]c12] | 427.3 |
| P-0318 | 1-(5-chloro-1H-indazol-7-yl)-2-methyl-2-(1-methylpiperidin-4-yl)propan-1-ol | 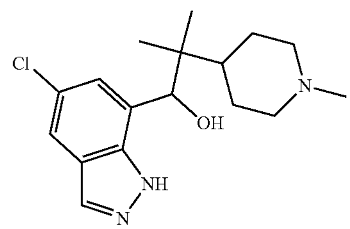 [SMILES: CN1CCC(C(C)(C)C(O)c2cc(Cl)cc3cn[nH]c23)CC1] | 322.2 |
| P-0319 | 1-(5-chloro-1H-indazol-7-yl)-2-(1-cyclopropylpiperidin-4-yl)-2-methylpropan-1-ol | 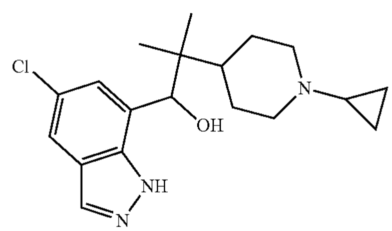 [SMILES: CC(C)(C1CCN(C2CC2)CC1)C(O)c1cc(Cl)cc2cn[nH]c12] | 348.3 |
| P-0320 | 1-(5-chloro-1H-indazol-7-yl)-2-(1-cyclopentylpiperidin-4-yl)-2-methylpropan-1-ol | 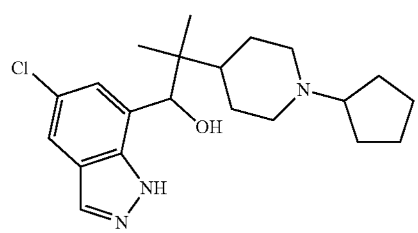 [SMILES: CC(C)(C1CCN(C2CCCC2)CC1)C(O)c1cc(Cl)cc2cn[nH]c12] | 376.2 |
| P-0321 | methyl 4-(1-(5-chloro-1H-indazol-7-yl)-1-hydroxy-2-methylpropan-2-yl)piperidine-1-carboxylate | 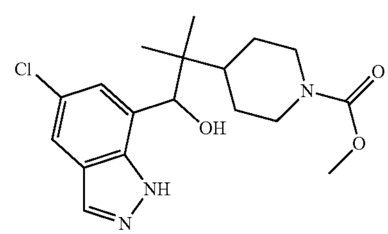 [SMILES: COC(=O)N1CCC(C(C)(C)C(O)c2cc(Cl)cc3cn[nH]c23)CC1] | 366.3 |
| P-0322 | ethyl 4-(1-(5-chloro-1H-indazol-7-yl)-1-hydroxy-2-methylpropan-2-yl)piperidine-1-carboxylate | 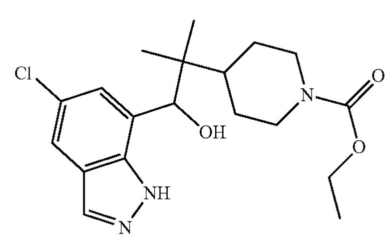 [SMILES: CCOC(=O)N1CCC(C(C)(C)C(O)c2cc(Cl)cc3cn[nH]c23)CC1] | 380.1 |

TABLE 1-continued

| Number | Compound Name | Compound Structure | (MH)+ |
|---|---|---|---|
| P-0323 | isopropyl 4-(1-(5-chloro-1H-indazol-7-yl)-1-hydroxy-2-methylpropan-2-yl)piperidine-1-carboxylate | 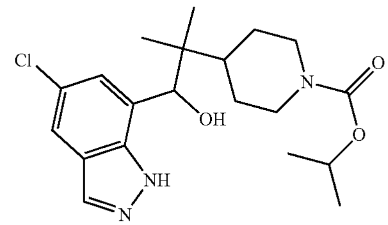 [SMILES: CC(C)OC(=O)N1CCC(C(C)(C)C(O)c2cc(Cl)cc3cn[nH]c23)CC1] | 394.3 |
| P-0324 | 4-(1-(5-chloro-1H-indazol-7-yl)-1-hydroxy-2-methylpropan-2-yl)piperidine-1-sulfonamide | 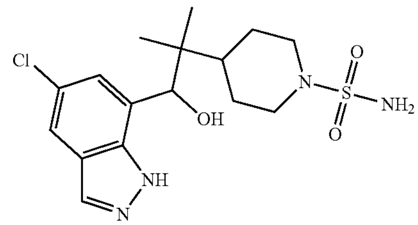 [SMILES: CC(C)(C1CCN(S(N)(=O)=O)CC1)C(O)c1cc(Cl)cc2cn[nH]c12] | 387.0 |
| P-0325 | 4-(1-(5-chloro-1H-indazol-7-yl)-1-hydroxy-2-methylpropan-2-yl)piperidine-1-carboxamide | 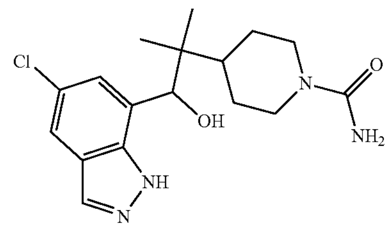 [SMILES: CC(C)(C1CCN(C(N)=O)CC1)C(O)c1cc(Cl)cc2cn[nH]c12] | 351.3 |
| P-0326 | methyl 4-((5-chloro-1H-indazol-7-yl)(hydroxy)methyl)bicyclo[2.2.2]octane-1-carboxylate | 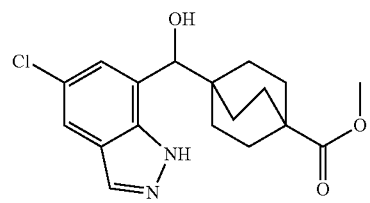 [SMILES: COC(=O)C12CCC(C(O)c3cc(Cl)cc4cn[nH]c34)(CC1)CC2] | 346.9 (MH)− |
| P-0327 | 4-((5-chloro-1H-indazol-7-yl)(hydroxy)methyl)bicyclo[2.2.2]octane-1-carboxylic acid | 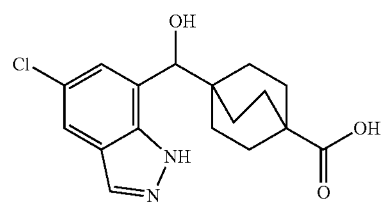 [SMILES: O=C(O)C12CCC(C(O)c3cc(Cl)cc4cn[nH]c34)(CC1)CC2] | 332.9 (MH)− |
| P-0328 | (5-chloro-1H-indazol-7-yl)(4-(hydroxymethyl)bicyclo[2.2.2]octan-1-yl)methanol | 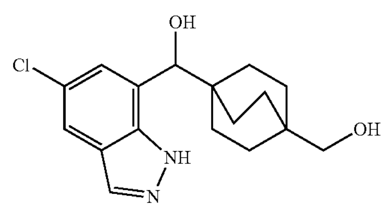 [SMILES: OCC12CCC(C(O)c3cc(Cl)cc4cn[nH]c34)(CC1)CC2] | 318.9 |
| P-0329 | methyl 8-(2-(5-chloro-1H-indazol-7-yl)-2-hydroxyethyl)-3-azabicyclo[3.2.1]octane-3-carboxylate | 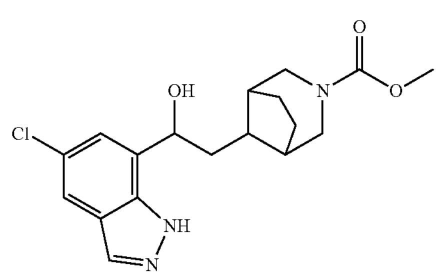 [SMILES: COC(=O)N1CC2CCC(C1)C2CC(O)c1cc(Cl)cc2cn[nH]c12] | 362.0 (MH)− |

TABLE 1-continued

| Compound Number | Compound Name | Compound Structure | (MH)+ |
|---|---|---|---|
| P-0330 | 4-(2-(5-chloro-1H-indazol-7-yl)-1,1-difluoro-2-hydroxyethyl)-N-methylpiperidine-1-sulfonamide | 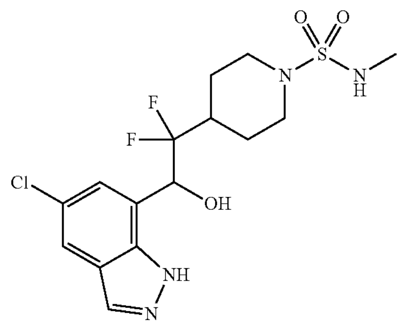 [SMILES: CNS(=O)(=O)N1CCC(C(F)(F)C(O)c2cc(Cl)cc3cn[nH]c23)CC1] | 409.0 |
| P-0331 | 4-(2-(5-chloro-1H-indazol-7-yl)-1,1-difluoro-2-hydroxyethyl)-N-ethylpiperidine-1-sulfonamide | 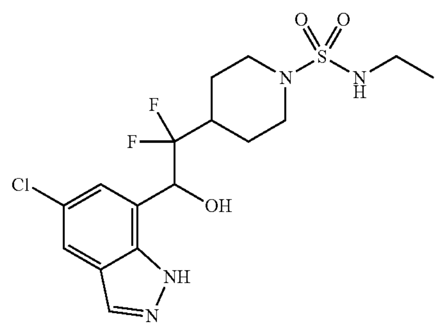 [SMILES: CCNS(=O)(=O)N1CCC(C(F)(F)C(O)c2cc(Cl)cc3cn[nH]c23)CC1] | 423.1 |
| P-0332 | 4-(2-(5-chloro-1H-indazol-7-yl)-1,1-difluoro-2-hydroxyethyl)-N-isopropylpiperidine-1-sulfonamide | 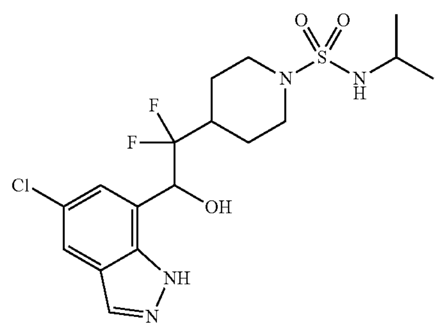 [SMILES: CC(C)NS(=O)(=O)N1CCC(C(F)(F)C(O)c2cc(Cl)cc3cn[nH]c23)CC1] | 437.1 |
| P-0333 | 4-(2-(5-chloro-1H-indazol-7-yl)-1,1-difluoro-2-hydroxyethyl)-N-(2,2,2-trifluoroethyl)piperidine-1-carboxamide | 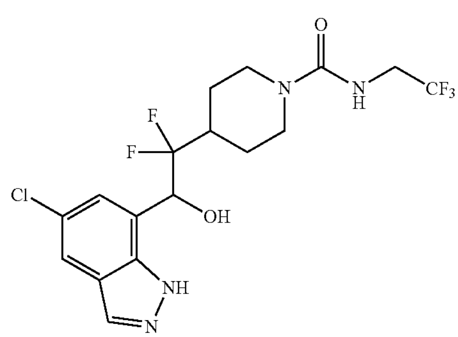 [SMILES: O=C(NCC(F)(F)F)N1CCC(C(F)(F)C(O)c2cc(Cl)cc3cn[nH]c23)CC1] | 441.1 |
| P-0334 | (S)-bicyclo[2.2.2]octan-1-yl(5-chloro-6-fluoro-1H-indazol-7-yl)methanol | 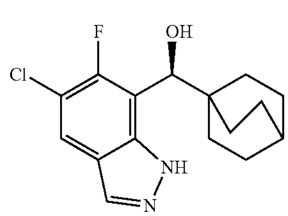 [SMILES: O[C@H](c1c(F)c(Cl)cc2cn[nH]c12)C12CCC(CC1)CC2] | 309.1 |

TABLE 1-continued

| Number | Compound Name | (MH)+ |
|---|---|---|
| P-0335 | (R)-bicyclo[2.2.2]octan-1-yl(5-chloro-6-fluoro-1H-indazol-7-yl)methanol | 309.1 |
| P-0336 | 2-(6-chloro-1H-indazol-4-yl)spiro[3.3]heptan-2-ol | 260.9 (MH)− |
| P-0337 | tert-butyl (S)-4-(1-(5-chloro-1H-indazol-7-yl)-1-hydroxy-2-methylpropan-2-yl)piperidine-1-carboxylate | 408.2 |
| P-0338 | tert-butyl (R)-4-(1-(5-chloro-1H-indazol-7-yl)-1-hydroxy-2-methylpropan-2-yl)piperidine-1-carboxylate | 408.2 |
| P-0339 | (R)-4-(1-(5-chloro-1H-indazol-7-yl)-1-hydroxy-2-methylpropan-2-yl)-N-(4-fluorophenyl)piperidine-1-carboxamide | 445.1 |
| P-0340 | (1R,3r,5S)-3-(1-(5-chloro-1H-indazol-7-yl)-1-hydroxy-2-methylpropan-azabicyclo[3.2.1]octane-8-carboxamide | 377.1 |

TABLE 1-continued

| Compound Number | Compound Name | Compound Structure | (MH)+ |
|---|---|---|---|
| P-0341 | (4-(2-(5-chloro-6-fluoro-1H-indazol-7-yl)-1,1-difluoro-2-hydroxyethyl)piperidin-1-yl)(pyridin-3-yl)methanone | 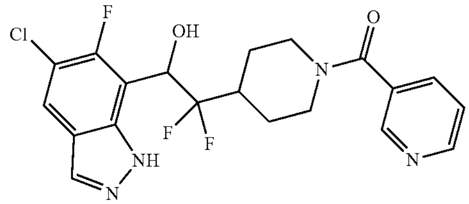 [SMILES: O=C(c1cccnc1)N1CCC(C(F)(F)C(O)c2c(F)c(Cl)cc3cn[nH]c23)CC1] | 439.0 |
| P-0342 | methyl 4-(2-(5-chloro-6-fluoro-1H-indazol-7-yl)-1,1-difluoro-2-hydroxyethyl)piperidine-1-carboxylate | 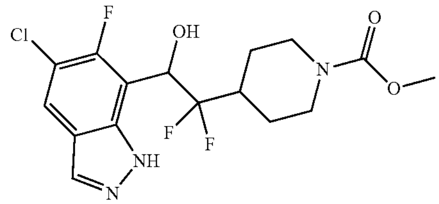 [SMILES: COC(=O)N1CCC(C(F)(F)C(O)c2c(F)c(Cl)cc3cn[nH]c23)CC1] | 392.0 |
| P-0343 | (4-(2-(5-chloro-6-fluoro-1H-indazol-7-yl)-1,1-difluoro-2-hydroxyethyl)piperidin-1-yl)(cyclopropyl)methanone | 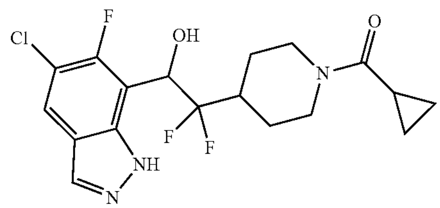 [SMILES: O=C(C1CC1)N1CCC(C(F)(F)C(O)c2c(F)c(Cl)cc3cn[nH]c23)CC1] | 402.0 |
| P-0344 | (S)-4-(1-(5-chloro-1H-indazol-7-yl)-1-hydroxy-2-methylpropan-2-yl)-N-(4-fluorophenyl)piperidine-1-carboxamide | 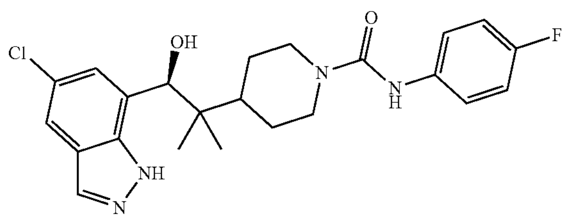 [SMILES: CC(C)(C1CCN(C(=O)Nc2ccc(F)cc2)CC1)[C@H](O)c1cc(Cl)cc2cn[nH]c12] | 445.2 |
| P-0345 | 4-(2-(5-chloro-1H-indazol-7-yl)-1,1-difluoro-2-hydroxyethyl)piperidine-1-sulfonamide | 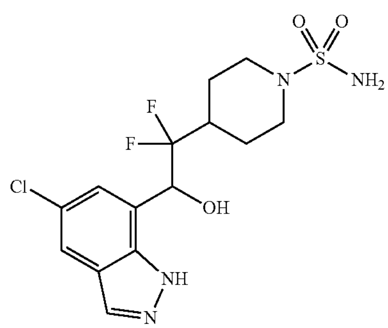 [SMILES: NS(=O)(=O)N1CCC(C(F)(F)C(O)c2cc(Cl)cc3cn[nH]c23)CC1] | 395.0 |
| P-0346 | 2-(5-chloro-1H-indazol-7-yl)-2-hydroxy-7-azaspiro[3.5]nonane-7-carboxamide | 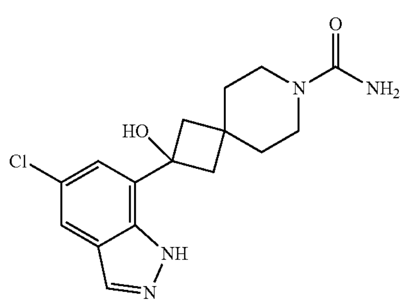 [SMILES: NC(=O)N1CCC2(CC1)CC(O)(c1cc(Cl)cc3cn[nH]c13)C2] | 335.1 |

TABLE 1-continued

| Number | Compound Name | Compound Structure | (MH)+ |
|---|---|---|---|
| P-0347 | (1R,3r,5S)-3-(1-(5-chloro-1H-indazol-7-yl)-1-hydroxy-2-methylpropan-2-yl)-8-azabicyclo[3.2.1]octane-8-sulfonamide | 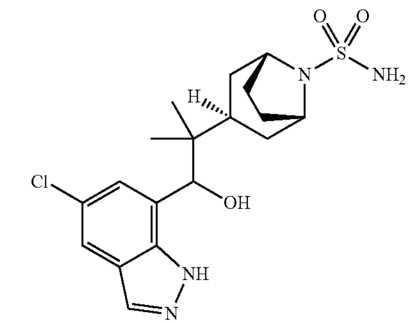 [SMILES: CC(C)(C(O)c1cc(Cl)cc2cn[nH]c12)[C@H]1C[C@H]2CC[C@@H](C1)N2S(N)(=O)=O] | 413.1 |
| P-0348 | (6-chloro-1H-indazol-4-yl)(4-methoxybicyclo[2.2.2]octan-1-yl)methanol | 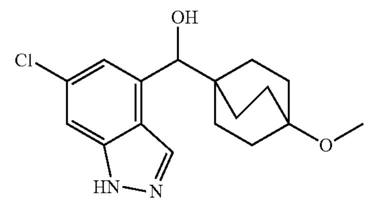 [SMILES: COC12CCC(C(O)c3cc(Cl)cc4[nH]ncc34)(CC1)CC2] | 321.0 |
| P-0349 | (4-(2-(5-chloro-1H-indazol-7-yl)-1,1-difluoro-2-hydroxyethyl)piperidin-1-yl)(cyclobutyl)methanone | 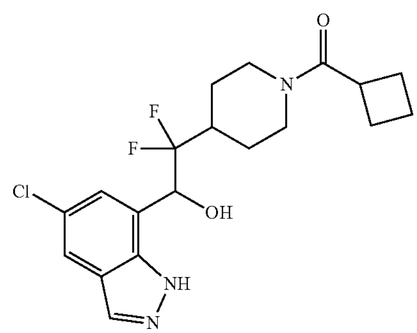 [SMILES: O=C(C1CCC1)N1CCC(C(F)(F)C(O)c2cc(Cl)cc3cn[nH]c23)CC1] | 398.1 |
| P-0350 | 1-(4-(2-(5-chloro-1H-indazol-7-yl)-1,1-difluoro-2-hydroxyethyl)piperidin-1-yl)-2-methoxyethan-1-one | 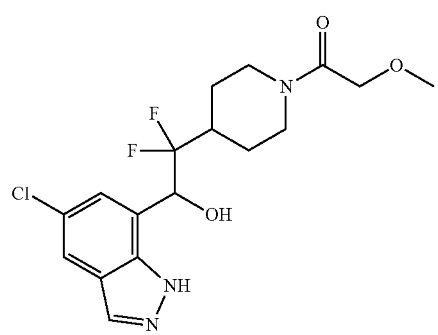 [SMILES: COCC(=O)N1CCC(C(F)(F)C(O)c2cc(Cl)cc3cn[nH]c23)CC1] | 388.1 |
| P-0351 | 1-(4-(2-(5-chloro-1H-indazol-7-yl)-1,1-difluoro-2-hydroxyethyl)piperidin-1-yl)-2-methylpropan-1-one | 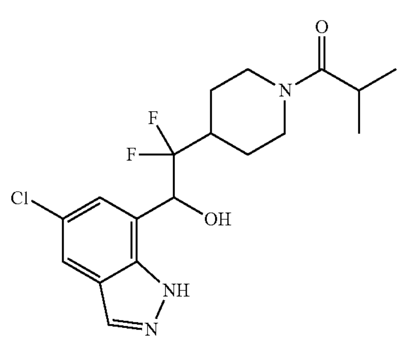 [SMILES: CC(C)C(=O)N1CCC(C(F)(F)C(O)c2cc(Cl)cc3cn[nH]c23)CC1] | 386.1 |

TABLE 1-continued

| Number | Compound Name | Compound Structure | (MH)+ |
|---|---|---|---|
| P-0352 | 5-(6-chloro-1H-indazol-4-yl)spiro[2.3]hexan-5-ol | 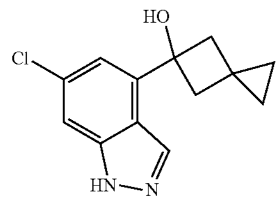 [SMILES: OC1(c2cc(Cl)cc3[nH]ncc23)CC2(CC2)C1] | 249.0 |
| P-0353 | 4-(1-(5-chloro-1H-indazol-7-yl)-1-hydroxy-2-methylpropan-2-yl)-N-(phenylsulfonyl)piperidine-1-carboxamide | 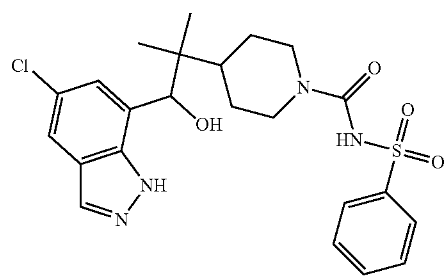 [SMILES: CC(C)(C1CCN(C(=O)NS(=O)(=O)c2ccccc2)CC1)C(O)c1cc(Cl)cc2cn[nH]c12] | 491.2 |
| P-0354 | 4-(1-(5-chloro-1H-indazol-7-yl)-1-hydroxy-2-methylpropan-2-yl)-N-((S)-1-phenylethyl)piperidine-1-carboxamide | 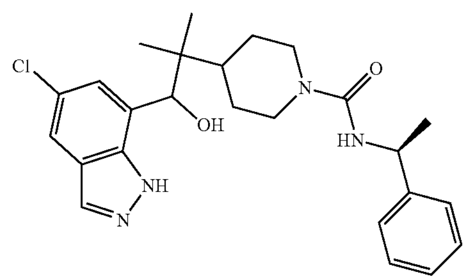 [SMILES: C[C@H](NC(=O)N1CCC(C(C)(C)C(O)c2cc(Cl)cc3cn[nH]c23)CC1)c1ccccc1] | 455.2 |
| P-0355 | 4-(1-(5-chloro-1H-indazol-7-yl)-1-hydroxy-2-methylpropan-2-yl)-N-propylpiperidine-1-carboxamide | 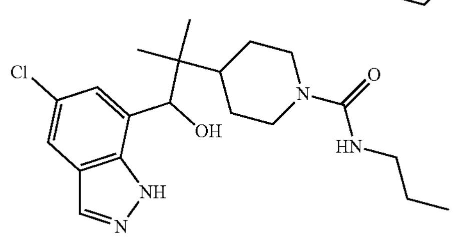 | 393.4 |
| P-0356 | N-(tert-butyl)-4-(1-(5-chloro-1H-indazol-7-yl)-1-hydroxy-2-methylpropan-2-yl)piperidine-1-carboxamide | 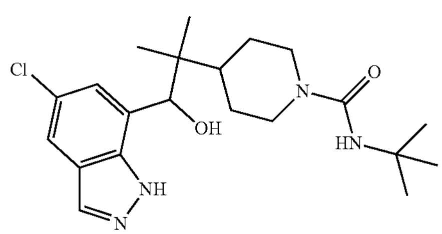 [SMILES: CC(C)(C)NC(=O)N1CCC(C(C)(C)C(O)c2cc(Cl)cc3cn[nH]c23)CC1] | 407.5 |
| P-0357 | 4-(1-(5-chloro-1H-indazol-7-yl)-1-hydroxy-2-methylpropan-2-yl)-N-(3-methoxypropyl)piperidine-1-carboxamide | 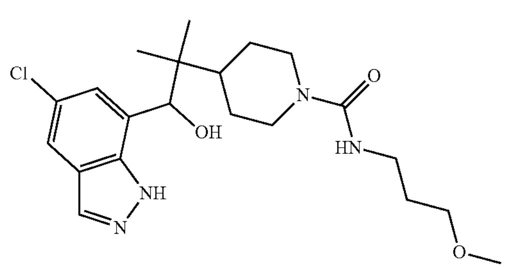 [SMILES: COCCCNC(=O)N1CCC(C(C)(C)C(O)c2cc(Cl)cc3cn[nH]c23)CC1] | 423.4 |

TABLE 1-continued

| Compound Number | Compound Name | Compound Structure | (MH)+ |
|---|---|---|---|
| P-0358 | 4-(1-(5-chloro-1H-indazol-7-yl)-1-hydroxy-2-methylpropan-2-yl)-N-(pyridin-3-yl)piperidine-1-carboxamide | 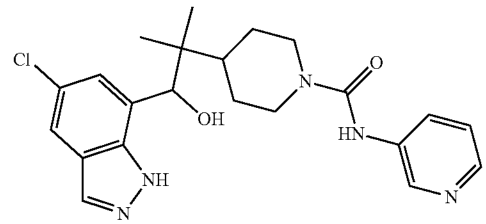 [SMILES: CC(C)(C1CCN(C(=O)Nc2cccnc2)CC1)C(O)c1cc(Cl)cc2cn[nH]c12] | 428.2 |
| P-0359 | 4-(1-(5-chloro-1H-indazol-7-yl)-1-hydroxy-2-methylpropan-2-yl)-N-(3-fluorophenyl)piperidine-1-carboxamide | 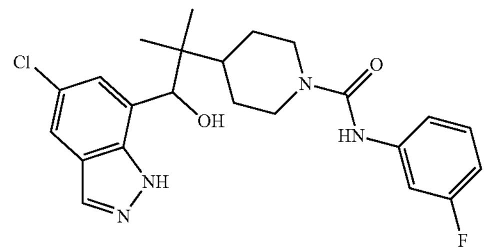 [SMILES: CC(C)(C1CCN(C(=O)Nc2cccc(F)c2)CC1)C(O)c1cc(Cl)cc2cn[nH]c12] | 445.3 |
| P-0360 | 4-(1-(5-chloro-1H-indazol-7-yl)-1-hydroxy-2-methylpropan-2-yl)-N-(3-cyanophenyl)piperidine-1-carboxamide | 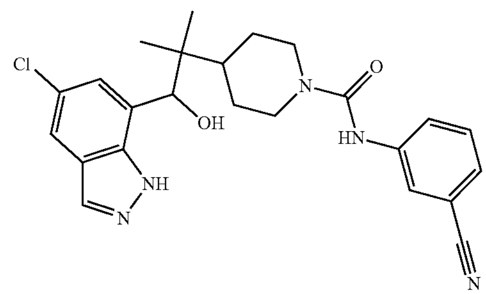 [SMILES: CC(C)(C1CCN(C(=O)Nc2cccc(C#N)c2)CC1)C(O)c1cc(Cl)cc2cn[nH]c12] | 452.2 |
| P-0361 | 4-(1-(5-chloro-1H-indazol-7-yl)-1-hydroxy-2-methylpropan-2-yl)-N-(4-chlorophenyl)piperidine-1-carboxamide | 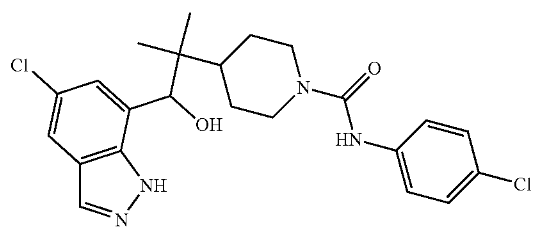 [SMILES: CC(C)(C1CCN(C(=O)Nc2ccc(Cl)cc2)CC1)C(O)c1cc(Cl)cc2cn[nH]c12] | 461.5 |
| P-0362 | (4-(1-(5-chloro-1H-indazol-7-yl)-1-hydroxy-2-methylpropan-2-yl)piperidin-1-yl)(pyridin-3-yl)methanone | 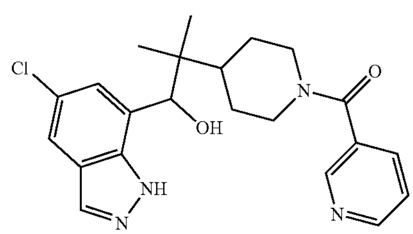 [SMILES: CC(C)(C1CCN(C(=O)c2cccnc2)CC1)C(O)c1cc(Cl)cc2cn[nH]c12] | 413.2 |
| P-0363 | (4-(1-(5-chloro-1H-indazol-7-yl)-1-hydroxy-2-methylpropan-2-yl)piperidin-1-yl)(6-(trifluoromethyl)pyridin-3-yl)methanone | 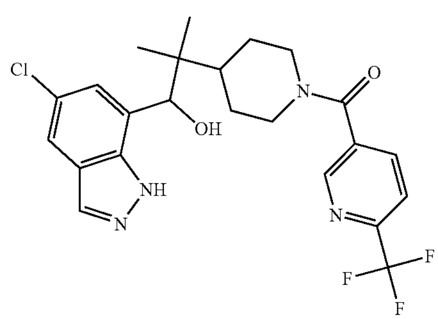 [SMILES: CC(C)(C1CCN(C(=O)c2ccc(C(F)(F)F)nc2)CC1)C(O)c1cc(Cl)cc2cn[nH]c12] | 481.0 |

TABLE 1-continued

| Compound Number | Compound Name | Compound Structure | (MH)+ |
|---|---|---|---|
| P-0364 | (4-(1-(5-chloro-1H-indazol-7-yl)-1-hydroxy-2-methylpropan-2-yl)piperidin-1-yl)(2-fluorophenyl)methanone | 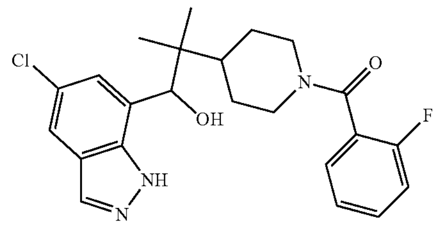 [SMILES: CC(C)(C1CCN(C(=O)c2ccccc2F)CC1)C(O)c1cc(Cl)cc2cn[nH]c12] | 430.3 |
| P-0365 | (4-(1-(5-chloro-1H-indazol-7-yl)-1-hydroxy-2-methylpropan-2-yl)piperidin-1-yl)(pyridin-2-yl)methanone | 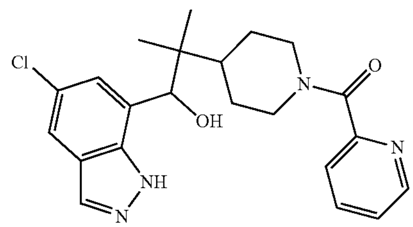 [SMILES: CC(C)(C1CCN(C(=O)c2ccccn2)CC1)C(O)c1cc(Cl)cc2cn[nH]c12] | 413.2 |
| P-0366 | (4-(1-(5-chloro-1H-indazol-7-yl)-1-hydroxy-2-methylpropan-2-yl)piperidin-1-yl)(2-(trifluoromethyl)phenyl)methanone | 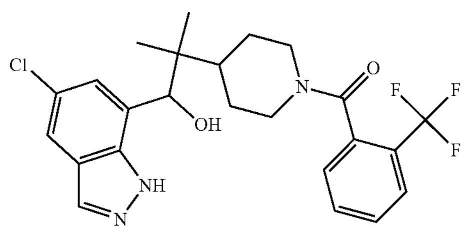 [SMILES: CC(C)(C1CCN(C(=O)c2ccccc2C(F)(F)F)CC1)C(O)c1cc(Cl)cc2cn[nH]c12] | 480.1 |
| P-0367 | (4-(1-(5-chloro-1H-indazol-7-yl)-1-hydroxy-2-methylpropan-2-yl)piperidin-1-yl)(6-morpholinopyridin-3-yl)methanone | 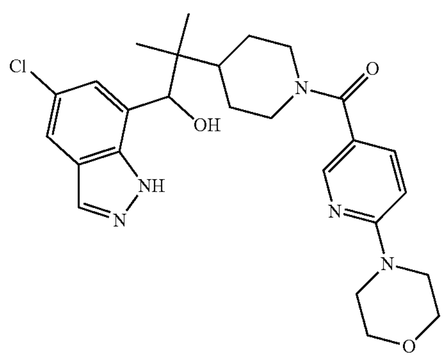 [SMILES: CC(C)(C1CCN(C(=O)c2ccc(N3CCOCC3)nc2)CC1)C(O)c1cc(Cl)cc2cn[nH]c12] | 498.4 |
| P-0368 | (4-(1-(5-chloro-1H-indazol-7-yl)-1-hydroxy-2-methylpropan-2-yl)piperidin-1-yl)(2-chlorophenyl)methanone | 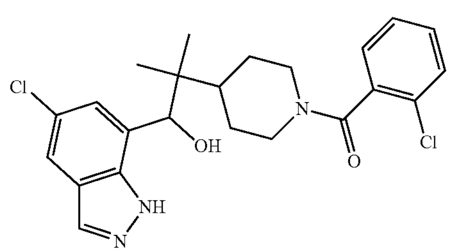 [SMILES: CC(C)(C1CCN(C(=O)c2ccccc2Cl)CC1)C(O)c1cc(Cl)cc2cn[nH]c12] | 446.2 |
| P-0369 | (4-(1-(5-chloro-1H-indazol-7-yl)-1-hydroxy-2-methylpropan-2-yl)piperidin-1-yl)(2-chloro-6-fluorophenyl)methanone | 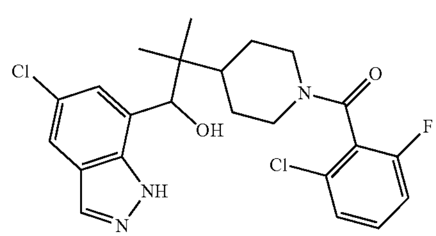 [SMILES: CC(C)(C1CCN(C(=O)c2c(F)cccc2Cl)CC1)C(O)c1cc(Cl)cc2cn[nH]c12] | 464.2 |

TABLE 1-continued

| Compound Number | Compound Name | Compound Structure | (MH)+ |
|---|---|---|---|
| P-0370 | tert-butyl 4-(1-(5-chloro-6-fluoro-1H-indazol-7-yl)-1-hydroxy-2-methylpropan-2-yl)piperidine-1-carboxylate | 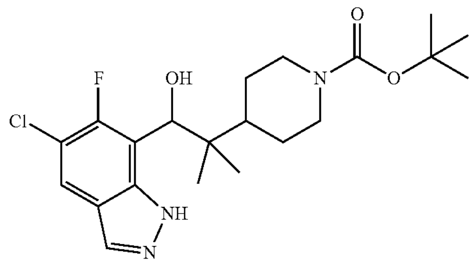 [SMILES: CC(C)(C)OC(=O)N1CCC(C(C)(C)C(O)c2c(F)c(Cl)cc3cn[nH]c23)CC1] | 426.1 |
| P-0371 | 2-(6-chloro-1H-indazol-4-yl)spiro[3.5]nonan-2-ol | 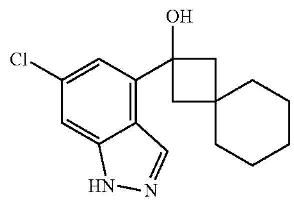 [SMILES: OC1(c2cc(Cl)cc3[nH]ncc23)CC2(CCCCC2)C1] | 291.0 |
| P-0372 | 2-(6-chloro-1H-indazol-4-yl)-7-oxaspiro[3.5]nonan-2-ol | 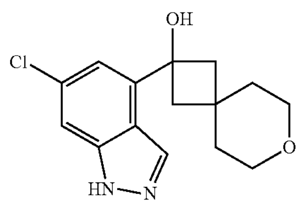 [SMILES: OC1(c2cc(Cl)cc3[nH]ncc23)CC2(CCOCC2)C1] | 290.9 (MH)− |
| P-0373 | 4-(1-(5-chloro-1H-indazol-7-yl)-1-hydroxy-2-methylpropan-2-yl)-N-((R)-1-phenylethyl)piperidine-1-carboxamide | 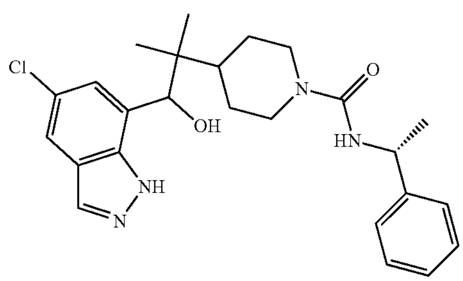 [SMILES: C[C@@H](NC(=O)N1CCC(C(C)(C)C(O)c2cc(Cl)cc3cn[nH]c23)CC1)c1ccccc1] | 455.2 |
| P-0374 | 1-(4-(2-(5-chloro-6-fluoro-1H-indazol-7-yl)-1,1-difluoro-2-hydroxyethyl)piperidin-1-yl)propan-1-one | 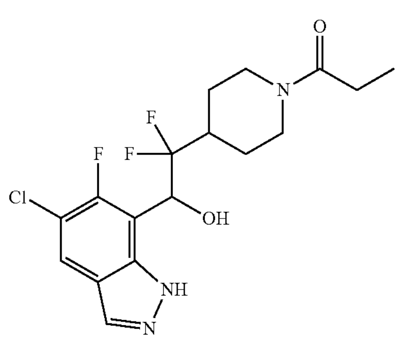 [SMILES: CCC(=O)N1CCC(C(F)(F)C(O)c2c(F)c(Cl)cc3cn[nH]c23)CC1] | 390.1 |

TABLE 1-continued

| Compound Number | Compound Name | Compound Structure | (MH)+ |
|---|---|---|---|
| P-0375 | 1-(4-(2-(5-chloro-6-fluoro-1H-indazol-7-yl)-1,1-difluoro-2-hydroxyethyl)piperidin-1-yl)-3-methylbutan-1-one | 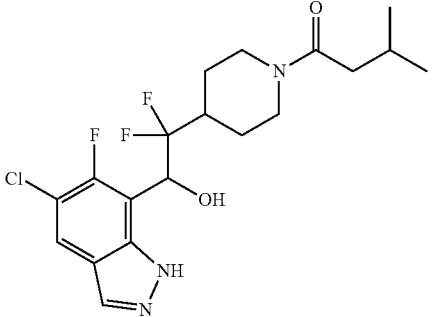 [SMILES: CC(C)CC(=O)N1CCC(C(F)(F)C(O)c2c(F)c(Cl)cc3cn[nH]c23)CC1] | 418.1 |
| P-0376 | 1-(4-(2-(5-chloro-6-fluoro-1H-indazol-7-yl)-1,1-difluoro-2-hydroxyethyl)piperidin-1-yl)-2-methoxyethan-1-one | 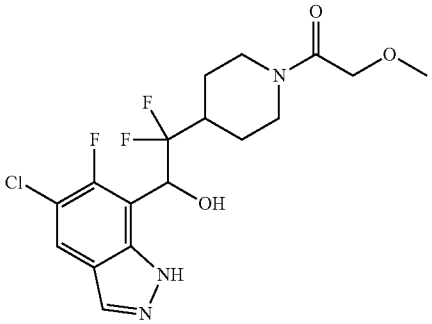 [SMILES: COCC(=O)N1CCC(C(F)(F)C(O)c2c(F)c(Cl)cc3cn[nH]c23)CC1] | 406.1 |
| P-0377 | 1-(4-(2-(5-chloro-6-fluoro-1H-indazol-7-yl)-1,1-difluoro-2-hydroxyethyl)piperidin-1-yl)-2-methylpropan-1-one | 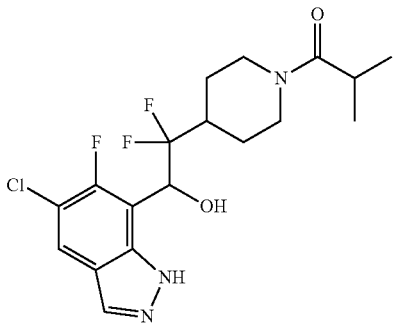 [SMILES: CC(C)C(=O)N1CCC(C(F)(F)C(O)c2c(F)c(Cl)cc3cn[nH]c23)CC1] | 404.1 |
| P-0378 | 4-(2-(5-chloro-6-fluoro-1H-indazol-7-yl)-1,1-difluoro-2-hydroxyethyl)-N-(2,2,2-trifluoroethyl)piperidine-1-carboxamide | 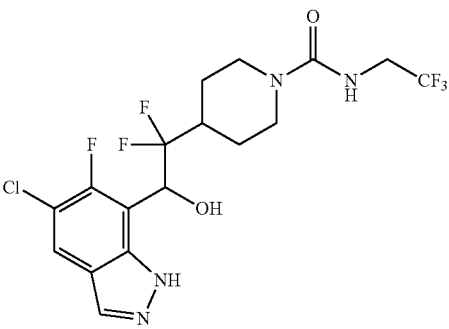 [SMILES: O=C(NCC(F)(F)F)N1CCC(C(F)(F)C(O)c2c(F)c(Cl)cc3cn[nH]c23)CC1] | 459.0 |

TABLE 1-continued

| Number | Compound Name | (MH)+ |
|---|---|---|
| P-0379 | 4-(2-(5-chloro-6-fluoro-1H-indazol-7-yl)-1,1-difluoro-2-hydroxyethyl)piperidine-1-carboxamide | 377.0 |
| P-0380 | (1R,2R,5S)-2-(5-chloro-1H-indazol-7-yl)adamantan-2-ol | 300.9 (MH)− |
| P-0381 | (S)-bicyclo[2.2.2]octan-1-yl(5-chloro-1H-indazol-7-yl)methanol | 291.0 |
| P-0382 | (R)-bicyclo[2.2.2]octan-1-yl(5-chloro-1H-indazol-7-yl)methanol | 291.0 |
| P-0383 | tert-butyl (S)-4-(1-(5-chloro-6-fluoro-1H-indazol-7-yl)-1-hydroxy-2-methylpropan-2-yl)piperidine-1-carboxylate | 426.2 |
| P-0384 | tert-butyl (R)-4-(1-(5-chloro-6-fluoro-1H-indazol-7-yl)-1-hydroxy-2-methylpropan-2-yl)piperidine-1-carboxylate | 426.2 |

TABLE 1-continued

| Compound Number | Compound Name | Compound Structure | (MH)+ |
|---|---|---|---|
| P-0385 | N-benzoyl-4-(1-(5-chloro-1H-indazol-7-yl)-1-hydroxy-2-methylpropan-2-yl)piperidine-1-carboxamide | 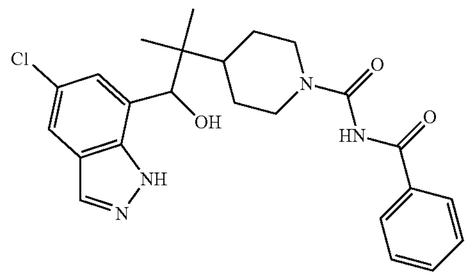 [SMILES: CC(C)(C1CCN(C(=O)NC(=O)c2ccccc2)CC1)C(O)c1cc(Cl)cc2cn[nH]c12] | 455.2 |
| P-0386 | N-benzyl-4-(1-(5-chloro-1H-indazol-7-yl)-1-hydroxy-2-methylpropan-2-yl)piperidine-1-carboxamide | 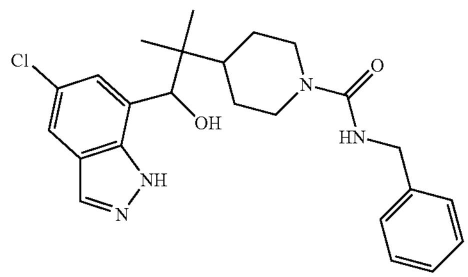 [SMILES: CC(C)(C1CCN(C(=O)NCc2ccccc2)CC1)C(O)c1cc(Cl)cc2cn[nH]c12] | 441.4 |
| P-0387 | 4-(1-(5-chloro-1H-indazol-7-yl)-1-hydroxy-2-methylpropan-2-yl)-N-cyclobutylpiperidine-1-carboxamide | 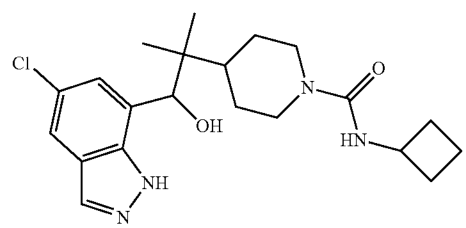 [SMILES: CC(C)(C1CCN(C(=O)NC2CCC2)CC1)C(O)c1cc(Cl)cc2cn[nH]c12] | 405.4 |
| P-0388 | 4-(1-(5-chloro-1H-indazol-7-yl)-1-hydroxy-2-methylpropan-2-yl)-N-(2-methoxyethyl)piperidine-1-carboxamide | 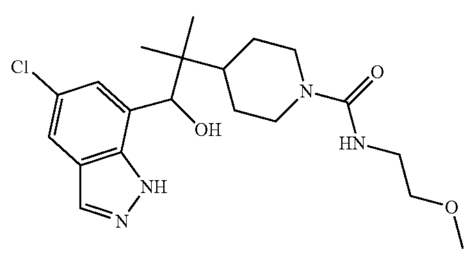 [SMILES: COCCNC(=O)N1CCC(C(C)(C)C(O)c2cc(Cl)cc3cn[nH]c23)CC1] | 409.3 |
| P-0389 | 4-(1-(5-chloro-1H-indazol-7-yl)-1-hydroxy-2-methylpropan-2-yl)-N-(pyridin-2-yl)piperidine-1-carboxamide | 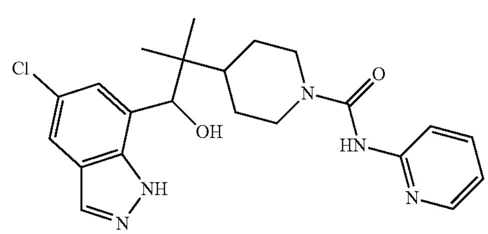 [SMILES: CC(C)(C1CCN(C(=O)Nc2ccccn2)CC1)C(O)c1cc(Cl)cc2cn[nH]c12] | 428.2 |

TABLE 1-continued

| Compound Number | Compound Name | Compound Structure | (MH)+ |
|---|---|---|---|
| P-0390 | 4-(1-(5-chloro-1H-indazol-7-yl)-1-hydroxy-2-methylpropan-2-yl)-N-(2-morpholinopyridin-4-yl)piperidine-1-carboxamide | 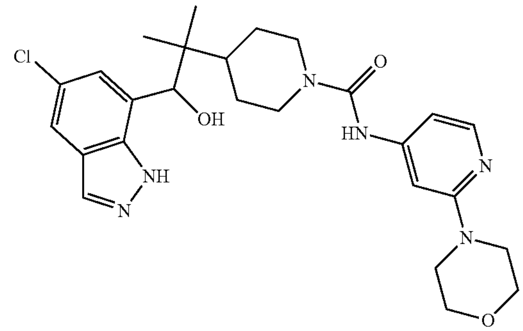 [SMILES: CC(C)(C1CCN(C(=O)Nc2ccnc(N3CCOCC3)c2)CC1)C(O)c1cc(Cl)cc2cn[nH]c12] | 513.4 |
| P-0391 | (4-(1-(5-chloro-1H-indazol-7-yl)-1-hydroxy-2-methylpropan-2-yl)piperidin-1-yl)(morpholino)methanone | 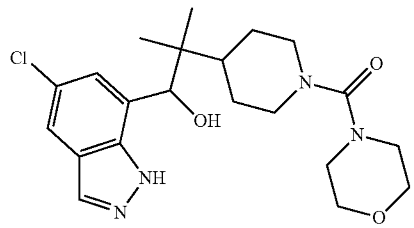 [SMILES: CC(C)(C1CCN(C(=O)N2CCOCC2)CC1)C(O)c1cc(Cl)cc2cn[nH]c12] | 421.3 |
| P-0392 | 4-(1-(5-chloro-1H-indazol-7-yl)-1-hydroxy-2-methylpropan-2-yl)-N-(3,5-dimethylisoxazol-4-yl)piperidine-1-carboxamide | 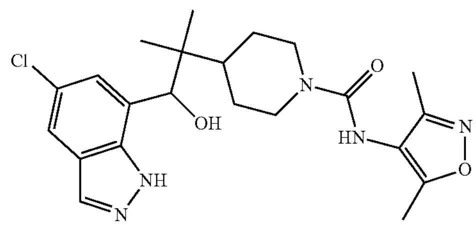 [SMILES: Cc1noc(C)c1NC(=O)N1CCC(C(C)(C)C(O)c2cc(Cl)cc3cn[nH]c23)CC1] | 446.2 |
| P-0393 | 4-(1-(5-chloro-1H-indazol-7-yl)-1-hydroxy-2-methylpropan-2-yl)-N-(4-chloro-3-(trifluoromethyl)phenyl)piperidine-1-carboxamide | 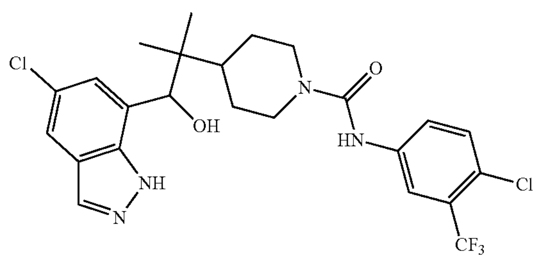 [SMILES: CC(C)(C1CCN(C(=O)Nc2ccc(Cl)c(C(F)(F)F)c2)CC1)C(O)c1cc(Cl)cc2cn[nH]c12] | 529.3 |
| P-0394 | 4-(1-(5-chloro-1H-indazol-7-yl)-1-hydroxy-2-methylpropan-2-yl)-N-(3-chloro-4-methylphenyl)piperidine-1-carboxamide | 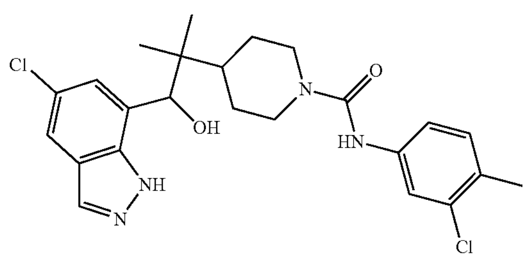 [SMILES: Cc1ccc(NC(=O)N2CCC(C(C)(C)C(O)c3cc(Cl)cc4cn[nH]c34)CC2)cc1Cl] | 475.3 |
| P-0395 | 4-(1-(5-chloro-1H-indazol-7-yl)-1-hydroxy-2-methylpropan-2-yl)-N-(3,5-dichlorophenyl)piperidine-1-carboxamide | 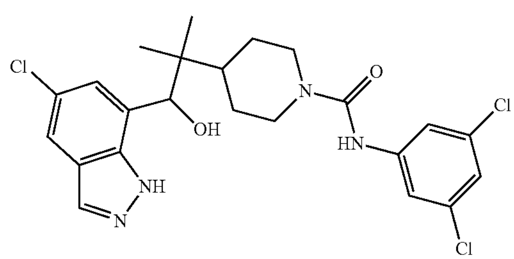 [SMILES: CC(C)(C1CCN(C(=O)Nc2cc(Cl)cc(Cl)c2)CC1)C(O)c1cc(Cl)cc2cn[nH]c12] | 495.4 |

TABLE 1-continued

| Compound Number | Compound Name | Compound Structure | (MH)+ |
|---|---|---|---|
| P-0396 | 4-(1-(5-chloro-1H-indazol-7-yl)-1-hydroxy-2-methylpropan-2-yl)-N-(3,5-dimethoxyphenyl)piperidine-1-carboxamide | 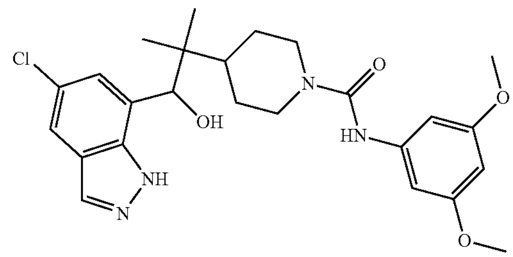 [SMILES: COc1cc(NC(=O)N2CCC(C(C)(C)C(O)c3cc(Cl)cc4cn[nH]c34)CC2)cc(OC)c1] | 487.3 |
| P-0397 | 4-(1-(5-chloro-1H-indazol-7-yl)-1-hydroxy-2-methylpropan-2-yl)-N-(p-tolyl)piperidine-1-carboxamide | 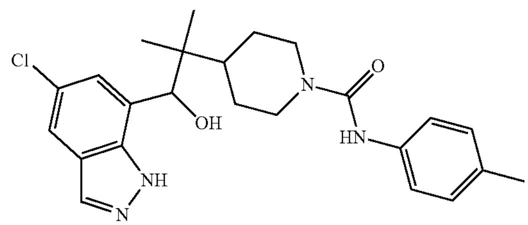 [SMILES: Cc1ccc(NC(=O)N2CCC(C(C)(C)C(O)c3cc(Cl)cc4cn[nH]c34)CC2)cc1] | 441.1 |
| P-0398 | 4-(1-(5-chloro-1H-indazol-7-yl)-1-hydroxy-2-methylpropan-2-yl)-N-(2,4-difluorophenyl)piperidine-1-carboxamide | 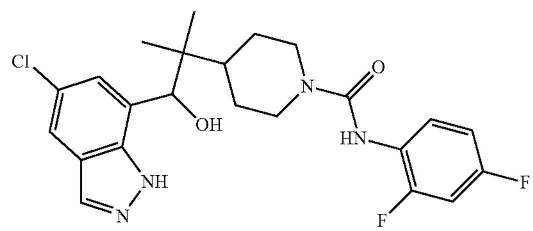 [SMILES: CC(C)(C1CCN(C(=O)Nc2ccc(F)cc2F)CC1)C(O)c1cc(Cl)cc2cn[nH]c12] | 463/3 |
| P-0399 | 4-(1-(5-chloro-1H-indazol-7-yl)-1-hydroxy-2-methylpropan-2-yl)-N-ethylpiperidine-1-carboxamide | 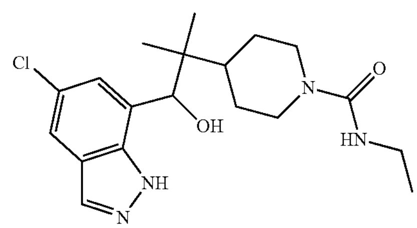 [SMILES: CCNC(=O)N1CCC(C(C)(C)C(O)c2cc(Cl)cc3cn[nH]c23)CC1] | 379.2 |
| P-0400 | 4-(1-(5-chloro-1H-indazol-7-yl)-1-hydroxy-2-methylpropan-2-yl)-N-(3-(trifluoromethyl)phenyl)piperidine-1-carboxamide | 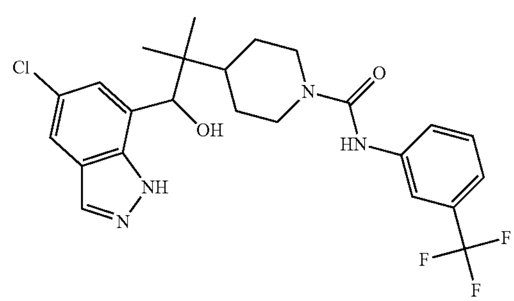 [SMILES: CC(C)(C1CCN(C(=O)Nc2cccc(C(F)(F)F)c2)CC1)C(O)c1cc(Cl)cc2cn[nH]c12] | 495.4 |
| P-0401 | 4-(1-(5-chloro-1H-indazol-7-yl)-1-hydroxy-2-methylpropan-2-yl)-N-(2-(trifluoromethyl)phenyl)piperidine-1-carboxamide | 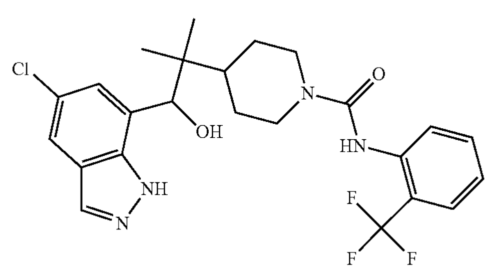 [SMILES: CC(C)(C1CCN(C(=O)Nc2ccccc2C(F)(F)F)CC1)C(O)c1cc(Cl)cc2cn[nH]c12] | 495.4 |

TABLE 1-continued

| Compound Number | Compound Name | Compound Structure | (MH)+ |
|---|---|---|---|
| P-0402 | 4-(1-(5-chloro-1H-indazol-7-yl)-1-hydroxy-2-methylpropan-2-yl)-N-(4-(dimethylamino)phenyl)piperidine-1-carboxamide | 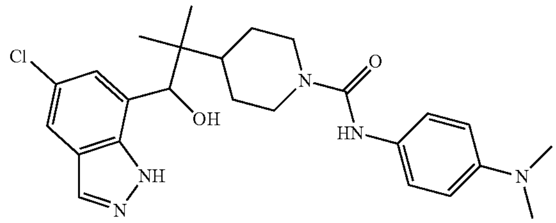 [SMILES: CN(C)c1ccc(NC(=O)N2CCC(C(C)(C)C(O)c3cc(Cl)cc4cn[nH]c34)CC2)cc1] | 470.5 |
| P-0403 | 4-(1-(5-chloro-1H-indazol-7-yl)-1-hydroxy-2-methylpropan-2-yl)-N-(4-(trifluoromethoxy)phenyl)piperidine-1-carboxamide | 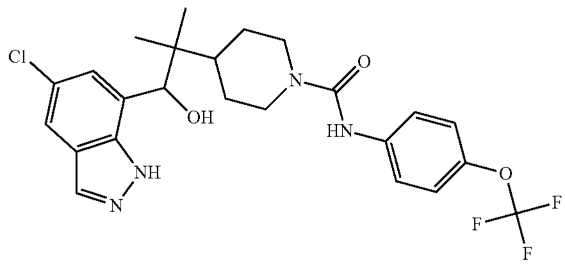 [SMILES: CC(C)(C1CCN(C(=O)Nc2ccc(OC(F)(F)F)cc2)CC1)C(O)c1cc(Cl)cc2cn[nH]c12] | 511.6 |
| P-0404 | 4-(1-(5-chloro-1H-indazol-7-yl)-1-hydroxy-2-methylpropan-2-yl)-N-(2,5-difluorophenyl)piperidine-1-carboxamide | 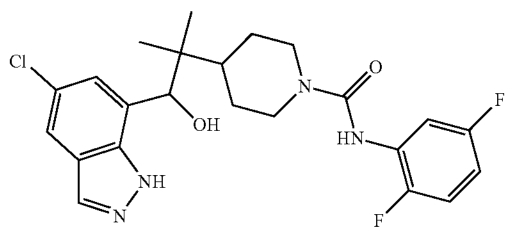 [SMILES: CC(C)(C1CCN(C(=O)Nc2cc(F)ccc2F)CC1)C(O)c1cc(Cl)cc2cn[nH]c12] | 463.3 |
| P-0405 | ethyl (4-(1-(5-chloro-1H-indazol-7-yl)-1-hydroxy-2-methylpropan-2-yl)piperidine-1-carbonyl)carbamate | 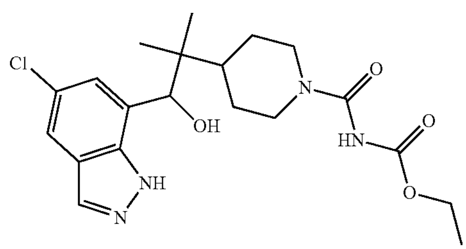 [SMILES: CCOC(=O)NC(=O)N1CCC(C(C)(C)C(O)c2cc(Cl)cc3cn[nH]c23)CC1] | 423.1 |
| P-0406 | 4-(1-(5-chloro-1H-indazol-7-yl)-1-hydroxy-2-methylpropan-2-yl)-N-(2-chloro-5-methylphenyl)piperidine-1-carboxamide | 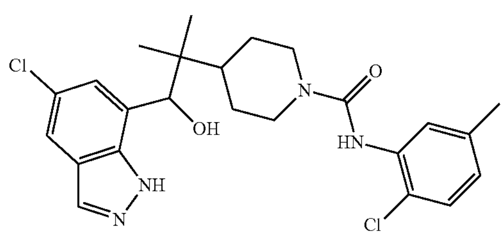 [SMILES: Cc1ccc(Cl)c(NC(=O)N2CCC(C(C)(C)C(O)c3cc(Cl)cc4cn[nH]c34)CC2)c1] | 475.3 |
| P-0407 | (1R,5S)-9-(5-chloro-1H-indazol-7-yl)bicyclo[3.3.1]nonan-9-ol | 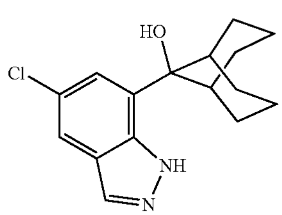 [SMILES: OC1(c2cc(Cl)cc3cn[nH]c23)C2CCCC1CCC2] | 288.9 (MH)− |

TABLE 1-continued

| Compound Number | Compound Name | Compound Structure | (MH)+ |
|---|---|---|---|
| P-0408 | 1-(4-(2-(5-chloro-6-fluoro-1H-indazol-7-yl)-1,1-difluoro-2-hydroxyethyl)piperidin-1-yl)-2-cyclopropylethan-1-one | 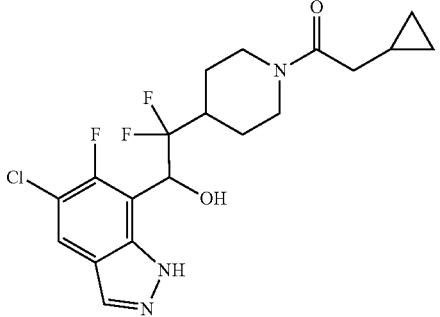 [SMILES: O=C(CC1CC1)N1CCC(C(F)(F)C(O)c2c(F)c(Cl)cc3cn[nH]c23)CC1] | 416.1 |
| P-0409 | (4-(2-(5-chloro-6-fluoro-1H-indazol-7-yl)-1,1-difluoro-2-hydroxyethyl)piperidin-1-yl)(cyclobutyl)methanone | 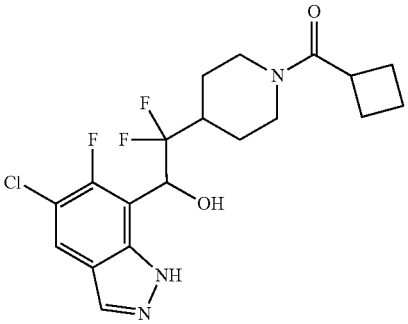 [SMILES: O=C(C1CCC1)N1CCC(C(F)(F)C(O)c2c(F)c(Cl)cc3cn[nH]c23)CC1] | 416.1 |
| P-0410 | 1-(4-(1-(5-chloro-1H-indazol-7-yl)-1-hydroxy-2-methylpropan-2-yl)piperidin-1-yl)-2-cyclopropylethan-1-one | 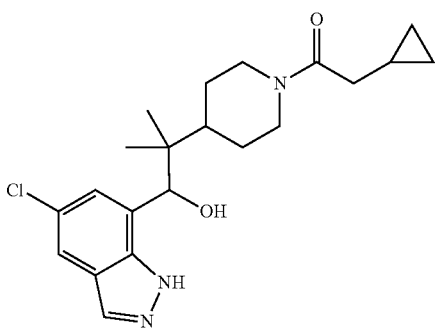 [SMILES: CC(C)(C1CCN(C(=O)CC2CC2)CC1)C(O)c1cc(Cl)cc2cn[nH]c12] | 390.2 |
| P-0411 | 1-(4-(1-(5-chloro-1H-indazol-7-yl)-1-hydroxy-2-methylpropan-2-yl)piperidin-1-yl)-3-methylbutan-1-one | 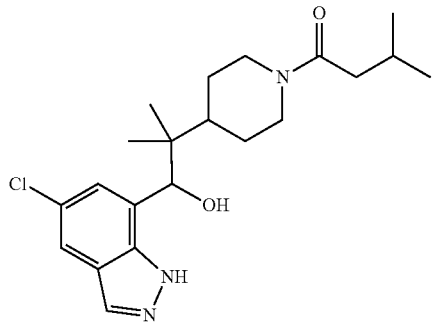 | 392.2 |

TABLE 1-continued

| Compound Number | Compound Name | Compound Structure | (MH)+ |
|---|---|---|---|
| P-0412 | (4-(1-(5-chloro-1H-indazol-7-yl)-1-hydroxy-2-methylpropan-2-yl)piperidin-1-yl)(cyclobutyl) methanone | 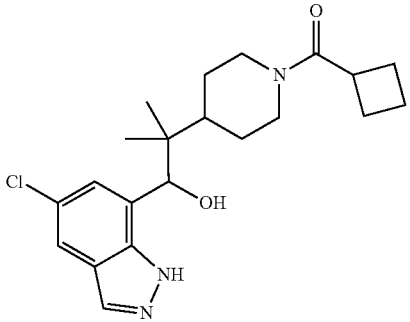 [SMILES: CC(C)(C1CCN(C(=O)C2CCC2)CC1)C(O)c1cc(Cl)cc2cn[nH]c12] | 390.2 |
| P-0413 | 1-(4-(1-(5-chloro-1H-indazol-7-yl)-1-hydroxy-2-methylpropan-2-yl)piperidin-1-yl)-2-methylpropan-1-one | 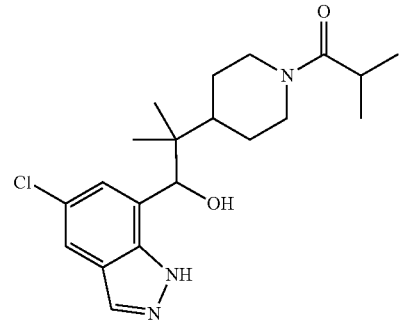 [SMILES: CC(C)C(=O)N1CCC(C(C)(C)C(O)c2cc(Cl)cc3cn[nH]c23)CC1] | 378.2 |
| P-0414 | 1-(4-(1-(5-chloro-1H-indazol-7-yl)-1-hydroxy-2-methylpropan-2-yl)piperidin-1-yl)-2-methoxyethan-1-one | 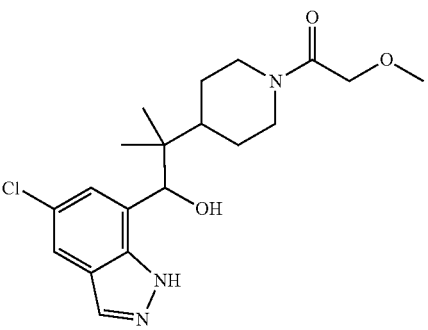 [SMILES: COCC(=O)N1CCC(C(C)(C)C(O)c2cc(Cl)cc3cn[nH]c23)CC1] | 380.1 |
| P-0415 | N-(4-((5-chloro-1H-indazol-7-yl)(hydroxy)methyl) bicyclo[2.2.2]octan-1-yl) methanesulfonamide | 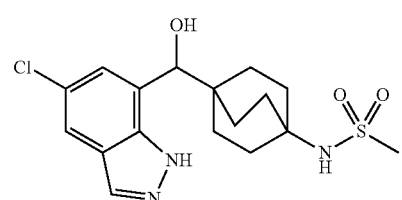 | 381.9 (MH)– |
| P-0416 | (4-(1-(5-chloro-6-fluoro-1H-indazol-7-yl)-1-hydroxy-2-methylpropan-2-yl)piperidin-1-yl)(cyclopropyl) methanone | 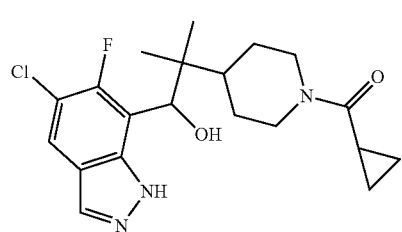 [SMILES: CC(C)(C1CCN(C(=O)C2CC2)CC1)C(O)c1c(F)c(Cl)cc2cn[nH]c12] | 394.3 |

TABLE 1-continued

| Compound Number | Compound Name | Compound Structure | (MH)+ |
|---|---|---|---|
| P-0417 | (4-(1-(5-chloro-6-fluoro-1H-indazol-7-yl)-1-hydroxy-2-methylpropan-2-yl)piperidin-1-yl)(phenyl)methanone | 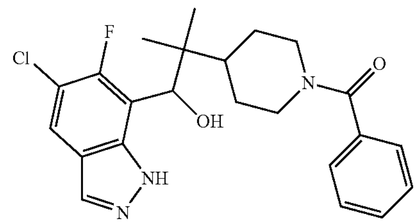 [SMILES: CC(C)(C1CCN(C(=O)c2ccccc2)CC1)C(O)c1c(F)c(Cl)cc2cn[nH]c12] | 430.3 |
| P-0418 | (4-(1-(5-chloro-6-fluoro-1H-indazol-7-yl)-1-hydroxy-2-methylpropan-2-yl)piperidin-1-yl)(pyridin-3-yl)methanone | 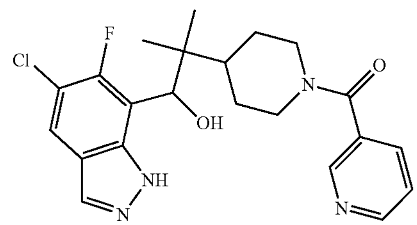 [SMILES: CC(C)(C1CCN(C(=O)c2cccnc2)CC1)C(O)c1c(F)c(Cl)cc2cn[nH]c12] | 431.2 |
| P-0419 | 4-(1-(5-chloro-6-fluoro-1H-indazol-7-yl)-1-hydroxy-2-methylpropan-2-yl)-N-(2-methoxyethyl)piperidine-1-carboxamide | 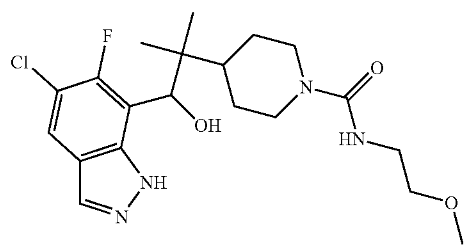 [SMILES: COCCNC(=O)N1CCC(C(C)(C)C(O)c2c(F)c(Cl)cc3cn[nH]c23)CC1] | 427.3 |
| P-0420 | 4-(1-(5-chloro-6-fluoro-1H-indazol-7-yl)-1-hydroxy-2-methylpropan-2-yl)-N-(3-methoxypropyl)piperidine-1-carboxamide | 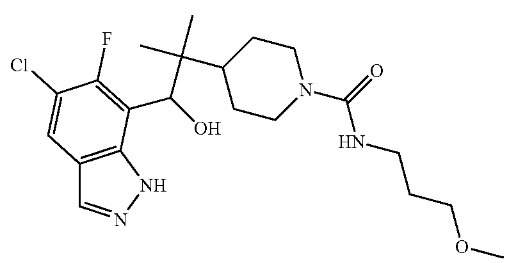 [SMILES: COCCCNC(=O)N1CCC(C(C)(C)C(O)c2c(F)c(Cl)cc3cn[nH]c23)CC1] | 441.1 |
| P-0421 | 1-(4-(1-(5-chloro-6-fluoro-1H-indazol-7-yl)-1-hydroxy-2-methylpropan-2-yl)piperidin-1-yl)propan-1-one | 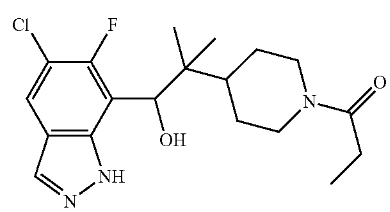 [SMILES: CCC(=O)N1CCC(C(C)(C)C(O)c2c(F)c(Cl)cc3cn[nH]c23)CC1] | 382.2 |
| P-0422 | (R)-1-(4-(1-(5-chloro-1H-indazol-7-yl)-1-hydroxy-2-methylpropan-2-yl)piperidin-1-yl)ethan-1-one | 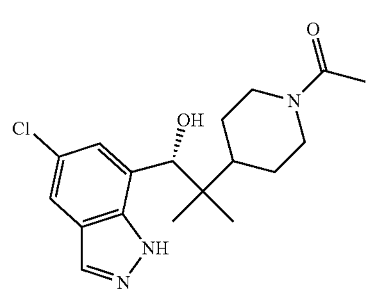 [SMILES: CC(=O)N1CCC(C(C)(C)[C@@H](O)c2cc(Cl)cc3cn[nH]c23)CC1] | 350.4 |

TABLE 1-continued

| Compound Number | Compound Name | Compound Structure | (MH)+ |
|---|---|---|---|
| P-0423 | (R)-1-(4-(1-(5-chloro-1H-indazol-7-yl)-1-hydroxy-2-methylpropan-2-yl)piperidin-1-yl)propan-1-one | 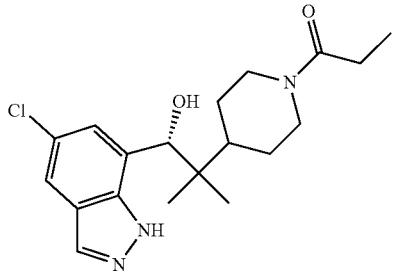 [SMILES: CCC(=O)N1CCC(C(C)(C)[C@@H](O)c2cc(Cl)cc3cn[nH]c23)CC1] | 364.2 |
| P-0424 | (R)-(4-(1-(5-chloro-1H-indazol-7-yl)-1-hydroxy-2-methylpropan-2-yl)piperidin-1-yl)(cyclopropyl)methanone | 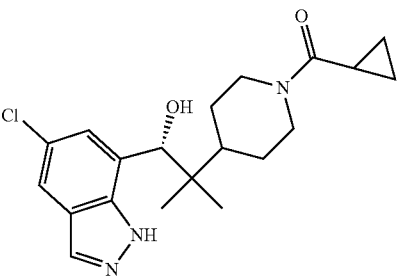 [SMILES: CC(C)(C1CCN(C(=O)C2CC2)CC1)[C@@H](O)c1cc(Cl)cc2cn[nH]c12] | 376.2 |
| P-0425 | (R)-4-(1-(5-chloro-1H-indazol-7-yl)-1-hydroxy-2-methylpropan-2-yl)-N-(2-methoxyethyl)piperidine-1-carboxamide | 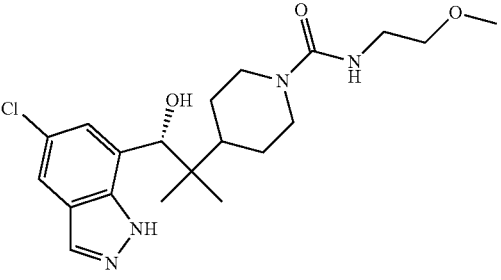 [SMILES: COCCNC(=O)N1CCC(C(C)(C)[C@@H](O)c2cc(Cl)cc3cn[nH]c23)CC1] | 409.3 |
| P-0426 | (R)-4-(1-(5-chloro-1H-indazol-7-yl)-1-hydroxy-2-methylpropan-2-yl)piperidine-1-carboxamide | 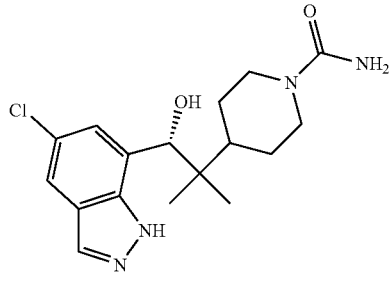 [SMILES: CC(C)(C1CCN(C(N)=O)CC1)[C@@H](O)c1cc(Cl)cc2cn[nH]c12] | 351.3 |
| P-0427 | (R)-4-(1-(5-chloro-1H-indazol-7-yl)-1-hydroxy-2-methylpropan-2-yl)-N-methylpiperidine-1-carboxamide | 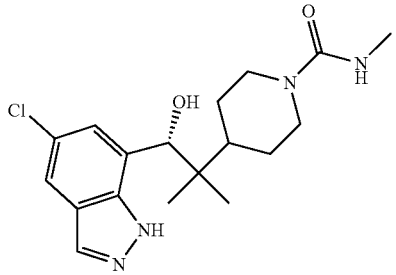 [SMILES: CNC(=O)N1CCC(C(C)(C)[C@@H](O)c2cc(Cl)cc3cn[nH]c23)CC1] | 365.1 |

TABLE 1-continued

| Compound Number | Compound Name | Compound Structure | (MH)+ |
|---|---|---|---|
| P-0428 | (R)-4-(1-(5-chloro-1H-indazol-7-yl)-1-hydroxy-2-methylpropan-2-yl)-N-ethylpiperidine-1-carboxamide | 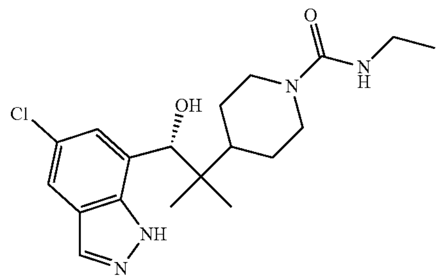 [SMILES: CCNC(=O)N1CCC(C(C)(C)[C@@H](O)c2cc(Cl)cc3cn[nH]c23)CC1] | 379.5 |
| P-0429 | (R)-4-(1-(5-chloro-1H-indazol-7-yl)-1-hydroxy-2-methylpropan-2-yl)-N-isopropylpiperidine-1-carboxamide | 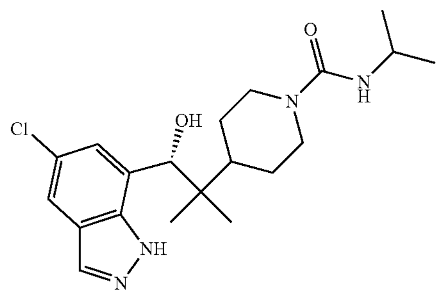 [SMILES: CC(C)NC(=O)N1CCC(C(C)(C)[C@@H](O)c2cc(Cl)cc3cn[nH]c23)CC1] | 393.4 |
| P-0430 | (R)-4-(1-(5-chloro-1H-indazol-7-yl)-1-hydroxy-2-methylpropan-2-yl)-N-(pyridin-3-yl)piperidine-1-carboxamide | 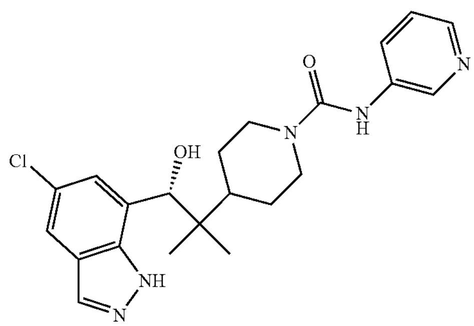 [SMILES: CC(C)(C1CCN(C(=O)Nc2cccnc2)CC1)[C@@H](O)c1cc(Cl)cc2cn[nH]c12] | 428.2 |
| P-0431 | (R)-4-(1-(5-chloro-1H-indazol-7-yl)-1-hydroxy-2-methylpropan-2-yl)-N-phenylpiperidine-1-carboxamide | 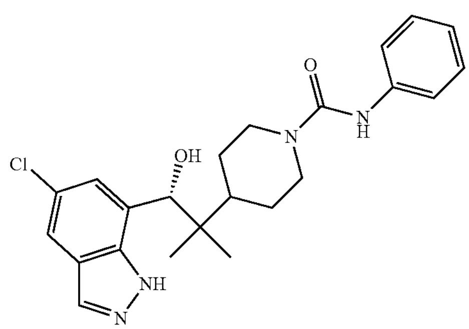 [SMILES: CC(C)(C1CCN(C(=O)Nc2ccccc2)CC1)[C@@H](O)c1cc(Cl)cc2cn[nH]c12] | 427.0 |
| P-0432 | (R)-4-(1-(5-chloro-1H-indazol-7-yl)-1-hydroxy-2-methylpropan-2-yl)-N-(2-chlorophenyl)piperidine-1-carboxamide | 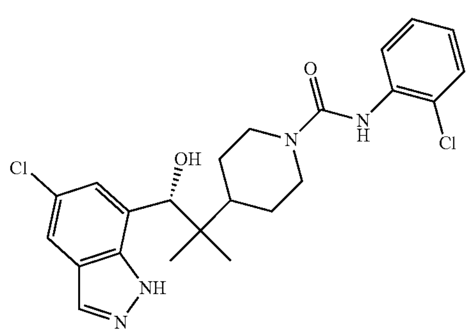 [SMILES: CC(C)(C1CCN(C(=O)Nc2ccccc2Cl)CC1)[C@@H](O)c1cc(Cl)cc2cn[nH]c12] | 461.2 |

TABLE 1-continued

| Number | Compound Name | Compound Structure | (MH)+ |
|---|---|---|---|
| P-0433 | (R)-4-(1-(5-chloro-1H-indazol-7-yl)-1-hydroxy-2-methylpropan-2-yl)-N-(4-chlorophenyl)piperidine-1-carboxamide | 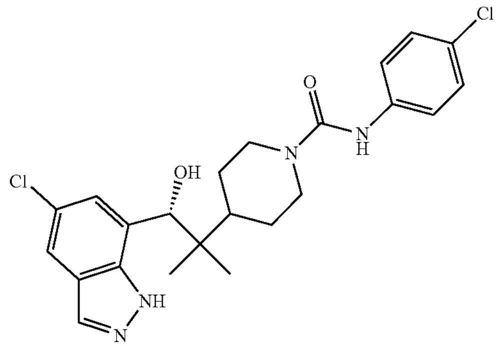 [SMILES: CC(C)(C1CCN(C(=O)Nc2ccc(Cl)cc2)CC1)[C@@H](O)c1cc(Cl)cc2cn[nH]c12] | 461.2 |
| P-0434 | (R)-4-(1-(5-chloro-1H-indazol-7-yl)-1-hydroxy-2-methylpropan-2-yl)-N-(3-fluorophenyl)piperidine-1-carboxamide | 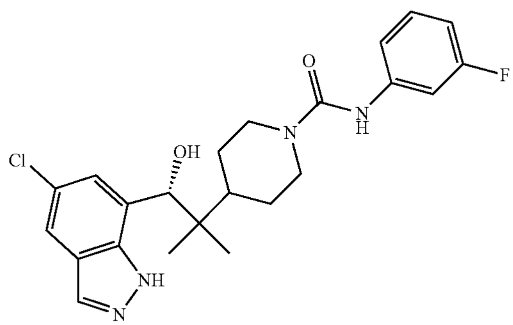 [SMILES: CC(C)(C1CCN(C(=O)Nc2cccc(F)c2)CC1)[C@@H](O)c1cc(Cl)cc2cn[nH]c12] | 445.3 |
| P-0435 | (R)-1-(4-(1-(5-chloro-1H-indazol-7-yl)-1-hydroxy-2-methylpropan-2-yl)piperidin-1-yl)-2-methoxyethan-1-one | 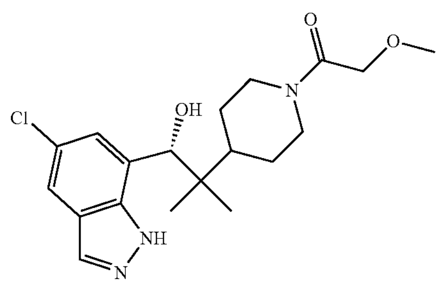 [SMILES: COCC(=O)N1CCC(C(C)(C)[C@@H](O)c2cc(Cl)cc3cn[nH]c23)CC1] | 380.1 |
| P-0436 | (R)-3-(4-(1-(5-chloro-1H-indazol-7-yl)-1-hydroxy-2-methylpropan-2-yl)piperidin-1-yl)-3-oxopropanenitrile | 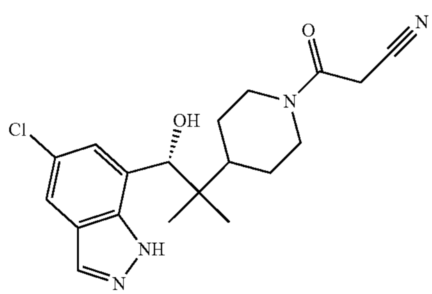 [SMILES: CC(C)(C1CCN(C(=O)CC#N)CC1)[C@@H](O)c1cc(Cl)cc2cn[nH]c12] | 375.3 |
| P-0437 | (R)-4-(1-(5-chloro-1H-indazol-7-yl)-1-hydroxy-2-methylpropan-2-yl)-N-(2-(trifluoromethyl)phenyl)piperidine-1-carboxamide | 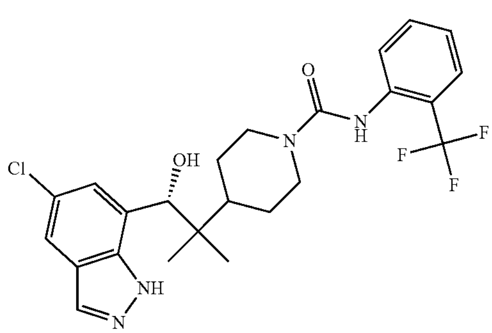 [SMILES: CC(C)(C1CCN(C(=O)Nc2ccccc2C(F)(F)F)CC1)[C@@H](O)c1cc(Cl)cc2cn[nH]c12] | 495.4 |

TABLE 1-continued

| Compound Number | Compound Name | Compound Structure | (MH)+ |
|---|---|---|---|
| P-0438 | (1R,3r,5S)-3-(1-(5-chloro-1H-indazol-7-yl)-1-hydroxy-2-methylpropan-2-yl)-N-(2,2,2-trifluoroethyl)-8-azabicyclo[3.2.1]octane-8-carboxamide | 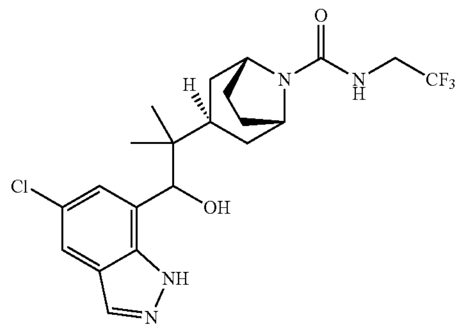 [SMILES: CC(C)(C(O)c1cc(Cl)cc2cn[nH]c12)[C@H]1C[C@H]2CC[C@@H](C1)N2C(=O)NCC(F)(F)F] | 459.1 |
| P-0439 | (1R,3r,5S)-3-(1-(5-chloro-1H-indazol-7-yl)-1-hydroxy-2-methylpropan-2-yl)-N-cyclopropyl-8-azabicyclo[3.2.1]octane-8-carboxamide | 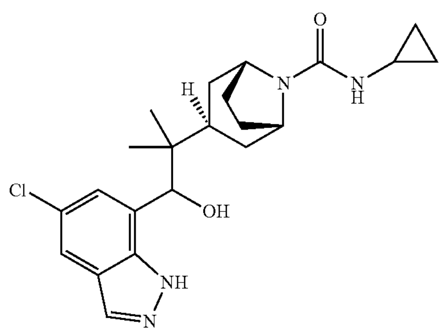 [SMILES: CC(C)(C(O)c1cc(Cl)cc2cn[nH]c12)[C@H]1C[C@H]2CC[C@@H](C1)N2C(=O)NC1CC1] | 417.2 |
| P-0440 | (1R,3r,5S)-3-(1-(5-chloro-1H-indazol-7-yl)-1-hydroxy-2-methylpropan-2-yl)-N-(4-fluorophenyl)-8-azabicyclo[3.2.1]octane-8-carboxamide | 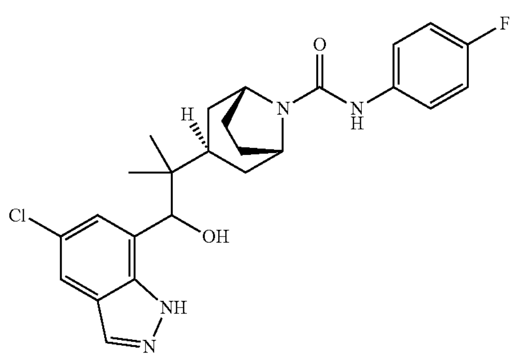 [SMILES: CC(C)(C(O)c1cc(Cl)cc2cn[nH]c12)[C@H]1C[C@H]2CC[C@@H](C1)N2C(=O)Nc1ccc(F)cc1] | 471.1 |
| P-0441 | 1-(4-(1-(5-chloro-1H-indazol-7-yl)-1-hydroxy-2-methylpropan-2-yl)piperidin-1-yl)-2-morpholinoethan-1-one | 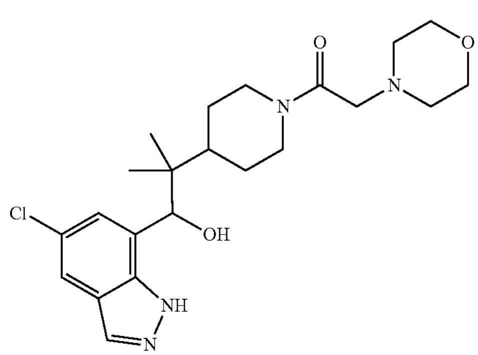 [SMILES: CC(C)(C1CCN(C(=O)CN2CCOCC2)CC1)C(O)c1cc(Cl)cc2cn[nH]c12] | 435.2 |

TABLE 1-continued

| Compound Number | Compound Name | Compound Structure | (MH)+ |
|---|---|---|---|
| P-0442 | (1R,3r,5S)-3-(1-(5-chloro-1H-indazol-7-yl)-1-hydroxy-2-methylpropan-2-yl)-N-methyl-8-azabicyclo[3.2.1]octane-8-carboxamide | 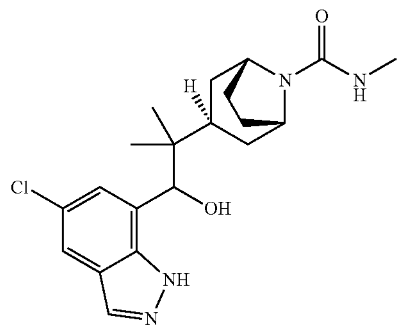 [SMILES: CNC(=O)N1[C@@H]2CC[C@H]1C[C@@H](C(C)(C)C(O)c1cc(Cl)cc3cn[nH]c13)C2] | 391.2 |
| P-0443 | 1-(4-(1-(5-chloro-1H-indazol-7-yl)-1-hydroxy-2-methylpropan-2-yl)piperidin-1-yl)-2-(tetrahydro-2H-pyran-4-yl)ethan-1-one | 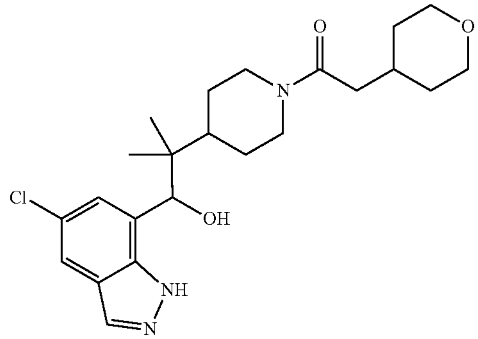 [SMILES: CC(C)(C1CCN(C(=O)CC2CCOCC2)CC1)C(O)c1cc(Cl)cc2cn[nH]c12] | 434.2 |
| P-0444 | (S)-1-(4-(1-(5-chloro-1H-indazol-7-yl)-1-hydroxy-2-methylpropan-2-yl)piperidin-1-yl)propan-1-one | 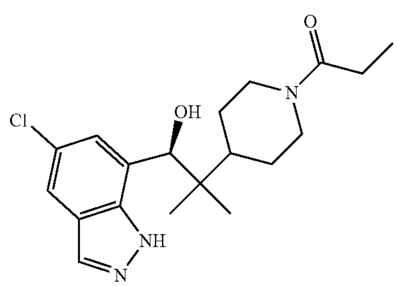 [SMILES: CCC(=O)N1CCC(C(C)(C)[C@H](O)c2cc(Cl)cc3cn[nH]c23)CC1] | 364.2 |
| P-0445 | (S)-4-(1-(5-chloro-1H-indazol-7-yl)-1-hydroxy-2-methylpropan-2-yl)-N-methylpiperidine-1-carboxamide | 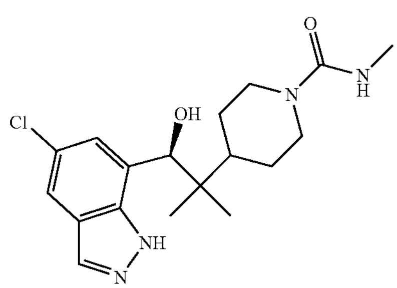 [SMILES: CNC(=O)N1CCC(C(C)(C)[C@H](O)c2cc(Cl)cc3cn[nH]c23)CC1] | 365.1 |
| P-0446 | (S)-4-(1-(5-chloro-1H-indazol-7-yl)-1-hydroxy-2-methylpropan-2-yl)-N-(2-methoxyethyl)piperidine-1-carboxamide | 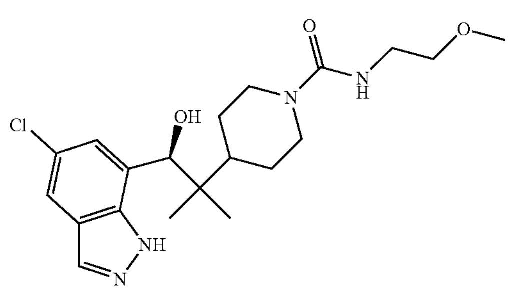 [SMILES: COCCNC(=O)N1CCC(C(C)(C)[C@H](O)c2cc(Cl)cc3cn[nH]c23)CC1] | 409.3 |

TABLE 1-continued

| Compound Number | Compound Name | Compound Structure | (MH)+ |
|---|---|---|---|
| P-0447 | (S)-4-(1-(5-chloro-1H-indazol-7-yl)-1-hydroxy-2-methylpropan-2-yl)-N-(4-cyanophenyl)piperidine-1-carboxamide | 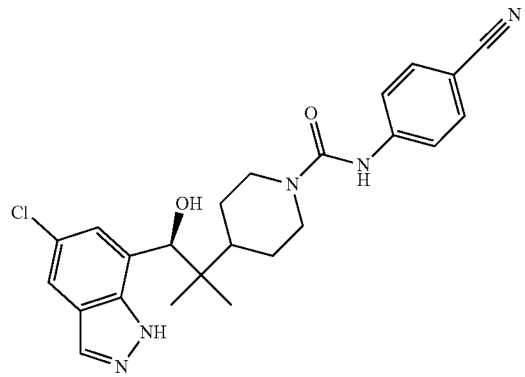 [SMILES: CC(C)(C1CCN(C(=O)Nc2ccc(C#N)cc2)CC1)[C@H](O)c1cc(Cl)cc2cn[nH]c12] | 454.2 |
| P-0448 | 1-(4-(1-(5-chloro-1H-indazol-7-yl)-1-hydroxy-2-methylpropan-2-yl)piperidin-l-yl)-2-(1,1-dioxidotetrahydro-2H-thiopyran-4-yl)ethan-1-one | 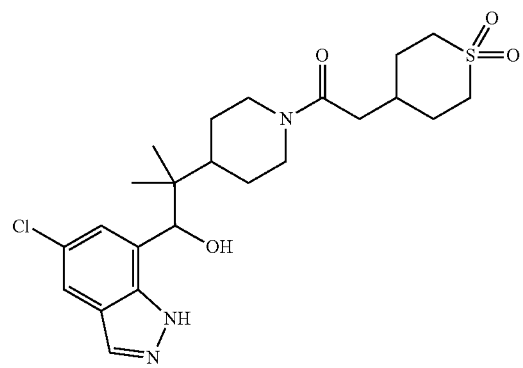 [SMILES: CC(C)(C1CCN(C(=O)CC2CCS(=O)(=O)CC2)CC1)C(O)c1cc(Cl)cc2cn[nH]c12] | 482.2 |
| P-0449 | 4-(1-(5-chloro-1H-indazol-7-yl)-1-hydroxy-2-methylpropan-2-yl)-N-((1r,4r)-4-methylcyclohexyl)piperidine-1-carboxamide | 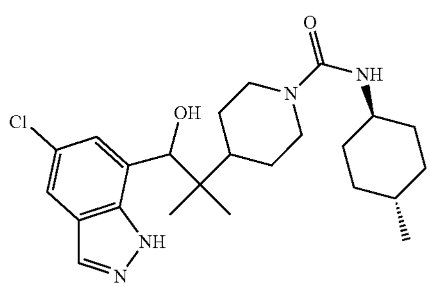 [SMILES: CC(C)(C1CCN(C(=O)N[C@H]2CC[C@H](C)CC2)CC1)C(O)c1cc(Cl)cc2cn[nH]c12] | 447.1 |
| P-0450 | 4-(1-(5-chloro-1H-indazol-7-yl)-1-hydroxy-2-methylpropan-2-yl)-N-(1-(methylsulfonyl)piperidin-4-yl)piperidine-1-carboxamide | 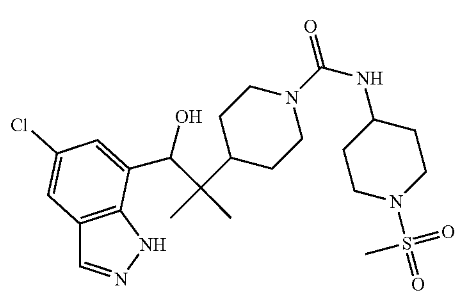 [SMILES: CC(C)(C1CCN(C(=O)NC2CCN(S(C)(=O)=O)CC2)CC1)C(O)c1cc(Cl)cc2cn[nH]c12] | 512.3 |

TABLE 1-continued

| Compound Number | Compound Name | Compound Structure | (MH)+ |
|---|---|---|---|
| P-0451 | 4-(1-(5-chloro-1H-indazol-7-yl)-1-hydroxy-2-methylpropan-2-yl)-N-(tetrahydro-2H-pyran-4-yl)piperidine-1-carboxamide | 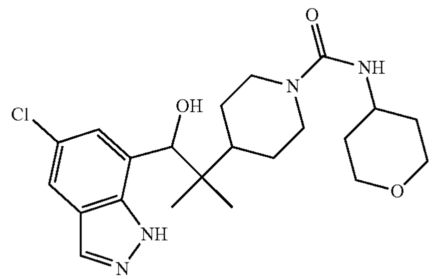 [SMILES: CC(C)(C1CCN(C(=O)NC2CCOCC2)CC1)C(O)c1cc(Cl)cc2cn[nH]c12] | 435.4 |
| P-0452 | 4-(1-(5-chloro-1H-indazol-7-yl)-1-hydroxy-2-methylpropan-2-yl)-N-(2-(methylsulfonyl)ethyl)piperidine-1-carboxamide | 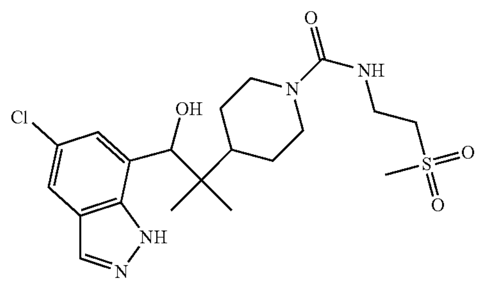 [SMILES: CC(C)(C1CCN(C(=O)NCCS(C)(=O)=O)CC1)C(O)c1cc(Cl)cc2cn[nH]c12] | 457.3 |
| P-0453 | 4-(1-(5-chloro-1H-indazol-7-yl)-1-hydroxy-2-methylpropan-2-yl)-N-(piperidin-4-yl)piperidine-1-carboxamide | 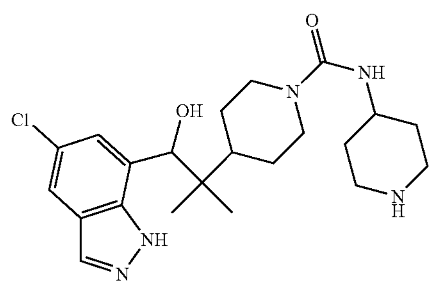 [SMILES: CC(C)(C1CCN(C(=O)NC2CCNCC2)CC1)C(O)c1cc(Cl)cc2cn[nH]c12] | 434.2 |
| P-0454 | 3-(4-(1-(5-chloro-1H-indazol-7-yl)-1-hydroxy-2-methylpropan-2-yl)piperidin-1-yl)-3-oxopropanenitrile | 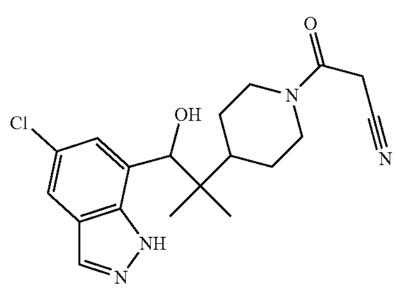 [SMILES: CC(C)(C1CCN(C(=O)CC#N)CC1)C(O)c1cc(Cl)cc2cn[nH]c12] | 375.3 |
| P-0455 | 1-(4-(1-(5-chloro-1H-indazol-7-yl)-1-hydroxy-2-methylpropan-2-yl)piperidin-1-yl)-2-(dimethylamino)ethan-1-one | 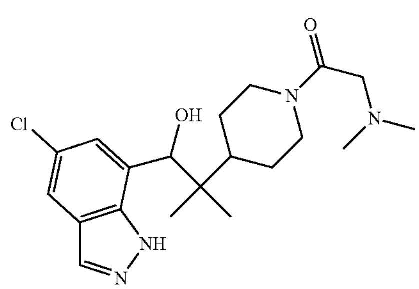 [SMILES: CN(C)CC(=O)N1CCC(C(C)(C)C(O)c2cc(Cl)cc3cn[nH]c23)CC1] | 393.4 |

TABLE 1-continued

| Compound Number | Compound Name | Compound Structure | (MH)+ |
|---|---|---|---|
| P-0456 | 1-(4-(1-(5-chloro-1H-indazol-7-yl)-1-hydroxy-2-methylpropan-2-yl)piperidin-1-yl)-3-(dimethylamino)propan-1-one | 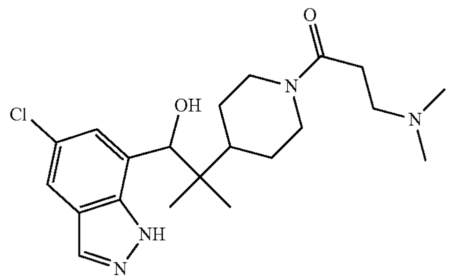 [SMILES: CN(C)CCC(=O)N1CCC(C(C)(C)C(O)c2cc(Cl)cc3cn[nH]c23)CC1] | 407.5 |
| P-0457 | (4-(1-(5-chloro-1H-indazol-7-yl)-1-hydroxy-2-methylpropan-2-yl)piperidin-1-yl)(1-methylcyclopropyl)methanone | 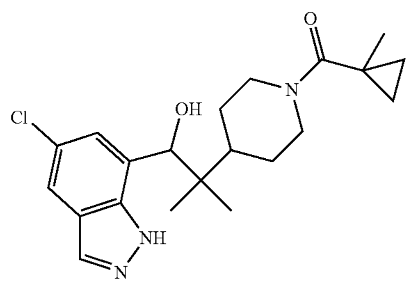 [SMILES: CC1(C(=O)N2CCC(C(C)(C)C(O)c3cc(Cl)cc4cn[nH]c34)CC2)CC1] | 390.4 |
| P-0458 | (4-(1-(5-chloro-1H-indazol-7-yl)-1-hydroxy-2-methylpropan-2-yl)piperidin-1-yl)(tetrahydro-2H-pyran-4-yl)methanone | 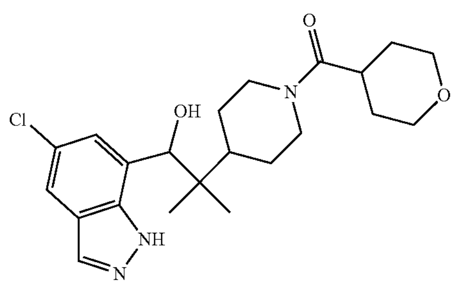 [SMILES: CC(C)(C1CCN(C(=O)C2CCOCC2)CC1)C(O)c1cc(Cl)cc2cn[nH]c12] | 420.1 |
| P-0459 | 1-(4-(1-(5-chloro-1H-indazol-7-yl)-1-hydroxy-2-methylpropan-2-yl)piperidin-1-yl)-3,3,3-trifluoropropan-1-one | 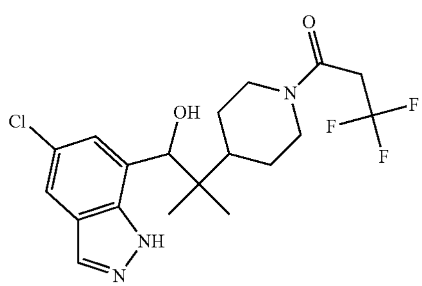 [SMILES: CC(C)(C1CCN(C(=O)CC(F)(F)F)CC1)C(O)c1cc(Cl)cc2cn[nH]c12] | 418.3 |
| P-0460 | 1-(4-(1-(5-chloro-1H-indazol-7-yl)-1-hydroxy-2-methylpropan-2-yl)piperidin-1-yl)butan-1-one | 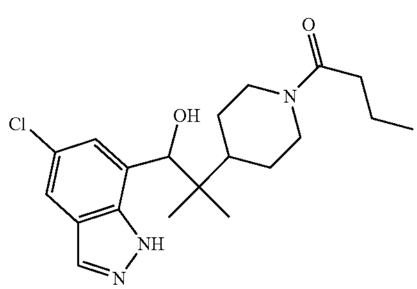 [SMILES: CCCC(=O)N1CCC(C(C)(C)C(O)c2cc(Cl)cc3cn[nH]c23)CC1] | 378.3 |

TABLE 1-continued

| Compound Number | Compound Name | Compound Structure | (MH)+ |
|---|---|---|---|
| P-0461 | 1-(4-(1-(5-chloro-1H-indazol-7-yl)-1-hydroxy-2-methylpropan-2-yl)piperidin-1-yl)-2-hydroxyethan-1-one | 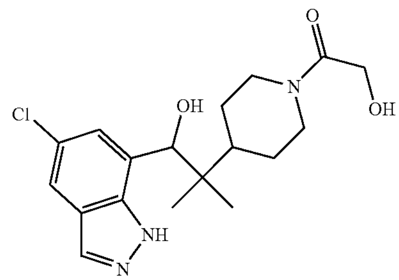 [SMILES: CC(C)(C1CCN(C(=O)CO)CC1)C(O)c1cc(Cl)cc2cn[nH]c12] | 366.3 |
| P-0462 | 4-(2-(5-chloro-1H-indazol-7-yl)-1,1-difluoro-2-hydroxyethyl)-N-(tetrahydro-2H-pyran-4-yl)piperidine-1-carboxamide | 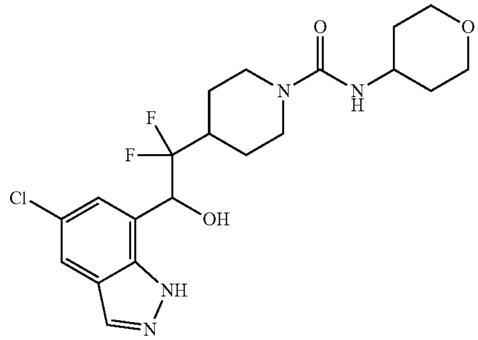 [SMILES: O=C(NC1CCOCC1)N1CCC(C(F)(F)C(O)c2cc(Cl)cc3cn[nH]c23)CC1] | 443.1 |
| P-0463 | 4-(2-(5-chloro-1H-indazol-7-yl)-1,1-difluoro-2-hydroxyethyl)-N-(1,1-dioxidotetrahydro-2H-thiopyran-4-yl)piperidine-1-carboxamide | 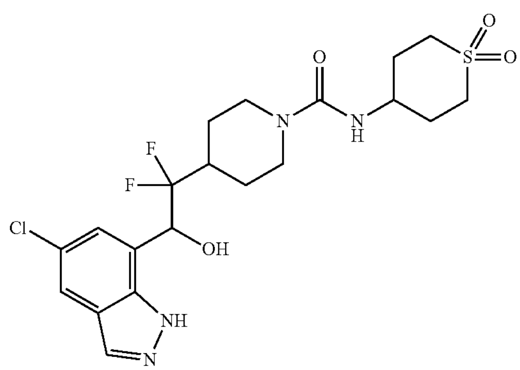 [SMILES: O=C(NC1CCS(=O)(=O)CC1)N1CCC(C(F)(F)C(O)c2cc(Cl)cc3cn[nH]c23)CC1] | 491.1 |
| P-0464 | 4-(2-(5-chloro-1H-indazol-7-yl)-1,1-difluoro-2-hydroxyethyl)-N-(oxetan-3-yl)piperidine-1-carboxamide | 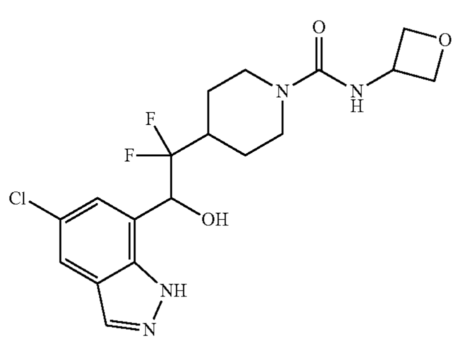 [SMILES: O=C(NC1COC1)N1CCC(C(F)(F)C(O)c2cc(Cl)cc3cn[nH]c23)CC1] | 415.1 |

TABLE 1-continued

| Compound Number | Compound Name | Compound Structure | (MH)+ |
|---|---|---|---|
| P-0465 | 4-(2-(5-chloro-1H-indazol-7-yl)-1,1-difluoro-2-hydroxyethyl)-N-((1-hydroxycyclopropyl)methyl)piperidine-1-carboxamide | 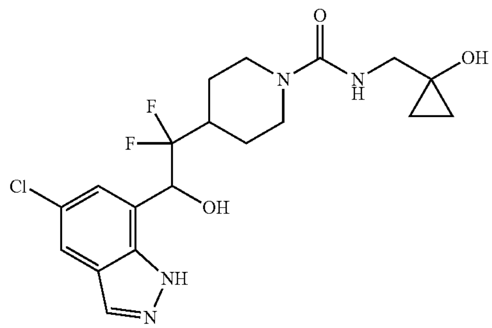 [SMILES: O=C(NCC1(O)CC1)N1CCC(C(F)(F)C(O)c2cc(Cl)cc3cn[nH]c23)CC1] | 429.1 |
| P-0466 | 4-(2-(5-chloro-1H-indazol-7-yl)-1,1-difluoro-2-hydroxyethyl)-N-(2-hydroxy-2-methylpropyl)piperidine-1-carboxamide | 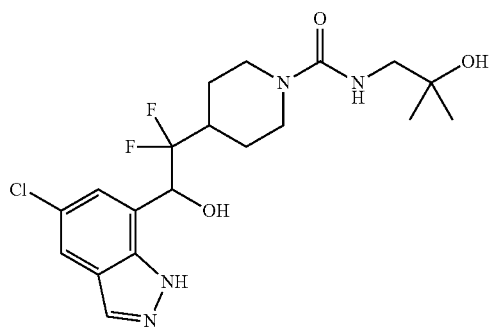 [SMILES: CC(C)(O)CNC(=O)N1CCC(C(F)(F)C(O)c2cc(Cl)cc3cn[nH]c23)CC1] | 431.1 |
| P-0467 | 4-(2-(5-chloro-1H-indazol-7-yl)-1,1-difluoro-2-hydroxyethyl)-N-((1,1-dioxidotetrahydro-2H-thiopyran-4-yl)methyl)piperidine-1-carboxamide | 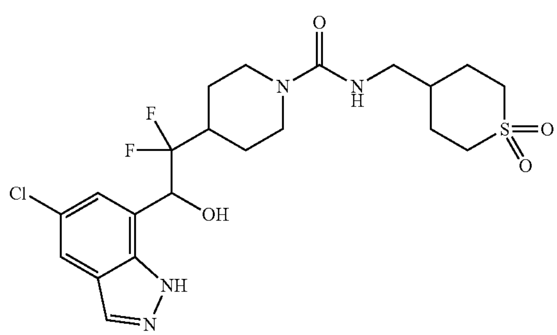 [SMILES: O=C(NCC1CCS(=O)(=O)CC1)N1CCC(C(F)(F)C(O)c2cc(Cl)cc3cn[nH]c23)CC1] | 505.1 |
| P-0468 | 4-(2-(5-chloro-1H-indazol-7-yl)-1,1-difluoro-2-hydroxyethyl)-N-((tetrahydro-2H-pyran-4-yl)methyl)piperidine-1-carboxamide | 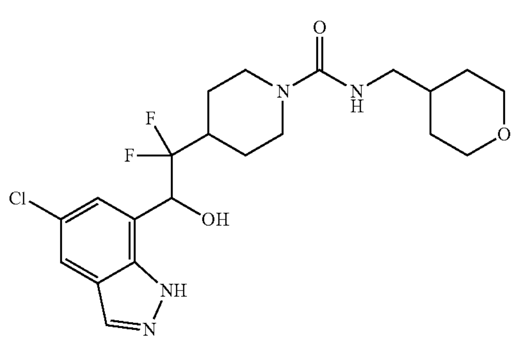 [SMILES: O=C(NCC1CCOCC1)N1CCC(C(F)(F)C(O)c2cc(Cl)cc3cn[nH]c23)CC1] | 457.1 |

TABLE 1-continued

| Compound Number | Compound Name | Compound Structure | (MH)+ |
|---|---|---|---|
| P-0469 | tert-butyl 4-(2-(5-chloro-1H-indazol-7-yl)-1,1-difluoro-2-hydroxyethyl)piperidine-1-carboxylate | 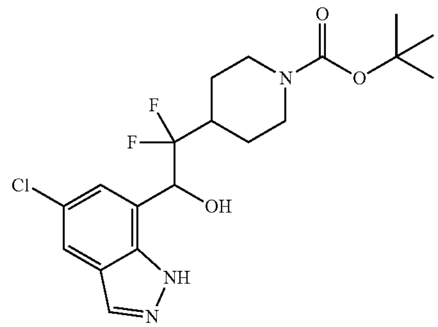 [SMILES: CC(C)(C)OC(=O)N1CCC(C(F)(F)C(O)c2cc(Cl)cc3cn[nH]c23)CC1] | 414.0 (MH)− |
| P-0470 | 4-(1-(5-chloro-1H-indazol-7-yl)-1-hydroxy-2-methylpropan-2-yl)-N-(thiophen-2-yl)piperidine-1-carboxamide | 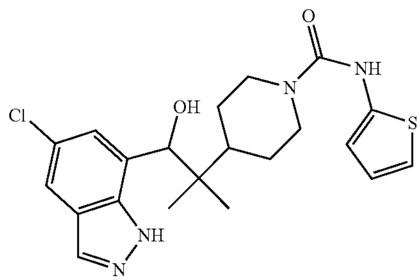 [SMILES: CC(C)(C1CCN(C(=O)Nc2cccs2)CC1)C(O)c1cc(Cl)cc2cn[nH]c12] | 433.3 |
| P-0471 | 4-(1-(5-chloro-1H-indazol-7-yl)-1-hydroxy-2-methylpropan-2-yl)-N-((methylsulfonyl)methyl)piperidine-1-carboxamide | 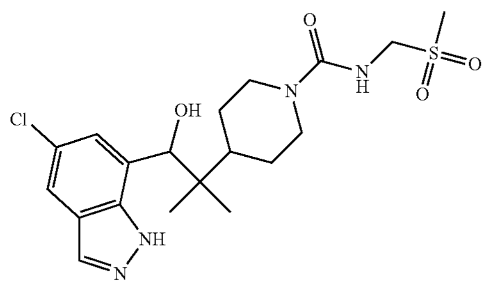 [SMILES: CC(C)(C1CCN(C(=O)NCS(C)(=O)=O)CC1)C(O)c1cc(Cl)cc2cn[nH]c12] | 443.5 |
| P-0472 | 4-(1-(5-chloro-1H-indazol-7-yl)-1-hydroxy-2-methylpropan-2-yl)-N-(3,3,3-trifluoropropyl)piperidine-1-carboxamide | 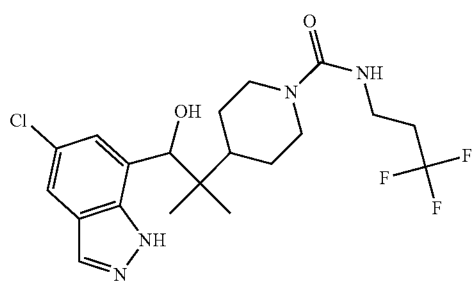 [SMILES: CC(C)(C1CCN(C(=O)NCCC(F)(F)F)CC1)C(O)c1cc(Cl)cc2cn[nH]c12] | 447.1 |
| P-0473 | 4-(1-(5-chloro-1H-indazol-7-yl)-1-hydroxy-2-methylpropan-2-yl)-N-(cyclopropylmethyl)piperidine-1-carboxamide | 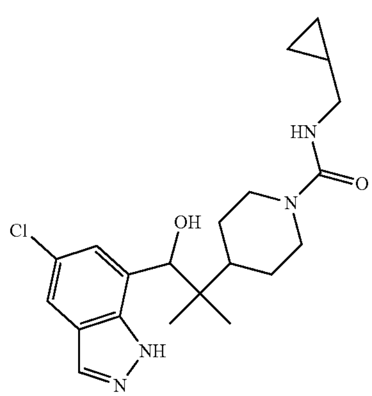 [SMILES: CC(C)(C1CCN(C(=O)NCC2CC2)CC1)C(O)c1cc(Cl)cc2cn[nH]c12] | 405.4 |

TABLE 1-continued

| Compound Number | Compound Name | Compound Structure | (MH)+ |
|---|---|---|---|
| P-0474 | (4-(1-(5-chloro-1H-indazol-7-yl)-1-hydroxy-2-methylpropan-2-yl)piperidin-1-yl)(2,2,3,3-tetramethylcyclopropyl)methanone | 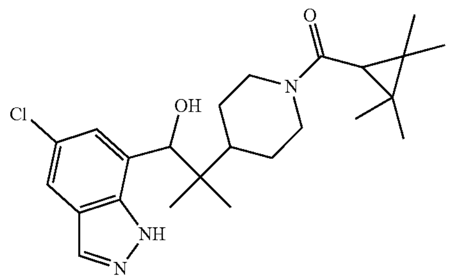 [SMILES: CC(C)(C1CCN(C(=O)C2C(C)(C)C2(C)C)CC1)C(O)c1cc(Cl)cc2cn[nH]c12] | 432.4 |
| P-0475 | 4-(1-(5-chloro-1H-indazol-7-yl)-1-hydroxy-2-methylpropan-2-yl)-N-(2-hydroxy-2-methylpropyl)piperidine-1-carboxamide | 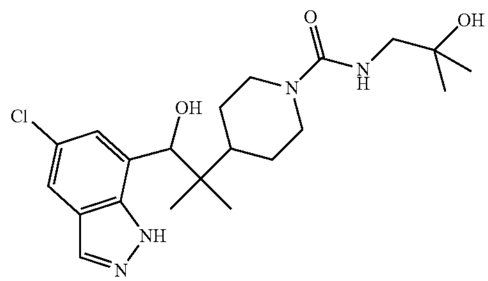 [SMILES: CC(C)(O)CNC(=O)N1CCC(C(C)(C)C(O)c2cc(Cl)cc3cn[nH]c23)CC1] | 423.4 |
| P-0476 | 4-(1-(5-chloro-1H-indazol-7-yl)-1-hydroxy-2-methylpropan-2-yl)-N-(2-hydroxyethyl)piperidine-1-carboxamide | 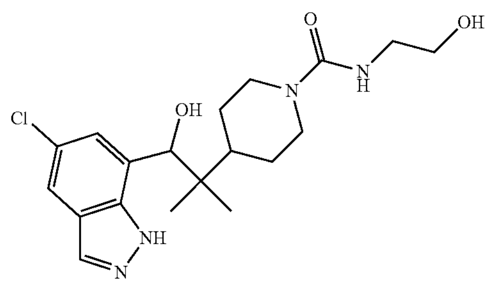 [SMILES: CC(C)(C1CCN(C(=O)NCCO)CC1)C(O)c1cc(Cl)cc2cn[nH]c12] | 395.2 |
| P-0477 | 4-(1-(5-chloro-1H-indazol-7-yl)-1-hydroxy-2-methylpropan-2-yl)-N-(pyridin-2-ylmethyl)piperidine-1-carboxamide | 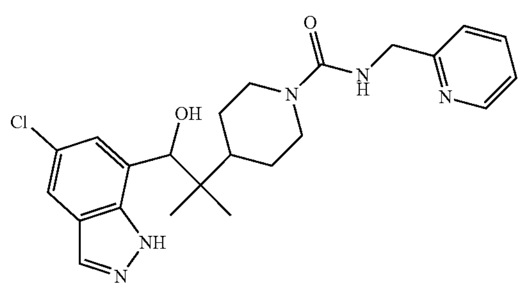 [SMILES: CC(C)(C1CCN(C(=O)NCc2ccccn2)CC1)C(O)c1cc(Cl)cc2cn[nH]c12] | 442.3 |
| P-0478 | 4-(1-(5-chloro-1H-indazol-7-yl)-1-hydroxy-2-methylpropan-2-yl)-N-((S)-1-(pyridin-2-yl)ethyl)piperidine-1-carboxamide | 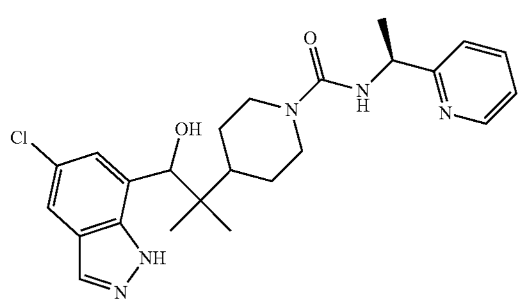 [SMILES: C[C@H](NC(=O)N1CCC(C(C)(C)C(O)c2cc(Cl)cc3cn[nH]c23)CC1)c1ccccn1] | 456.4 |

TABLE 1-continued

| Compound Number | Compound Name | Compound Structure | (MH)+ |
|---|---|---|---|
| P-0479 | 4-(1-(5-chloro-1H-indazol-7-yl)-1-hydroxy-2-methylpropan-2-yl)-N-((R)-1-(pyridin-2-yl)ethyl)piperidine-1-carboxamide | 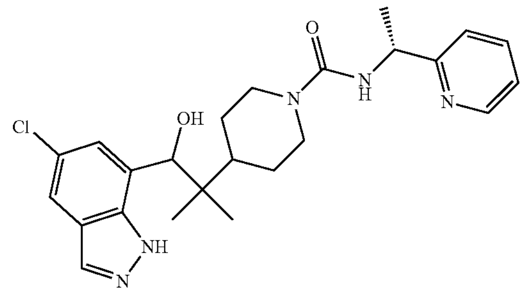 [SMILES: C[C@@H](NC(=O)N1CCC(C(C)(C)C(O)c2cc(Cl)cc3cn[nH]c23)CC1)c1ccccn1] | 456.4 |
| P-0480 | 1-(4-(2-(5-chloro-1H-indazol-7-yl)-1,1-difluoro-2-hydroxyethyl)piperidin-1-yl)-2-(tetrahydro-2H-pyran-4-yl)ethan-1-one | 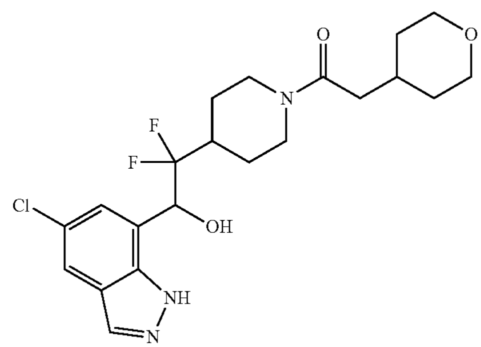 | 442.1 |
| P-0481 | 1-(4-(2-(5-chloro-1H-indazol-7-yl)-1,1-difluoro-2-hydroxyethyl)piperidin-1-yl)-2-(1,1-dioxidotetrahydro-2H-thiopyran-4-yl)ethan-1-one | 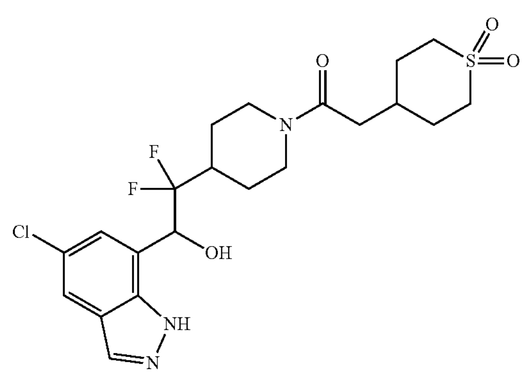 [SMILES: O=C(CC1CCS(=O)(=O)CC1)N1CCC(C(F)(F)C(O)c2cc(Cl)cc3cn[nH]c23)CC1] | 490.1 |
| P-0482 | 4-(2-(5-chloro-1H-indazol-7-yl)-1,1-difluoro-2-hydroxyethyl)-N-(oxetan-3-ylmethyl)piperidine-1-carboxamide | 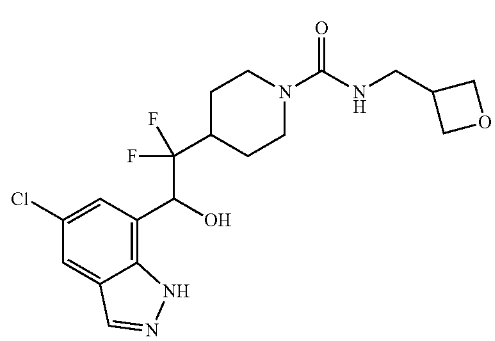 [SMILES: O=C(NCC1COC1)N1CCC(C(F)(F)C(O)c2cc(Cl)cc3cn[nH]c23)CC1] | 429.1 |

TABLE 1-continued

| Compound Number | Compound Name | Compound Structure | (MH)+ |
|---|---|---|---|
| P-0483 | 4-(2-(5-chloro-1H-indazol-7-yl)-1,1-difluoro-2-hydroxyethyl)-N-(4-cyanophenyl)piperidine-1-carboxamide | 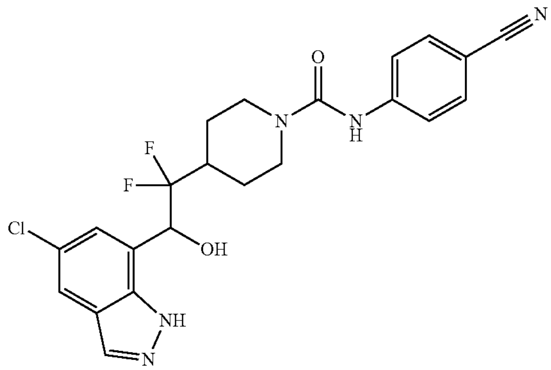 [SMILES: N#Cc1ccc(NC(=O)N2CCC(C(F)(F)C(O)c3cc(Cl)cc4cn[nH]c34)CC2)cc1] | 460.0 |
| P-0484 | 4-(2-(5-chloro-1H-indazol-7-yl)-1,1-difluoro-2-hydroxyethyl)-N-(4-chlorophenyl)piperidine-1-carboxamide | 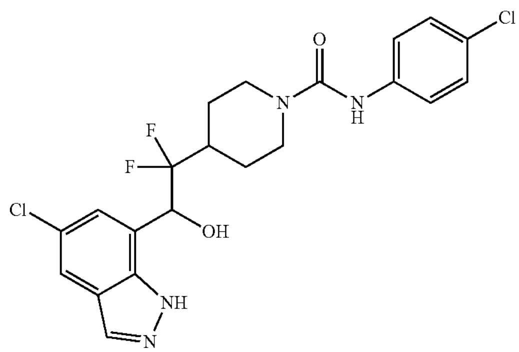 [SMILES: O=C(Nc1ccc(Cl)cc1)N1CCC(C(F)(F)C(O)c2cc(Cl)cc3cn[nH]c23)CC1] | 469.0 |
| P-0485 | 1-(4-(2-(5-chloro-1H-indazol-7-yl)-1,1-difluoro-2-hydroxyethyl)piperidin-1-yl)-2-(1,1-dioxidothiomorpholino)ethan-1-one | 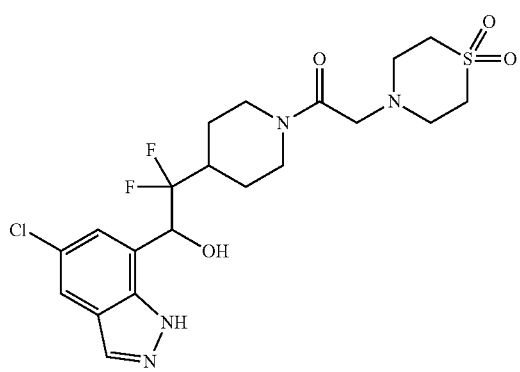 | 491.1 |
| P-0486 | 1-(4-(1-(5-chloro-1H-indazol-7-yl)-1-hydroxy-2-methylpropan-2-yl)piperidin-1-yl)-2-(1,1-dioxidoisothiazolidin-2-yl)ethan-1-one | 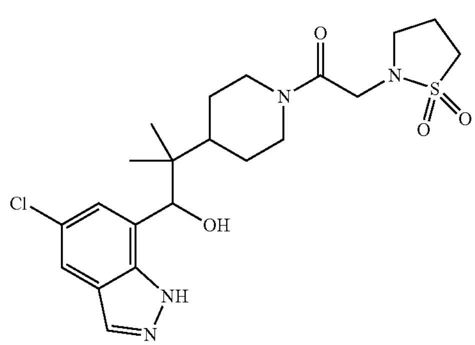 [SMILES: CC(C)(C1CCN(C(=O)CN2CCCS2(=O)=O)CC1)C(O)c1cc(Cl)cc2cn[nH]c12] | 469.1 |

TABLE 1-continued

| Compound Number | Compound Name | Compound Structure | (MH)+ |
|---|---|---|---|
| P-0487 | 1-(4-(1-(5-chloro-1H-indazol-7-yl)-1-hydroxy-2-methylpropan-2-yl)piperidin-1-yl)-2-(1,1-dioxidothiomorpholino)ethan-1-one | 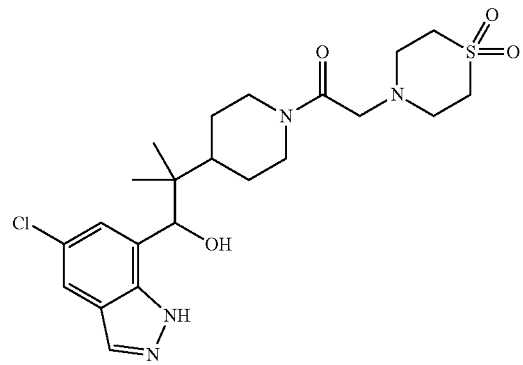 [SMILES: CC(C)(C1CCN(C(=O)CN2CCS(=O)(=O)CC2)CC1)C(O)c1cc(Cl)cc2cn[nH]c12] | 483.2 |
| P-0488 | 4-(2-(5-chloro-1H-indazol-7-yl)-1,1-difluoro-2-hydroxyethyl)-N-(3-chlorophenyl)piperidine-1-carboxamide | 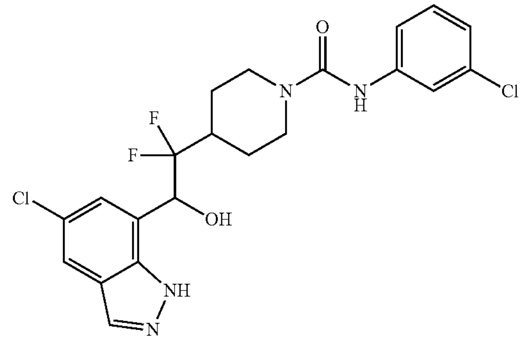 [SMILES: O=C(Nc1cccc(Cl)c1)N1CCC(C(F)(F)C(O)c2cc(Cl)cc3cn[nH]c23)CC1] | 469.0 |
| P-0489 | 1-(4-(2-(5-chloro-1H-indazol-7-yl)-1,1-difluoro-2-hydroxyethyl)piperidin-1-yl)-2-(1,1-dioxidoisothiazolidin-2-yl)ethan-1-one | 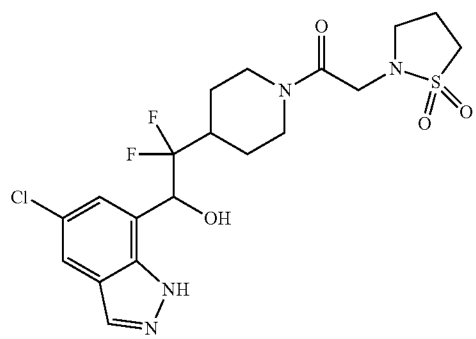 [SMILES: O=C(CN1CCCS1(=O)=O)N1CCC(C(F)(F)C(O)c2cc(Cl)cc3cn[nH]c23)CC1] | 477.1 |
| P-0490 | tert-butyl 4-(2-(5,6-dihydro-1H-cyclobuta[f]indazol-7-yl)-1,1-difluoro-2-hydroxyethyl)piperidine-1-carboxylate | 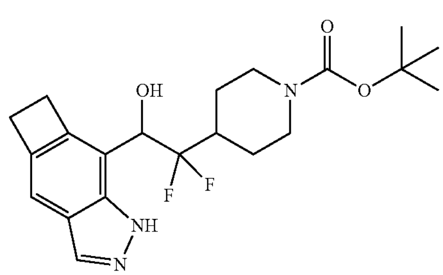 [SMILES: CC(C)(C)OC(=O)N1CCC(C(F)(F)C(O)c2c3c(cc4cn[nH]c24)CC3)CC1] | 408.1 |

TABLE 1-continued

| Compound Number | Compound Name | Compound Structure | (MH)+ |
|---|---|---|---|
| P-0491 | 4-(1-(5-chloro-1H-indazol-7-yl)-1-hydroxy-2-methylpropan-2-yl)-N-(4-((4-methylpiperazin-1-yl)methyl)phenyl)piperidine-1-carboxamide | 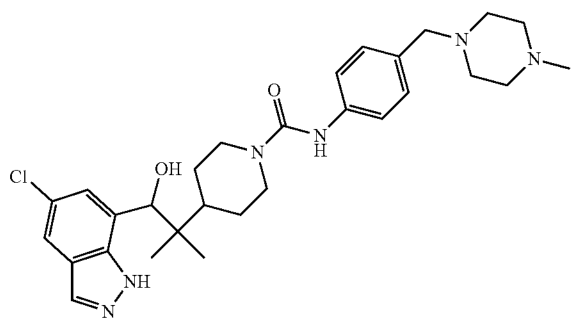 [SMILES: CN1CCN(Cc2ccc(NC(=O)N3CCC(C(C)(C)C(O)c4cc(Cl)cc5cn[nH]c45)CC3)cc2)CC1] | 539.5 |
| P-0492 | 4-(1-(5-chloro-1H-indazol-7-yl)-1-hydroxy-2-methylpropan-2-yl)-N-(2-(1,1-dioxidoisothiazolidin-2-yl)ethyl)piperidine-1-carboxamide | 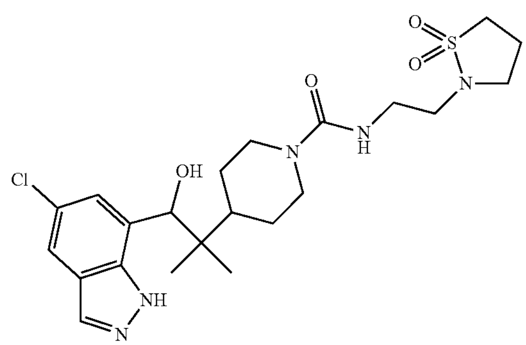 [SMILES: CC(C)(C1CCN(C(=O)NCCN2CCCS2(=O)=O)CC1)C(O)c1cc(Cl)cc2cn[nH]c12] | 498.4 |
| P-0493 | 4-(1-(5-chloro-1H-indazol-7-yl)-1-hydroxy-2-methylpropan-2-yl)-N-(2-(methylsulfonamido)ethyl)piperidine-1-carboxamide | 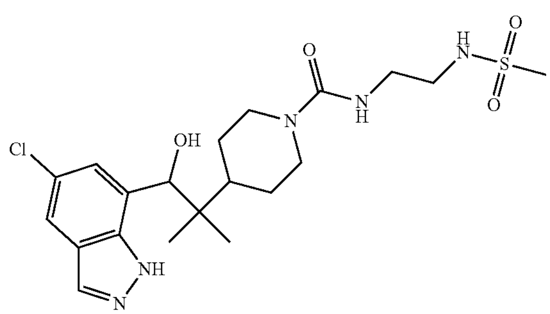 [SMILES: CC(C)(C1CCN(C(=O)NCCNS(C)(=O)=O)CC1)C(O)c1cc(Cl)cc2cn[nH]c12] | 472.3 |
| P-0494 | 1-(4-(2-(5-chloro-1H-indazol-7-yl)-1,1-difluoro-2-hydroxyethyl)piperidin-1-yl)-2-(4-chlorophenyl)ethan-1-one | 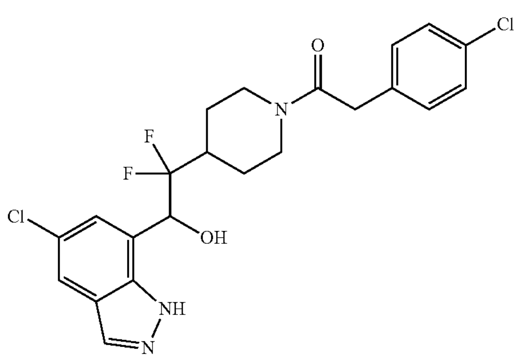 [SMILES: O=C(Cc1ccc(Cl)cc1)N1CCC(C(F)(F)C(O)c2cc(Cl)cc3cn[nH]c23)CC1] | 468.1 |

TABLE 1-continued

| Compound Number | Compound Name | Compound Structure | (MH)+ |
|---|---|---|---|
| P-0495 | 1-(4-(2-(5-chloro-1H-indazol-7-yl)-1,1-difluoro-2-hydroxyethyl)piperidin-1-yl)-2-(6-chloropyridin-3-yl)ethan-1-one | 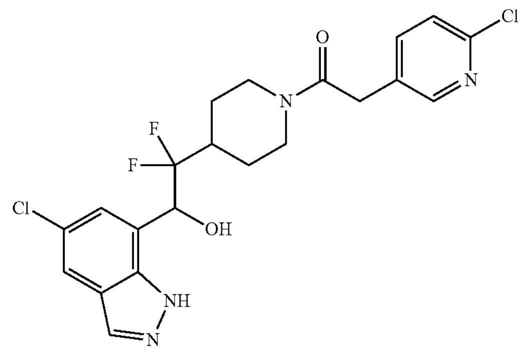 [SMILES: O=C(Cc1ccc(Cl)nc1)N1CCC(C(F)(F)C(O)c2cc(Cl)cc3cn[nH]c23)CC1] | 469.1 |
| P-0496 | 1-(4-(2-(5-chloro-1H-indazol-7-yl)-1,1-difluoro-2-hydroxyethyl)piperidin-1-yl)-2-(4-methoxyphenyl)ethan-1-one | 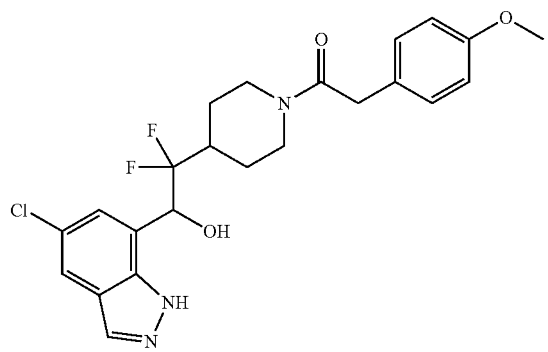 | 464.1 |
| P-0497 | (S)-1-(4-(1-(5-chloro-1H-indazol-7-yl)-1-hydroxy-2-methylpropan-2-yl)piperidin-1-yl)-2-(1,1-dioxidothiomorpholino)ethan-1-one | 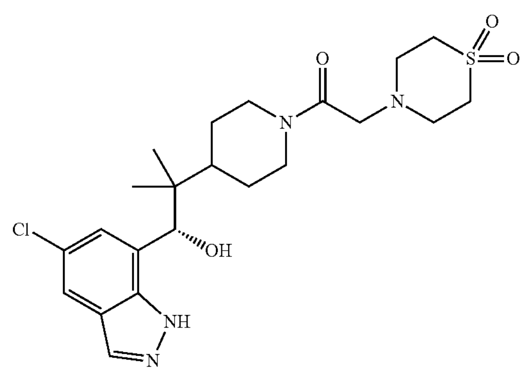 [SMILES: CC(C)(C1CCN(C(=O)CN2CCS(=O)(=O)CC2)CC1)[C@H](O)c1cc(Cl)cc2cn[nH]c12] | 483.1 |
| P-0498 | (S)-(4-(1-(5-chloro-1H-indazol-7-yl)-1-hydroxy-2-methylpropan-2-yl)piperidin-1-yl)(cyclobutyl)methanone | 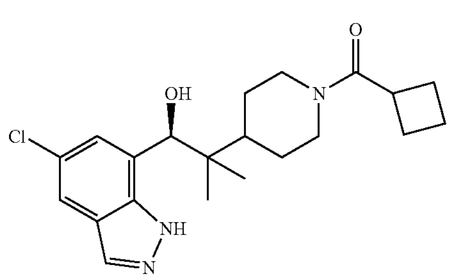 [SMILES: CC(C)(C1CCN(C(=O)C2CCC2)CC1)[C@H](O)c1cc(Cl)cc2cn[nH]c12] | 390.2 |

TABLE 1-continued

| Compound Number | Compound Name | Compound Structure | (MH)+ |
|---|---|---|---|
| P-0499 | (S)-4-(1-(5-chloro-1H-indazol-7-yl)-1-hydroxy-2-methylpropan-2-yl)-N-(2-hydroxyethyl)piperidine-1-carboxamide | 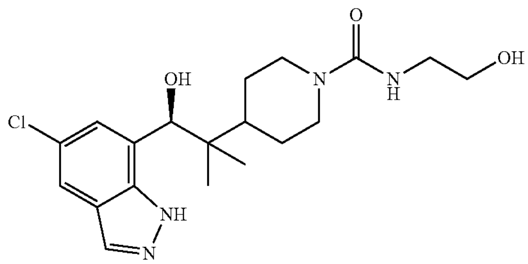 [SMILES: CC(C)(C1CCN(C(=O)NCCO)CC1)[C@H](O)c1cc(Cl)cc2cn[nH]c12] | 395.5 |
| P-0500 | (S)-1-(4-(1-(5-chloro-1H-indazol-7-yl)-1-hydroxy-2-methylpropan-2-yl)piperidin-1-yl)-2-(1,1-dioxidothiomorpholino)ethan-1-one | 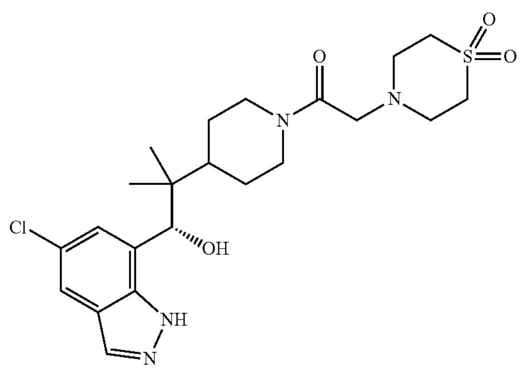 [SMILES: CC(C)(C1CCN(C(=O)CN2CCS(=O)(=O)CC2)CC1)[C@H](O)c1cc(Cl)cc2cn[nH]c12] | 483.1 |
| P-0501 | (S)-1-(4-(1-(5-chloro-1H-indazol-7-yl)-1-hydroxy-2-methylpropan-2-yl)piperidin-1-yl)-2-morpholinoethan-1-one | 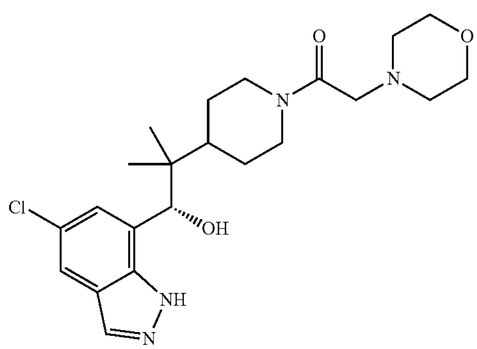 | 435.2 |
| P-0502 | (S)-1-(4-(1-(5-chloro-1H-indazol-7-yl)-1-hydroxy-2-methylpropan-2-yl)piperidin-1-yl)-2-(1,1-dioxidotetrahydro-2H-thiopyran-4-yl)ethan-1-one | 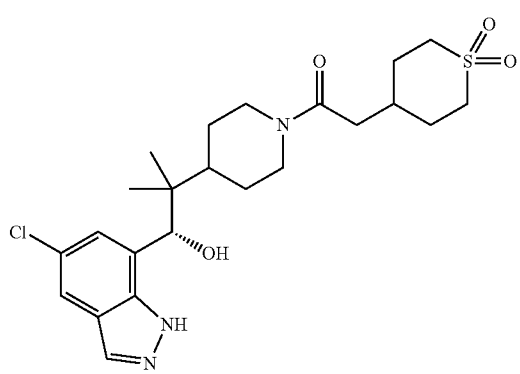 [SMILES: CC(C)(C1CCN(C(=O)CC2CCS(=O)(=O)CC2)CC1)[C@H](O)c1cc(Cl)cc2cn[nH]c12] | 482.1 |

TABLE 1-continued

| Compound Number | Compound Name | Compound Structure | (MH)+ |
|---|---|---|---|
| P-0503 | (S)-4-(1-(5-chloro-6-fluoro-1H-indazol-7-yl)-1-hydroxy-2-methylpropan-2-yl)-N-(4-cyanophenyl)piperidine-1-carboxamide | 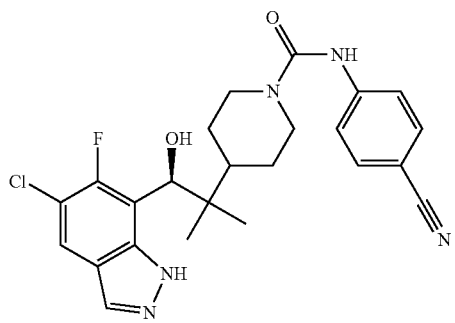 [SMILES: CC(C)(C1CCN(C(=O)Nc2ccc(C#N)cc2)CC1)[C@H](O)c1c(F)c(Cl)cc2cn[nH]c12] | 470.2 |
| P-0504 | (S)-(4-(1-(5-chloro-6-fluoro-1H-indazol-7-yl)-1-hydroxy-2-methylpropan-2-yl)piperidin-1-yl)(cyclopropyl)methanone | 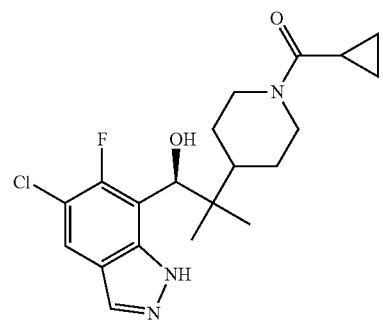 [SMILES: CC(C)(C1CCN(C(=O)C2CC2)CC1)[C@H](O)c1c(F)c(Cl)cc2cn[nH]c12] | 394.0 |
| P-0505 | (S)-3-(4-(1-(5-chloro-6-fluoro-1H-indazol-7-yl)-1-hydroxy-2-methylpropan-2-yl)piperidin-1-yl)-3-oxopropanenitrile | 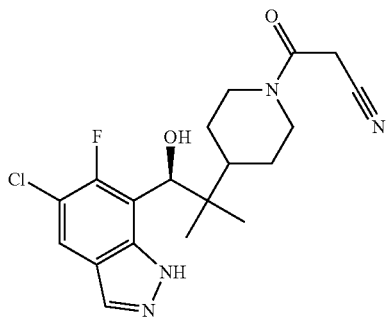 [SMILES: CC(C)(C1CCN(C(=O)CC#N)CC1)[C@H](O)c1c(F)c(Cl)cc2cn[nH]c12] | 393.1 |
| P-0506 | (S)-1-(4-(1-(5-chloro-6-fluoro-1H-indazol-7-yl)-1-hydroxy-2-methylpropan-2-yl)piperidin-1-yl)-2-methoxyethan-1-one | 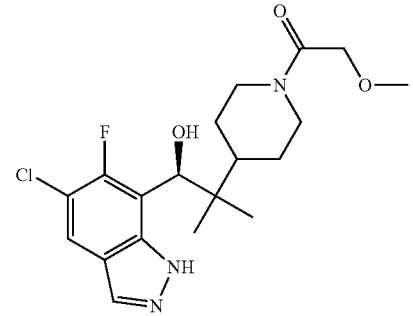 [SMILES: COCC(=O)N1CCC(C(C)(C)[C@H](O)c2c(F)c(Cl)cc3cn[nH]c23)CC1] | 397.9 |

TABLE 1-continued

| Compound Number | Compound Name | Compound Structure | (MH)+ |
|---|---|---|---|
| P-0507 | (S)-(4-(1-(5-chloro-6-fluoro-1H-indazol-7-yl)-1-hydroxy-2-methylpropan-2-yl)piperidin-1-yl)(tetrahydro-2H-pyran-4-yl)methanone | 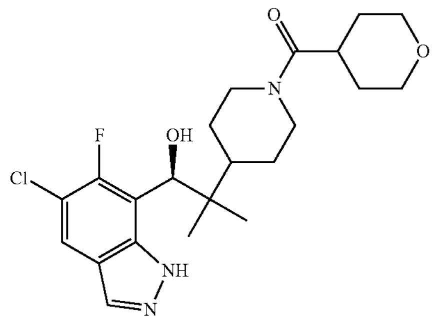 [SMILES: CC(C)(C1CCN(C(=O)C2CCOCC2)CC1)[C@H](O)c1c(F)c(Cl)cc2cn[nH]c12] | 438.1 |
| P-0508 | (S)-4-(1-(5-chloro-6-fluoro-1H-indazol-7-yl)-1-hydroxy-2-methylpropan-2-yl)-N-methylpiperidine-1-carboxamide | 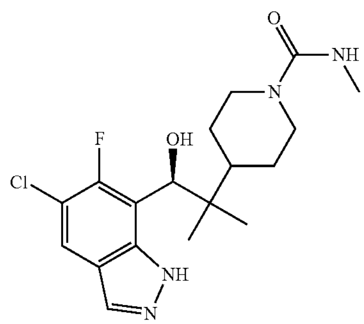 [SMILES: CNC(=O)N1CCC(C(C)(C)[C@H](O)c2c(F)c(Cl)cc3cn[nH]c23)CC1] | 383.1 |
| P-0509 | (S)-4-(1-(5-chloro-6-fluoro-1H-indazol-7-yl)-1-hydroxy-2-methylpropan-2-yl)-N-cyclopropylpiperidine-1-carboxamide | 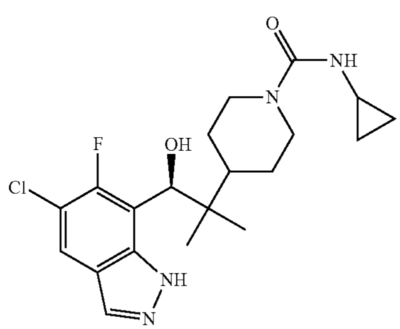 [SMILES: CC(C)(C1CCN(C(=O)NC2CC2)CC1)[C@H](O)c1c(F)c(Cl)cc2cn[nH]c12] | 409.3 |
| P-0510 | (S)-4-(1-(5-chloro-6-fluoro-1H-indazol-7-yl)-1-hydroxy-2-methylpropan-2-yl)-N-(2-methoxyethyl)piperidine-1-carboxamide | 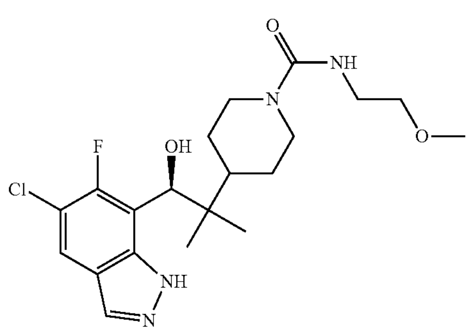 [SMILES: COCCNC(=O)N1CCC(C(C)(C)[C@H](O)c2c(F)c(Cl)cc3cn[nH]c23)CC1] | 427.0 |

TABLE 1-continued

| Compound Number | Compound Name | Compound Structure | (MH)+ |
|---|---|---|---|
| P-0511 | (S)-4-(1-(5-chloro-6-fluoro-1H-indazol-7-yl)-1-hydroxy-2-methylpropan-2-yl)-N-(2,2,2-trifluoroethyl)piperidine-1-carboxamide | 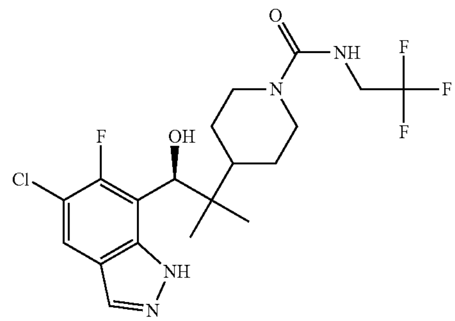 [SMILES: CC(C)(C1CCN(C(=O)NCC(F)(F)F)CC1)[C@H](O)c1c(F)c(Cl)cc2cn[nH]c12] | 451.0 |
| P-0512 | (S)-4-(1-(5-chloro-6-fluoro-1H-indazol-7-yl)-1-hydroxy-2-methylpropan-2-yl)-N-(4-fluorophenyl)piperidine-1-carboxamide | 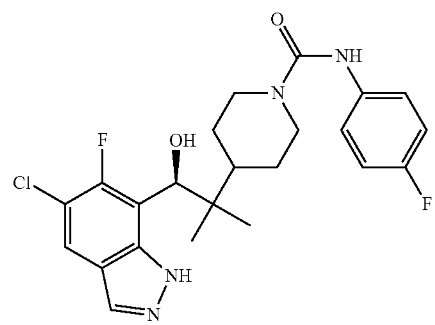 [SMILES: CC(C)(C1CCN(C(=O)Nc2ccc(F)cc2)CC1)[C@H](O)c1c(F)c(Cl)cc2cn[nH]c12] | 463.3 |
| P-0513 | ethyl (S)-(4-(1-(5-chloro-6-fluoro-1H-indazol-7-yl)-1-hydroxy-2-methylpropan-2-yl)piperidine-1-carbonyl)carbamate | 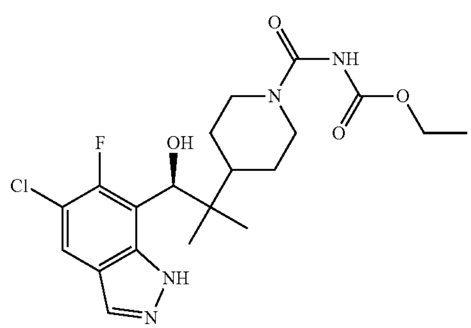 [SMILES: CCOC(=O)NC(=O)N1CCC(C(C)(C)[C@H](O)c2c(F)c(Cl)cc3cn[nH]c23)CC1] | 441.1 |
| P-0514 | (S)-N-benzoyl-4-(1-(5-chloro-6-fluoro-1H-indazol-7-yl)-1-hydroxy-2-methylpropan-2-yl)piperidine-1-carboxamide | 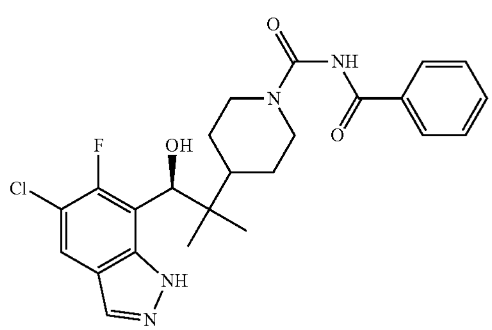 [SMILES: CC(C)(C1CCN(C(=O)NC(=O)c2ccccc2)CC1)[C@H](O)c1c(F)c(Cl)cc2cn[nH]c12] | 473.2 |

TABLE 1-continued

| Compound Number | Compound Name | Compound Structure | (MH)+ |
|---|---|---|---|
| P-0515 | (S)-1-(5-chloro-6-fluoro-1H-indazol-7-yl)-2-methyl-2-(1-(methylsulfonyl)piperidin-4-yl)propan-1-ol | 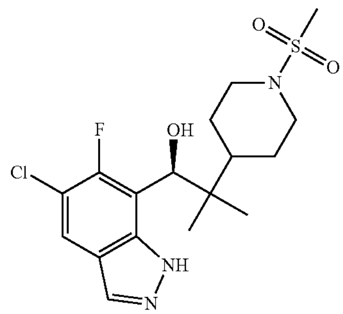 [SMILES: CC(C)(C1CCN(S(C)(=O)=O)CC1)[C@H](O)c1c(F)c(Cl)cc2cn[nH]c12] | 403.9 |
| P-0516 | tert-butyl (R)-4-(2-(5-chloro-1H-indazol-7-yl)-1,1-difluoro-2-hydroxyethyl)piperidine-1-carboxylate | 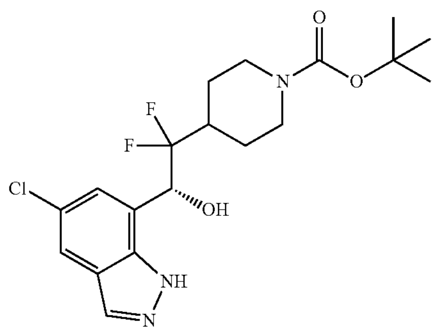 [SMILES: CC(C)(C)OC(=O)N1CCC(C(F)(F)[C@H](O)c2cc(Cl)cc3cn[nH]c23)CC1] | 416.1 |
| P-0517 | tert-butyl (S)-4-(2-(5-chloro-1H-indazol-7-yl)-1,1-difluoro-2-hydroxyethyl)piperidine-1-carboxylate | 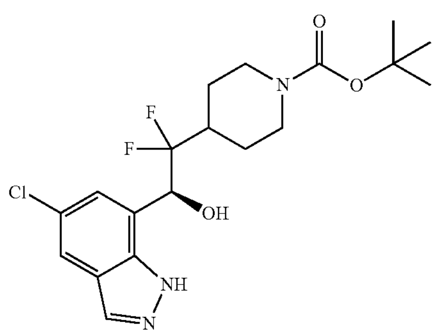 [SMILES: CC(C)(C)OC(=O)N1CCC(C(F)(F)[C@@H](O)c2cc(Cl)cc3cn[nH]c23)CC1] | 416.1 |
| P-0518 | (S)-1-(4-(1-(5-chloro-1H-indazol-7-yl)-1-hydroxy-2-methylpropan-2-yl)piperidin-1-yl)-2-(4-chloro-3-fluorophenyl)ethan-1-one | 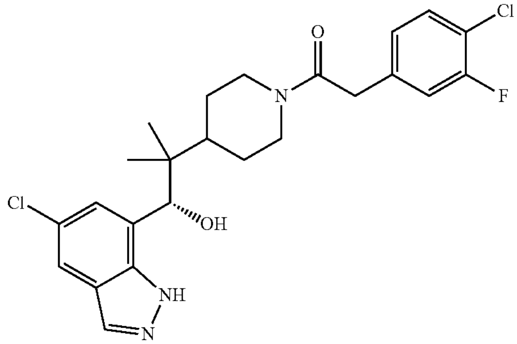 [SMILES: CC(C)(C1CCN(C(=O)Cc2ccc(Cl)c(F)c2)CC1)[C@H](O)c1cc(Cl)cc2cn[nH]c12] | 468.1 |

TABLE 1-continued

| Compound Number | Compound Name | Compound Structure | (MH)+ |
|---|---|---|---|
| P-0519 | (S)-1-(4-(1-(5-chloro-1H-indazol-7-yl)-1-hydroxy-2-methylpropan-2-yl)piperidin-1-yl)-2-(3-chloro-4-fluorophenyl)ethan-1-one | 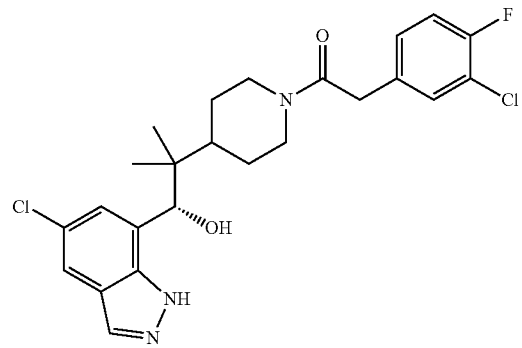 [SMILES: CC(C)(C1CCN(C(=O)Cc2ccc(F)c(Cl)c2)CC1)[C@H](O)c1cc(Cl)cc2cn[nH]c12] | 465.1 |
| P-0520 | 1-(4-(2-(5-chloro-1H-indazol-7-yl)-1,1-difluoro-2-hydroxyethyl)piperidin-1-yl)-2-(3-chlorophenyl)ethan-1-one | 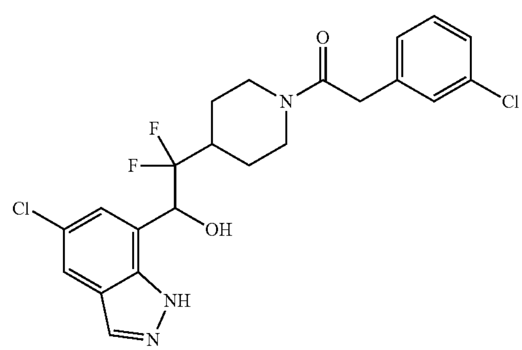 [SMILES: O=C(Cc1cccc(Cl)c1)N1CCC(C(F)(F)C(O)c2cc(Cl)cc3cn[nH]c23)CC1] | 464.2 |
| P-0521 | 1-(4-(2-(5-chloro-1H-indazol-7-yl)-1,1-difluoro-2-hydroxyethyl)piperidin-1-yl)-2-(6-methoxypyridin-3-yl)ethan-1-one | 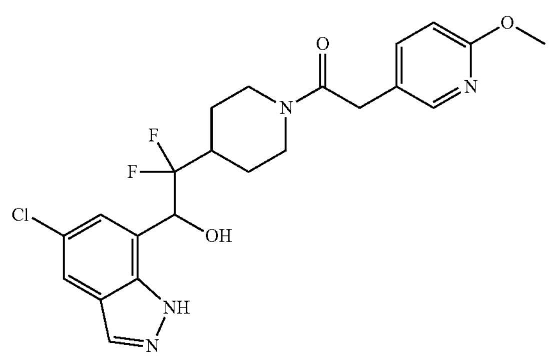 | 486.1 |
| P-0522 | 1-(4-(2-(5-chloro-1H-indazol-7-yl)-1,1-difluoro-2-hydroxyethyl)piperidin-1-yl)-2-(3-methoxyphenyl)ethan-1-one | 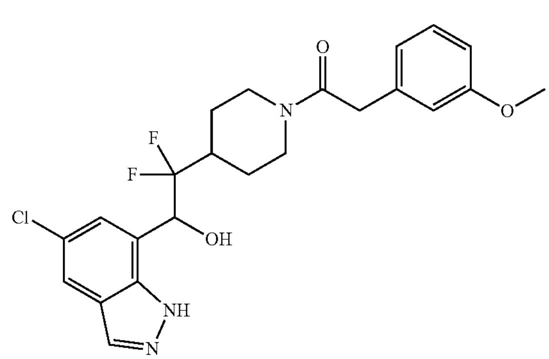 [SMILES: COc1cccc(CC(=O)N2CCC(C(F)(F)C(O)c3cc(Cl)cc4cn[nH]c34)CC2)c1] | 486.1 |

TABLE 1-continued

| Compound Number | Compound Name | Compound Structure | (MH)+ |
|---|---|---|---|
| P-0523 | 1-(4-(2-(5-chloro-1H-indazol-7-yl)-1,1-difluoro-2-hydroxyethyl)piperidin-1-yl)-2-(4-chloro-3-fluorophenyl)ethan-1-one | 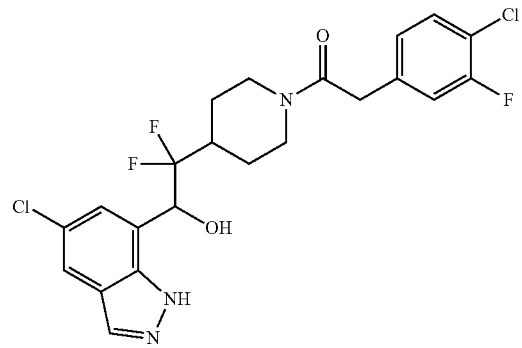 [SMILES: O=C(Cc1ccc(Cl)c(F)c1)N1CCC(C(F)(F)C(O)c2cc(Cl)cc3cn[nH]c23)CC1] | 469.0 |
| P-0524 | 1-(4-(2-(5-chloro-1H-indazol-7-yl)-1,1-difluoro-2-hydroxyethyl)piperidin-1-yl)-2-(3-chloro-4-fluorophenyl)ethan-1-one | 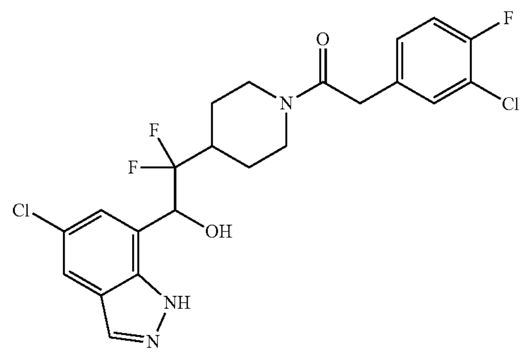 [SMILES: O=C(Cc1ccc(F)c(Cl)c1)N1CCC(C(F)(F)C(O)c2cc(Cl)cc3cn[nH]c23)CC1] | 465.1 |
| P-0525 | 1-(4-(2-(5-chloro-1H-indazol-7-yl)-1,1-difluoro-2-hydroxyethyl)piperidin-1-yl)-2-(2-chloropyridin-4-yl)ethan-1-one | 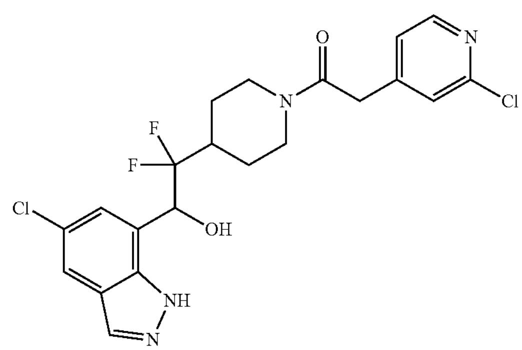 [SMILES: O=C(Cc1ccnc(Cl)c1)N1CCC(C(F)(F)C(O)c2cc(Cl)cc3cn[nH]c23)CC1] | 408.2 |
| P-0526 | 1-(4-(2-(5-chloro-1H-indazol-7-yl)-1,1-difluoro-2-hydroxyethyl)piperidin-1-yl)-2-(2-methoxypyridin-4-yl)ethan-1-one | 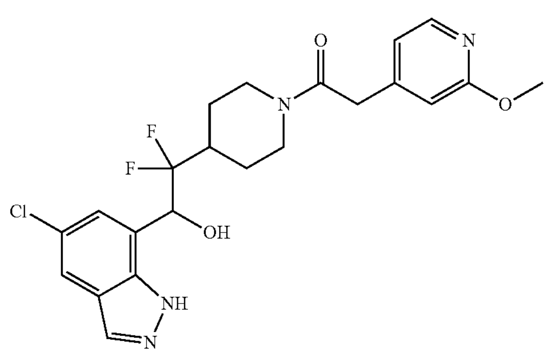 [SMILES: COc1cc(CC(=O)N2CCC(C(F)(F)C(O)c3cc(Cl)cc4cn[nH]c34)CC2)ccn1] | 478.1 |

TABLE 1-continued

| Compound Number | Compound Name | Compound Structure | (MH)+ |
|---|---|---|---|
| P-0527 | tert-butyl (R)-4-(2-(5,6-dihydro-1H-cyclobuta[f]indazol-7-yl)-1,1-difluoro-2-hydroxyethyl)piperidine-1-carboxylate | 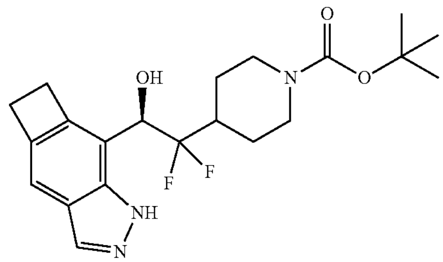 [SMILES: CC(C)(C)OC(=O)N1CCC(C(F)(F)[C@H](O)c2c3c(cc4cn[nH]c24)CC3)CC1] | 478.05 |
| P-0528 | tert-butyl (S)-4-(2-(5,6-dihydro-1H-cyclobuta[f]indazol-7-yl)-1,1-difluoro-2-hydroxyethyl)piperidine-1-carboxylate | 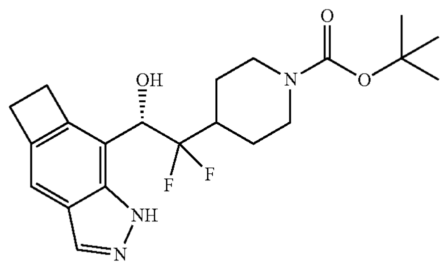 | 408.2 |
| P-0529 | (S)-(4-(1-(5-chloro-1H-indazol-7-yl)-1-hydroxy-2-methylpropan-2-yl)piperidin-1-yl)(cyclopropyl)methanone | 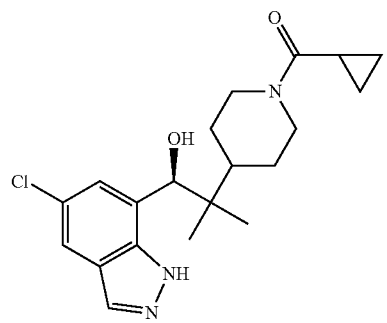 [SMILES: CC(C)(C1CCN(C(=O)C2CC2)CC1)[C@H](O)c1cc(Cl)cc2cn[nH]c12] | 376.2 |
| P-0530 | (S)-1-(4-(1-(5-chloro-1H-indazol-7-yl)-1-hydroxy-2-methylpropan-2-yl)piperidin-1-yl)-2-cyclopropylethan-1-one | 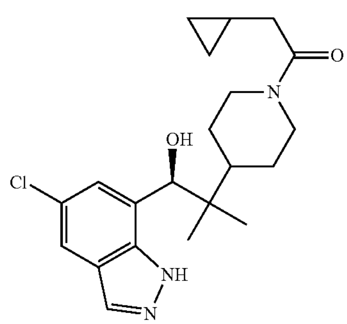 [SMILES: CC(C)(C1CCN(C(=O)CC2CC2)CC1)[C@H](O)c1cc(Cl)cc2cn[nH]c12] | 390.350 1587 |
| P-0531 | (S)-1-(4-(1-(5-chloro-1H-indazol-7-yl)-1-hydroxy-2-methylpropan-2-yl)piperidin-1-yl)-3,3,3-trifluoropropan-1-one | 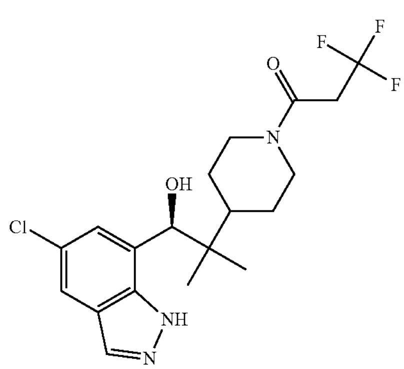 [SMILES: CC(C)(C1CCN(C(=O)CC(F)(F)F)CC1)[C@H](O)c1cc(Cl)cc2cn[nH]c12] | 418.3 |

TABLE 1-continued

| Compound Number | Compound Name | Compound Structure | (MH)+ |
|---|---|---|---|
| P-0532 | (S)-1-(4-(1-(5-chloro-1H-indazol-7-yl)-1-hydroxy-2-methylpropan-2-yl)piperidin-1-yl)-2-(tetrahydro-2H-pyran-4-yl)ethan-1-one | 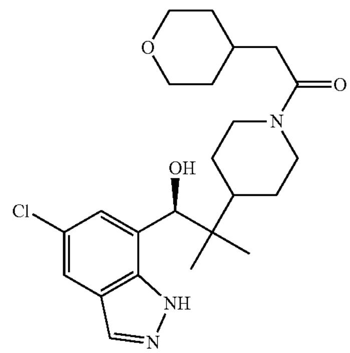 [SMILES: CC(C)(C1CCN(C(=O)CC2CCOCC2)CC1)[C@H](O)c1cc(Cl)cc2cn[nH]c12] | 434.2 |
| P-0533 | (S)-1-(4-(1-(5-chloro-1H-indazol-7-yl)-1-hydroxy-2-methylpropan-2-yl)piperidin-1-yl)-2-methoxyethan-1-one | 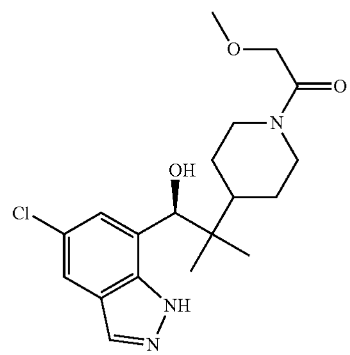 [SMILES: COCC(=O)N1CCC(C(C)(C)[C@H](O)c2cc(Cl)cc3cn[nH]c23)CC1] | 380.1 |
| P-0534 | (S)-3-(4-(1-(5-chloro-1H-indazol-7-yl)-1-hydroxy-2-methylpropan-2-yl)piperidin-1-yl)-3-oxopropanenitrile | 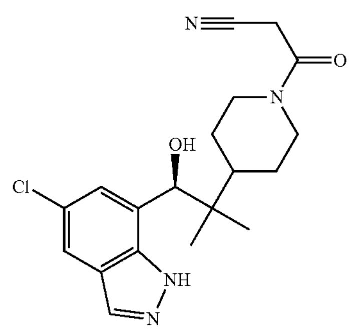 [SMILES: CC(C)(C1CCN(C(=O)CC#N)CC1)[C@H](O)c1cc(Cl)cc2cn[nH]c12] | 375.3 |
| P-0535 | (S)-1-(4-(1-(5-chloro-1H-indazol-7-yl)-1-hydroxy-2-methylpropan-2-yl)piperidin-1-yl)-2-hydroxyethan-1-one | 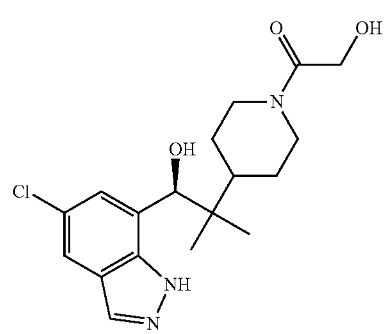 [SMILES: CC(C)(C1CCN(C(=O)CO)CC1)[C@H](O)c1cc(Cl)cc2cn[nH]c12] | 366.3 |

TABLE 1-continued

| Compound Number | Compound Name | Compound Structure | (MH)+ |
|---|---|---|---|
| P-0536 | (S)-(4-(1-(5-chloro-1H-indazol-7-yl)-1-hydroxy-2-methylpropan-2-yl)piperidin-1-yl)(pyridin-3-yl)methanone | 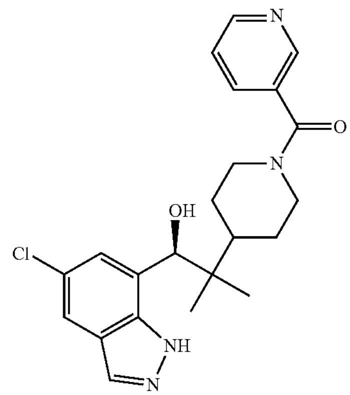 [SMILES: CC(C)(C1CCN(C(=O)c2cccnc2)CC1)[C@H](O)c1cc(Cl)cc2cn[nH]c12] | 413.5 |
| P-0537 | (S)-(4-(1-(5-chloro-1H-indazol-7-yl)-1-hydroxy-2-methylpropan-2-yl)piperidin-1-yl)(6-(trifluoromethyl)pyridin-3-yl)methanone | 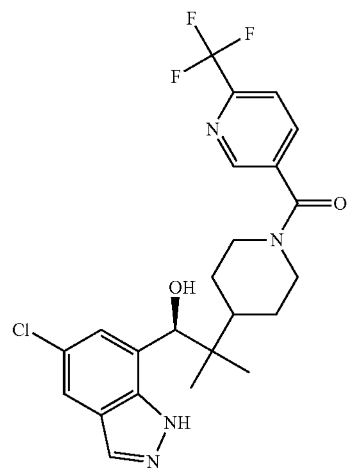 [SMILES: CC(C)(C1CCN(C(=O)c2ccc(C(F)(F)F)nc2)CC1)[C@H](O)c1cc(Cl)cc2cn[nH]c12] | 481.3 |
| P-0538 | (S)-(4-(1-(5-chloro-1H-indazol-7-yl)-1-hydroxy-2-methylpropan-2-yl)piperidin-1-yl)(6-morpholinopyridin-3-yl)methanone | 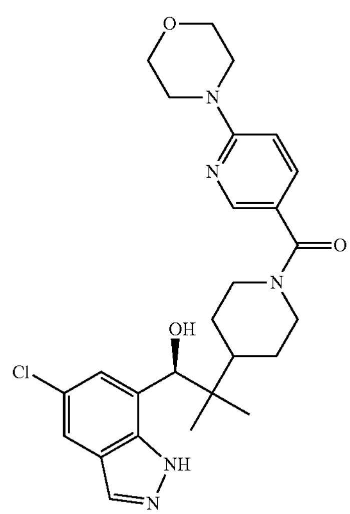 [SMILES: CC(C)(C1CCN(C(=O)c2ccc(N3CCOCC3)nc2)CC1)[C@H](O)c1cc(Cl)cc2cn[nH]c12] | 498.4055176 |

TABLE 1-continued

| Compound Number | Compound Name | Compound Structure | (MH)+ |
|---|---|---|---|
| P-0539 | (S)-(4-(1-(5-chloro-1H-indazol-7-yl)-1-hydroxy-2-methylpropan-2-yl)piperidin-1-yl)(2,2,3,3-tetramethylcyclopropyl)methanone | 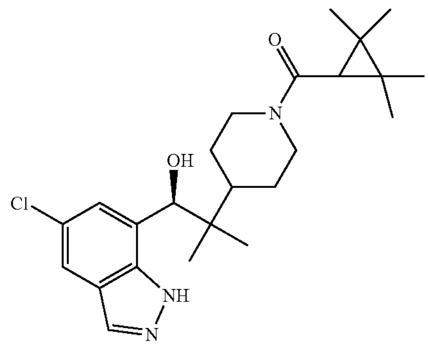 [SMILES: CC(C)(C1CCN(C(=O)C2C(C)(C)C2(C)C)CC1)[C@H](O)c1cc(Cl)cc2cn[nH]c12] | 432.4 |
| P-0540 | methyl (S)-4-(1-(5-chloro-1H-indazol-7-yl)-1-hydroxy-2-methylpropan-2-yl)piperidine-1-carboxylate | 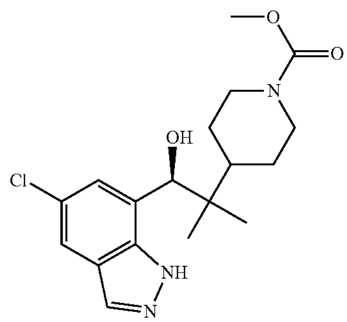 [SMILES: COC(=O)N1CCC(C(C)(C)[C@H](O)c2cc(Cl)cc3cn[nH]c23)CC1] | 366.0 |
| P-0541 | ethyl (S)-4-(1-(5-chloro-1H-indazol-7-yl)-1-hydroxy-2-methylpropan-2-yl)piperidine-1-carboxylate | 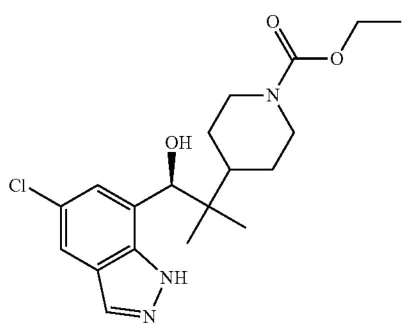 | 380.1 |
| P-0542 | (S)-1-(4-(1-(5-chloro-1H-indazol-7-yl)-1-hydroxy-2-methylpropan-2-yl)piperidin-1-yl)ethan-1-one | 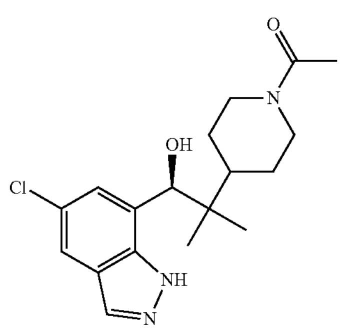 [SMILES: CC(=O)N1CCC(C(C)(C)[C@H](O)c2cc(Cl)cc3cn[nH]c23)CC1] | 350.1 |

TABLE 1-continued

| Compound Number | Compound Name | Compound Structure | (MH)+ |
|---|---|---|---|
| P-0543 | (S)-1-(4-(1-(5-chloro-1H-indazol-7-yl)-1-hydroxy-2-methylpropan-2-yl)piperidin-1-yl)butan-1-one | 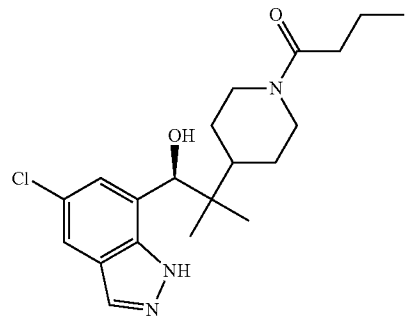 [SMILES: CCCC(=O)N1CCC(C(C)(C)[C@H](O)c2cc(Cl)cc3cn[nH]c23)CC1] | 378.3 |
| P-0544 | (S)-1-(4-(1-(5-chloro-1H-indazol-7-yl)-1-hydroxy-2-methylpropan-2-yl)piperidin-1-yl)-2-methylpropan-1-one | 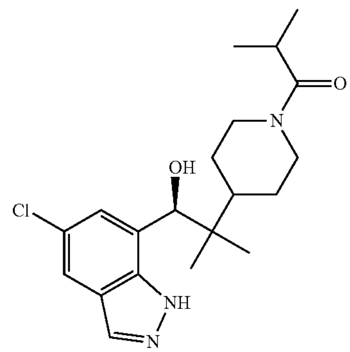 [SMILES: CC(C)C(=O)N1CCC(C(C)(C)[C@H](O)c2cc(Cl)cc3cn[nH]c23)CC1] | 378.3 |
| P-0545 | (S)-1-(4-(1-(5-chloro-1H-indazol-7-yl)-1-hydroxy-2-methylpropan-2-yl)piperidin-1-yl)-3-methylbutan-1-one | 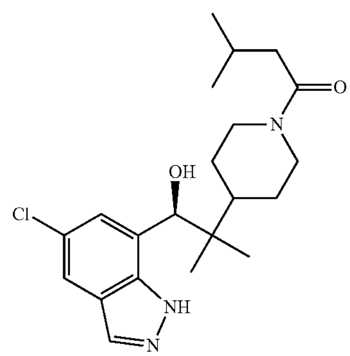 [SMILES: CC(C)CC(=O)N1CCC(C(C)(C)[C@H](O)c2cc(Cl)cc3cn[nH]c23)CC1] | 392.2 |
| P-0546 | (S)-(4-(1-(5-chloro-1H-indazol-7-yl)-1-hydroxy-2-methylpropan-2-yl)piperidin-1-yl)(tetrahydro-2H-pyran-4-yl)methanone | 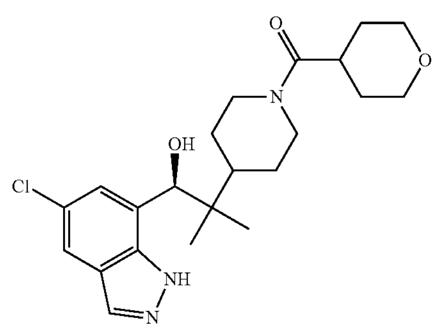 [SMILES: CC(C)(C1CCN(C(=O)C2CCOCC2)CC1)[C@H](O)c1cc(Cl)cc2cn[nH]c12] | 420.1 |

TABLE 1-continued

| Compound Number | Compound Name | Compound Structure | (MH)+ |
|---|---|---|---|
| P-0547 | (S)-1-(4-(1-(5-chloro-1H-indazol-7-yl)-1-hydroxy-2-methylpropan-2-yl)piperidin-1-yl)-2-(dimethylamino)ethan-1-one | 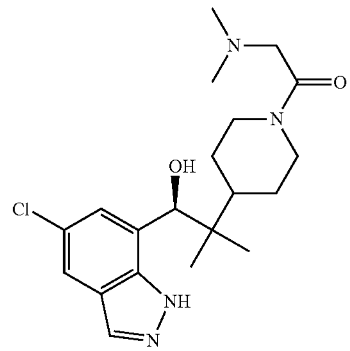 [SMILES: CN(C)CC(=O)N1CCC(C(C)(C)[C@H](O)c2cc(Cl)cc3cn[nH]c23)CC1] | 393.4 |
| P-0548 | (S)-(4-(1-(5-chloro-1H-indazol-7-yl)-1-hydroxy-2-methylpropan-2-yl)piperidin-1-yl)(5-chloropyridin-2-yl)methanone | 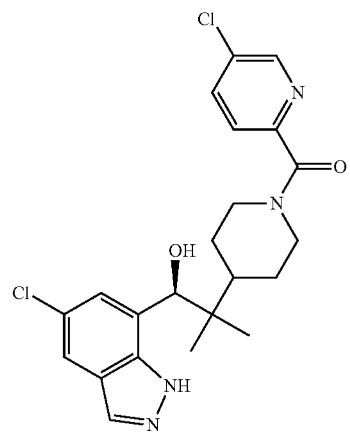 [SMILES: CC(C)(C1CCN(C(=O)c2ccc(Cl)cn2)CC1)[C@H](O)c1cc(Cl)cc2cn[nH]c12] | 447.1 |
| P-0550 | (S)-4-(1-(5-chloro-1H-indazol-7-yl)-1-hydroxy-2-methylpropan-2-yl)-N-ethylpiperidine-1-carboxamide | 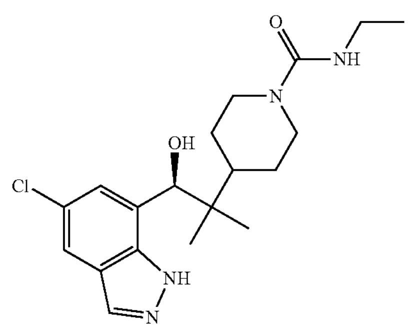 [SMILES: CCNC(=O)N1CCC(C(C)(C)[C@H](O)c2cc(Cl)cc3cn[nH]c23)CC1] | 379.2 |
| P-0551 | (S)-4-(1-(5-chloro-1H-indazol-7-yl)-1-hydroxy-2-methylpropan-2-yl)-N-cyclopropylpiperidine-1-carboxamide | 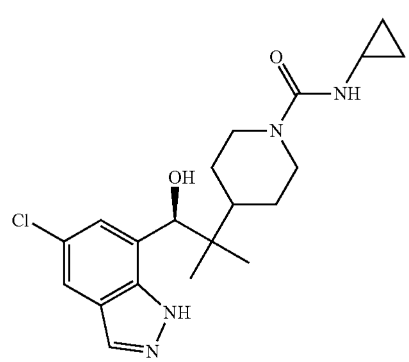 [SMILES: CC(C)(C1CCN(C(=O)NC2CC2)CC1)[C@H](O)c1cc(Cl)cc2cn[nH]c12] | 391.3 |

TABLE 1-continued

| Compound Number | Compound Name | Compound Structure | (MH)+ |
|---|---|---|---|
| P-0552 | (S)-4-(1-(5-chloro-1H-indazol-7-yl)-1-hydroxy-2-methylpropan-2-yl)-N-cyclobutylpiperidine-1-carboxamide | 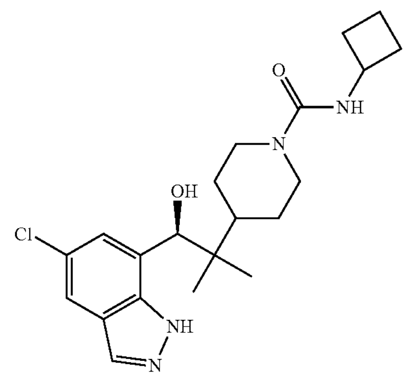 [SMILES: CC(C)(C1CCN(C(=O)NC2CCC2)CC1)[C@H](O)c1cc(Cl)cc2cn[nH]c12] | 405.4 |
| P-0553 | (S)-4-(1-(5-chloro-1H-indazol-7-yl)-1-hydroxy-2-methylpropan-2-yl)-N-(3-methoxypropyl)piperidine-1-carboxamide | 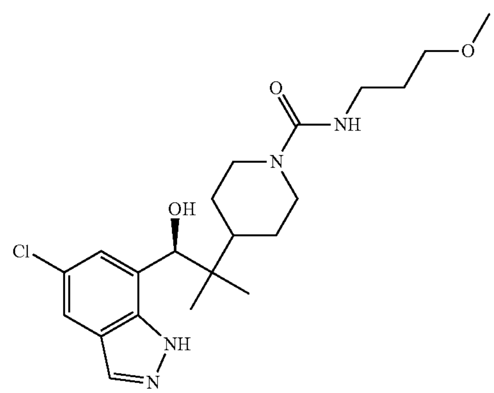 [SMILES: COCCCNC(=O)N1CCC(C(C)(C)[C@H](O)c2cc(Cl)cc3cn[nH]c23)CC1] | 423.4 |
| P-0554 | (S)-4-(1-(5-chloro-1H-indazol-7-yl)-1-hydroxy-2-methylpropan-2-yl)-N-(pyridin-3-yl)piperidine-1-carboxamide | 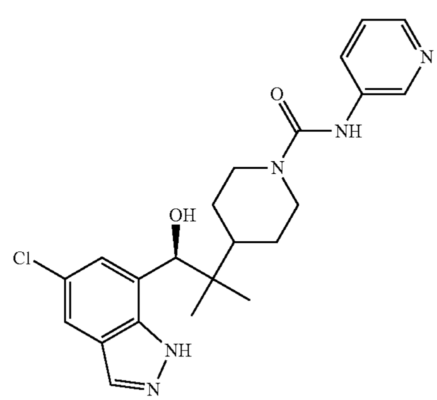 [SMILES: CC(C)(C1CCN(C(=O)Nc2cccnc2)CC1)[C@H](O)c1cc(Cl)cc2cn[nH]c12] | 428.5 |
| P-0555 | (S)-N-benzoyl-4-(1-(5-chloro-1H-indazol-7-yl)-1-hydroxy-2-methylpropan-2-yl)piperidine-1-carboxamide | 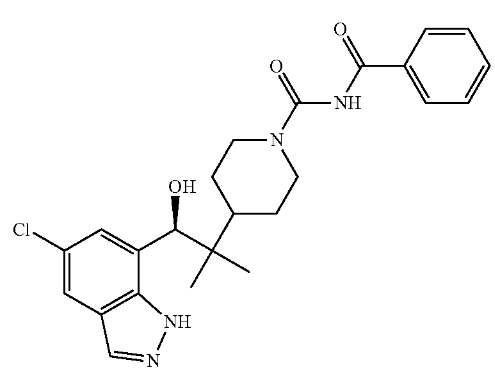 [SMILES: CC(C)(C1CCN(C(=O)NC(=O)c2ccccc2)CC1)[C@H](O)c1cc(Cl)cc2cn[nH]c12] | 455.2 |

TABLE 1-continued

| Compound Number | Compound Name | (MH)+ |
|---|---|---|
| P-0556 | (S)-4-(1-(5-chloro-1H-indazol-7-yl)-1-hydroxy-2-methylpropan-2-yl)-N-(2-(methylsulfonyl)ethyl)piperidine-1-carboxamide | 457.3 |
| P-0557 | (S)-1-(5-chloro-1H-indazol-7-yl)-2-(1-(ethylsulfonyl)piperidin-4-yl)-2-methylpropan-1-ol | 400.3 |
| P-0558 | 4-(1-(5-chloro-1H-indazol-7-yl)-1-hydroxy-2-methylpropan-2-yl)-N-(6-fluoropyridin-3-yl)piperidine-1-carboxamide | 446.0 |
| P-0559 | (S)-4-(1-(5-chloro-1H-indazol-7-yl)-1-hydroxy-2-methylpropan-2-yl)-N-(6-fluoropyridin-3-yl)piperidine-1-carboxamide | 446.0 |
| P-0560 | (S)-4-(1-(5-chloro-1H-indazol-7-yl)-1-hydroxy-2-methylpropan-2-yl)-N-(cyclopropylmethyl)piperidine-1-carboxamide | 405.4 |

TABLE 1-continued

| Compound Number | Compound Name | Compound Structure | (MH)+ |
|---|---|---|---|
| P-0561 | (S)-4-(1-(5-chloro-1H-indazol-7-yl)-1-hydroxy-2-methylpropan-2-yl)-N-(3,3,3-trifluoropropyl)piperidine-1-carboxamide | 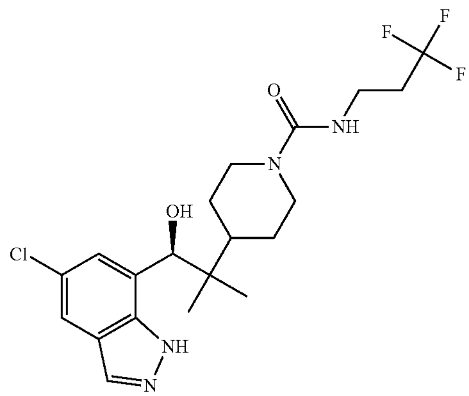 [SMILES: CC(C)(C1CCN(C(=O)NCCC(F)(F)F)CC1)[C@H](O)c1cc(Cl)cc2cn[nH]c12] | 447.4 |
| P-0562 | (S)-4-(1-(5-chloro-1H-indazol-7-yl)-1-hydroxy-2-methylpropan-2-yl)-N-(2,2,2-trifluoroethyl)piperidine-1-carboxamide | 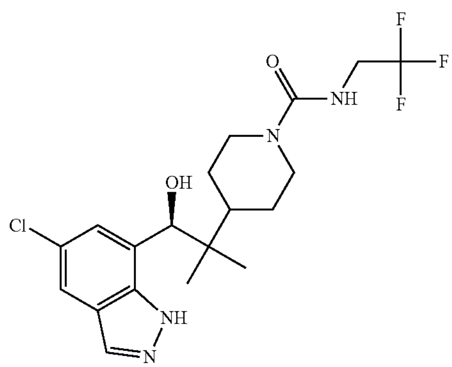 [SMILES: CC(C)(C1CCN(C(=O)NCC(F)(F)F)CC1)[C@H](O)c1cc(Cl)cc2cn[nH]c12] | 433.3 |
| P-0563 | (S)-4-(1-(5-chloro-1H-indazol-7-yl)-1-hydroxy-2-methylpropan-2-yl)-N-phenylpiperidine-1-carboxamide | 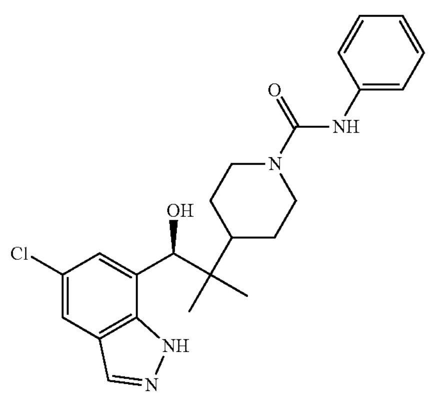 [SMILES: CC(C)(C1CCN(C(=O)Nc2ccccc2)CC1)[C@H](O)c1cc(Cl)cc2cn[nH]c12] | 427.3 |
| P-0564 | (S)-4-(1-(5-chloro-1H-indazol-7-yl)-1-hydroxy-2-methylpropan-2-yl)-N-isobutylpiperidine-1-carboxamide | 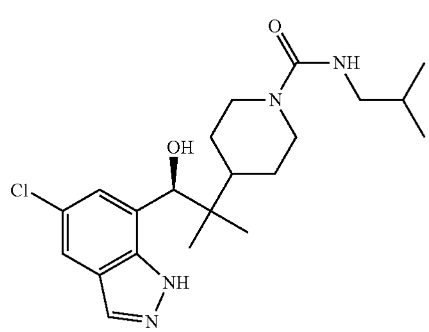 [SMILES: CC(C)CNC(=O)N1CCC(C(C)(C)[C@H](O)c2cc(Cl)cc3cn[nH]c23)CC1] | 407.5 |

TABLE 1-continued

| Compound Number | Compound Name | Compound Structure | (MH)+ |
|---|---|---|---|
| P-0565 | 4-((S)-1-(5-chloro-1H-indazol-7-yl)-1-hydroxy-2-methylpropan-2-yl)-N-(((R)-tetrahydrofuran-2-yl)methyl)piperidine-1-carboxamide | 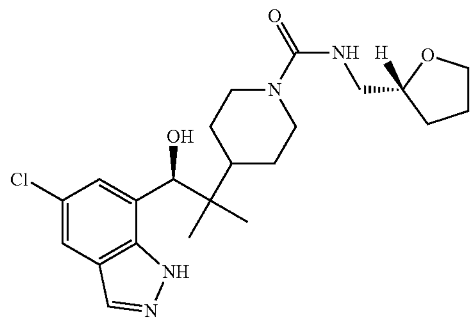 [SMILES: CC(C)(C1CCN(C(=O)NC[C@H]2CCCO2)CC1)[C@H](O)c1cc(Cl)cc2cn[nH]c12] | 435.4 |
| P-0566 | 4-((S)-1-(5-chloro-1H-indazol-7-yl)-1-hydroxy-2-methylpropan-2-yl)-N-(((S)-tetrahydrofuran-2-yl)methyl)piperidine-1-carboxamide | 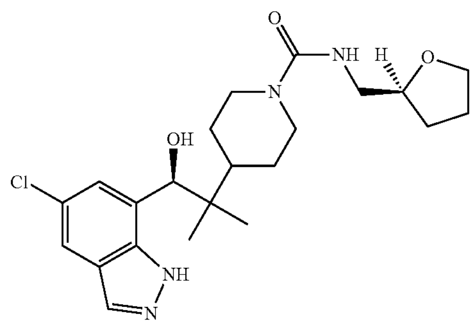 [SMILES: CC(C)(C1CCN(C(=O)NC[C@@H]2CCCO2)CC1)[C@H](O)c1cc(Cl)cc2cn[nH]c12] | 435.4 |
| P-0567 | (S)-4-(1-(5-chloro-1H-indazol-7-yl)-1-hydroxy-2-methylpropan-2-yl)-N-propylpiperidine-1-carboxamide | 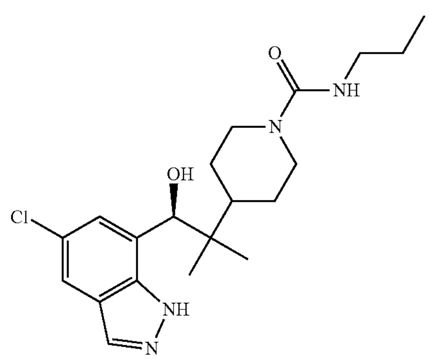 [SMILES: CCCNC(=O)N1CCC(C(C)(C)[C@H](O)c2cc(Cl)cc3cn[nH]c23)CC1] | 393.4 |
| P-0568 | (S)-4-(1-(5-chloro-1H-indazol-7-yl)-1-hydroxy-2-methylpropan-2-yl)-N-(prop-2-yn-1-yl)piperidine-1-carboxamide | 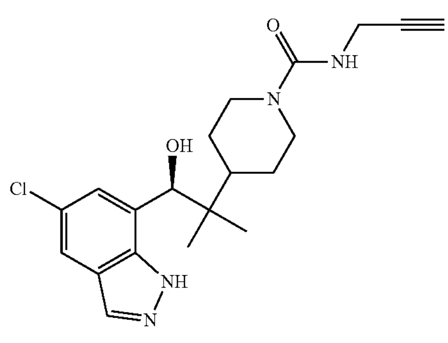 [SMILES: C#CCNC(=O)N1CCC(C(C)(C)[C@H](O)c2cc(Cl)cc3cn[nH]c23)CC1] | 389.4 |

TABLE 1-continued

| Number | Compound Name | Compound Structure | (MH)+ |
|---|---|---|---|
| P-0569 | (S)-4-(1-(5-chloro-1H-indazol-7-yl)-1-hydroxy-2-methylpropan-2-yl)-N-(3-cyanophenyl)piperidine-1-carboxamide | 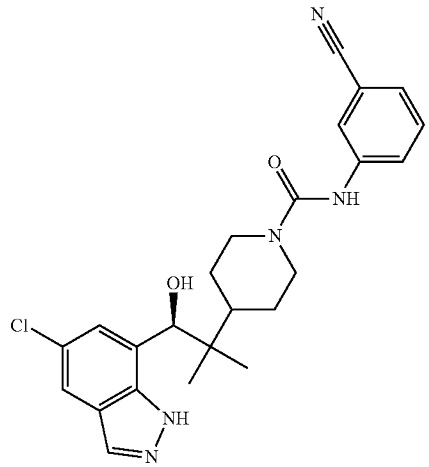 [SMILES: CC(C)(C1CCN(C(=O)Nc2cccc(C#N)c2)CC1)[C@H](O)c1cc(Cl)cc2cn[nH]c12] | 451.9 |
| P-0570 | 4-(1-(5-chloro-1H-indazol-7-yl)-1-hydroxy-2-methylpropan-2-yl)-N-(6-cyanopyridin-3-yl)piperidine-1-carboxamide | 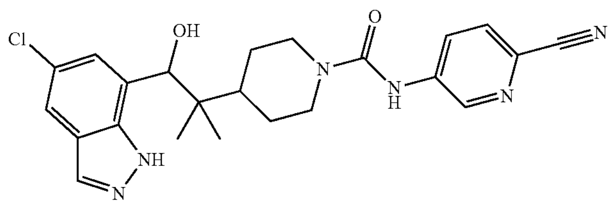 [SMILES: CC(C)(C1CCN(C(=O)Nc2ccc(C#N)nc2)CC1)C(O)c1cc(Cl)cc2cn[nH]c12] | 487.6 |
| P-0571 | (R)-1-(4-(2-(5-chloro-1H-indazol-7-yl)-1,1-difluoro-2-hydroxyethyl)piperidin-1-yl)-2-(4-chloro-3-fluorophenyl)ethan-1-one | 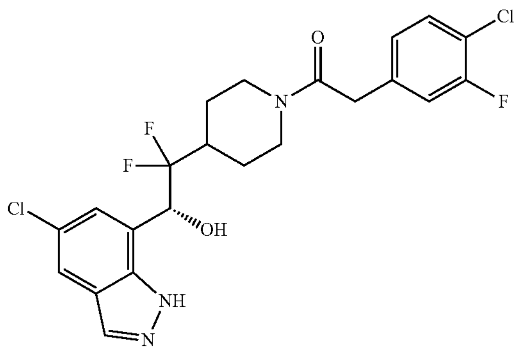 [SMILES: O=C(Cc1ccc(Cl)c(F)c1)N1CCC(C(F)(F)[C@H](O)c2cc(Cl)cc3cn[nH]c23)CC1] | 453.1 |
| P-0572 | (R)-1-(4-(2-(5-chloro-1H-indazol-7-yl)-1,1-difluoro-2-hydroxyethyl)piperidin-1-yl)-2-(3-chloro-4-fluorophenyl)ethan-1-one | 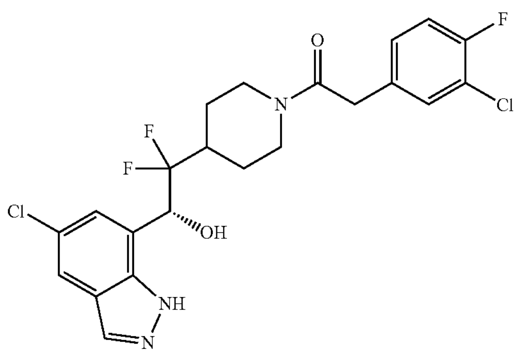 [SMILES: O=C(Cc1ccc(F)c(Cl)c1)N1CCC(C(F)(F)[C@H](O)c2cc(Cl)cc3cn[nH]c23)CC1] | 487.1 |
| P-0573 | (E)-4-(1-(5-chloro-1H-indazol-7-yl)-1-hydroxy-2-methylpropan-2-yl)-N'-cyanopiperidine-1-carboximidamide | 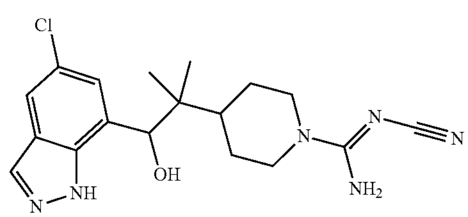 [SMILES: CC(C)(C1CCN(/C(N)=N/C#N)CC1)C(O)c1cc(Cl)cc2cn[nH]c12] | 375.1 |

TABLE 1-continued

| Compound Number | Compound Name | Compound Structure | (MH)+ |
|---|---|---|---|
| P-0574 | (R)-1-(4-(2-(5-chloro-1H-indazol-7-yl)-1,1-difluoro-2-hydroxyethyl)piperidin-1-yl)propan-1-one | 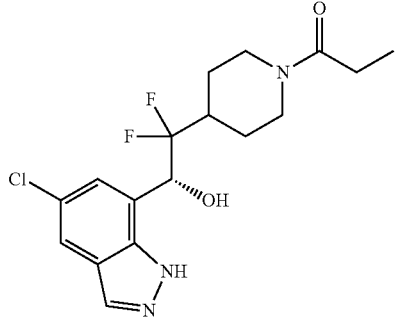 [SMILES: CCC(=O)N1CCC(C(F)(F)[C@H](O)c2cc(Cl)cc3cn[nH]c23)CC1] | 373.1 |
| P-0575 | (R)-4-(2-(5-chloro-1H-indazol-7-yl)-1,1-difluoro-2-hydroxyethyl)-N-methylpiperidine-1-carboxamide | 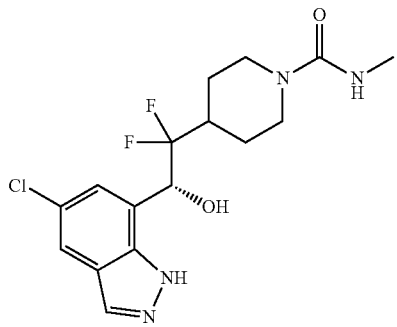 | 372.1 |
| P-0576 | (R)-1-(4-(2-(5-chloro-1H-indazol-7-yl)-1,1-difluoro-2-hydroxyethyl)piperidin-1-yl)-2-(2-chloropyridin-4-yl)ethan-1-one | 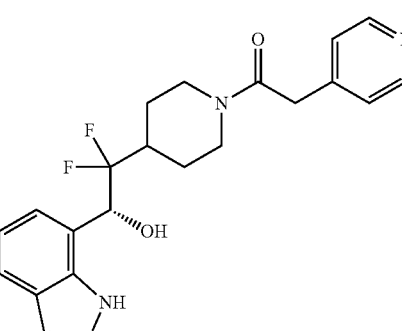 | 373.1 |
| P-0577 | 1-(4-(2-(6-chloro-1H-indazol-4-yl)-1,1-difluoro-2-hydroxyethyl)piperidin-1-yl)propan-1-one | 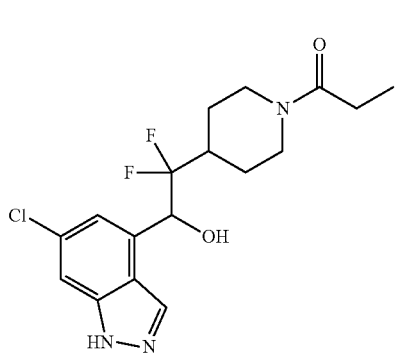 [SMILES: CCC(=O)N1CCC(C(F)(F)C(O)c2cc(Cl)cc3[nH]ncc23)CC1] | 443.2 |

TABLE 1-continued

| Compound Number | Compound Name | Compound Structure | (MH)+ |
|---|---|---|---|
| P-0578 | 4-(2-(6-chloro-1H-indazol-4-yl)-1,1-difluoro-2-hydroxyethyl)-N-methylpiperidine-1-carboxamide | 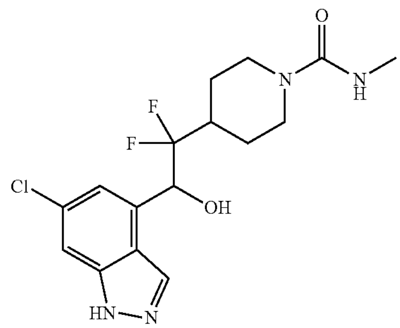 [SMILES: CNC(=O)N1CCC(C(F)(F)C(O)c2cc(Cl)cc3[nH]ncc23)CC1] | 397.3 |
| P-0579 | (S)-4-(1-(5-chloro-1H-indazol-7-yl)-1-hydroxy-2-methylpropan-2-yl)-N-((methylsulfony)methyl)piperidine-1-carboxamide | 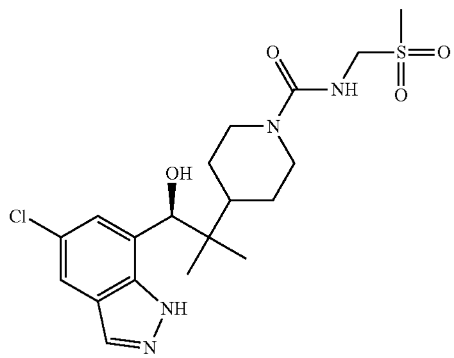 [SMILES: CC(C)(C1CCN(C(=O)NCS(C)(=O)=O)CC1)[C@H](O)c1cc(Cl)cc2cn[nH]c12] | 415.3 |
| P-0580 | (S)-4-(1-(5-chloro-1H-indazol-7-yl)-1-hydroxy-2-methylpropan-2-yl)-N-(2-fluoroethyl)piperidine-1-carboxamide | 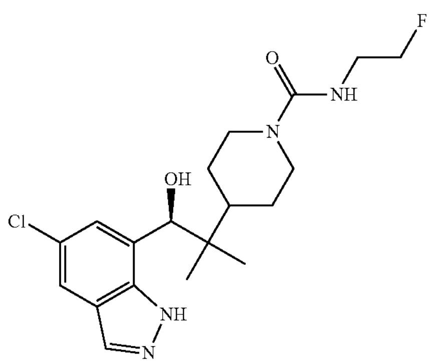 [SMILES: CC(C)(C1CCN(C(=O)NCCF)CC1)[C@H](O)c1cc(Cl)cc2cn[nH]c12] | 419.2 |
| P-0581 | (S)-4-(1-(5-chloro-1H-indazol-7-yl)-1-hydroxy-2-methylpropan-2-yl)-N-(2,2-difluoroethyl)piperidine-1-carboxamide | 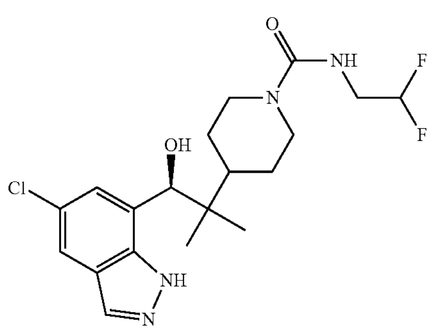 [SMILES: CC(C)(C1CCN(C(=O)NCC(F)F)CC1)[C@H](O)c1cc(Cl)cc2cn[nH]c12] | 422.2 |

TABLE 1-continued

| Compound Number | Compound Name | Compound Structure | (MH)+ |
|---|---|---|---|
| P-0582 | (S)-4-(1-(5-chloro-1H-indazol-7-yl)-1-hydroxy-2-methylpropan-2-yl)-N-(cyclobutylmethyl)piperidine-1-carboxamide | 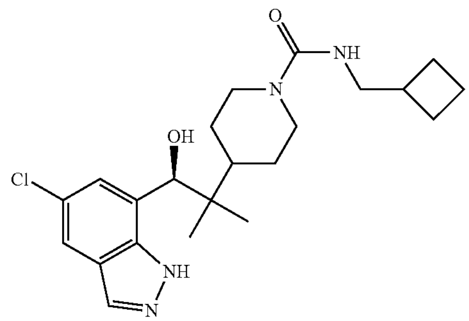 [SMILES: CC(C)(C1CCN(C(=O)NCC2CCC2)CC1)[C@H](O)c1cc(Cl)cc2cn[nH]c12] | 466.3 |
| P-0583 | (S)-4-(1-(5-chloro-1H-indazol-7-yl)-1-hydroxy-2-methylpropan-2-yl)-N-(2-(methylamino)-2-oxoethyl)piperidine-1-carboxamide | 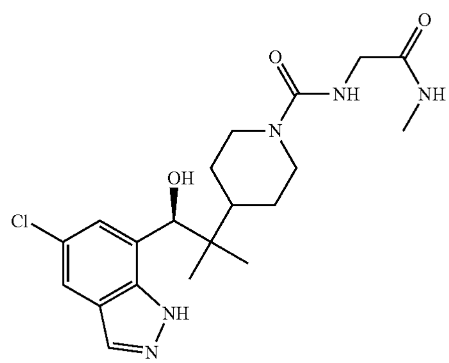 [SMILES: CNC(=O)CNC(=O)N1CCC(C(C)(C)[C@H](O)c2cc(Cl)cc3cn[nH]c23)CC1] | 472.3 |
| P-0584 | (S)-4-(1-(5-chloro-1H-indazol-7-yl)-1-hydroxy-2-methylpropan-2-yl)-N-(4-cyanobenzyl)piperidine-1-carboxamide | 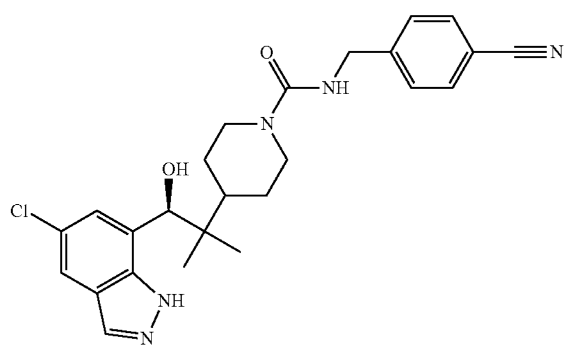 [SMILES: CC(C)(C1CCN(C(=O)NCc2ccc(C#N)cc2)CC1)[C@H](O)c1cc(Cl)cc2cn[nH]c12] | 372.1 |
| P-0585 | (S)-4-(1-(5-chloro-1H-indazol-7-yl)-1-hydroxy-2-methylpropan-2-yl)-N-((6-methoxypyridin-3-yl)methyl)piperidine-1-carboxamide | 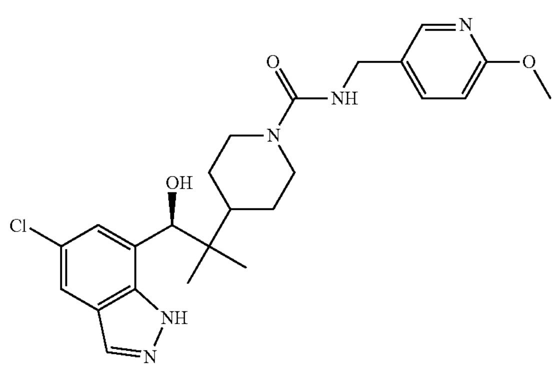 [SMILES: COc1ccc(CNC(=O)N2CCC(C(C)(C)[C@H](O)c3cc(Cl)cc4cn[nH]c34)CC2)cn1] | 469.1 |

TABLE 1-continued

| Compound Number | Compound Name | Compound Structure | (MH)+ |
|---|---|---|---|
| P-0586 | (S)-4-(1-(5-chloro-1H-indazol-7-yl)-1-hydroxy-2-methylpropan-2-yl)-N-((6-(dimethylamino)pyridin-3-yl)methyl)piperidine-1-carboxamide | 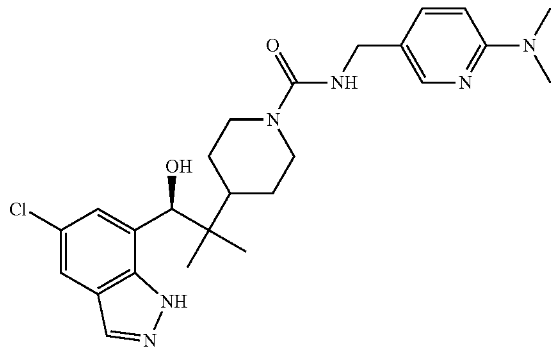 [SMILES: CN(C)c1ccc(CNC(=O)N2CCC(C(C)(C)[C@H](O)c3cc(Cl)cc4cn[nH]c34)CC2)cn1] | 427.1 |
| P-0587 | (S)-4-(1-(5-chloro-1H-indazol-7-yl)-1-hydroxy-2-methylpropan-2-yl)-N-(cyanomethyl)piperidine-1-carboxamide | 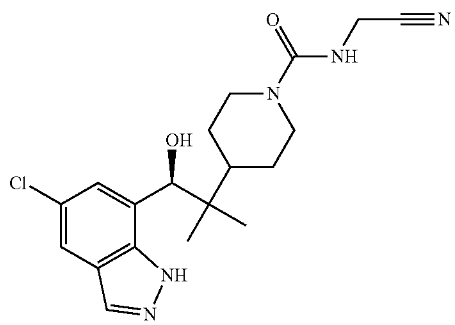 [SMILES: CC(C)(C1CCN(C(=O)NCC#N)CC1)[C@H](O)c1cc(Cl)cc2cn[nH]c12] | 458.2 |
| P-0588 | (S)-4-(1-(5-chloro-1H-indazol-7-yl)-1-hydroxy-2-methylpropan-2-yl)-N-(4,4-difluorocyclohexyl)piperidine-1-carboxamide | 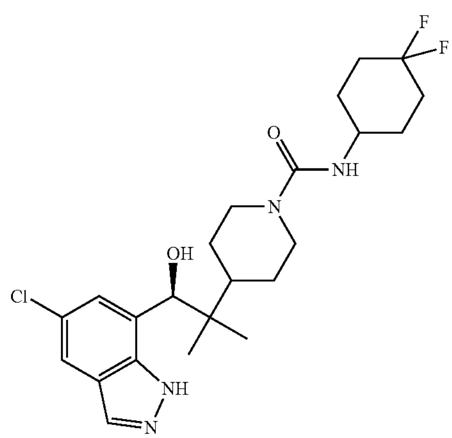 [SMILES: CC(C)(C1CCN(C(=O)NC2CCC(F)(F)CC2)CC1)[C@H](O)c1cc(Cl)cc2cn[nH]c12] | 485.5 |
| P-0589 | 4-((S)-1-(5-chloro-1H-indazol-7-yl)-1-hydroxy-2-methylpropan-2-yl)-N-((S)-tetrahydrofuran-3-yl)piperidine-1-carboxamide | 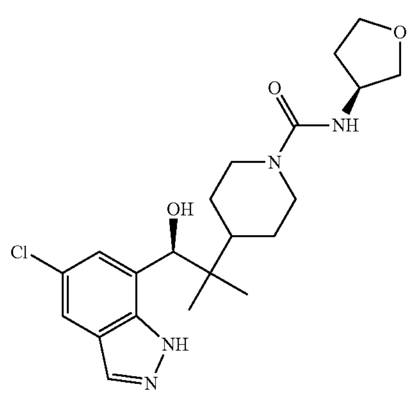 [SMILES: CC(C)(C1CCN(C(=O)N[C@H]2CCOC2)CC1)[C@H](O)c1cc(Cl)cc2cn[nH]c12] | 390.4 |

TABLE 1-continued

| Number | Compound Name | Compound Structure | (MH)+ |
|---|---|---|---|
| P-0590 | (S)-4-(1-(5-chloro-1H-indazol-7-yl)-1-hydroxy-2-methylpropan-2-yl)-N-((6-cyanopyridin-3-yl)methyl)piperidine-1-carboxamide | 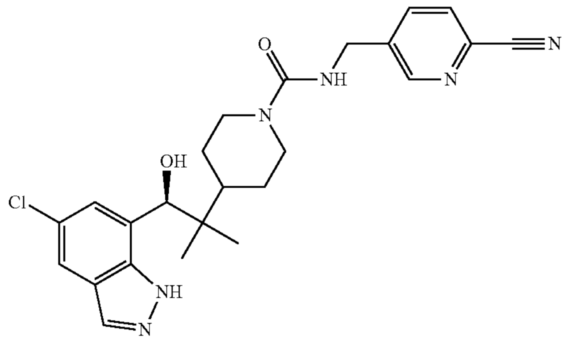 [SMILES: CC(C)(C1CCN(C(=O)NCc2ccc(C#N)nc2)CC1)[C@H](O)c1cc(Cl)cc2cn[nH]c12] | 469.3 |
| P-0591 | 4-((S)-1-(5-chloro-1H-indazol-7-yl)-1-hydroxy-2-methylpropan-2-yl)-N-((1R,3R)-3-hydroxycyclopentyl)piperidine-1-carboxamide | 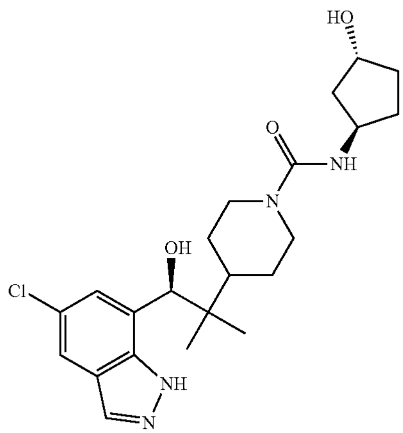 [SMILES: CC(C)(C1CCN(C(=O)N[C@@H]2CC[C@@H](O)C2)CC1)[C@H](O)c1cc(Cl)cc2cn[nH]c12] | 421.3 |
| P-0592 | (S)-4-(1-(5-chloro-1H-indazol-7-yl)-1-hydroxy-2-methylpropan-2-yl)-N-(3,3-difluorocyclobutyl)piperidine-1-carboxamide | 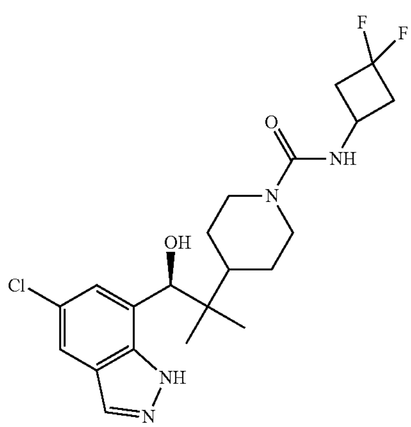 [SMILES: CC(C)(C1CCN(C(=O)NC2CC(F)(F)C2)CC1)[C@H](O)c1cc(Cl)cc2cn[nH]c12] | 467.2 |
| P-0593 | 4-((S)-1-(5-chloro-1H-indazol-7-yl)-1-hydroxy-2-methylpropan-2-yl)-N-((R)-tetrahydrofuran-3-yl)piperidine-1-carboxamide | 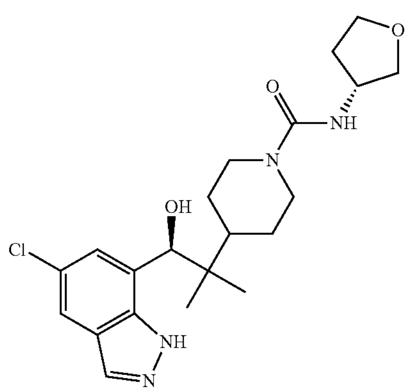 [SMILES: CC(C)(C1CCN(C(=O)N[C@@H]2CCOC2)CC1)[C@H](O)c1cc(Cl)cc2cn[nH]c12] | 435.4 |

TABLE 1-continued

| Compound Number | Compound Name | Compound Structure | (MH)+ |
|---|---|---|---|
| P-0594 | (S)-4-(1-(5-chloro-1H-indazol-7-yl)-1-hydroxy-2-methylpropan-2-yl)-N-isopropylpiperidine-1-carboxamide | 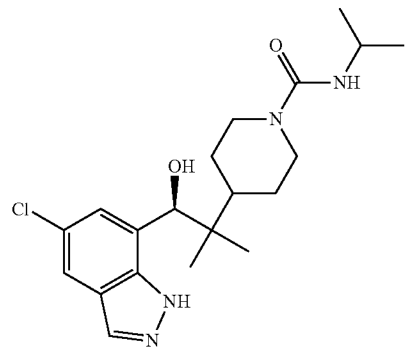 [SMILES: CC(C)NC(=O)N1CCC(C(C)(C)[C@H](O)c2cc(Cl)cc3cn[nH]c23)CC1] | 441.4 |
| P-0595 | (S)-4-(1-(5-chloro-1H-indazol-7-yl)-1-hydroxy-2-methylpropan-2-yl)-N-(oxetan-3-yl)piperidine-1-carboxamide | 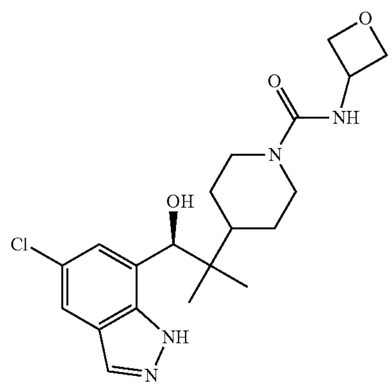 [SMILES: CC(C)(C1CCN(C(=O)NC2COC2)CC1)[C@H](O)c1cc(Cl)cc2cn[nH]c12] | 421.3 |
| P-0596 | (S)-4-(1-(5-chloro-1H-indazol-7-yl)-1-hydroxy-2-methylpropan-2-yl)-N-(3-fluoropropyl)piperidine-1-carboxamide | 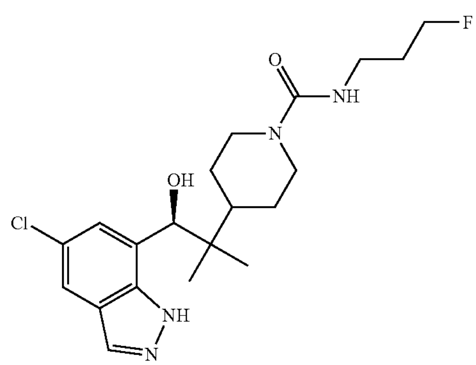 [SMILES: CC(C)(C1CCN(C(=O)NCCCF)CC1)[C@H](O)c1cc(Cl)cc2cn[nH]c12] | 393.4 |
| P-0597 | (S)-4-(1-(5-chloro-1H-indazol-7-yl)-1-hydroxy-2-methylpropan-2-yl)-N-(3-cyanopropyl)piperidine-1-carboxamide | 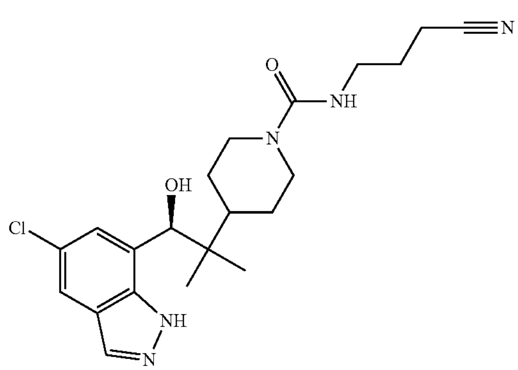 [SMILES: CC(C)(C1CCN(C(=O)NCCCC#N)CC1)[C@H](O)c1cc(Cl)cc2cn[nH]c12] | 407.2 |

TABLE 1-continued

| Compound Number | Compound Name | Compound Structure | (MH)+ |
|---|---|---|---|
| P-0598 | (S)-4-(1-(5-chloro-1H-indazol-7-yl)-1-hydroxy-2-methylpropan-2-yl)-N-methoxypiperidine-1-carboxamide | 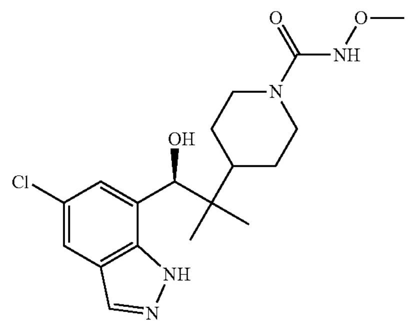 [SMILES: CONC(=O)N1CCC(C(C)(C)[C@H](O)c2cc(Cl)cc3cn[nH]c23)CC1] | 411.4 |
| P-0599 | (S)-4-(1-(5-chloro-1H-indazol-7-yl)-1-hydroxy-2-methylpropan-2-yl)-N-((1-methylcyclopropyl)methyl)piperidine-1-carboxamide | 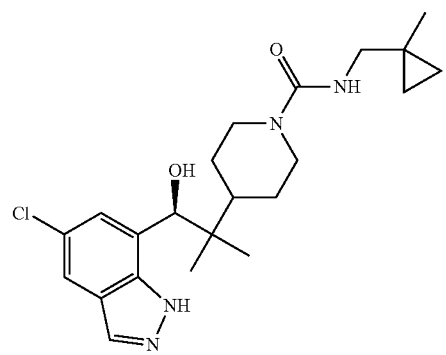 [SMILES: CC1(CNC(=O)N2CCC(C(C)(C)[C@H](O)c3cc(Cl)cc4cn[nH]c34)CC2)CC1] | 418.3 |
| P-0600 | 4-((S)-1-(5-chloro-1H-indazol-7-yl)-1-hydroxy-2-methylpropan-2-yl)-N-((1r,3S)-3-hydroxycyclobutyl)piperidine-1-carboxamide | 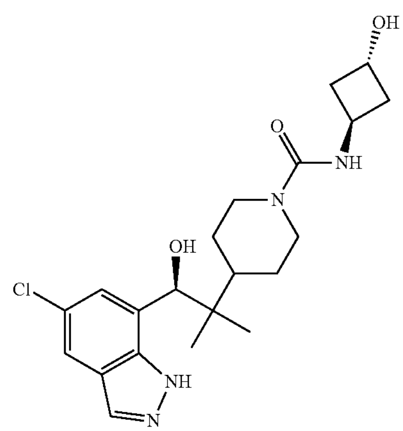 [SMILES: CC(C)(C1CCN(C(=O)N[C@H]2C[C@H](O)C2)CC1)[C@H](O)c1cc(Cl)cc2cn[nH]c12] | 381.0 |
| P-0601 | (S)-4-(1-(5-chloro-1H-indazol-7-yl)-1-hydroxy-2-methylpropan-2-yl)-N-((5-fluoropyridin-2-yl)methyl)piperidine 1-carboxamide | 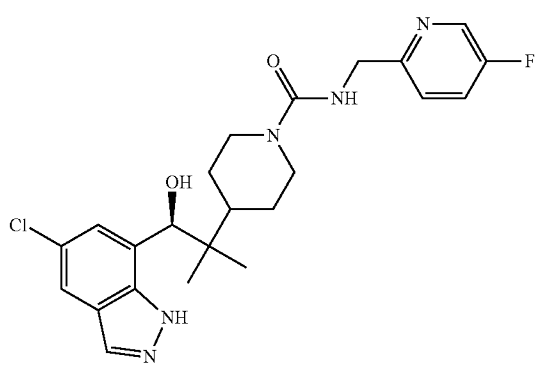 [SMILES: CC(C)(C1CCN(C(=O)NCc2ccc(F)cn2)CC1)[C@H](O)c1cc(Cl)cc2cn[nH]c12] | 419.2 |

TABLE 1-continued

| Compound Number | Compound Name | Compound Structure | (MH)+ |
|---|---|---|---|
| P-0602 | (S)-4-(1-(5-chloro-1H-indazol-7-yl)-1-hydroxy-2-methylpropan-2-yl)-N-(4-fluorobenzyl)piperidine-1-carboxamide | 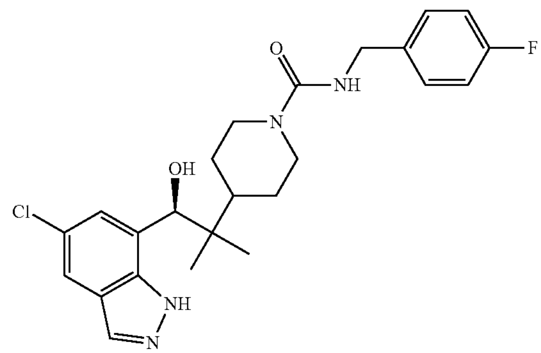 [SMILES: CC(C)(C1CCN(C(=O)NCc2ccc(F)cc2)CC1)[C@H](O)c1cc(Cl)cc2cn[nH]c12] | 421.0 |
| P-0603 | 4-(1-(6-chloro-1H-indazol-4-yl)-1-hydroxy-2-methylpropan-2-yl)-N-phenylpiperidine-1-carboxamide | 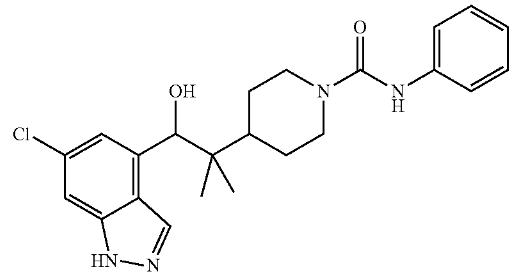 [SMILES: CC(C)(C1CCN(C(=O)Nc2ccccc2)CC1)C(O)c1cc(Cl)cc2[nH]ncc12] | 460.3 |
| P-0604 | 4-(1-(5-chloro-1H-indazol-7-yl)-1-hydroxy-2-methylpropan-2-yl)-N-(6-chloropyridin-3-yl)piperidine-1-carboxamide | 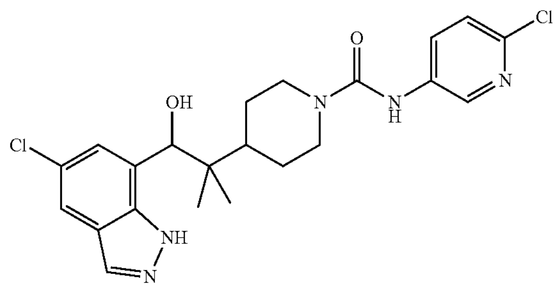 [SMILES: CC(C)(C1CCN(C(=O)Nc2ccc(Cl)nc2)CC1)C(O)c1cc(Cl)cc2cn[nH]c12] | 459.4 |
| P-0605 | 4-(1-(5-chloro-1H-indazol-7-yl)-1-hydroxy-2-methylpropan-2-yl)-N-(6-methoxypyridin-3-yl)piperidine-1-carboxamide | 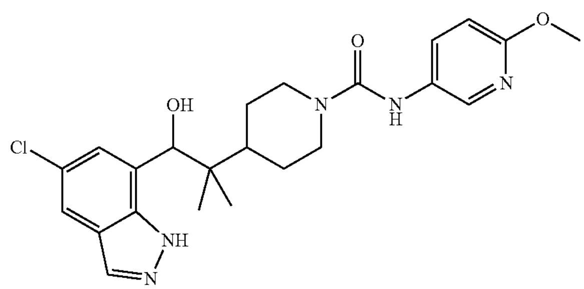 [SMILES: COc1ccc(NC(=O)N2CCC(C(C)(C)C(O)c3cc(Cl)cc4cn[nH]c34)CC2)cn1] | 462.0 |
| P-0606 | 4-(1-(6-chloro-1H-indazol-4-yl)-1-hydroxy-2-methylpropan-2-yl)piperidine-1-carboxamide | 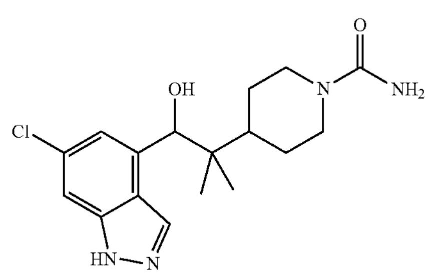 [SMILES: CC(C)(C1CCN(C(N)=O)CC1)C(O)c1cc(Cl)cc2[nH]ncc12] | 351.2 |

TABLE 1-continued

| Compound Number | Compound Name | Compound Structure | (MH)+ |
|---|---|---|---|
| P-0607 | tert-butyl 4-(1-(6-chloro-1H-indazol-4-yl)-1-hydroxy-2-methylpropan-2-yl)piperidine-1-carboxylate | 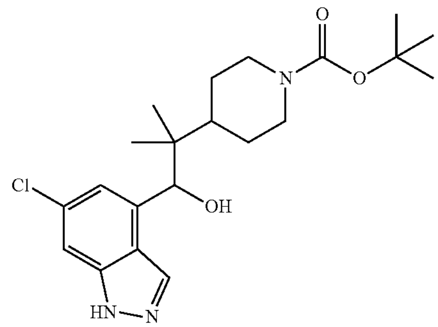 [SMILES: CC(C)(C)OC(=O)N1CCC(C(C)(C)C(O)c2cc(Cl)cc3[nH]ncc23)CC1] | |
| P-0608 | 1-(4-(1-(6-chloro-1H-indazol-4-yl)-1-hydroxy-2-methylpropan-2-yl)piperidin-1-yl)-2-cyclopropylethan-1-one | 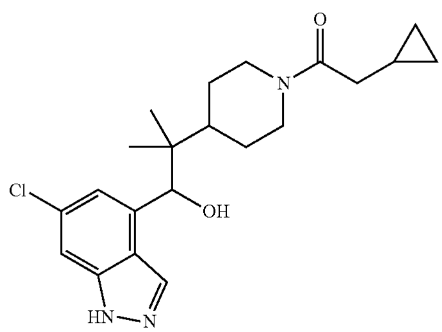 [SMILES: CC(C)(C1CCN(C(=O)CC2CC2)CC1)C(O)c1cc(Cl)cc2[nH]ncc12] | |
| P-0609 | 1-(4-(1-(6-chloro-1H-indazol-4-yl)-1-hydroxy-2-methylpropan-2-yl)piperidin-1-yl)-2-morpholinoethan-1-one | 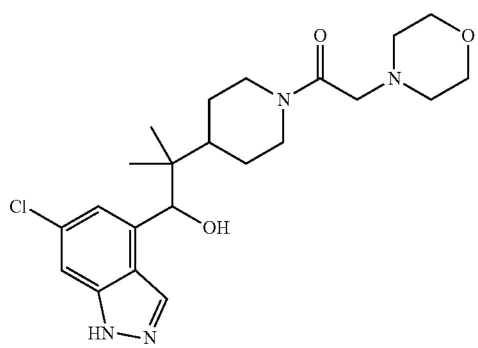 [SMILES: CC(C)(C1CCN(C(=O)CN2CCOCC2)CC1)C(O)c1cc(Cl)cc2[nH]ncc12] | 435.2 |
| P-0610 | 1-(4-(1-(6-chloro-1H-indazol-4-yl)-1-hydroxy-2-methylpropan-2-yl)piperidin-1-yl)-2-(1,1-dioxidotetrahydro-2H-thiopyran-4-yl)ethan-1-one | 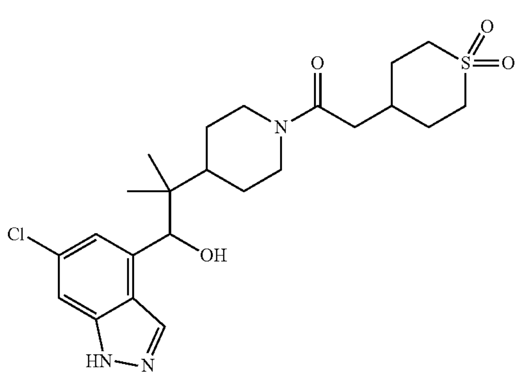 [SMILES: CC(C)(C1CCN(C(=O)CC2CCS(=O)(=O)CC2)CC1)C(O)c1cc(Cl)cc2[nH]ncc12] | 482.2 |

TABLE 1-continued

| Compound Number | Compound Name | Compound Structure | (MH)+ |
|---|---|---|---|
| P-0611 | (R)-cyclopropyl(4-(2-(5,6-dihydro-1H-cyclobuta[f]indazol-7-yl)-1,1-difluoro-2-hydroxyethyl)piperidin-1-yl)methanone | 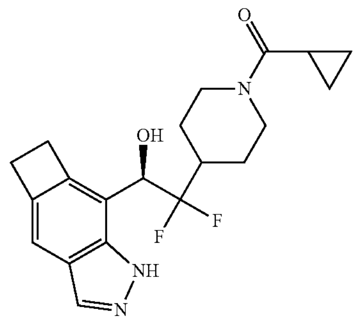 [SMILES: O=C(C1CC1)N1CCC(C(F)(F)[C@H](O)c2c3c(cc4cn[nH]c24)CC3)CC1] | 376.5 |
| P-0612 | (R)-1-(4-(2-(5,6-dihydro-1H-cyclobuta[f]indazol-7-yl)-1,1-difluoro-2-hydroxyethyl)piperidin-1-yl)propan-1-one | 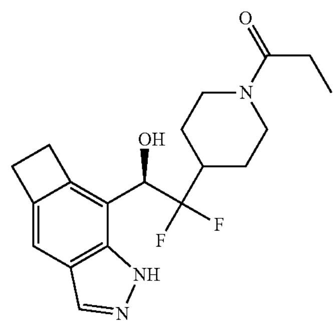 [SMILES: CCC(=O)N1CCC(C(F)(F)[C@H](O)c2c3c(cc4cn[nH]c24)CC3)CC1] | 364.2 |
| P-0613 | (R)-3-(4-(2-(5,6-dihydro-1H-cyclobuta[f]indazol-7-yl)-1,1-difluoro-2-hydroxyethyl)piperidin-1-yl)-3-oxopropanenitrile | 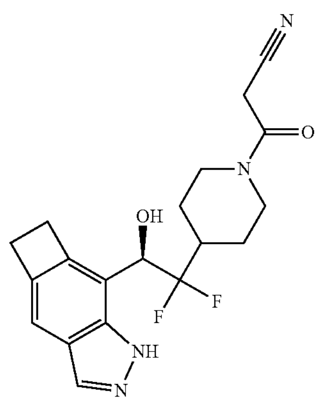 [SMILES: N#CCC(=O)N1CCC(C(F)(F)[C@H](O)c2c3c(cc4cn[nH]c24)CC3)CC1] | 375.3 |
| P-0614 | (R)-1-(4-(2-(5,6-dihydro-1H-cyclobuta[f]indazol-7-yl)-1,1-difluoro-2-hydroxyethyl)piperidin-1-yl)-2-methoxyethan-1-one | 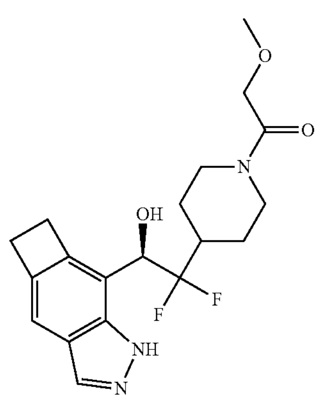 [SMILES: COCC(=O)N1CCC(C(F)(F)[C@H](O)c2c3c(cc4cn[nH]c24)CC3)CC1] | 380.4 |

TABLE 1-continued

| Compound Number | Compound Name | Compound Structure | (MH)+ |
|---|---|---|---|
| P-0615 | (R)-1-(4-(2-(5,6-dihydro-1H-cyclobuta[f]indazol-7-yl)-1,1-difluoro-2-hydroxyethyl)piperidin-1-yl)-2-hydroxyethan-1-one | 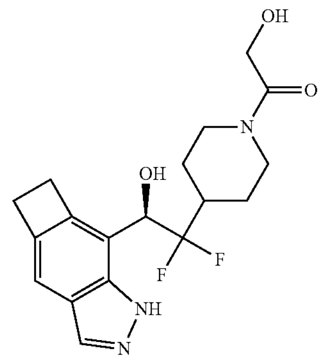 [SMILES: O=C(CO)N1CCC(C(F)(F)[C@H](O)c2c3c(cc4cn[nH]c24)CC3)CC1] | 366.4 |
| P-0616 | (R)-(4-(2-(5,6-dihydro-1H-cyclobuta[f]indazol-7-yl)-1,1-difluoro-2-hydroxyethyl)piperidin-1-yl)(2,2,3,3-tetramethylcyclopropyl)methanone | 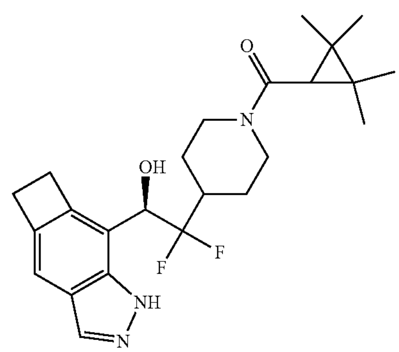 [SMILES: CC1(C)C(C(=O)N2CCC(C(F)(F)[C@H](O)c3c4c(cc5cn[nH]c35)CC4)CC2)C1(C)C] | 432.7 |
| P-0617 | (R)-1-(4-(2-(5,6-dihydro-1H-cyclobuta[f]indazol-7-yl)-1,1-difluoro-2-hydroxyethyl)piperidin-1-yl)-2-(tetrahydro-2H-pyran-4-yl)ethan-1-one | 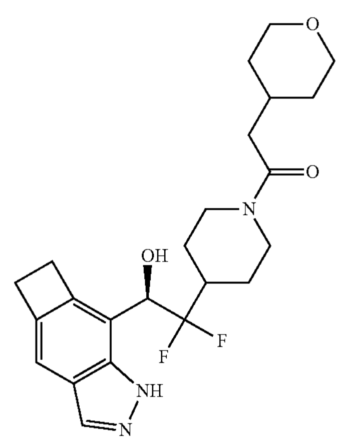 | 434.5 |
| P-0618 | (R)-(4-(2-(5,6-dihydro-1H-cyclobuta[f]indazol-7-yl)-1,1-difluoro-2-hydroxyethyl)piperidin-1-yl)(tetrahydro-2H-pyran-4-yl)methanone | 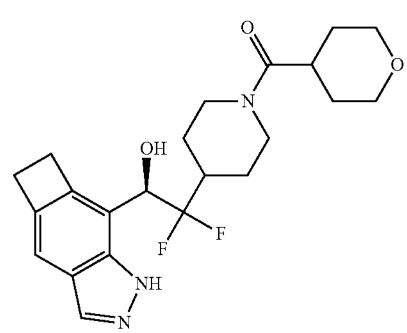 [SMILES: O=C(C1CCOCC1)N1CCC(C(F)(F)[C@H](O)c2c3c(cc4cn[nH]c24)CC3)CC1] | 420.4 |

TABLE 1-continued

| Compound Number | Compound Name | Compound Structure | (MH)+ |
|---|---|---|---|
| P-0619 | (R)-(4-(2-(5,6-dihydro-1H-cyclobuta[f]indazol-7-yl)-1,1-difluoro-2-hydroxyethyl)piperidin-1-yl)(pyridin-3-yl)methanone | 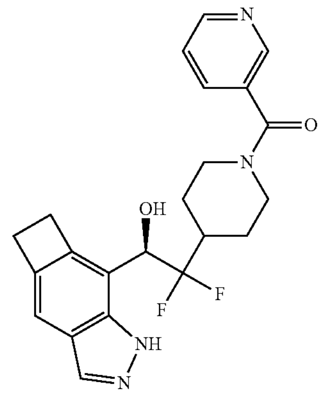 [SMILES: O=C(c1cccnc1)N1CCC(C(F)(F)[C@H](O)c2c3c(cc4cn[nH]c24)CC3)CC1] | 413.5 |
| P-0620 | (R)-(4-(2-(5,6-dihydro-1H-cyclobuta[f]indazol-7-yl)-1,1-difluoro-2-hydroxyethyl)piperidin-1-yl)(6-(trifluoromethyl)pyridin-3-yl)methanone | 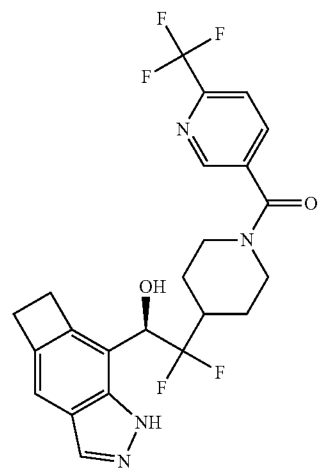 [SMILES: O=C(c1ccc(C(F)(F)F)nc1)N1CCC(C(F)(F)[C@H](O)c2c3c(cc4cn[nH]c24)CC3)CC1] | 481.3 |
| P-0621 | (R)-(5-chloropyridin-2-yl)(4-(2-(5,6-dihydro-1H-cyclobuta[f]indazol-7-yl)-1,1-difluoro-hydroxyethyl)piperidin-1-yl)methanone | 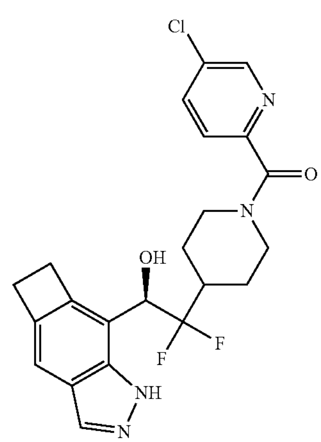 [SMILES: O=C(c1ccc(Cl)cn1)N1CCC(C(F)(F)[C@H](O)c2c3c(cc4cn[nH]c24)CC3)CC1] | 447.1 |

TABLE 1-continued

| Compound Number | Compound Name | Compound Structure | (MH)+ |
|---|---|---|---|
| P-0622 | (R)-1-(4-(2-(5,6-dihydro-1H-cyclobuta[f]indazol-7-yl)-1,1-difluoro-2-hydroxyethyl)piperidin-1-yl)-2-morpholinoethan-1-one | 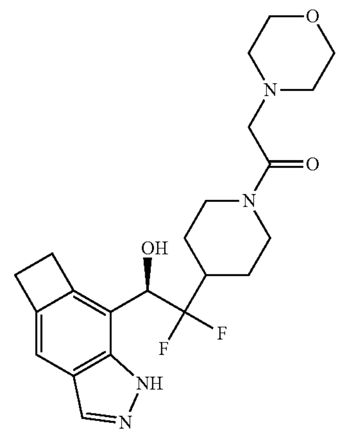 [SMILES: O=C(CN1CCOCC1)N1CCC(C(F)(F)[C@H](O)c2c3c(cc4cn[nH]c24)CC3)CC1] | 435.4 |
| P-0623 | (R)-1-(4-(2-(5,6-dihydro-1H-cyclobuta[f]indazol-7-yl)-1,1-difluoro-2-hydroxyethyl)piperidin-1-yl)-2-(1,1-dioxidothiomorpholino)ethan-1-one | 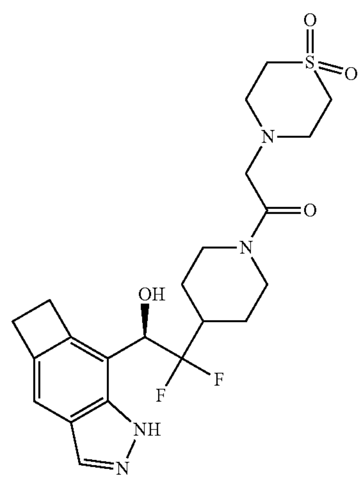 [SMILES: O=C(CN1CCS(=O)(=O)CC1)N1CCC(C(F)(F)[C@H](O)c2c3c(cc4cn[nH]c24)CC3)CC1] | 483.4 |
| P-0624 | (R)-1-(4-(2-(5,6-dihydro-1H-cyclobuta[f]indazol-7-yl)-1,1-difluoro-2-hydroxyethyl)piperidin-1-yl)-2-(1,1-dioxidotetrahydro-2H-thiopyran-4-yl)ethan-1-one | 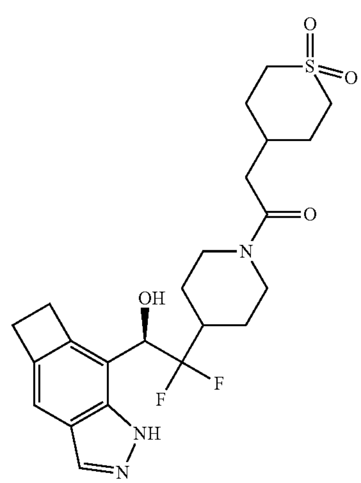 [SMILES: O=C(CC1CCS(=O)(=O)CC1)N1CCC(C(F)(F)[C@H](O)c2c3c(cc4cn[nH]c24)CC3)CC1] | 482.2 |

TABLE 1-continued

| Compound Number | Compound Name | Compound Structure | (MH)+ |
|---|---|---|---|
| P-0625 | (R)-2-(3-chloro-4-fluorophenyl)-1-(4-(2-(5,6-dihydro-1H-cyclobuta[f]indazol-7-yl)-1,1-difluoro-2-hydroxyethyl)piperidin-1-yl)ethan-1-one | 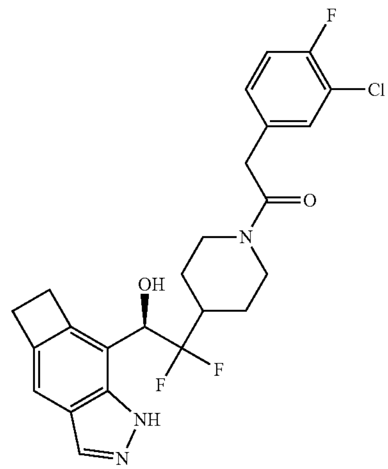 [SMILES: O=C(Cc1ccc(F)c(Cl)c1)N1CCC(C(F)(F)[C@H](O)c2c3c(cc4cn[nH]c24)CC3)CC1] | 478.3 |
| P-0626 | (R)-2-(4-chloro-3-fluorophenyl)-1-(4-(2-(5,6-dihydro-1H-cyclobuta[f]indazol-7-yl)-1,1-difluoro-2-hydroxyethyl)piperidin-1-yl)ethan-1-one | 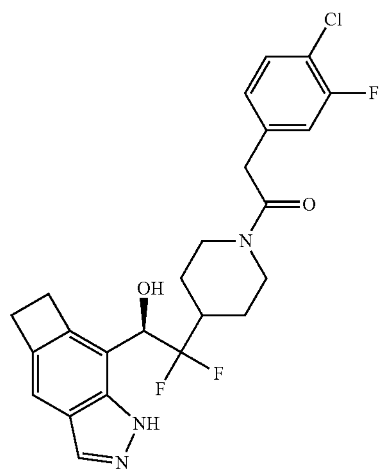 [SMILES: O=C(Cc1ccc(Cl)c(F)c1)N1CCC(C(F)(F)[C@H](O)c2c3c(cc4cn[nH]c24)CC3)CC1] | 478.3 |
| P-0627 | (R)-4-(2-(5,6-dihydro-1H-cyclobuta[f]indazol-7-yl)-1,1-difluoro-2-hydroxyethyl)-N-ethylpiperidine-1-carboxamide | 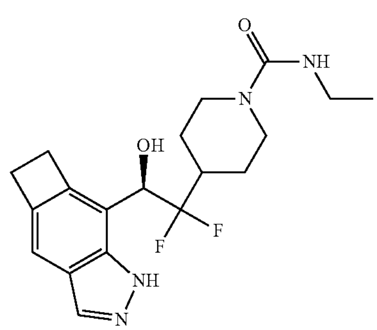 [SMILES: CCNC(=O)N1CCC(C(F)(F)[C@H](O)c2c3c(cc4cn[nH]c24)CC3)CC1] | 379.2 |

TABLE 1-continued

| Compound Number | Compound Name | (MH)+ |
|---|---|---|
| P-0628 | (R)-N-cyclopropyl-4-(2-(5,6-dihydro-1H-cyclobuta[f]indazol-7-yl)-1,1-difluoro-2-hydroxyethyl)piperidine-1-carboxamide | 391.6 |
| P-0629 | (R)-N-cyclobutyl-4-(2-(5,6-dihydro-1H-cyclobuta[f]indazol-7-yl)-1,1-difluoro-2-hydroxyethyl)piperidine-1-carboxamide | 405.4 |
| P-0630 | (R)-4-(2-(5,6-dihydro-1H-cyclobuta[f]indazol-7-yl)-1,1-difluoro-2-hydroxyethyl)-N-(2-methoxyethyl)piperidine-1-carboxamide | 409.3 |

TABLE 1-continued

| Compound Number | Compound Name | (MH)+ |
|---|---|---|
| P-0631 | (R)-N-(cyclopropylmethyl)-4-(2-(5,6-dihydro-1H-cyclobuta[f]indazol-7-yl)-1,1-difluoro-2-hydroxyethyl)piperidine-1-carboxamide | 405.4 |
| P-0632 | (R)-4-(2-(5,6-dihydro-1H-cyclobuta[f]indazol-7-yl)-1,1-difluoro-2-hydroxyethyl)-N-(3,3,3-trifluoropropyl)piperidine-1-carboxamide | 447.4 |
| P-0633 | (R)-4-(2-(5,6-dihydro-1H-cyclobuta[f]indazol-7-yl)-1,1-difluoro-2-hydroxyethyl)-N-methylpiperidine-1-carboxamide | 365.1 |
| P-0634 | (R)-4-(2-(5,6-dihydro-1H-cyclobuta[f]indazol-7-yl)-1,1-difluoro-2-hydroxyethyl)-N-(2,2,2-trifluoroethyl)piperidine-1-carboxamide | 433.3 |

TABLE 1-continued

| Compound Number | Compound Name | Compound Structure | (MH)+ |
|---|---|---|---|
| P-0635 | ethyl (R)-(4-(2-(5,6-dihydro-1H-cyclobuta[f]indazol-7-yl)-1,1-difluoro-2-hydroxyethyl)piperidine-1-carbonyl)carbamate | 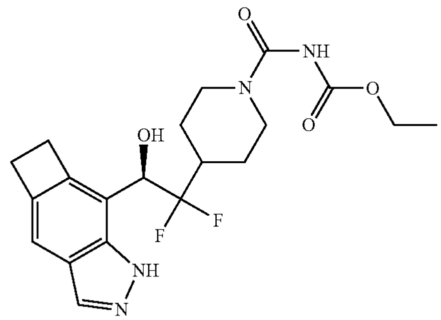 [SMILES: CCOC(=O)NC(=O)N1CCC(C(F)(F)[C@H](O)c2c3c(cc4cn[nH]c24)CC3)CC1] | 423.4 |
| P-0636 | (R)-4-(2-(5,6-dihydro-1H-cyclobuta[f]indazol-7-yl)-1,1-difluoro-2-hydroxyethyl)-N-(pyridin-3-yl)piperidine-1-carboxamide | 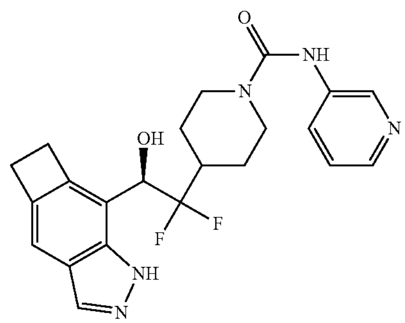 [SMILES: O=C(Nc1cccnc1)N1CCC(C(F)(F)[C@H](O)c2c3c(cc4cn[nH]c24)CC3)CC1] | 428.2 |
| P-0637 | (R)-4-(2-(5,6-dihydro-1H-cyclobuta[f]indazol-7-yl)-1,1-difluoro-2-hydroxyethyl)-N-(4-fluorophenyl)piperidine-1-carboxamide | 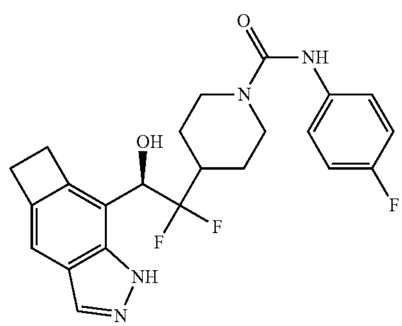 [SMILES: O=C(Nc1ccc(F)cc1)N1CCC(C(F)(F)[C@H](O)c2c3c(cc4cn[nH]c24)CC3)CC1] | 445.3 |
| P-0638 | (R)-N-(4-cyanophenyl)-4-(2-(5,6-dihydro-1H-cyclobuta[f]indazol-7-yl)-1,1-difluoro-2-hydroxyethyl)piperidine-1-carboxamide | 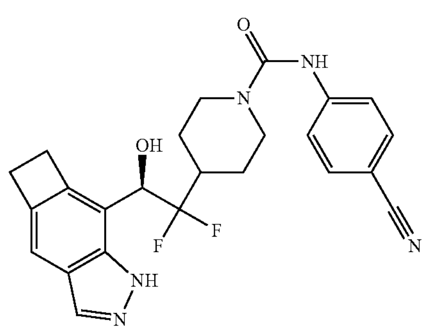 [SMILES: N#Cc1ccc(NC(=O)N2CCC(C(F)(F)[C@H](O)c3c4c(cc5cn[nH]c35)CC4)CC2)cc1] | 452.2 |

TABLE 1-continued

| Compound Number | Compound Name | (MH)+ |
|---|---|---|
| P-0639 | (R)-N-benzoyl-4-(2-(5,6-dihydro-1H-cyclobuta[f]indazol-7-yl)-1,1-difluoro-2-hydroxyethyl)piperidine-1-carboxamide | 455.2 |
| P-0640 | (R)-1-(5,6-dihydro-1H-cyclobuta[f]indazol-7-yl)-2-(1-(ethylsulfonyl)piperidin-4-yl)-2,2-difluoroethan-1-ol | 400.3 |
| P-0641 | (R)-1-(5,6-dihydro-1H-cyclobuta[f]indazol-7-yl)-2,2-difluoro-(methylsulfonyl)piperidin-4-yl)ethan-1-ol | 386.2 |
| P-0642 | 1-(4-(2-(6-chloro-1H-indazol-4-yl)-1,1-difluoro-2-hydroxyethyl)piperidin-1-yl)-2-(4-chloro-3-fluorophenyl)ethan-1-one | 486.05 |

TABLE 1-continued

| Compound Number | Compound Name | Compound Structure | (MH)+ |
|---|---|---|---|
| P-0643 | 1-(4-(2-(6-chloro-1H-indazol-4-yl)-1,1-difluoro-2-hydroxyethyl)piperidin-1-yl)-2-(3-chloro-4-fluorophenyl)ethan-1-one | 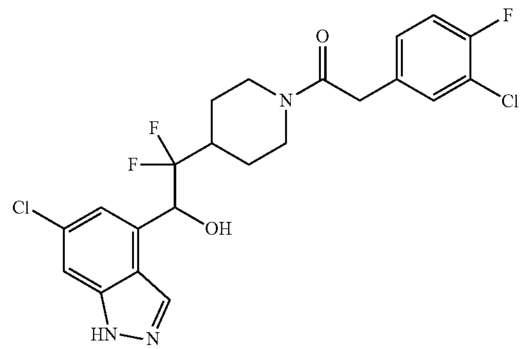 [SMILES: O=C(Cc1ccc(F)c(Cl)c1)N1CCC(C(F)(F)C(O)c2cc(Cl)cc3[nH]ncc23)CC1] | 486.05 |
| P-0644 | 1-(4-(2-(6-chloro-1H-indazol-4-yl)-1,1-difluoro-2-hydroxyethyl)piperidin-1-yl)-2-(2-chloropyridin-4-yl)ethan-1-one | 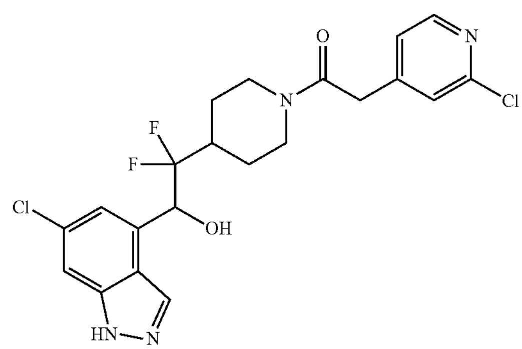 [SMILES: O=C(Cc1ccnc(Cl)c1)N1CCC(C(F)(F)C(O)c2cc(Cl)cc3[nH]ncc23)CC1] | 469.1 |
| P-0645 | (S)-4-(1-(5-chloro-1H-indazol-7-yl)-1-hydroxy-2-methylpropan-2-yl)-N-(5-fluoropyridin-2-yl)piperidine-1-carboxamide | 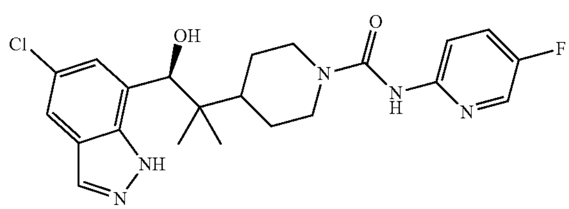 [SMILES: CC(C)(C1CCN(C(=O)Nc2ccc(F)cn2)CC1)[C@H](O)c1cc(Cl)cc2cn[nH]c12] | 446.0 |
| P-0646 | 1-(4-(1-(6-chloro-1H-indazol-4-yl)-1-hydroxy-2-methylpropan-2-yl)piperidin-1-yl)propan-1-one | 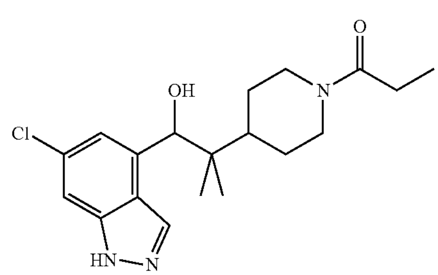 [SMILES: CCC(=O)N1CCC(C(C)(C)C(O)c2cc(Cl)cc3[nH]ncc23)CC1] | 364.0 |
| P-0647 | 4-(1-(6-chloro-1H-indazol-4-yl)-1-hydroxy-2-methylpropan-2-yl)-N-(4-cyanophenyl)piperidine-1-carboxamide | 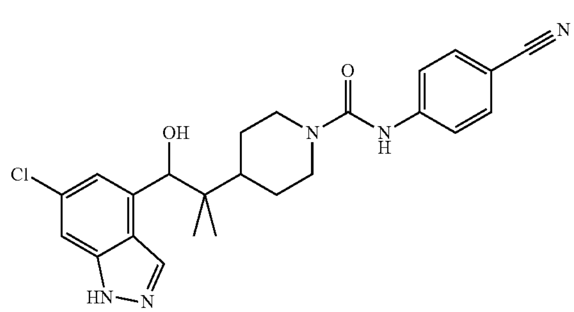 [SMILES: CC(C)(C1CCN(C(=O)Nc2ccc(C#N)cc2)CC1)C(O)c1cc(Cl)cc2[nH]ncc12] | 452.1 |

TABLE 1-continued

| Compound Number | Compound Name | (MH)+ |
|---|---|---|
| P-0648 | 4-(1-(6-chloro-1H-indazol-4-yl)-1-hydroxy-2-methylpropan-2-yl)-N-(4-chlorophenyl)piperidine-1-carboxamide | 459.0 |
| P-0650 | (5-chloro-4-fluoro-1H-indazol-7-yl)(3,3-difluoro-1-methylcyclobutyl)methanol | 305.1 |
| P-0651 | (S)-4-(1-(5-chloro-1H-indazol-7-yl)-1-hydroxy-2-methylpropan-2-yl)-N-(pyridin-4-ylmethyl)piperidine-1-carboxamide | 442.6 |
| P-0652 | (S)-4-(1-(5-chloro-1H-indazol-7-yl)-1-hydroxy-2-methylpropan-2-yl)-N-(2-morpholinoethyl)piperidine-1-carboxamide | 464.5 |

TABLE 1-continued

| Compound Number | Compound Name | Compound Structure | (MH)+ |
|---|---|---|---|
| P-0653 | 4-((S)-1-(5-chloro-1H-indazol-7-yl)-1-hydroxy-2-methylpropan-2-yl)-N-((S)-1-(pyridin-2-yl)ethyl)piperidine-1-carboxamide | 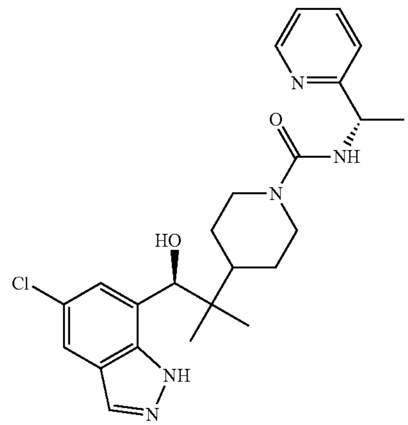 [SMILES: C[C@H](NC(=O)N1CCC(C(C)(C)[C@H](O)c2cc(Cl)cc3cn[nH]c23)CC1)c1ccccn1] | 456.4 |
| P-0654 | (S)-(4-(1-(5-chloro-1H-indazol-7-yl)-1-hydroxy-2-methylpropan-2-yl)piperidin-1-yl)(1,1-dioxidothiomorpholino)methanone | 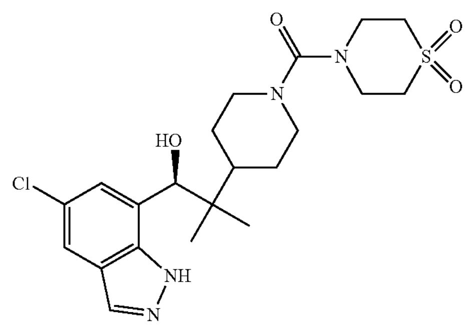 [SMILES: CC(C)(C1CCN(C(=O)N2CCS(=O)(=O)CC2)CC1)[C@H](O)c1cc(Cl)cc2cn[nH]c12] | 469.3 |
| P-0655 | (S)-4-(1-(5-chloro-1H-indazol-7-yl)-1-hydroxy-2-methylpropan-2-yl)-N-(oxetan-3-ylmethyl)piperidine-1-carboxamide | 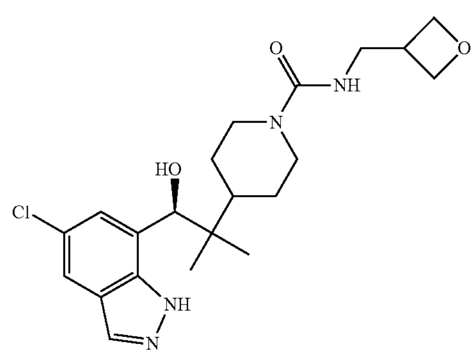 [SMILES: CC(C)(C1CCN(C(=O)NCC2COC2)CC1)[C@H](O)c1cc(Cl)cc2cn[nH]c12] | 421.3 |
| P-0656 | 4-((S)-1-(5-chloro-1H-indazol-7-yl)-1-hydroxy-2-methylpropan-2-yl)-N-((1S,2S)-2-hydroxycyclopentyl)piperidine-1-carboxamide | 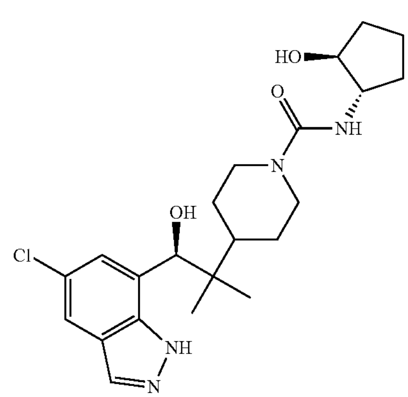 [SMILES: CC(C)(C1CCN(C(=O)N[C@H]2CCC[C@@H]2O)CC1)[C@H](O)c1cc(Cl)cc2cn[nH]c12] | 435.1 |

TABLE 1-continued

| Compound Number | Compound Name | Compound Structure | (MH)+ |
|---|---|---|---|
| P-0657 | 1-(4-(2-(6-chloro-1H-indazol-4-yl)-1,1-difluoro-2-hydroxyethyl)piperidin-1-yl)-2-(2-chloropyridin-4-yl)ethan-1-one | 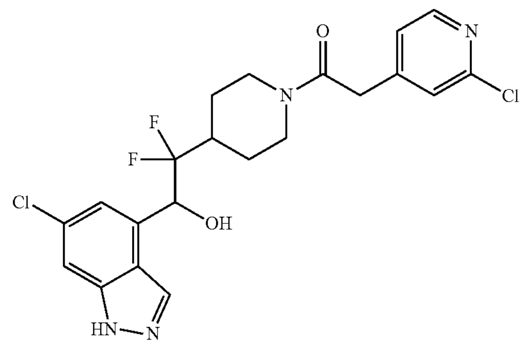 [SMILES: O=C(Cc1ccnc(Cl)c1)N1CCC(C(F)(F)C(O)c2cc(Cl)cc3[nH]ncc23)CC1] | 469.1 |
| P-0658 | (S)-4-(1-(5-chloro-1H-indazol-7-yl)-1-hydroxy-2-methylpropan-2-yl)-N-(5-fluoropyridin-2-yl)piperidine-1-carboxamide | 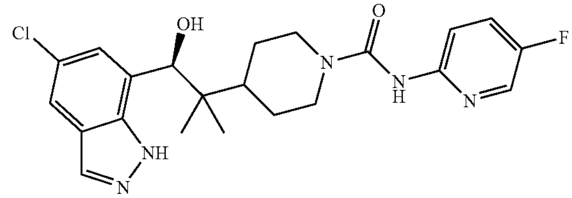 [SMILES: CC(C)(C1CCN(C(=O)Nc2ccc(F)cn2)CC1)[C@H](O)c1cc(Cl)cc2cn[nH]c12] | 446.0 |
| P-0659 | (S)-(4-(1-(5-chloro-1H-indazol-7-yl)-1-hydroxy-2-methylpropan-2-yl)piperidin-1-yl)(1-fluorocyclopropyl)methanone | 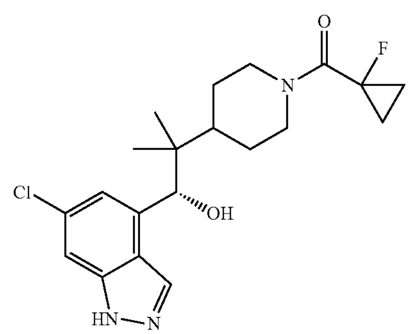 | 394.1 |
| P-0660 | 4-(1-(6-chloro-1H-indazol-4-yl)-1-hydroxy-2-methylpropan-2-yl)-N-(4-fluorophenyl)piperidine-1-carboxamide | 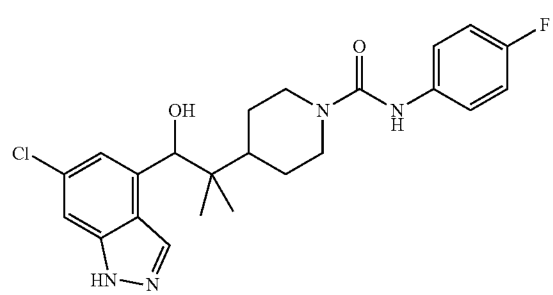 [SMILES: CC(C)(C1CCN(C(=O)Nc2ccc(F)cc2)CC1)C(O)c1cc(Cl)cc2[nH]ncc12] | 445.1 |
| P-0661 | (4-(1-(6-chloro-1H-indazol-4-yl)-1-hydroxy-2-methylpropan-2-yl)piperidin-1-yl)(1-fluorocyclopropyl)methanone | 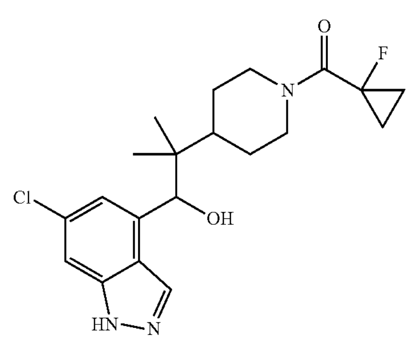 [SMILES: CC(C)(C1CCN(C(=O)C2(F)CC2)CC1)C(O)c1cc(Cl)cc2[nH]ncc12] | 394.10 |

TABLE 1-continued

| Compound Number | Compound Name | Compound Structure | (MH)+ |
|---|---|---|---|
| P-0662 | (S)-4-(1-(5-chloro-1H-indazol-7-yl)-1-hydroxy-2-methylpropan-2-yl)-N,N-dimethylpiperidine-1-carboxamide | 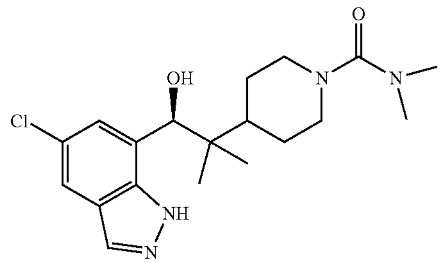 [SMILES: CN(C)C(=O)N1CCC(C(C)(C)[C@H](O)c2cc(Cl)cc3cn[nH]c23)CC1] | 379.2 |
| P-0663 | (S)-1-(4-(1-(5-chloro-1H-indazol-7-yl)-1-hydroxy-2-methylpropan-2-yl)piperidin-1-yl)-2,2,2-trifluoroethan-1-one | 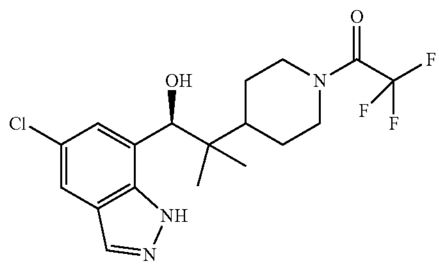 [SMILES: CC(C)(C1CCN(C(=O)C(F)(F)F)CC1)[C@H](O)c1cc(Cl)cc2cn[nH]c12] | 404.5 |
| P-0664 | (S)-4-(1-(5-chloro-1H-indazol-7-yl)-1-hydroxy-2-methylpropan-2-yl)-N-(2-hydroxyethyl)piperidine-1-carboxamide | 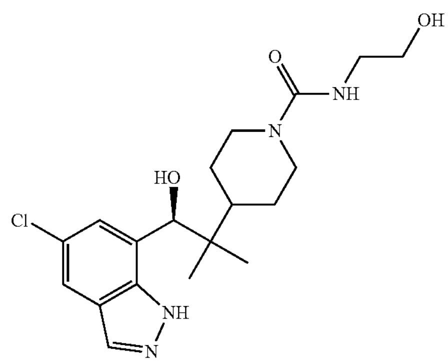 [SMILES: CC(C)(C1CCN(C(=O)NCCO)CC1)[C@H](O)c1cc(Cl)cc2cn[nH]c12] | 395.2 |
| P-0665 | (S)-4-(1-(5-chloro-1H-indazol-7-yl)-1-hydroxy-2-methylpropan-2-yl)-N-(3-hydroxypropyl)piperidine-1-carboxamide | 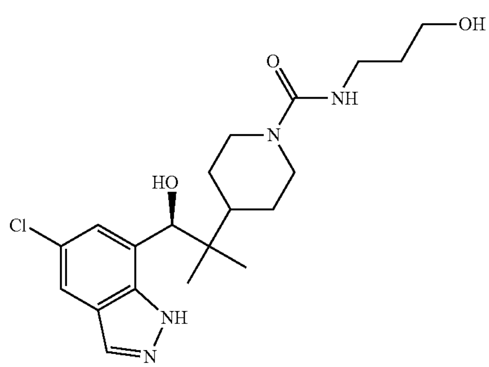 [SMILES: CC(C)(C1CCN(C(=O)NCCCO)CC1)[C@H](O)c1cc(Cl)cc2cn[nH]c12] | 409.3 |

TABLE 1-continued

| Compound Number | Compound Name | Compound Structure | (MH)+ |
|---|---|---|---|
| P-0666 | (S)-4-(1-(5-chloro-1H-indazol-7-yl)-1-hydroxy-2-methylpropan-2-yl)-N-(2-hydroxymethylpropyl)piperidine-1-carboxamide | 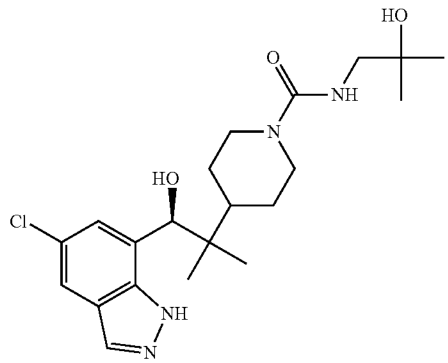 [SMILES: CC(C)(O)CNC(=O)N1CCC(C(C)(C)[C@H](O)c2cc(Cl)cc3cn[nH]c23)CC1] | 423.4 |
| P-0667 | (S)-4-(1-(5-chloro-1H-indazol-7-yl)-1-hydroxy-2-methylpropan-2-yl)-N-((3-hydroxyoxetan-3-yl)methyl)piperidine-1-carboxamide | 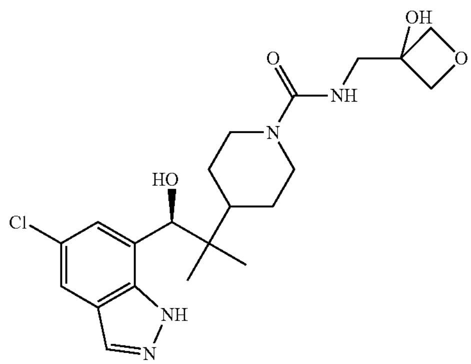 [SMILES: CC(C)(C1CCN(C(=O)NCC2(O)COC2)CC1)[C@H](O)c1cc(Cl)cc2cn[nH]c12] | 437.2 |
| P-0668 | 4-((S)-1-(5-chloro-1H-indazol-7-yl)-1-hydroxy-2-methylpropan-2-yl)-N-((R)-1-hydroxypropan-2-yl)piperidine-1-carboxamide | 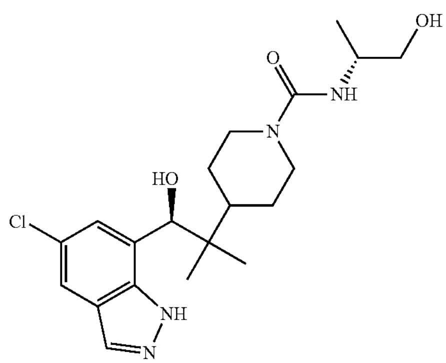 [SMILES: C[C@H](CO)NC(=O)N1CCC(C(C)(C)[C@H](O)c2cc(Cl)cc3cn[nH]c23)CC1] | 409.3 |
| P-0669 | 4-((S)-1-(5-chloro-1H-indazol-7-yl)-1-hydroxy-2-methylpropan-2-yl)-N-((S)-1-hydroxypropan-2-yl)piperidine-1-carboxamide | 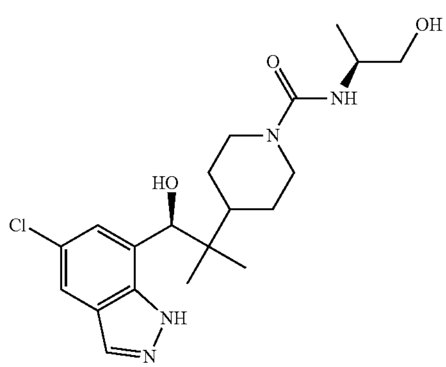 [SMILES: C[C@@H](CO)NC(=O)N1CCC(C(C)(C)[C@H](O)c2cc(Cl)cc3cn[nH]c23)CC1] | 409.3 |

TABLE 1-continued

| Compound Number | Compound Name | Compound Structure | (MH)+ |
|---|---|---|---|
| P-0670 | 4-((S)-1-(5-chloro-1H-indazol-7-yl)-1-hydroxy-2-methylpropan-2-yl)-N-((R)-2-hydroxypropyl)piperidine-1-carboxamide | 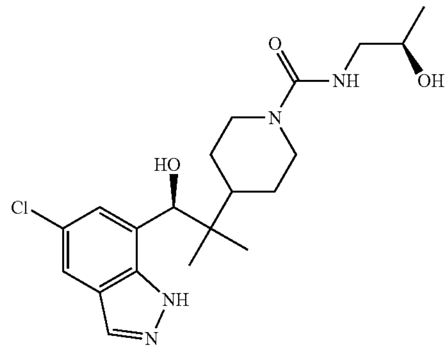 [SMILES: C[C@@H](O)CNC(=O)N1CCC(C(C)(C)[C@H](O)c2cc(Cl)cc3cn[nH]c23)CC1] | 409.3 |
| P-0671 | 4-((S)-1-(5-chloro-1H-indazol-7-yl)-1-hydroxy-2-methylpropan-2-yl)-N-((S)-2-hydroxypropyl)piperidine-1-carboxamide | 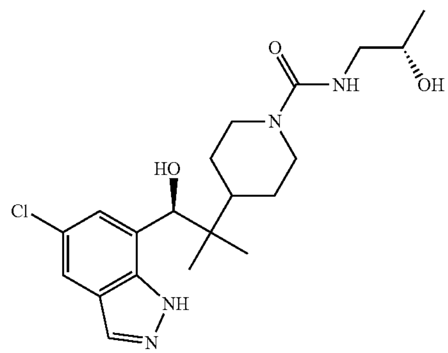 [SMILES: C[C@H](O)CNC(=O)N1CCC(C(C)(C)[C@H](O)c2cc(Cl)cc3cn[nH]c23)CC1] | 409.3 |
| P-0672 | (S)-4-(1-(5-chloro-1H-indazol-7-yl)-1-hydroxy-2-methylpropan-2-yl)-N-(1-cyanocyclopropyl)piperidine-1-carboxamide | 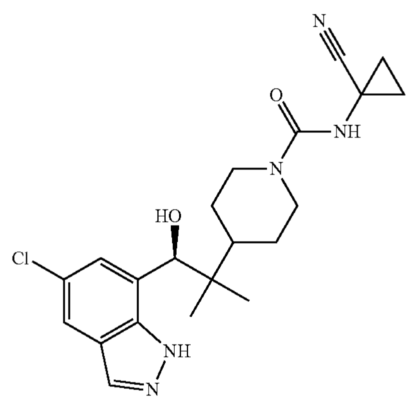 [SMILES: CC(C)(C1CCN(C(=O)NC2(C#N)CC2)CC1)[C@H](O)c1cc(Cl)cc2cn[nH]c12] | 416.5 |
| P-0673 | (S)-(4-(1-(5-chloro-1H-indazol-7-yl)-1-hydroxy-2-methylpropan-2-yl)piperidine-1-carbonyl)glycine | 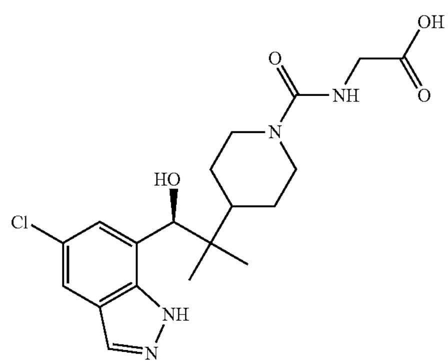 [SMILES: CC(C)(C1CCN(C(=O)NCC(=O)O)CC1)[C@H](O)c1cc(Cl)cc2cn[nH]c12] | 409.3 |

TABLE 1-continued

| Compound Number | Compound Name | Compound Structure | (MH)+ |
|---|---|---|---|
| P-0674 | (S)-4-(1-(5-chloro-1H-indazol-7-yl)-1-hydroxy-2-methylpropan-2-yl)-N-(1,1-dioxidotetrahydro-2H-thiopyran-4-yl)piperidine-1-carboxamide | 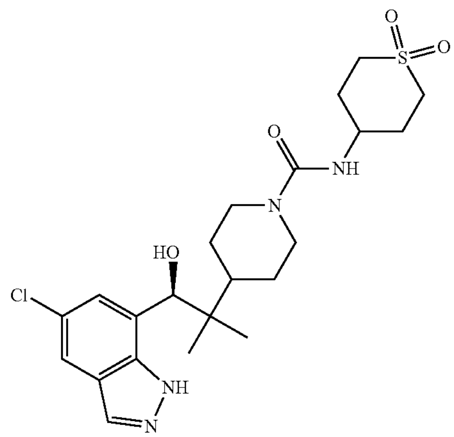 [SMILES: CC(C)(C1CCN(C(=O)NC2CCS(=O)(=O)CC2)CC1)[C@H](O)c1cc(Cl)cc2cn[nH]c12] | 483.4 |
| P-0675 | (S)-4-(1-(5-chloro-1H-indazol-7-yl)-1-hydroxy-2-methylpropan-2-yl)-N-((1-cyanocyclopropyl)methyl)piperidine-1-carboxamide | 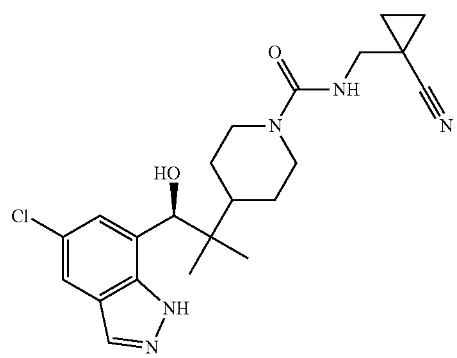 [SMILES: CC(C)(C1CCN(C(=O)NCC2(C#N)CC2)CC1)[C@H](O)c1cc(Cl)cc2cn[nH]c12] | 430.6 |
| P-0676 | (S)-4-(1-(5-chloro-1H-indazol-7-yl)-1-hydroxy-2-methylpropan-2-yl)-N-(4-((4-methylpiperazin-1-yl)methyl)phenyl)piperidine-1-carboxamide | 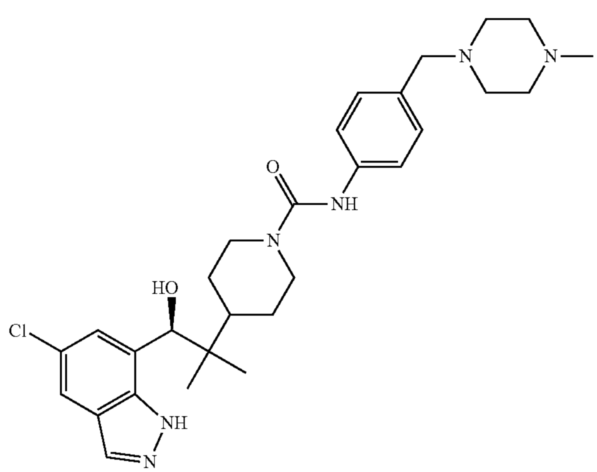 [SMILES: CN1CCN(Cc2ccc(NC(=O)N3CCC(C(C)(C)[C@H](O)c4cc(Cl)cc5cn[nH]c45)CC3)cc2)CC1] | 539.5 |

TABLE 1-continued

| Compound Number | Compound Name | Compound Structure | (MH)+ |
|---|---|---|---|
| P-0677 | (S)-4-(1-(5-chloro-1H-indazol-7-yl)-1-hydroxy-2-methylpropan-2-yl)-N-(2-(methylsulfonamido)ethyl)piperidine-1-carboxamide | 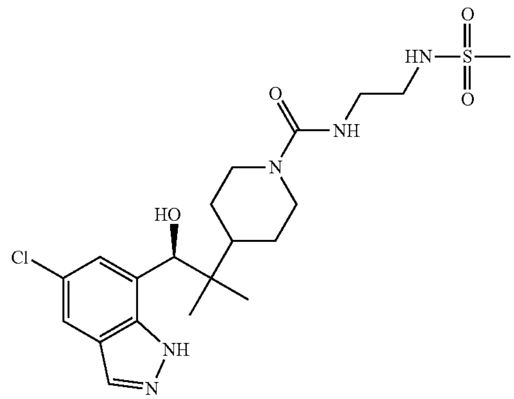 [SMILES: CC(C)(C1CCN(C(=O)NCCNS(C)(=O)=O)CC1)[C@H](O)c1cc(Cl)cc2cn[nH]c12] | 472.3 |
| P-0678 | (S)-4-(1-(5-chloro-1H-indazol-7-yl)-1-hydroxy-2-methylpropan-2-yl)-N-(2-(1,1-dioxidoisothiazolidin-2-yl)ethyl)piperidine-1-carboxamide | 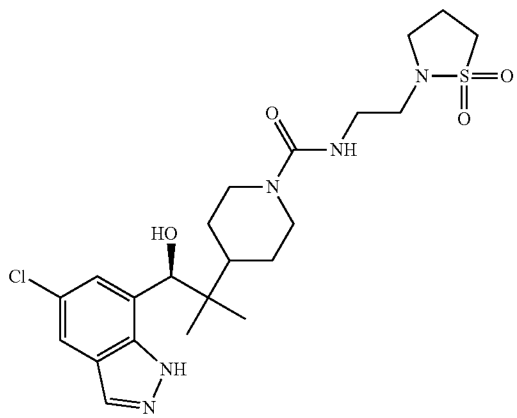 [SMILES: CC(C)(C1CCN(C(=O)NCCN2CCCS2(=O)=O)CC1)[C@H](O)c1cc(Cl)cc2cn[nH]c12] | 498.4 |
| P-0679 | (S)-4-(1-(5-chloro-1H-indazol-7-yl)-1-hydroxy-2-methylpropan-2-yl)-N-(pyridin-3-ylmethyl)piperidine-1-carboxamide | 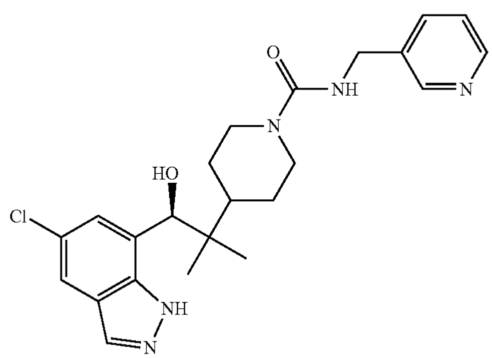 [SMILES: CC(C)(C1CCN(C(=O)NCc2cccnc2)CC1)[C@H](O)c1cc(Cl)cc2cn[nH]c12] | 442.6 |
| P-0680 | (S)-4-(1-(5-chloro-1H-indazol-7-yl)-1-hydroxy-2-methylpropan-2-yl)-N-(pyrazin-2-ylmethyl)piperidine-1-carboxamide | 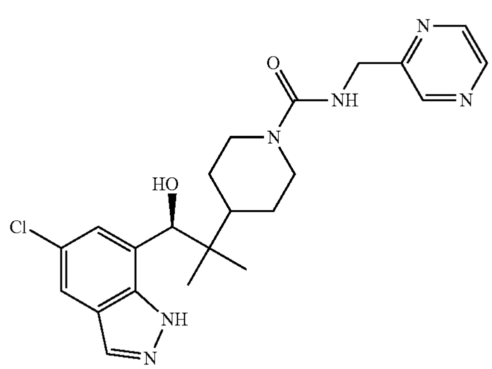 [SMILES: CC(C)(C1CCN(C(=O)NCc2cnccn2)CC1)[C@H](O)c1cc(Cl)cc2cn[nH]c12] | 443.5 |

TABLE 1-continued

| Compound Number | Compound Name | Compound Structure | (MH)+ |
|---|---|---|---|
| P-0681 | (S)-4-(1-(5-chloro-1H-indazol-7-yl)-1-hydroxy-2-methylpropan-2-yl)-N-(pyridazin-4-ylmethyl)piperidine-1-carboxamide | 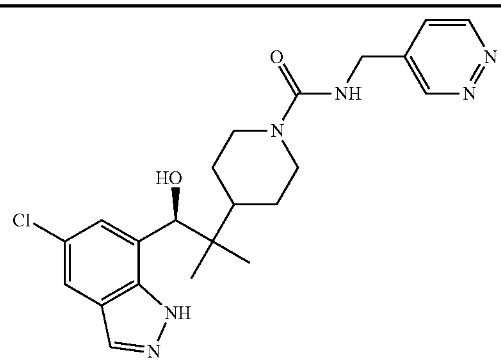 | 443.5 |

Biological Examples

Human Indoleamine 2,3-dioxygenase (IDO) and Tryptophan 2,3-dioxygenase (TDO) enzymatic assay Human IDO or TDO with N-terminal His tag is purified in E. coli. The IDO enzymatic assay is performed using 6 nM IDO and 10 µM L-Trp in the presence of 10 mM ascorbic acid, 5 µM methylene blue, 100 nM catalase and 0.01% Tween 20 in 50 mM sodium phosphate buffer (pH 6.5). 19 µL of above reaction mixture is added to wells of 384 well reaction plate containing 14 of various concentrations of test compound or DMSO vehicle and incubated for 20 minutes at room temperature. The TDO enzymatic reaction assay is performed using 1 nM TDO and 350 µM L-Trp in the presence of 10 mM ascorbic acid, 0.4 µM methylene blue, 100 nM catalase and 0.01% Tween 20 in 50 mM sodium phosphate buffer (pH 6.5). 19 µL of above reaction mixture is added to wells of 384 well reaction plate containing 1 µL of various concentrations of test compound or DMSO vehicle and incubated for 70 minutes at room temperature. 16 wells containing all the components of reaction mixture and 5% DMSO serve as high control. 16 well containing all the components except enzyme of reaction mixture and 5% DMSO serves as low control. Both IDO and TDO enzymatic reactions are stopped by addition of 44 of 30% TCA and incubated 30 minutes at 50° C. to hydrolyze N-formylkynurenine produced by IDO or TDO to kynurenine. Upon measuring the kynurenine level, the percentage inhibition is calculated at individual concentrations relative to high and low controls. The data is analyzed by using nonlinear regression to generate $IC_{50}$ values.

Determine Inhibitor Activity Against IDO or TDO in Cell Based Kynurenine Assay

IDO1-expressing or TDO-expressing HEK293 cell clones are generated upon stable transfection of plasmids expressing human IDO or human TDO under the control of CMV promoter. Cells are selected in DMEM media supplemented with 10% fetal bovine serum and 1 mg/ml G418 at 37° C. in a humidified incubator supplied with 5% $CO_2$. The assays are performed as follows.

Cells were seeded in a 96 well plate in 50 µL of culture media at a density of $2.5 \times 10^4$ per well. Serial dilutions of compounds (in total volume of 50 µL culture media) are added into cells. 4 wells containing 0.2% DMSO treated cells serve as high controls and 4 wells containing media only with 0.2% DMSO serve as low controls. After 24 hours of incubation, the supernatant was transferred to a 384 well reaction plate and the kynurenine level determined. The percentage inhibition at individual concentrations relative to high and low controls is calculated. The data is analyzed by using nonlinear regression to generate $IC_{50}$ values.

Cytotoxicity of each compound after 24 hours of incubation with cells is measured by CellTiter-Glo luminescence cell viability assay according to instructions form the manufacturer. Briefly, after the incubation with each compound and the removal of 20 µL of the supernatant from each well, 25 µL of reconstituted CellTiter Glo Reagent is added to each well. Plates are shaken for approximately 15 minutes at room temperature and then the luminescent signal is read on Tecan microplate reader. The measured luminescence correlates directly with cell number. DMSO treated cells serve as the uninhibited high control. Percentage control at individual concentrations relative to high controls is calculated. The data is analyzed by using nonlinear regression to generate $IC_{50}$ values.

The following Table 2 provides data indicating IDO1 and TDO biochemical and/or cell inhibitory activity for exemplary compounds as described herein. In the table below, activity is provided as follows: +++=0.0001 µM<$IC_{50}$<10 nM; ++=10 µM<$IC_{50}$<100 µM, +=100 µM<$IC_{50}$<200 µM, X=undetectable.

TABLE 2

| P # | IDO1 GMean: $IC_{50}$ (µM) (Biochemical Assay) | TDO GMean: $IC_{50}$ (µM) (Biochemical Assay) | HEK293 IDO1 Kynurenine GMean $IC_{50}$ (µM) (Cellular Assay) | HEK293 TDO Kynurenine GMean $IC_{50}$ (µM) (Cellular Assay) |
|---|---|---|---|---|
| P-0001 | +++ | +++ | X | X |
| P-0002 | +++ | +++ | +++ | +++ |
| P-0003 | +++ | +++ | | |
| P-0004 | +++ | +++ | +++ | +++ |
| P-0005 | +++ | +++ | +++ | +++ |
| P-0006 | +++ | +++ | +++ | +++ |
| P-0007 | +++ | +++ | +++ | +++ |
| P-0008 | +++ | +++ | +++ | +++ |
| P-0009 | +++ | +++ | +++ | X |
| P-0010 | +++ | +++ | +++ | +++ |
| P-0011 | +++ | +++ | +++ | +++ |
| P-0012 | +++ | +++ | X | +++ |
| P-0013 | +++ | +++ | +++ | +++ |
| P-0014 | +++ | +++ | +++ | +++ |
| P-0015 | +++ | +++ | +++ | |

TABLE 2-continued

| P # | IDO1 GMean: IC$_{50}$ (µM) (Biochemical Assay) | TDO GMean: IC$_{50}$ (µM) (Biochemical Assay) | HEK293 IDO1 Kynurenine GMean IC$_{50}$ (µM) (Cellular Assay) | HEK293 TDO Kynurenine GMean IC$_{50}$ (µM) (Cellular Assay) |
|---|---|---|---|---|
| P-0016 | +++ | +++ | +++ | +++ |
| P-0017 | +++ | +++ | +++ | +++ |
| P-0018 | +++ | +++ | +++ | +++ |
| P-0019 | +++ | +++ | X | +++ |
| P-0020 | +++ | X | X | X |
| P-0021 | +++ | +++ | +++ | +++ |
| P-0022 | +++ | +++ | +++ | +++ |
| P-0023 | +++ | +++ | X | +++ |
| P-0024 | +++ | +++ | X | +++ |
| P-0025 | +++ | +++ | +++ | +++ |
| P-0026 | +++ | +++ | +++ | +++ |
| P-0027 | +++ | +++ | +++ | +++ |
| P-0028 | ++ | +++ | X | +++ |
| P-0029 | +++ | +++ | +++ | +++ |
| P-0030 | +++ | +++ | X | X |
| P-0031 | +++ | +++ | X | X |
| P-0032 | +++ | +++ | +++ | +++ |
| P-0033 | +++ | +++ | +++ | +++ |
| P-0034 | +++ | +++ | +++ | +++ |
| P-0035 | +++ | +++ | X | +++ |
| P-0036 | +++ | +++ | +++ | X |
| P-0037 | +++ | +++ | +++ | X |
| P-0038 | +++ | +++ | X | +++ |
| P-0039 | +++ | +++ | +++ | +++ |
| P-0040 | +++ | +++ | +++ | +++ |
| P-0041 | +++ | +++ | +++ | +++ |
| P-0042 | +++ | +++ | +++ | +++ |
| P-0043 | +++ | +++ | +++ | X |
| P-0044 | + | ++ | X | X |
| P-0045 | ++ | +++ | X | +++ |
| P-0046 | +++ | +++ | X | X |
| P-0047 | +++ | +++ | X | +++ |
| P-0048 | +++ | +++ | +++ | +++ |
| P-0049 | +++ | +++ | +++ | +++ |
| P-0050 | +++ | +++ | +++ | X |
| P-0051 | +++ | +++ | +++ | +++ |
| P-0052 | +++ | +++ | +++ | +++ |
| P-0053 | +++ | +++ | +++ | +++ |
| P-0054 | +++ | +++ | +++ | X |
| P-0055 | +++ | +++ | +++ | +++ |
| P-0056 | ++ | +++ | X | +++ |
| P-0057 | +++ | +++ | X | |
| P-0058 | +++ | +++ | +++ | X |
| P-0059 | +++ | +++ | +++ | X |
| P-0060 | +++ | +++ | +++ | X |
| P-0061 | +++ | +++ | +++ | X |
| P-0062 | +++ | +++ | X | X |
| P-0063 | +++ | +++ | X | X |
| P-0064 | +++ | ++ | | |
| P-0065 | +++ | ++ | | |
| P-0066 | +++ | +++ | | |
| P-0067 | + | +++ | | |
| P-0068 | +++ | +++ | | |
| P-0069 | ++ | ++ | | |
| P-0070 | + | + | | |
| P-0071 | +++ | ++ | | |
| P-0072 | ++ | ++ | | |
| P-0073 | +++ | ++ | | |
| P-0074 | +++ | ++ | X | X |
| P-0075 | +++ | +++ | | |
| P-0076 | ++ | +++ | X | X |
| P-0077 | X | ++ | | |
| P-0078 | +++ | ++ | | |
| P-0079 | +++ | +++ | +++ | X |
| P-0080 | +++ | +++ | X | X |
| P-0081 | +++ | +++ | X | X |
| P-0082 | +++ | +++ | +++ | +++ |
| P-0083 | +++ | +++ | +++ | +++ |
| P-0084 | +++ | +++ | X | X |
| P-0085 | +++ | +++ | X | X |
| P-0086 | +++ | +++ | +++ | +++ |
| P-0087 | +++ | +++ | +++ | X |
| P-0088 | +++ | +++ | +++ | X |
| P-0089 | +++ | +++ | +++ | +++ |
| P-0090 | +++ | +++ | +++ | +++ |
| P-0091 | +++ | +++ | +++ | +++ |
| P-0092 | +++ | +++ | +++ | +++ |
| P-0093 | +++ | +++ | +++ | +++ |
| P-0094 | +++ | +++ | X | +++ |
| P-0095 | +++ | +++ | +++ | +++ |
| P-0096 | +++ | +++ | X | +++ |
| P-0097 | +++ | +++ | +++ | +++ |
| P-0098 | +++ | +++ | +++ | X |
| P-0099 | +++ | +++ | +++ | +++ |
| P-0100 | +++ | +++ | +++ | +++ |
| P-0105 | +++ | +++ | +++ | +++ |
| P-0106 | +++ | +++ | +++ | +++ |
| P-0110 | +++ | +++ | +++ | +++ |
| P-0111 | +++ | +++ | +++ | +++ |
| P-0112 | +++ | +++ | +++ | +++ |
| P-0113 | +++ | +++ | +++ | +++ |
| P-0114 | +++ | +++ | +++ | +++ |
| P-0115 | +++ | +++ | +++ | +++ |
| P-0116 | +++ | +++ | +++ | +++ |
| P-0117 | +++ | +++ | +++ | +++ |
| P-0118 | +++ | +++ | +++ | +++ |
| P-0119 | +++ | +++ | +++ | +++ |
| P-0120 | +++ | +++ | +++ | +++ |
| P-0121 | +++ | +++ | +++ | +++ |
| P-0122 | +++ | +++ | +++ | +++ |
| P-0123 | +++ | +++ | +++ | +++ |
| P-0125 | +++ | +++ | +++ | +++ |
| P-0126 | +++ | +++ | +++ | +++ |
| P-0127 | +++ | +++ | +++ | +++ |
| P-0128 | +++ | +++ | +++ | +++ |
| P-0129 | +++ | +++ | +++ | +++ |
| P-0130 | +++ | +++ | +++ | +++ |
| P-0131 | +++ | +++ | +++ | +++ |
| P-0132 | +++ | +++ | +++ | +++ |
| P-0133 | +++ | +++ | +++ | +++ |
| P-0134 | +++ | +++ | +++ | +++ |
| P-0135 | +++ | +++ | +++ | +++ |
| P-0136 | +++ | +++ | +++ | +++ |
| P-0137 | +++ | +++ | +++ | +++ |
| P-0138 | +++ | +++ | +++ | +++ |
| P-0139 | +++ | +++ | +++ | +++ |
| P-0141 | +++ | +++ | +++ | +++ |
| P-0142 | +++ | +++ | +++ | +++ |
| P-0143 | +++ | +++ | +++ | +++ |
| P-0144 | +++ | +++ | +++ | +++ |
| P-0145 | +++ | +++ | X | +++ |
| P-0146 | +++ | +++ | X | +++ |
| P-0147 | +++ | +++ | +++ | +++ |
| P-0148 | +++ | +++ | +++ | +++ |
| P-0149 | +++ | +++ | +++ | +++ |
| P-0150 | +++ | +++ | +++ | +++ |
| P-0151 | +++ | +++ | +++ | +++ |
| P-0152 | +++ | +++ | +++ | +++ |
| P-0153 | +++ | +++ | +++ | +++ |
| P-0154 | +++ | +++ | +++ | +++ |
| P-0155 | +++ | +++ | +++ | +++ |
| P-0156 | +++ | +++ | +++ | +++ |
| P-0157 | +++ | +++ | +++ | +++ |
| P-0158 | +++ | +++ | +++ | +++ |
| P-0159 | +++ | +++ | +++ | +++ |
| P-0160 | +++ | +++ | +++ | +++ |
| P-0161 | +++ | +++ | +++ | +++ |
| P-0162 | +++ | +++ | +++ | +++ |
| P-0163 | +++ | +++ | +++ | +++ |
| P-0164 | +++ | +++ | +++ | +++ |
| P-0165 | +++ | +++ | +++ | +++ |
| P-0166 | +++ | +++ | +++ | +++ |
| P-0167 | +++ | +++ | +++ | +++ |
| P-0168 | +++ | +++ | +++ | +++ |
| P-0169 | +++ | +++ | +++ | +++ |
| P-0170 | +++ | +++ | X | X |

TABLE 2-continued

| P # | IDO1 GMean: IC$_{50}$ (μM) (Biochemical Assay) | TDO GMean: IC$_{50}$ (μM) (Biochemical Assay) | HEK293 IDO1 Kynurenine GMean IC$_{50}$ (μM) (Cellular Assay) | HEK293 TDO Kynurenine GMean IC$_{50}$ (μM) (Cellular Assay) |
|---|---|---|---|---|
| P-0171 | +++ | +++ | X | +++ |
| P-0172 | +++ | +++ | +++ | +++ |
| P-0173 | +++ | +++ | X | +++ |
| P-0174 | +++ | +++ | +++ | +++ |
| P-0175 | +++ | +++ | +++ | +++ |
| P-0176 | +++ | +++ | +++ | +++ |
| P-0177 | +++ | +++ | +++ | +++ |
| P-0178 | +++ | +++ | +++ | +++ |
| P-0179 | +++ | +++ | +++ | +++ |
| P-0180 | +++ | +++ | +++ | +++ |
| P-0181 | +++ | +++ | +++ | +++ |
| P-0182 | +++ | +++ | +++ | +++ |
| P-0183 | +++ | +++ | +++ | +++ |
| P-0184 | +++ | +++ | +++ | +++ |
| P-0185 | +++ | +++ | +++ | +++ |
| P-0186 | +++ | +++ | +++ | +++ |
| P-0187 | +++ | +++ | +++ | +++ |
| P-0188 | +++ | +++ | +++ | X |
| P-0189 | X | X | X | +++ |
| P-0190 | +++ | +++ | +++ | +++ |
| P-0191 | +++ | +++ | +++ | +++ |
| P-0192 | +++ | +++ | +++ | +++ |
| P-0193 | +++ | +++ | +++ | +++ |
| P-0194 | +++ | +++ | +++ | +++ |
| P-0195 | +++ | +++ | +++ | +++ |
| P-0196 | +++ | +++ | +++ | +++ |
| P-0197 | +++ | +++ | +++ | +++ |
| P-0198 | +++ | +++ | +++ | +++ |
| P-0199 | +++ | +++ | +++ | +++ |
| P-0201 | +++ | +++ | X | X |
| P-0202 | ++ | +++ | X | X |
| P-0203 | +++ | +++ | +++ | +++ |
| P-0204 | +++ | +++ | +++ | +++ |
| P-0205 | ++ | ++ | X | +++ |
| P-0206 | ++ | ++ | X | +++ |
| P-0207 | +++ | ++ | +++ | +++ |
| P-0208 | +++ | +++ | +++ | +++ |
| P-0209 | +++ | +++ | +++ | +++ |
| P-0210 | +++ | +++ | +++ | +++ |
| P-0211 | +++ | +++ | +++ | +++ |
| P-0212 | +++ | +++ | +++ | +++ |
| P-0213 | +++ | +++ | +++ | +++ |
| P-0214 | +++ | +++ | +++ | +++ |
| P-0215 | +++ | +++ | +++ | +++ |
| P-0216 | X | ++ | X | X |
| P-0217 | +++ | +++ | +++ | +++ |
| P-0218 | +++ | +++ | +++ | +++ |
| P-0219 | ++ | +++ | X | X |
| P-0220 | +++ | +++ | +++ | +++ |
| P-0221 | +++ | +++ | +++ | +++ |
| P-0222 | +++ | +++ | +++ | +++ |
| P-0223 | +++ | +++ | +++ | +++ |
| P-0224 | +++ | +++ | +++ | +++ |
| P-0225 | +++ | +++ | +++ | +++ |
| P-0226 | +++ | +++ | +++ | X |
| P-0227 | +++ | +++ | +++ | +++ |
| P-0228 | +++ | +++ | +++ | +++ |
| P-0229 | +++ | +++ | +++ | +++ |
| P-0230 | ++ | ++ | X | X |
| P-0231 | + | ++ | X | X |
| P-0232 | +++ | +++ | +++ | +++ |
| P-0233 | ++ | ++ | X | X |
| P-0234 | +++ | +++ | +++ | +++ |
| P-0235 | +++ | +++ | +++ | +++ |
| P-0236 | +++ | +++ | +++ | +++ |
| P-0237 | +++ | +++ | +++ | +++ |
| P-0238 | +++ | +++ | +++ | +++ |
| P-0239 | +++ | +++ | +++ | +++ |
| P-0240 | +++ | +++ | +++ | +++ |
| P-0243 | +++ | +++ | +++ | +++ |
| P-0244 | +++ | +++ | +++ | +++ |
| P-0246 | +++ | +++ | +++ | +++ |
| P-0247 | +++ | +++ | +++ | +++ |
| P-0248 | +++ | +++ | +++ | X |
| P-0249 | +++ | +++ | +++ | X |
| P-0250 | +++ | +++ | +++ | +++ |
| P-0251 | +++ | +++ | +++ | +++ |
| P-0252 | +++ | +++ | +++ | X |
| P-0253 | +++ | +++ | +++ | +++ |
| P-0254 | +++ | +++ | +++ | +++ |
| P-0255 | +++ | +++ | +++ | +++ |
| P-0256 | +++ | +++ | +++ | +++ |
| P-0257 | +++ | +++ | +++ | +++ |
| P-0258 | +++ | +++ | +++ | +++ |
| P-0259 | +++ | +++ | +++ | +++ |
| P-0260 | +++ | +++ | +++ | +++ |
| P-0261 | +++ | +++ | +++ | +++ |
| P-0262 | +++ | +++ | +++ | +++ |
| P-0263 | +++ | +++ | +++ | +++ |
| P-0264 | +++ | +++ | +++ | X |
| P-0265 | +++ | +++ | +++ | +++ |
| P-0266 | +++ | +++ | X | X |
| P-0267 | +++ | +++ | +++ | +++ |
| P-0268 | +++ | +++ | +++ | +++ |
| P-0269 | +++ | +++ | +++ | +++ |
| P-0270 | +++ | +++ | +++ | +++ |
| P-0271 | +++ | +++ | +++ | +++ |
| P-0272 | +++ | +++ | +++ | +++ |
| P-0273 | +++ | +++ | +++ | +++ |
| P-0274 | ++ | ++ | X | X |
| P-0275 | +++ | +++ | +++ | +++ |
| P-0276 | +++ | +++ | +++ | +++ |
| P-0277 | +++ | +++ | +++ | X |
| P-0278 | +++ | +++ | +++ | X |
| P-0279 | +++ | +++ | +++ | X |
| P-0280 | +++ | +++ | +++ | X |
| P-0281 | +++ | +++ | +++ | +++ |
| P-0282 | +++ | +++ | +++ | +++ |
| P-0283 | +++ | +++ | X | +++ |
| P-0284 | +++ | +++ | +++ | +++ |
| P-0285 | +++ | +++ | +++ | +++ |
| P-0286 | +++ | +++ | +++ | +++ |
| P-0287 | +++ | +++ | +++ | X |
| P-0288 | +++ | +++ | +++ | +++ |
| P-0289 | +++ | +++ | +++ | +++ |
| P-0290 | +++ | +++ | +++ | +++ |
| P-0291 | +++ | +++ | +++ | +++ |
| P-0292 | +++ | +++ | +++ | +++ |
| P-0293 | +++ | +++ | +++ | +++ |
| P-0294 | +++ | +++ | +++ | +++ |
| P-0295 | +++ | +++ | +++ | +++ |
| P-0296 | +++ | +++ | +++ | X |
| P-0297 | +++ | +++ | +++ | +++ |
| P-0298 | +++ | +++ | +++ | +++ |
| P-0299 | +++ | +++ | +++ | +++ |
| P-0300 | +++ | +++ | +++ | +++ |
| P-0301 | +++ | +++ | +++ | +++ |
| P-0302 | +++ | +++ | +++ | +++ |
| P-0303 | +++ | +++ | +++ | +++ |
| P-0304 | +++ | +++ | +++ | +++ |
| P-0305 | +++ | +++ | +++ | +++ |
| P-0306 | +++ | +++ | +++ | +++ |
| P-0307 | +++ | +++ | +++ | +++ |
| P-0308 | +++ | +++ | +++ | +++ |
| P-0309 | +++ | +++ | +++ | +++ |
| P-0310 | +++ | +++ | +++ | +++ |
| P-0311 | +++ | +++ | +++ | +++ |
| P-0312 | +++ | +++ | +++ | +++ |
| P-0314 | +++ | +++ | +++ | +++ |
| P-0315 | +++ | +++ | +++ | +++ |
| P-0316 | +++ | +++ | +++ | +++ |
| P-0317 | +++ | +++ | +++ | +++ |
| P-0318 | +++ | +++ | +++ | +++ |
| P-0319 | +++ | +++ | +++ | +++ |
| P-0320 | +++ | +++ | +++ | +++ |
| P-0321 | +++ | +++ | +++ | +++ |

TABLE 2-continued

| P # | IDO1 GMean: IC$_{50}$ (μM) (Biochemical Assay) | TDO GMean: IC$_{50}$ (μM) (Biochemical Assay) | HEK293 IDO1 Kynurenine GMean IC$_{50}$ (μM) (Cellular Assay) | HEK293 TDO Kynurenine GMean IC$_{50}$ (μM) (Cellular Assay) |
|---|---|---|---|---|
| P-0322 | +++ | +++ | +++ | +++ |
| P-0323 | +++ | +++ | +++ | +++ |
| P-0324 | +++ | +++ | +++ | +++ |
| P-0325 | +++ | +++ | +++ | +++ |
| P-0326 | +++ | +++ | +++ | +++ |
| P-0327 | +++ | +++ | +++ | +++ |
| P-0328 | +++ | +++ | +++ | +++ |
| P-0329 | +++ | +++ | +++ | +++ |
| P-0330 | +++ | +++ | +++ | +++ |
| P-0331 | +++ | +++ | +++ | +++ |
| P-0332 | +++ | +++ | +++ | +++ |
| P-0333 | +++ | +++ | +++ | +++ |
| P-0334 | +++ | +++ | +++ | +++ |
| P-0335 | +++ | +++ | +++ | X |
| P-0336 | ++ | +++ | X | +++ |
| P-0337 | +++ | +++ | +++ | +++ |
| P-0338 | +++ | +++ | X | +++ |
| P-0339 | +++ | +++ | +++ | +++ |
| P-0340 | +++ | +++ | +++ | +++ |
| P-0341 | +++ | +++ | +++ | +++ |
| P-0342 | +++ | +++ | +++ | +++ |
| P-0343 | +++ | +++ | +++ | +++ |
| P-0344 | +++ | +++ | +++ | +++ |
| P-0345 | +++ | +++ | +++ | +++ |
| P-0346 | +++ | +++ | +++ | +++ |
| P-0347 | +++ | +++ | +++ | +++ |
| P-0348 | +++ | +++ | X | +++ |
| P-0349 | +++ | +++ | +++ | +++ |
| P-0350 | +++ | +++ | +++ | +++ |
| P-0351 | +++ | +++ | +++ | +++ |
| P-0352 | ++ | +++ | X | +++ |
| P-0353 | +++ | +++ | +++ | +++ |
| P-0354 | +++ | +++ | +++ | +++ |
| P-0355 | +++ | +++ | +++ | +++ |
| P-0356 | +++ | +++ | +++ | +++ |
| P-0357 | +++ | +++ | +++ | +++ |
| P-0358 | +++ | +++ | +++ | +++ |
| P-0359 | +++ | +++ | +++ | +++ |
| P-0360 | +++ | +++ | +++ | +++ |
| P-0361 | +++ | +++ | +++ | +++ |
| P-0362 | +++ | +++ | +++ | +++ |
| P-0363 | +++ | +++ | +++ | +++ |
| P-0364 | +++ | +++ | +++ | +++ |
| P-0365 | +++ | +++ | +++ | +++ |
| P-0366 | +++ | +++ | +++ | +++ |
| P-0367 | +++ | +++ | +++ | +++ |
| P-0368 | +++ | +++ | +++ | +++ |
| P-0369 | +++ | +++ | +++ | +++ |
| P-0370 | +++ | +++ | +++ | +++ |
| P-0371 | ++ | +++ | X | +++ |
| P-0372 | X | +++ | +++ | X |
| P-0373 | +++ | +++ | +++ | +++ |
| P-0374 | +++ | +++ | +++ | +++ |
| P-0375 | +++ | +++ | +++ | +++ |
| P-0376 | +++ | +++ | +++ | +++ |
| P-0377 | +++ | +++ | +++ | +++ |
| P-0378 | +++ | +++ | +++ | +++ |
| P-0379 | +++ | +++ | +++ | +++ |
| P-0380 | +++ | +++ | X | +++ |
| P-0381 | +++ | +++ | +++ | +++ |
| P-0382 | +++ | X | +++ | X |
| P-0383 | +++ | +++ | +++ | +++ |
| P-0384 | +++ | +++ | X | X |
| P-0385 | +++ | +++ | +++ | +++ |
| P-0386 | +++ | +++ | +++ | +++ |
| P-0387 | +++ | +++ | +++ | +++ |
| P-0388 | +++ | +++ | +++ | +++ |
| P-0389 | +++ | +++ | +++ | +++ |
| P-0390 | +++ | +++ | +++ | +++ |
| P-0391 | +++ | +++ | +++ | +++ |
| P-0392 | +++ | +++ | +++ | +++ |
| P-0393 | +++ | +++ | +++ | +++ |
| P-0394 | +++ | +++ | +++ | +++ |
| P-0395 | +++ | +++ | +++ | +++ |
| P-0396 | +++ | +++ | +++ | +++ |
| P-0397 | +++ | +++ | +++ | +++ |
| P-0398 | +++ | +++ | +++ | +++ |
| P-0399 | +++ | +++ | +++ | +++ |
| P-0400 | +++ | +++ | +++ | +++ |
| P-0401 | +++ | +++ | +++ | +++ |
| P-0402 | +++ | +++ | +++ | +++ |
| P-0403 | +++ | +++ | +++ | +++ |
| P-0404 | +++ | +++ | +++ | +++ |
| P-0405 | +++ | +++ | +++ | +++ |
| P-0406 | +++ | +++ | +++ | +++ |
| P-0407 | +++ | +++ | X | +++ |
| P-0408 | +++ | +++ | +++ | +++ |
| P-0409 | +++ | +++ | +++ | +++ |
| P-0410 | +++ | +++ | +++ | +++ |
| P-0411 | +++ | +++ | +++ | +++ |
| P-0412 | +++ | +++ | +++ | +++ |
| P-0413 | +++ | +++ | +++ | +++ |
| P-0414 | +++ | +++ | +++ | +++ |
| P-0415 | +++ | +++ | +++ | X |
| P-0416 | +++ | +++ | +++ | +++ |
| P-0417 | +++ | +++ | +++ | +++ |
| P-0418 | +++ | +++ | +++ | +++ |
| P-0419 | +++ | +++ | +++ | +++ |
| P-0420 | +++ | +++ | +++ | +++ |
| P-0421 | +++ | +++ | +++ | +++ |
| P-0422 | +++ | +++ | +++ | +++ |
| P-0423 | +++ | +++ | +++ | +++ |
| P-0424 | +++ | +++ | X | +++ |
| P-0425 | +++ | +++ | +++ | +++ |
| P-0426 | +++ | +++ | X | +++ |
| P-0427 | +++ | +++ | +++ | +++ |
| P-0428 | +++ | +++ | X | +++ |
| P-0429 | +++ | +++ | X | +++ |
| P-0430 | +++ | +++ | +++ | +++ |
| P-0431 | ++ | +++ | +++ | +++ |
| P-0432 | +++ | +++ | X | +++ |
| P-0433 | X | +++ | +++ | +++ |
| P-0434 | ++ | +++ | +++ | +++ |
| P-0435 | +++ | +++ | +++ | +++ |
| P-0436 | +++ | +++ | +++ | +++ |
| P-0437 | +++ | +++ | X | X |
| P-0438 | +++ | +++ | +++ | +++ |
| P-0439 | +++ | +++ | +++ | +++ |
| P-0440 | +++ | +++ | +++ | +++ |
| P-0441 | +++ | +++ | +++ | +++ |
| P-0442 | +++ | +++ | +++ | +++ |
| P-0443 | +++ | +++ | +++ | +++ |
| P-0444 | +++ | +++ | +++ | +++ |
| P-0445 | +++ | +++ | +++ | +++ |
| P-0446 | +++ | +++ | +++ | +++ |
| P-0447 | +++ | +++ | +++ | +++ |
| P-0448 | +++ | +++ | +++ | +++ |
| P-0449 | +++ | +++ | +++ | +++ |
| P-0450 | +++ | +++ | +++ | +++ |
| P-0451 | +++ | +++ | +++ | +++ |
| P-0452 | +++ | +++ | +++ | +++ |
| P-0453 | +++ | +++ | X | X |
| P-0454 | +++ | +++ | +++ | +++ |
| P-0455 | +++ | +++ | +++ | +++ |
| P-0456 | +++ | +++ | +++ | +++ |
| P-0457 | +++ | +++ | +++ | +++ |
| P-0458 | +++ | +++ | +++ | +++ |
| P-0459 | +++ | +++ | +++ | +++ |
| P-0460 | +++ | +++ | +++ | +++ |
| P-0461 | +++ | +++ | +++ | +++ |
| P-0462 | +++ | +++ | +++ | +++ |
| P-0463 | +++ | +++ | +++ | X |
| P-0464 | +++ | +++ | +++ | +++ |
| P-0465 | +++ | +++ | +++ | +++ |
| P-0466 | +++ | +++ | +++ | +++ |
| P-0467 | +++ | +++ | +++ | X |

TABLE 2-continued

| P # | IDO1 GMean: IC$_{50}$ (µM) (Biochemical Assay) | TDO GMean: IC$_{50}$ (µM) (Biochemical Assay) | HEK293 IDO1 Kynurenine GMean IC$_{50}$ (µM) (Cellular Assay) | HEK293 TDO Kynurenine GMean IC$_{50}$ (µM) (Cellular Assay) |
|---|---|---|---|---|
| P-0468 | +++ | +++ | +++ | +++ |
| P-0469 | +++ | +++ | +++ | +++ |
| P-0470 | +++ | +++ | +++ | +++ |
| P-0471 | +++ | +++ | +++ | +++ |
| P-0472 | +++ | +++ | +++ | +++ |
| P-0473 | +++ | +++ | +++ | +++ |
| P-0474 | +++ | +++ | +++ | +++ |
| P-0475 | +++ | +++ | +++ | +++ |
| P-0476 | +++ | +++ | +++ | +++ |
| P-0477 | +++ | +++ | +++ | +++ |
| P-0478 | +++ | +++ | +++ | +++ |
| P-0479 | +++ | +++ | +++ | +++ |
| P-0480 | +++ | +++ | +++ | +++ |
| P-0481 | +++ | +++ | +++ | X |
| P-0482 | +++ | +++ | +++ | +++ |
| P-0483 | +++ | +++ | +++ | +++ |
| P-0484 | +++ | +++ | +++ | +++ |
| P-0485 | +++ | +++ | +++ | X |
| P-0486 | +++ | +++ | +++ | +++ |
| P-0487 | +++ | +++ | +++ | +++ |
| P-0488 | +++ | +++ | +++ | +++ |
| P-0489 | +++ | +++ | +++ | +++ |
| P-0490 | +++ | +++ | +++ | +++ |
| P-0491 | +++ | +++ | +++ | +++ |
| P-0492 | +++ | +++ | +++ | +++ |
| P-0493 | +++ | +++ | +++ | +++ |
| P-0494 | +++ | +++ | +++ | +++ |
| P-0495 | +++ | +++ | +++ | +++ |
| P-0496 | +++ | +++ | +++ | +++ |
| P-0497 | +++ | +++ | +++ | +++ |
| P-0498 | +++ | +++ | +++ | +++ |
| P-0499 | +++ | +++ | +++ | +++ |
| P-0500 | +++ | +++ | +++ | +++ |
| P-0501 | +++ | +++ | +++ | +++ |
| P-0502 | +++ | +++ | +++ | +++ |
| P-0503 | +++ | +++ | +++ | +++ |
| P-0504 | +++ | +++ | +++ | +++ |
| P-0505 | +++ | +++ | +++ | +++ |
| P-0506 | +++ | +++ | +++ | +++ |
| P-0507 | +++ | +++ | +++ | +++ |
| P-0508 | +++ | +++ | +++ | +++ |
| P-0509 | +++ | +++ | +++ | +++ |
| P-0510 | +++ | +++ | +++ | +++ |
| P-0511 | +++ | +++ | +++ | +++ |
| P-0512 | +++ | +++ | +++ | +++ |
| P-0513 | +++ | +++ | +++ | +++ |
| P-0514 | +++ | +++ | +++ | +++ |
| P-0515 | +++ | +++ | +++ | +++ |
| P-0516 | +++ | +++ | +++ | +++ |
| P-0517 | +++ | X | X | X |
| P-0518 | +++ | +++ | +++ | +++ |
| P-0519 | +++ | +++ | +++ | +++ |
| P-0520 | +++ | +++ | +++ | +++ |
| P-0521 | +++ | +++ | +++ | +++ |
| P-0522 | +++ | +++ | +++ | +++ |
| P-0523 | +++ | +++ | +++ | +++ |
| P-0524 | +++ | +++ | +++ | +++ |
| P-0525 | +++ | +++ | +++ | +++ |
| P-0526 | +++ | +++ | +++ | +++ |
| P-0527 | +++ | ++ | +++ | +++ |
| P-0528 | +++ | X | +++ | +++ |
| P-0529 | +++ | +++ | +++ | +++ |
| P-0530 | +++ | +++ | +++ | +++ |
| P-0531 | +++ | +++ | +++ | +++ |
| P-0532 | +++ | +++ | +++ | +++ |
| P-0533 | +++ | +++ | +++ | +++ |
| P-0534 | +++ | +++ | +++ | +++ |
| P-0535 | +++ | +++ | +++ | +++ |
| P-0536 | +++ | +++ | +++ | +++ |
| P-0537 | +++ | +++ | +++ | +++ |
| P-0538 | +++ | +++ | +++ | +++ |
| P-0539 | +++ | +++ | +++ | +++ |
| P-0540 | +++ | +++ | +++ | +++ |
| P-0541 | +++ | +++ | +++ | +++ |
| P-0542 | +++ | +++ | +++ | +++ |
| P-0543 | +++ | +++ | +++ | +++ |
| P-0544 | +++ | +++ | +++ | +++ |
| P-0545 | +++ | +++ | +++ | +++ |
| P-0546 | +++ | +++ | +++ | +++ |
| P-0547 | +++ | +++ | +++ | +++ |
| P-0548 | +++ | +++ | +++ | +++ |
| P-0550 | +++ | +++ | +++ | +++ |
| P-0551 | +++ | +++ | +++ | +++ |
| P-0552 | +++ | +++ | +++ | +++ |
| P-0553 | +++ | +++ | +++ | +++ |
| P-0554 | +++ | +++ | +++ | +++ |
| P-0555 | +++ | +++ | +++ | +++ |
| P-0556 | +++ | +++ | +++ | +++ |
| P-0557 | +++ | +++ | +++ | +++ |
| P-0558 | +++ | +++ | +++ | +++ |
| P-0559 | +++ | +++ | +++ | +++ |
| P-0560 | +++ | +++ | +++ | +++ |
| P-0561 | +++ | +++ | +++ | +++ |
| P-0562 | +++ | +++ | +++ | +++ |
| P-0563 | +++ | +++ | +++ | +++ |
| P-0564 | +++ | +++ | +++ | +++ |
| P-0565 | +++ | +++ | +++ | +++ |
| P-0566 | +++ | +++ | +++ | +++ |
| P-0567 | +++ | +++ | +++ | +++ |
| P-0568 | +++ | +++ | +++ | +++ |
| P-0569 | +++ | +++ | +++ | +++ |
| P-0570 | +++ | +++ | +++ | +++ |
| P-0571 | +++ | +++ | | |
| P-0572 | +++ | +++ | | |
| P-0573 | +++ | +++ | | |
| P-0574 | +++ | +++ | | |
| P-0575 | +++ | +++ | | |
| P-0576 | +++ | +++ | | |
| P-0577 | +++ | +++ | | |
| P-0578 | +++ | +++ | | |
| P-0579 | +++ | +++ | | |
| P-0580 | +++ | +++ | | |
| P-0581 | +++ | +++ | | |
| P-0582 | +++ | +++ | | |
| P-0583 | +++ | +++ | | |
| P-0584 | +++ | +++ | | |
| P-0585 | +++ | +++ | | |
| P-0586 | +++ | +++ | | |
| P-0587 | +++ | +++ | | |
| P-0588 | +++ | +++ | | |
| P-0589 | +++ | +++ | | |
| P-0590 | +++ | +++ | | |
| P-0591 | +++ | +++ | | |
| P-0592 | +++ | +++ | | |
| P-0593 | +++ | +++ | | |
| P-0594 | +++ | +++ | | |
| P-0595 | +++ | +++ | | |
| P-0596 | +++ | +++ | | |
| P-0597 | +++ | +++ | | |
| P-0598 | +++ | +++ | | |
| P-0599 | +++ | +++ | | |
| P-0600 | +++ | +++ | | |
| P-0601 | +++ | +++ | | |
| P-0602 | +++ | +++ | | |
| P-0603 | +++ | +++ | | |
| P-0604 | +++ | +++ | | |
| P-0605 | +++ | +++ | | |
| P-0606 | +++ | +++ | | |
| P-0607 | +++ | +++ | | |
| P-0608 | +++ | +++ | | |
| P-0609 | +++ | +++ | | |
| P-0610 | +++ | +++ | | |
| P-0611 | +++ | +++ | | |
| P-0612 | +++ | +++ | | |
| P-0613 | +++ | +++ | | |
| P-0614 | +++ | +++ | | |

TABLE 2-continued

| P # | IDO1 GMean: IC$_{50}$ (μM) (Biochemical Assay) | TDO GMean: IC$_{50}$ (μM) (Biochemical Assay) | HEK293 IDO1 Kynurenine GMean IC$_{50}$ (μM) (Cellular Assay) | HEK293 TDO Kynurenine GMean IC$_{50}$ (μM) (Cellular Assay) |
|---|---|---|---|---|
| P-0615 | +++ | +++ | | |
| P-0616 | +++ | ++ | | |
| P-0617 | +++ | +++ | | |
| P-0618 | +++ | +++ | | |
| P-0619 | +++ | +++ | | |
| P-0620 | +++ | +++ | | |
| P-0621 | +++ | +++ | | |
| P-0622 | +++ | +++ | | |
| P-0623 | +++ | +++ | | |
| P-0624 | +++ | +++ | | |
| P-0625 | +++ | +++ | | |
| P-0626 | +++ | +++ | | |
| P-0627 | +++ | +++ | | |
| P-0628 | +++ | +++ | | |
| P-0629 | +++ | +++ | | |
| P-0630 | +++ | +++ | | |
| P-0631 | +++ | +++ | | |
| P-0632 | | | | |
| P-0633 | | | | |
| P-0634 | | | | |
| P-0635 | | | | |
| P-0636 | +++ | +++ | | |
| P-0637 | +++ | +++ | | |
| P-0638 | +++ | +++ | | |
| P-0650 | +++ | +++ | | |
| P-0651 | +++ | +++ | | |
| P-0652 | +++ | +++ | | |
| P-0653 | +++ | +++ | | |
| P-0654 | +++ | +++ | | |
| P-0655 | +++ | +++ | | |
| P-0656 | +++ | +++ | | |
| P-0657 | +++ | +++ | | |
| P-0658 | +++ | +++ | | |
| P-0659 | +++ | +++ | | |
| P-0660 | +++ | +++ | | |
| P-0661 | +++ | +++ | | |
| P-0662 | +++ | +++ | | |
| P-0663 | +++ | +++ | | |
| P-0664 | +++ | +++ | | |
| P-0665 | +++ | +++ | | |
| P-0666 | +++ | +++ | | |
| P-0667 | +++ | +++ | | |
| P-0668 | +++ | +++ | | |
| P-0669 | +++ | +++ | | |
| P-0670 | +++ | +++ | | |
| P-0671 | +++ | +++ | | |
| P-0672 | +++ | +++ | | |
| P-0673 | +++ | +++ | | |
| P-0674 | +++ | +++ | | |
| P-0675 | +++ | +++ | | |
| P-0676 | +++ | +++ | | |
| P-0677 | +++ | +++ | | |
| P-0678 | +++ | +++ | | |
| P-0679 | +++ | +++ | | |
| P-0680 | +++ | +++ | | |
| P-0681 | +++ | +++ | | |

It has been found that the compounds the of this disclosure that 4,6 indazole compounds having the general core structure:

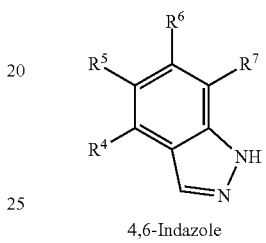

4,6-Indazole have surprising and unexpected IDO1 biochemical and cellular potency, as measured by the biochemical and cellular assays described in this disclosure, when compared to 5,7 indazole compounds compounds having the following core structure:

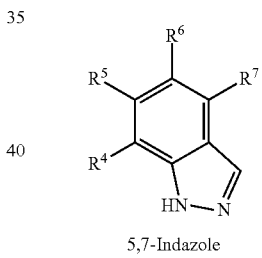

5,7-Indazole

The following 6 comparative examples below demonstrate the surprisingly and unexpected IDO1 biochemical and cellular potency of the 4,6 indazole compounds of this disclosure as compared to the respective 5,7 indazole compounds.

| | 4,6 indazole | 5,7 indazole |
|---|---|---|
| 1. Structure | | |
| 2. IDO1 | 0.05 (μM) | 3.25 (μM) |
| 3. TDO | 0.17 (μM) | 6.06 (μM) |
| 4. hIDO1 | 0.23 (μM) | 10.00 (μM) |
| 5. hTDO | 1.20 (μM) | 0.05 (μM) |

| 1. Structure | 4,6 indazole | 5,7 indazole |
|---|---|---|
| 2. IDO1 | 0.11 (μM) | 6.60 (μM) |
| 3. TDO | 1.18 (μM) | 0.16 (μM) |
| 4. hIDO1 | 0.08 (μM) | 10.00 (μM) |
| 5. hTDO | 2.63 (μM) | 0.17 (μM) |

| 1. Structure | 4,6 indazole | 5,7 indazole |
|---|---|---|
| 2. IDO1 | 0.03 (μM) | 0.70 (μM) |
| 3. TDO | 0.15 (μM) | 0.10 (μM) |
| 4. hIDO1 | 0.08 (μM) | 10.00 (μM) |
| 5. hTDO | 0.42 (μM) | 0.01 (μM) |

| 1. Structure | 4,6 indazole | 5,7 indazole |
|---|---|---|
| 2. IDO1 | 0.11 (μM) | 0.95 (μM) |
| 3. TDO | 1.18 (μM) | 0.08 (μM) |
| 4. hIDO1 | 0.08 (μM) | 6.94 (μM) |
| 5. hTDO | 2.63 (μM) | 0.01 (μM) |

| 1. Structure | 4,6 indazole | 5,7 indazole |
|---|---|---|
| 2. IDO1 | 0.14 (μM) | 22.02 (μM) |
| 3. TDO | 0.04 (μM) | 0.04 (μM) |

-continued

| 1. Structure | 4,6 indazole | 5,7 indazole |
|---|---|---|
| 4. hIDO1 | 10.00 (μM) | 10.00 (μM) |
| 5. hTDO | 2.94 (μM) | 0.03 (μM) |

| 1. Structure | 4,6 indazole | 5,7 indazole |
|---|---|---|
| 2. IDO1 | 0.16 (μM) | 200.00 (μM) |
| 3. TDO | 0.22 (μM) | 0.18 (μM) |
| 4. hIDO1 | 0.40 (μM) | 10.00 (μM) |
| 5. hTDO | 2.41 (μM) | 0.57 (μM) |

Other embodiments of this disclosure relate to one or more of the compounds in Tables 1 and 2 that have greater IDO1 biochemical inhibitory activity than TDO biochemical inhibitory activity as measured by the biochemical assays described in this disclosure. Other embodiments of this disclosure relate to one or more of the compounds in Tables 1 and 2 that have at least three fold greater IDO1 biochemical inhibitory activity than TDO biochemical inhibitory activity as measured by the biochemical assays described in this disclosure. Other embodiments of this disclosure relate to one or more of the compounds in Tables 1 and 2 that have at least five fold greater IDO1 biochemical inhibitory activity than TDO biochemical inhibitory activity as measured by the biochemical assays described in this disclosure.

Other embodiments of this disclosure relate to one or more of the compounds in Tables 1 and 2 that have at least ten fold greater IDO1 biochemical inhibitory activity than TDO biochemical inhibitory activity as measured by the biochemical assays described in this disclosure.

Other embodiments of this disclosure relate to one or more of the compounds in Tables 1 and 2 that have greater IDO1 cellular inhibitory activity than TDO cellular inhibitory activity as measured by the cellular assays described in this disclosure. Other embodiments of this disclosure relate to one or more of the compounds in Tables 1 and 2 that have at least three fold greater IDO1 cellular inhibitory activity than TDO cellular inhibitory activity as measured by the cellular assays described in this disclosure. Other embodiments of this disclosure relate to one or more of the compounds in Tables 1 and 2 that have at least five fold greater IDO1 cellular inhibitory activity than TDO cellular inhibitory activity as measured by the cellular assays described in this disclosure.

Other embodiments of this disclosure relate one or more of the compounds in Tables 1 and 2 that have at least ten fold greater IDO1 cellular inhibitory activity than TDO cellular inhibitory activity as measured by the cellular assays described in this disclosure.

Other embodiments of this disclosure relate to one or more of the compounds in Tables 1 and 2 that have greater TDO biochemical inhibitory activity than IDO1 biochemical inhibitory activity as measured by the biochemical assays described in this disclosure. Other embodiments of this disclosure relate to one or more of the compounds in Tables 1 and 2 that have at least three fold greater TDO biochemical inhibitory activity than IDO1 biochemical inhibitory activity as measured by the biochemical assays described in this disclosure. Other embodiments of this disclosure relate to one or more of the compounds in Tables 1 and 2 that have at least five fold greater TDO biochemical inhibitory activity than IDO1 biochemical inhibitory activity as measured by the biochemical assays described in this disclosure.

Other embodiments of this disclosure relate to one or more of the compounds in Tables 1 and 2 that have at least ten fold greater TDO biochemical inhibitory activity than IDO1 biochemical inhibitory activity as measured by the biochemical assays described in this disclosure.

Other embodiments of this disclosure relate to one or more of the compounds in Tables 1 and 2 that have greater TDO cellular inhibitory activity than IDO1 cellular inhibitory activity as measured by the cellular assays described in this disclosure. Other embodiments of this disclosure relate to one or more of the compounds in Table 1 that have at least three fold greater TDO cellular inhibitory activity than IDO1 cellular inhibitory activity as measured by the cellular assays described in this disclosure. Other embodiments of this disclosure relate to one or more of the compounds in Table 1 that have at least five fold greater TDO cellular inhibitory activity than IDO1 cellular inhibitory activity as measured by the cellular assays described in this disclosure. Other embodiments of this disclosure relate to one or more of the compounds in Tables 1 and 2 that have at least ten fold greater TDO cellular inhibitory activity than IDO1 cellular inhibitory activity as measured by the cellular assays described in this disclosure.

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of the compounds of this disclosure and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

Reference to particular amino acid residues in human IDO1 polypeptide is defined by the numbering corresponding to the IDO1 sequence in GenBank GI:4504577 (SEQ ID NO. 1). Reference to particular nucleotide positions in a nucleotide sequence encoding all or a portion of IDO1 is defined by the numbering corresponding to the sequence provided in GenBank GI:323668304 (SEQ ID NO:2).

Reference to particular amino acid residues in human TDO polypeptide is defined by the numbering corresponding to the TDO sequence in GenBank GI:5032165 (SEQ ID NO. 3). Reference to particular nucleotide positions in a nucleotide sequence encoding all or a portion of TDO is defined by the numbering corresponding to the sequence provided in GenBank (SEQ ID NO. 4).

```
GI:4504577
                                                      SEQ ID NO: 1
MAHAMENSWTISKEYHIDEEVGFALPNPQENLPDFYNDWMFIAKHLPDLIESGQLRERV

EKLNMLSIDHLTDHKSQRLARLVLGCITMAYVWGKGHGDVRKVLPRNIAVPYCQLSK

KLELPPILVYADCVLANWKKKDPNKPLTYENMDVLFSFRDGDCSKGFFLVSLLVEIAAA

SAIKVIPTVFKAMQMQERDTLLKALLEIASCLEKALQVFHQIHDHVNPKAFFSVLRIYLS

GWKGNPQLSDGLVYEGFWEDPKEFAGGSAGQSSVFQCFDVLLGIQQTAGGGHAAQFL

QDMRRYMPPAHRNFLCSLESNPSVREFVLSKGDAGLREAYDACVKALVSLRSYHLQIV

TKYILIPASQQPKENKTSEDPSKLEAKGTGGTDLMNFLKTVRSTTEKSLLKEG

GI:323668304
                                                      SEQ ID NO: 2
AATTTCTCACTGCCCCTGTGATAAACTGTGGTCACTGGCTGTGGCAGCAACTATTAT

AAGATGCTCTGAAAACTCTTCAGACACTGAGGGGCACCAGAGGAGCAGACTACAA

GAATGGCACACGCTATGGAAAACTCCTGGACAATCAGTAAAGAGTACCATATTGAT

GAAGAAGTGGGCTTTGCTCTGCCAAATCCACAGGAAAATCTA

CCTGATTTTTATAATGACTGGATGTTCATTGCTAAACATCTGCCTGATCTCATAGAG

TCTGGCCAGCTTCGAGAAAGAGTTGAGAAGTTAAACATGCTCAGCATTGATCATCT

CACAGACCACAAGTCACAGCGCCTTGCACGTCTAGTTCTGGGATGCATCACCATGG
```

-continued
```
CATATGTGTGGGGCAAAGGTCATGGAGATGTCCGTAAGGTCTTGCCAAGAAATATT

GCTGTTCCTTACTGCCAACTCTCCAAGAAACTGGAACTGCCTCCTATTTTGGTTTATG

CAGACTGTGTCTTGGCAAACTGGAAGAAAAGGATCCTAATAAGCCCCTGACTTAT

GAGAACATGGACGTTTTGTTCTCATTTCGTGATGGAGACTGCAGTAAAGGATTCTTC

CTGGTCTCTCTATTGGTGGAAATAGCAGCTGCTTCTGCAATCAAAGTAATTCCTACT

GTATTCAAGGCAATGCAAATGCAAGAACGGGACACTTTGCTAAAGGCGCTGTTGGA

AATAGCTTCTTGCTTGGAGAAAGCCCTTCAAGTGTTTCACCAAATCCACGATCATGT

GAACCCAAAAGCATTTTTCAGTGTTCTTCGCATATATTTGTCTGGCTGGAAAGGCAA

CCCCCAGCTATCAGACGGTCTGGTGTATGAAGGGTTCTGGGAAGACCCAAAGGAGT

TTGCAGGGGGCAGTGCAGGCCAAAGCAGCGTCTTTCAGTGCTTTGACGTCCTGCTG

GGCATCCAGCAGACTGCTGGTGGAGGACATGCTGCTCAGTTCCTCCAGGACATGAG

AAGATATATGCCACCAGCTCACAGGAACTTCCTGTGCTCATTAGAGTCAAATCCCTC

AGTCCGTGAGTTTGTCCTTTCAAAAGGTGATGCTGGCCTGCGGGAAGCTTATGACGC

CTGTGTGAAAGCTCTGGTCTCCCTGAGGAGCTACCATCTGCAAATCGTGACTAAGTA

CATCCTGATTCCTGCAAGCCAGCAGCCAAAGGAGAATAAGACCTCTGAAGACCCTT

CAAAACTGGAAGCCAAAGGAACTGGAGGCACTGATTTAATGAATTTCCTGAAGACT

GTAAGAAGTACAACTGAGAAATCCCTTTTGAAGGAAGGTTAATGTAACCCAACAAG

AGCACATTTTATCATAGCAGAGACATCTGTATGCATTCCTGTCATTACCCATTGTAACAG

AGCCACAAACTAATACTATGCAATGTTTTACCAATAATGCAATACAAAAGACCTCA

AAATACCTGTGCATTTCTTGTAGGAAAACAACAAAAGGTAATTATGTGTAATTATAC

TAGAAGTTTTGTAATCTGTATCTTATCATTGGAATAAAATGACATTCAATAAATAAA

AATGCATAAGATATATTCTGTCGGCTGGGCGCGGTGGCTCACGCCTGTAATCCCAGC

ACTTTGGGAGGCCGAGGCGGGCGGATCACAAGGTCAGGAGATCGAGACCATCT

TGGCTAACACGGTGAAACCCCGTCTCTACTAAAAATACAAAAAATTAGCCGGGCGC

GGTGGCGGGCACCTGTAGTCCCAGCTACTCGGGAGGCTGAGGCAGGAGAATGGCGT

GAACCTGGGAGGCGGAGCTTGCAGTGAGCCAAGATTGTGCCACTGCAATCCGGCCT

GGGCTAAAGAGCGGGACTCCGTCTCAAAAAAAAAAAAAAAAAGATATATTCTGTC

ATAATAAATAAAAATGCATAAGATATAAAAAAAAAAAAAA

GI:5032165
                                                    SEQ ID NO: 3
MSGCPFLGNNFGYTFKKLPVEGSEEDKSQTGVNRASKGGLIYGNYLHLEKVLNAQELQ

SETKGNKIHDEHLFIITHQAYELWFKQILWELDSVREIFQNGHVRDERNMLKVVSRMHR

VSVILKLLVQQFSILETMTALDFNDFREYLSPASGFQSLQFRLLENKIGVLQNMRVPYNR

RHYRDNFKGEENELLLKSEQEKTLLELVEAWLERTPGLEPHGFNFWGKLEKNITRGLEE

EFIRIQAKEESEEKEEQVAEFQKQKEVLLSLFDEKRHEHLLSKGERRLSYRALQGALMIY

FYREEPRFQVPFQLLTSLMDIDSLMTKWRYNHVCMVHRMLGSKAGTGGSSGYHY

LRSTVSDRYKVFVDLFNLSTYLIPRHWIPKMNPTIHKFLYTAEYCDSSYFSSDESD

GI 375151559
                                                    SEQ ID NO: 4
GGAAGGTCAATGATAGCATCTGCCTAGAGTCAAACCTCCGTGCTTCTCAGACAGTG

CCTTTTCACCATGAGTGGGTGCCCATTTTTAGGAAACAACTTTGGATATACTTTTAA

AAAACTCCCCGTAGAAGGCAGCGAAGAAGACAAATCACAAACTGGTGTGAATAGA

GCCAGCAAAGGAGGTCTTATCTATGGGAACTACCTGCATTTGGAAAAAGTTTTGAA
```

-continued

```
TGCACAAGAACTGCAAAGTGAAACAAAAGGAAATAAAATCCATGATGAACATCTTT

TTATCATAACTCATCAAGCTTATGAACTCTGGTTTAAGCAAATCCTCTGGGAGTTGG

ATTCTGTTCGAGAGATCTTTCAGAATGGCCATGTCAGAGATGAAAGGAACATGCTT

AAGGTTGTTTCTCGGATGCACCGAGTGTCAGTGATCCTGAAACTGCTGGTGCAGCA

GTTTTCCATTCTGGAGACGATGACAGCCTTGGACTTCAATGACTTCAGAGAGTACTT

ATCTCCAGCATCAGGCTTCCAGAGTTTGCAATTCCGACTATTAGAAAACAAGAT

AGGTGTTCTTCAGAACATGAGAGTCCCTTATAACAGAAGACATTATCGTGATAACTT

CAAAGGAGAAGAAAATGAACTGCTACTTAAATCTGAGCAGGAAAAGACACTTCTG

GAATTAGTGGAGGCATGGCTGGAAAGAACTCCAGGTTTAGAGCCACATGGATTTAA

CTTCTGGGGAAAGCTTGAAAAAAATATCACCAGAGGCCTGGAAGAGGAATTCATAA

GGATTCAGGCTAAAGAAGAGTCTGAAGAAAAGAGGAACAGGTGGCTGAATTTCAG

AAGCAAAAGAGGTGCTACTGTCCTTATTTGATGAGAAACGTCATGAACATCTCCTT

AGTAAAGGTGAAAGACGGCTGTCATACAGAGCACTTCAGGGAGCATTGATGATATA

TTTTTACAGGGAAGAGCCTAGGTTCCAGGTGCCTTTTCAGTTGCTGACTTCTCTTATG

GACATAGATTCACTGATGACCAAATGGAGATATAACCATGTGTGCATGGTGCACAG

AATGCTGGGCAGCAAAGCTGGCACCGGTGGTTCCTCAGGCTATCACTACCTGC

GATCAACTGTGAGTGATAGGTACAAGGTATTTGTAGATTTATTTAATCTTTCAACAT

ACCTGATTCCCCGACACTGGATACCGAAGATGAACCCAACCATTCACAAATTTCTAT

ATACAGCAGAATACTGTGATAGCTCC

TACTTCAGCAGTGATGAATCAGATTAAAATCGTCTGCAAAATCTATGAAGAATACT

GGTTTCACAGCCTATTTTTTATTTTCTATGGATTTTCATAAATACAGTTTGAATATAT

GTATGCATATATTGTTCAGCACCACGATGCTCTGATTTAATTCTAGAAACAATTTGA

TTACCTCTTGTTTGTGACAAGACTAAGCATTAAGATGAGAAAGAATACATTTAAATA

GTAACATTGTACATAGGGTGTTTTCCTATTAAAAATTCAGTTTCCCCTGAGACTTAA

TGTAACCACTTAATGTAATCACTATCTCATTGTTTCATCTTTATAAACTTGTAAACTT

CATCTATTTCAAATATTTTATGCAGTACATTATATTATTCTGTACAAAGGCTTTCAAA

CAAAATTTTTAAAATAATAAAGTATTAATCTTTCTCCCTGTA
```

---

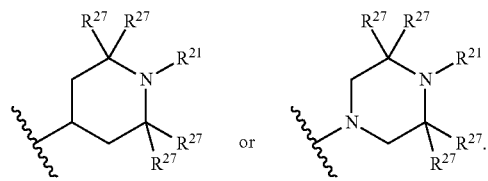

We claim:

1. A compound of Formula I(c):

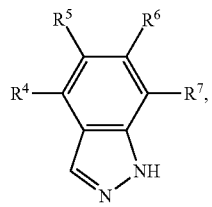

(Ic)

or a pharmaceutically acceptable salt, a solvate, a tautomer, a stereoisomer or a deuterated analog thereof, wherein:

$R^4$, $R^5$ and $R^6$ are each independently H, halogen, alkyl, haloalkyl, —$OCH_3$ optionally substituted with 1-3 halogens, or $C_3$-$C_6$cycloalkyl optionally substituted with 1-3 halogens, provided that at least one of $R^4$, $R^5$ or $R^6$ is not H;

$R^7$ is one of the following groups (a)-(f):
  (a) cycloalkenyl optionally substituted with 1-7 $Z^1$ and optionally substituted with 1 $Z^4$;
  (b) heterocycloalkyl substituted with 1-9 $Z^2$ and optionally substituted with 1 $Z^5$;
  (c) a bridged heterocyclic ring optionally substituted with 1-5 $Z^2$ and optionally substituted with 1 $Z^5$;
  (d) a spiro ring system containing two heterocycloalkyl groups joined by one common spiro carbon atom, wherein the spiro ring system is optionally substituted on its carbon atoms with 1-8 $Z^3$, and wherein the spiro ring system is optionally N-substituted with alkyl, haloalkyl, —$CO_2$-alkyl, —C(O)$NR^{10}R^{11}$, —$SO_2NR^{10}R^{11}$, —$SO_2$-alkyl, $SO_2$-haloalkyl, or —$SO_2$-cycloalkyl substituted with 1-6 halogens;

(e)

[Structure: C bonded to OH, R⁸, R⁹]

or (f)

[Structure: C(=O) bonded to CY₂Y and CH(R⁹)(R⁸ᵇ)]

each Y is independently H, D, halogen, alkyl, or haloalkyl, or 2 Y groups join together with the carbon atom to which they are attached to form a cycloalkyl optionally substituted with 1-3 halogens;

$R^8$ is H, —$CH_3$, —$CFH_2$, —$CF_2H$ or —$CF_3$;

$R^{8b}$ is H, F, Cl, —$CH_3$, —$CFH_2$, —$CF_2H$ or —$CF_3$;

$R^9$ is —$(CY_2)_{0-3}$—$R^{12}$;

or $R^8$ and $R^9$ join together with the carbon atom to which they are attached to form one of the following groups (a)-(e):

(a) a cycloalkyl optionally substituted with 1-9 $Z^2$ and optionally substituted with 1 $Z^5$ or 1-2 $Z^6$;

(b) a heterocycloalkyl optionally substituted with 1-9 $Z^2$ and optionally substituted with 1 $Z^5$;

(c) a spiro ring system containing two cycloalkyl groups joined by one common spiro carbon atom, wherein the spiro ring system is optionally substituted with 1-9 $Z^2$ and optionally substituted with 1 $Z^5$ or 1-2 $Z^6$;

(d) a spiro ring system containing one cycloalkyl and one heterocycloalkyl joined by one common spiro carbon atom, wherein the spiro ring system is optionally substituted on its carbon atoms with 1-9 $Z^3$, and wherein the spiro ring system is optionally N-substituted with alkyl, haloalkyl, —$CO_2$-alkyl, —C(O)$NR^{10}R^{11}$, —$SO_2NR^{10}R^{11}$, —$SO_2$-alkyl, $SO_2$-haloalkyl, or —$SO_2$-cycloalkyl substituted with 1-6 halogens; or (e) a spiro ring system containing one cycloalkyl and one a bridged ring joined by one common spiro carbon atom, wherein the spiro ring system is optionally substituted with 1-5 $Z^2$ and optionally substituted with 1 $Z^5$;

$R^{10}$ is H, alkyl, or haloalkyl;

$R^{11}$ is H, alkyl, haloalkyl, cyanoalkyl, CN, alkynyl, phenyl optionally substituted with 1-4 $J^3$, heteroaryl optionally substituted with 1-4 $J^3$, heterocycloalkyl optionally substituted with 1-4 $J^3$, -alkylene-C(O)—OH, -alkylene-C(O)—$NH_2$, -alkylene-C(O)—N(H)-alkyl, -alkylene-C(O)—N(alkyl)₂, alkoxy, -alkylene-C(O)-phenyl optionally substituted with 1-4 $J^3$, —C(O)—O-alkyl, alkylene-C(O)—O-alkyl, hydroxyalkyl, cycloalkyl optionally substituted with 1-4 $J^3$, cycloalkylalkyl optionally substituted with 1-4 $J^3$, -alkylene-phenyl optionally substituted with 1-4 $J^3$, -alkylene-$SO_2$-phenyl optionally substituted with 1-4 $J^3$, -alkylene-$SO_2$-alkyl, -alkylene-NH—$SO_2$—$C_1$-$C_6$ alkyl, alkoxyalkyl, alkoxycarbonyl, alkylcycloalkyl optionally substituted with 1-4 $J^3$, -alkylene-heterocycloalkyl optionally substituted with 1-4 $J^3$, -alkylene-heteroaryl optionally substituted with 1-4 $J^3$, or —C(O)— phenyl optionally substituted with 1-4 $J^3$;

$R^{12}$ is one of the following groups (a)-(g):

(a) a saturated cycloalkyl optionally substituted with 1-9 $Z^2$ and optionally substituted with 1 $Z^5$ or 1-2 $Z^6$;

(b) an unsaturated cycloalkyl optionally substituted with 1-7 $Z^2$ and optionally substituted with 1 $Z^5$;

(c) a heterocycloalkyl optionally substituted 1-9 $Z^2$ and optionally substituted with 1 $Z^5$;

(d) phenyl optionally substituted with 1-2 $Z^2$;

(e) a bridged ring optionally substituted with 1-5 $Z^2$ and the bridged ring is optionally substituted on a carbon atom with —N(H)(SO)₂-alkyl and the bridged ring is optionally N-substituted with alkyl, haloalkyl, —$SO_2$-alkyl, —$SO_2$-haloalkyl; —$CO_2$-alkyl, —C(O)$NR^{10}R^{11}$, —$SO_2NR^{10}R^{11}$, or —$SO_2$-cycloalkyl substituted with 1-5 halogens;

(f) heteroaryl optionally substituted with 1-2 $Z^2$; or (g) alkyl optionally substituted with 1-2 G groups;

each G is independently —$CF_3$, $C_{3-6}$cycloalkyl, CN, $NH_2$, N(H)alkyl, —N(H)C(O)-alkyl, or —N($C_1$-$C_6$alkyl)₂;

$J^1$ is $C_1$-$C_6$alkyl optionally substituted with 1-4 $J^3$, —$C_1$-$C_6$alkylene-$C_1$-$C_6$alkoxy, $C_1$-$C_6$cyanoalkyl, $C_1$-$C_6$hydroxyalkyl, $C_0$-$C_3$ alkylene-$C_3$-$C_6$ cycloalkyl optionally substituted with 1-4 $J^3$, $C_0$-$C_3$ alkylene-phenyl optionally substituted with 1-4 $J^3$, —$C_0$-$C_3$ alkylene-5-6 membered heteroaryl optionally substituted with 1-4 $J^3$, —$C_0$-$C_3$ alkylene-4-6 membered heterocycloalkyl optionally substituted with 1-4 $J^3$;

$J^2$ is H, $C_1$-$C_6$alkyl, or $C_1$-$C_6$haloalkyl;

each $J^3$ is independently halogen, $C_1$-$C_6$alkyl, $C_1$-$C_6$haloalkyl, OH, $C_1$-$C_6$alkoxy optionally substituted with 1-3 halogens, CN, —$C_0$-$C_3$ alkylene-4-6 membered heterocycloalkyl optionally substituted with $C_1$-$C_3$alkyl, —S(O)₂—$C_1$-$C_6$alkyl, —$NH_2$, —N(H)—$C_1$-$C_6$alkyl, or —N($C_1$-$C_6$alkyl)₂, provided that when $J^3$ is attached to nitrogen, $J^3$ cannot be halogen, OH, CN, $NH_2$, —N(H)—$C_1$-$C_6$alkyl, or —N($C_1$-$C_6$alkyl)₂;

each $Z^1$ is independently CN, halogen, alkyl, or haloalkyl;

each $Z^2$ is independently —OH, CN, halogen, alkyl, cycloalkyl optionally substituted with 1-3 halogens, hydroxyalkyl, haloalkyl, —$NH_2$, —N(H)alkyl, —N(alkyl)₂, alkoxyl optionally substituted with halo or phenyl, 5-6 membered heterocycloalkyl, or 5-6 membered heteroaryl, provided that when $Z^2$ is attached to nitrogen, $Z^2$ cannot be —OH, CN, halogen, alkoxyl, —$NH_2$, —N(H)alkyl, or —N(alkyl)₂;

each $Z^3$ is independently CN, halogen, alkyl or haloalkyl;

$Z^4$ is alkoxyalkyl, phenyl optionally substituted with 1-3 halogens, —$SO_2$-alkyl, —$SO_2$-haloalkyl, —$SO_2$-cycloalkyl optionally substituted with 1-6 halogens, —C(O)$NR^{10}R^{11}$, —$SO_2NR^{10}R^{11}$, —N(H)$SO_2$-alkyl, —N(H)$SO_2$-cycloalkyl optionally substituted with 1-6 halogens, or —N(H)$SO_2$-haloalkyl;

$Z^5$ is alkoxyalkyl, —$SO_2$-alkyl, —$CO_2$-alkyl, —C(O)$J^1$, $CO_2J^2$, —$C_0$-$C_4$alkylene-phenyl optionally substituted with 1-4 $J^3$, —$C_0$-$C_4$alkylene-CH(phenyl)₂ optionally substituted with 1-4 $J^3$, —$C_0$-$C_4$alkylene-CH($C_3$-$C_6$cycloalkyl)₂ optionally substituted with 1-4 $J^3$, —$SO_2$-haloalkyl, —$SO_2$-cycloalkyl optionally substituted with 1-6 $J^3$, —$SO_2$-heterocycloalkyl optionally substituted with 1-6 $J^3$, —$SO_2$-heteroaryl optionally substituted with 1-6 $J^3$, —$SO_2$-aryl optionally substituted with 1-6 $J^3$, —C(O)$NR^{10}R^{11}$, —$SO_2NR^{10}R^{11}$, —N(H)$SO_2$-alkyl optionally substituted with 1-6 $J^3$, —N(H)$SO_2$-aryl optionally substituted with 1-6 $J^3$, —N(H)$SO_2$-cycloalkyl optionally substituted with 1-6 $J^3$, —N(H)$SO_2$-heterocyloalkyl optionally substituted with 1-6 $J^3$, —N(H)$SO_2$-heteroaryl optionally substituted with 1-6 $J^3$, —N(H)$SO_2$-haloalkyl, optionally substituted with 1-6 $J^3$, —C(O)—N(H)$SO_2$-alkyl optionally substituted with 1-6 $J^3$, —C(O)—N(H)$SO_2$- aryl optionally substituted with 1-6 $J^3$, —C(O)—N(H)SO$_2$-cycloalkyl optionally substituted with 1-6 $J^3$, —C(O)—N(H)SO$_2$-heterocyloalkyl optionally substituted with 1-6 $J^3$, —C(O)N(H)SO$_2$-heteroaryl optionally substituted with 1-6 $J^3$, —C(O)N(H)SO$_2$-haloalkyl, or —C(NW$_2$)=N—T, provided that when $Z^5$ is attached to nitrogen, $Z^5$ cannot be —N(H)SO$_2$-alkyl, —N(H)SO$_2$-aryl, —N(H)SO$_2$-cycloalkyl, —N(H)SO$_2$-heterocyloalkyl, —N(H)SO$_2$-heteroaryl, or —N(H)SO$_2$-haloalkyl;

each W is independently H, alkyl or haloalkyl;

T is alkyl, haloalkyl, hydroxyalkyl, alkoxy or CN; and each $Z^6$ is independently halo, alkyl, haloalkyl, CN, OH, cycloalkyl, aryl or heteroaryl, provided that only one $Z^6$ can be OH.

2. The compound of claim 1, wherein:

$R^4$ is H, F, Cl, Br, —OCH$_3$ optionally substituted with 1-3 halogens, cyclopropyl, $C_1$-$C_3$alkyl, or $C_1$-$C_3$haloalkyl;

$R^5$ and $R^6$ are each independently H, F, Cl, Br, —OCH$_3$ optionally substituted with 1-3 halogens, $C_1$-$C_3$alkyl, $C_1$-$C_3$haloalkyl, or $C_3$-$C_5$cycloalkyl optionally substituted with 1-3 halogens, provided that at least one of $R^5$ or $R^6$ is not H;

$R^7$ is one of the following groups (a)-(f):

(a) cycloalkenyl optionally substituted with 1-6 $Z^1$ and optionally substituted with 1 $Z^4$;

(b) heterocycloalkyl substituted with 1-8 $Z^2$ and optionally substituted with 1 $Z^5$;

(c) a bridged nitrogen-containing heterocyclic ring optionally substituted with 1-4 $Z^2$ and optionally substituted with 1 $Z^5$; or (d) a spiro ring system containing two nitrogen-containing heterocycloalkyl groups joined by one common spiro carbon atom, wherein the spiro ring system is optionally substituted on its carbon atoms with 1-7 $Z^3$, and wherein the spiro ring system is optionally N-substituted with alkyl, haloalkyl, —SO$_2$-alkyl, —SO$_2$-haloalkyl, —CO$_2$-alkyl, —C(O)NR$^{10}$R$^{11}$, —SO$_2$NR$^{10}$R$^{11}$, or —SO$_2$-cycloalkyl substituted with 1-5 halogens;

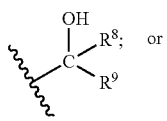
(e)

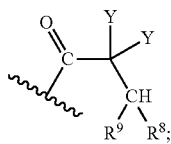
(f)

each Y is independently H, F, Cl, $C_1$-$C_3$alkyl or $C_1$-$C_3$haloalkyl, or 2 Y groups join together with the carbon atom to which they are attached to form a $C_3$-$C_5$cycloalkyl optionally substituted with 1-3 halogens;

$R^8$ is H or CH$_3$;

$R^{8b}$ is H or —CH$_3$;

$R^9$ is —(CY$_2$)$_{0-2}$—R$^{12}$;

or $R^8$ and $R^9$ join together with the carbon atom to which they are attached to form one of the following groups (a), (b), (c), (d1), (d2), or (e):

(a) a cycloalkyl optionally substituted with 1-8 $Z^2$ and optionally substituted with 1 $Z^5$ or 1-2 $Z^6$;

(b) a heterocycloalkyl optionally substituted with 1-8 $Z^2$ and optionally substituted with 1 $Z^5$;

(c) a spiro ring system containing two cycloalkyl groups joined by one common spiro carbon atom, wherein the spiro ring system is optionally substituted with 1-8 $Z^2$ and optionally substituted with 1 $Z^5$ or 1-2 $Z^6$;

(d1) a spiro ring system containing one cycloalkyl and one nitrogen-containing heterocycloalkyl joined by one common spiro carbon atom, wherein the spiro ring system is optionally substituted on its carbon atoms with 1-8 $Z^3$, and wherein the spiro ring system is optionally N-substituted with alkyl, haloalkyl, —SO$_2$-alkyl, —SO$_2$-haloalkyl, —CO$_2$-alkyl, —C(O)NR$^{10}$R$^{11}$, —SO$_2$NR$^{10}$R$^{11}$, or —SO$_2$-cycloalkyl substituted with 1-5 halogens;

(d2) a spiro ring system containing one cycloalkyl and one heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-8 $Z^3$; or (e) a spiro ring system containing one cycloalkyl and one bridged ring joined by one common spiro carbon atom, wherein the spiro ring system is optionally substituted with 1-4 $Z^2$, and further optionally substituted with 1 $Z^5$;

$R^{10}$ is H, $C_1$-$C_6$alkyl, or $C_1$-$C_6$haloalkyl;

$R^{11}$ is H, $C_1$-$C_6$alkyl, $C_1$-$C_6$haloalkyl, $C_1$-$C_6$cyanoalkyl, CN, $C_2$-$C_6$alkynyl, $C_1$-$C_6$alkylene-C(O)—OH, -alkylene-C(O)—NH$_2$, -alkylene-C(O)—N(H)—$C_1$-$C_6$alkyl, —$C_1$-$C_6$alkylene-C(O)—N($C_1$-$C_6$alkyl)$_2$, alkoxy, —$C_0$-$C_6$ alkylene-C(O)—O—$C_1$-$C_6$ alkyl, $C_1$-$C_6$hydroxyalkyl, —$C_0$-$C_6$alkylene-phenyl optionally substituted with 1-4 $J^3$, —$C_1$-$C_3$ alkylene-SO$_2$-phenyl optionally substituted with 1-4 $J^3$, $C_1$-$C_3$ alkylene-SO$_2$—$C_1$-$C_6$ alkyl, —$C_1$-$C_3$ alkylene-NH—SO$_2$—$C_1$-$C_6$ alkyl, —$C_1$-$C_6$alkylene-$C_1$-$C_6$alkoxy, $C_1$-$C_6$alkoxycarbonyl, —$C_0$-$C_6$ alkylene-$C_3$-$C_6$cycloalkyl optionally substituted with 1-4 $J^3$, —$C_0$-$C_6$ alkylene-$C_3$-$C_6$heterocycloalkyl optionally substituted with 1-4 $J^3$, —$C_0$-$C_6$ alkylene-5-6 membered heteroaryl optionally substituted with 1-4 $J^3$, or —$C_0$-$C_6$ alkylene-C(O)-phenyl optionally substituted with 1-4 $J^3$;

$R^{12}$ is one of the following groups (a), (b), (c), (d), (e), or (g):

(a) a saturated cycloalkyl optionally substituted with 1-8 $Z^2$ and optionally substituted with 1 $Z^5$ or 1-2 $Z^6$;

(b) a cycloalkenyl optionally substituted with 1-6 $Z^2$ and optionally substituted with 1 $Z^5$;

(c) a heterocycloalkyl optionally substituted with 1-8 $Z^2$ and optionally substituted with 1 $Z^5$;

(d) phenyl optionally substituted with 1-2 substituents independently selected from the group consisting of CN, halogen, $C_1$-$C_4$alkyl, $C_1$-$C_4$haloalkyl, —NH$_2$, —N(H)$C_1$-$C_4$alkyl, —N($C_1$-$C_4$alkyl)$_2$, $C_1$-$C_4$alkoxyl optionally substituted with phenyl, 5-6 membered heterocycloalkyl, and 5-6 membered heteroaryl;

(e) a bridged ring optionally substituted with 1-4 $Z^2$, wherein the bridged ring is optionally N-substituted with alkyl, haloalkyl, —SO$_2$-alkyl, —SO$_2$-haloalkyl, —CO$_2$-alkyl, —C(O)NR$^{10}$R$^{11}$, —SO$_2$NR$^{10}$R$^{11}$, or —SO$_2$-cycloalkyl substituted with 1-5 halogens; or (g) alkyl optionally substituted with 1-2 G groups;

each G is independently —CF$_3$, cyclopropyl, CN, NH$_2$, N(H)alkyl, —N(H)C(O)-alkyl or —N(C$_1$-C$_6$alkyl)$_2$;

J$^1$ is C$_1$-C$_6$alkyl optionally substituted with 1-4 J$^3$, —C$_1$-C$_6$alkoxy, C$_1$-C$_6$cyanoalkyl, C$_1$-C$_6$hydroxyalkyl, C$_0$-C$_3$ alkylene-C$_3$-C$_6$ cycloalkyl optionally substituted with 1-4 J$^3$, C$_0$-C$_3$ alkylene-phenyl optionally substituted with 1-4 J$^3$, —C$_0$-C$_3$ alkylene-5-6 membered heteroaryl optionally substituted with 1-4 J$^3$, or —C$_0$-C$_3$ alkylene-4-6 membered heterocycloalkyl optionally substituted with 1-4 J$^3$;

J$^2$ is H, C$_1$-C$_6$alkyl, or C$_1$-C$_6$haloalkyl;

each J$^3$ is independently halogen, C$_1$-C$_6$alkyl, C$_1$-C$_6$haloalkyl, OH, C$_1$-C$_6$alkoxy optionally substituted with 1-3 halogens, CN, 4-6 membered heterocycloalkyl, —S(O)$_2$—C$_1$-C$_6$alkyl, —NH$_2$, —N(H)—C$_1$-C$_6$alkyl, or —N(C$_1$-C$_6$alkyl)$_2$ provided that when J$^3$ is attached to nitrogen, J$^3$ cannot be halogen, OH, CN, —NH$_2$, —N(H)—C$_1$-C$_6$alkyl, or —N(C$_1$-C$_6$alkyl)$_2$;

each Z$^1$ is independently CN, F, Cl, alkyl, or haloalkyl;

each Z$^2$ is independently —OH, CN, F, Cl, alkyl, alkoxy, C$_3$-C$_6$ cycloalkyl optionally substituted with 1-3 halogens, cyclopropyl, hydroxyalkyl, or haloalkyl, provided that when Z$^2$ is attached to nitrogen, Z$^2$ cannot be —OH, CN, F, Cl, or alkoxy;

each Z$^3$ is independently CN, F, Cl, alkyl or haloalkyl;

Z$^4$ is —C$_1$-C$_3$alkylene-C$_1$-C$_3$alkoxy, —SO$_2$-alkyl, —SO$_2$-haloalkyl, —C(O)NR$^{10}$R$^{11}$, —SO$_2$NR$^{10}$R$^{11}$, —SO$_2$-cycloalkyl optionally substituted with 1-5 halogens, —N(H)SO$_2$-alkyl, —N(H)SO$_2$-cycloalkyl optionally substituted with 1-5 halogens, or —N(H)SO$_2$-haloalkyl;

Z$^5$ is —C$_1$-C$_3$alkylene-C$_1$-C$_3$alkoxy, —C$_0$-C$_3$alkylene-phenyl optionally substituted with 1-3 J$^3$, —SO$_2$-alkyl, SO$_2$-haloalkyl, —C$_0$-C$_3$alkylene-CH(phenyl)$_2$ optionally substituted with 1-3 J$^3$, —C$_0$-C$_3$alkylene-CH(C$_3$-C$_6$cycloalkyl)$_2$ optionally substituted with 1-3 J$^3$, —C(O)NR$^{10}$R$^{11}$, —CO$_2$-alkyl, —C(O)J$^1$, CO$_2$J$^2$, —SO$_2$NR$^{10}$R$^{11}$, —SO$_2$-cycloalkyl optionally substituted with 1-5 J$^3$, —SO$_2$-heterocycloalkyl optionally substituted with 1-5 J$^3$, —SO$_2$-heteroaryl optionally substituted with 1-5 J$^3$, —SO$_2$-phenyl optionally substituted with 1-3 J$^3$, —C(O)N(H)SO$_2$-cycloalkyl optionally substituted with 1-5 J$^3$, —C(O)N(H)SO$_2$-heterocycloalkyl optionally substituted with 1-5 J$^3$, —C(O)N(H)SO$_2$-heteroaryl optionally substituted with 1-5 J$^3$, —C(O)N(H)SO$_2$-phenyl optionally substituted with 1-3 J$^3$, —N(H)SO$_2$-alkyl, —N(H)SO$_2$-cycloalkyl optionally substituted with 1-5 J$^3$, —N(H)SO$_2$-heterocycloalkyl optionally substituted with 1-5 J$^3$, —N(H)SO$_2$-heteroaryl optionally substituted with 1-5 J$^3$, —N(H)SO$_2$-haloalkyl, or —C(NW$_2$)=N—T, provided that when Z$^5$ is attached to nitrogen, Z$^5$ cannot be —N(H)SO$_2$-alkyl, —N(H)SO$_2$-cycloalkyl, —N(H)SO$_2$-heterocycloalkyl, —N(H)SO$_2$-heteroaryl, or N(H)SO$_2$—C$_1$-C$_6$haloalkyl;

each W is independently H, C$_1$-C$_3$alkyl or C$_1$-C$_3$haloalkyl;

T is C$_1$-C$_6$alkyl, C$_1$-C$_6$haloalkyl, C$_1$-C$_6$hydroxyalkyl, C$_1$-C$_6$alkoxy or CN; and each Z$^6$ is independently halo, C$_1$-C$_3$alkyl, C$_1$-C$_3$haloalkyl, CN, OH, C$_3$-C$_5$cycloalkyl, phenyl or 5-6 membered heteroaryl, provided that only one Z$^6$ can be OH.

3. The compound of claim 1, wherein:

R$^7$ is one of the following groups (a), (b), (c), or (e):

(a) C$_5$-C$_6$cycloalkenyl optionally substituted with 1-5 Z$^1$ and optionally substituted with 1 Z$^4$;

(b) 5 or 6-membered nitrogen-containing heterocycloalkyl substituted with 1-7 Z$^2$ and optionally substituted with 1 Z$^5$;

(c) a 5-9 membered nitrogen-containing bridged heterocyclic ring optionally substituted with 1-3 Z$^2$ and optionally substituted with 1 Z$^5$; or (e)

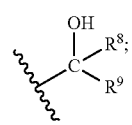

R$^8$ is H;

R$^9$ is —(CY$_2$)$_{0-2}$—R$^{12}$;

or R$^8$ and R$^9$ join together with the carbon atom to which they are attached to form one of the following groups (a), (b), (c), (d1), (d2), or (e):

(a) a C$_3$-C$_6$cycloalkyl optionally substituted with 1-7 Z$^2$ and optionally substituted with 1 Z$^5$ or 1-2 Z$^6$;

(b) a 4-6 membered heterocycloalkyl optionally substituted with 1-7 Z$^2$ and optionally substituted with 1 Z$^5$;

(c) a spiro ring system containing two C$_4$-C$_6$cycloalkyl groups joined by one common spiro carbon atom, wherein the spiro ring system is optionally substituted with 1-7 Z$^2$ and optionally substituted with 1 Z$^5$ or 1-2 Z$^6$;

(d1) a spiro ring system containing one C$_4$-C$_6$cycloalkyl and one 4-6 membered nitrogen-containing heterocycloalkyl joined by one common spiro carbon atom, wherein the spiro ring system is optionally substituted on its carbon atoms with 1-7 Z$^3$, and wherein the spiro ring system is optionally N-substituted with C$_1$-C$_6$alkyl, C$_1$-C$_6$haloalkyl, —SO$_2$—C$_1$-C$_6$alkyl, —SO$_2$—C$_1$-C$_6$haloalkyl, —C(O)NR$^{10}$R$^{11}$, —SO$_2$NR$^{10}$R$^{11}$, or —SO$_2$—C$_3$-C$_6$cycloalkyl substituted with 1-4 halogens;

(d2) a spiro ring system containing one cycloalkyl and one heterocycloalkyl containing —O—, —S—, —S(O)—, or —S(O)$_2$—, wherein the spiro ring system is joined by one common spiro carbon atom, and wherein the spiro ring system is optionally substituted on its carbon atoms with 1-7 Z$^3$; or (e) a spiro ring system containing one cycloalkyl and one bridged ring joined by one common spiro carbon atom, wherein the spiro ring system is optionally substituted with 1-3 Z$^2$;

R$^{10}$ is H, C$_1$-C$_3$alkyl, or C$_1$-C$_3$haloalkyl;

R$^{11}$ is H, C$_1$-C$_3$alkyl, C$_1$-C$_3$haloalkyl, C$_1$-C$_4$cyanoalkyl, C$_2$-C$_4$alkynyl, —C$_1$-C$_4$alkylene-C(O)—NH$_2$, —C$_1$-C$_4$alkylene-C(O)—N(H)—C$_1$-C$_4$alkyl, —C$_1$-C$_4$alkylene-C(O)—N(C$_1$-C$_4$alkyl)$_2$, —C$_0$-C$_4$ alkylene-C(O)—O—C$_1$-C$_4$alkyl, C$_1$-C$_4$hydroxyalkyl, —C$_0$-C$_4$alkylene-phenyl optionally substituted with 1-4 J$^3$, —C$_1$-C$_3$ alkylene-SO$_2$-phenyl optionally substituted with 1-4 J$^3$, —C$_1$-C$_3$ alkylene-SO$_2$—C$_1$-C$_6$ alkyl, —C$_1$-C$_3$ alkylene-NH—SO$_2$—C$_1$-C$_6$ alkyl, —C$_1$-C$_4$alkylene-C$_1$-C$_4$alkoxy, C$_1$-C$_4$alkoxycarbonyl, —C$_0$-C$_4$ alkylene-C$_3$-C$_6$cycloalkyl optionally substituted with 1-4 J$^3$, —C$_0$-C$_4$ alkylene-5-6 membered heterocycloalkyl optionally substituted with 1-4 J$^3$, —C$_0$-C$_4$ alkylene-5-6 membered heteroaryl optionally substituted with 1-4 J$^3$, or —C(O)-phenyl optionally substituted with 1-4 J$^3$;

$R^{12}$ is one of the following groups (a)-(e):
(a) a saturated $C_3$-$C_6$cycloalkyl optionally substituted with 1-7 $Z^2$ and optionally substituted with 1 $Z^5$ or 1-2 $Z^6$;
(b) a $C_5$-$C_6$cycloalkenyl optionally substituted with 1-5 $Z^2$ and optionally substituted with 1 $Z^5$;
(c) a 4-6 membered heterocycloalkyl optionally substituted with 1-7 $Z^2$ and optionally substituted with 1 $Z^5$;
(d) phenyl optionally substituted with 1-2 substituents independently selected from the group consisting of CN, halogen, $C_1$-$C_4$alkyl, and $C_1$-$C_4$haloalkyl; or
(e) a 5-10 membered bridged carbocyclic or heterocyclic ring, wherein the 5-10 membered bridged carbocyclic or heterocyclic ring are each optionally substituted with 1-3 $Z^2$, and wherein the bridged heterocyclic ring is optionally N-substituted with $C_1$-$C_6$alkyl, $C_1$-$C_6$haloalkyl, —$SO_2$—$C_1$-$C_6$alkyl, —$SO_2$—$C_1$-$C_6$haloalkyl, —C(O)$NR^{10}R^{11}$, —$SO_2NR^{10}R^{11}$, or —$SO_2$—$C_3$-$C_6$cycloalkyl substituted with 1-4 halogens;

$J^1$ is $C_1$-$C_5$alkyl optionally substituted with 1-4 $J^3$, —$C_1$-$C_5$alkylene-$C_1$-$C_5$alkoxy, $C_1$-$C_5$cyanoalkyl, $C_1$-$C_5$hydroxyalkyl, $C_0$-$C_3$ alkylene-$C_3$-$C_6$ cycloalkyl optionally substituted with 1-3 $J^3$, —$C_0$-$C_3$ alkylene-phenyl optionally substituted with 1-3 $J^3$, —$C_0$-$C_3$ alkylene-5-6 membered heteroaryl optionally substituted with 1-3 $J^3$, or —$C_0$-$C_3$ alkylene-4-6 membered heterocycloalkyl optionally substituted with 1-3 $J^3$;

$J^2$ is H, $C_1$-$C_5$alkyl, or $C_1$-$C_5$haloalkyl;

each $J^3$ is independently halogen, $C_1$-$C_5$alkyl, $C_1$-$C_5$haloalkyl, OH, $C_1$-$C_5$alkoxy optionally substituted with 1-3 halogens, CN, 4-6 membered heterocycloalkyl, —$S(O)_2$—$C_1$-$C_5$alkyl, —$NH_2$, —N(H)—$C_1$-$C_5$alkyl, or —N($C_1$-$C_5$alkyl)$_2$, provided that when $J^3$ is attached to nitrogen, $J^3$ cannot be halogen, OH, CN, —$NH_2$, —N(H)—$C_1$-$C_5$alkyl, or —N($C_1$-$C_5$alkyl)$_2$;

each Y is independently H, D, F, Cl, $C_1$-$C_2$alkyl or $C_1$-$C_2$haloalkyl, or 2 Y groups join together with the carbon atom to which they are attached to form a $C_3$-$C_4$cycloalkyl optionally substituted with 1-3 halogens;

each $Z^1$ is independently CN, halogen, $C_1$-$C_6$alkyl, or $C_1$-$C_6$haloalkyl;

each $Z^2$ is independently —OH, CN, F, Cl, $C_1$-$C_6$alkyl, alkoxy, $C_3$-$C_6$ cycloalkyl optionally substituted with 1-3 halogens, cyclopropyl, hydroxyalkyl, or $C_1$-$C_6$haloalkyl, provided that when $Z^2$ is attached to nitrogen, $Z^2$ cannot be —OH, CN, F, Cl, or alkoxy;

each $Z^3$ is independently CN, F, Cl, $C_1$-$C_6$alkyl or $C_1$-$C_6$haloalkyl;

$Z^4$ is —$SO_2$—$C_1$-$C_6$alkyl, —$SO_2$—$C_3$-$C_6$cycloalkyl optionally substituted with 1-3 halogens, —$SO_2$—$C_1$-$C_6$haloalkyl, —N(H)$SO_2$—$C_1$-$C_6$alkyl, —N(H)$SO_2$—$C_3$-$C_6$cycloalkyl optionally substituted with 1-3 halogens, or —N(H)$SO_2$—$C_1$-$C_6$haloalkyl;

$Z^5$ is —$C_1$-$C_2$alkylene-$C_1$-$C_2$alkoxy, —$C_0$-$C_2$alkylene-phenyl optionally substituted with 1-3 $J^3$, —$SO_2$—$C_1$-$C_6$alkyl, —$SO_2$—$C_1$-$C_6$haloalkyl, —$SO_2$—($C_3$-$C_6$cycloalkyl) optionally substituted with 1-3 $J^3$, —$SO_2$-4-6 membered heterocycloalkyl optionally substituted with 1-3 $J^3$, —$SO_2$-5-6 membered heteroaryl optionally substituted with 1-3 $J^3$, —C(O)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_3$alkylene-CH(phenyl)$_2$ optionally substituted with 1-3 $J^3$, —$C_0$-$C_3$alkylene-CH($C_3$-$C_6$cycloalkyl)$_2$ optionally substituted with 1-3 $J^3$, —C(O)$NR^{10}R^{11}$, C(O)$J^1$, $CO_2J^2$, —$SO_2NR^{10}R^{11}$, —$SO_2$-phenyl optionally substituted with 1-3 $J^3$, —N(H)$SO_2$—$C_1$-$C_6$alkyl, —N(H)$SO_2$—$C_3$-$C_6$cycloalkyl optionally substituted with 1-3 $J^3$, —N(H)$SO_2$—$C_1$-$C_6$haloalkyl, or —C($NH_2$)=N—T; provided that when $Z^5$ is attached to nitrogen, $Z^5$ cannot be —N(H)$SO_2$—$C_1$-$C_6$alkyl, —N(H)$SO_2$—$C_3$-$C_6$cycloalkyl optionally substituted with 1-3 $J^3$, or —N(H)$SO_2$—$C_1$-$C_6$haloalkyl;

T is $C_1$-$C_3$alkyl, $C_1$-$C_3$haloalkyl, $C_1$-$C_3$hydroxyalkyl, $C_1$-$C_3$alkoxy or CN; and each $Z^6$ is independently halo, $C_1$-$C_2$alkyl, $C_1$-$C_2$haloalkyl, CN, OH, $C_3$-$C_6$cycloalkyl, phenyl or 5-6 membered heteroaryl, provided that only one $Z^6$ can be OH.

4. The compound according to claim 1 having one of Formula (IIa), (IIb), (IIc), (IId), (IIj), or (IIi):

(IIa)

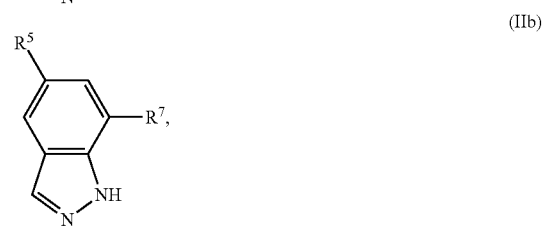

(IIb)

(IIc)

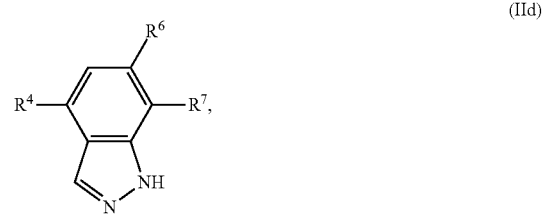

(IId)

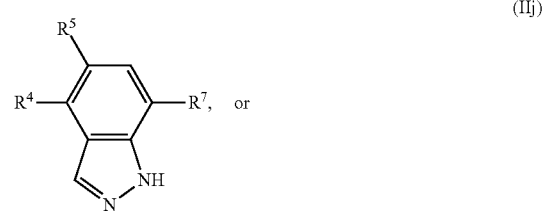

(IIj)

or

-continued

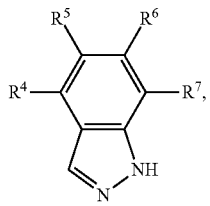

(IIi)

or a pharmaceutically acceptable salt, a solvate, a tautomer, a stereoisomer or a deuterated analog thereof, wherein:
$R^4$, $R^5$ and $R^6$ are each independently F, Cl, $C_1$-$C_3$alkyl, $C_1$-$C_3$haloalkyl, —$OCH_3$ optionally substituted with 1-3 F, or cyclopropyl.

5. The compound according to claim 4, wherein:
$R^4$, $R^5$ and $R^6$ are each independently F, Cl, methyl optionally substituted with 1-3 F, —$OCH_3$ optionally substituted with 1-3 F, or cyclopropyl;
$R^7$ is one of the following groups (a), (b), (c), or (e):
(a) cyclohexenyl optionally substituted with 1-4 $Z^1$ and optionally substituted with 1 $Z^4$;
(b) a six-membered nitrogen-containing heterocycloalkyl substituted with 1-6 $Z^2$ and optionally substituted with 1 $Z^5$;
(c) an 8-9 membered bridged nitrogen-containing heterocyclic ring optionally substituted with 1-2 $Z^2$ and optionally substituted with 1 Z; or

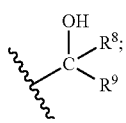

(e)

$R^8$ is H;
$R^9$ is —$(CY_2)_{0-2}$—$R^{12}$;
or $R^8$ and $R^9$ join together with the carbon atom to which they are attached to form one of the following groups (a), (b), (c), (d1), (d2), or (e):
(a) a $C_3$-$C_6$cycloalkyl optionally substituted with 1-7 $Z^2$ and optionally substituted with 1 $Z^5$ or 1-2 $Z^6$;
(b) a 4-6 membered nitrogen-containing heterocycloalkyl optionally substituted with 1-6 $Z^2$ and optionally substituted with 1 $Z^5$;
(c) a spiro ring system containing two $C_4$-$C_6$cycloalkyl groups joined by one common spiro carbon atom, wherein the spiro ring system is optionally substituted with 1-6 $Z^2$ and optionally substituted with 1 $Z^5$ or 1-2 $Z^6$;
(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-6 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl; or
(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-6 $Z^3$; or
(e) a spiro ring system containing one $C_4$-$C_6$cycloalkyl and one 7-10 membered bridged ring joined by one common spiro carbon atom, wherein the spiro ring system is optionally substituted with 1-2 $Z^2$;
$R^{10}$ is H, $C_1$-$C_2$alkyl, or $C_1$-$C_2$haloalkyl;
$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—$N(C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_4$alkylene-phenyl optionally substituted with 1-3 $J^3$, —$C_1$-$C_3$ alkylene-$SO_2$-phenyl optionally substituted with 1-3 $J^3$, —$C_1$-$C_3$ alkylene-$SO_2$—$C_1$-$C_6$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-3 $J^3$, —$C_0$-$C_4$ alkylene-$C_3$-$C_6$heterocycloalkyl optionally substituted with 1-3 $J^3$, —$C_0$-$C_4$ alkylene-5-6 membered heteroaryl optionally substituted with 1-3 $J^3$, or —C(O)-phenyl optionally substituted with 1-3 $J^3$;
$R^{12}$ is one of the following groups (a)-(e):
(a) a saturated $C_3$-$C_8$cycloalkyl optionally substituted with 1-6 $Z^2$ and optionally substituted with 1 $Z^5$ or 1-2 $Z^6$;
(b) $C_5$-$C_6$cycloalkenyl optionally substituted with 1-6 $Z^2$ and optionally substituted with 1 $Z^5$;
(c) a 4-6 membered nitrogen-containing heterocycloalkyl optionally substituted with 1-6 $Z^2$, and further optionally substituted with 1 $Z^5$;
(d) phenyl optionally substituted with 1-2 $Z^2$; or
(e) a 6-9 membered bridged carbocyclic or nitrogen-containing heterocyclic ring, wherein the bridged carbocyclic or nitrogen-containing heterocyclic ring are each optionally substituted with 1-2 $Z^2$, and wherein 6-9 membered bridged nitrogen-containing heterocyclic ring is optionally N-substituted with $C_1$-$C_4$alkyl, $C_1$-$C_4$haloalkyl, —$SO_2$—$C_1$-$C_4$alkyl, —$SO_2$—$C_1$-$C_4$haloalkyl, —C(O)$NR^{10}R^{11}$, —$SO_2NR^{10}R^{11}$, or —$SO_2$—$C_3$-$C_6$cycloalkyl optionally substituted with 1-3 halogens;
$J^1$ is $C_1$-$C_4$alkyl optionally substituted with 1-4 $J^3$, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, —$C_0$-$C_3$ alkylene-5-6 membered heteroaryl optionally substituted with 1-3 $J^3$, or —$C_0$-$C_3$ alkylene-4-6 membered heterocycloalkyl optionally substituted with 1-3 $J^3$;
$J^2$ is H, $C_1$-$C_4$alkyl, or $C_1$-$C_4$haloalkyl;
each $J^3$ is independently halogen, $C_1$-$C_4$alkyl, $C_1$-$C_4$haloalkyl, OH, $C_1$-$C_4$alkoxy optionally substituted with 1-3 halogens, CN, 4-6 membered heterocycloalkyl, —$S(O)_2$—$C_1$-$C_4$alkyl, —$NH_2$, —N(H)—$C_1$-$C_4$alkyl, or —$N(C_1$-$C_4$alkyl)$_2$ provided that when $J^3$ is attached to nitrogen, $J^3$ cannot be halogen, OH, CN, —$NH_2$, —N(H)—$C_1$-$C_4$alkyl, or —$N(C_1$-$C_4$alkyl)$_2$;
each Y is independently H, D, F, $CH_3$, —$CFH_2$, —$CF_2H$ or —$CF_3$, or 2 Y groups join together with the carbon atom to which they are attached to form a $C_3$-$C_4$cycloalkyl optionally substituted with 1-3 F;
each $Z^1$ is independently CN, F, Cl, $C_1$-$C_4$alkyl, of $C_1$-$C_4$haloalkyl;

each $Z^2$ is independently —OH, CN, F, Cl, $C_1$-$C_4$alkyl, or $C_1$-$C_4$haloalkyl;

each $Z^3$ is independently CN, F, Cl, $C_1$-$C_4$alkyl, or $C_1$-$C_4$haloalkyl;

$Z^4$ is-$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

$Z^5$ is —$C_1$-$C_2$alkylene-$C_1$-$C_2$alkoxy, —$C_0$-$C_1$alkylene-phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)NR$^{10}$R$^{11}$, —C(O)J$^1$, CO$_2$J$^2$, —SO$_2$NR$^{10}$R$^{11}$, —$SO_2$—$C_3$-$C_6$cycloalkyl optionally substituted with 1-3 halogens, —$CO_2$-alkyl, —N(H)$SO_2$—$C_1$-$C_4$alkyl, —N(H)$SO_2$—$C_3$-$C_6$cycloalkyl optionally substituted with 1-3 $J^3$, —N(H)$SO_2$—$C_1$-$C_4$haloalkyl, or C(NH$_2$)=N—T, provided that when $Z^5$ is attached to nitrogen, $Z^5$ cannot be —N(H)$SO_2$—$C_1$-$C_4$alkyl, —N(H)$SO_2$—$C_3$-$C_6$cycloalkyl optionally substituted with 1-3 $J^3$, or —N(H)$SO_2$—$C_1$-$C_4$haloalkyl;

T is $C_1$-$C_2$alkyl, $C_1$-$C_2$haloalkyl, $C_1$-$C_2$hydroxyalkyl, $C_1$-$C_2$alkoxy or CN; and each $Z^6$ is independently halo, $C_1$-$C_2$alkyl, $C_1$-$C_2$haloalkyl, CN, OH, $C_3$-$C_6$cycloalkyl, phenyl or 5-6 membered heteroaryl, provided that only one $Z^6$ can be OH.

6. The compound according to claim 4, wherein:

$R^6$ is F, Cl, —CH$_3$, —CFH$_2$, —CF$_2$H, —CF$_3$, —O—CH$_3$, —O—CFH$_2$, —OCF$_3$, or cyclopropyl;

$R^7$ is one of the following groups (a), (b), (c), or (e):

(a) cyclohexenyl optionally substituted with 1-3 $Z^1$ and optionally substituted with 1 $Z^4$;

(b) a six-membered nitrogen-containing heterocycloalkyl substituted with 1-5 $Z^2$ and optionally substituted with 1 $Z^5$;

(c) an 8 membered bridged heterocyclic ring containing 1-2 nitrogen atoms, said 8 membered bridged heterocyclic ring optionally substituted with 1 $Z^2$ and optionally substituted with 1 $Z^5$; or (e)

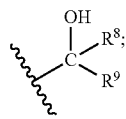

$R^8$ is H;
$R^9$ is —(CY$_2$)$_{0-2}$—R$^{12}$;
or $R^8$ and $R^9$ join together with the carbon atom to which they are attached to form one of the following groups (a), (b), (c), (d1), (d2), or (e):

(a) a $C_3$-$C_6$cycloalkyl optionally substituted with 1-6 $Z^2$ and optionally substituted with 1 $Z^5$ or 1-2 $Z^6$;

(b) a 4-6 membered nitrogen-containing heterocycloalkyl optionally substituted with 1-5 $Z^2$ and optionally substituted with 1 $Z^5$;

(c) a spiro ring system containing two $C_4$-$C_6$cycloalkyl groups joined by one common spiro carbon atom, wherein the spiro ring system is optionally substituted with 1-6 $Z^2$ and optionally substituted with 1 $Z^5$ or 1-2 $Z^6$;

(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system is optionally N-substituted with $C_1$-$C_6$alkyl, $C_1$-$C_6$haloalkyl, —$SO_2$—$C_1$-$C_6$alkyl, —$SO_2$—$C_3$-$C_6$cycloalkyl optionally substituted with 1-3 halogens, or —$SO_2$—$C_1$-$C_6$haloalkyl; or (d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$; or (e) a spiro ring system containing one $C_4$-$C_6$cycloalkyl and one 7-10 membered bridged ring joined by one common spiro carbon atom, wherein the spiro ring system is optionally substituted with 1 $Z^2$;

$R^{12}$ is one of the following groups (a), (b), (c), (d), (e1), or (e2):

(a) a saturated $C_3$-$C_8$cycloalkyl optionally substituted with 1-6 $Z^2$ and optionally substituted with 1 $Z^5$ or 1-2 $Z^6$;

(b) a $C_5$-$C_6$cycloalkenyl optionally substituted with 1-3 $Z^2$ and optionally substituted with 1 $Z^5$;

(c) a 4-6 membered nitrogen-containing heterocycloalkyl optionally substituted with 1-5 $Z^2$ and optionally substituted with 1 $Z^5$;

(d) phenyl optionally substituted with 1-2 $Z^2$;

(e1) a 5-10 membered bridged carbocyclic ring, wherein the bridged carbocyclic ring is optionally substituted with 1 $Z^2$; or (e2) a 6-9 membered bridged nitrogen-containing heterocyclic ring optionally N-substituted with $C_1$-$C_3$alkyl, $C_1$-$C_3$haloalkyl, —$SO_2$—$C_1$-$C_3$alkyl, —$SO_2$—$C_1$-$C_3$haloalkyl, —C(O)NR$^{10}$R$^{11}$, —SO$_2$NR$^{10}$R$^{11}$, or —$SO_2$—$C_3$-$C_6$cycloalkyl optionally substituted with 1-3 halogens;

each Y is independently H, D, F, CH$_3$, —CFH$_2$, —CF$_2$H or —CF$_3$, or 2 Y groups join together with the carbon atom to which they are attached to form a $C_3$-$C_4$cycloalkyl optionally substituted with 1-2 F; and each $Z^6$ is independently F, $C_1$-$C_2$alkyl, $C_1$-$C_2$haloalkyl, CN, OH, $C_3$-$C_6$cycloalkyl, phenyl or 6 membered heteroaryl, provided that only one $Z^6$ can be OH.

7. The compound according to claim 4, wherein:

$R^6$ is F, Cl, —CH$_3$, —CFH$_2$, —CF$_2$H, —CF$_3$, —OCH$_3$, —OCFH$_2$, —OCF$_3$, or cyclopropyl;

$R^7$ is one of the following groups (a), (b), (c), or (e):

(a) cyclohexenyl optionally substituted with 1-3 $Z^1$ and optionally substituted with 1 $Z^4$;

(b) a six-membered nitrogen-containing heterocycloalkyl substituted with 1-4 $Z^2$ and optionally substituted with 1 $Z^5$;

(c) an 8 membered bridged heterocyclic ring containing 1-2 nitrogen atoms, said 8 membered bridged heterocyclic ring optionally N-substituted with 1 $Z^5$; or

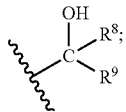
(e)

$R^8$ is H;
$R^9$ is —(CY$_2$)$_{0-2}$—$R^{12}$;
or $R^8$ and $R^9$ join together with the carbon atom to which they are attached to form one of the following groups (a), (b), (c), (d1), (d2), or (e):
(a) a $C_3$-$C_6$cycloalkyl optionally substituted with 1-6 $Z^2$ and optionally substituted with 1 $Z^5$ or 1-2 $Z^6$;
(b) a 4-6 membered nitrogen-containing heterocycloalkyl optionally substituted with 1-5 $Z^2$ and optionally substituted with 1 $Z^5$;
(c) a spiro ring system containing two $C_4$-$C_6$cycloalkyl groups joined by one common spiro carbon atom, wherein the spiro ring system is optionally substituted with 1-6 $Z^2$ and optionally substituted with 1 $Z^5$ or 1-2 $Z^6$;
(d1) a spiro ring system containing one $C_4$-$C_6$cycloalkyl and one 4-6 membered nitrogen-containing heterocycloalkyl joined by one common spiro carbon atom, wherein the spiro ring system is optionally substituted on its carbon atoms with 1-5 $Z^3$, and wherein the spiro ring system can also be optionally N-substituted with $C_1$-$C_6$alkyl, $C_1$-$C_6$haloalkyl, —SO$_2$—$C_1$-$C_6$alkyl, —SO$_2$—$C_3$-$C_6$cycloalkyl optionally substituted with 1-3 halogens, or —SO$_2$—$C_1$-$C_6$haloalkyl; or
(d2) a spiro ring system containing one $C_4$-$C_6$cycloalkyl and one 4-6 membered heterocycloalkyl containing —O—, —S—, —S(O)— or —S(O)$_2$—, wherein the spiro ring system is joined by one common spiro carbon atom, and wherein the spiro ring system is optionally substituted on its carbon atoms with 1-5 $Z^3$; or
(e) a spiro ring system containing one $C_4$-$C_6$cycloalkyl and one 7-10 membered bridged ring joined by one common spiro carbon atom, wherein the spiro ring system is optionally substituted with 1 $Z^2$;
$R^{12}$ is one of the following groups (a2), (b), (c), (d), or (e):
(a1) a saturated $C_3$-$C_6$cycloalkyl optionally substituted with 1-5 $Z^2$ and optionally substituted with 1 $Z^5$ or 1-2 $Z^6$;
(a2) cubane;
(b) a $C_5$-$C_6$cycloalkenyl optionally substituted with 1-3 $Z^2$ and optionally substituted with 1 $Z^5$;
(c) a 4-6 membered nitrogen-containing heterocycloalkyl optionally substituted with 1-5 $Z^2$ and optionally substituted with 1 $Z^5$;
(d) phenyl optionally substituted with 1-2 $Z^2$; or
(e) a 5-10 membered bridged carbocyclic ring, wherein the bridged carbocyclic ring is optionally substituted with 1 $Z^2$;
each Y is independently H, F, CH$_3$, —CFH$_2$, —CF$_2$H or —CF$_3$, or 2 Y groups join together with the carbon atom to which they are attached to form a cyclopropyl or cyclobutyl group;
each $Z^1$ is independently CN, F, Cl, $C_1$-$C_4$alkyl, or $C_1$-$C_4$haloalkyl;

each $Z^2$ is independently —OH, CN, F, Cl, $C_1$-$C_4$alkyl, or $C_1$-$C_4$haloalkyl;
each $Z^3$ is independently CN, F, Cl, $C_1$-$C_4$alkyl, or $C_1$-$C_4$haloalkyl;
$Z^4$ is —SO$_2$—$C_1$-$C_4$alkyl, —SO$_2$—$C_3$-$C_6$cycloalkyl optionally substituted with 1-3 halogens, —SO$_2$—$C_1$-$C_4$haloalkyl, —N(H)SO$_2$—$C_1$-$C_4$alkyl, —N(H)SO$_2$—$C_3$-$C_6$cycloalkyl optionally substituted with 1-3 halogens, or —N(H)SO$_2$—$C_1$-$C_4$haloalkyl;
$Z^5$ is —SO$_2$—$C_1$-$C_4$alkyl, SO$_2$—$C_1$-$C_4$haloalkyl, —SO$_2$—$C_3$-$C_6$cycloalkyl optionally substituted with 1-3 $J^3$, —C(O)NR$^{10}$R$^{11}$, —CO$_2$-alkyl, COJ$^1$, CO$_2$J$^2$, —N(H)SO$_2$—$C_1$-$C_4$alkyl, —N(H)SO$_2$—$C_3$-$C_6$cycloalkyl optionally substituted with 1-3 $J^3$, or —N(H)SO$_2$—$C_1$-$C_4$haloalkyl, provided that when $Z^5$ is attached to nitrogen, $Z^5$ cannot be —N(H)SO$_2$—$C_1$-$C_4$alkyl, —N(H)SO$_2$—$C_3$-$C_6$cycloalkyl optionally substituted with 1-3 $J^3$, or —N(H)SO$_2$—$C_1$-$C_4$haloalkyl; and
each $Z^6$ is independently F, CH$_3$ optionally substituted with 1-3 F, CN, OH, $C_3$-$C_4$cycloalkyl, phenyl or 6 membered heteroaryl, provided that only one $Z^6$ can be OH.

8. The compound according to claim 1 having any one of the following Formulae:

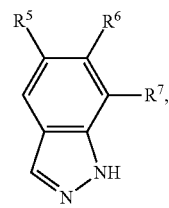
(IIIa)

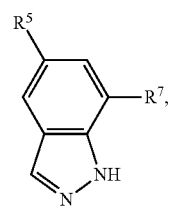
(IIIb)

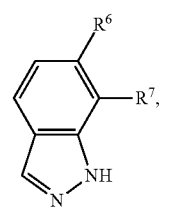
(IIIc)

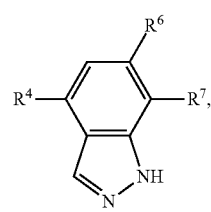
(IIId)

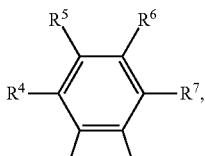

(IIIe)

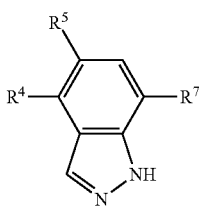

(IIIf)

or a pharmaceutically acceptable salt, a solvate, a tautomer, a stereoisomer or a deuterated analog thereof, wherein:

$R^4$, $R^5$ and $R^6$ are each independently F, Cl, —CH₃, —CFH₂, —CF₂H, —CF₃, —OCH₃, —OCFH₂, —OCF₂H or —OCF₃.

9. The compound according to claim 1 wherein $R^4$ is H; $R^5$ is Cl; and $R^6$ is H, C₁ or F.

10. The compound according to claim 8 having one of the following Formulae:

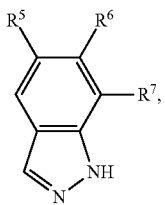

(IIIa)

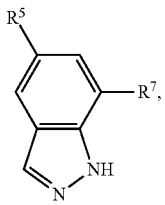

(IIIb)

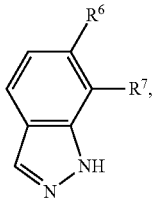

(IIIc)

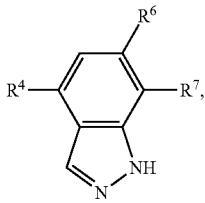

(IIId)

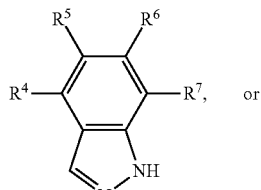

(IIIe)

or

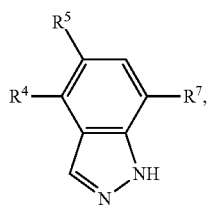

(IIIf)

or a pharmaceutically acceptable salt, a solvate, a tautomer, a stereoisomer or a deuterated analog thereof.

11. The compound according to claim 1, wherein $Z^5$ is: —C(O)—O—CH₃, —C(O)—O—CH₂CH₃, C(O)—O—C(CH₃)₃, —C(O)—O—CH₂CF₃, —C(O)—O—(CH₂)₂CH₃, —C(O)—O—CH(CH₃)₂, —C(O)—O—C(CH₃)₃, —C(O)—O—CH₂CH(CH₃)₂, —C(O)—N(H)—SO₂—CH₃, —C(O)—N(H)—SO₂—CH₂CF₃, —C(O)—N(H)—SO₂—CH₂CH₃, —C(O)—N(H)—SO₂—(CH₂)₂CH₃, —C(O)—N(H)—SO₂—CH(CH₃)₂, —C(O)—N(H)—SO₂—C(CH₃)₃, —C(O)—N(H)—SO₂—CH₂CH(CH₃)₂, —C(O)—N(H)—SO₂—cyclopropyl, —C(O)—N(H)—SO₂-cyclobutyl, —C(O)—N(H)—SO₂-cyclopentyl, —C(O)—N(H)—SO₂—cyclohexyl, —C(O)—N(H)—SO₂-phenyl, —C(O)—N(H)—SO₂-tetrahydro-2H-pyran, —C(O)—N(H)—SO₂—tetrahydro-2H-thiopyran, —C(O)—N(H)—SO₂-piperidinyl, —C(O)—N(H)—SO₂-piperazinyl, —C(O)—N(H)—SO₂-pyridyl, —C(O)—N(H)—SO₂-isoxazolyl, —C(O)—N(H)—SO₂-thiophenyl, —SO₂—CH₃, —SO₂—CH₂CH₃, —SO₂—CH₂CF₃, —SO₂—(CH₂)₂—CH₃, —SO₂—CH(CH₃)₂, —SO₂—CH₂CH(CH₃)₂, —SO₂-cyclopropyl, —SO₂-cyclobutyl, —SO₂-cyclopentyl, —SO₂-cyclohexyl, —SO₂-phenyl, —SO₂-tetrahydro-2H-pyran, —SO₂—tetrahydro-2H-thiopyran, —SO₂-pyridyl, —SO₂-isoxazolyl, —SO₂-thiophenyl, —C(O)—CH₂—OH, —C(O)(CH₂)₂—OH, —C(O)CH₂—C(CH₃)₂—OH, —CH(phenyl)₂, —CH(C₃-C₆cycloalkyl)₂-SO₂—N(CH₃)₂, —C(O)CH₃, —C(O)CH₂CH₃—C(O)CH₂CF₃, —C(O)(CH₂)₂CH₃, —C(O)CH(CH₃)₂, —C(O)C(CH₃)₃, —C(O)CH₂CH(CH₃)₂, —C(O)-cyclopropyl, —C(O)cyclobutyl, —C(O)cyclopentyl, —C(O)cyclohexyl, —C(O)phenyl, —C(O)tetrahydro-2H-pyran, —C(O)-tetrahydro-2H-thiopyranyl, —C(O)-piperidinyl, —C(O)piperazinyl, —C(O)-pyridyl, —C(O)-isoxazolyl, —C(O)-thiophenyl, —C(O)N(H)CH₃, —C(O)N(H)—CH₂CF₃, —C(O)—N(H)—CH₂CH₃, —C(O)N(H)—(CH₂)₂CH₃, —C(O)—N(H)—CH(CH₃)₂, —C(O)—N(H)—C(CH₃)₃, —C(O)—N(H)—CH₂CH(CH₃)₂, C(O)—N(H)-cyclopropyl, —C(O)—N(H)-cyclobutyl, —C(O)—N(H)-cyclopentyl, —C(O)—N(H)-cyclohexyl, —C(O)—N(H)-phenyl, —C(O)—N(H)-heterocycloalkyl, —C(O)—N(H)-pyridyl, —C(O)—N(H)-isoxazolyl, or —C(O)—N(H)-thiophenyl, wherein the heterocycloalkyl, phenyl, pyridyl, isoxazolyl, or thiophenyl moieties of $Z^5$ can be optionally substituted with 1-3 substituents independently selected from the group consisting of F, Cl, CN, $CH_3$, $CF_3$, OH, $OCH_3$ and $OCF_3$.

12. The compound according to claim 1, wherein $R^{11}$ is —$(CH_2)_2$—$CF_3$, $CH_2$—$CF_3$, $CH_3$, —$CH(CH_3)_2$, —$CH_2$—$CH_3$, —$CH(CH_3)_2$, —$C(CH_3)_3$, —$CH_2CH_2CH_3$, —CH($CH_3$)-phenyl, —$C_3$-$C_6$cycloalkyl, phenyl optionally substituted with 1-2 $J^3$, —$(CH_2)_{0-1}$cyclopropyl, —$(CH_2)_{0-1}$cyclobutyl, —$(CH_2)_{0-1}$cyclopentyl, —$(CH_2)_{0-1}$cyclohexyl, —$(CH_2)_{0-1}$ tetrahydro-2H-thiopyran 1,1-dioxide, —$(CH_2)_{0-1}$tetrahydro-2H-pyran, —$(CH_2)_{0-1}$oxetane, —$(CH_2)_{0-1}$morpholinyl, —$(CH_2)_{0-1}$ thiomorpholinyl 1,1-dioxide, —$(CH_2)_{0-1}$ isothiozolidine 1,1-dioxide, —$CH_2$—CN, methoxymethyl, methoxypropyl, methoxyethyl, morpholinyl, pyridyl, or phenyl optionally substituted with 1-3 substituents independently selected from F, Cl, $C_1$-$C_6$ alkoxy, and CN.

13. The compound according to claim 2, wherein $R^7$ is:

[structures]

14. The compound according to claim 2, wherein $R^7$ is:

[structures]

15. The compound according to claim 1, wherein $R^7$ is one of the following groups:

[structures]

wherein:
E is bicyclo[2.2.2]octane-1-yl, bicyclo[2.2.1]heptan-1-yl, 1-fluorobicyclo[2.2.2]octan-1-yl, (1r,2R,4S,5r,6R,8S)-tetracyclo[3.3.1.0$^{2,4}$.0$^{6,8}$]nonan-9-yl, (1s,5s)-bicyclo[3.3.1]nonan-9-yl, cuban-1-yl, adamantanyl, (1R,5S)-8-azabicyclo[3.2.1]octanyl, (1R,5S)-3,8-diazabicyclo[3.2.1]octanyl, or (1R,5S)-3-azabicyclo[3.2.1]octane;

$X^1$ is —$CR^{13}$—;
$X^2$ is —$C(R^{14})_2$— or —$C(R^{14})_2$—$C(R^{14})_2$—;
$X^3$ is —$C(R^{14})_2$— or —$C(R^{14})_2$—$C(R^{14})_2$—;
$X^4$ is —$N(R^{15})$— or —$C(R^{16})(R^{17})$—;
$X^5$ is —$N(R^{18})$— or —$C(R^{19})(R^{20})$—;
$X^6$ is —$N(R^{21})$— or —O—;
$X^8$ is —C(H)— or

[structure]

$X^9$ is CH or N;
$X^{10}$ is $NR^{21}$;
$R^{10}$ is H, $C_1$-$C_3$alkyl, or $C_1$-$C_3$haloalkyl;
$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—N($C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_3$ alkylene-$C_3$-$C_6$cycloalkyl optionally substituted with 1-4 $J^3$, —$C_0$-$C_4$alkylene-phenyl optionally substituted with 1-3 $J^3$, —$C_1$-$C_3$ alkylene-$SO_2$-phenyl optionally substituted with 1-3 $J^3$, —$C_1$-$C_3$ alkylene-$SO_2$—$C_1$-$C_6$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-3 $J^3$, —$C_0$-$C_4$ alkylene-$C_3$-$C_6$heterocycloalkyl optionally substituted with 1-3 $J^3$, —$C_0$-$C_4$ alkylene-5-6 membered heteroaryl optionally substituted with 1-3 $J^3$, or —C(O)-phenyl optionally substituted with 1-3 $J^3$;

$R^{13}$ is H, F, $CH_3$, $CFH_2$, $CF_2H$, or $CF_3$;
each $R^{14}$ is independently H, halogen, $CH_3$, —$CFH_2$, —$CF_2H$ or —$CF_3$, provided that no more than four $R^{14}$ is other than H;
$R^{15}$ is $C_1$-$C_2$alkylene-$C_1$-$C_2$alkoxy, —$C_0$-$C_1$alkylene-phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-

5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)N$R^{10}R^{11}$, —C(O)$J^1$, $CO_2J^2$, —$SO_2NR^{10}R^{11}$, —$CO_2$-alkyl, or —C(N$W_2$)=N—T;

$R^{16}$ is H, halogen, CN, OH, cyclopropyl, cyclobutyl, $C_1$-$C_4$alkyl or $C_1$-$C_4$haloalkyl;

$R^{17}$ is H, halogen, CN, OH, cyclopropyl, cyclobutyl, $C_1$-$C_4$alkyl, $C_1$-$C_4$haloalkyl, $SO_2$—$C_1$-$C_4$alkyl, $SO_2$—$C_1$-$C_4$haloalkyl, —$SO_2$—$C_3$-$C_6$cycloalkyl optionally substituted with 1-3 halogens, —C(O)N$R^{10}R^{11}$, —$CO_2$-alkyl, $COJ^1$, $CO_2J^2$, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

each Y is independently H, F, $CH_3$, —$CFH_2$, —$CF_2H$ or —$CF_3$, or two Y groups join together, with the carbon atom to which they are attached, to form a cyclopropyl or cyclobutyl group;

$R^{18}$ is H, $C_1$-$C_4$alkyl, $C_1$-$C_4$haloalkyl, —$SO_2$—$C_1$-$C_4$alkyl, —$SO_2$—$C_3$-$C_6$cycloalkyl optionally substituted with 1-3 halogens, —$SO_2$—$C_1$-$C_4$haloalkyl, $C_3$-$C_6$cycloalkyl optionally substituted with 1-3 halogens, —C(O)N$R^{10}R^{11}$, —$CO_2$-alkyl, $COJ^1$, or $CO_2J^2$;

$R^{19}$ is H, halogen, CN, OH, cyclopropyl, cyclobutyl, $C_1$-$C_4$alkyl, or —$C_1$-$C_4$haloalkyl;

$R^{20}$ is H, halogen, CN, OH, cyclopropyl, cyclobutyl, $C_1$-$C_4$alkyl, $C_1$-$C_4$haloalkyl, —$SO_2$—$C_1$-$C_4$alkyl, $SO_2$—$C_1$-$C_4$haloalkyl, —$SO_2$—$C_3$-$C_6$cycloalkyl optionally substituted with 1-3 halogens, —$CO_2$-alkyl, $COJ^1$, $CO_2J^2$, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

or $R^{19}$ and $R^{20}$ join together with the carbon atom to which they are attached to form one of the following groups (a)-(d):

(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl is optionally substituted with —N(H)$SO_2$—$C_1$-$C_3$alkyl, —N(H)$SO_2$—$C_1$-$C_3$haloalkyl, or —N(H)$SO_2$—$C_3$-$C_6$cycloalkyl optionally substituted with 1-3 halogens;

(b) a 4-6 membered nitrogen-containing heterocycloalkyl optionally substituted on its carbon atoms with 1-3 groups independently selected from the group consisting of CN, F, $C_1$-$C_4$alkyl, and $C_1$-$C_4$haloalkyl, and wherein the nitrogen-containing heterocycloalkyl can also be optionally N-substituted with —$SO_2$—$C_1$-$C_3$alkyl, —$SO_2$—$C_1$-$C_3$haloalkyl or —$SO_2$—$C_3$-$C_6$cycloalkyl optionally substituted with 1-3 halogens;

(c) a 4-6 membered heterocycloalkyl containing —O—, —S—, —SO—, or $SO_2$—, wherein the 4-6 membered heterocycloalkyl is optionally substituted on its carbon atoms with 1-3 groups independently selected from the group consisting of CN, F, $C_1$-$C_4$alkyl, and $C_1$-$C_4$haloalkyl; or (d) a 7-10 membered bridged ring;

$R^{21}$ is $C_1$-$C_3$alkylene-$C_1$-$C_3$alkoxy, —$C_0$-$C_2$alkylene-phenyl optionally substituted with 1-3 $J^3$, —$SO_2$—$C_1$-$C_6$alkyl, —$SO_2$—$C_1$-$C_6$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —(CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_2$alkylene-CH(phenyl)$_2$ optionally substituted with 1-3 $J^3$, —$C_1$-$C_2$alkylene-CH($C_3$-$C_6$cycloalkyl)$_2$ optionally substituted with 1-3 $J^3$, —C(O)N$R^{10}R^{11}$, —C(O)$J^1$, $CO_2J^2$, —$SO_2NR^{10}R^{11}$, or —$CO_2$-alkyl;

each $R^{27}$ is independently H, D, F, Cl, $CH_3$, —$CFH_2$, —$CF_2H$ or —$CF_3$, provided that no more than four $R^{27}$ is other than H and at least one $R^{27}$ is F, Cl, $CH_3$, —$CFH_2$, —$CF_2H$ or —$CF_3$;

$R^{70}$ is selected from the group consisting of CN, halogen, $C_1$-$C_4$alkyl, $C_1$-$C_4$haloalkyl, —$NH_2$, —N(H)$C_1$-$C_4$alkyl, —N($C_1$-$C_4$alkyl)$_2$, $C_1$-$C_4$alkoxyl optionally substituted with phenyl, 5-6 membered heterocycloalkyl, and 5-6 membered heteroaryl;

$J^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, —$C_0$-$C_3$ alkylene-5-6 membered heteroaryl optionally substituted with 1-3 $J^3$, or —$C_0$-$C_3$ alkylene-4-6 membered heterocycloalkyl optionally substituted with 1-3 $J^3$;

$J^2$ is H, $C_1$-$C_4$alkyl, or $C_1$-$C_4$haloalkyl; and each $J^3$ is independently halogen, $C_1$-$C_4$alkyl, $C_1$-$C_4$haloalkyl, OH, $C_1$-$C_4$alkoxy optionally substituted with 1-3 halogens, CN, 4-6 membered heterocycloalkyl, —S(O)$_2$—$C_1$-$C_4$alkyl, —$NH_2$, —N(H)—$C_1$-$C_4$alkyl, or —N($C_1$-$C_4$alkyl)$_2$ provided that when $J^3$ is attached to nitrogen, $J^3$ cannot be halogen, OH, CN, —$NH_2$, —N(H)—$C_1$-$C_4$alkyl, or —N($C_1$-$C_4$alkyl)$_2$.

16. The compound according to claim 1, wherein $R^7$ is one of the following groups:

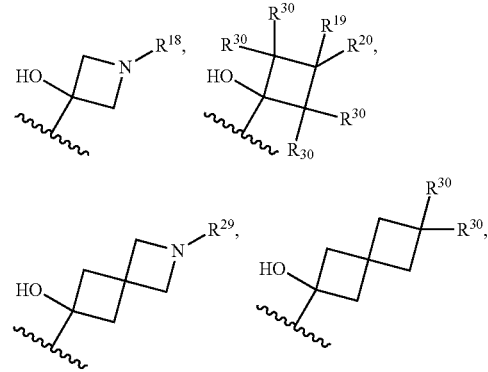

-continued
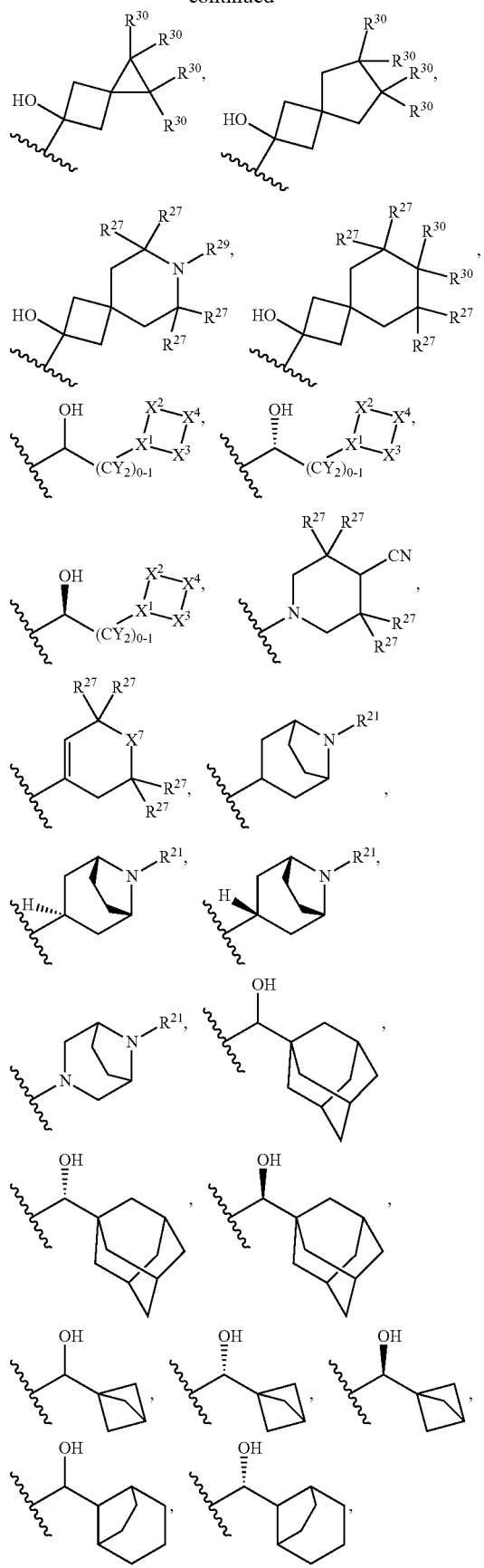
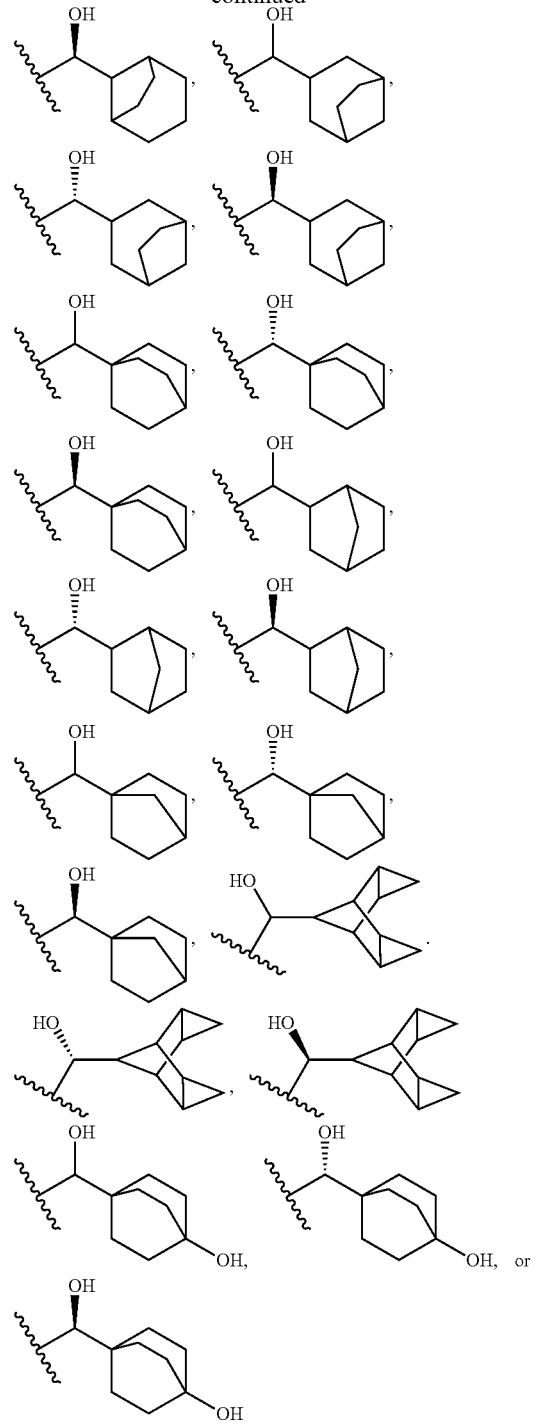
wherein:
each Y is independently H, F, CH$_3$, —CFH$_2$, —CF$_2$H or —CF$_3$, or two Y groups join together, with the carbon atom to which they are attached, to form a cyclopropyl or cyclobutyl group;
X$^1$ is —CR$^{13}$—;
X$^2$ is —C(R$^{14}$)$_2$— or —C(R$^{14}$)$_2$—C(R$^{14}$)$_2$—;
X$^3$ is —C(R$^{14}$)$_2$— or —C(R$^{14}$)$_2$—C(R$^{14}$)$_2$—;
X$^4$ is —N(R$^{15}$)— or —C(R$^{16}$)(R$^{17}$)—;
X$^7$ is —C(R$^{25}$)(R$^{26}$)—;
R$^{10}$ is H, C$_1$-C$_2$alkyl, or C$_1$-C$_2$haloalkyl;

$R^{11}$ is H, $C_1$-$C_3$alkyl, $C_1$-$C_3$haloalkyl, $C_1$-$C_4$cyanoalkyl, $C_2$-$C_4$alkynyl, —$C_1$-$C_4$alkylene-C(O)—$NH_2$, —$C_1$-$C_4$alkylene-C(O)—N(H)—$C_1$-$C_4$alkyl, —$C_1$-$C_4$alkylene-C(O)—N($C_1$-$C_4$alkyl)$_2$, —$C_0$-$C_4$ alkylene-C(O)—O—$C_1$-$C_4$alkyl, $C_1$-$C_4$hydroxyalkyl, —$C_0$-$C_4$alkylene-phenyl optionally substituted with 1-3 $J^3$, —$C_1$-$C_3$ alkylene-$SO_2$-phenyl optionally substituted with 1-2 $J^3$, $C_1$-$C_3$ alkylene-$SO_2$—$C_1$-$C_6$ alkyl, —$C_1$-$C_3$ alkylene-NH—$SO_2$—$C_1$-$C_6$ alkyl, —$C_1$-$C_4$alkylene-$C_1$-$C_4$alkoxy, $C_1$-$C_4$alkoxycarbonyl, —$C_0$-$C_4$ alkylene-$C_3$-$C_6$cycloalkyl optionally substituted with 1-2 $J^3$, —$C_0$-$C_4$ alkylene-$C_3$-$C_6$heterocycloalkyl optionally substituted with 1-2 $J^3$, —$C_0$-$C_4$ alkylene-5-6 membered heteroaryl optionally substituted with 1-2 $J^3$, or —C(O)-phenyl optionally substituted with 1-2 $J^3$;

$R^{13}$ is H, F, $CH_3$, $CFH_2$, $CF_2H$, or $CF_3$;

each $R^{14}$ is independently H, halogen, $CH_3$, —$CFH_2$, —$CF_2H$ or —$CF_3$, provided that no more than four $R^{14}$ is other than H;

$R^{15}$ is $C_1$-$C_2$alkylene-$C_1$-$C_2$alkoxy, —$C_0$-$C_1$alkylene-phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, —C(O)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$-5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)$NR^{10}R^{11}$, —C(O)$J^1$, c $CO_2J^2$, —$SO_2NR^{10}R^{11}$, —$CO_2$-alkyl, or —C($NW_2$)=N—T, $R^{16}$ is H, halogen, CN, OH, cyclopropyl, cyclobutyl, $C_1$-$C_4$alkyl or $C_1$-$C_4$haloalkyl;

$R^{17}$ is H, halogen, CN, OH, cyclopropyl, cyclobutyl, $C_1$-$C_4$alkyl, $C_1$-$C_4$haloalkyl, $SO_2$—$C_1$-$C_4$alkyl, $SO_2$—$C_1$-$C_4$haloalkyl, —$SO_2$—$C_3$-$C_6$cycloalkyl optionally substituted with 1-3 halogens, —C(O)$NR^{10}R^{11}$, —$CO_2$-alkyl, $COJ^1$, $CO_2J^2$, —N(H)$SO_2$—$C_1$-$C_4$alkyl, —N(H)$SO_2$—$C_3$-$C_6$cycloalkyl optionally substituted with 1-3 halogens, or —N(H)$SO_2$—$C_1$-$C_4$haloalkyl;

$R^{18}$ is H, $C_1$-$C_3$alkyl, $C_1$-$C_3$haloalkyl, —C(O)$NR^{10}R^{11}$, —$CO_2$-alkyl, $COJ^1$, $CO_2J^2$, or $C_3$-$C_6$cycloalkyl optionally substituted with 1-3 F; $SO_2$—$C_1$-$C_4$alkyl, $SO_2$—$C_1$-$C_4$haloalkyl, —$SO_2$—$C_3$-$C_6$cycloalkyl optionally substituted with 1-3 halogens, $R^{19}$ is H, F, CN, cyclopropyl, cyclobutyl, $C_1$-$C_3$alkyl, or —$C_1$-$C_3$fluoroalkyl;

$R^{20}$ is H, F, CN $C_1$-$C_3$alkyl, $C_1$-$C_3$fluoroalkyl, —N(H)$SO_2$—$C_1$-$C_4$alkyl, —N(H)$SO_2$—$C_3$-$C_6$cycloalkyl optionally substituted with 1-3 halogens, —N(H)$SO_2$—$C_1$-$C_4$fluoroalkyl, or $C_3$-$C_6$cycloalkyl optionally substituted with 1-3 F;

or $R^{19}$ and $R^{20}$ join together with the carbon atom to which they are attached to form one of the following groups (a)-(d):

(a) a $C_3$-$C_6$cycloalkyl optionally substituted with 1-4 groups independently selected from the group consisting of CN, F, $C_1$-$C_4$alkyl, and $C_1$-$C_4$haloalkyl, and wherein the $C_3$-$C_6$cycloalkyl is optionally substituted with —N(H)$SO_2$—$C_1$-$C_3$alkyl, —N(H)$SO_2$—$C_1$-$C_3$haloalkyl, or —N(H)$SO_2$—$C_3$-$C_6$cycloalkyl optionally substituted with 1-3 halogens;

(b) a 4-6 membered nitrogen-containing heterocycloalkyl optionally substituted on its carbon atoms with 1-3 groups independently selected from the group consisting of CN, F, $C_1$-$C_3$alkyl, and $C_1$-$C_3$fluoroalkyl, and wherein the nitrogen-containing heterocycloalkyl can also be optionally N-substituted with —$SO_2$—$C_1$-$C_3$alkyl, —$SO_2$—$C_1$-$C_3$fluoroalkyl or —$SO_2$—$C_3$-$C_6$cycloalkyl optionally substituted with 1-3 F;

(c) a 4-6 membered heterocycloalkyl containing —O—, —S—, —SO—, or —$SO_2$—, wherein the 4-6 membered heterocycloalkyl is optionally substituted on its carbon atoms with 1-3 groups independently selected from the group consisting of CN, F, $C_1$-$C_3$alkyl, and $C_1$-$C_3$fluoroalkyl; or (d) a 7-10 membered bridged ring;

$R^{21}$ is H, $C_1$-$C_2$alkylene-$C_1$-$C_2$alkoxy, —$C_0$-$C_1$alkylene-phenyl optionally substituted with 1-3 $J^3$, —$SO_2$—$C_1$-$C_4$alkyl, —$SO_2$—$C_1$-$C_4$haloalkyl, —$SO_2$—$C_3$-$C_6$cycloalkyl optionally substituted with 1-3 $J^3$, —$SO_2$-5-6 membered heterocycloalkyl optionally substituted with 1-3 $J^3$, —$SO_2$-5-6 membered heteroaryl optionally substituted with 1-3 $J^3$, —$SO_2$-phenyl optionally substituted with 1-3 $J^3$, (CO)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$-4-6 membered heterocycloalkyl optionally substituted with 1-3 $J^3$, —C(O)N(H)$SO_2$—5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)$NR^{10}R^{11}$, —C(O)$J^1$, $CO_2J^2$, —$SO_2NR^{10}R^{11}$, —$CO_2$-alkyl, or —C($NH_2$)=N—T;

$R^{25}$ is H, F, $C_1$-$C_3$alkyl, or $C_1$-$C_3$fluoroalkyl;

$R^{26}$ is H, F, $C_1$-$C_3$alkyl, $C_1$-$C_3$fluoroalkyl, CN, —N(H)$SO_2$—$C_1$-$C_3$alkyl, —N(H)$SO_2$—$C_1$-$C_3$fluoroalkyl, or —N(H)$SO_2$—$C_3$-$C_6$cycloalkyl optionally substituted with 1-3 F;

each $R^{27}$ is independently H, D, F, $CH_3$, —$CFH_2$, —$CF_2H$ or —$CF_3$, provided that no more than two $R^{27}$ is other than H;

$R^{29}$ is H, $C_1$-$C_3$alkyl, $C_1$-$C_3$fluoroalkyl, —$SO_2$—$C_1$-$C_3$alkyl, —$SO_2$—$C_1$-$C_3$fluoroalkyl, —$SO_2$—$C_3$-$C_6$cycloalkyl optionally substituted with 1-3 F, —C(O)$NR^{10}R^{11}$, or —$CO_2$-alkyl;

$R^{30}$ is H, F, or $C_1$-$C_3$ alkyl optionally substituted with 1-3 F;

T is $C_1$-$C_3$alkyl, $C_1$-$C_3$haloalkyl, $C_1$-$C_3$hydroxyalkyl, $C_1$-$C_3$alkoxy or CN;

$J^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 $J^3$, $C_0$-$C_3$ alkylene-phenyl optionally substituted with 1-3 $J^3$, $C_0$-$C_3$ alkylene-5-6 membered heteroaryl optionally substituted with 1-3 $J^3$, or —$C_0$-$C_3$ alkylene-4-6 membered heterocycloalkyl optionally substituted with 1-3 $J^3$;

$J^2$ is H, $C_1$-$C_4$alkyl, or $C_1$-$C_4$haloalkyl; and each $J^3$ is independently halogen, $C_1$-$C_4$alkyl, $C_1$-$C_4$haloalkyl, OH, —$C_1$-$C_4$alkoxy optionally substituted with 1-3 halogens, CN, 4-6 membered heterocycloalkyl, —$S(O)_2$—$C_1$-$C_4$alkyl, —$NH_2$, —N(H)—$C_1$-$C_4$alkyl, or —N($C_1$-$C_4$alkyl)$_2$ provided that when $J^3$ is attached to nitrogen, $J^3$ cannot be halogen, OH, CN, —$NH_2$, —N(H)—$C_1$-$C_4$alkyl, or —N($C_1$-$C_4$alkyl)$_2$.
17. The compound according to claim 16, wherein $R^7$ is one of the following groups:
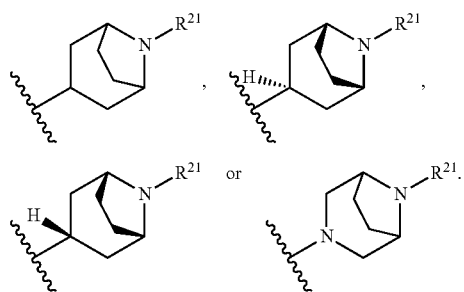
18. The compound according to claim 16, wherein $R^7$ is one of the following groups:
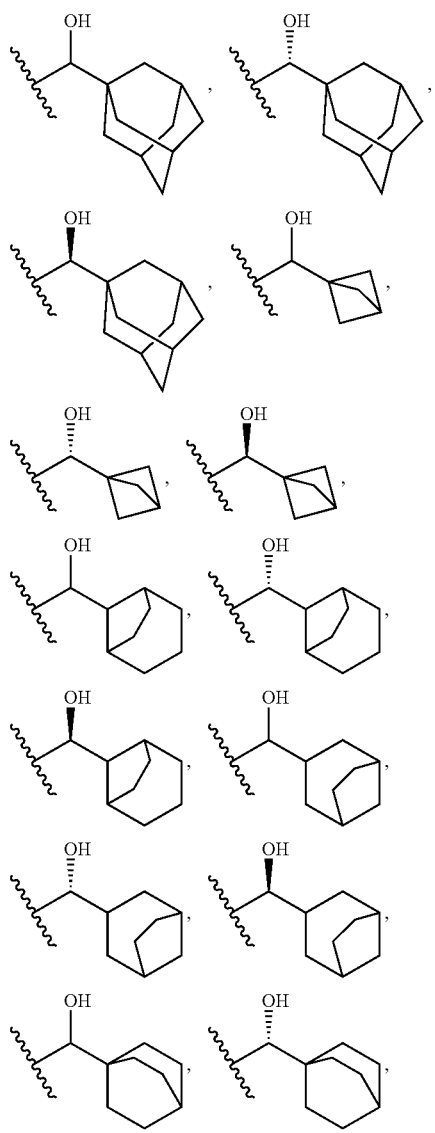
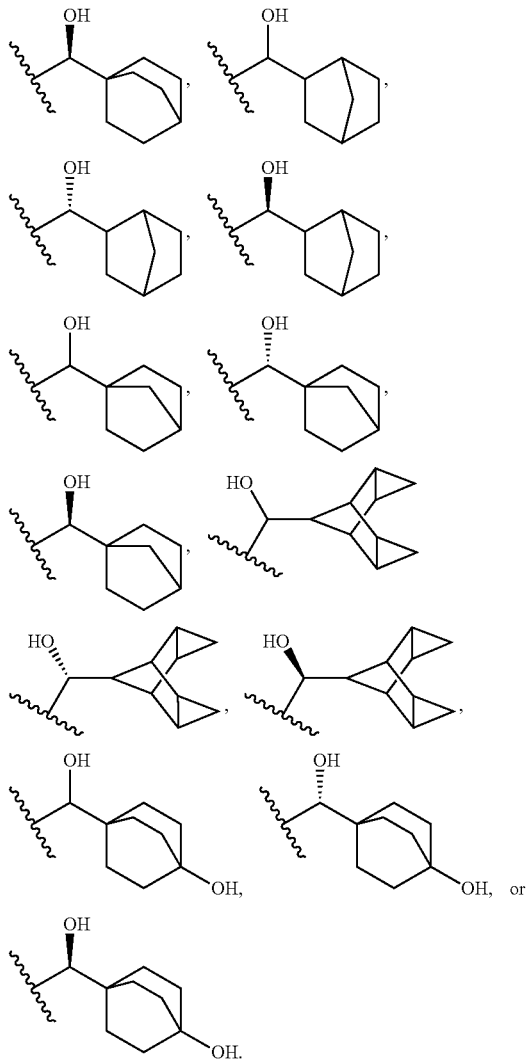
19. The compound according to claim 1, wherein $R^7$ is one of the following groups:
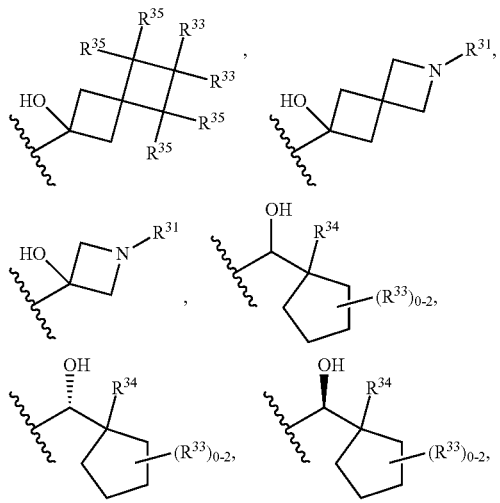

-continued

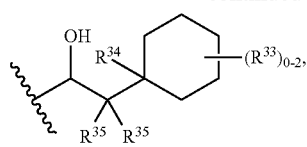
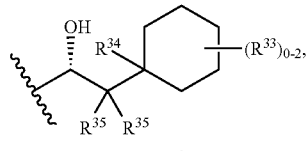
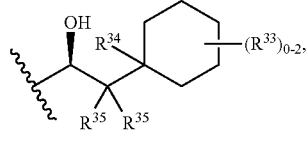
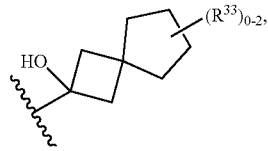
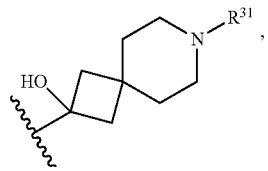
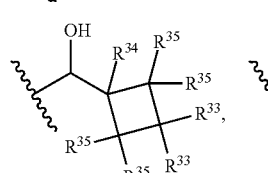
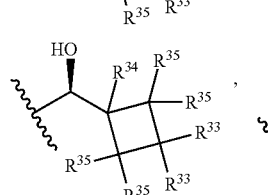
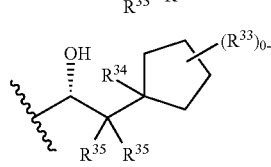
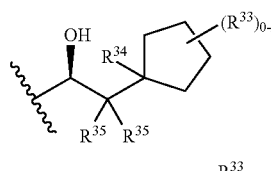
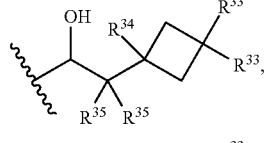
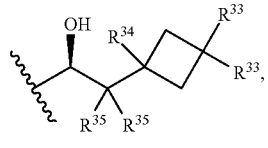

-continued

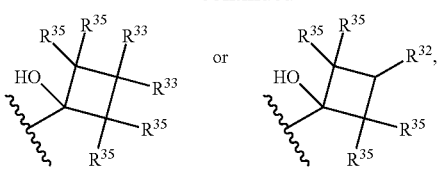

$R^{31}$ is H, $C_1$-$C_3$ alkyl optionally substituted with 1-3 F, —$SO_2$alkyl, or —$SO_2$-haloalkyl;

$R^{32}$ is —$SO_2$-alkyl or —N(H)$SO_2$-alkyl;

$R^{33}$ is H, F, CN, cyclopropyl, or $C_1$-$C_3$ alkyl optionally substituted with 1-3 F;

$R^{34}$ is H, F, or $C_1$-$C_3$ alkyl optionally substituted with 1-3 F; and $R^{35}$ is H, F, or methyl optionally substituted with 1-3 F.

20. The compound according to claim 1, wherein $R^7$ is one of the following groups:

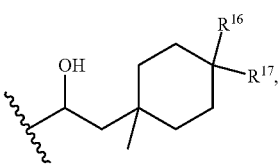
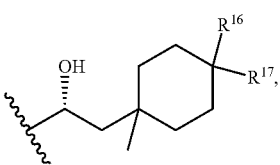
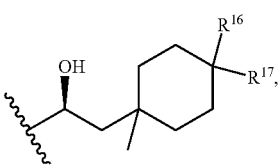
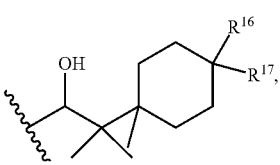
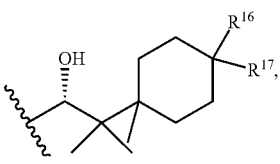
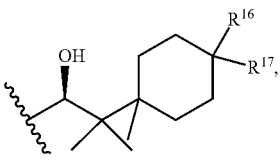
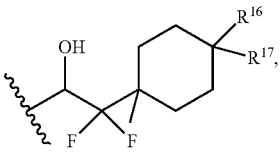

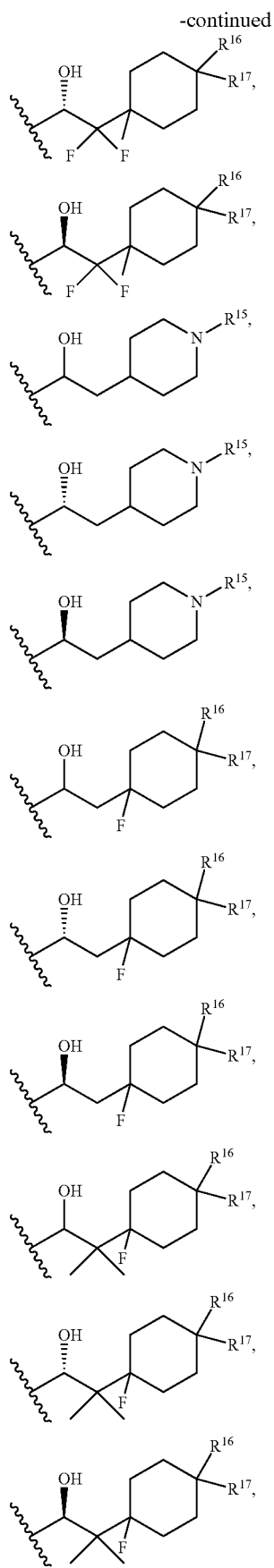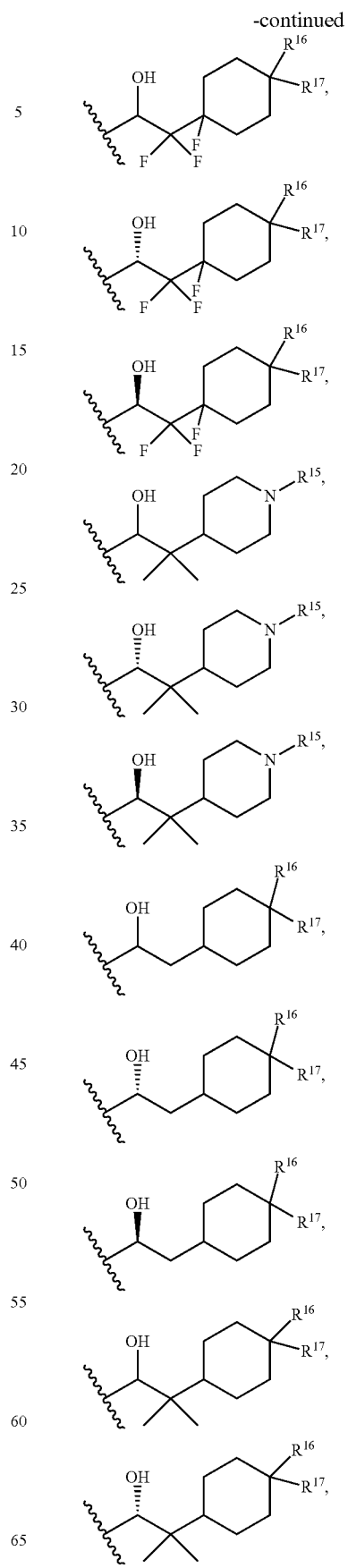

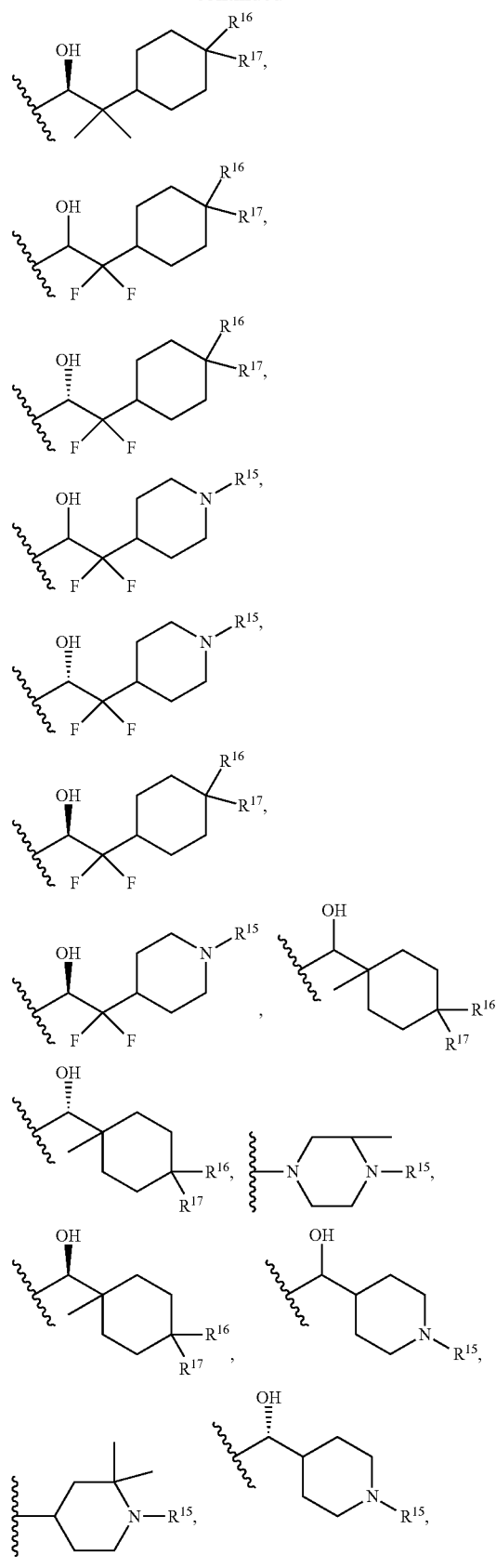
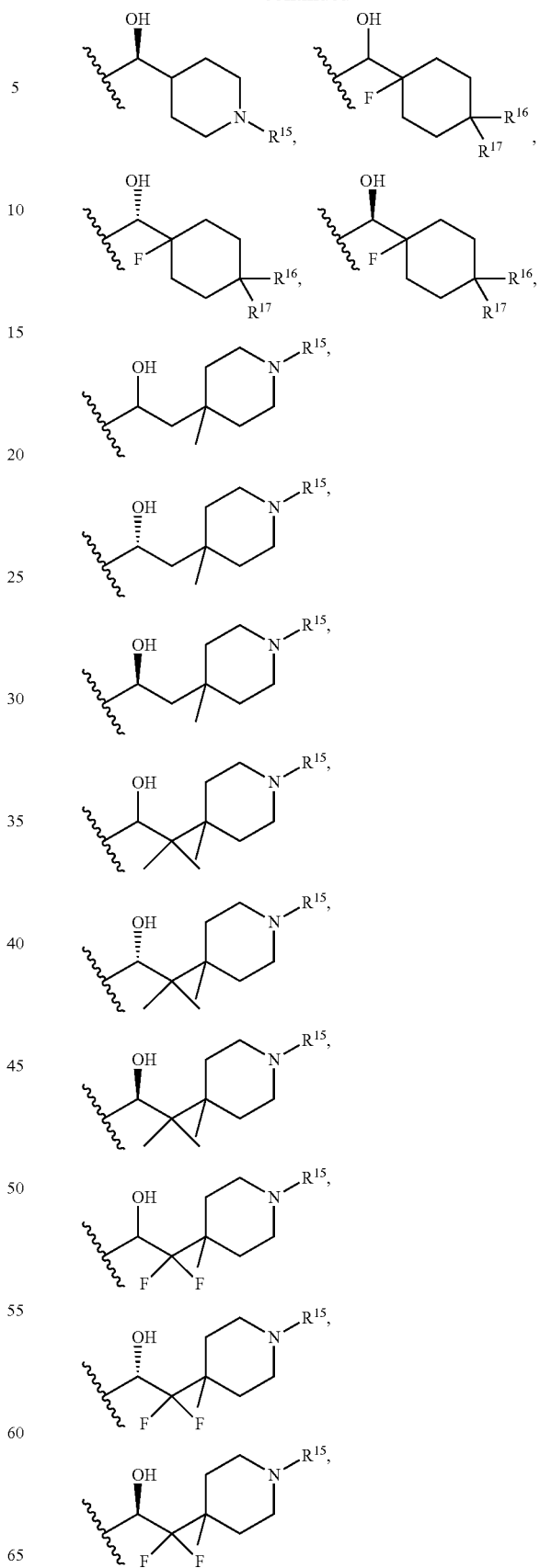

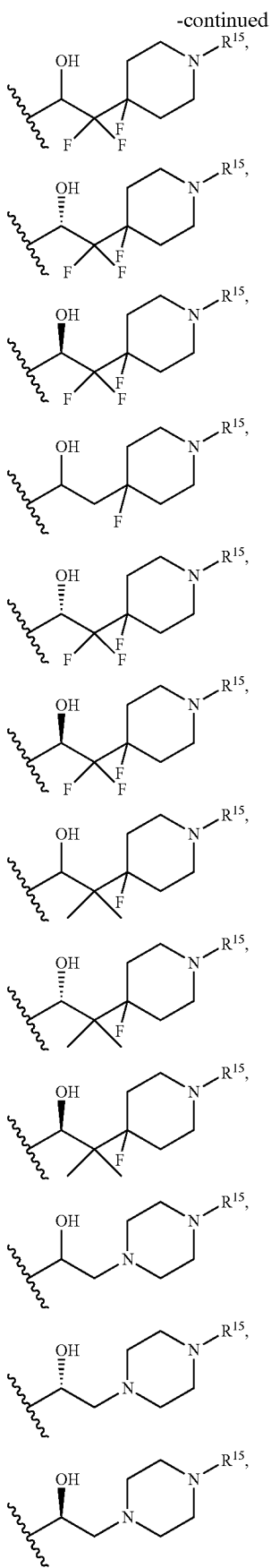
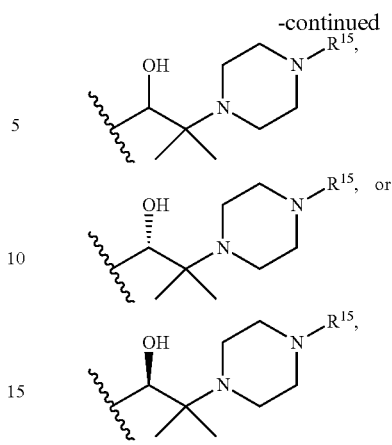

wherein:

$R^{10}$ is H or $C_1$-$C_2$alkyl;

$R^{11}$ is H, $C_1$-$C_3$alkyl, $C_1$-$C_3$haloalkyl, $C_1$-$C_3$cyanoalkyl, $C_2$-$C_3$alkynyl, —$C_1$-$C_3$alkylene-C(O)—$NH_2$, —$C_1$-$C_3$alkylene-C(O)—N(H)—$C_1$-$C_3$alkyl, —$C_1$-$C_3$alkylene-C(O)—N($C_1$-$C_3$alkyl)$_2$, —$C_0$-$C_3$ alkylene-C(O)—O—$C_1$-$C_3$alkyl, $C_1$-$C_3$hydroxyalkyl, —$C_0$-$C_3$ alkylene-$C_3$-$C_6$cycloalkyl optionally substituted with 1-2 $J^3$, —$C_0$-$C_4$alkylene-phenyl optionally substituted with 1 $J^3$, —$C_1$-$C_3$ alkylene-$SO_2$-phenyl optionally substituted with 1 $J^3$, —$C_1$-$C_3$ alkylene-$SO_2$—$C_1$-$C_3$ alkyl, —$C_1$-$C_3$ alkylene-NH—$SO_2$—$C_1$-$C_3$ alkyl, $C_1$-$C_3$alkylene-$C_1$-$C_3$alkoxy, $C_1$-$C_3$alkoxycarbonyl, —$C_0$-$C_3$ alkylene-$C_3$-$C_6$heterocycloalkyl optionally substituted with 1 $J^3$, —$C_0$-$C_3$ alkylene-5-6 membered heteroaryl optionally substituted with 1 $J^3$, or —C(O)-phenyl optionally substituted with 1 $J^3$;

$R^{15}$ is —$C_1$-$C_2$alkylene-$C_1$-$C_2$alkoxy, —$C_0$-$C_1$alkylene-phenyl optionally substituted with 1-3 $J^3$, —$SO_2$—$C_1$-$C_3$alkyl, —$SO_2$—$C_1$-$C_3$haloalkyl, —$SO_2$—$C_3$-$C_6$cycloalkyl optionally substituted with 1-3 $J^3$, —$SO_2$—5-6 membered heterocycloalkyl optionally substituted with 1-3 $J^3$, —$SO_2$—5-6 membered heteroaryl optionally substituted with 1-3 $J^3$, —$SO_2$-phenyl optionally substituted with 1-3 $J^3$, —C(O)N(H)$SO_2$—$C_1$-$C_6$alkyl, —C(O)N(H)$SO_2$—$C_1$-$C_6$haloalkyl, —C(O)N(H)$SO_2$—$C_3$-$C_6$cycloalkyl optionally substituted with 1-3 $J^3$, —C(O)N(H)$SO_2$—4-6 membered heterocycloalkyl optionally substituted with 1-3 $J^3$, —C(O)N(H)$SO_2$—5-6 membered heteroaryl optionally substituted with 1-3 $J^3$, —$C_0$-$C_2$alkylene-CH(phenyl)$_2$ optionally substituted with 1-3 $J^3$, —$C_0$-$C_2$alkylene-CH($C_3$-$C_6$cycloalkyl)$_2$ optionally substituted with 1-3 $J^3$, —C(O)N$R^{10}R^{11}$, —$SO_2$N$R^{10}R^{11}$, —$SO_2$—$C_3$-$C_6$cycloalkyl optionally substituted with 1-3 halogens, —$CO_2$-alkyl, $COJ^1$, —$CO_2J^2$, or —C($NH_2$)=N—CN;

$R^{16}$ is H, F, $C_1$-$C_3$alkyl or $C_1$-$C_3$fluoroalkyl;

$R^{17}$ is H, F, $C_1$-$C_3$ alkyl, $C_1$-$C_3$fluoroalkyl, —N(H)$SO_2$—$C_1$-$C_3$alkyl, —$SO_2$—$C_3$-$C_6$cycloalkyl optionally substituted with 1-3 F, —N(H)$SO_2$—$C_1$-$C_3$haloalkyl, or $C_3$-$C_6$cycloalkyl optionally substituted with 1-3 F;

$J^1$ is $C_1$-$C_4$alkyl, —$C_1$-$C_4$alkylene-$C_1$-$C_4$alkoxy, $C_1$-$C_4$cyanoalkyl, $C_1$-$C_4$hydroxyalkyl, $C_0$-$C_3$ alkylene-$C_3$-$C_6$ cycloalkyl optionally substituted with 1-3 J³, C₀-C₁alkylene-phenyl optionally substituted with 1-3 J³, —C₀-C₁alkylene-5-6 membered heteroaryl optionally substituted with 1 J³, or —C₀-C₃alkylene-4-6 membered heterocycloalkyl optionally substituted with 1-3 J³;

J² is H, C₁-C₃ alkyl, or C₁-C₃ haloalkyl; and each J³ is independently halogen, C₁-C₄alkyl, C₁-C₄haloalkyl, OH, —C₁-C₃ alkoxy optionally substituted with 1-3 halogens, CN, 5-6 membered heterocycloalkyl, —S(O)₂—C₁-C₄alkyl, —NH₂, —N(H)—C₁-C₃ alkyl, or —N(C₁-C₃ alkyl)₂ provided that when J³ is attached to nitrogen, J³ cannot be halogen, OH, CN, —NH₂, —N(H)—C₁-C₃ alkyl, or —N(C₁-C₃ alkyl)₂.

21. The compound according to claim 20, wherein R⁷ is one of the following groups:

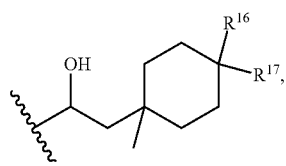

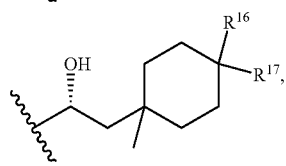

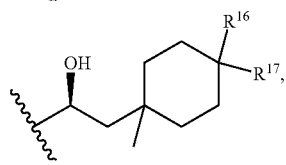

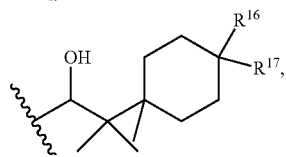

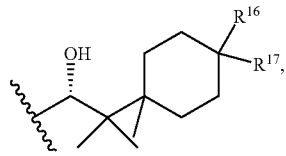

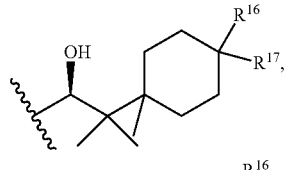

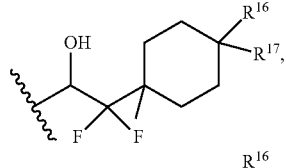

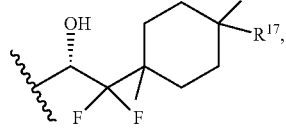

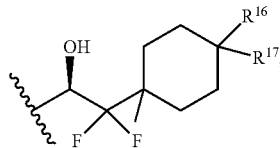

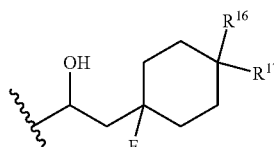

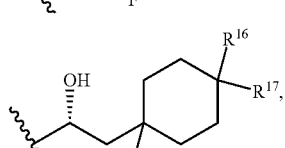

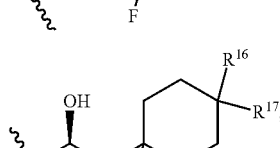

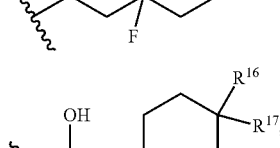

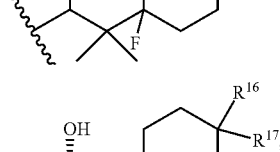

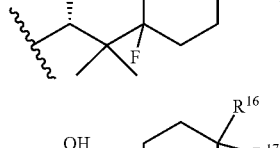

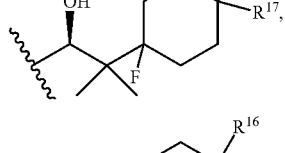

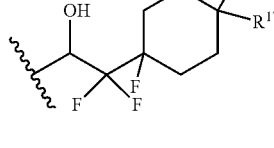

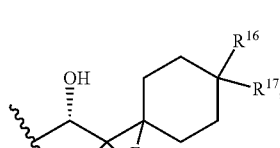

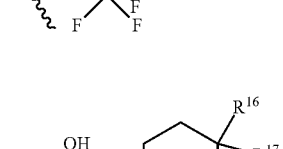

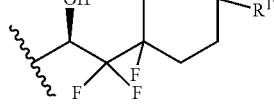

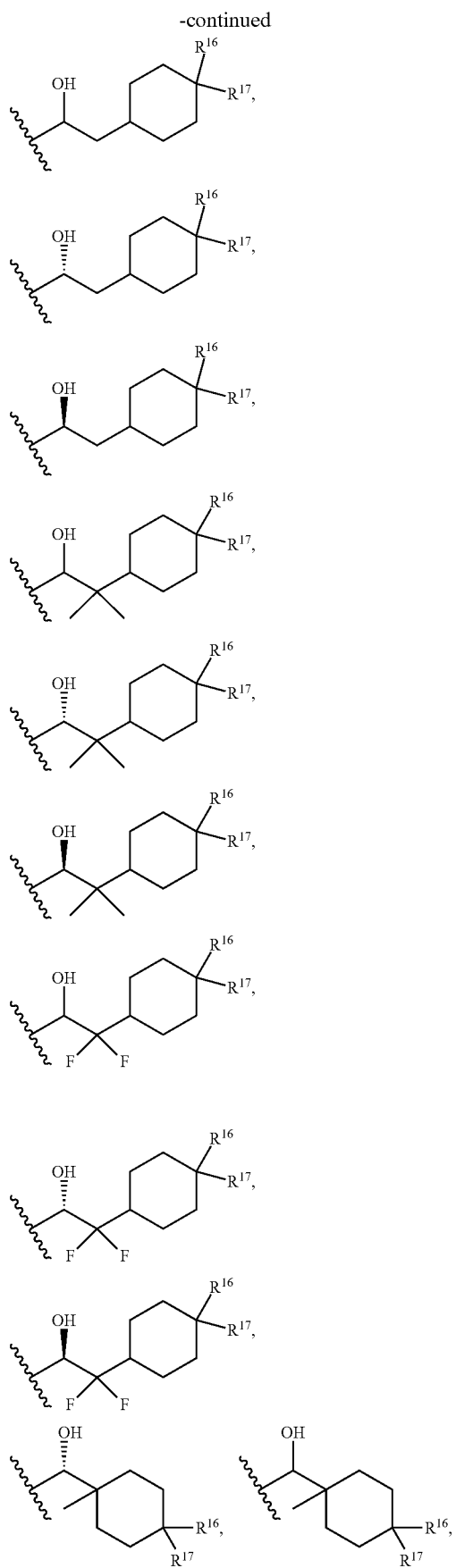
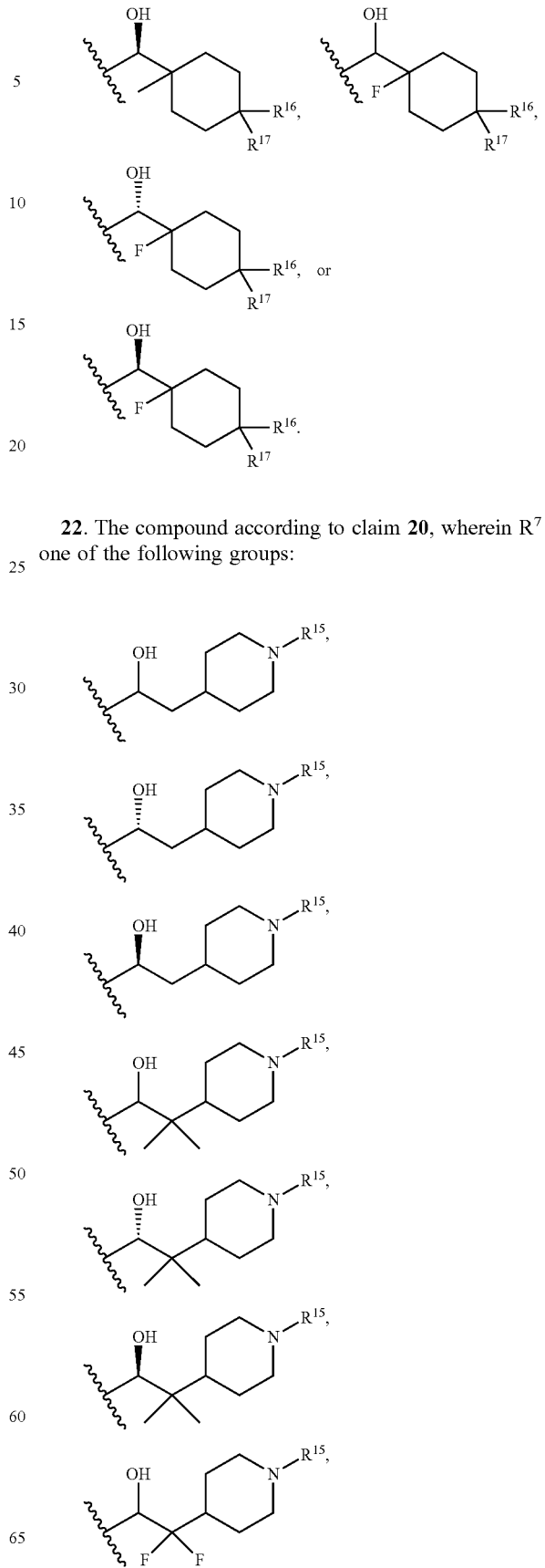
22. The compound according to claim 20, wherein $R^7$ is one of the following groups:

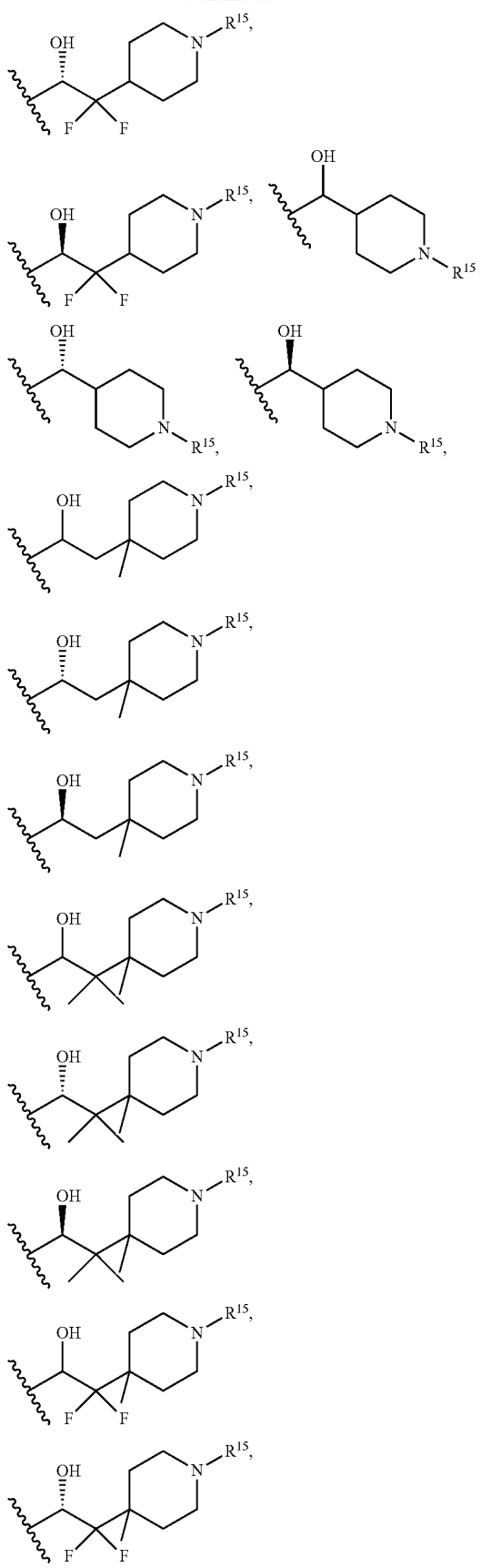
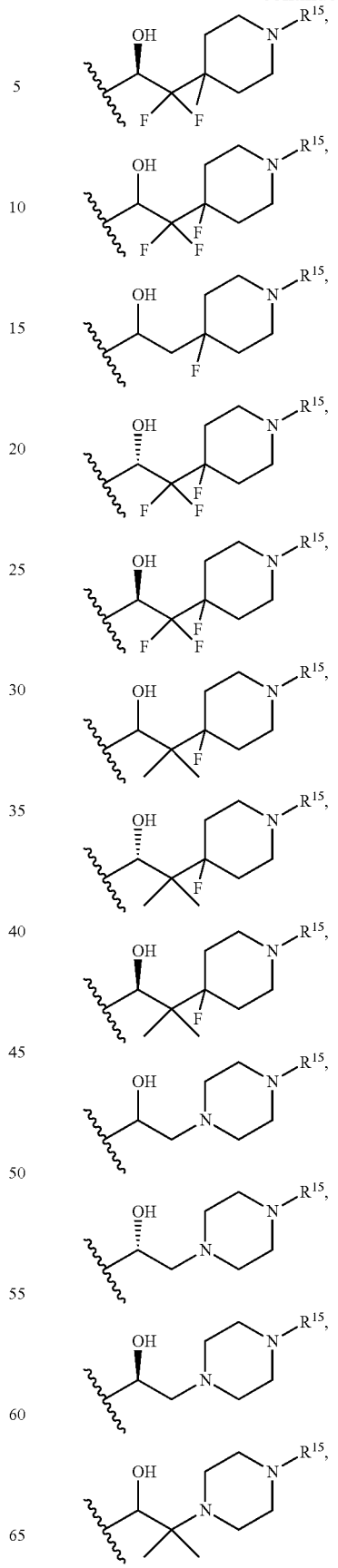

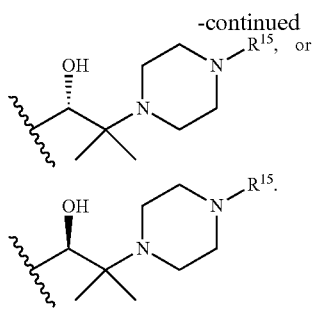

23. The compounds according to claim 20, wherein $R^{15}$ is one of the following groups: —S(O)$_2$—(CH$_2$)$_2$—CF$_3$, —S(O)$_2$—CH$_2$—CF$_3$, —S(O)$_2$—CH$_3$, —S(O)$_2$—CH(CH$_3$)$_2$, —S(O)$_2$—CH$_2$—CH$_3$, —S(O)$_2$—CH(CH$_3$)$_2$, —S(O)$_2$—CH$_2$CH$_2$CH$_3$, —S(O)$_2$—N(H)propyl, —S(O)$_2$—C$_3$-C$_6$cycloalkyl, —S(O)$_2$-morpholinyl, —S(O)$_2$-pyridyl, —S(O)$_2$-isoxazolyl optionally substituted with 1-3 methyl, —S(O)$_2$-phenyl optionally substituted with 1-3 substituents selected from the group consisting of F, Cl, C$_1$-C$_3$alkoxy, and CN, —C(O)—CH$_3$, —C(O)—CH(CH$_3$)$_2$, —C(O)—CH$_2$—CH$_3$, —C(O)—CH(CH$_3$)$_2$, —C(O)—C(CH$_3$)$_3$, —C(O)—CH$_2$CH$_2$CH$_3$, —C(O)—CH(CH$_3$)-phenyl, —C(O)—N(H)propyl, —C(O)—(CH$_2$)$_{0-1}$cyclopropyl, —C(O)—(CH$_2$)$_{0-1}$cyclobutyl, —C(O)—(CH$_2$)$_{0-1}$cyclopentyl, —C(O)—(CH$_2$)$_{0-1}$cyclohexyl, —C(O)—(CH$_2$)$_{0-1}$tetrahydro-2H-thiopyran 1,1-dioxide, —C(O)—(CH$_2$)$_{0-1}$tetrahydro-2H-pyran, —C(O)—(CH$_2$)$_{0-1}$oxetane, —C(O)—(CH$_2$)$_{0-1}$morpholinyl, —C(O)—(CH$_2$)$_{0-1}$thiomorpholinyl 1,1-dioxide, —C(O)—(CH$_2$)$_{0-1}$ isothiozolidine 1,1-dioxide, —C(O)—CH$_2$—CN, —C(O)-methoxymethyl, —C(O)-methoxypropyl, —C(O)-methoxyethyl, —C(O)-pyridyl, —C(O)-isoxazolyl optionally substituted with 1-3 methyl, —C(O)-phenyl optionally substituted with 1-3 substituents independently selected from the group consisting of F, Cl, C$_1$-C$_3$alkoxy, and CN, —S(O)$_2$—N(H)—(CH$_2$)$_2$—CF$_3$, —S(O)$_2$—N(H)—CH$_2$—CF$_3$, —S(O)$_2$—N(H)—CH$_3$, —S(O)$_2$—N(H)—CH(CH$_3$)$_2$, —S(O)$_2$—N(H)—CH$_2$—CH$_3$, —S(O)$_2$—N(H)—CH(CH$_3$)$_2$, —S(O)$_2$—N(H)—CH$_2$CH$_2$CH$_3$, —S(O)$_2$—N(H)—CH(CH$_3$)-phenyl, —S(O)$_2$—N(H)—(CH$_2$)$_{0-1}$cyclopropyl, —S(O)$_2$—N(H)—(CH$_2$)$_{0-1}$cyclobutyl, —S(O)$_2$—N(H)—(CH$_2$)$_{0-1}$cyclopentyl, —S(O)$_2$—N(H)—(CH$_2$)$_{0-1}$cyclohexyl, —S(O)$_2$—N(H)—(CH$_2$)$_{0-1}$ tetrahydro-2H-thiopyran 1,1-dioxide, —S(O)$_2$—N(H)—(CH$_2$)$_{0-1}$tetrahydro-2H-pyran, —S(O)$_2$—N(H)—(CH$_2$)$_{0-1}$oxetane, —S(O)$_2$—N(H)—(CH$_2$)$_{0-1}$-morpholinyl, —S(O)$_2$—N(H)—(CH$_2$)$_{0-1}$ thiomorpholinyl 1,1-dioxide, —S(O)$_2$—N(H)—(CH$_2$)$_{0-1}$ isothiozolidine 1,1-dioxide, —S(O)$_2$—N(H)—CH$_2$—CN, —S(O)$_2$—N(H)-methoxymethyl, —S(O)$_2$—N(H)-methoxypropyl, —S(O)$_2$—N(H)-methoxyethyl, —S(O)$_2$—N(H)-pyridyl, —S(O)$_2$—N(H)-isoxazolyl optionally substituted with 1-3 methyl, —S(O)$_2$—N(H)-phenyl optionally substituted with 1-3 substituents independently selected from the group consisting of F, Cl, C$_1$-C$_3$ alkoxy, and CN, —C(O)—N(H)(CH$_2$)$_2$—CF$_3$, —C(O)—N(H)CH$_2$—CF$_3$, —C(O)—N(H)CH$_3$, —C(O)—N(H)CH(CH$_3$)$_2$, —C(O)—N(H)CH$_2$—CH$_3$, —C(O)—N(H)CH(CH$_3$)$_2$, —C(O)—N(H)CH$_2$CH$_2$CH$_3$, —C(O)—N(H)—CH$_2$—CH$_2$—S(O)$_2$—CH$_3$, —C(O)—N(H)—CH$_2$—CN, —C(O)—N(H)—CH$_2$—CH$_2$—F, —C(O)—NH$_2$, —C(O)—N(H)CH(CH$_3$)-phenyl, —C(O)—N(H)(CH$_2$)$_{0-1}$-cyclopropyl, —C(O)—N(H)(CH$_2$)$_{0-1}$-cyclobutyl, —C(O)—N(H)(CH$_2$)$_{0-1}$-cyclopentyl, —C(O)—N(H)(CH$_2$)$_{0-1}$-cyclohexyl, —C(O)—N(H)(CH$_2$)$_{0-1}$ tetrahydro-2H-thiopyran 1,1-dioxide, —C(O)—N(H)(CH$_2$)$_{0-1}$-tetrahydro-2H-pyran, —C(O)—N(H)(CH$_2$)$_{0-1}$oxetane, —C(O)—N(H)(CH$_2$)$_{0-1}$-morpholinyl, —C(O)—N(H)(CH$_2$)$_{0-1}$ thiomorpholinyl 1,1-dioxide, —C(O)—N(H)(CH$_2$)$_{0-1}$ isothiozolidine 1,1-dioxide, —C(O)—N(H)CH$_3$—CN, —C(O)—N(H)-methoxymethyl, —C(O)—N(H)-methoxypropyl, —C(O)—N(H)-methoxyethyl, —C(O)—N(H)-pyridyl, —C(O)—N(H)isoxazolyl optionally substituted with 1-3 methyl, —C(O)—N(H)phenyl optionally substituted with 1-3 substituents independently selected from the group consisting of F, Cl, C$_1$-C$_3$alkoxy, and CN, —C(O)—N(H)—SO$_2$—(CH$_2$)$_2$—CF$_3$, —C(O)—N(H)—SO$_2$—CH$_2$—CF$_3$, —C(O)—N(H)—SO$_2$—CH$_3$, —C(O)—N(H)—SO$_2$—CH(CH$_3$)$_2$, —C(O)—N(H)—SO$_2$—CH$_2$—CH$_3$, —C(O)—N(H)—SO$_2$—CH(CH$_3$)$_2$, —C(O)—N(H)—SO$_2$—C(CH$_3$)$_3$, —C(O)—N(H)—SO$_2$—CH$_2$CH$_2$CH$_3$, —C(O)—N(H)—SO$_2$—C$_3$-C$_6$cycloalkyl, —C(O)—N(H)—SO$_2$-morpholinyl, —C(O)—N(H)—SO$_2$-pyridyl, —C(O)—N(H)—SO$_2$—isoxazolyl optionally substituted with 1-3 methyl, —C(NH$_2$)=N—CN, or —C(O)—N(H)—C$_0$-phenyl optionally substituted with 1-3 substituents independently selected from the group consisting of F, Cl, C$_1$-C$_3$alkoxy, and CN.

24. The compound according to claim 1, wherein $R^7$ is one of the following groups:

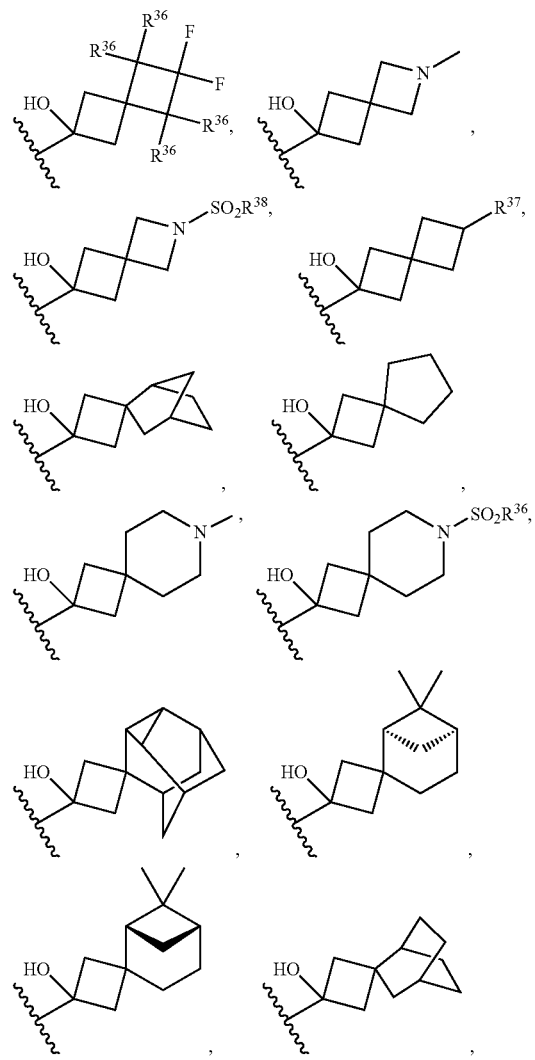

-continued
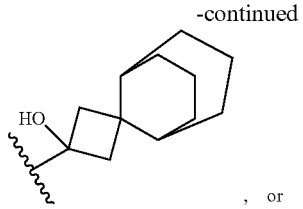
, or
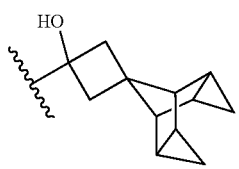
wherein:
R^{36} is H or $C_1$-$C_3$ alkyl optionally substituted with 1-3 F;
R^{37} is H, —N(H)SO$_2$-alkyl, or —SO$_2$-alkyl; and
R^{38} is $C_1$-$C_3$ alkyl optionally substituted with 1-3 F.
25. The compound according to claim 24, wherein $R^7$ is one of the following groups:
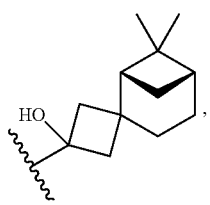, 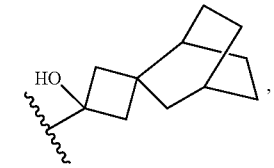,
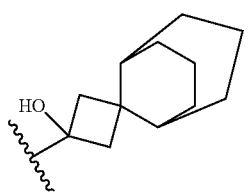, 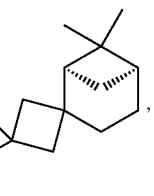,
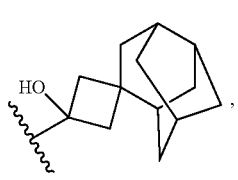, 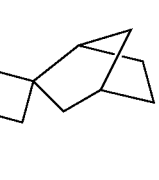, or
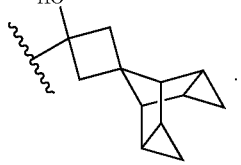.
26. The compound according to claim 1, wherein $R^7$ is one of the following groups:
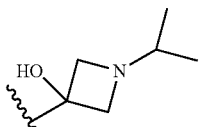, 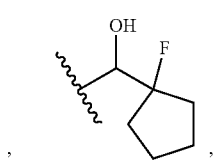,
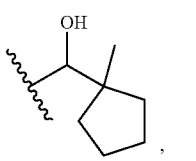, 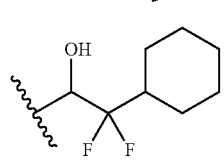,
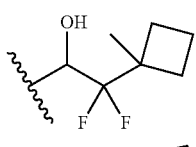, 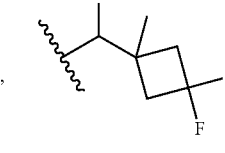,
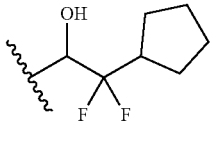, 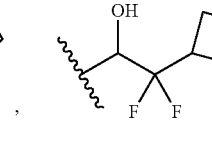,
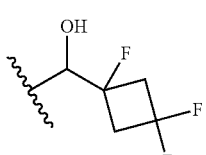, 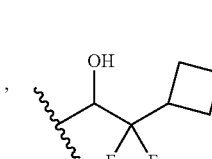,
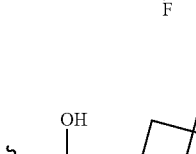, 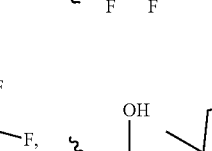,
, 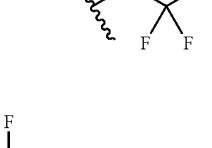,
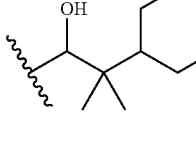, 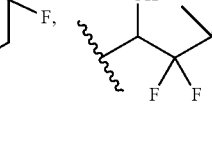,
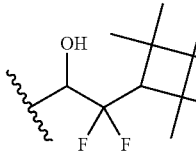, 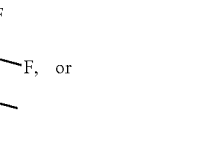, or
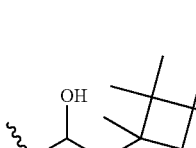.

27. A compound selected from:
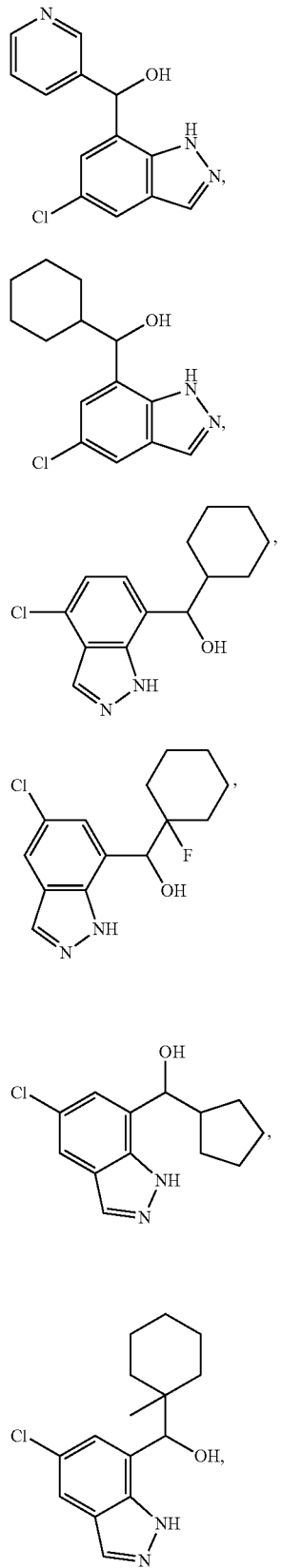
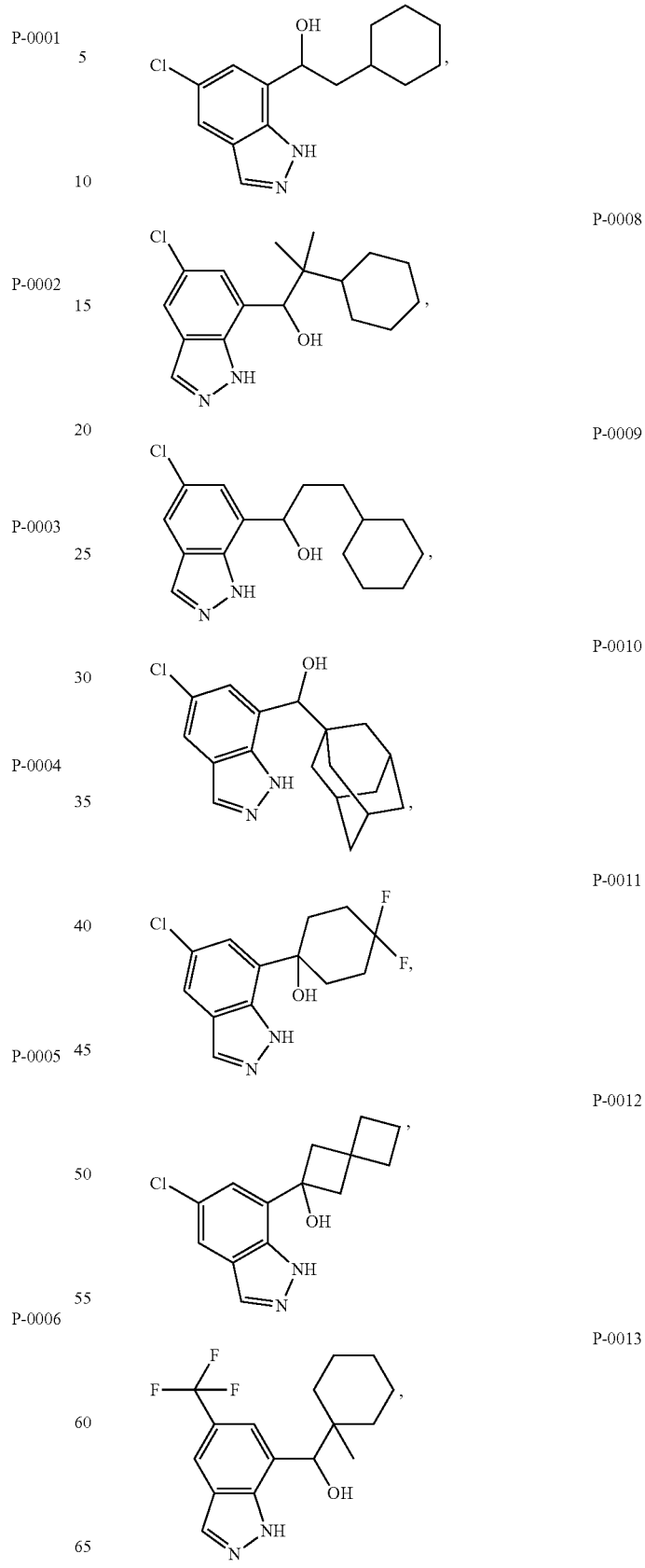

-continued
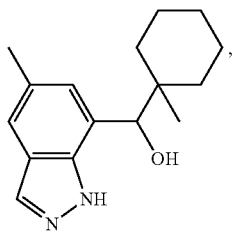
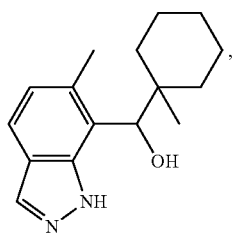
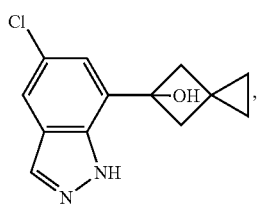
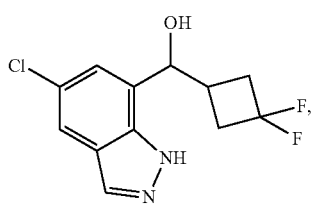
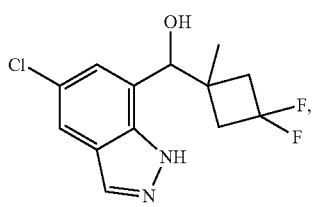
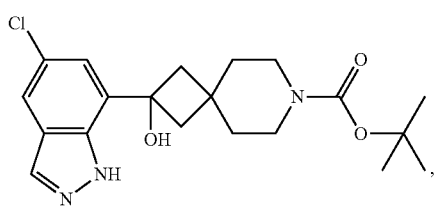
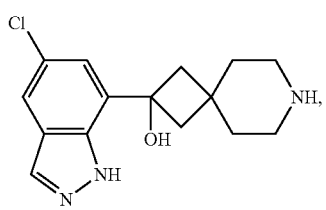
-continued
P-0014
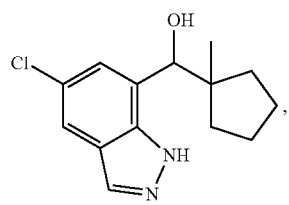
P-0021
P-0015
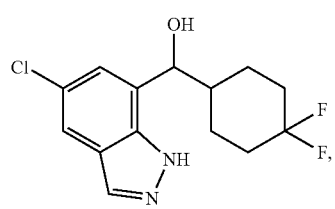
P-0022
P-0016
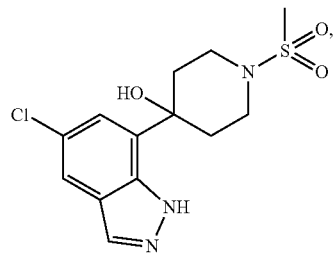
P-0023
P-0017
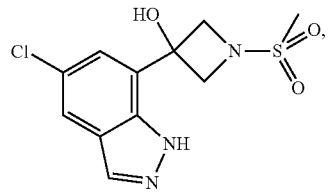
P-0024
P-0018
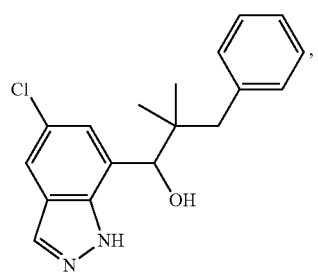
P-0026
P-0019
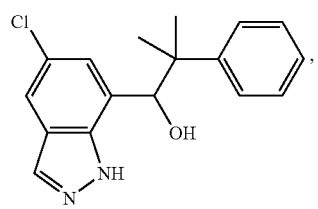
P-0027
P-0020
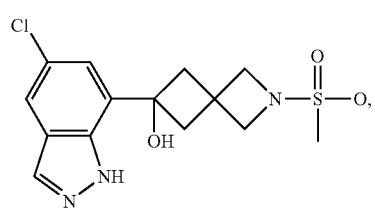
P-0028

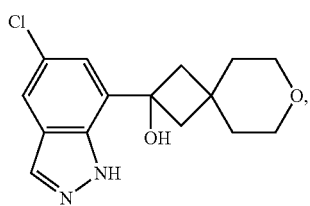
P-0029
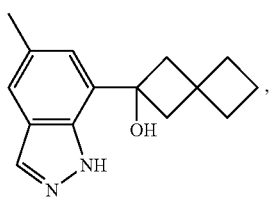
P-0030
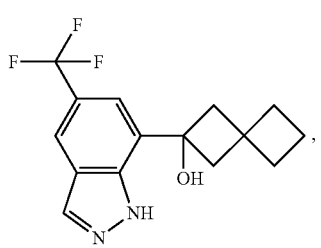
P-0031
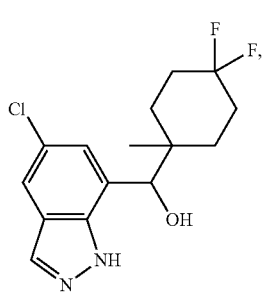
P-0032
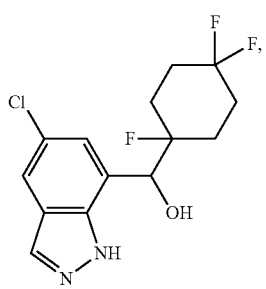
P-0033
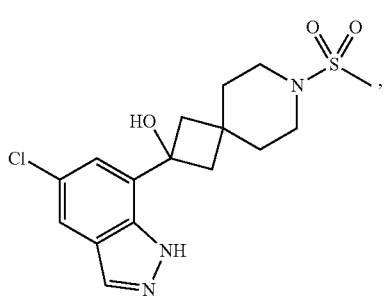
P-0034
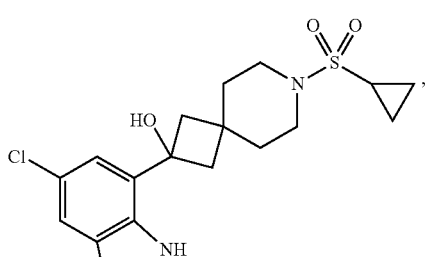
P-0035
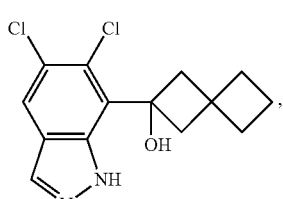
P-0036
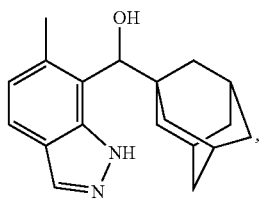
P-0037
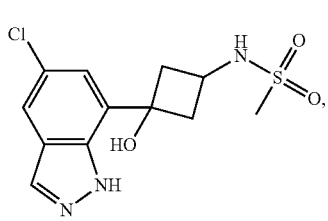
P-0038
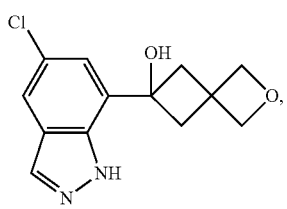
P-0039
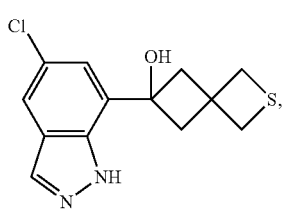
P-0040
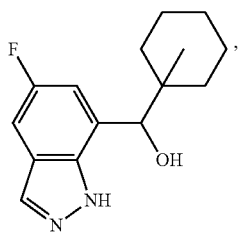
P-0041

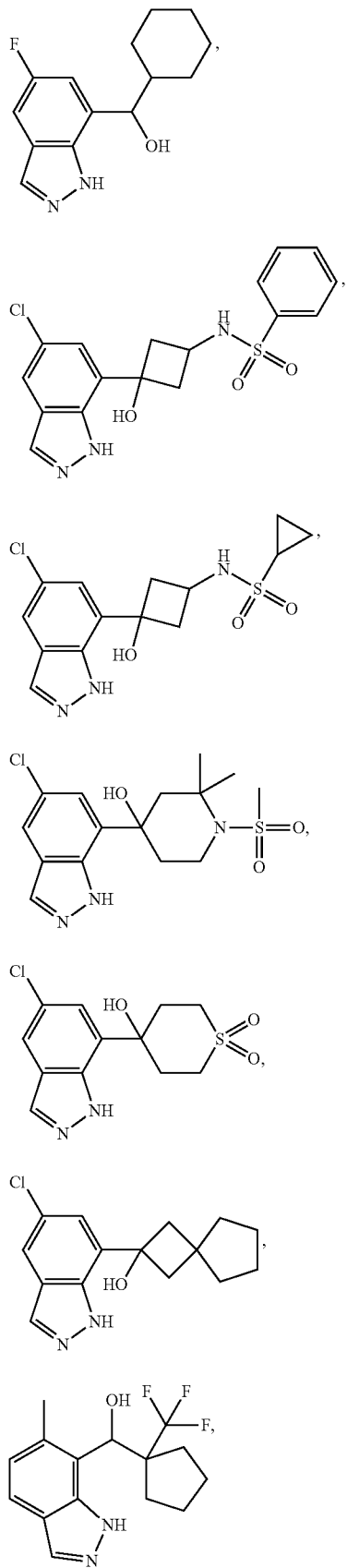
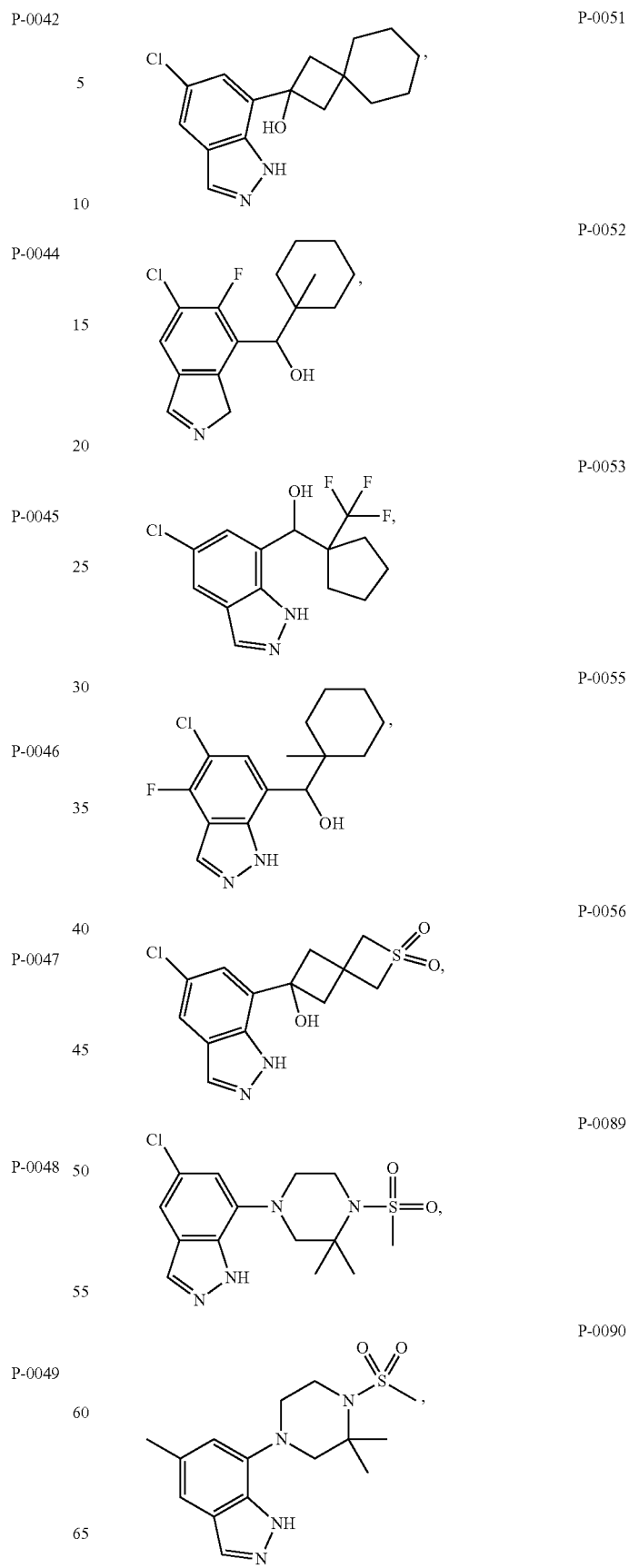

-continued
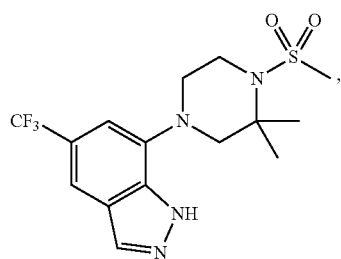
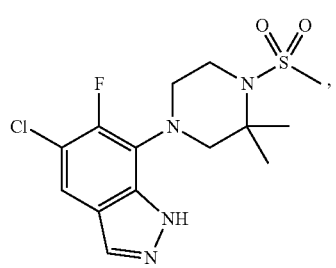
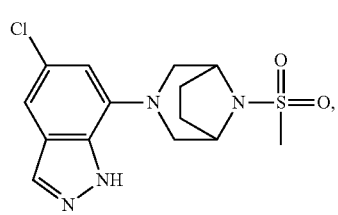
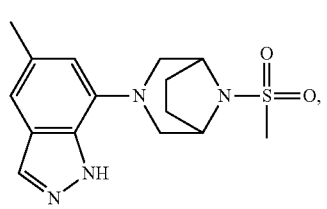
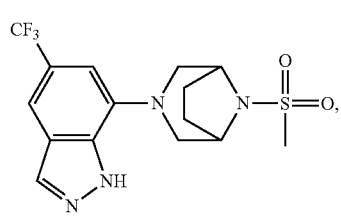
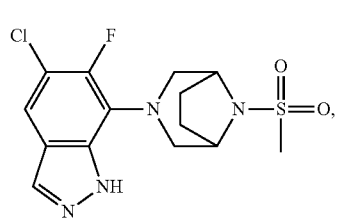
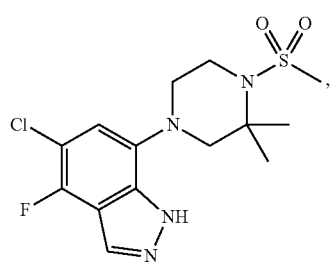
-continued
P-0091 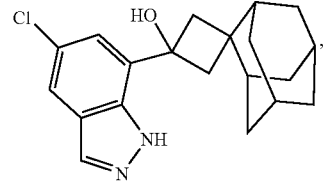 P-0100
P-0092 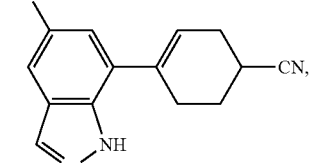 P-0105
P-0093 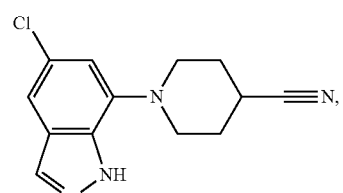 P-0106
P-0094 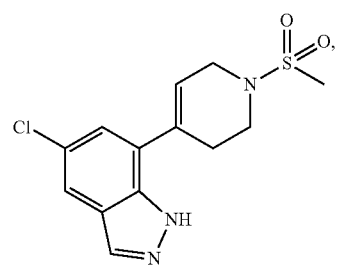 P-0110
P-0095 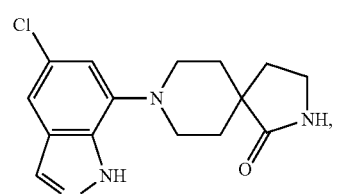 P-0111
P-0096 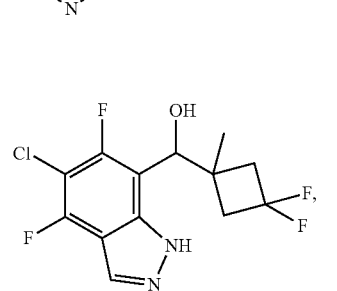 P-0112
P-0097 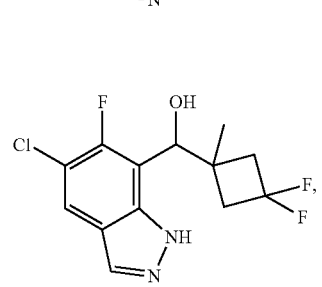 P-0114

P-0115 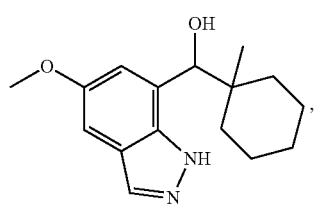
P-0116 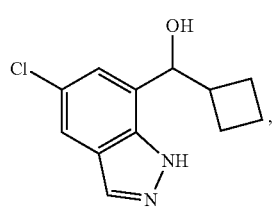
P-0117 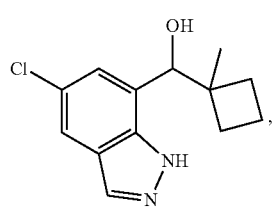
P-0118 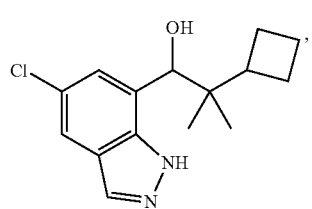
P-0119 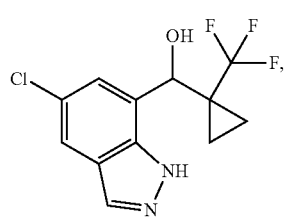
P-0120 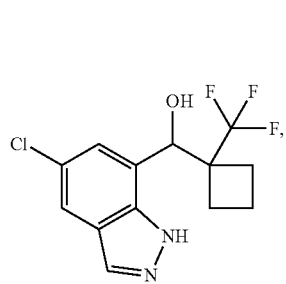
P-0121 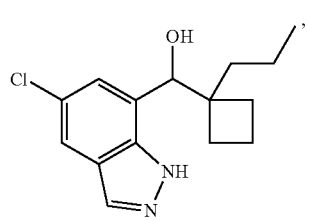
P-0123 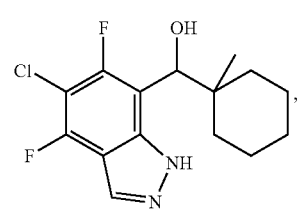
P-0124 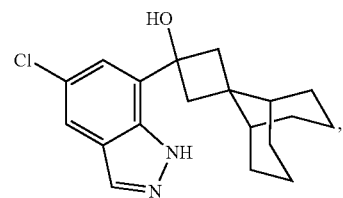
P-0125 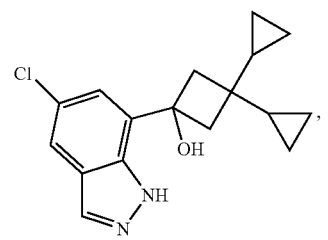
P-0126 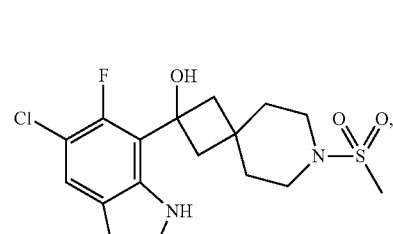
P-0127 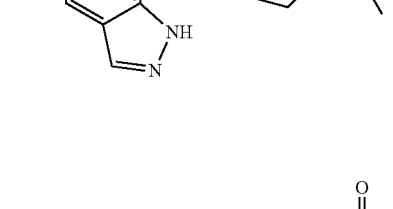
P-0128 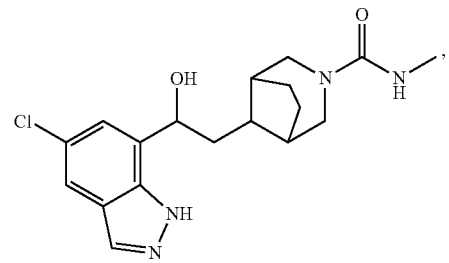
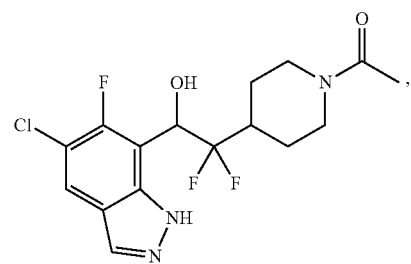

P-0130 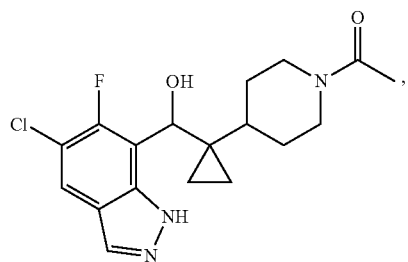
P-0131 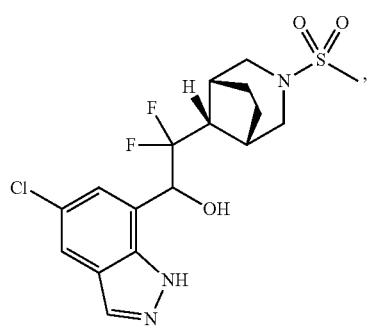
P-0132 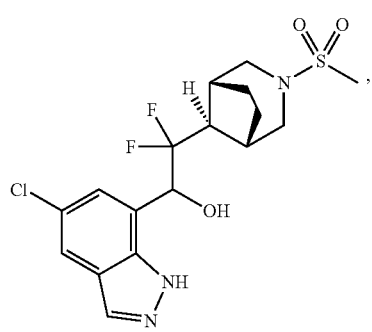
P-0133 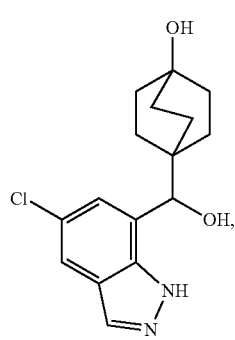
P-0134 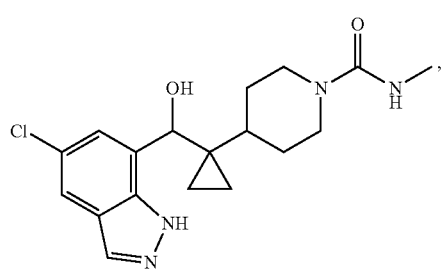
P-0135 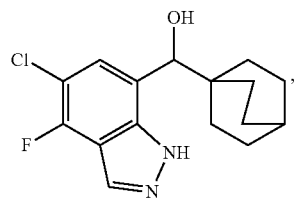
P-0136 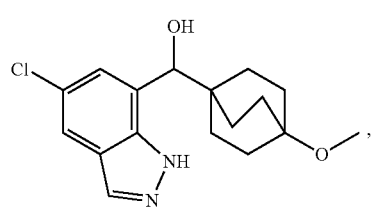
P-0137 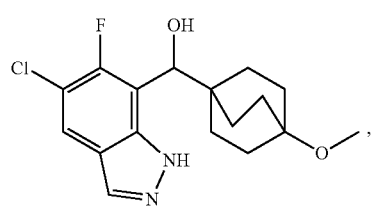
P-0138 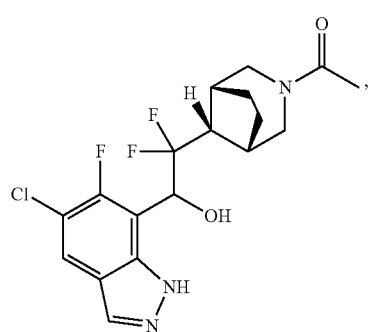
P-0139 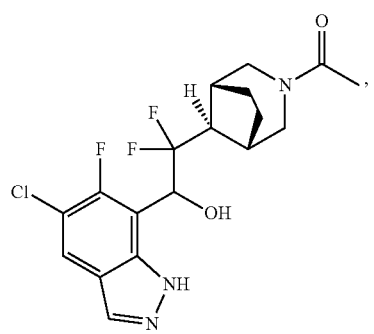
P-0141 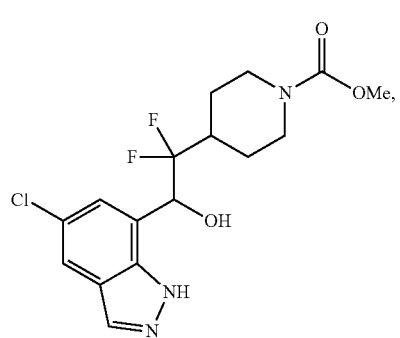

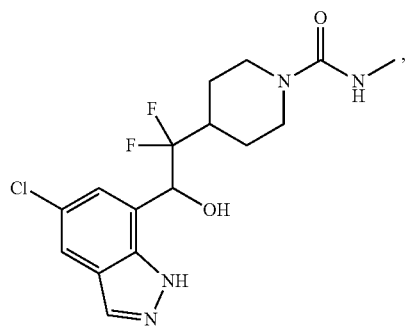
P-0142
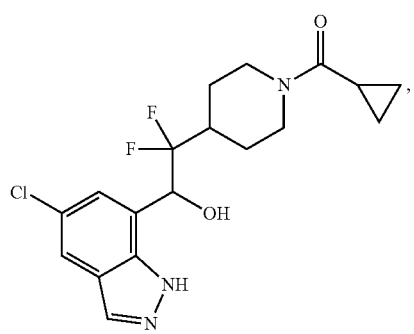
P-0143
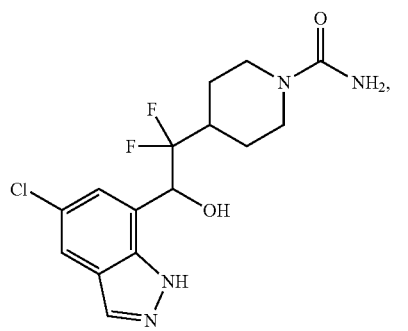
P-0144
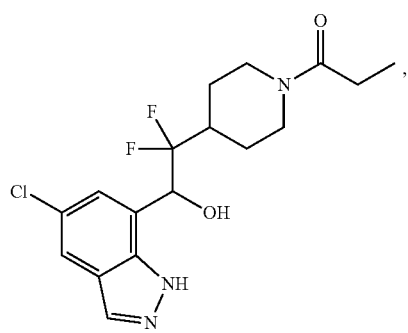
P-0147
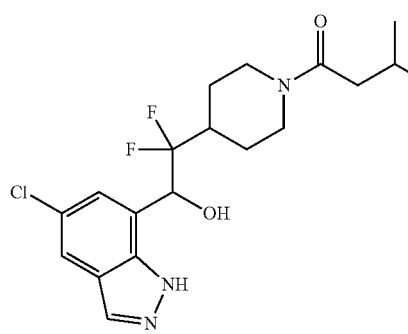
P-0148
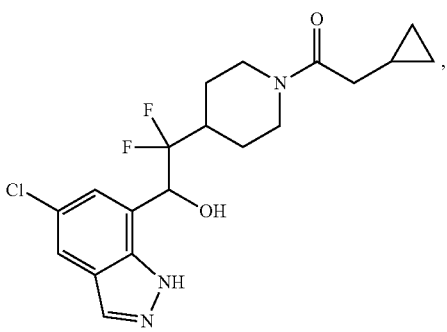
P-0149
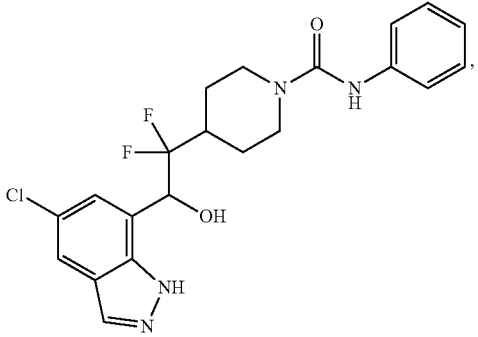
P-0150
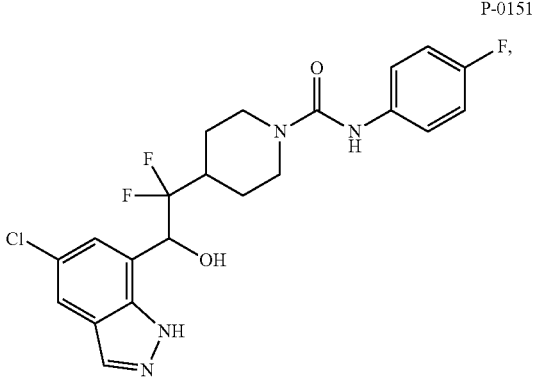
P-0151
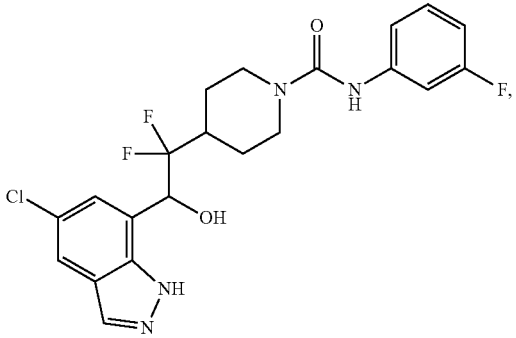
P-0152

P-0153
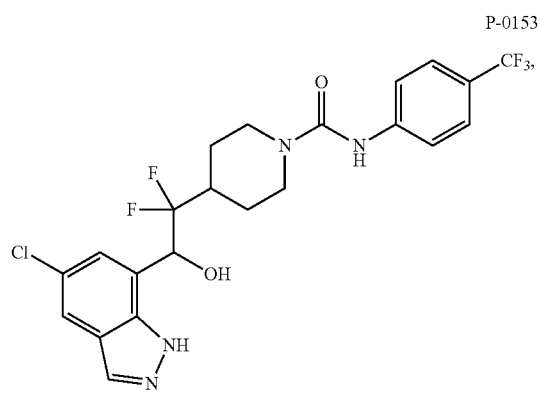
P-0154
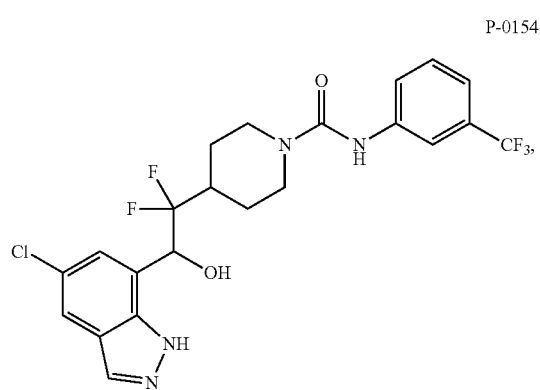
P-0155
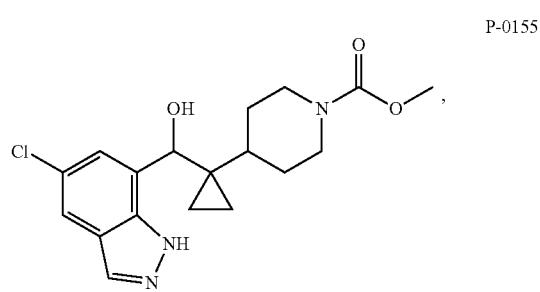
P-0156
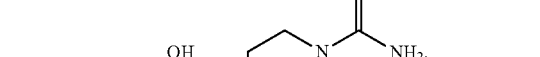
P-0157
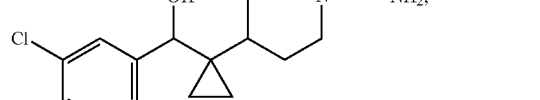
P-0163
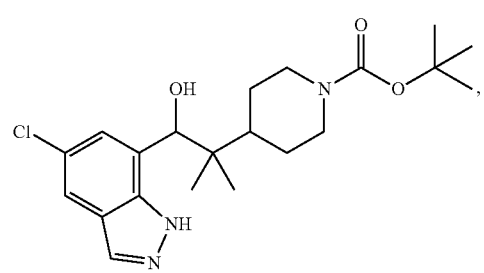
P-0164
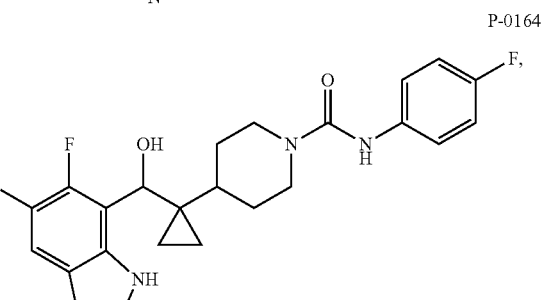
P-0165
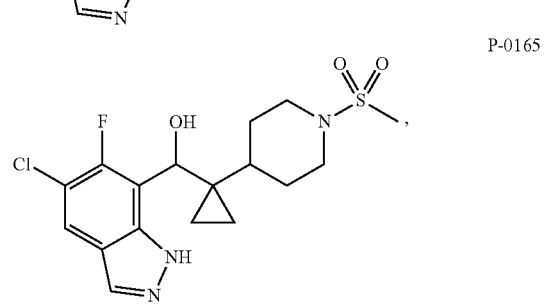
P-0166
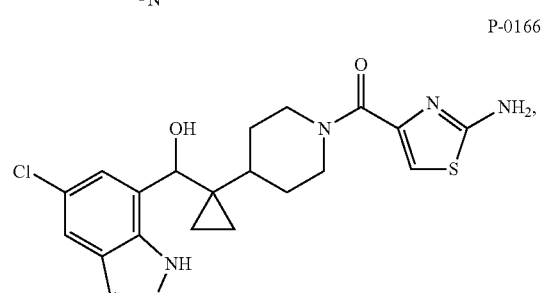
P-0167
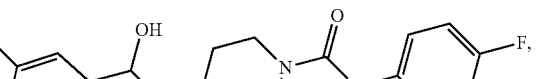
P-0158
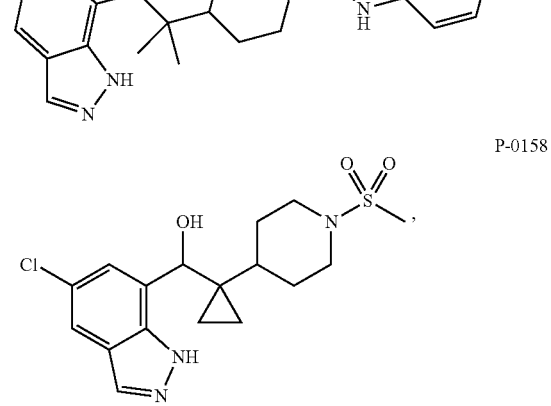

P-0159
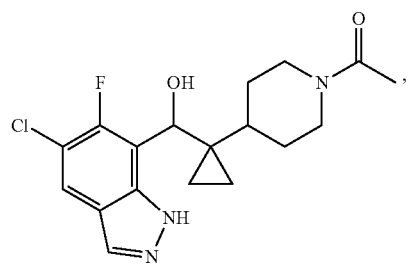
P-0160
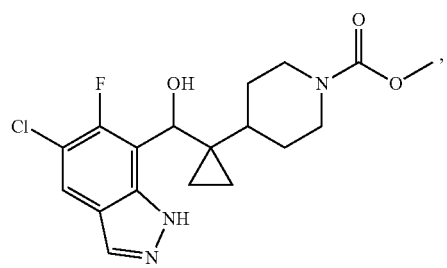
P-0161
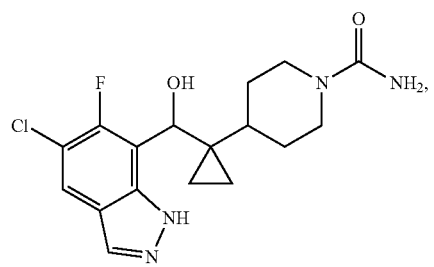
P-0162
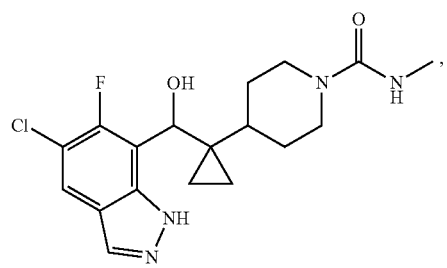
P-0168
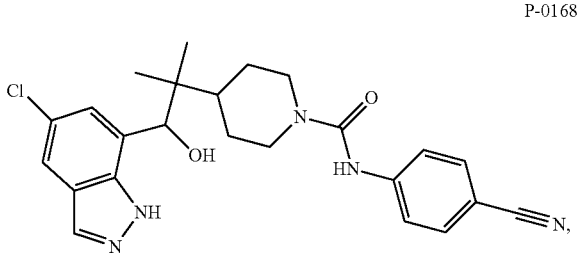
P-0170
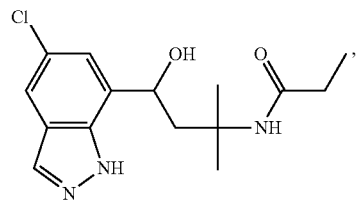
P-0175
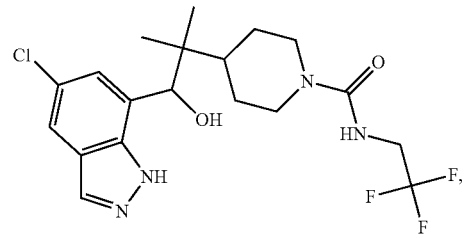
P-0176
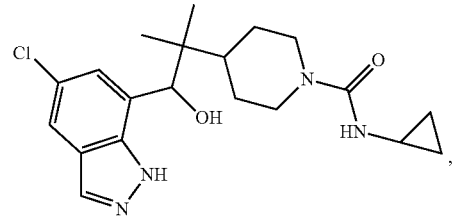
P-0177
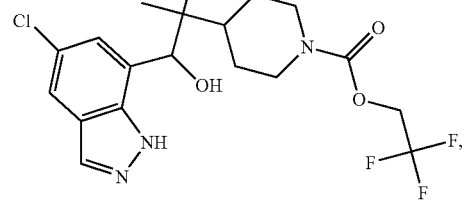
P-0178
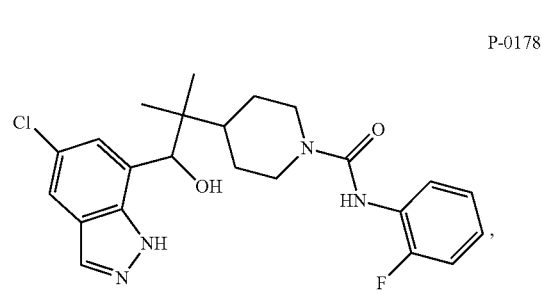
P-0179
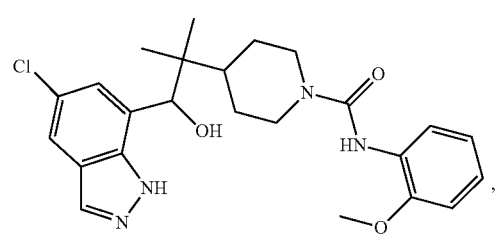
P-0180
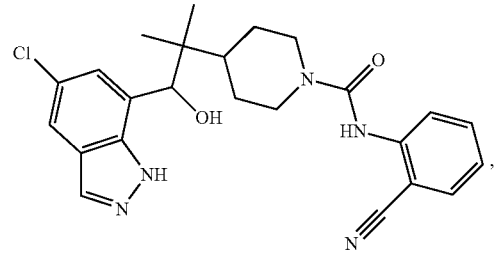

P-0181
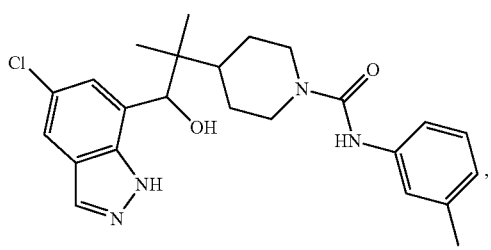
P-0182
P-0183
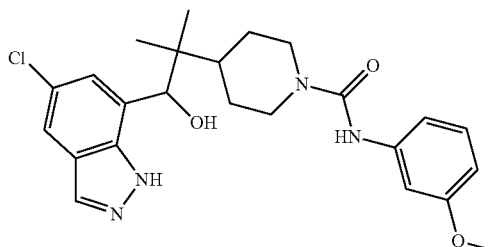
P-0184
P-0185
P-0186
P-0187
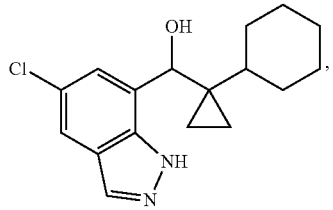
P-0188
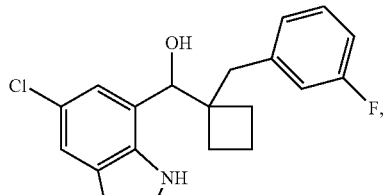
P-0189
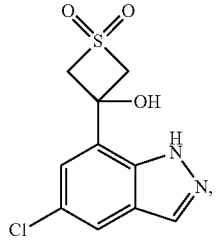
P-0190
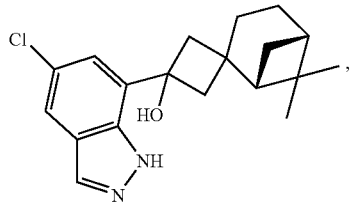
P-0191
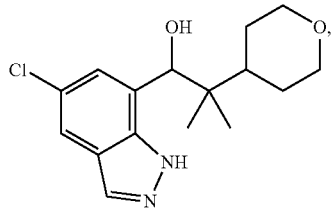
P-0192
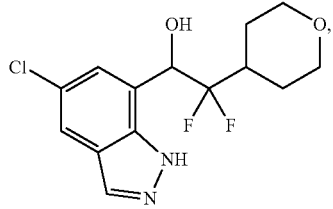
P-0193
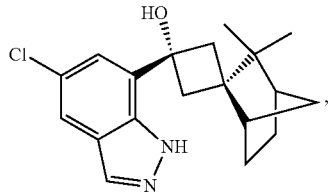

| | |
|---|---|
| P-0194 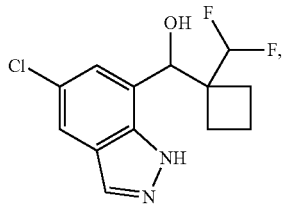 | P-0202 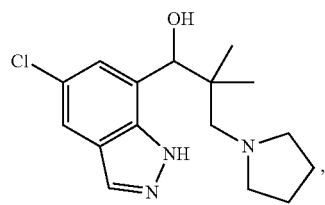 |
| P-0195 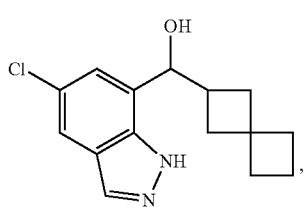 | P-0203 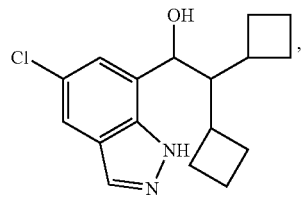 |
| P-0196 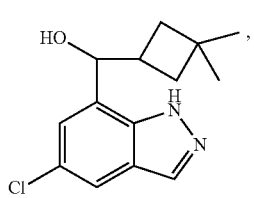 | P-0204 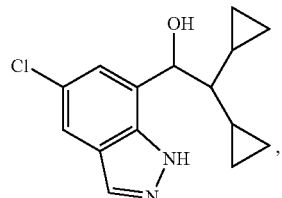 |
| P-0197 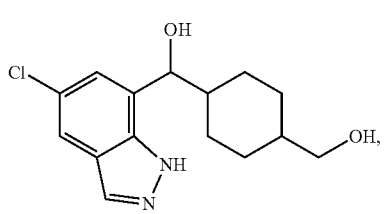 | P-0205 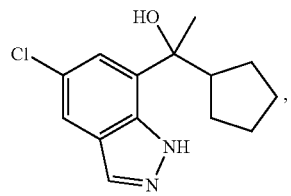 |
| P-0198 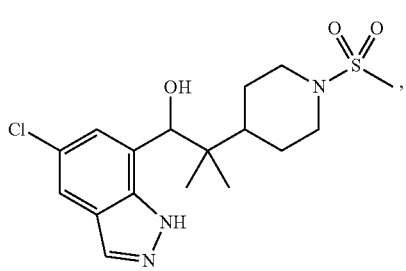 | P-0206 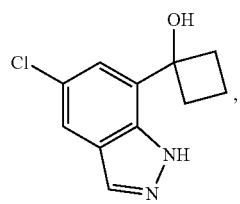 |
| P-0199 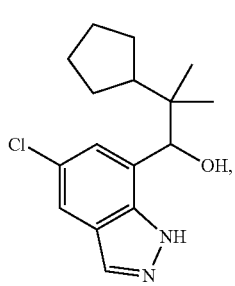 | P-0207 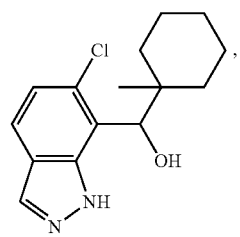 |
| P-0201 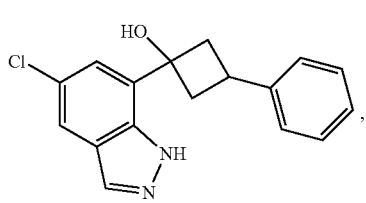 | P-0208 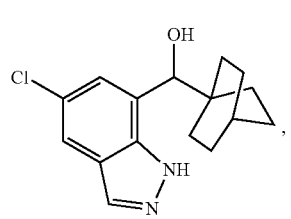 |

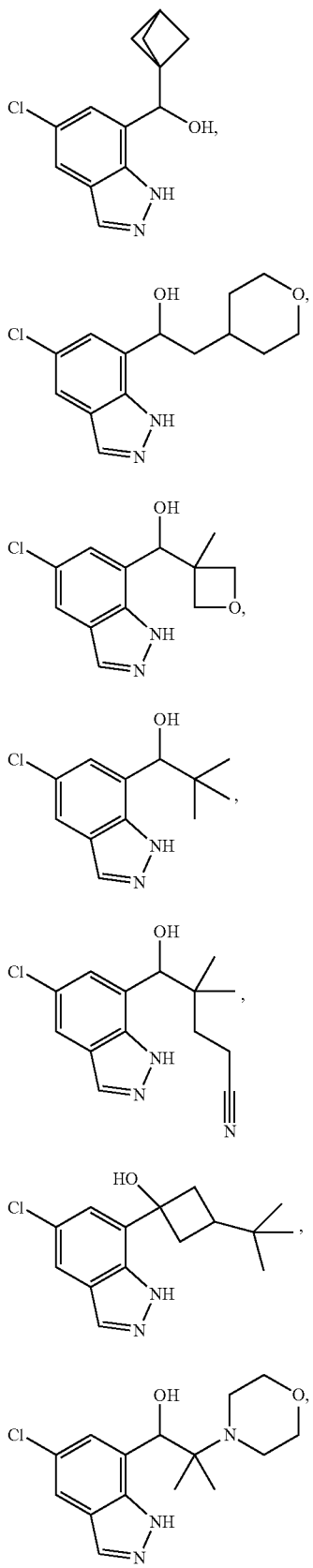
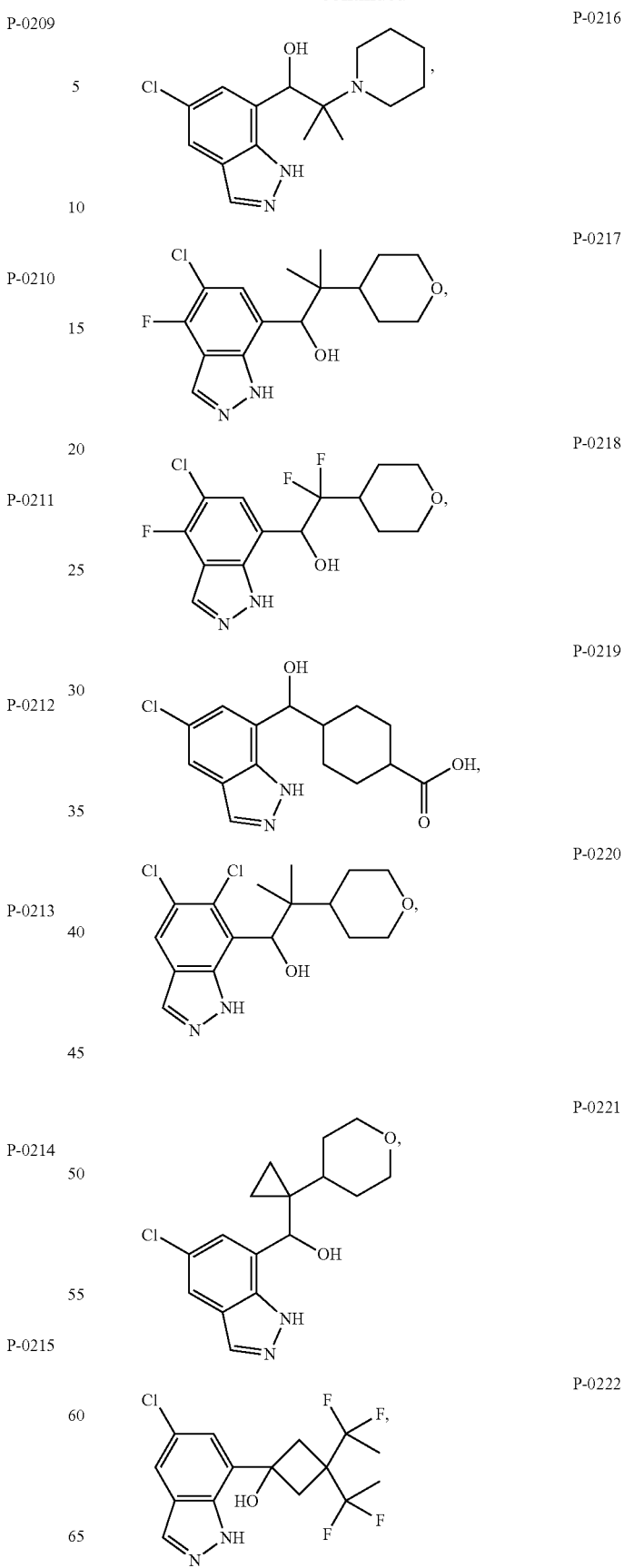

P-0223 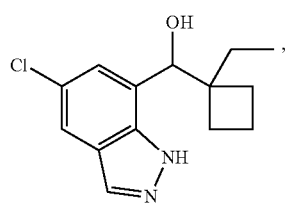
P-0224 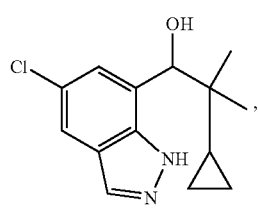
P-0225 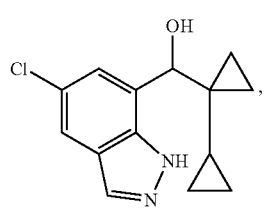
P-0226 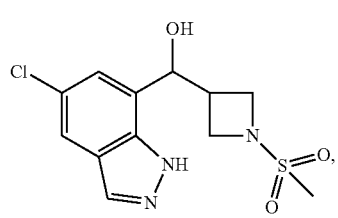
P-0227 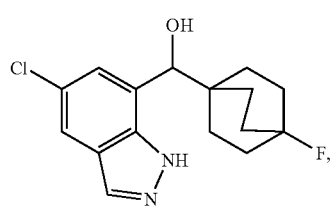
P-0228 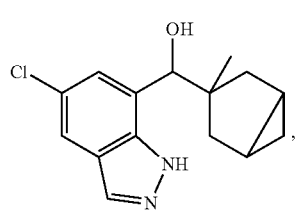
P-0229 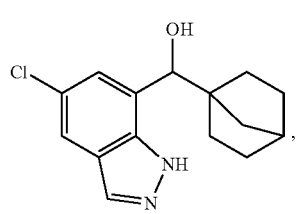
P-0230 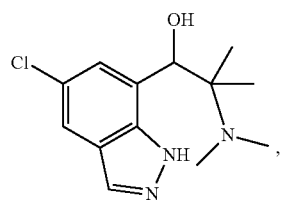
P-0231 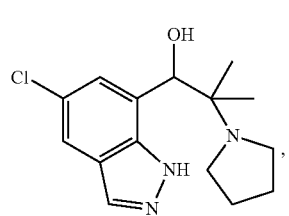
P-0232 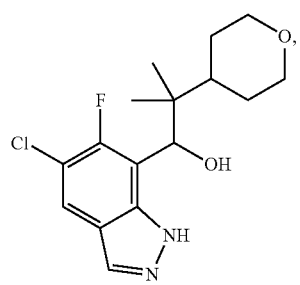
P-0233 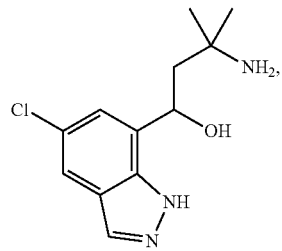
P-0234 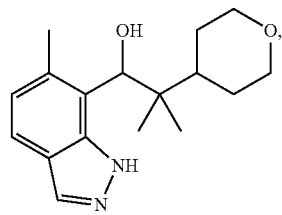
P-0235 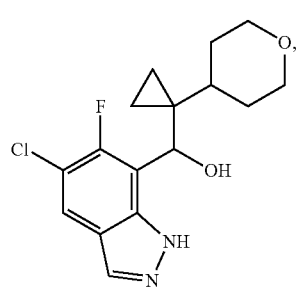

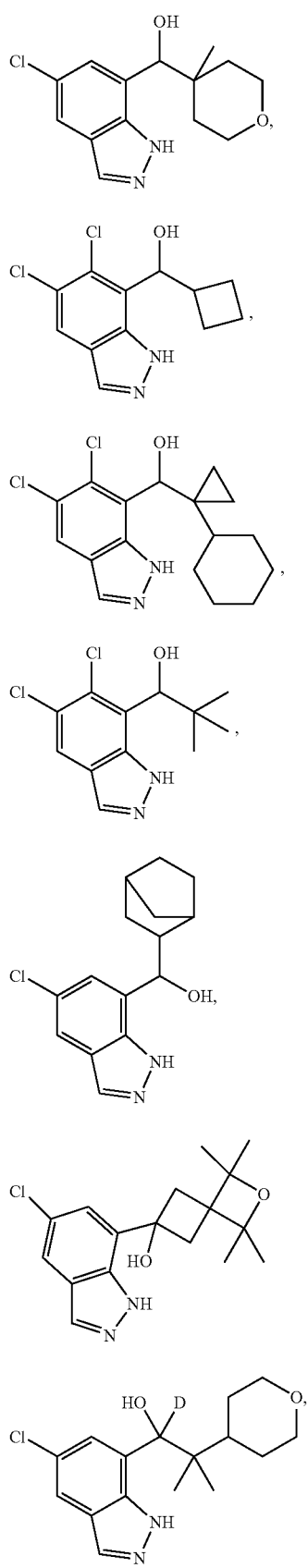
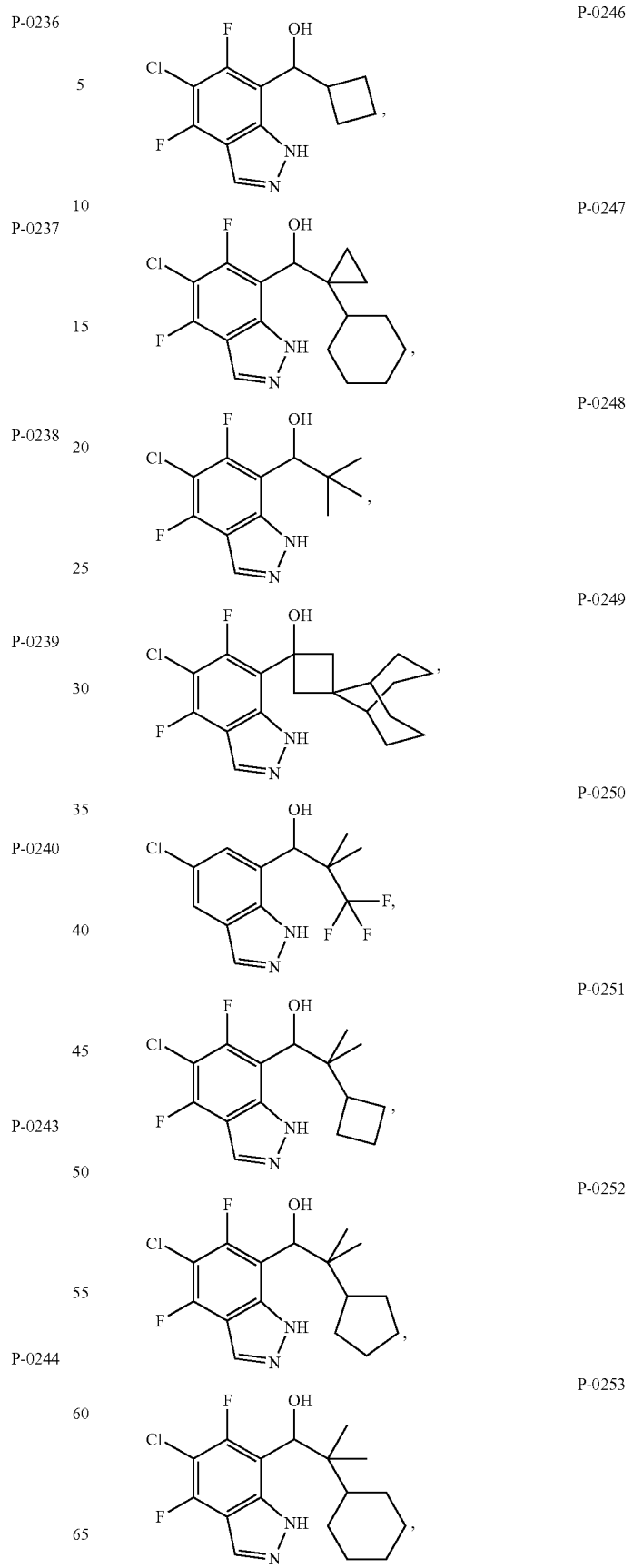

553
-continued
P-0254
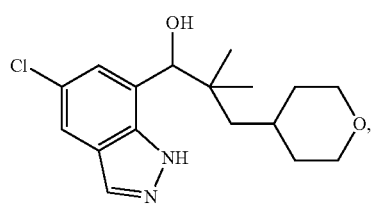
P-0255
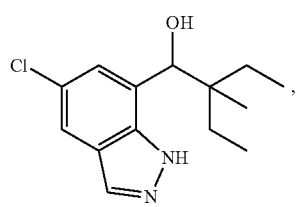
P-0256
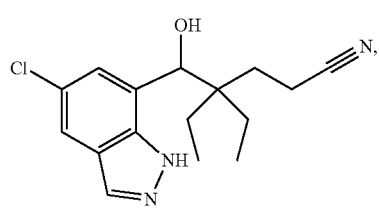
P-0257
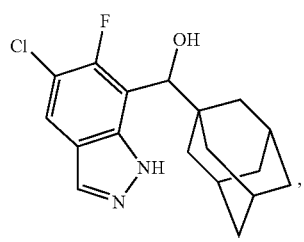
P-0263
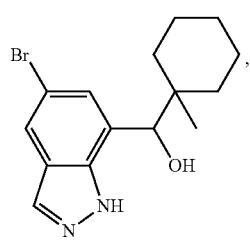
P-0264
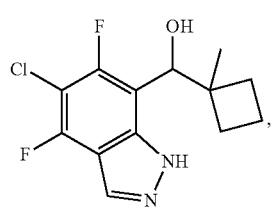
P-0265
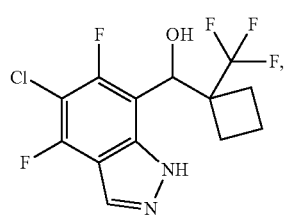
554
-continued
P-0266
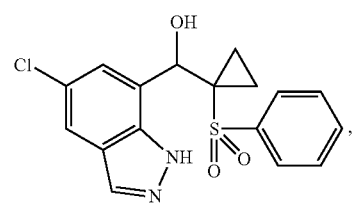
P-0267
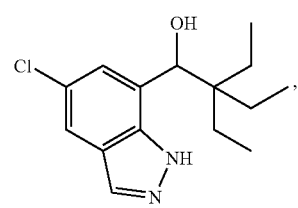
P-0268
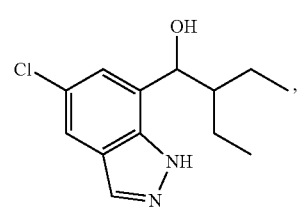
P-0258
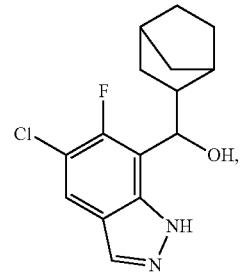
P-0259
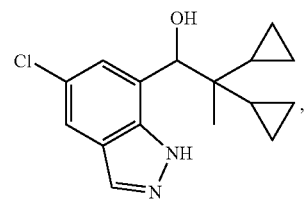
P-0260
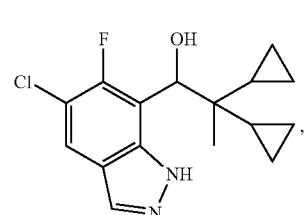
P-0261
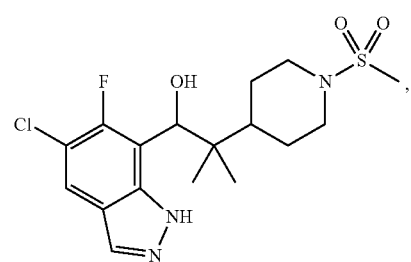

P-0262
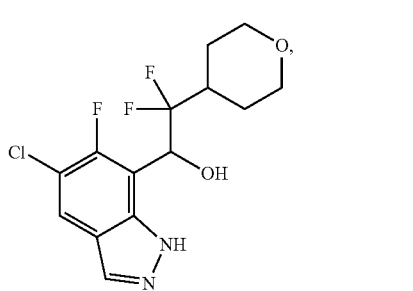
P-0269
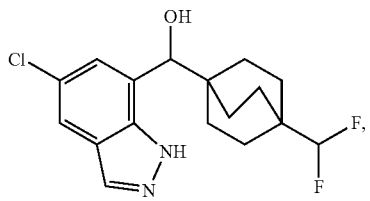
P-0270
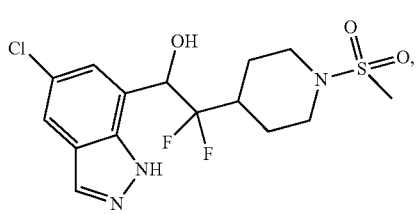
P-0271
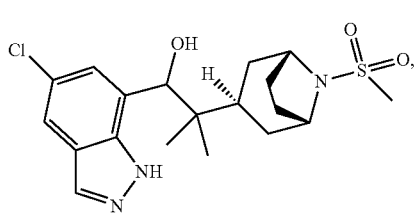
P-0272
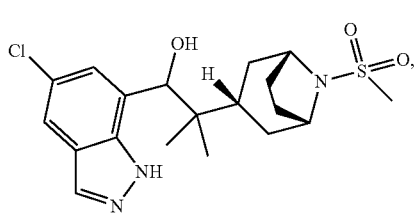
P-0273
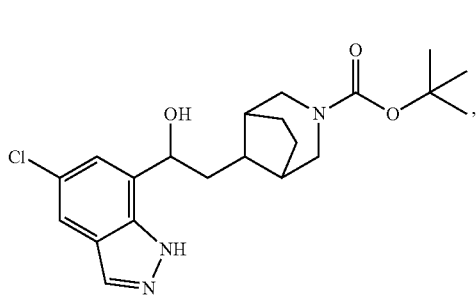
P-0274
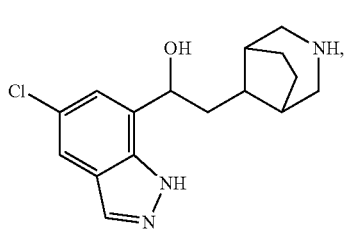
P-0276
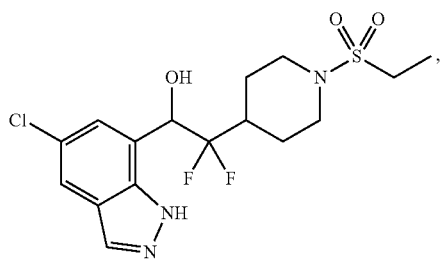
P-0281
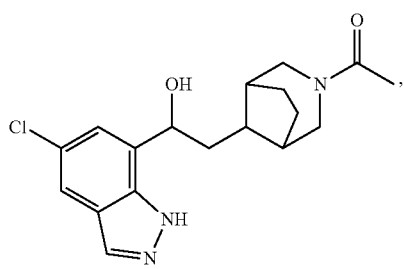
P-0282
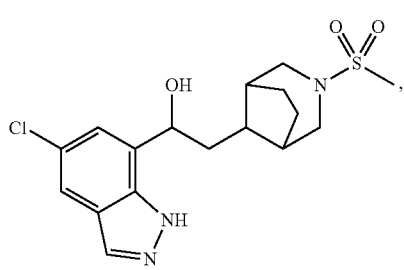
P-0283
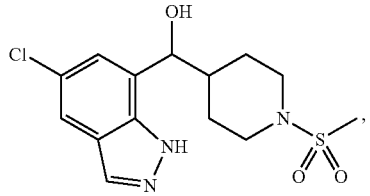
P-0284
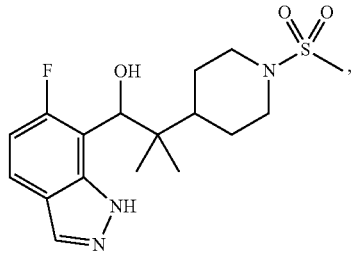
P-0285
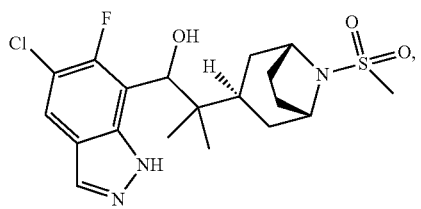

P-0286 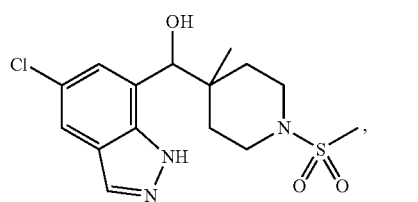
P-0287 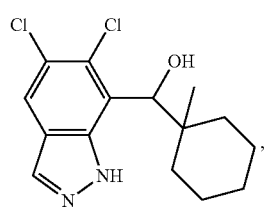
P-0288 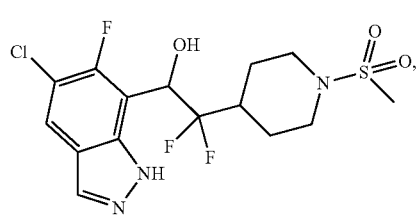
P-0289 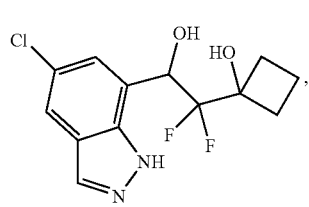
P-0290 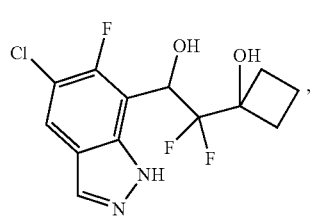
P-0291 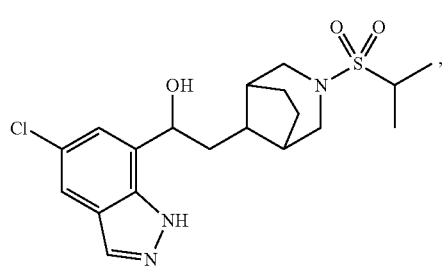
P-0294 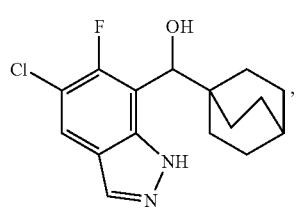
P-0295 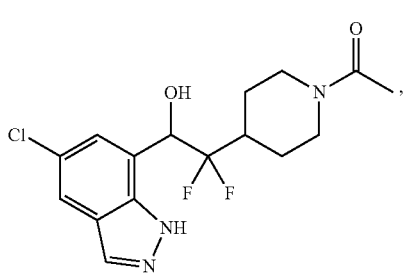
P-0297 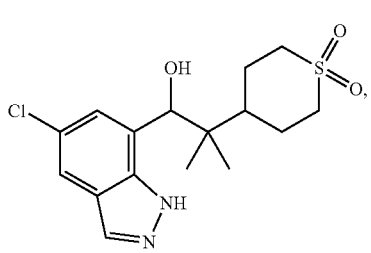
P-0298 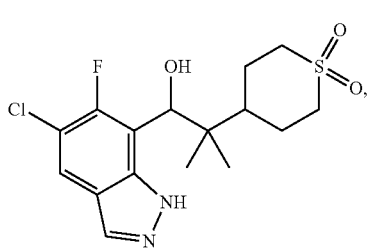
P-0299 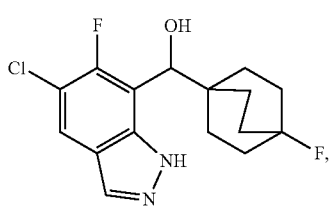
P-0300 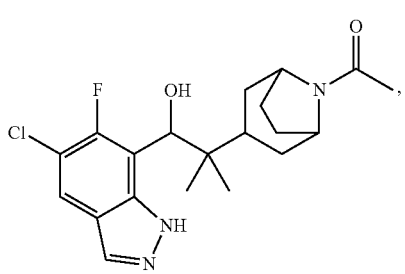
P-0301 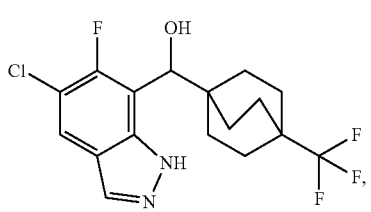

P-0302 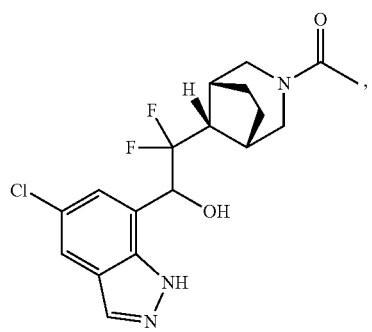
P-0303 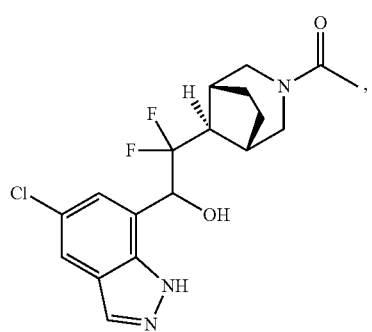
P-0304 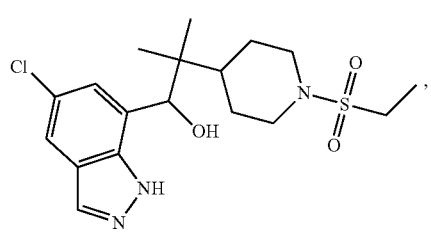
P-0305 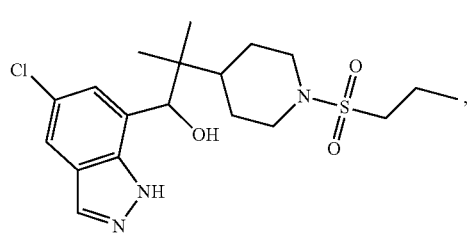
P-0306 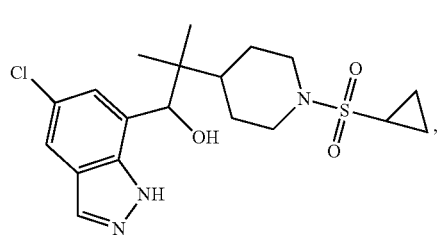
P-0307 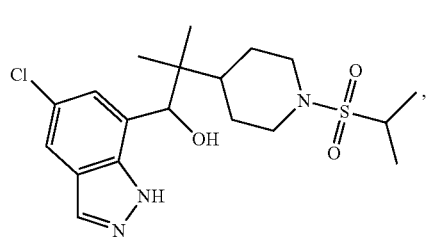
P-0308 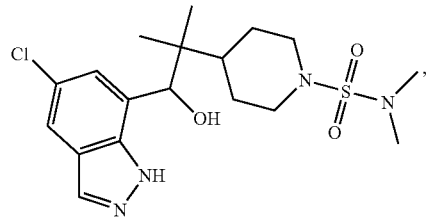
P-0309 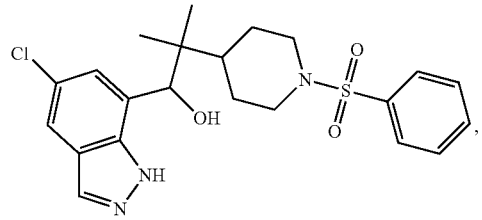
P-0310 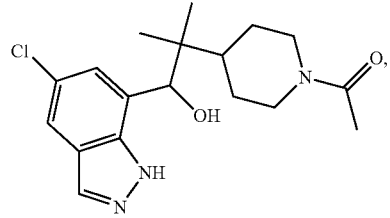
P-0311 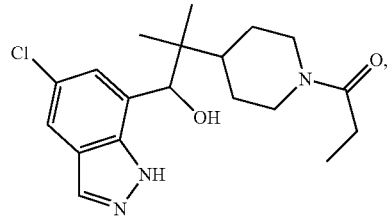
P-0312 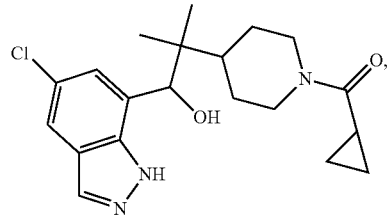
P-0313 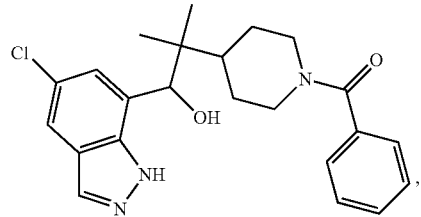
P-0314 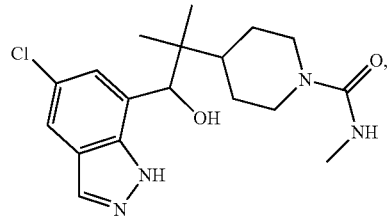

P-0315
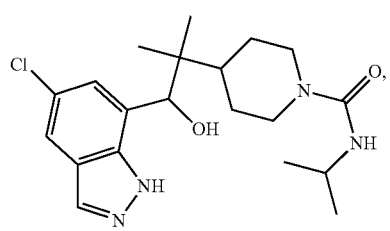
P-0316
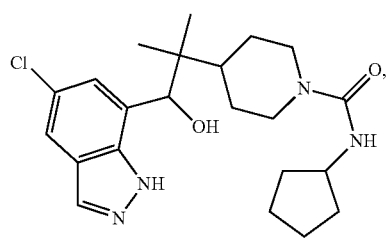
P-0317
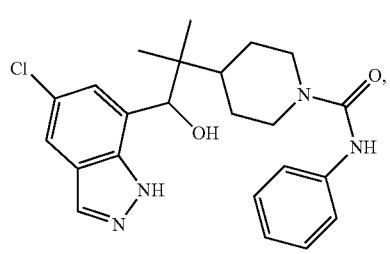
P-0318
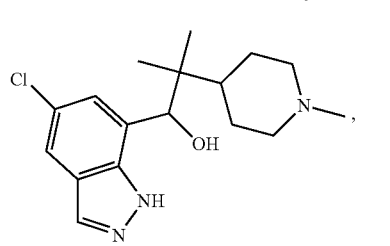
P-0319
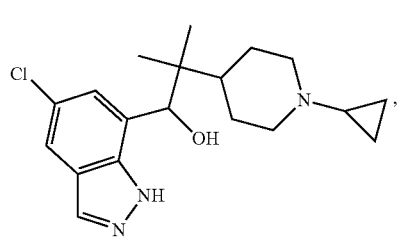
P-0320
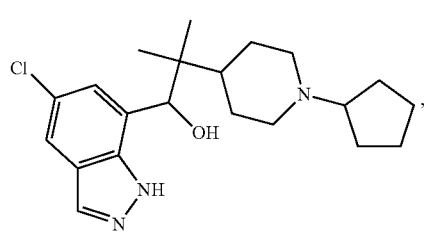
P-0321
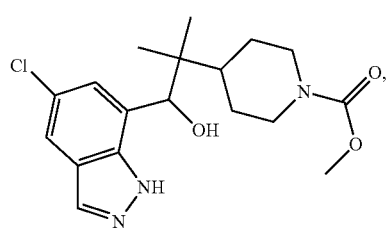
P-0322
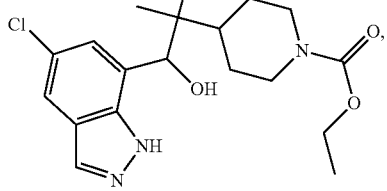
P-0323
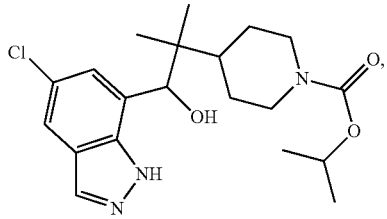
P-0324
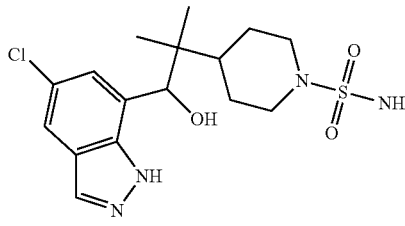
P-0325
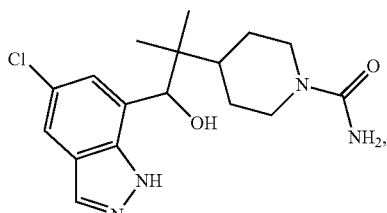
P-0326
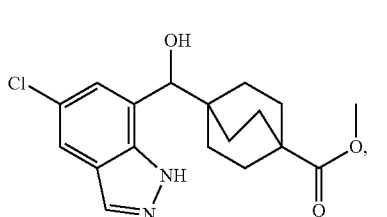
P-0327
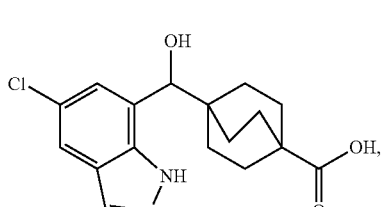
P-0328
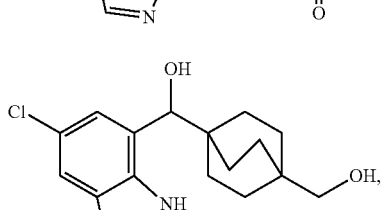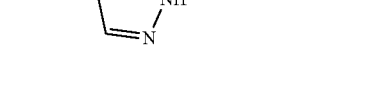

P-0329 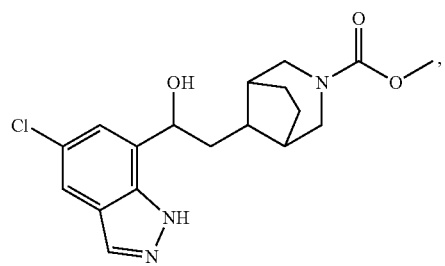
P-0330 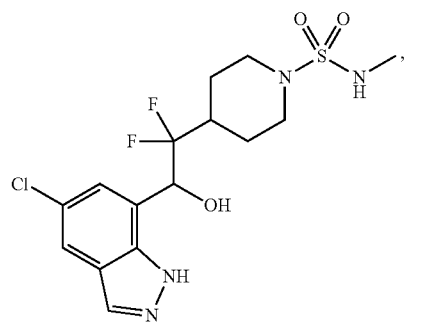
P-0331 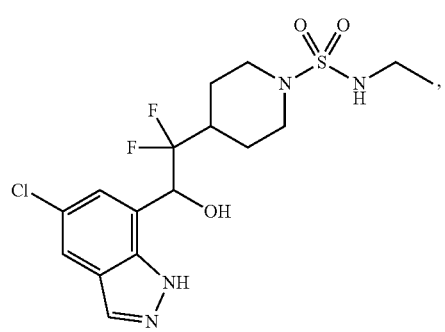
P-0332 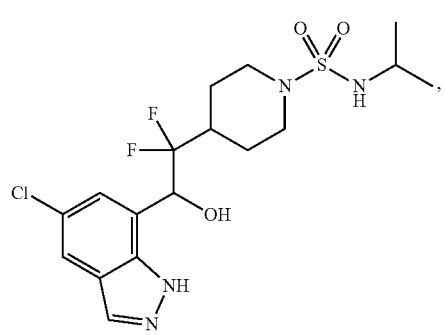
P-0333 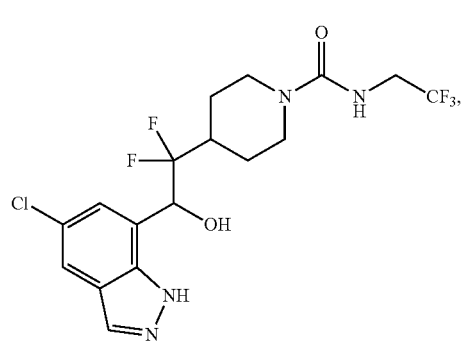
P-0334 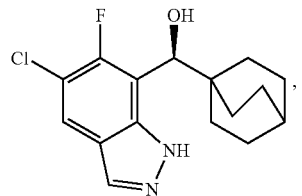
P-0335 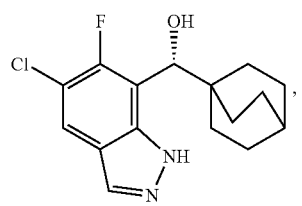
P-0337 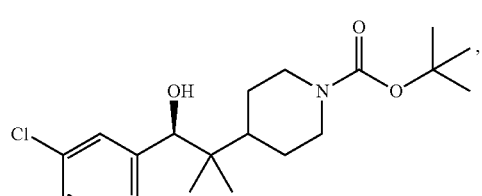
P-0338 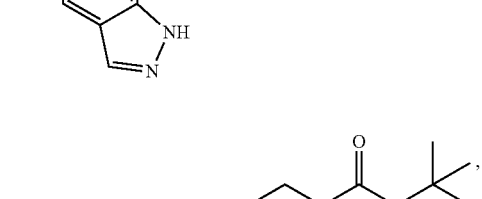
P-0339 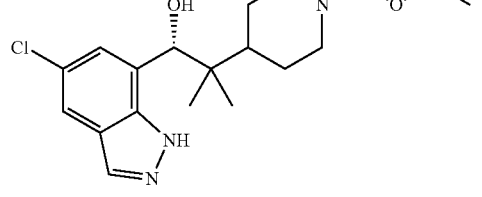
P-0340 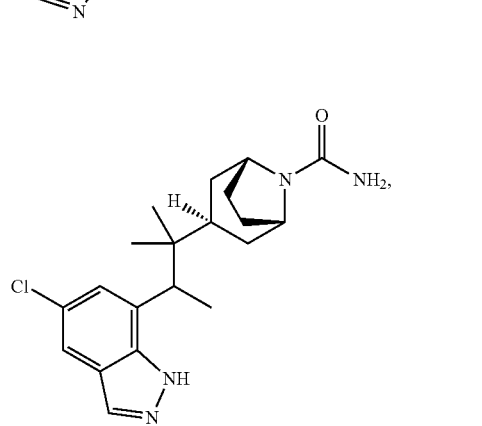

P-0341
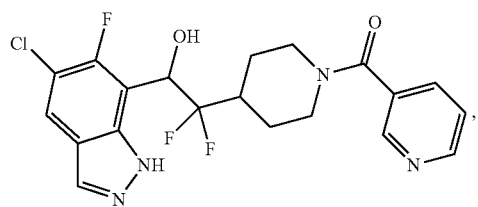
P-0342
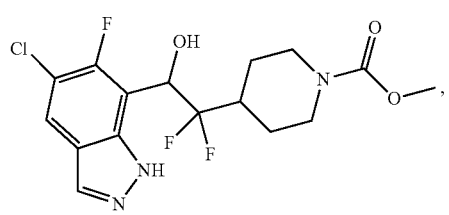
P-0343
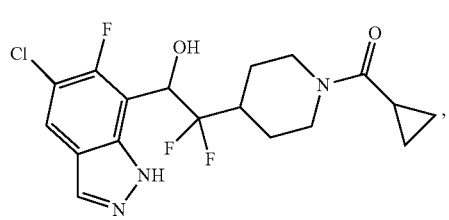
P-0344
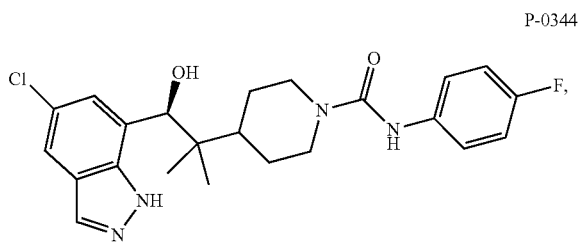
P-0345
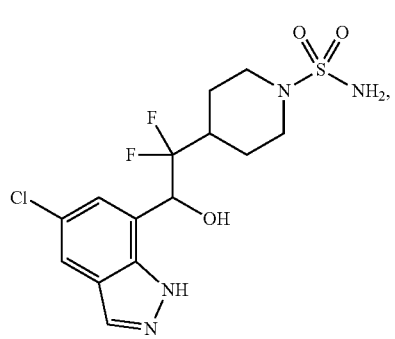
P-0346
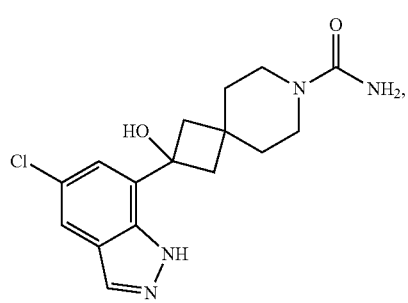
P-0347
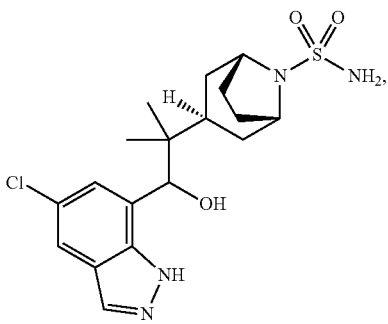
P-0349
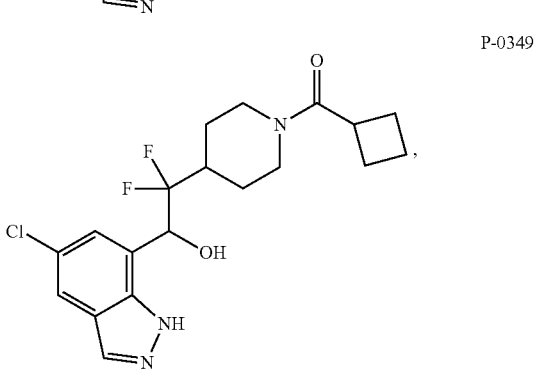
P-0350
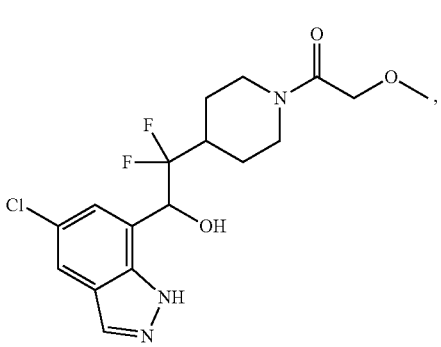
P-0351
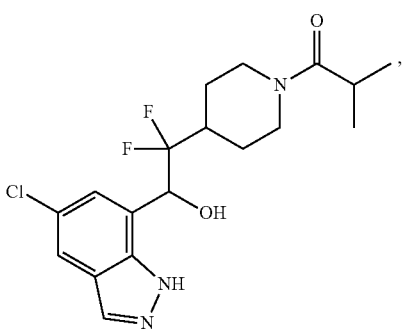
P-0353
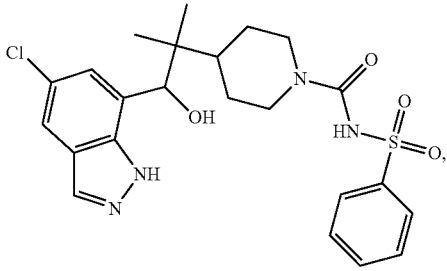

P-0354
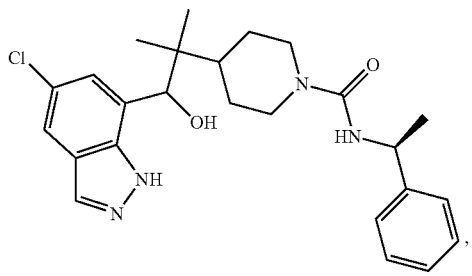
P-0355
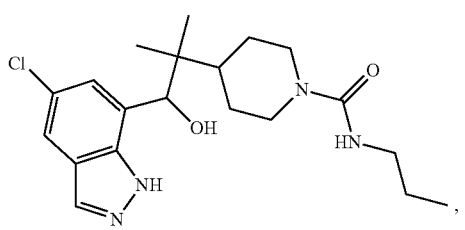
P-0356
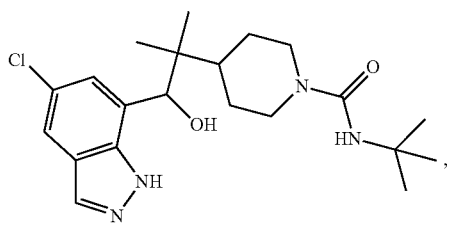
P-0357
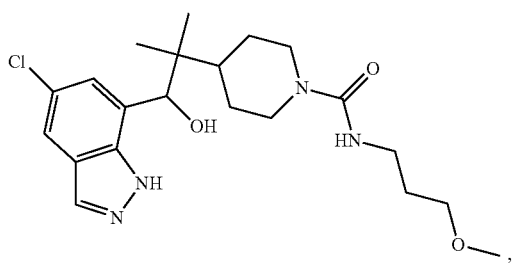
P-0358
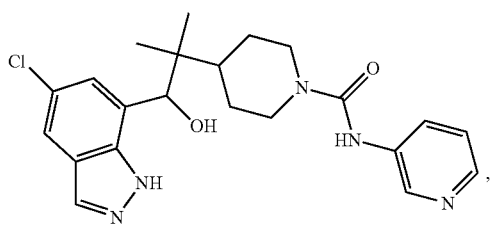
P-0359
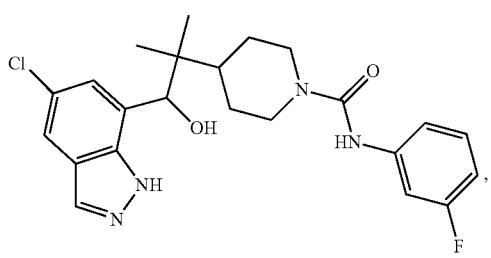
P-0360
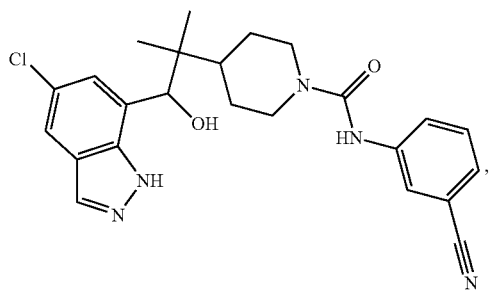
P-0361
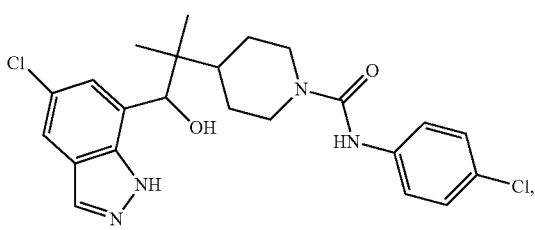
P-0362
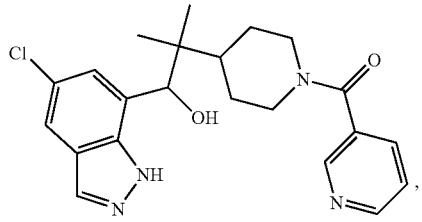
P-0363
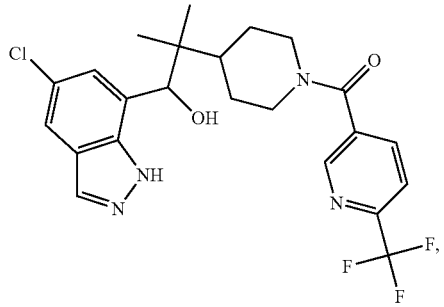
P-0364
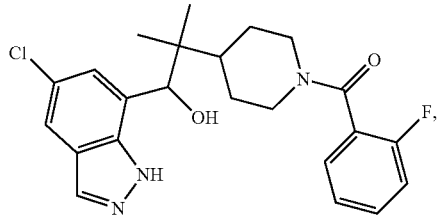
P-0365
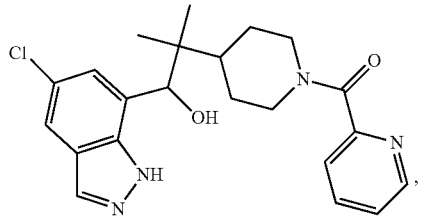

P-0366
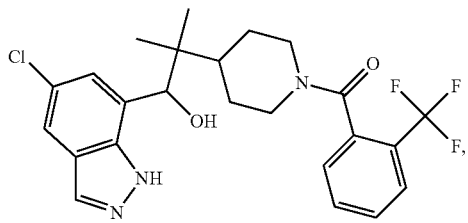
P-0367
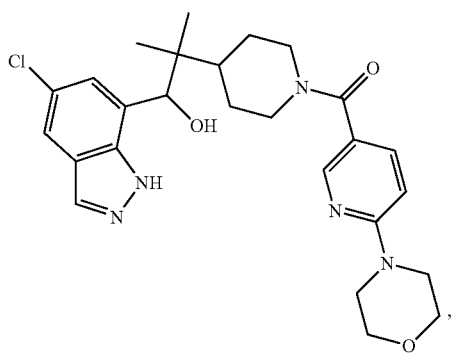
P-0368
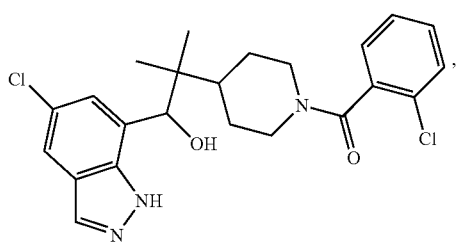
P-0369
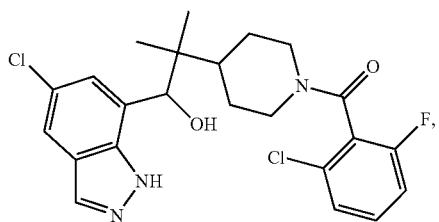
P-0370
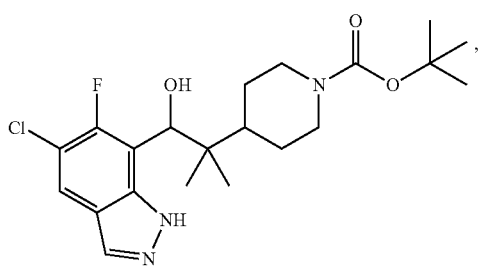
P-0373
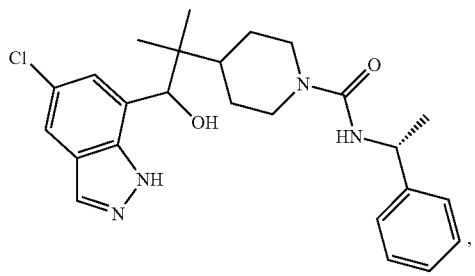
P-0374
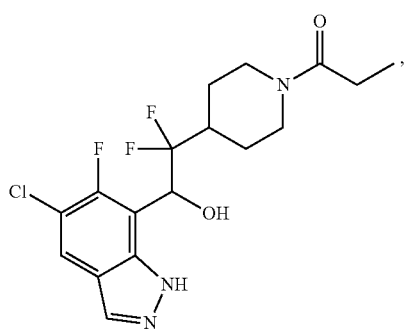
P-0375
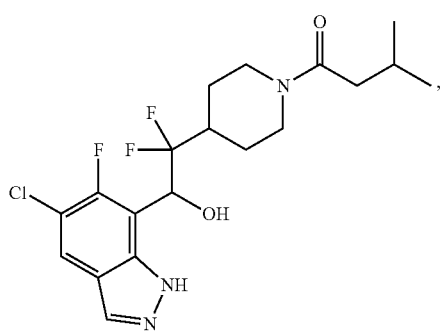
P-0376
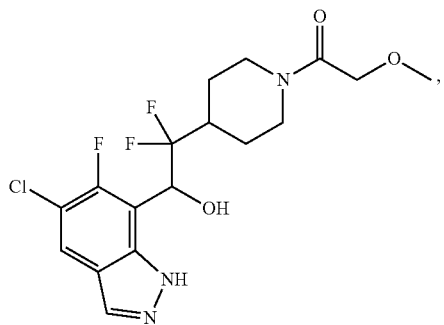
P-0377
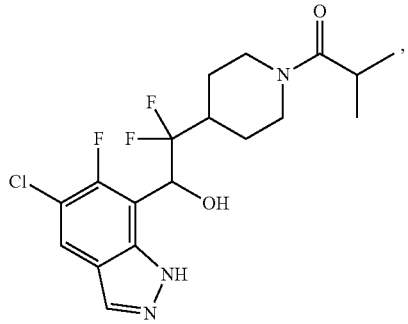

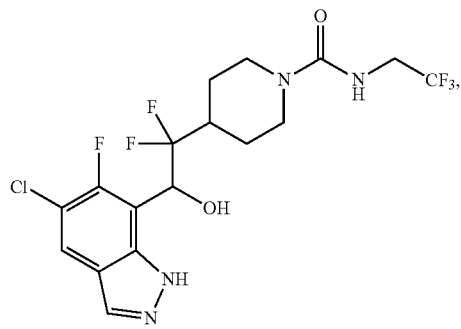 P-0378
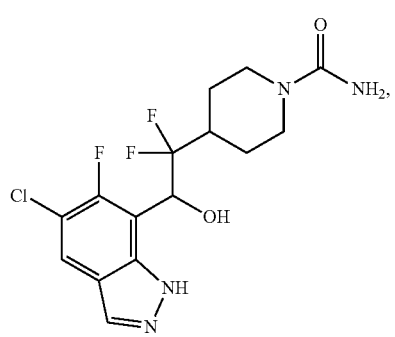 P-0379
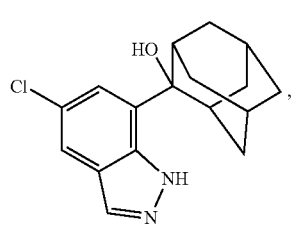 P-0380
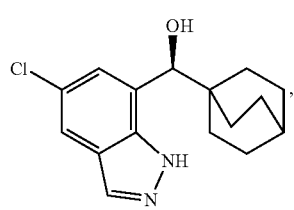 P-0381
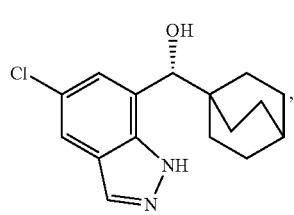 P-0382
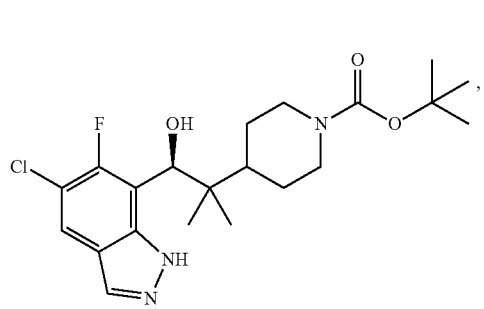 P-0383
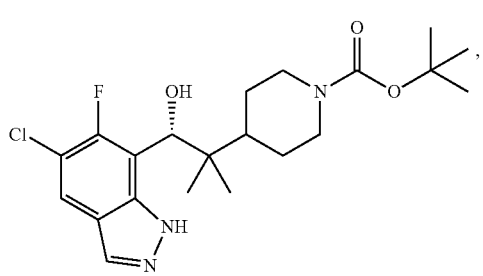 P-0384
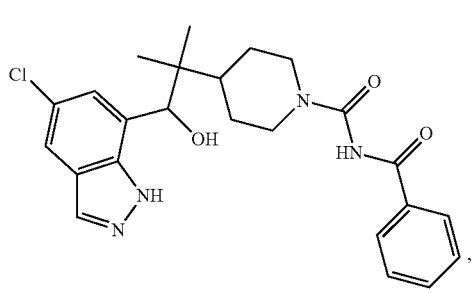 P-0385
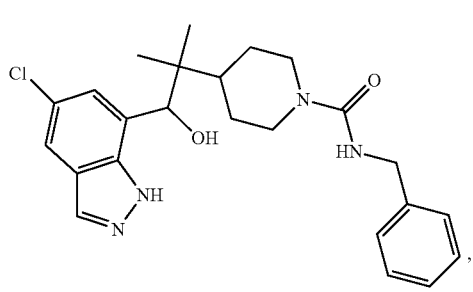 P-0386
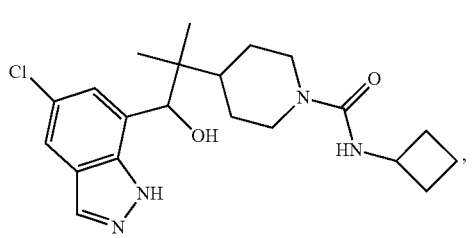 P-0387
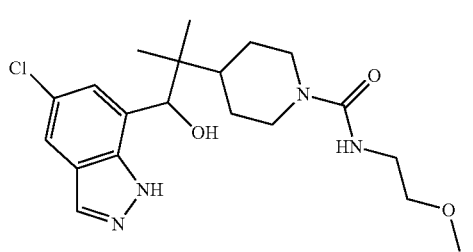 P-0388

P-0389
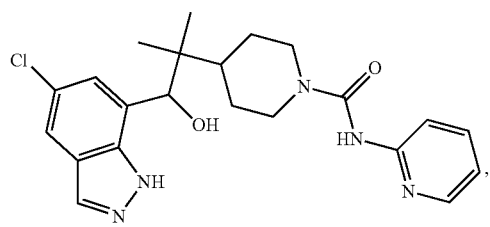
P-0390
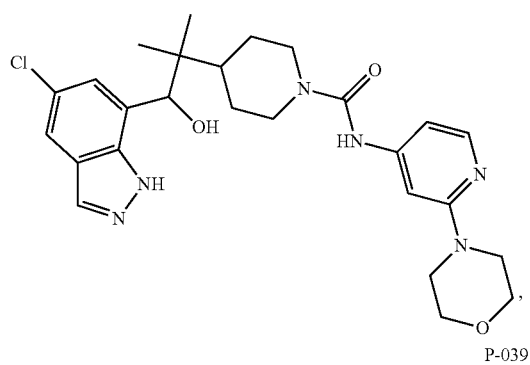
P-0391
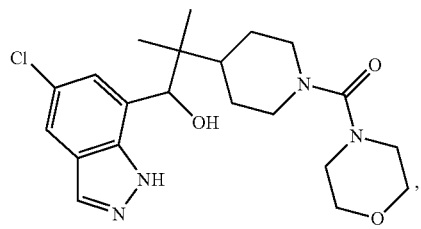
P-0392
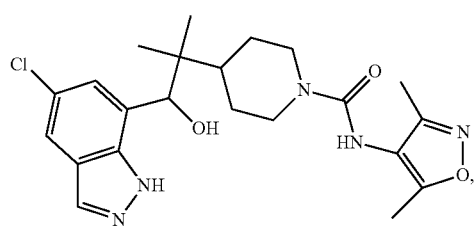
P-0393
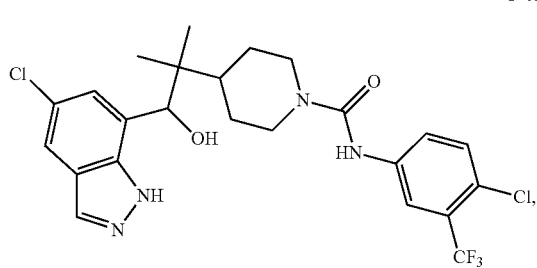
P-0394
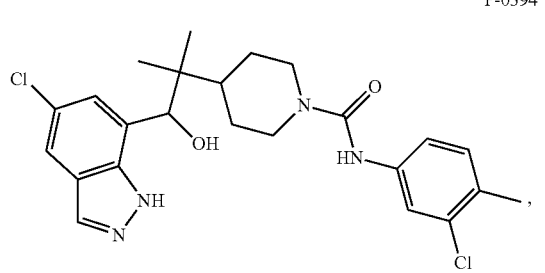
P-0395
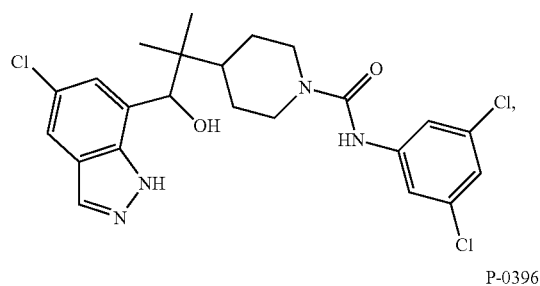
P-0396
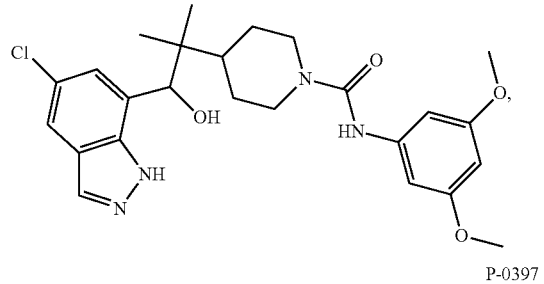
P-0397
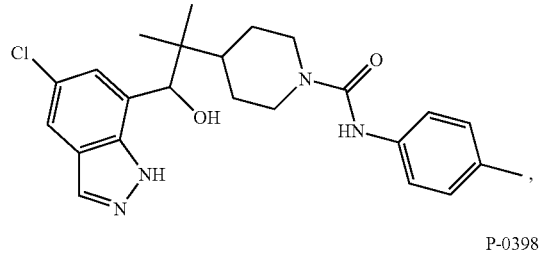
P-0398
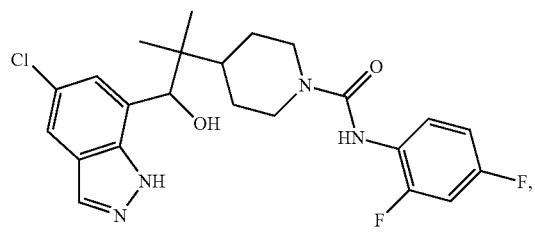
P-0399
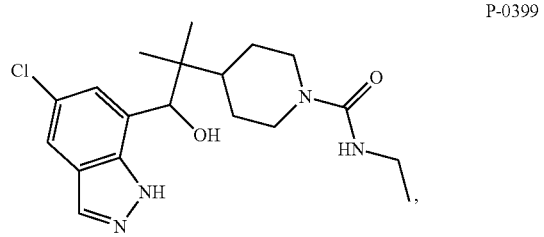
P-0400
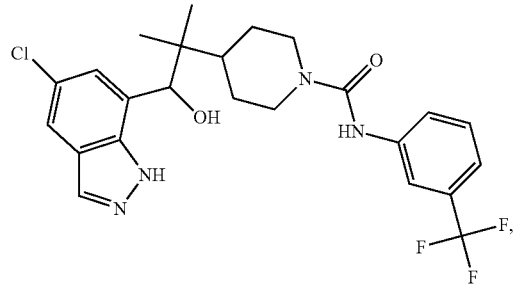

| | |
|---|---|
| P-0401 | P-0407 |
| P-0402 | P-0408 |
| P-0403 | P-0409 |
| P-0404 | P-0410 |
| P-0405 | |
| P-0406 | P-0411 |

P-0412
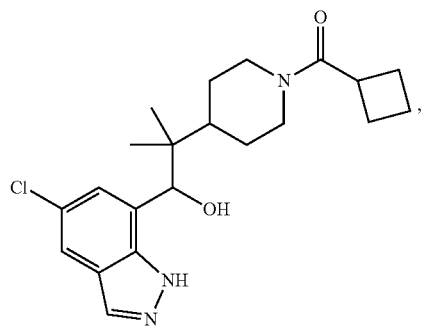
P-0413
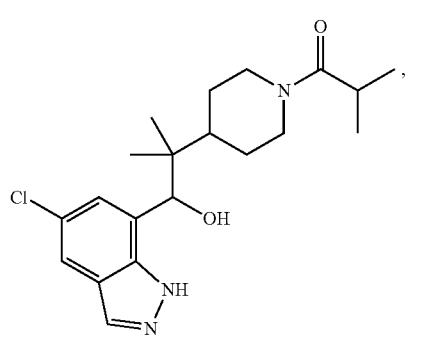
P-0414
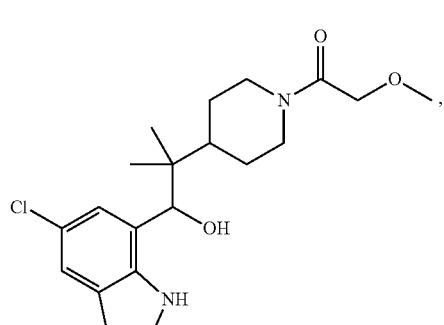
P-0415
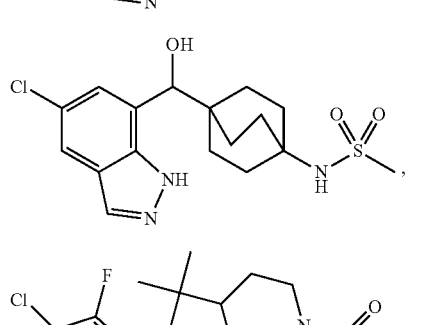
P-0416
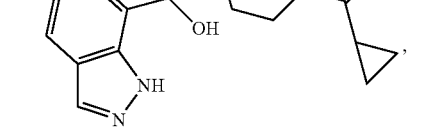
P-0417
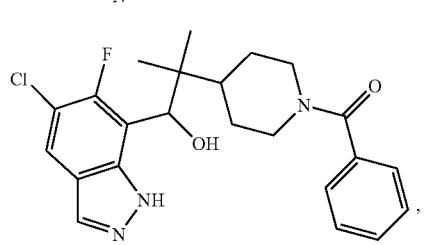
P-0418
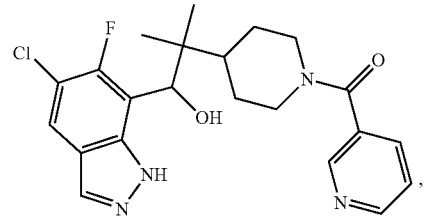
P-0419
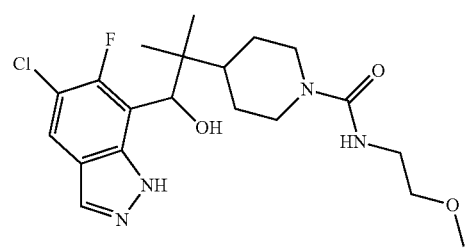
P-0420
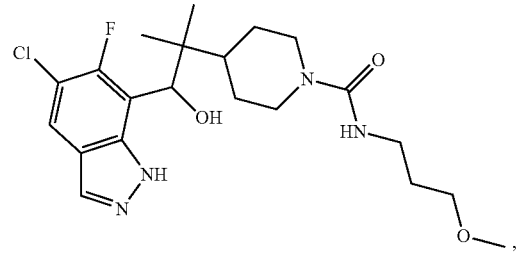
P-0421
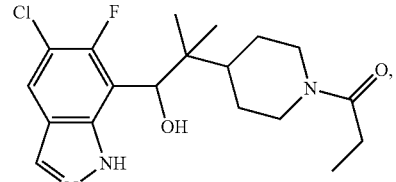
P-0422
P-0423
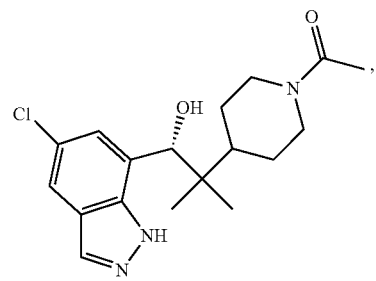

P-0424, P-0425, P-0426, P-0427, P-0428, P-0429, P-0430, P-0431, P-0432

P-0433
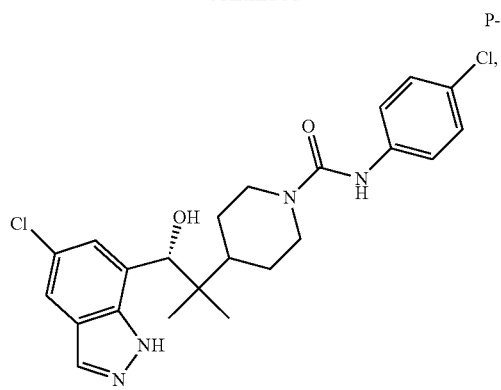
P-0434
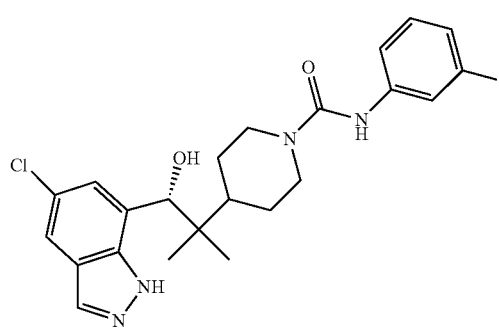
P-0435
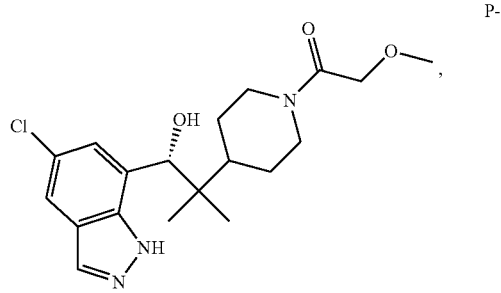
P-0436
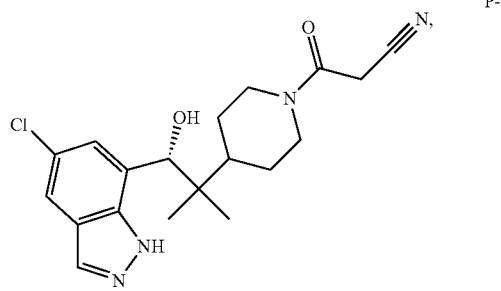
P-0437
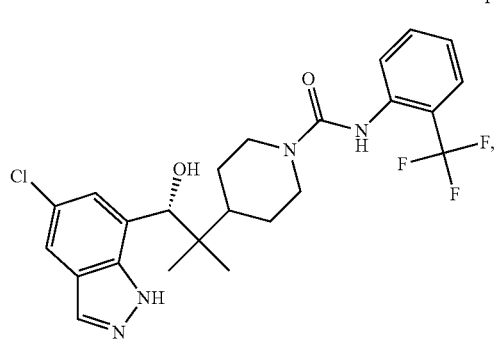
P-0438
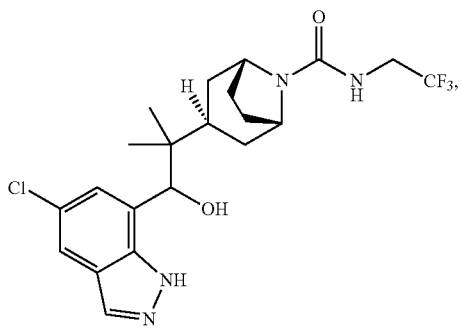
P-0439
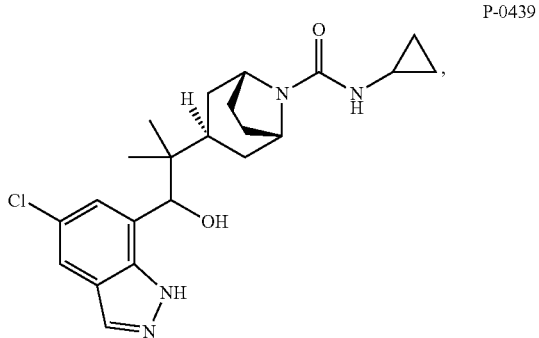
P-0440
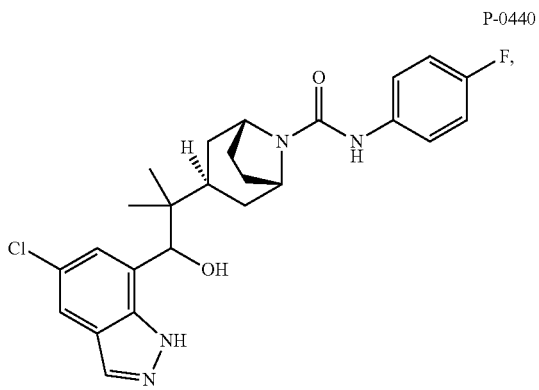
P-0441
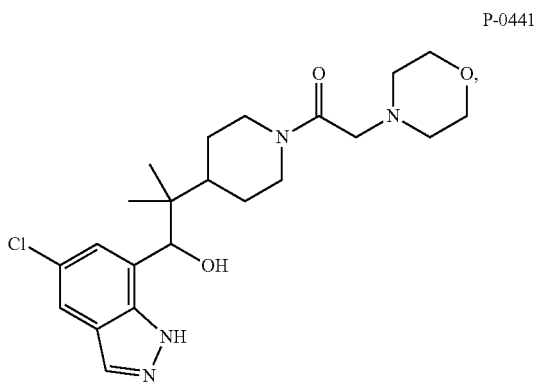

P-0442
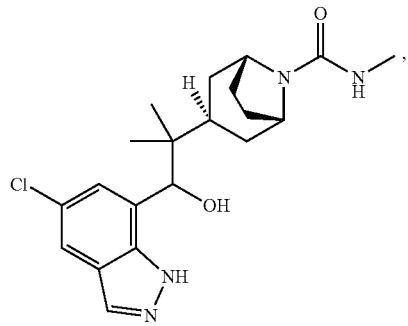
P-0443
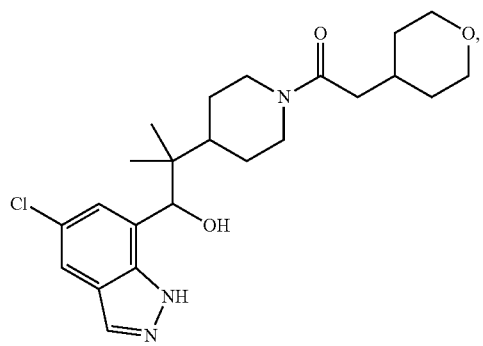
P-0444
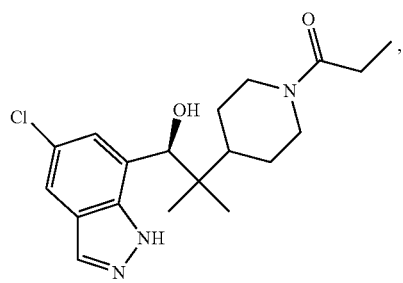
P-0445
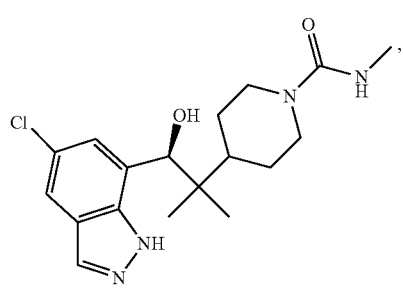
P-0446
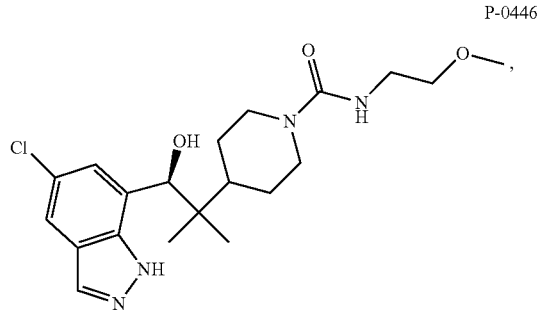
P-0447
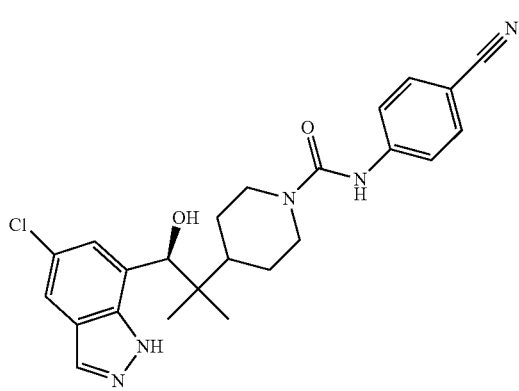
P-0448
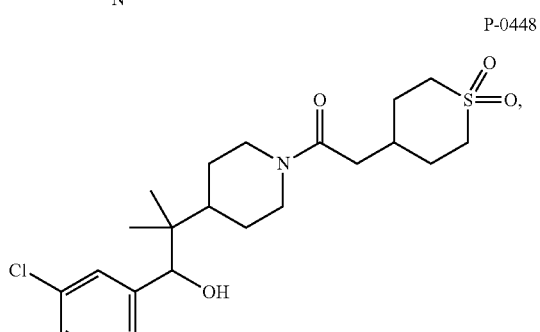
P-0449
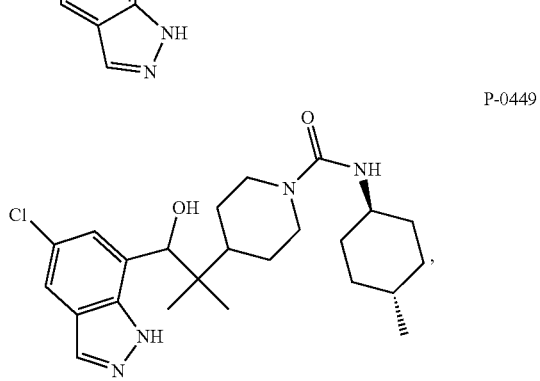
P-0450
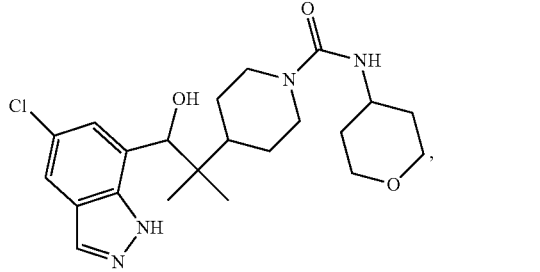
P-0451
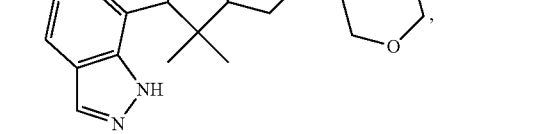

P-0452
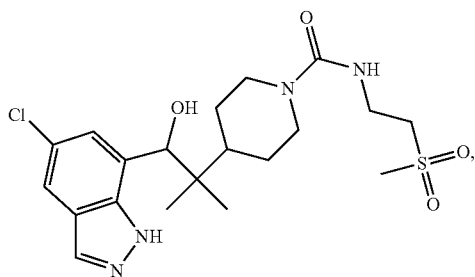
P-0453
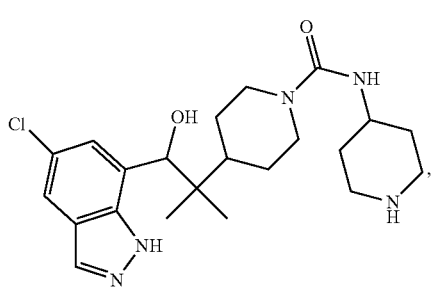
P-0454
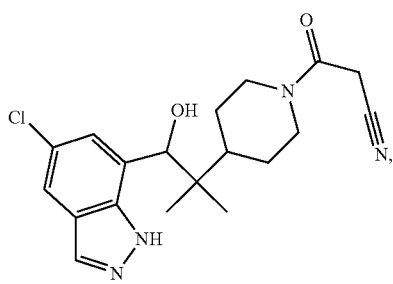
P-0455
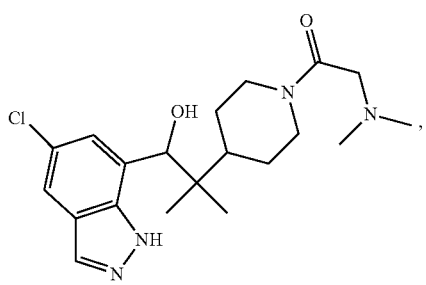
P-0456
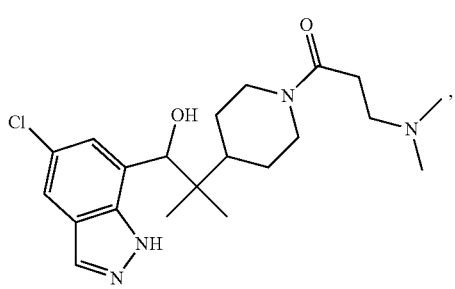
P-0457
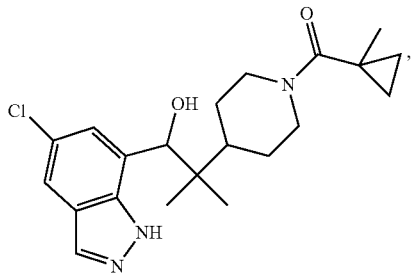
P-0458
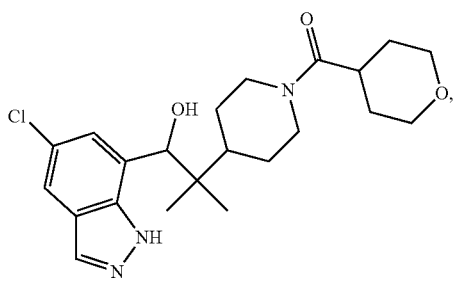
P-0459
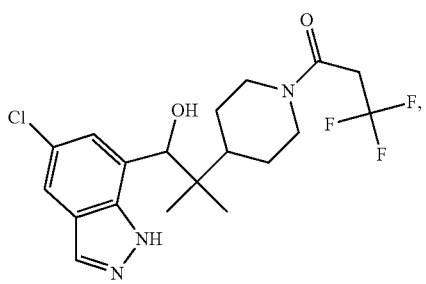
P-0460
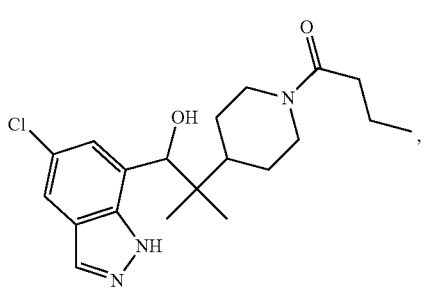
P-0461
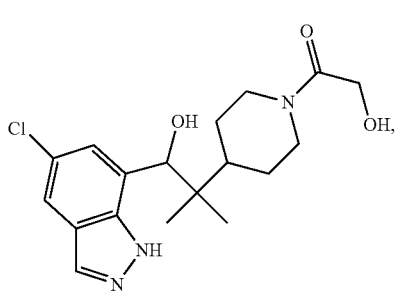

P-0462
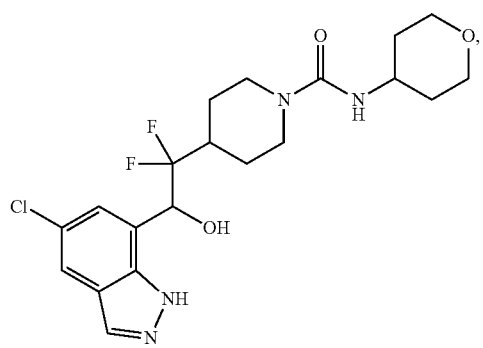
P-0463
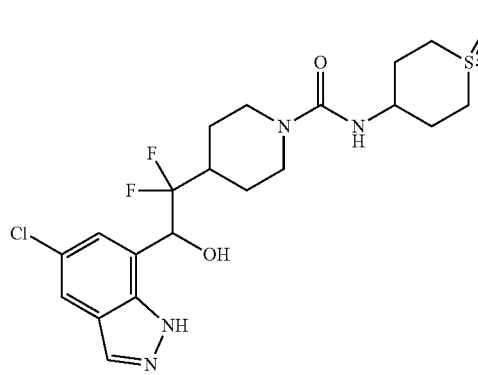
P-0464
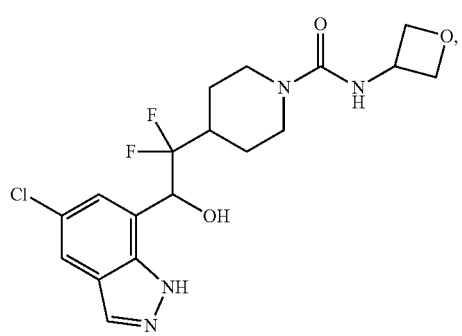
P-0465
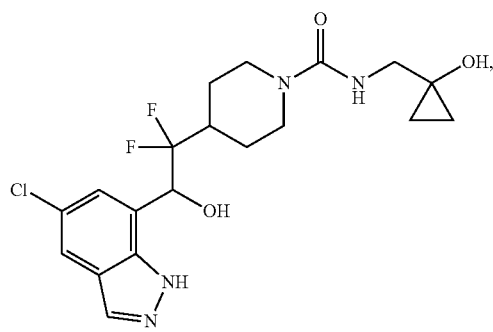
P-0466
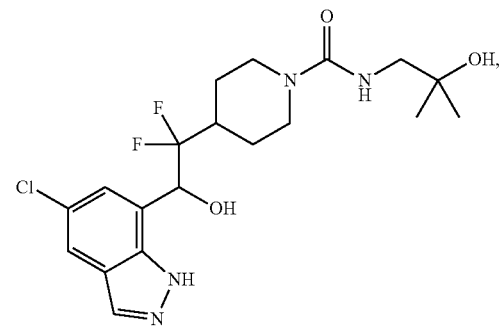
P-0467
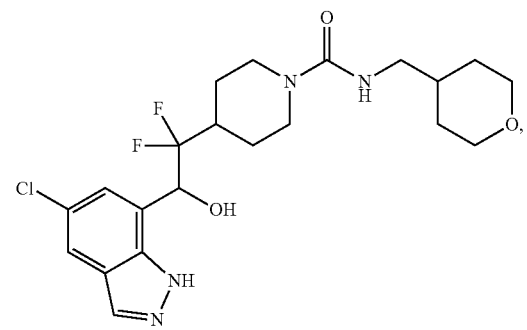
P-0468
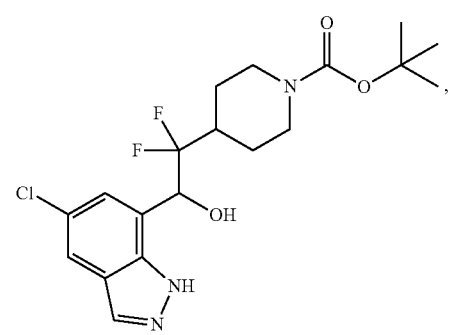
P-0469

P-0470
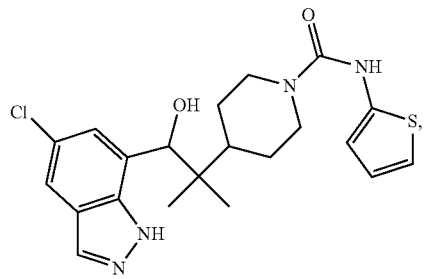
P-0471
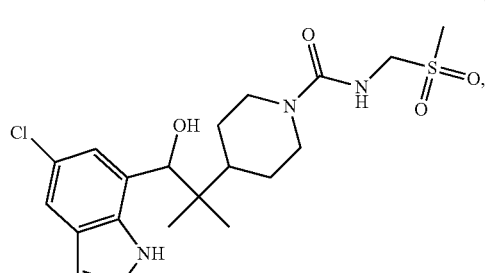
P-0472
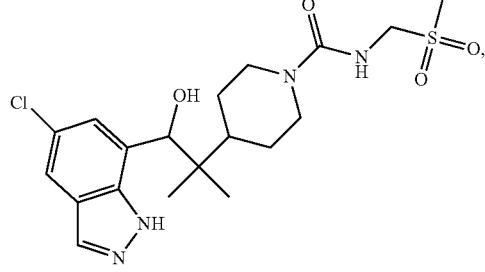
P-0473
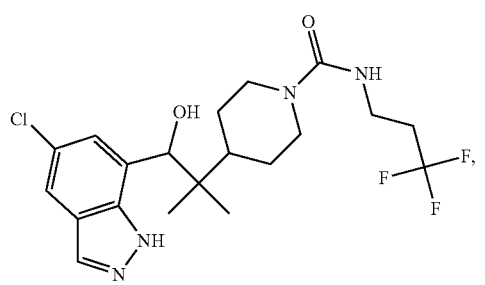
P-0474
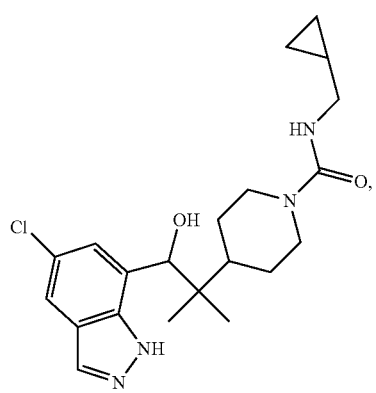
P-0475
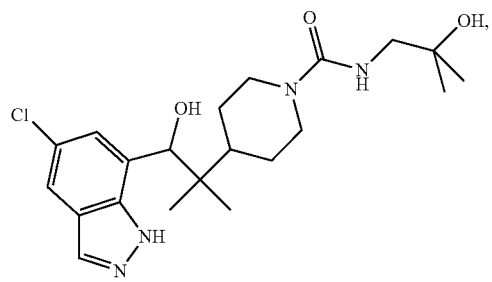
P-0476
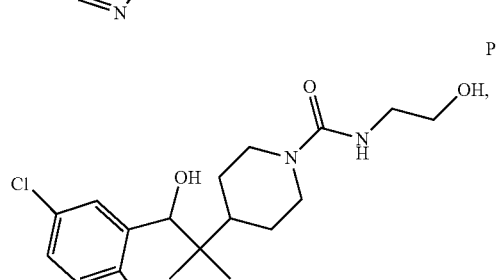
P-0477
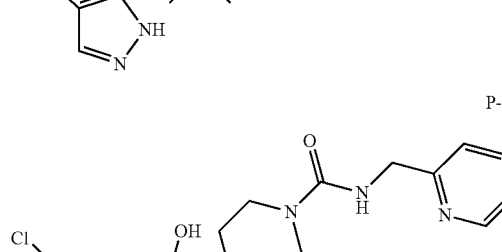
P-0478
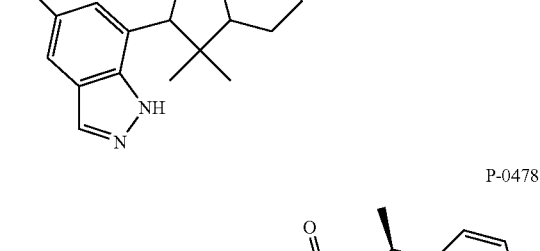
P-0479
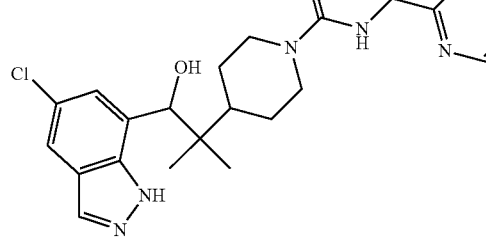

P-0480
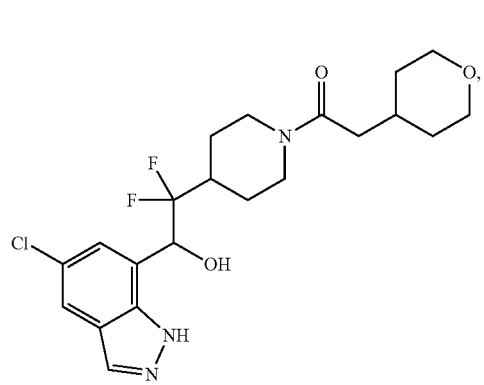
P-0481
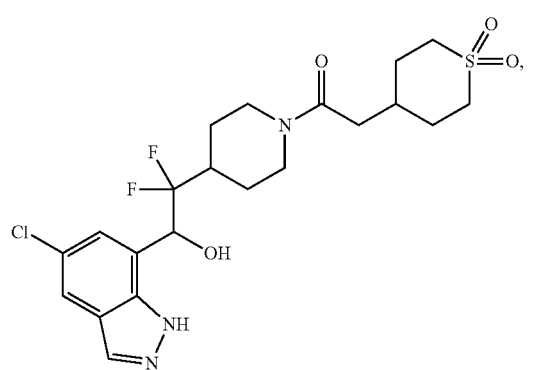
P-0482
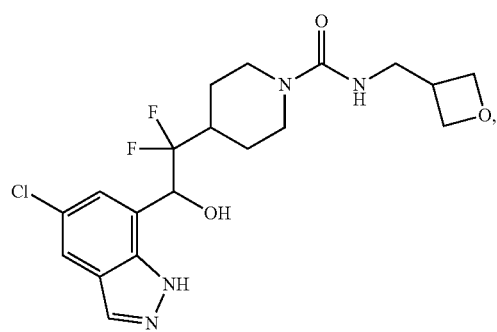
P-0483
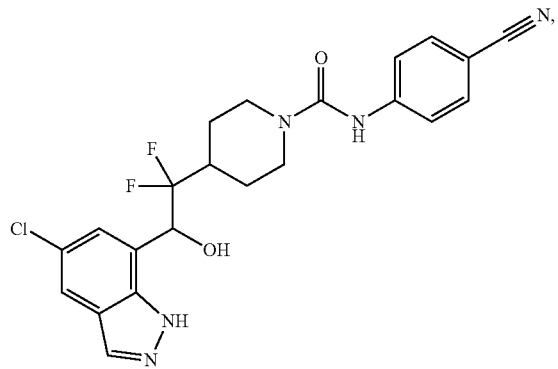
P-0484
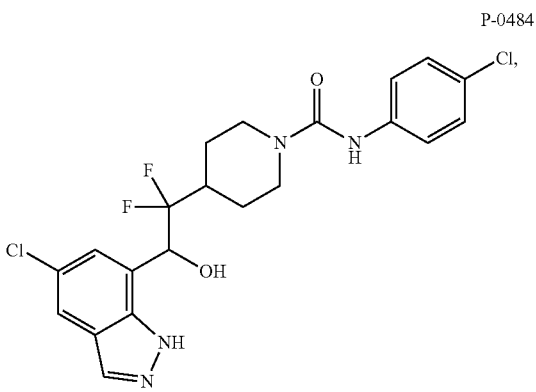
P-0485
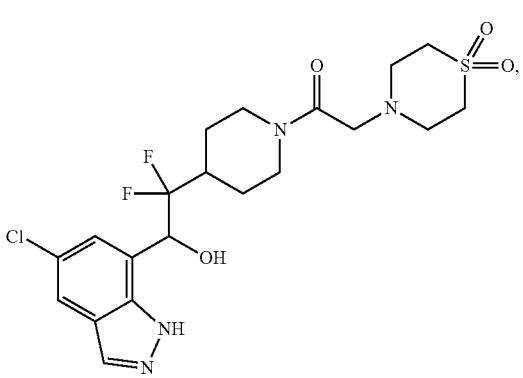
P-0486
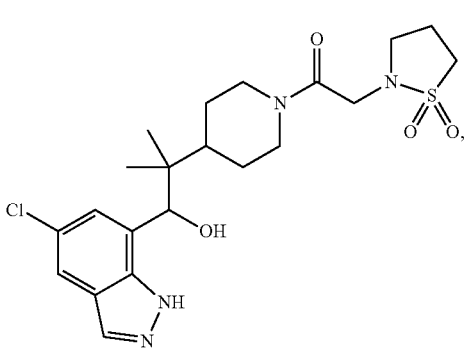
P-0487
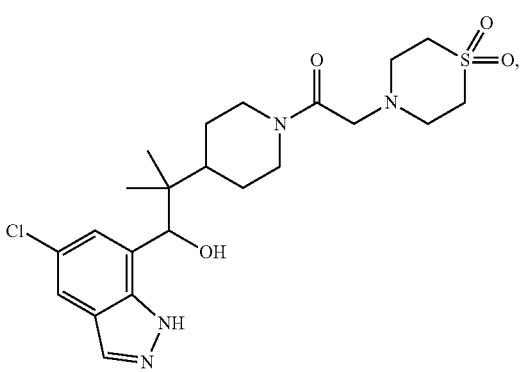

P-0488
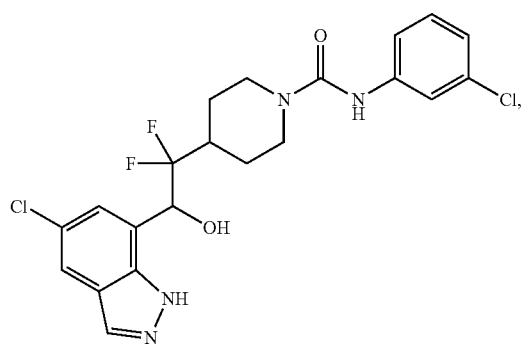
P-0493
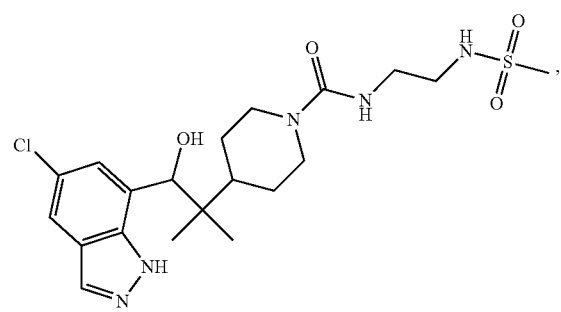
P-0489
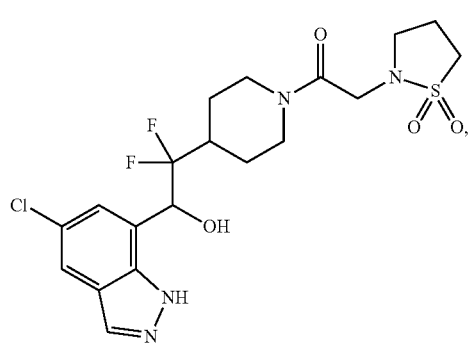
P-0494
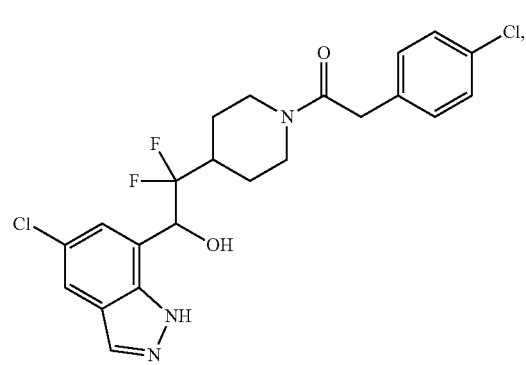
P-0491
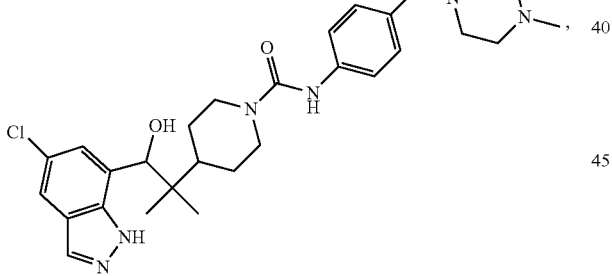
P-0495
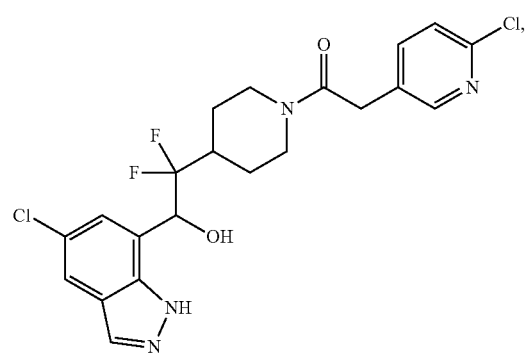
P-0492
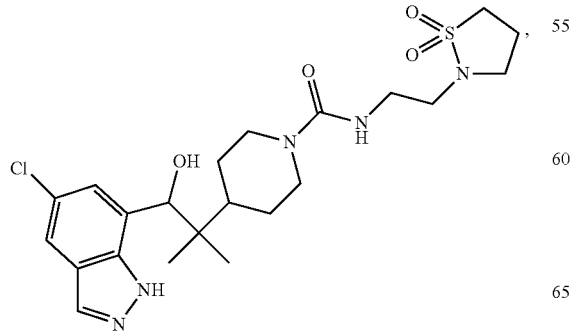
P-0496
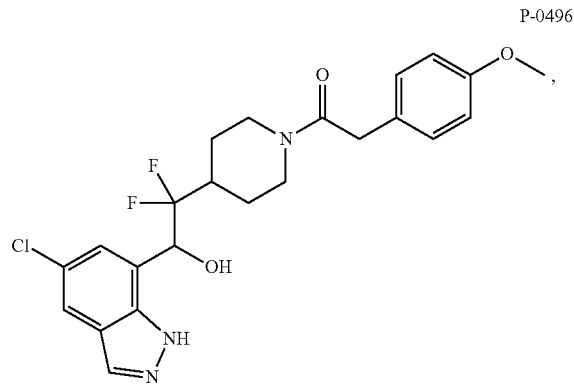

P-0497
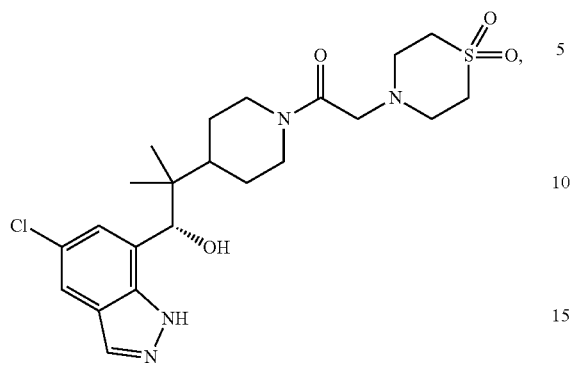
P-0498
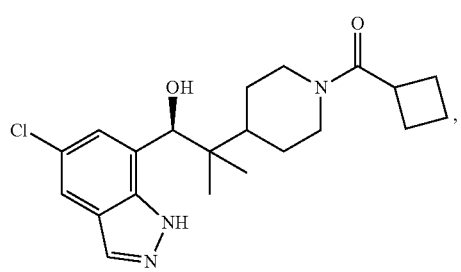
P-0499
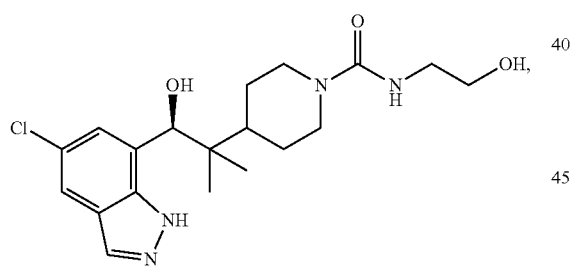
P-0501
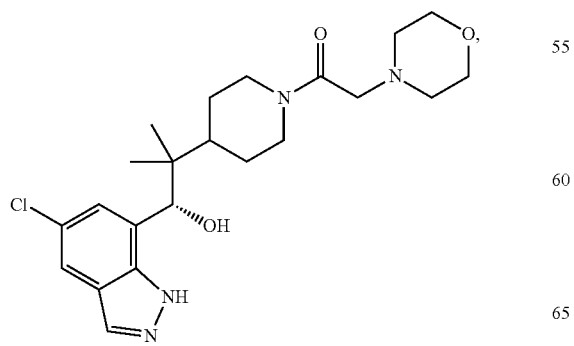
P-0502
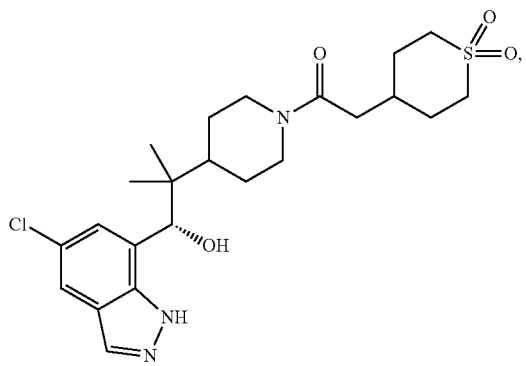
P-0503
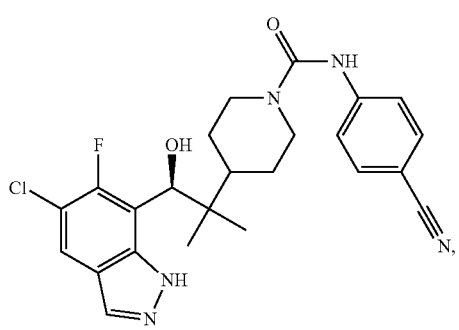
P-0504
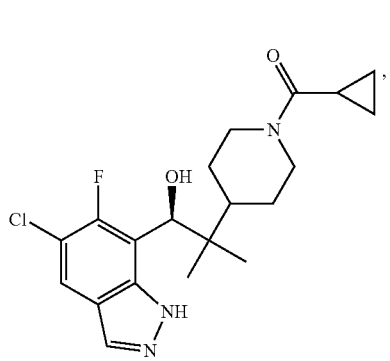
P-0505
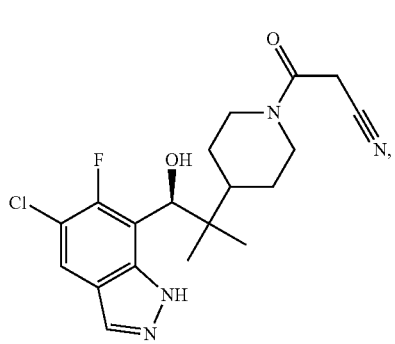

P-0506
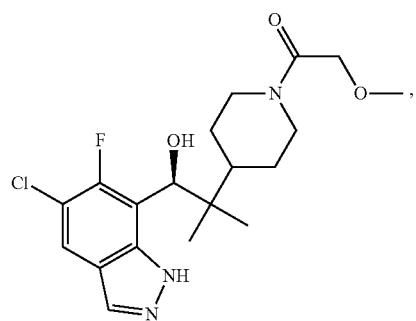
P-0507
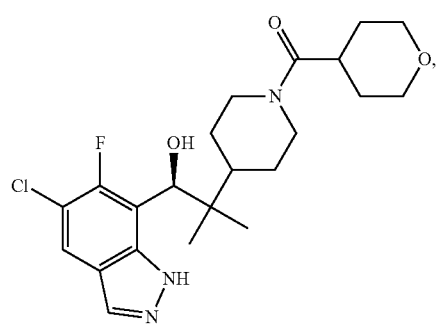
P-0508
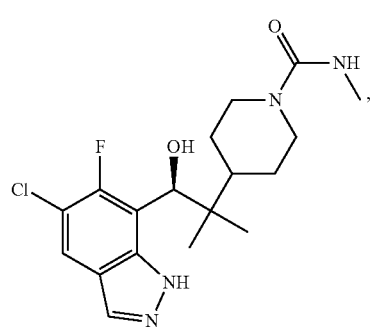
P-0509
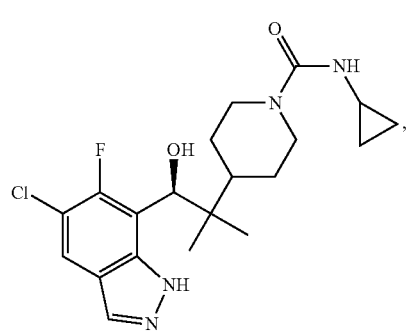
P-0510
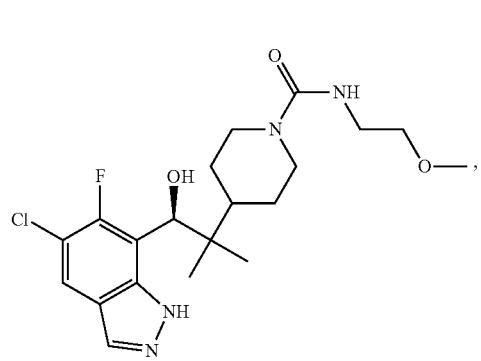
P-0511
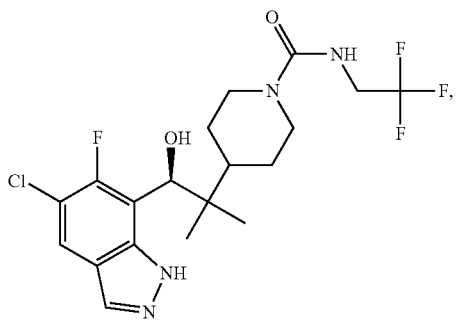
P-0512
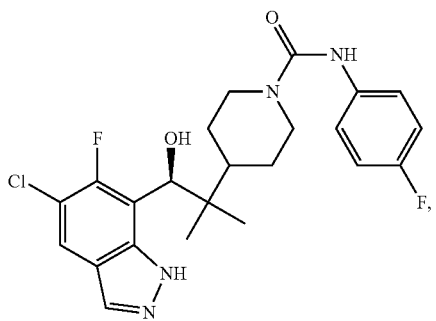
P-0513
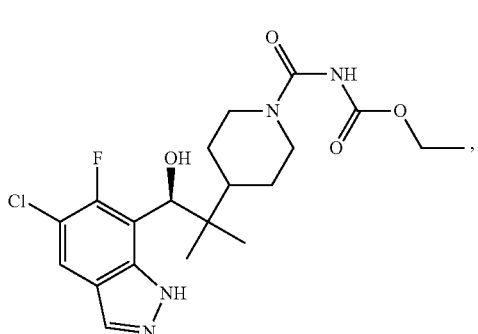
P-0514
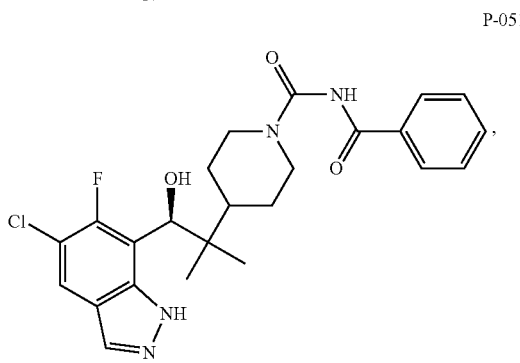
P-0515
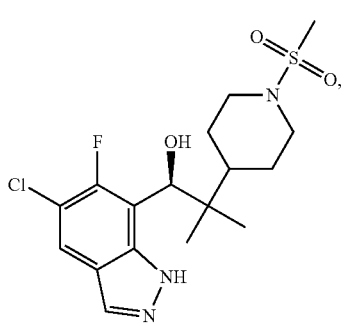

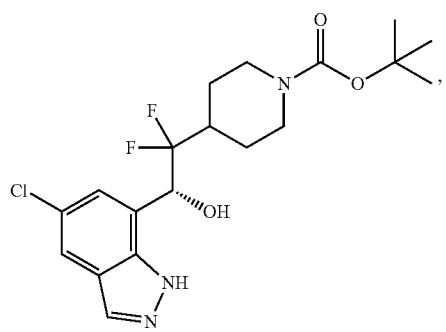
P-0516
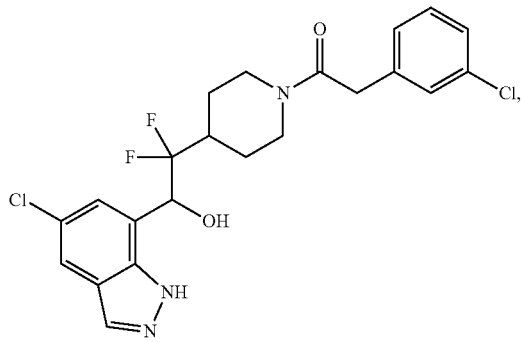
P-0520
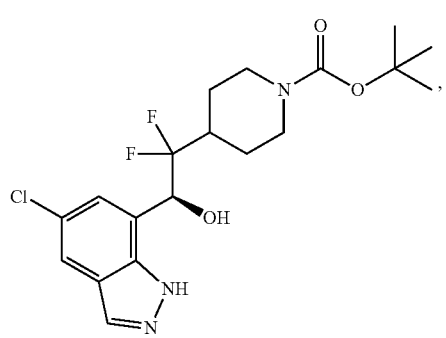
P-0517
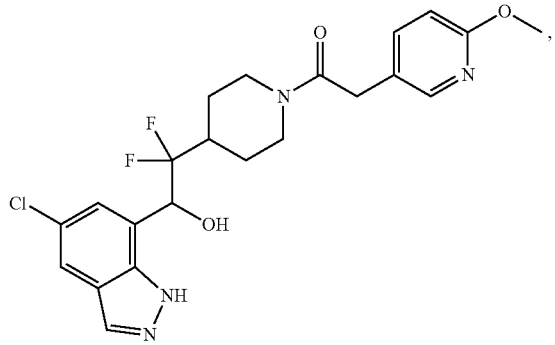
P-0521
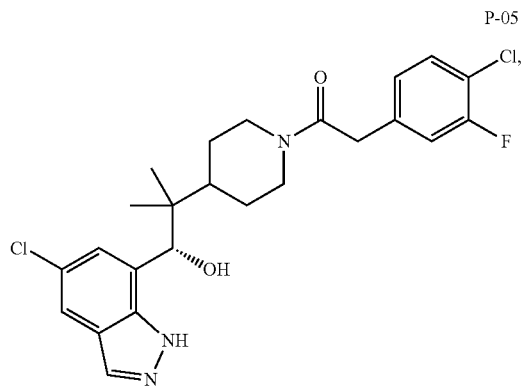
P-0518
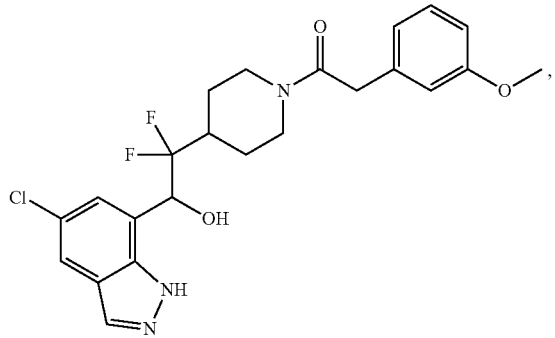
P-0522
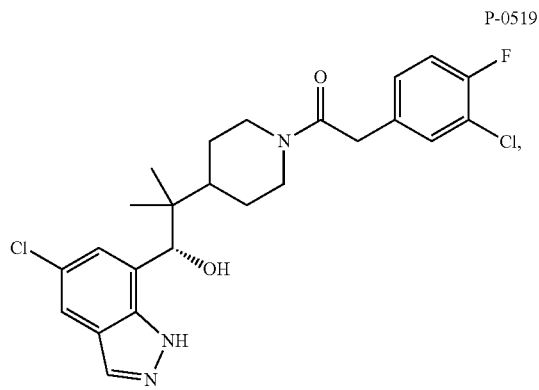
P-0519
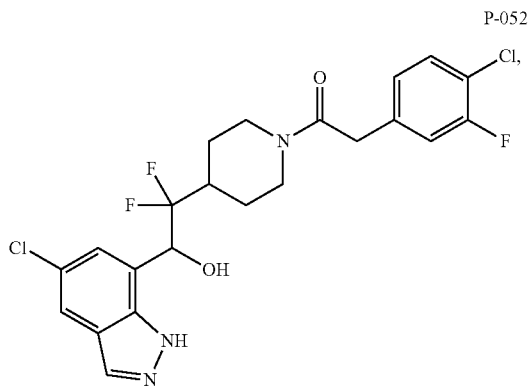
P-0523

-continued

P-0524

P-0525

P-0526

P-0529

P-0530

P-0531

P-0532

P-0533

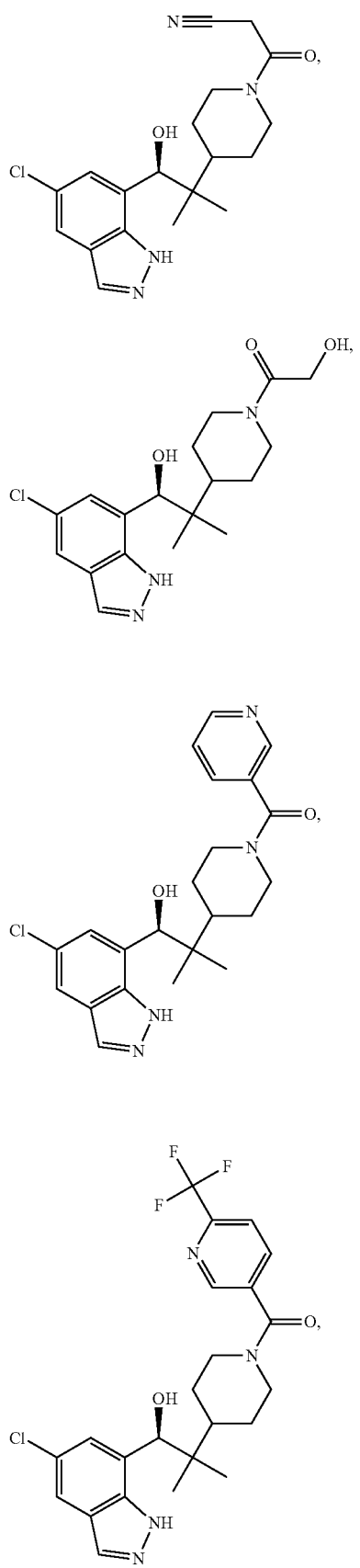
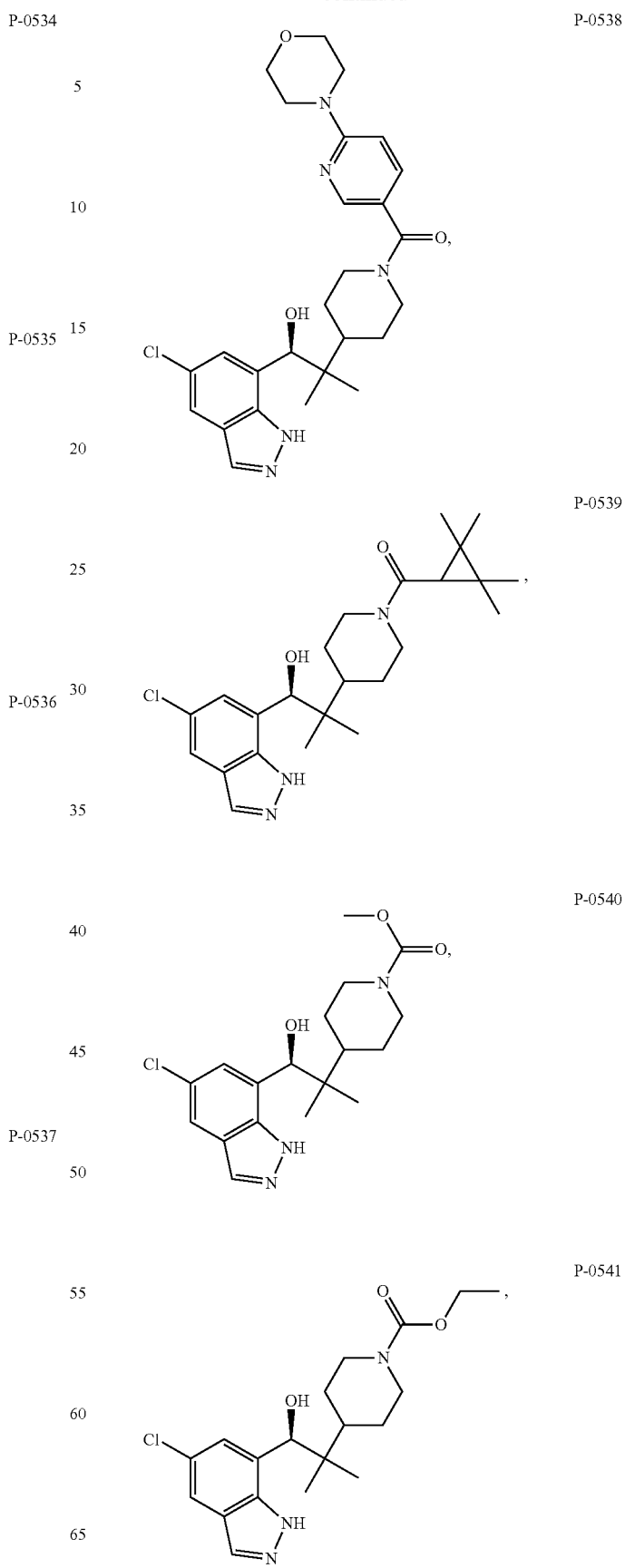

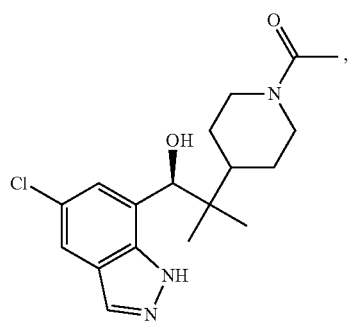 P-0542
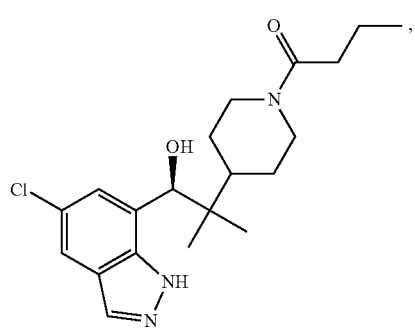 P-0543
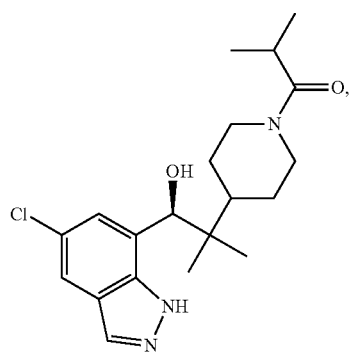 P-0544
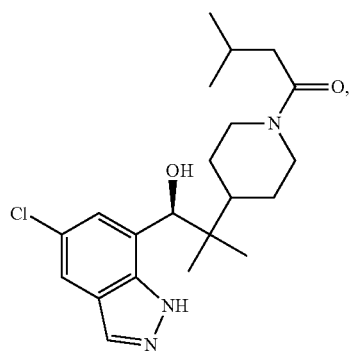 P-0545
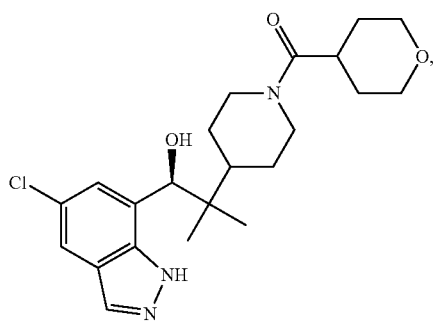 P-0546
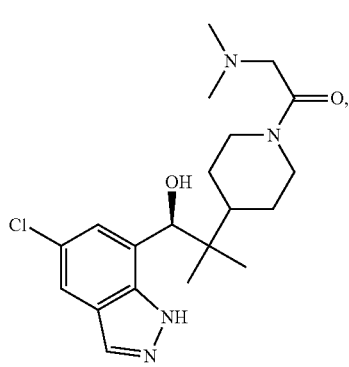 P-0547
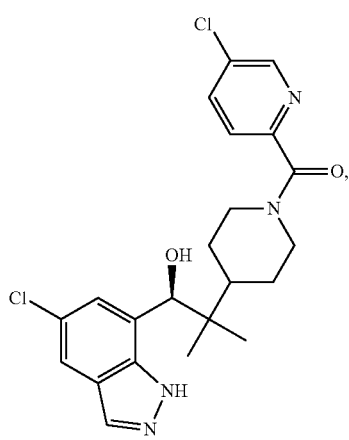 P-0548
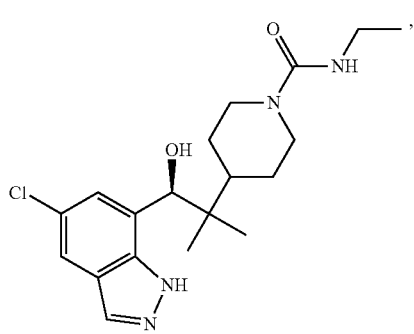 P-0550

P-0551
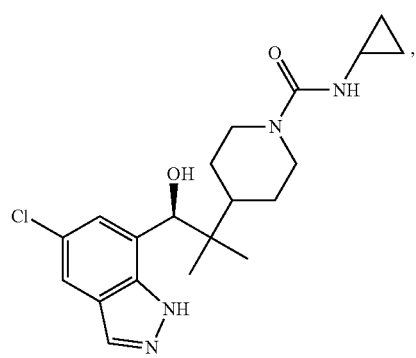
P-0552
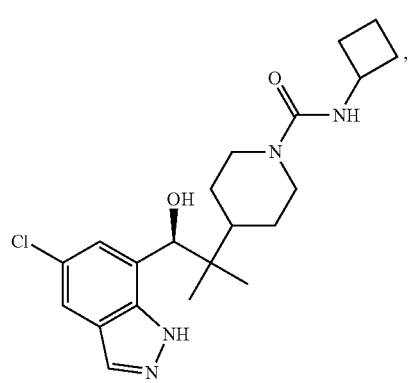
P-0553
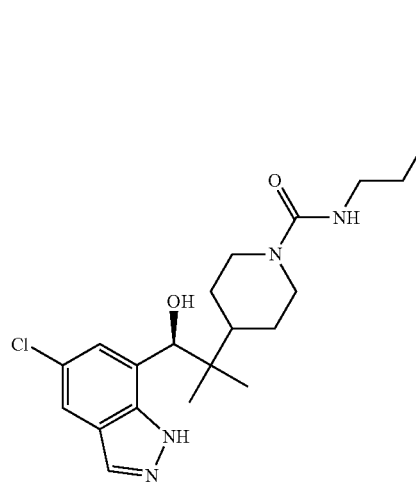
P-0554
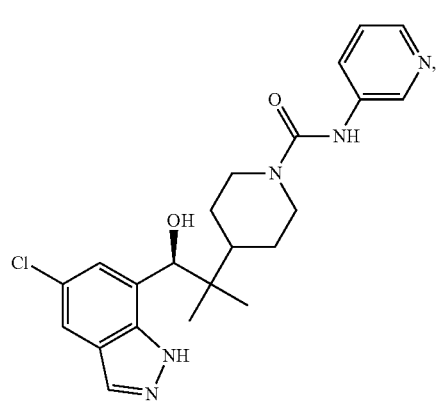
P-0555
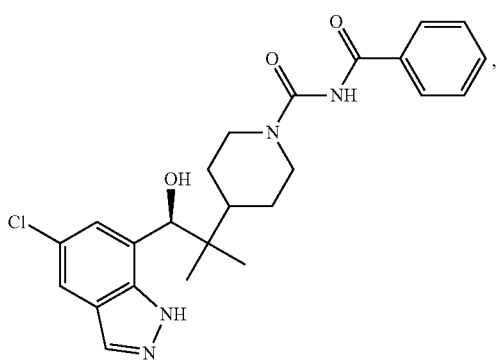
P-0556
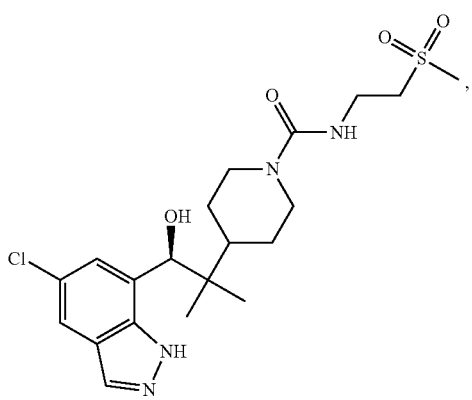
P-0557
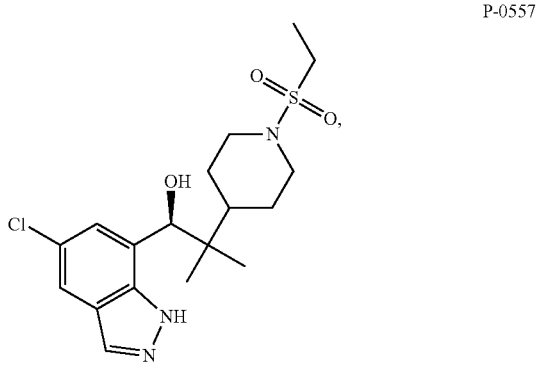
P-0558
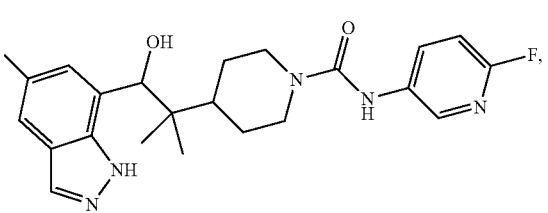
P-0559
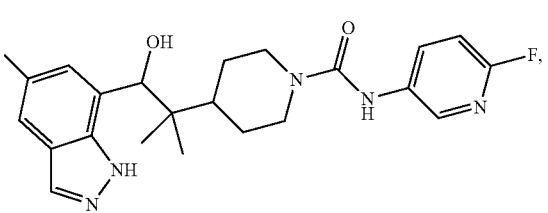

P-0560 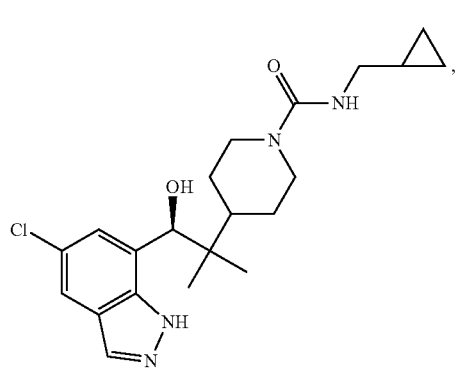
P-0561 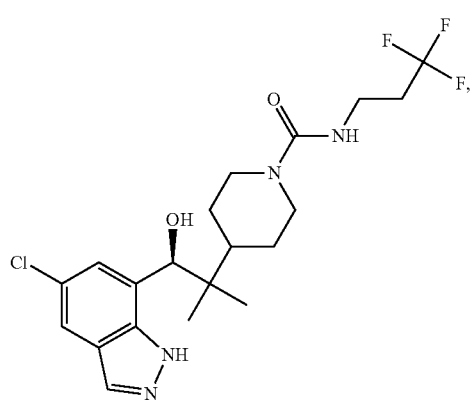
P-0562 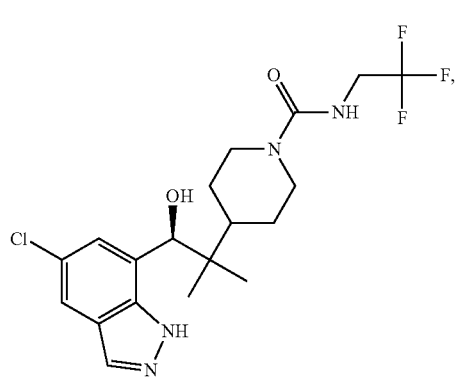
P-0563 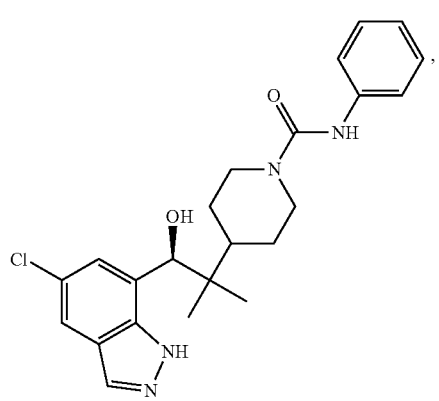
P-0564 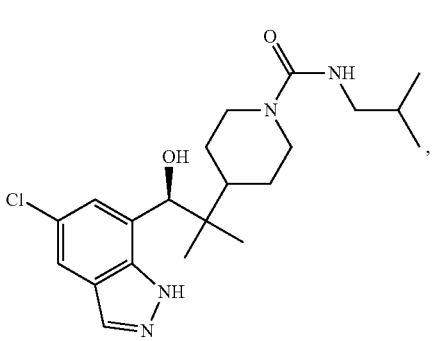
P-0565 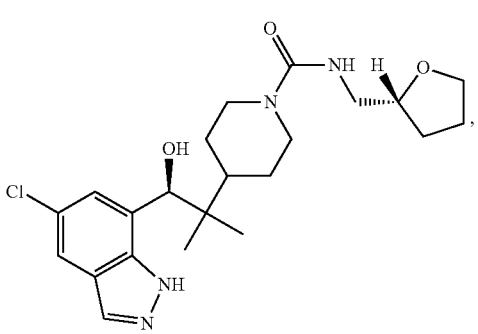
P-0566 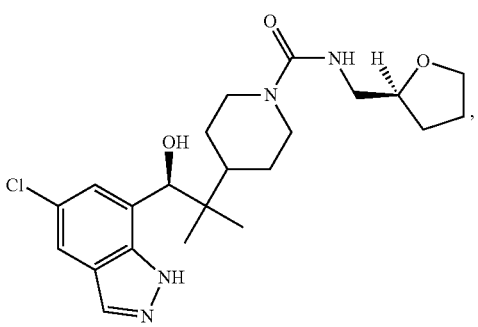
P-0567 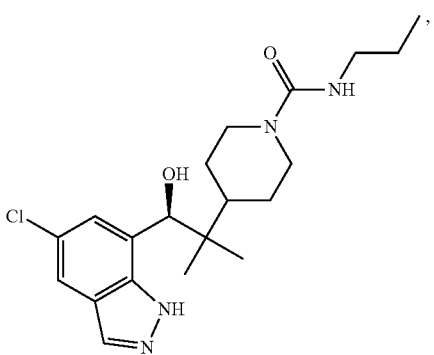

-continued
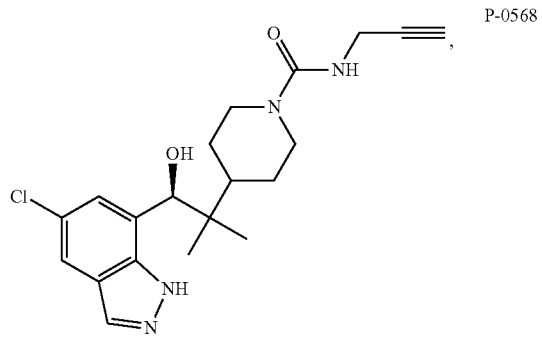
P-0568
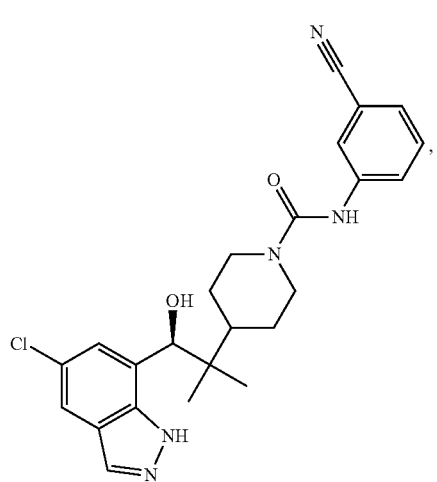
P-0569
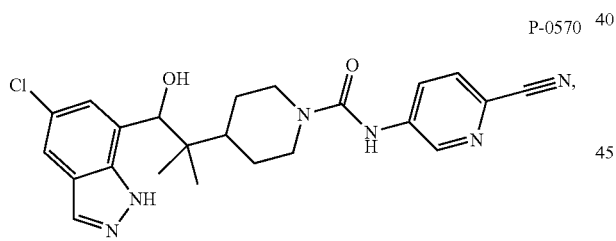
P-0570
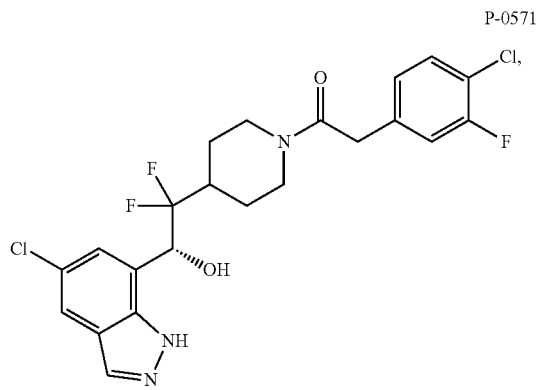
P-0571
-continued
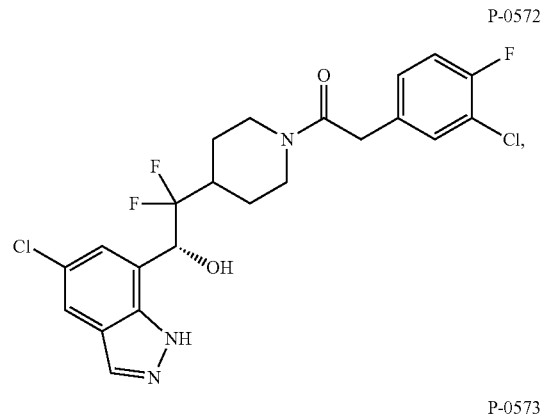
P-0572
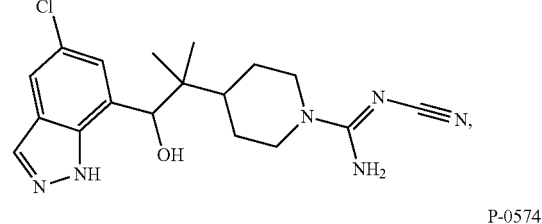
P-0573
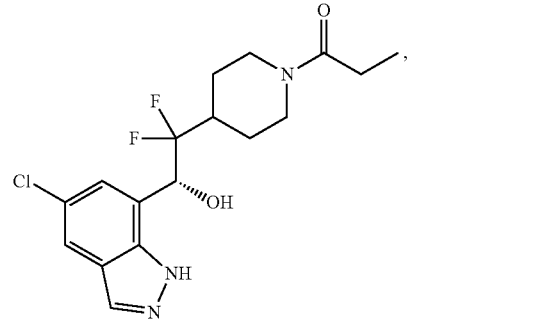
P-0574
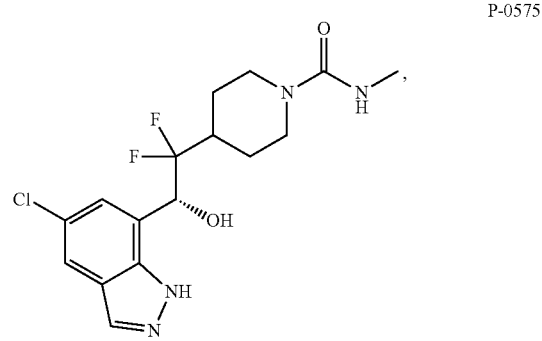
P-0575
P-0576

P-0579
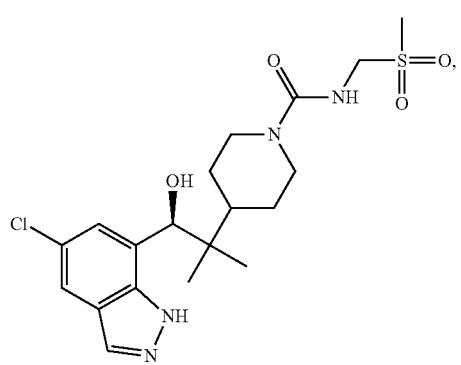
P-0583
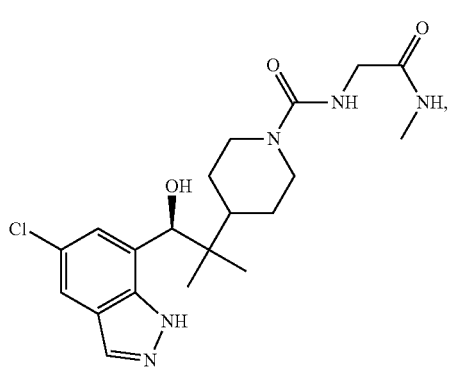
P-0580
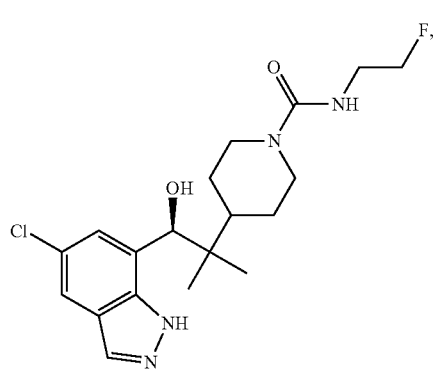
P-0584
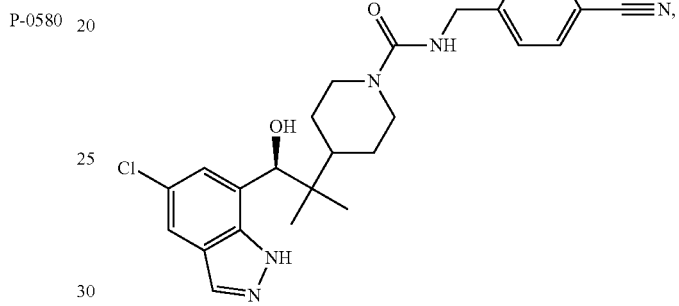
P-0581
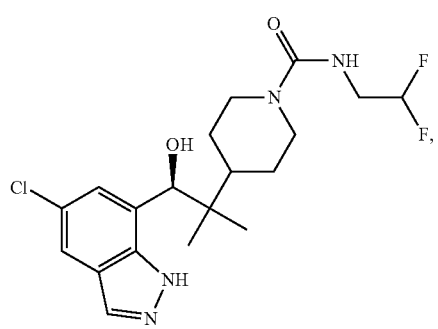
P-0585
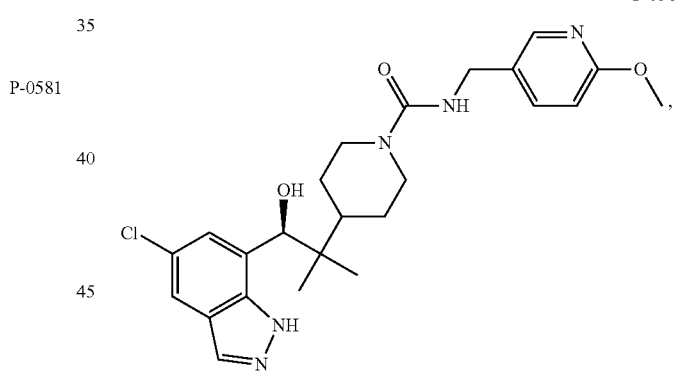
P-0582
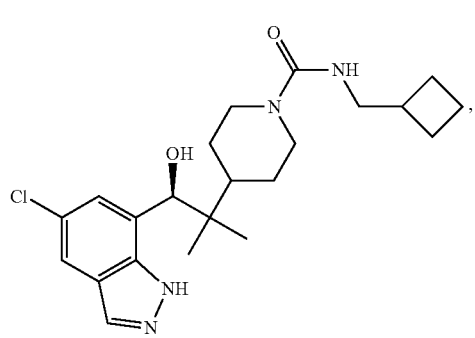
P-0586
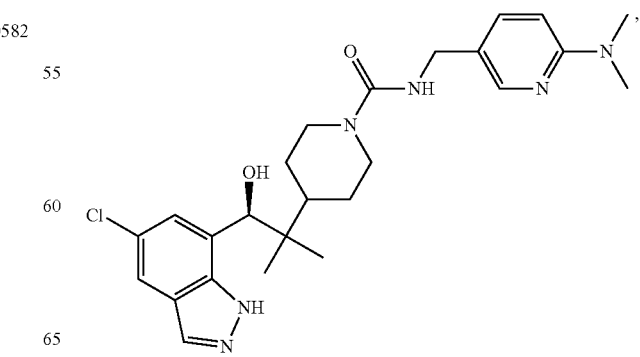

P-0587
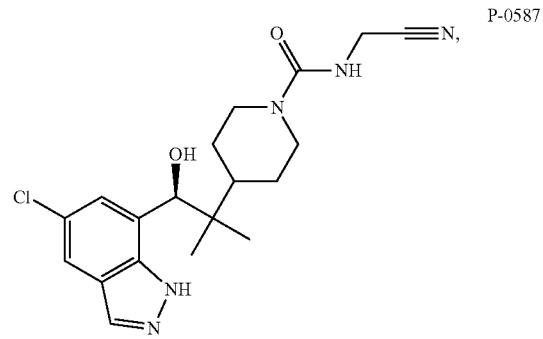
P-0588
P-0589
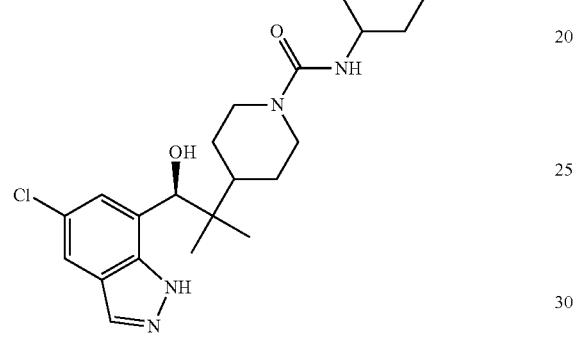
P-0590
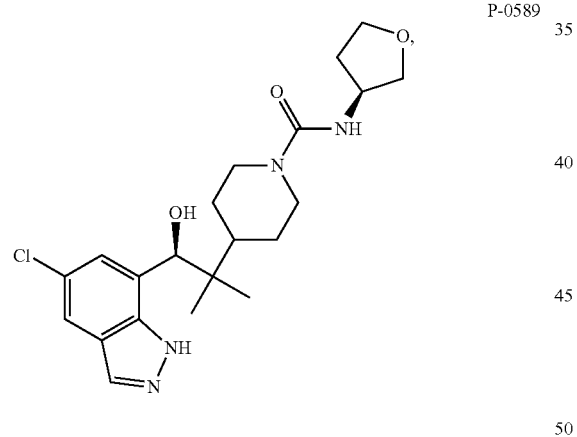
P-0591
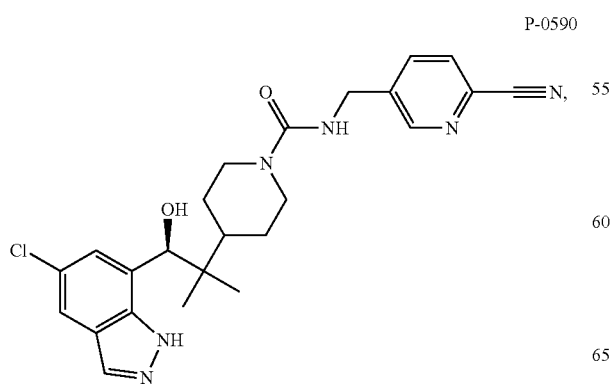
P-0592
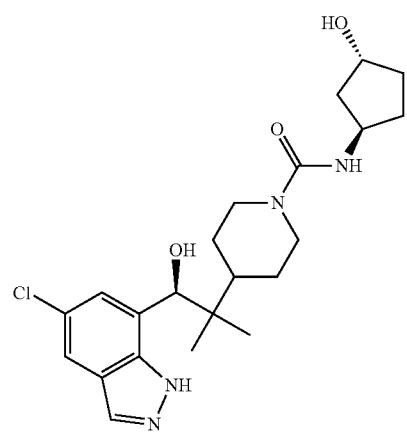
P-0593
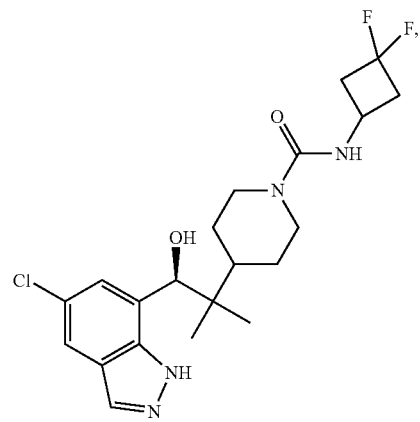
P-0594
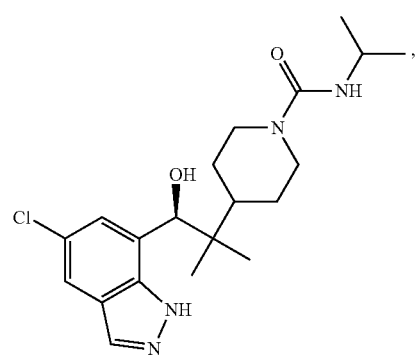

617
-continued
P-0595
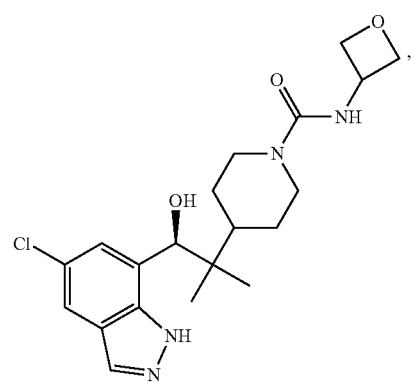
P-0596
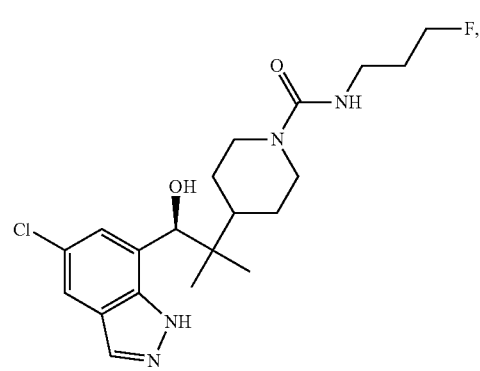
P-0597
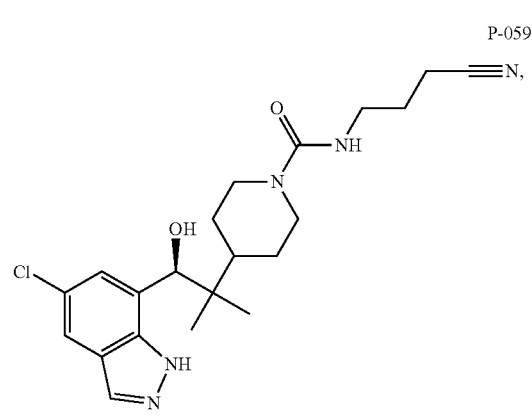
P-0598
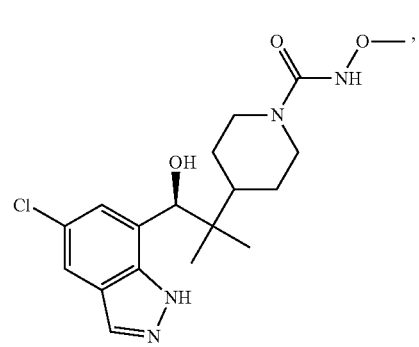
618
-continued
P-0599
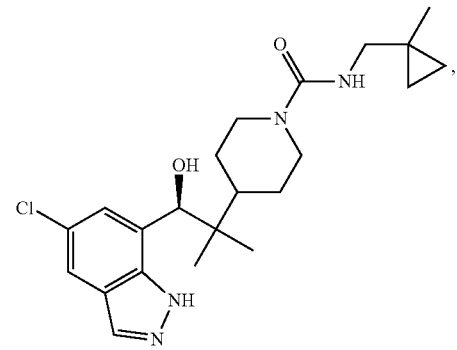
P-0600
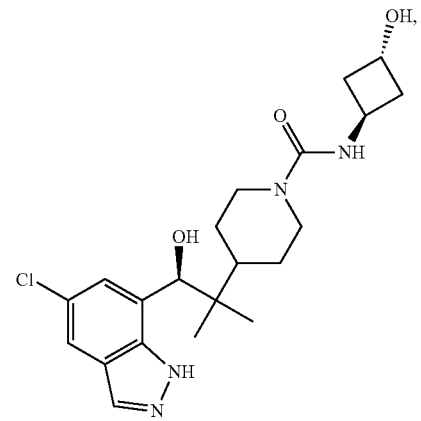
P-0601
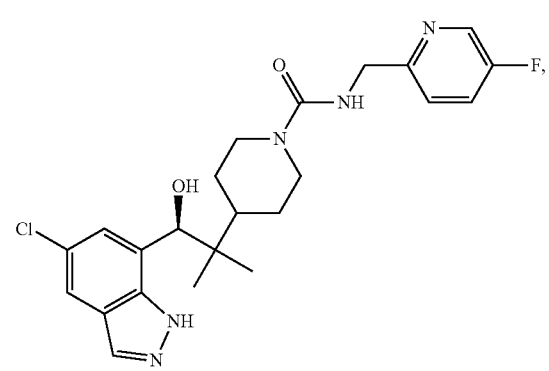
P-0602
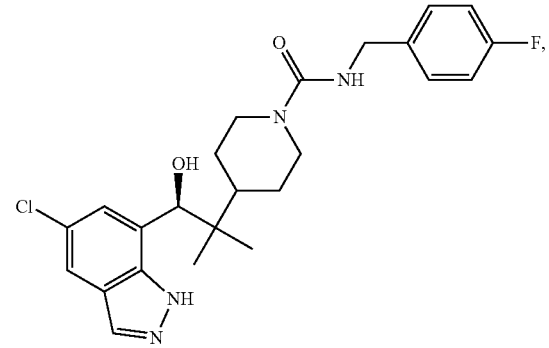

P-0604
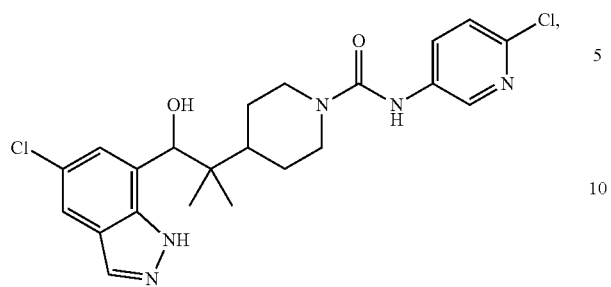
P-0605
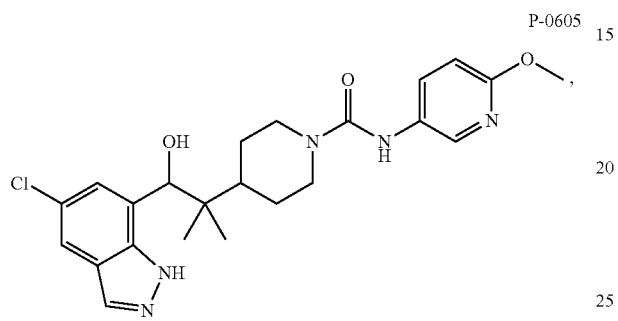
P-0645
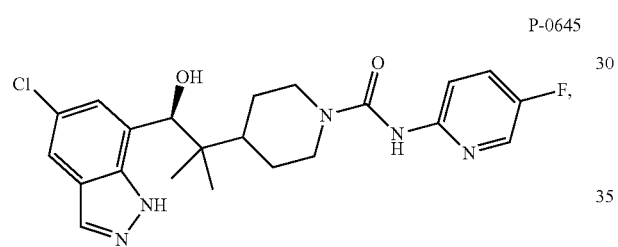
P-0650
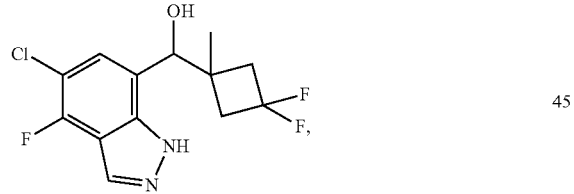
P-0651
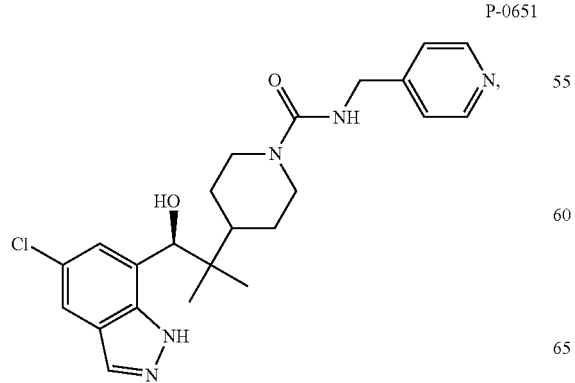
P-0652
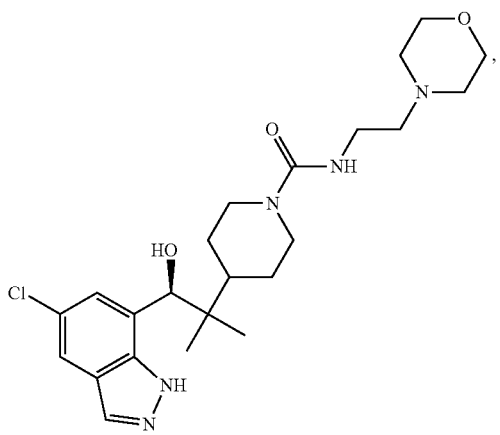
P-0653
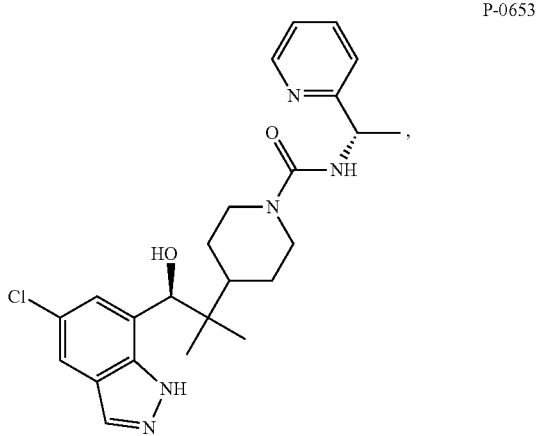
P-0654
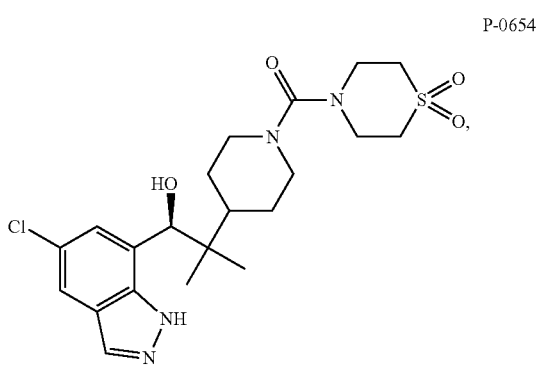
P-0655
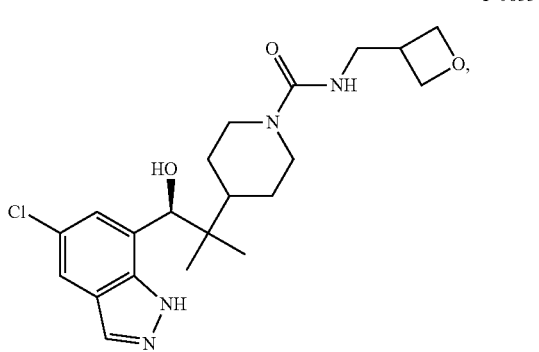

621
-continued
P-0656
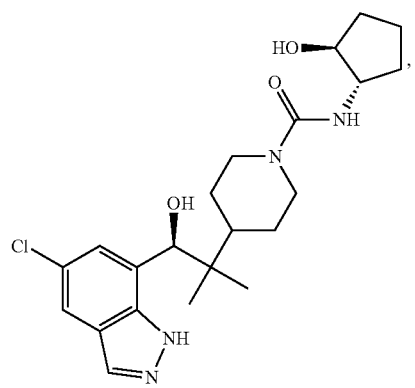
P-0659
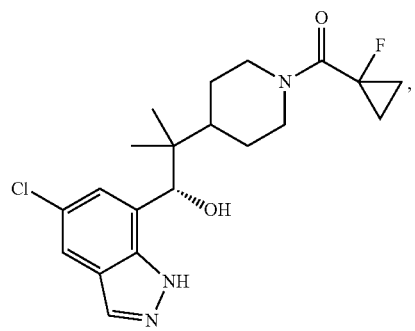
P-0662
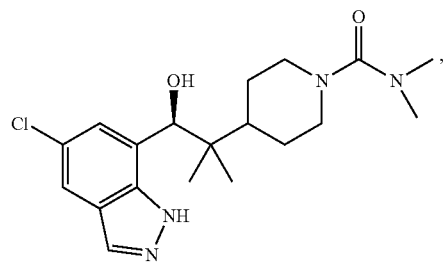
P-0663
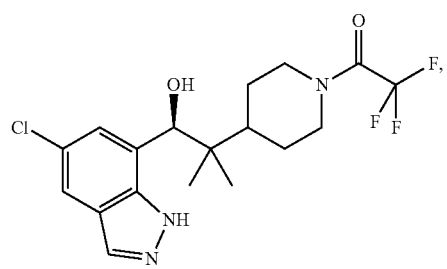
P-0665
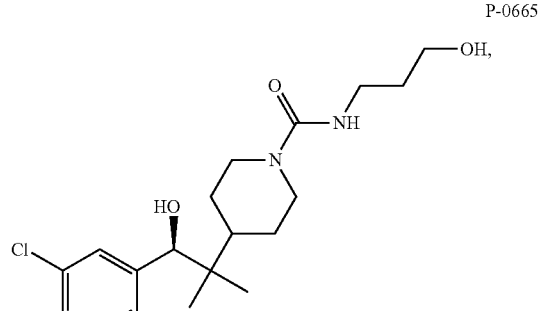
622
-continued
P-0666
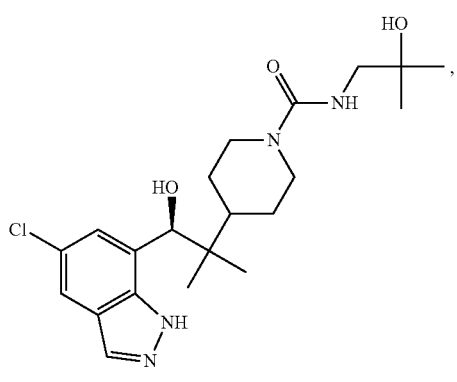
P-0667
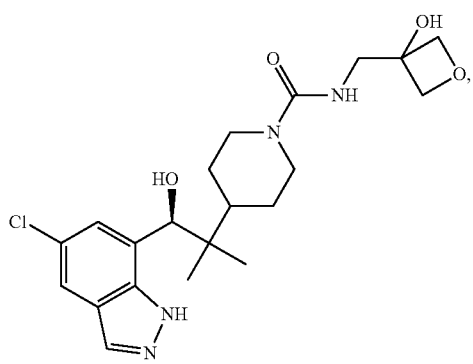
P-0668
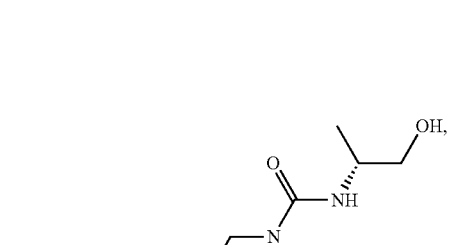
P-0669
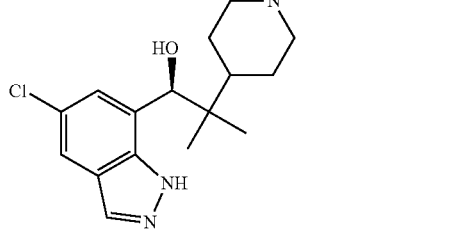

623
-continued
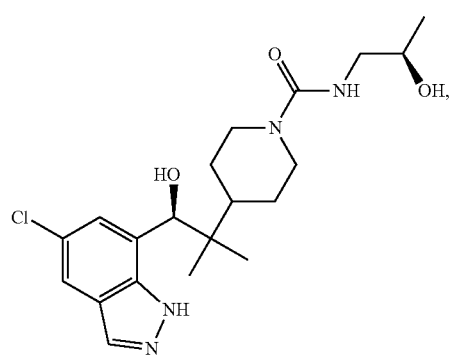
P-0670
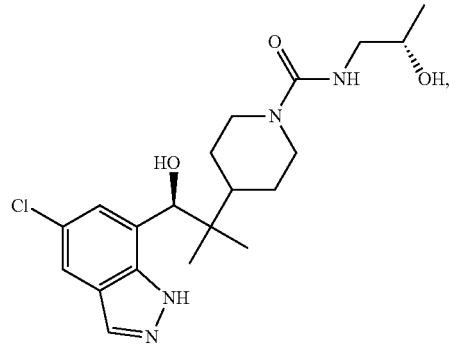
P-0671
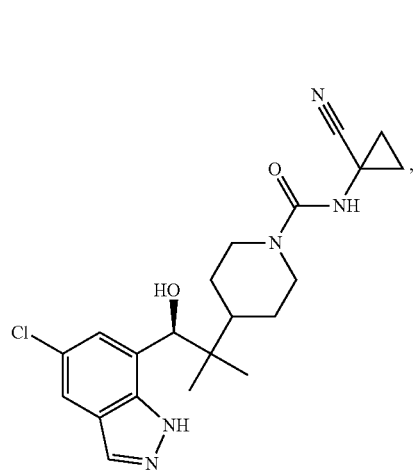
P-0672
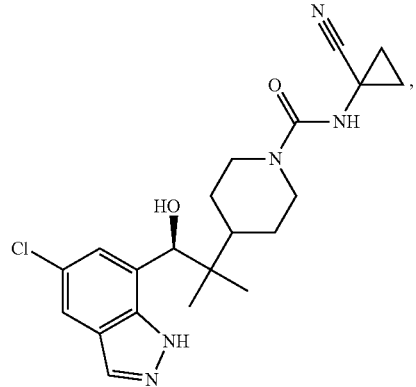
P-0673
624
-continued
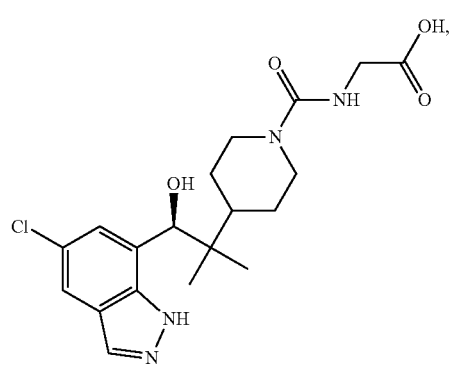
P-0674
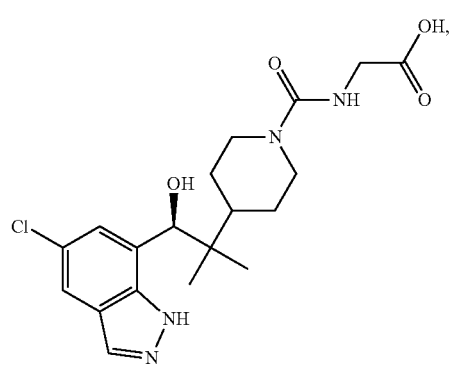
P-0675
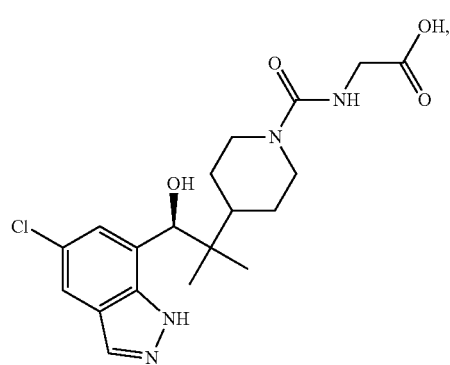
P-0676
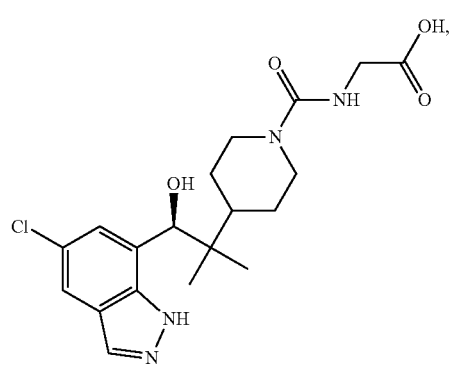
P-0677

-continued

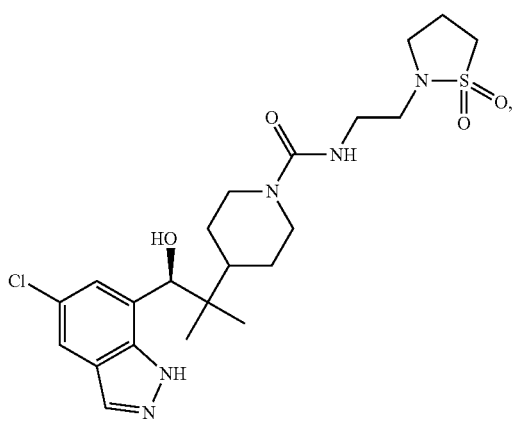
P-0678

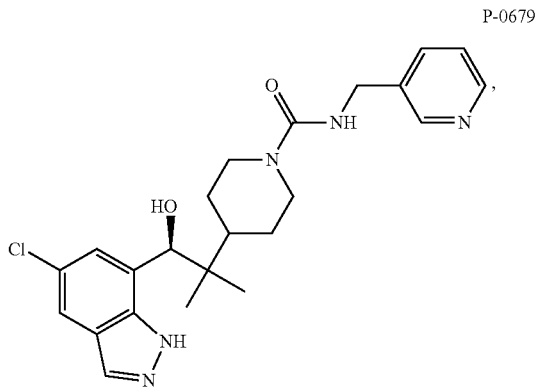
P-0679

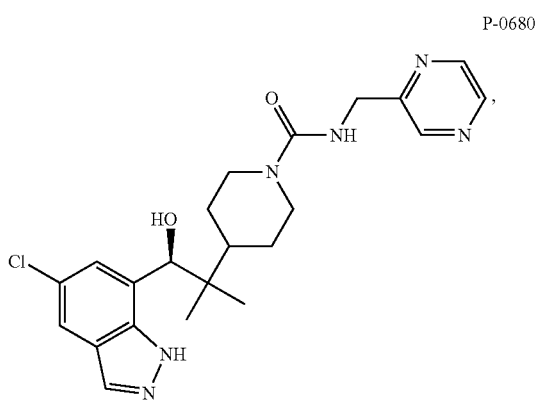
P-0680

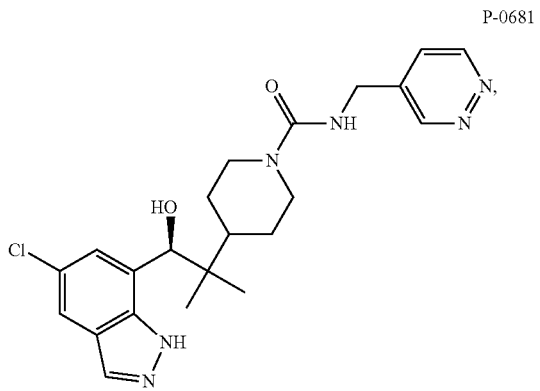
P-0681 or a pharmaceutically acceptable salt, a solvate, a tautomer, a stereoisomer or a deuterated analog thereof.

28. A pharmaceutical composition comprising a compound of claim 1, and a pharmaceutically acceptable carrier.

29. The pharmaceutical composition according claim 28, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxycamptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor selected from temsirolimus, everolimus, and deforolimus, a PI3K inhibitor selected from BEZ235, GDC-0941, XL147, and XL765, PD-332991, tanespimycin, or tipifarnib; xv) a Mek inhibitor selected from AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), and TAK-733; or xviii) an anti-retroviral agent selected from maraviroc; enfuvirtide; lamivudine and zidovudine; emtricitabine: lamivudine; abacavir and lamivudine; zalcitabine; zidovudine; abacavir, zidovudine, and lamivudine; tenofovir disoproxil fumarate and emtricitabine; enteric coated didanosine; didanosine; tenofovir disoproxil fumarate; stavudine; abacavir sulfate; rilpivirine; etravirine; delavirdine; efavirenz;

nevirapine; raltegravir; dolutegravir; elvitegravir; amprenavir; tipranavir; indinavir; saquinavir; saquinavir mesylate; lopinavir and ritonavir; Fosamprenavir Calcium; ritonavir; darunavir; atazanavir sulfate; nelfinavir mesylate; favirenz, emtricitabine and tenofovir disoproxil fumarate; emtricitabine, rilpivirine, and tenofovir disoproxil fumarate; atazanavir sulfate and combicistat; cobicistat and darunavir ethanolate; and elvitegravir, cobicistat, emtricitabine and tenofovir disoproxil fumarate.

30. A method for treating a subject with a disease or condition mediated by IDO1, TDO, or both IDO1 and TDO, wherein the method comprises administering to a subject an effective amount of a compound of claim 1, wherein the disease or condition is selected from the group consisting of rheumatoid arthritis, type 1 diabetes, lupus, Hashimoto's thyroid disease, multiple sclerosis, inflammatory bowel disease, Crohn's disease, ulcerative colitis, celiac disease, asthma, HIV, skin cancer promoted by chronic inflammation, Alzheimer's disease, Parkinson's disease, Huntington's disease, amyotrophic lateral sclerosis, multiple sclerosis, schizophrenia, bipolar disorder, depression, inflammation-associated depression, end-stage renal disease, chronic kidney disease and atherosclerosis.

31. The method of claim 30, further comprising administering to said subject a second pharmaceutical agent, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-a and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor selected from temsirolimus, everolimus, and deforolimus, a PI3K inhibitor selected from BEZ235, GDC-0941, XL147, and XL765, PD-332991, tanespimycin, or tipifarnib; xv) a Mek inhibitor selected from AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), and TAK-733; or xviii) an anti-retroviral agent selected from maraviroc; enfuvirtide; lamivudine and zidovudine; emtricitabine; lamivudine; abacavir and lamivudine; zalcitabine; zidovudine; abacavir, zidovudine, and lamivudine; tenofovir disoproxil fumarate and emtricitabine; enteric coated didanosine; didanosine; tenofovir disoproxil fumarate; stavudine; abacavir sulfate; rilpivirine; etravirine; delavirdine; efavirenz; nevirapine; raltegravir; dolutegravir; elvitegravir; amprenavir; tipranavir; indinavir; saquinavir; saquinavir mesylate; lopinavir and ritonavir; Fosamprenavir Calcium; ritonavir; darunavir; atazanavir sulfate; nelfinavir mesylate; favirenz, emtricitabine and tenofovir disoproxil fumarate; emtricitabine, rilpivirine, and tenofovir disoproxil fumarate; atazanavir sulfate and combicistat; cobicistat and darunavir ethanolate; and elvitegravir, cobicistat, emtricitabine and tenofovir disoproxil fumarate.

32. The compound according to claim 20, wherein $R^{15}$ is one of the following groups: —C(O)—CH$_3$, —C(O)—CH(CH$_3$)$_2$, —C(O)—CH$_2$—CH$_3$, —C(O)—CH(CH$_3$)$_2$, —C(O)—C(CH$_3$)$_3$, —C(O)—CH$_2$CH$_2$CH$_3$, —C(O)—CH(CH$_3$)-phenyl, —C(O)—N(H)propyl, —C(O)—(CH$_2$)$_{0-1}$cyclopropyl, —C(O)—(CH$_2$)$_{0-1}$cyclobutyl, —C(O)—(CH$_2$)$_{0-1}$cyclopentyl, —C(O)—(CH$_2$)$_{0-1}$cyclohexyl, —C(O)—(CH$_2$)$_{0-1}$ tetrahydro-2H-thiopyran 1,1-dioxide, —C(O)—(CH$_2$)$_{0-1}$tetrahydro-2H-pyran, —C(O)—(CH$_2$)$_{0-1}$oxetane, —C(O)—(CH$_2$)$_{0-1}$morpholinyl, —C(O)—(CH$_2$)$_{0-1}$ thiomorpholinyl 1,1-dioxide, —C(O)—(CH$_2$)$_{0-1}$ isothiozolidine 1,1-dioxide, —C(O)—CH$_2$—CN, —C(O)-methoxymethyl, —C(O)-methoxypropyl, —C(O)-methoxyethyl, —C(O)-pyridyl, —C(O)-isoxazolyl optionally substituted with 1-3 methyl, or —C(O)-phenyl optionally substituted with 1-3 substituents independently selected from the group consisting of F, Cl, C$_1$-C$_3$alkoxy, and CN.

33. The compound according to claim 20, wherein $R^{15}$ is one of the following groups: —C(O)—N(H)(CH$_2$)$_2$—CF$_3$, —C(O)—N(H)CH$_2$—CF$_3$, —C(O)—N(H)CH$_3$, —C(O)—N(H)CH(CH$_3$)$_2$, —C(O)—N(H)CH$_2$—CH$_3$, —C(O)—N(H)CH(CH$_3$)$_2$, —C(O)—N(H)CH$_2$CH$_2$CH$_3$, —C(O)—N(H)CH(CH$_3$)-phenyl, —C(O)—N(H)(CH$_2$)$_{0-1}$cyclopropyl, —C(O)—N(H)(CH$_2$)$_{0-1}$ cyclobutyl, —C(O)—N(H)(CH$_2$)$_{0-1}$ cyclopentyl, —C(O)—N(H)(CH$_2$)$_{0-1}$cyclohexyl, —C(O)—N(H)(CH$_2$)$_{0-1}$ tetrahydro-2H-thiopyran 1,1-dioxide, —C(O)—N(H)(CH$_2$)$_{0-1}$tetrahydro-2H-pyran, —C(O)—N(H)(CH$_2$)$_{0-1}$oxetane, —C(O)—N(H)(CH$_2$)$_{0-1}$morpholinyl, —C(O)—N(H)(CH$_2$)$_{0-1}$ thiomorpholinyl 1,1-dioxide, —C(O)—N(H)(CH$_2$)$_{0-1}$ isothiozolidine 1,1-dioxide, —C(O)—N(H)CH$_2$—CN, —C(O)—N(H)-methoxymethyl, —C(O)—N(H)-methoxypropyl, —C(O)—N(H)-methoxyethyl, —C(O)—N(H)-pyridyl, —C(O)—N(H)isoxazolyl optionally substituted with 1-3 methyl, or —C(O)—N(H)phenyl optionally substituted with 1-3 substituents independently selected from the group consisting of F, Cl, C$_1$-C$_3$alkoxy, and CN.

34. The compound according to claim 20, wherein $R^{15}$ is one of the following groups: —C(O)—N(H)—SO$_2$—(CH$_2$)$_2$—CF$_3$, —C(O)—N(H)—SO$_2$—CH$_2$—CF$_3$, —C(O)—N(H)—SO$_2$—CH$_3$, —C(O)—N(H)—SO$_2$—CH(CH$_3$)$_2$, —C(O)—N(H)—SO$_2$—CH$_2$—CH$_3$, —C(O)—N(H)—SO$_2$—CH(CH$_3$)$_2$, —C(O)—N(H)—SO$_2$—C(CH$_3$)$_3$, —C(O)—N(H)—SO$_2$—CH$_2$CH$_2$CH$_3$, —C(O)—N(H)—SO$_2$—C$_3$-C$_6$cycloalkyl, —C(O)—N(H)—SO$_2$tetrahydro-2H-thiopyran 1,1-dioxide, —C(O)—N(H)—SO$_2$-tetrahydro-2H-pyran, —C(O)—N(H)—SO$_2$-oxetane, —C(O)—N(H)—SO$_2$-morpholinyl, —C(O)—N(H)—SO$_2$-thiomorpholinyl 1,1-dioxide, —C(O)—N(H)—SO$_2$-isothiozolidine 1,1-dioxide, —C(O)—N(H)—SO$_2$-pyridyl, or —C(O)—N(H)—SO$_2$—isoxazolyl optionally substituted with 1-3 methyl.

35. The compound according to claim 4, wherein $R^5$ is F, Cl, C$_1$-C$_3$alkyl, C$_1$-C$_3$haloalkyl, or —OCH$_3$ optionally substituted with 1-3 F.

36. The compound according to claim 1, wherein $R^7$ is:

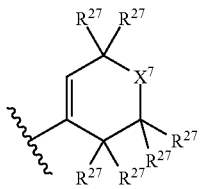

wherein:

$X^7$ is —C(R$^{25}$)(R$^{26}$)—;

$R^{25}$ is H, halogen, C$_1$-C$_4$alkyl, or C$_1$-C$_4$haloalkyl;

$R^{26}$ is H, halogen, C$_1$-C$_4$alkyl, C$_1$-C$_4$haloalkyl, CN, —N(H)SO$_2$—C$_1$-C$_4$alkyl, —N(H)SO$_2$—C$_1$-C$_4$haloalkyl, or —N(H)SO$_2$—C$_3$-C$_6$cycloalkyl optionally substituted with 1-3 halogens;

each $R^{27}$ is independently H, D, F, Cl, CH$_3$, —CFH$_2$, —CF$_2$H or —CF$_3$, provided that no more than four $R^{27}$ is other than H.

37. The compound according to claim, wherein $R^7$ is: